United States Patent
Kawanishi et al.

(10) Patent No.: US 6,699,891 B1
(45) Date of Patent: Mar. 2, 2004

(54) NPYY5 ANTAGONISTS

(75) Inventors: Yasuyuki Kawanishi, Osaka (JP); Hideyuki Takenaka, Shiga (JP); Kohji Hanasaki, Osaka (JP); Tetsuo Okada, Sakai (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/111,981

(22) PCT Filed: Nov. 21, 2000

(86) PCT No.: PCT/JP00/08197

§ 371 (c)(1),
(2), (4) Date: May 1, 2002

(87) PCT Pub. No.: WO01/37826

PCT Pub. Date: May 31, 2001

(30) Foreign Application Priority Data

Nov. 26, 1999 (JP) .......................... 11/336469
Dec. 14, 1999 (JP) .......................... 11/353786

(51) Int. Cl.[7] .................... A61K 31/44; C07D 213/75
(52) U.S. Cl. ................................ 514/352; 546/309
(58) Field of Search ............................. 514/352; 546/309

(56) References Cited

U.S. PATENT DOCUMENTS

| | | | |
|---|---|---|---|
| 4,948,809 A | 8/1990 | Witte et al. ............ | 514/538 |
| 4,981,873 A | 1/1991 | Witte et al. ............ | 514/562 |
| 5,817,677 A | 10/1998 | Linz et al. ............. | 514/326 |
| 6,124,331 A | * 9/2000 | Marzabadi ............. | 514/336 |
| 6,140,354 A | * 10/2000 | Dax ..................... | 514/357 |
| 6,172,108 B1 | 1/2001 | Vega et al. ............ | 514/485 |
| 6,380,224 B1 | * 4/2002 | Dax ..................... | 514/357 |

FOREIGN PATENT DOCUMENTS

| | | |
|---|---|---|
| EP | 0 148 725 A1 | 7/1985 |
| EP | 0 226 346 A1 | 6/1987 |
| EP | 0 837 052 A1 | 4/1996 |
| EP | 0 757 037 A2 | 2/1997 |
| EP | 0 915 086 A1 | 5/1999 |
| EP | 0 950 656 A1 | 10/1999 |
| EP | 1 010 691 A2 | 6/2000 |
| EP | 1 184 373 A1 | 3/2002 |
| JP | 59-16871 A | 1/1984 |
| JP | 2-180862 A | 7/1990 |
| JP | 4-364158 A | 12/1992 |
| JP | 5-194370 A | 8/1993 |
| JP | 5-26243 A | 10/1993 |
| JP | 8-92249 A | 4/1996 |
| JP | 2001-122865 A | 5/2001 |
| JP | 2001-172257 A | 6/2001 |
| WO | 95/35276 A1 | 12/1995 |
| WO | 96/00214 A1 | 1/1996 |
| WO | WO 97/15567 | 5/1997 |
| WO | 97/20820 A1 | 6/1997 |
| WO | 97/20821 A | 6/1997 |
| WO | 97/20823 A1 | 6/1997 |
| WO | 97/28137 A1 | 8/1997 |
| WO | 97/44315 A1 | 11/1997 |
| WO | 99/32466 A1 | 7/1999 |
| WO | 99/64394 A1 | 12/1999 |
| WO | 01/07409 A1 | 7/2000 |
| WO | 00/63171 A1 | 10/2000 |
| WO | 00/64880 A1 | 11/2000 |
| WO | 00/68197 A1 | 11/2000 |
| WO | 01/02379 A1 | 1/2001 |
| WO | 01/09120 A1 | 2/2001 |

OTHER PUBLICATIONS

Shionogi et al. "Sulfonamide type benzamides" CA 100:209423 (1984).*
Linz et al. "Five memebered heterocycles . . . " CA 127:17681 (1997).*
Taniguchi et al. "Preparation of acylamino substituted . . . " CA 129:40984 (1998).*
Rubini et al. "Synthesis of isosteric methylene–oxy . . . " Tetrahedron V.42, p. 6039–6054 (1996).*
Bundgaard "Design of prodrugs" Elsevier p. 1–10, 27–43 (1985).*
McNally et al., Biorganic & Medical Chemistry Letters, vol. 10, pp. 213–216 (2000).
Youngman et al., J. Med. Chem., vol. 43, pp. 346–350 (2000).

* cited by examiner

Primary Examiner—Ceila Chang
(74) Attorney, Agent, or Firm—Birch, Stewart, Kolasch & Birch, LLP

(57) ABSTRACT

The present invention provides a pharmaceutical composition for use as an NPY Y5 receptor antagonist comprising a compound of the formula (I):

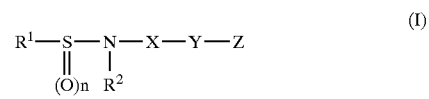

wherein $R^1$ is lower alkyl, cycloalkyl or the like, $R^2$ is hydrogen, lower alkyl or the like, n is 1 or 2, X is lower alkylene, lower alkenylene, arylene, cycloalkylene or the like, Y is $CONR^7$, $CSNR^7$, $NR^7CO$, $NR^7CS$ or the like, Z is lower alkyl, optionally substituted carbocyclyl, optionally substituted heterocyclyl or the like and $R^7$ is hydrogen or lower alkyl, prodrug, pharmaceutically acceptable salt or solvate thereof.

10 Claims, No Drawings

NPYY5 ANTAGONISTS

TECHNICAL FIELD

The present invention relates to a pharmaceutical composition for use as an NPY Y5 receptor antagonist, specifically, anti-obestic agent and novel compounds having an anti-obestic activity.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulating activity of food intake, an anti-seizure activity, a learning-promoting activity, an anti-anxiety activity, an anti-stress activity etc. in central nervous system, and it may be pivotally involved in the central nervous system diseases such as depression, Alzheimer's disease and Parkinson's disease. NPY is thought to be associated with the cardiovascular diseases, since it induces a contraction of smooth muscles such as blood vessels or cardiac muscles in the peripheral tissues. Furthermore, NPY is also known to be involved in the metabolic diseases such as obesity, diabetes, and hormone abnormalities (Trends in Pharmacological Sciences, Vol.15, and 153 (1994)). Therefore, an NPY receptor antagonist is expected as a medicine for preventing or treating various diseases involved in the NPY receptor.

Subtypes of Y1, Y2, Y3, Y4, Y5, and Y6 have now been identified as the NPY receptor (Trends in Pharmacological Sciences, Vol.18, and 372 (1997)). It has been suggested that the Y5 receptor is at least involved in the feeding behavior and its antagonist is expected as an anti-obestic agent (Peptides, Vol.18, and 445 (1997)).

Quinazoline compounds having similar structures to those of the compounds of the present invention and exhibiting an NPY receptor antagonistic activity are described in WO97/20820, WO97/20821, WO97/20823 and the like. In addition, it is described that urea derivatives having a sulfonamide group and amide derivatives having a sulfonyl group in WO 99/64349 and benzyl sulfonamide derivatives in EP1010691-A, have an NPY antagonistic activity.

Compounds having similar structures to those of the compounds of the present invention are described in JP59-16871-A and WO97/15567. Their activities are quite different from that of the present invention and these documents do not suggest the present invention.

DISCLOSURE OF INVENTION

The object of the present invention is to provide a superior pharmaceutical composition for use as an NPY Y5 receptor antagonist and novel compounds having the activity.

The present invention provides

[1] A pharmaceutical composition for use as an NPY Y5 receptor antagonist comprising a compound of the formula (I):

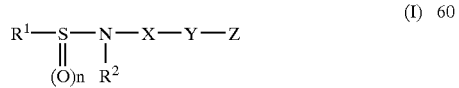
(I)

wherein $R^1$ is optionally substituted lower alkyl, optionally substituted cycloalkyl or optionally substituted aryl, $R^2$ is hydrogen or lower alkyl, and $R^1$ and $R^2$ taken together may form lower alkylene, n is 1 or 2, X is optionally substituted lower alkylene,
optionally substituted lower alkenylene,
optionally substituted —CO-lower alkylene,
optionally substituted —CO-lower alkenylene or

wherein $R^3$, $R^4$, $R^5$ and $R^6$ are each independently hydrogen or lower alkyl,

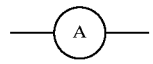

is optionally substituted cycloalkylene, optionally substituted cycloalkenylene, optionally substituted bicycloalkylene, optionally substituted arylene or optionally substituted heterocyclediyl and p and q are each independently 0 or 1, —$NR^2$—X— may be

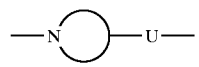

wherein

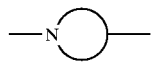

is piperidinediyl, piperazinediyl, pyridinediyl, pyrazinediyl, pyrrolidinediyl or pyrrolediyl and U is single bond, lower alkylene or lower alkenylene, Y is $OCONR^7$, $CONR^7$, $CSNR^7$, $NR^7CO$ or $NR^7CS$, $R^7$ is hydrogen or lower alkyl, and Z is optionally substituted lower alkyl, optionally substituted lower alkenyl, optionally substituted amino, optionally substituted lower alkoxy, optionally substituted carbocyclyle or optionally substituted heterocyclyl, prodrug, pharmaceutically acceptable salt or solvate thereof,

[2] The pharmaceutical composition for use as an NPY Y5 receptor antagonist described in [1] wherein $R^2$ is hydrogen or lower alkyl and Z is optionally substituted lower alkyl, optionally substituted lower alkenyl, optionally substituted lower alkoxy, optionally substituted carbocyclyl, optionally substituted heterocyclyl or optionally substituted amino, provided that $R^1$ is optionally substituted C3 to C10 alkyl when Z is optionally substituted amino,

[3] The pharmaceutical composition for use as an NPY Y5 receptor antagonist described in [1] wherein $R^1$ is optionally substituted lower alkyl or optionally substituted cycloalkyl, X is optionally substituted lower alkylene, optionally substituted lower alkenylene or

wherein

is the same as defined in [1], and Z is optionally substituted lower alkyl, optionally substituted carbocyclyl or optionally substituted heterocyclyl,

[4] The pharmaceutical composition for use as an NPY Y5 receptor antagonist described in any one of [1] to [3] wherein $R^1$ is optionally substituted C3 to C10 alkyl,

[5] The pharmaceutical composition for use as an NPY Y5 receptor antagonist described in any one of [1] to [4] which is an anti-obestic agent,

[6] The pharmaceutical composition for use as an NPY Y5 receptor antagonist described in any one of [1] to [4] which is an anorectic agent,

[7] A method for treating and/or preventing obesity comprising administering an effective dose of an NPY Y5 receptor antagonist described in any one of [1] to [4],

[8] A method for suppressing food intake comprising administering an effective dose of an NPY Y5 receptor antagonist described in any one of [1] to [4],

[9] Use of an NPY Y5 receptor antagonist described in any one of [1] to [4] for manufacturing a medicine for treating and/or preventing obesity,

[10] Use of an NPY Y5 receptor antagonist described in any one of [1] to [4] for manufacturing a medicine for suppressing food intake,

[11] A compound of the formula (I):

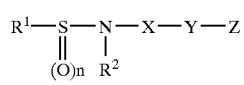

wherein X is C2 to C6 alkylene or C3 to C6 alkenylene, $R^1$ is optionally substituted C3 to C10 alkyl or optionally substituted C5 to C6 cycloalkyl and the other symbols are the same as defined in [1], provided that Z is not lower alkylphenylamino, hydroxy(lower)alkylphenylamino and acylphenylamino when Y is $NR^7CO$, prodrug, pharmaceutically acceptable salt or solvate thereof,

[12] The compound described in [11] wherein Z is optionally substituted lower alkyl or optionally substituted phenyl, prodrug, pharmaceutically acceptable salt or solvate thereof,

[13] A compound of the formula (I):

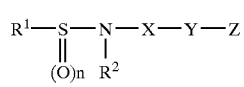

wherein X is

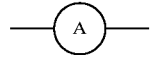

is optionally substituted cycloalkylene, optionally substituted cycloalkenylene, optionally substituted bicycloalkylene or optionally substituted piperidinylene, $R^1$ is optionally substituted C3 to C10 alkyl or optionally substituted C5 to C6 cycloalkyl and the other symbols are the same as defined in [1], prodrug, pharmaceutically acceptable salt or solvate thereof,

[14] The compound described in [13] wherein is optionally substituted cyclohexylene or optionally substituted piperidinylene and p and q are simultaneously 0, prodrug, pharmaceutically acceptable salt or solvate thereof,

[15] The compound described in [13] or [14] wherein Y is CONH, prodrug, pharmaceutically acceptable salt or solvate thereof,

[16] The compound described in any one of [13] to [15] wherein Z is optionally substituted lower alkyl, optionally substituted phenyl, optionally substituted pyridyl or optionally substituted benzopyranyl, prodrug, pharmaceutically acceptable salt or solvate thereof,

[17] A compound of the formula (I):

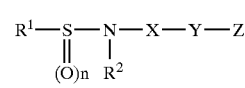

wherein X is

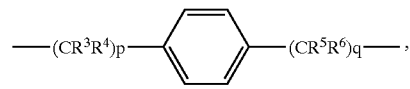

$R^1$ is optionally substituted C3 to C10 alkyl or optionally substituted C5 to C6 cycloalkyl, Z is p-(lower)alkylphenyl and the other symbols are the same as defined in [1], provided that Z is not p-n-butylphenyl when $R^1$ is isopropyl, prodrug, pharmaceutically acceptable salt or solvate thereof,

[18] A compound of the formula (I):

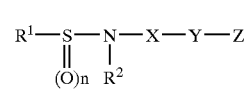

wherein X is

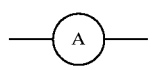

is heteroarylene, $R^1$ is optionally substituted C3 to C10 alkyl or optionally substituted C5 to C6 cycloalkyl and the other symbols are the same as defined in [1], prodrug, pharmaceutically acceptable salt or solvate thereof,

[19] The compound described in [18] wherein

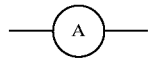

is thiophenediyl or furandiyl, prodrug, pharmaceutically acceptable salt or solvate thereof and

[20] A pharmaceutical composition comprising the compound described in any one of [11] to [19], prodrug, pharmaceutically acceptable salt or solvate thereof.

BEST MODE FOR CARRYING OUT THE INVENTION

In the present specification, the term "halogen" includes fluorine, chlorine, bromine and iodine. Fluorine or chlorine is preferable.

The term "protective group" in "optionally protected hydroxy" and "optionally protected hydroxy(lower)alkyl" includes all of hydroxy protecting groups usually used. For example, acyl such as acetyl, trichloroacetyl and benzoyl, lower alkoxycarbonyl such as t-butoxycarbonyl, lower alkylsulfonyl such as methane sulfonyl, lower alkoxy(lower)alkyl such as methoxymethyl, trialkylsilyl such as t-butyldimethylsilyl are included.

The term "lower alkyl" includes C1 to C10 straight or branched alkyl. The examples of "lower alkyl" are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl.

"Lower alkyl" represented by $R^1$ is preferably C3 to C10 alkyl, more preferably C3 to C6 alkyl and most preferably isopropyl or t-butyl.

"Lower alkyl" in other cases is preferably C1 to C6 alkyl and more preferably C1 to C4 alkyl.

The examples of substituents of "optionally substituted lower alkyl" represented by Z are, (1) halogen; (2) cyano;
(3) the following groups (i) to (xvi), which are optionally substituted with one or more substituents selected from "a substituents group β" defined below,
  (i) hydroxy, (ii) lower alkoxy, (iii) mercapto, (iv) lower alkylthio, (v) acyl, (vi) acyloxy, (vii) carboxy, (viii) lower alkoxycarbonyl, (ix) imino, (x) carbamoyl, (xi) thiocarbamoyl, (xii) lower alkylcarbamoyl, (xiii) lower alkylthiocarbamoyl, (xiv) amino, (xv) lower alkylamino or (xvi) heterocyclylcarbonyl; or
(4) a group of the formula:

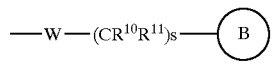

wherein $R^{10}$ and $R^{11}$ are each independently hydrogen or lower alkyl and when this group has two or more of $R^{10}$ and/or two or more of $R^{11}$, each $R^{10}$ and/or each $R^{11}$ may be different, W is single bond, O, S or $NR^{12}$, $R^{12}$ is hydrogen, lower alkyl or phenyl,

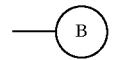

is cycloalkyl, bicycloalkyl, cycloalkenyl, aryl or heterocyclyl, each of which is optionally substituted with one or more of substituents selected from "a substituents group α" defined below and s is an integer of 0 to 4.

In the present specification, "a substituents group α" is a group constituting of (1) halogen; (2) oxo; (3) cyano; (4) nitro; (5) imino optionally substituted with lower alkyl or hydroxy;
  (6) the following groups (i) to (xxi), which are optionally substituted with one or more of groups selected from the substituents group A,
    (i) hydroxy, (ii) lower alkyl, (iii) lower alkenyl, (iv) lower alkoxy, (v) carboxy, (vi) lower alkoxycarbonyl, (vii) acyl, (viii) acyloxy, (ix) imino, (x) mercapto, (xi) lower alkylthio, (xii) carbamoyl, (xiii) lower alkylcarbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl and (xxi) cycloalkylsulfamoyl;
  (7) the following groups (i) to (v), which are optionally substituted with the substituents group β, lower alkyl, lower alkoxy(lower)alkyl, optionally protected hydroxy(lower)alkyl, halogeno(lower)alkyl, lower alkylsulfonyl and/or arylsulfonyl,
    (i) cycloalkyl, (ii) cycloalkenyl, (iii) cycloalkyloxy, (iv) amino and (v) alkylenedioxy; and
  (8) the following groups (i) to (xii), which are optionally substituted with the substituents group β, lower alkyl, halogeno(lower)alkyl and/or oxo,
    (i) phenyl, (ii) naphthyl, (iii) phenoxy, (iv) phenyl(lower)alkoxy, (v) phenylthio, (vi) phenyl(lower)alkylthio, (vii) phenylazo, (viii) heterocyclyl, (ix) heterocyclyloxy, (x) heterocyclylthio, (xi) heterocyclylcarbonyl and (xii) heterocyclylsulfonyl.

The preferable examples of the substituents group α as substituents for B ring are halogen; nitro; hydroxy;

optionally substituted lower alkyl wherein the substituents is halogen, cyano, phenyl, carboxy and/or lower alkoxycarbonyl;

lower alkenyl; lower alkoxycarbonyl(lower)alkenyl;

optionally substituted lower alkoxy wherein the substituents is halogen, hydroxy, lower alkoxy, carboxy, lower alkoxycarbonyl, lower alkylamino and/or cyano;

acyl; hydroxyimino; lower alkylthio; lower alkylsulfinyl; sulfamoyl;

optionally substituted amino wherein the substituents is lower alkyl, optionally protected hydroxy(lower)alkyl, phenyl and/or acyl;

alkylenedioxy; cyanophenyl; heterocyclylphenyl; biphenylyl; phenoxy; phenylazo optionally substituted with lower alkyl; or optionally substituted heterocyclyl wherein the substituents is optionally protected hydroxy, mercapto, halogen, lower alkyl, cycloalkyl, lower alkoxycarbonyl, amino, lower alkoxycarbonyl amino, carbamoyl, oxo, phenyl, lower alkoxyphenyl or heterocyclyl. More preferable examples are halogen; lower alkyl optionally substituted with halogen; or lower alkoxy optionally substituted with halogen.

"A substituents group β" is a group consisting of halogen, optionally protected hydroxy, mercapto, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, phenoxy, lower alkylphenyl, lower alkoxyphenyl, halogenophenyl, naphthyl and heterocyclyl.

Examples of the substituents for "optionally substituted lower alkyl" represented by any other than Z (e.g., $R^1$) are one or more substituents selected from the substituents group β. The lower alkyl may be substituted with these substituents at any possible positions.

The lower alkyl part in "lower alkoxy", "lower alkoxycarbonyl", "lower alkoxycarbonyl(lower)alkyl", "lower alkylphenyl", "lower alkoxyphenyl", "lower alkylcarbamoyl", "lower alkylthiocarbamoyl", "lower alkylamino", "halogeno(lower)alkyl", "hydroxy(lower) alkyl", "phenyl(lower)alkoxy", "lower alkylthio", "phenyl (lower)alkylthio", "lower alkoxycarbonylamino", "lower alkoxycarbonyl(lower)alkenyl", "lower alkylsulfinyl", "lower alkylsulfonyl", "aryl(lower)alkoxycarbonyl", "lower alkylbenzoyl" and "lower alkoxybenzoyl" is the same as defined in the above "lower alkyl".

Examples of substituents for "optionally substituted lower alkoxy" are one or more substituents selected from the substituents group β. Preferable examples are phenyl, lower alkylphenyl, lower alkoxyphenyl, naphthyl and heterocyclyl.

The term "cycloalkyl" includes C3 to C8 cyclic alkyl and preferably C5 to C6 cyclic alkyl. Examples are cyclopropyl, cyclobutyl, cyclopentyl, cyclohexyl, cycloheptyl and cyclooctyl.

Examples of substituents for "optionally substituted cycloalkyl" are one or more substituents selected from the substituents group α and the cycloalkyl may be substituted with these substituents at any possible positions.

The term "bicycloalkyl" includes a group which is formed by excluding one hydrogen from a C5 to C8 aliphatic cycle containing two rings which possess two or more of atoms in common. Examples are bicyclo[2.1.0]pentyl, bicyclo[2.2.1] heptyl, bicyclo[2.2.2]octyl and bicyclo[3.2.1]octyl.

The term "lower alkenyl" includes C2 to C10, preferably C2 to C8 and more preferably C3 to C6 straight or branched alkenyl having one or more double bonds at any possible positions. Examples are vinyl, propenyl, isopropenyl, butenyl, isobutenyl, phenyl, butadienyl, pentenyl, isopentenyl, pentadienyl, hexenyl, isohexenyl, hexadienyl, heptenyl, octenyl, nonenyl and decenyl.

The "lower alkenyl" part in "lower alkoxycarbonyl (lower)alkenyl" is the same as the above "lower alkenyl".

Examples of the substituents for "optionally substituted lower alkenyl" are halogen, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, lower alkylphenyl, lower alkoxyphenyl, naphthyl and/or heterocyclyl.

The term "acyl" includes (1) C1 to C10, preferably C1 to C6 and more preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl and benzoyl.

The "acyl" part in "acyloxy" is the same as the above.

The term "cycloalkenyl" includes a group having at least one double bond at any possible positions in the above cycloalkyl. Examples are cyclopropenyl, cyclobutenyl, cyclopentenyl, cyclohexenyl and cyclohexadienyl.

Examples of substituents for "optionally substituted cycloalkenyl" are one or more substituents selected from the substituents group β.

Examples of substituents for "optionally substituted amino" are the substituents group β, optionally substituted benzoyl and/or optionally substituted heterocyclylcarbonyl wherein the substituents is hydroxy, lower alkyl, lower alkoxy and/or lower alkylthio.

The term "aryl" includes a monocyclic of polycyclic aromatic carbocyclyl group and examples are phenyl, naphthyl, anthryl and phenanthryl. "Aryl" includes aryl fused with other a non-aromatic carbocyclyl group, for example, indanyl, indenyl, biphenylyl, acenaphthyl, tetrahydronaphthyl and fluorenyl. Phenyl is preferable.

The aryl part in "aryl lower alkoxycarbonyl" is the same as the above.

The term "optionally substituted aryl" and "optionally substituted phenyl" represented by Z include the above "aryl" and "phenyl" respectively, which may be substituted with the substituents group α or lower alkyl which may be substituted with one or more group selected from the substituents group α.

Examples of the substituents for "optionally substituted aryl" and "optionally substituted phenyl" represented by any other than Z are one or more groups selected from the substituents group β.

The term "carbocyclyl" includes the above "cycloalkyl", "cycloalkenyl", "bicycloalkyl" and "aryl".

The term "non-aromatic carbocyclyl" includes the above "cycloalkyl", "cycloalkenyl" and "bicycloalkyl".

The term "optionally substituted carbocyclyl" includes the above "optionally substituted cycloalkyl", "optionally substituted cycloalkenyl", "optionally substituted bicycloalkyl" and "optionally substituted aryl".

The term "heterocyclyl" includes a heterocyclic group containing at least one heteroatom arbitrarily selected from O, S and N. For example, 5- or 6-membered heteroaryl such as pyrrolyl, imidazolyl, pyrazolyl, pyridyl, pyridazinyl, pyrimidinyl, oxazolyl, oxadiazolyl, isothiazolyl, thiazolyl, thiadiazolyl, furyl and thienyl; fused heterocyclyl consisting of two rings such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl benbzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, quinazolinyl, quinolyl, isoquinolyl, naphthyridinyl, dihydropyridyl, tetrahydroquinolyl and tetrahydrobenzothienyl; fused heterocyclyl consisting of three rings such as carbazolyl, acridinyl, xanthenyl, phenothiazinyl, phenoxathiinyl, phenoxazinyl and dibenzofuryl; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

"Fused heterocyclyl" fused with a ring other than a heterocycle (e.g., benzothiazolyl), may connect at any possible position.

Substituents for "optionally substituted heterocyclyl" are the same as those for the above "optionally substituted aryl".

Heterocyclyl parts in "heterocyclylcarbonyl", "heterocyclyloxy", "heterocyclylthio" and "heterocyclyl substituted phenyl" are the same as the above "heterocyclyl".

The term "lower alkylene" includes a bivalent group comprising 1 to 6 of methylene, preferably 2 to 6 of methylene and more preferably 3 to 6 of methylene. For example, methylene, ethylene, trimethylene, tetramethylene, pentamethylene and hexamethylene are included. Tetramethylene is preferable.

"$R^1$ and $R^2$ taken together may form lower alkylene" includes the case

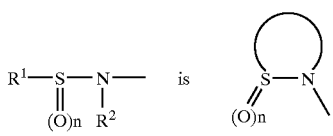   is   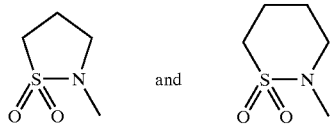

Preferable examples are

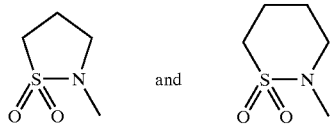

Lower alkylene part in "lower alkylenedioxy" is the same as the above "lower alkylene". Methylenedioxy or ethylenedioxy is preferable.

The term "lower alkenylene" includes a bivalent group comprising 2 to 6 of methylene, preferably 3 to 6 of methylene and more preferably 4 to 5 of methylene and including at least one double bond.

The term "cycloalkylene" includes a bivalent group which is formed by excluding one hydrogen from the above "cycloalkyl". A preferable example of cycloalkylene represented by X is 1,4-cyclohexanediyl.

The term "cycloalkenylene" includes a group containing at least one double bonds in the above cycloalkylene.

The term "bicycloalkylene" includes a group which is formed by excluding one hydrogen from the above "bicycloalkyl". Examples are bicyclo[2.1.0]pentylene, bicyclo[2.2.1]heptylene, bicyclo[2.2.2]octylene, and bicyclo[3.2.1]octylene.

The term "heterocyclediyl" includes a bivalent group which is formed by excluding one hydrogen from the above "heterocyclyl". Piperidinediyl, piperazinediyl, pyridinediyl, pyrimidinediyl, pyrazinediyl, pyrrolidinediyl or pyrrolediyl is preferable and piperidindiyl is more preferable.

The term "arylene" includes a bivalent group which is formed by excluding one hydrogen from the above "aryl". Phenylene is preferable.

The term "heteroarylene" includes aromatic groups in the above "heterocyclediyl". Examples are pyrrolediyl, imidazolediyl, pyrazolediyl, pyridinediyl, pyridazinediyl, pyrimidinediyl, pyrazinediyl, triazolediyl, triazinediyl, isoxazolediyl, oxazolediyl, oxadiazolediyl, isothiazolediyl, thiazolediyl, thiadiazolediyl, furandiyl and thiophenediyl.

One or more groups selected from the substituents group β are examples of substituents for "optionally substituted lower alkylene", "optionally substituted lower alkenylene", "optionally substituted cycloalkylene", "optionally substituted cyclohexylene", "optionally substituted bicycloalkylene", "optionally substituted cycloalkenylene", "optionally substituted phenylene", "optionally substituted heterocyclediyl" and "optionally substituted piperidinylene". Halogen, hydroxy, lower alkyl, halogeno(lower)alkyl, lower alkoxy, amino, lower alkylamino, acyl, carboxy or lower alkoxycarbonyl is preferable. These substituents may attach to any possible positions.

When $-NR^2-X-$ is

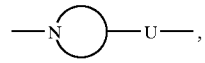

U is preferably single bond or methylene. More preferably,

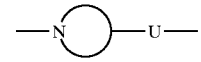

is

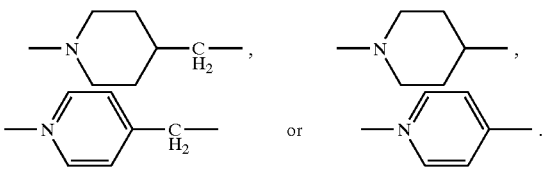

The compounds of the present invention include any formable and pharmaceutically acceptable salts thereof. Examples of "the pharmaceutically acceptable salt" are salts with mineral acids such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of the present invention include solvates thereof. Hydrate is preferable and arbitrary numbers of water molecules may coordinate to the compound of the present invention.

The compounds of the present invention include prodrugs thereof. Prodrug includes derivatives of the compounds of the present invention which have a chemically or metabolically decomposable group and can be converted into pharmaceutically active compounds of the present invention in vivo by solvolysis or under the physiological conditions. The methods for selecting and producing suitable prodrugs are described in Design of Prodrugs, Elsevier, Amsterdam 1985.

When a compound (I) of the present invention has carboxy, examples of prodrugs are an ester derivative and an amide derivative, which can be produced by reacting a compound (I) having carboxy with a suitable alcohol or a suitable amine, respectively.

When a compound (I) of the present invention has hydroxy, an example of prodrugs is an acyloxy derivative, which can be synthesized by reacting a compound (I) having hydroxy with a suitable acyl halide or a suitable acid anhydride.

When a compound (I) of the present invention has amino, an example of prodrugs is an amide derivative, which can be synthesized by reacting a compound (I) having amino with a suitable acid halide or a suitable mixed acid anhydride.

When the compound (I) of the present invention has an asymmetric carbon atom, it includes racemates, all of enantiomers and all of stereoisomers such as diastereomer, epimer and enantiomer thereof.

When the compound (I) of the present invention having one or more double bonds forms an E isomer or Z isomer, the compound (I) includes both isomers. When X is cycloalkylene, the compound (I) includes both of cis isomer and trans isomer.

For example, the compound (I) of the present invention can be synthesized by the following methods.
(Compounds Wherein Y=CONR$^7$)

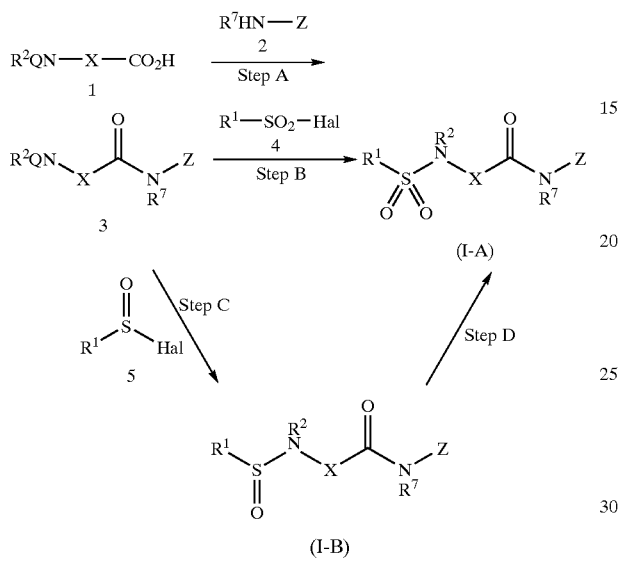

wherein Hal is halogen, Q is an amino protecting group and the other symbols are the same as the above.

Step A

Compound 1 is reacted with Amino Compound 2 having the desired substituent Z and R$^7$ in a suitable solvent at 0° C. to 50° C. for several minutes to several hours. As solvents, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, a mixture thereof etc. can be used. An activator such as thionyl chloride, acid halide, acid anhydride and activated ester can be used, if necessary.

Step B

Compound 3 is deprotected by the usual method and reacted with Sulfonyl Halide 4 having the desired substituent R$^1$ in a suitable solvent at 0° C. to 50° C. for several minutes to several hours to give Compound (I-A) wherein n is 2. Tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and the mixture thereof etc. can be used as a solvent.

Step C

Compound (I-B) wherein n is 1 can be synthesized by reacting Compound 3 with Sulfinyl Halide 5 having substituent R$^1$. The conditions for the reaction are the same as those of the above Step B.

Step D

Compound (I-B) obtained in Step C is oxidized by the usual method to give Compound (I-A) wherein n is 2. m-Chloroperbenzoic acid, peracetic acid, hydrogen peroxide, trifluoroperacetic acid, sodium periodate, sodium hypochlorite, potassium permanganate etc. can be used as an oxidizer and the reaction may be carried out at 0° C. to 50° C. Examples of solvents are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, methanol, ethanol, isopropanol and mixture thereof.

In case X is heterocyclediyl containing at least one N atom and the N atom connects to CONR$^7$—Z in the compound (I), the following reaction may be employed to obtain Compound (I-A') or (I-B'). Step D may be carried out just after Step C or Step E.

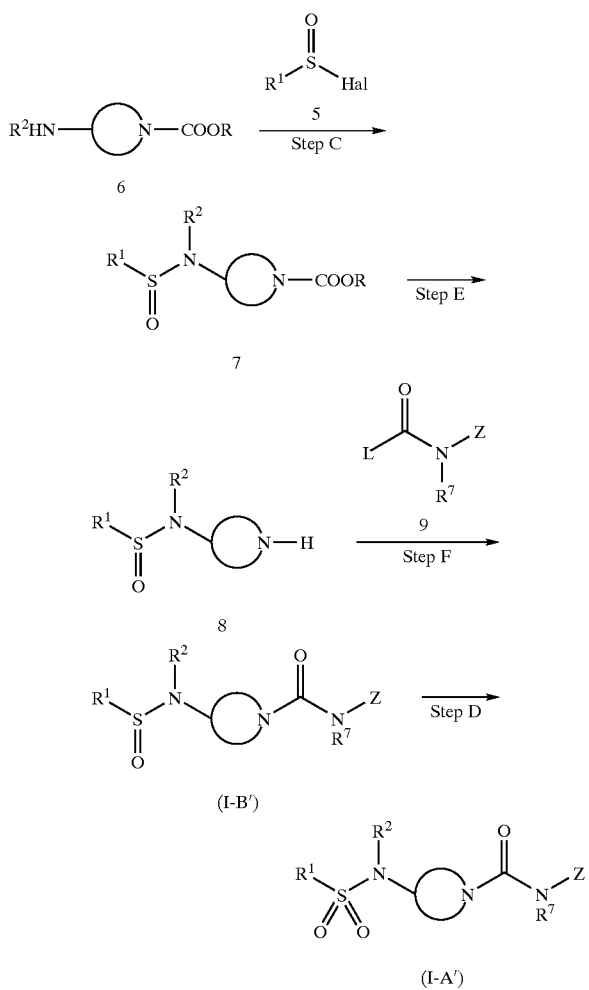

wherein R is lower alkyl or aryl and L is a leaving group.

Step C

Compound 5 is reacted with Compound 6 in a similar manner to the above Step C to give Compound 7.

Step E

Thus obtained Compound 7 is treated with a base in a suitable solvent to give Compound 8. For example, barium hydroxide, sodium hydroxide, potassium hydroxide, hydrazine or lithium propanethiolate can be used as a base. As a solvent, tetrahydrofuran, dimethylformamide, dioxane, acetone, acetonitrile, methanol, ethanol, propanol, water, the mixture thereof or the like can be used. The reaction can be carried out at 0° C. to 100° C. for several minutes to several tens hours.

Step F

Compound 8 is reacted with Compound 9 having a leaving group and a desired substituent in a suitable solvent in the presence or absence of a base at 0° C. to 100° C. for several minutes to several days to give Compound (I-B'). Examples of the leaving group are phenoxy, chloro and trichloromethyl. Examples of the base are triethylamine, pyridine, diisopropylethylamine, sodium hydroxide, potassium carbonate and sodium hydrogencarbonate. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, methanol, ethanol and the mixture thereof.

Step D

Compound (I-B') is reacted in a similar manner to the above Step D to give Compound (I-A').

(Compound Wherein Y=NR⁷CO)

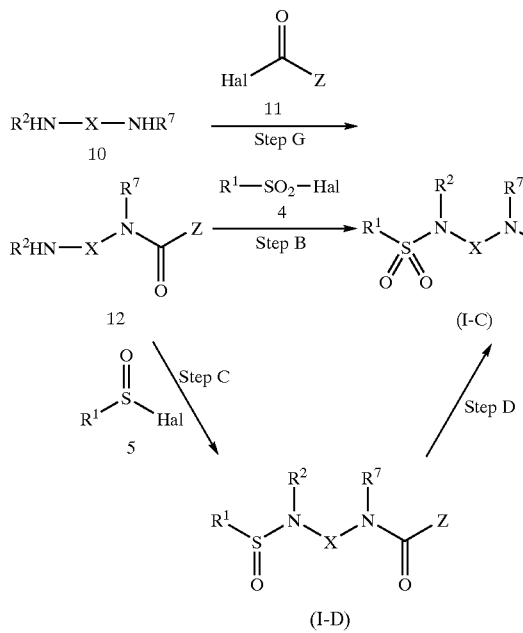

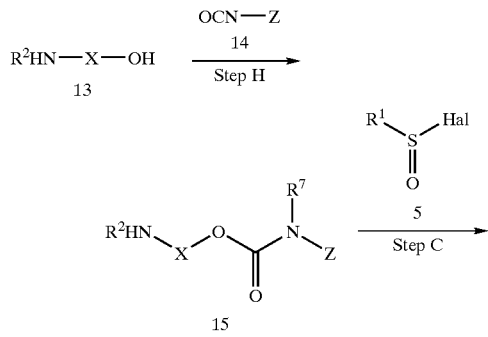

wherein each of the symbols is the same as the above.

Step G and Step B

Compound 10 is reacted with Compound 11 under the same reaction condition as that in Step B. Thus obtained Compound 12 is reacted in a similar manner to the above Step B to give Compound (I-C) wherein n=2.

Step C and Step D

To synthesize Compound (I-D), Compound 12 obtained in Step G may be reacted in similar manners to the above Step C and Step D.

(Compound Wherein Y=OCONR⁷)

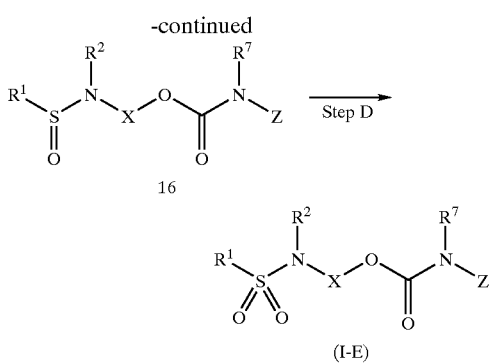

wherein each of symbols is the same as the above.

Step H

Compound 13 is reacted with Isocianate Compound 14 having a substituent Z in a suitable solvent in the presence or absence of a suitable catalyst at 0° C. to 100° C. for several minutes to several days to give Compound 15. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and the mixture thereof.

Step C and Step D

Thus obtained Compound 15 is reacted in similar manners to Step C and Step D to give Compound (I-E) of the present invention.

(Compound Wherein Y=CSNR⁷ or NR⁷CS)

Compound (I) wherein Y is CSNR⁷ or NR⁷CS can be synthesized by reacting Compound (I) wherein Y is CONR⁷ or NR⁷CO synthesized in any one of the above methods with the Lawesson's reagent or phosphorus pentasulfide in a suitable solvent at 30° C. to 100° C. for several minutes to several hours. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and the mixture thereof.

Amino groups may be protected with a suitable protecting group in the usual manner at a suitable step. For example, phthalimide, lower alkoxycarbonyl, lower alkenyloxycarbonyl, halogenoalkoxycarbonyl, aryl(lower) alkoxycarbonyl, trialkylsilyl, lower alkylsulfonyl, halogeno (lower)alkylsulfonyl, arylsulfonyl, lower alkylcarbonyl and arylcarbonyl can be used as the protecting group.

After protection of the amino group, the compound is subjected to the above-mentioned reactions and the obtained compound is deprotected by treatment of an acid or a base in a suitable solvent at a suitable stage. Examples of a solvent is tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and the mixture thereof. Examples of a base are hydrazine, pyridine, sodium hydroxide and potassium hydroxide and examples of an acid are hydrochloric acid, trifluoroacetic acid and hydrofluoric acid.

All of the compounds of the present invention have an NPY Y5 antagonistic activity and the following compounds are specifically preferable.

In the formula (I), a compound wherein R¹ is optionally substituted lower alkyl or optionally substituted cycloalkyl (hereinafter referred to as "R¹ is R1-1"), a compound wherein $R^1$ is C3 to C10 alkyl or C5 to C6 cycloalkyl, each of which is optionally substituted with halogen (hereinafter referred to as "$R^1$ is R1-2"), a compound wherein $R^1$ is C3 to C10 alkyl optionally substituted with halogen (hereinafter referred to as "$R^1$ is R1-3"), a compound wherein $R^1$ is isopropyl or t-butyl (hereinafter referred to as "$R^1$ is R1-4"), a compound wherein $R^2$ is hydrogen or C1 to C3 alkyl (hereinafter referred to as "$R^2$ is R2-1"), a compound wherein $R^2$ is hydrogen (hereinafter referred to as "$R^2$ is R2-2"), a compound wherein X is optionally substituted lower alkylene, optionally substituted lower alkenylene or

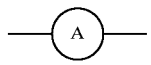

wherein

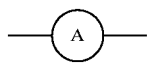

is optionally substituted cycloalkylene, optionally substituted cycloalkenylene, optionally substituted bicycloalkylene, optionally substituted phenylene or optionally substituted heterocyclediyl (hereinafter referred to as "X is X-1"), a compound wherein X is C2 to C6 alkylene, C3 to C6 alkenylene or

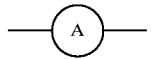

wherein

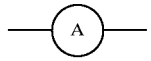

is optionally substituted cycloalkylene, optionally substituted cycloalkenylene, optionally substituted bicycloalkylene, optionally substituted phenylene, optionally substituted piperidinylene, optionally substituted thiophenediyl or optionally substituted furandiyl (hereinafter referred to as "X is X-2"), a compound wherein X is C2 to C6 alkylene or

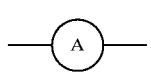

wherein is optionally substituted cycloalkylene, optionally substituted phenylene, optionally substituted piperidinylene, optionally substituted thiophenediyl or optionally substituted furandiyl (hereinafter referred to as "X is X-3"), a compound wherein X is (i) C2 to C6 alkylene or (ii) cycloalkylene or phenylene, each of which is optionally substituted with halogen, hydroxy, lower alkyl or halogeno(lower)alkyl (hereinafter referred to as "X is X-4"), a compound wherein X is C2 to C6 alkylene or to C5 to C6 cycloalkylene (hereinafter referred to as "X is X-5"), a compound wherein X is C3 to C6 alkylene or 1,4-cyclohexylene (hereinafter referred to as "X is X-6"), a compound wherein Y is $CONR^7$, $CSNR^7$, $NR^7CO$ or $NR^7CS$ and $R^7$ is hydrogen or C1 to C3 alkyl (hereinafter referred to as "Y is Y-1"), a compound wherein Y is CONH, CSNH or NHCO (hereinafter referred to as "Y is Y-2"), a compound wherein Y is CONH (hereinafter referred to as "Y is Y-3"), a compound wherein Z is optionally substituted lower alkyl, optionally substituted carbocyclyl or optionally substituted heterocyclyl (hereinafter referred to as "Z is Z-1"), a compound wherein Z is —$(CR^8R^9)$r-W—$(CR^{10}R^{11})$s-V wherein $R^8$, $R^9$, $R^{10}$ and $R^{11}$ are each independently hydrogen or lower alkyl and when Z has two or more of $R^8$, two or more of $R^9$, two or more of $R^{10}$ and/or two or more of $R^{11}$, each of $R^8$, $R^9$, $R^{10}$ and $R^{11}$ may be different, W is single bond, O, S or $NR^{12}$, $R^{12}$ is hydrogen, lower alkyl or phenyl, V is hydrogen, optionally substituted cycloalkyl, optionally substituted bicycloalkyl, optionally substituted aryl or optionally substituted heterocyclyl, r is an integer of 1 to 4 and s is an integer of 0 to 4 (hereinafter referred to as "Z is Z-2"), a compound wherein Z is —(CH2)r-W—$(CH_2)$s-V wherein W is single bond, O, S or $NR^{12}$, $R^{12}$ is hydrogen or lower alkyl, V is optionally substituted aryl or optionally substituted heterocyclyl wherein the substituents is halogen, hydroxy, lower alkyl, halogeno(lower)alkyl, lower alkoxy, lower alkenyl, amino, lower alkylamino, acyl, carboxy, lower alkoxycarbonyl, phenyl or monocyclic heteroaryl, r is an integer of 1 to 4 and s is an integer of 0 to 4 (hereinafter referred to as "Z is Z-3"), a compound wherein Z is —$(CH_2)$r-W—(CH2)s-V wherein W is single bond, O, S, NH or NMe, V is optionally substituted phenyl or optionally substituted heteroaryl wherein the substituents is halogen, lower alkyl, halogeno(lower)alkyl, lower alkoxy, amino or lower alkylamino, r is an integer of 1 to 3 and s is an integer of 0 or 1 (hereinafter referred to as "Z is Z-4"), a compound wherein Z is optionally substituted carbocyclyl,
wherein the substituent is halogen; hydroxy;
optionally substituted lower alkyl wherein the substituents is halogen, hydroxy, carboxy, lower alkoxycarbonyl, cyano and/or phenyl;
lower alkenyl optionally substituted with lower alkoxycarbonyl;
optionally substituted lower alkoxy wherein the substituents is halogen, hydroxy, lower alkoxy, carboxy, lower alkoxycarbonyl, lower alkylamino, cycloalkyl, cyano and/or heterocyclyl;
cycloalkyl; cycloalkyloxy; acyl; lower alkylthio; carbamoyl; lower alkylcarbamoyl; cycloalkylcarbamoyl; hydroxy imino;
optionally substituted amino wherein the substituents is lower alkyl, optionally protected hydroxy(lower)alkyl, lower alkoxy(lower)alkyl, acyl, lower alkylsulfonyl, arylsulfonyl and/or phenyl;
phenyl optionally substituted with halogen, cyano, phenyl and/or heterocyclyl;
lower alkylsulfinyl; lower alkylsulfamoyl; cycloalkylsulfamoyl;

nitro; cyano; alkylenedioxy; phenylazo optionally substituted with lower alkyl; phenoxy; oxo;
optionally substituted heterocyclyl wherein the substituents is optionally protected hydroxy, mercapto, halogen, lower alkyl, cycloalkyl, lower alkoxycarbonyl, acyl, amino, lower alkoxycarbonylamino, carbamoyl, oxo, phenyl, lower alkoxyphenyl, halogenophenyl, heterocyclyl and/or oxo;
heterocyclylsulfonyl optionally substituted with lower alkyl; heterocyclyloxy; heterocyclylcarbonyl optionally substituted with lower alkyl
(hereinafter referred to as "Z is Z-5"),
a compound wherein Z is optionally substituted phenyl
wherein the substituents is halogen; hydroxy; lower alkyl optionally substituted with halogen, hydroxy, lower alkoxycarbonyl, cyano and/or phenyl; lower alkoxycarbonyl(lower)alkenyl; lower alkoxy optionally substituted with halogen, lower alkoxy, lower alkoxycarbonyl, cycloalkyl and/or heterocyclyl; cycloalkyl; cycloalkyloxy; acyl; lower alkylthio; carbamoyl; lower alkycarbamoyl; amino optionally substituted with lower alkyl, hydroxy(lower)alkyl, acyl, lower alkylsulfonyl and/or phenyl; phenyl optionally substituted with halogen, cyano, phenyl and/or heterocyclyl;
lower alkyl sulfamoyl; cycloalkylsulfamoyl; nitro; alkylenedioxy; phenylazo optionally substituted with lower alkyl; phenoxy; oxo;
heterocyclyl optionally substituted with hydroxy, halogen, lower alkyl, lower alkoxycarbonyl, amino, carbamoyl, phenyl, halogenophenyl, heterocyclyl and/or oxo;
heterocyclyloxy; and/or heterocyclylsulfonyl optionally substituted with lower alkyl
(hereinafter referred to as " Z is Z-6"),
a compound wherein Z is optionally substituted phenyl
wherein the substituents is halogen; lower alkyl optionally substituted with halogen, hydroxy, lower alkoxycarbonyl and/or phenyl; lower alkoxy optionally substituted with halogen and/or cycloalkyl; cycloalkyl; cycloalkyloxy; acyl; lower alkylthio; lower alkylcarbamoyl; amino optionally substituted with lower alkyl, hydroxy(lower)alkyl, acyl and/or phenyl; phenyl optionally substituted with piperidyl; cycloalkylsulfamoyl; alkylenedioxy; phenoxy;
morpholinyl or morpholino, each of which is optionally substituted with lower alkyl; piperidyl optionally substituted with hydroxy, lower alkyl, lower alkoxycarbonyl, phenyl, halogenophenyl and/or oxo; pyrrolidinyl optionally substituted with hydroxy, carbamoyl and/or oxo;
piperazinyl optionally substituted with phenyl or pyrimidinyl; dihydropyridyl; pyrrolyl; pyrrolinyl; imidazolyl optionally substituted with halogen and/or lower alkyl; pyrazolyl; thienyl; thiadiazolyl; furyl; oxazolyl; isoxazolyl; tetrazolyl optionally substituted with lower alkyl and/or phenyl; indolinyl; indolyl; tetrahydroquinolyl; benzothiazolyl optionally substituted with lower alkyl; tetrahydroisothiazolyl optionally substituted with oxo; benzopyranyl optionally substituted with oxo; tetrahydropyranyloxy; tetrahydrofuryloxy; morpholinosulfonyl optionally substituted with lower alkyl; and/or piperidylsulfonyl optionally substituted with lower alkyl
(hereinafter referred to as "Z is Z-7"), a compound wherein Z is optionally substituted phenyl
wherein the substituents is halogen, lower alkyl, halogeno(lower)alkyl, lower alkoxy, cycloalkyloxy, lower alkylcarbamoyl, phenyl, lower alkyl morpholino and/or tetrahydropyranyloxy
(hereinafter referred to as "Z is Z-8"),
a compound wherein Z is optionally substituted heterocyclyl
wherein the substituents is halogen, hydroxy, lower alkyl, halogeno(lower)alkyl, lower alkoxy, mercapto, lower alkylthio, acyl, carboxy, lower alkoxycarbonyl, amino, lower alkylamino, phenyl, naphthyl, phenylthio optionally substituted with halogen, phenoxy optionally substituted with halogen, oxo, and/or heterocyclyl optionally substituted with lower alkyl
(hereinafter referred to as "Z is Z-9"),
a compound wherein Z is thienyl, pyrazolyl, thiazolyl, thiadiazolyl, pyridyl, pyrimidinyl, pyrazinyl, triazinyl, indolyl, isoindolyl, indolinyl, isoindolinyl, indazolyl, benzopyranyl, benzoxazolyl, benzothienyl, benzothiazolyl, benzothiazolinyl, benzothiadiazolyl, quinolyl, isoquinolyl, dihydrobenzofuryl, carbazolyl, acridinyl or dibenzofuryl, each of which is optionally substituted with substituents selected from the group of lower alkyl;
halogeno(lower)alkyl; lower alkoxy; lower alkoxycarbonyl; acyl; lower alkoxycarbonyl(lower)alkyl; mercapto; phenyl, naphthyl, phenylthio or phenoxy, each of which is optionally substituted with halogen; furyl; nitro; oxo; and morpholino optionally substituted with lower alkyl) (hereinafter referred to as "Z is Z-10"),
a compound wherein Z is thienyl, thiazolyl, thiadiazolyl, pyridyl, pyrazinyl, indolyl, isoindolinyl, benzopyranyl, quinolyl, carbazolyl, dibenzofuryl, benzopyranyl, benzothienyl or benzothiazolyl, each of which is optionally substituted with one or more substituents selected from the group of lower alkyl, halogeno(lower)alkyl, lower alkoxy, lower alkoxycarbonyl, acyl, phenyl, naphthyl, phenylthio, lower alkyl morpholino and oxo) (hereinafter referred to as "Z is Z-11),
a compound wherein $R^1$ is R1-2, $R^2$ is R2-2, n is 2 and a combination of X, Y and Z, i.e., (X, Y, Z), is any one of the followings.
(X, Y, Z)=(X-3, Y-2, Z-1), (X-3, Y-2, Z-2), (X-3, Y-2, Z-3), (X-3, Y-2, Z-4), (X-3, Y-2, Z-5), (X-3, Y-2, Z-6), (X-3, Y-2, Z-7), (X-3, Y-2, Z-8), (X-3, Y-2, Z-9), (X-3, Y-2, Z-10), (X-3, Y-2, Z-11), (X-3, Y-3, Z-1), (X-3, Y-3, Z-2), (X-3, Y-3, Z-3), (X-3, Y-3, Z-4), (X-3, Y-3, Z-5), (X-3, Y-3, Z-6), (X-3, Y-3, Z-7), (X-3, Y-3, Z-8), (X-3, Y-3, Z-9), (X-3, Y-3, Z-10), (X-3, Y-3, Z-11), (X-4, Y-2, Z-1), (X-4, Y-2, Z-2), (X-4, Y-2, Z-3), (X-4, Y-2, Z-4), (X-4, Y-2, Z-5), (X-4, Y-2, Z-6), (X-4, Y-2, Z-7), (X-4, Y-2, Z-8), (X-4, Y-2, Z-9), (X-4, Y-2, Z-10), (X-4, Y-2, Z-11), (X-4, Y-3, Z-1), (X-4, Y-3, Z-2), (X-4, Y-3, Z-3), (X-4, Y-3, Z-4), (X-4, Y-3, Z-5), (X-4, Y-3, Z-6), (X-4, Y-3, Z-7), (X-4, Y-3, Z-8), (X-4, Y-3, Z-9), (X-4, Y-3, Z-10), (X-4, Y-3, Z-11), (X-5, Y-2, Z-1), (X-5, Y-2, Z-2), (X-5, Y-2, Z-3), (X-5, Y-2, Z-4), (X-5, Y-2, Z-5), (X-5, Y-2, Z-6), (X-5, Y-2, Z-7), (X-5, Y-2, Z-8), (X-5, Y-2, Z-9), (X-5, Y-2, Z-10), (X-5, Y-2, Z-11), (X-5, Y-3, Z-1), (X-5, Y-3, Z-2), (X-5, Y-3, Z-3), (X-5, Y-3, Z-4), (X-5, Y-3, Z-5), (X-5, Y-3, Z-6), (X-5, Y-3, Z-7), (X-5, Y-3, Z-8), (X-5, Y-3, Z-9), (X-5, Y-3, Z-10), (X-5, Y-3, Z-11), the pharmaceutically acceptable salt, solvate or prodrug thereof.

The NPY Y5 receptor antagonist of the present invention is effective for all of the diseases in which NPY Y5 is involved and it is especially useful for preventing and/or treating obesity and suppressing food intake. Moreover, the antagonist is effective for preventing and/or treating the diseases in which obesity acts as a risk factor, for example, diabetes, hypertension, hyperlipemia, atherosclerosis and acute coronary syndrome.

In addition, the NPY Y5 receptor antagonist of the present invention has a low affinity for NPY Y1 and Y2 receptors, and has a high selectivity for NPY Y5 receptor. NPY causes a sustained vasoconstrictive action in the periphery and this action is mainly via Y1 receptor. Since Y5 receptor is not involved in this action at all, the NPY Y5 receptor antagonist has a low risk of inducing side effects based on the peripheral vasoconstriction, and is expected to be suitably used as a safe medicine.

The NPY Y5 receptor antagonist shows an anti-obestic effect by suppressing food intake. Therefore, it is one of the features that this antagonist does not induce side effects, e.g., an indigestion caused by an anti-obestic agent which inhibits digestion and absorption, and a central side effect such as anti-depression caused by a serotonin transporter inhibitor showing an anti-obesity effect.

A compound of the present invention can be administered orally or parenterally as an anti-obestic agent or anorectic agent. In the case of oral administration, it may be in any usual form such as tablets, granules, powders, capsules, pills, solutions, syrups, buccal tablets and sublingual tablets. When the compound is parenterally administered, any usual form is preferable, for example, injections (e.g., intravenous, intramuscular), suppositories, endermic agents and vapors. Oral administration is particularly preferable because the compounds of the present invention show a high oral absorbability.

A pharmaceutical composition may be manufactured by mixing an effective amount of a compound of the present invention with various pharmaceutical additives suitable for the administration form, such as excipients, binders, moistening agents, disintegrators, lubricants and diluents. When the composition is of an injection, an active ingredient together with a suitable carrier can be sterilized to give a pharmaceutical composition.

Examples of the excipients include lactose, saccharose, glucose, starch, calcium carbonate and crystalline cellulose. Examples of the binders include methylcellulose, carboxymethylcellulose, hydroxypropylcellulose, gelatin and polyvinylpyrrolidone. Examples of the disintegrators include carboxymethylcellulose, sodium carboxymethylcellulose, starch, sodium alginate, agar and sodium lauryl sulfate. Examples of the lubricants include talc, magnesium stearate and macrogol. Cacao oil, macrogol, methylcellulose etc. may be used as base materials of suppositories. When the composition is manufactured as solutions, emulsified injections or suspended injections, dissolving accelerators, suspending agents, emulsifiers, stabilizers, preservatives, isotonic agents and the like may be added. For oral administration, sweetening agents, flavors and the like may be added.

Although the dosage of a compound of the present invention as an anti-obestic agent or anorectic agent should be determined in consideration of the patient's age and body weight, the type and degree of diseases, the administration route etc., a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day, preferably, 0.01 to 1 mg/kg/day. The dosage may be administered in one to several divisions per day.

The present invention is further explained by the following Examples and Experiments, which are not intended to limit the scope of the present invention.

EXAMPLES

Example 1

Synthesis of Compound (I-7)

Step 1

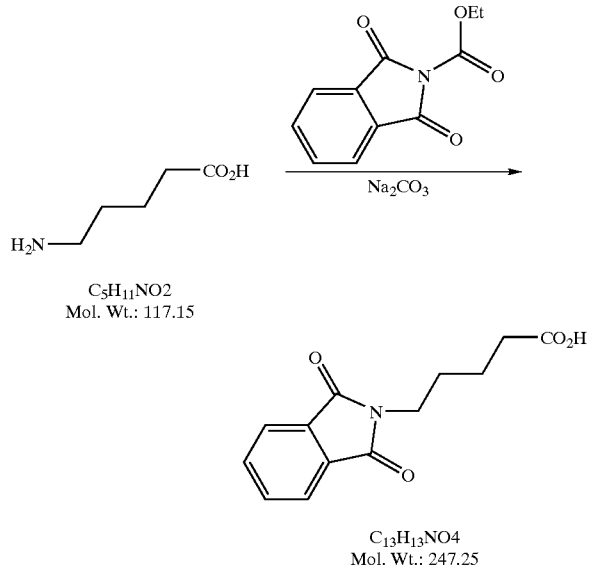

Sodium carbonate (995 mg, 9.38 mmol) was dissolved in 30 ml of water and starting material amino acid (1.0 g, 8.53 mmol) and N-carbethoxyphthalimide (2.49 g, 11.4 mmol) were added thereto. The mixture was stirred at room temperature overnight. The pH of the mixture was adjusted to 1 by adding conc. hydrochloric acid. Precipitated crystals were washed with water and dried to give the desired compound (1.72 g, 82% yield).

$^1$H-NMR (CD$_3$OD) δ ppm: 1.59–1.77 (m, 4H), 2.34 (t, 2H, J=6.3 Hz), 3.69 (t, 2H, J=6.6 Hz), 7.78–7.87 (m, 4H).

Step 2

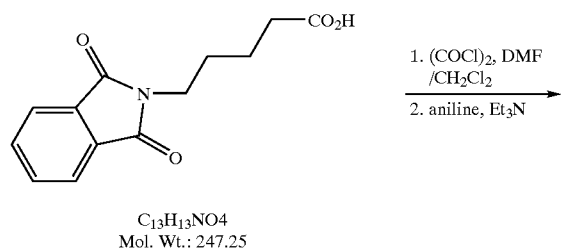

-continued

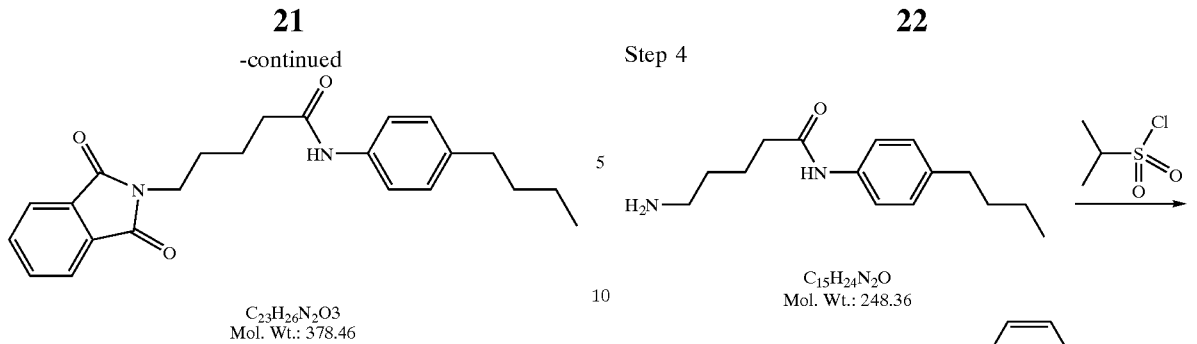

C₂₃H₂₆N₂O₃
Mol. Wt.: 378.46

The compound obtained in Step 1 (1.0 g, 4.0 mmol) was dissolved in 5 ml of dichloromethane at room temperature. Oxalyl chloride (0.459 ml, 5.2 mmol) and trace amounts of DMF were added to the mixture under ice-cooling and the mixture was reacted under ice-cooling and at room temperature, each for 30 min. After the solvent was removed under reduced pressure, 5 ml of dichloromethane was added. Under ice-cooling, 4-butylaniline (664 mg, 4.4 mmol) and triethylamine (0.564 ml, 4.4 mmol) were added thereto and the mixture was reacted for 30 min. at room temperature. The reactant was poured into water and extracted with chloroform. The organic layer was washed with water and dried over magnesium sulfate anhydride. The solvent was removed under reduced pressure and the residue was purified by silica gel chromatography to give the desired compound (1.49 g, 97% yield).

¹H-NMR (CDCl₃) δ ppm: 0.91 (t, 3H, J=7.5 Hz), 1.27–1.39 (m, 2H), 1.51–1.62 (m, 2H), 1.72–1.84 (m, 4H), 2.40–2.46 (m, 2H), 2.56 (t, 2H, J=7.5 Hz), 3.76 (t, 1H, J=5.7 Hz), 7.12 (d, 2H, J=7.8 Hz), 7.33 (s, 1H), 7.42 (d, 2H, J=8.1 Hz), 7.71–7.73 (m, 2H), 7.83–7.86 (m, 2H).

Step 3

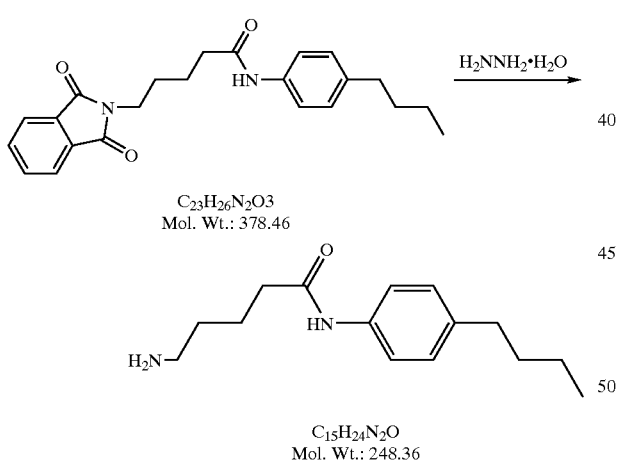

C₂₃H₂₆N₂O₃
Mol. Wt.: 378.46

C₁₅H₂₄N₂O
Mol. Wt.: 248.36

After the compound obtained in Step 2 (1.49 g, 3.9 mmol) was dissolved in 30 ml of ethanol, hydrazine monohydrate (0.591 mg, 11.8 mmol) was added and the mixture was reacted at 50° C. for 3 hours. The solvent was removed, 1 mol/l aqueous NaOH was added and the solution was extracted with ethyl acetate. The organic layer was washed with water and dried over magnesium sulfate anhydride. The solvent was removed under reduced pressure to give the desired compound (808 mg, 83% yield).

¹H-NMR (CD₃OD) δ ppm: 0.93 (t, 3H, J=7.2 Hz), 1.28–1.40 (m, 2H), 1.50–1.62 (m, 4H), 1.67–1.77 (m, 2H), 2.37 (t, 2H, J=7.5 Hz), 2.56 (t, 2H, J=7.8 Hz), 2.68 (t, 2H, J=7.2 Hz), 7.11 (d, 2H, J=8.1 Hz), 7.42 (d, 2H, J=8.4 Hz).

Step 4

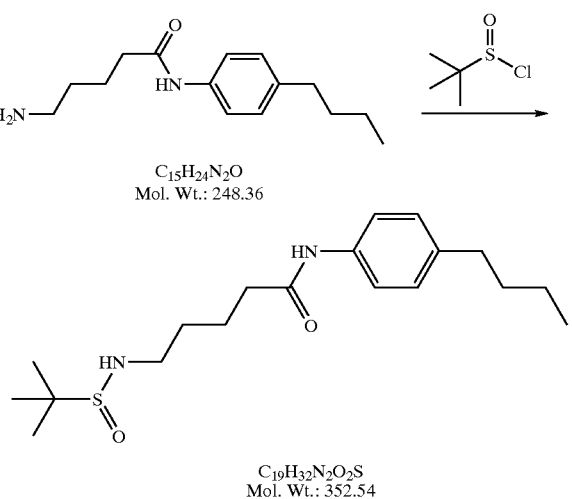

C₁₅H₂₄N₂O
Mol. Wt.: 248.36

The compound obtained in Step 3 (808 mg, 3.25 mmol) was suspended in 5 ml of dichloromethane under ice-cooling and isopropylsulfonyl chloride (696 mg, 4.9 mmol) and triethylamine (494 mg, 4.9 mmol) were added. After the mixture was reacted under ice-cooling for an hour, the reactant was poured into water and extracted with chloroform. The organic layer was washed with water and dried over magnesium sulfate anhydride. The solvent was removed under reduced pressure and the residue was purified by silica gel chromatography to give the desired compound quantitatively.

¹H-NMR (CDCl₃) δ ppm: 0.91 (t, 3H, J=7.2 Hz), 1.27–1.40 (m, 2H), 1.36 (d, 6H, J=6.6 Hz), 1.51–1.69 (m, 4H), 1.77–1.86 (m, 2H), 2.38 (t, 2H, J=7.2 Hz), 2.56 (t, 2H, J=7.5 Hz), 3.12–3.21 (m, 3H), 4.38 (t, 1H, J=5.7 Hz), 7.11 (d, 2H, J=8.4 Hz), 7.36–7.41 (m, 3H).

Example 2

Synthesis of Compound (I-10)

C₁₅H₂₄N₂O
Mol. Wt.: 248.36

C₁₉H₃₂N₂O₂S
Mol. Wt.: 352.54

The desired compound was synthesized in a similar manner to Step 4 in Example 1 except that tert-butylsulfinyl chloride (689 mg, 4.9 mmol) and triethylamine (494 mg, 4.9 mmol) were added to the compound obtained in Step 3 in Example 1.

¹H-NMR (CDCl₃) δ ppm: 0.91 (t, 3H, J=7.5 Hz), 1.22 (s, 9H), 1.30–1.37 (m, 2H), 1.51–1.68 (m, 4H), 1.76–1.86 (m, 2H), 2.31–2.40 (m, 2H), 2.56 (t, 2H, J=7.5 Hz), 3.15–3.26 (m, 3H), 7.11 (t, 2H, J=8.7 Hz), 7.42 (d, 2H, J=8.1 Hz), 7.54 (s, 1H).

Example 3

Synthesis of Compound (I-11)

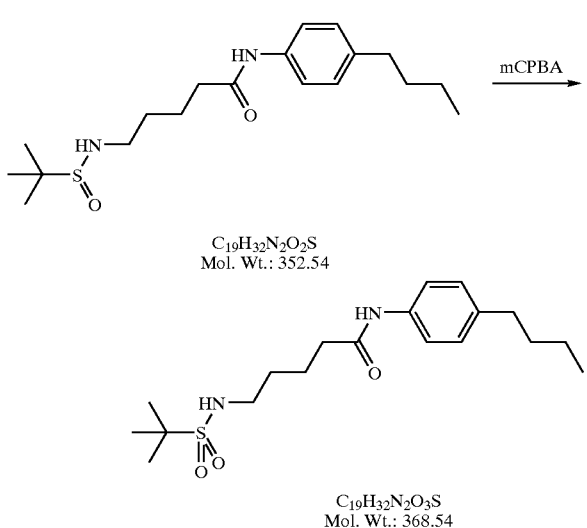

The compound obtained in Example 2 (352 mg, 1.0 mmol) was dissolved in 5 ml of dichloromethane under ice-cooling and mCPBA (259 mg, 1.5 mmol) was added to the solution. The solution was reacted at room temperature for an hour and the insoluble material was filtered off. The filtrate was washed with 1 mol/l NaOH, Na₂S₂O₅ and water, successively, and dried over magnesium sulfate anhydride. The solvent was removed under reduced pressure and the residue was purified by silica gel chromatography to give the desired compound (338 mg, 92% yield).

¹H-NMR (CDCl₃) δ ppm: 0.91 (t, 3H, J=7.5 Hz), 1.29–1.39 (m, 2H), 1.39 (s, 9H), 1.51–1.68 (m, 4H), 1.76–1.84 (m, 2H), 2.37 (t, 2H, J=7.5 Hz), 2.56 (t, 2H, J=7.8 Hz), 3.19–3.26 (m, 2H), 4.20 (t, 1H, J=5.7 Hz), 7.11 (t, 2H, J=8.1 Hz), 7.42 (d, 2H, J=8.7 Hz), 7.46 (s, 1H).

Example 4

Synthesis of Compound (1–72)

Step 1

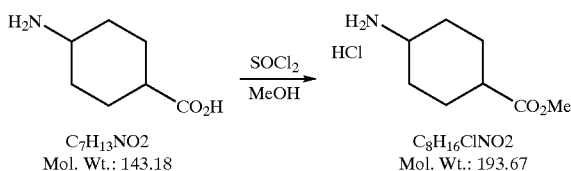

Starting material amino acid (a mixture of cis isomer and trans isomer) (1.0 g, 8.53 mmol) was dissolved in 7.5 ml of methanol. Thionyl chloride (1.0 ml, 13.7 mmol) was added to the mixture under ice-cooling and the mixture was stirred at room temperature overnight. After the mixture was concentrated under reduced pressure, diethylether was added and precipitated crystals were obtained by filtration. The crystals were washed with diethylether and dried to give the desired compound (1.25 g, 93% yield).

¹H-NMR (CDCl₃) δ ppm: 1.50–2.60 (m, 9H), 3.08–3.36 (m, 1H), 3.67 (s, 3H, CO₂Me of cis isomer), 3.71 (s, 3H, CO₂Me of trans isomer), 8.15–8.55 (m, 3H).

Step 2

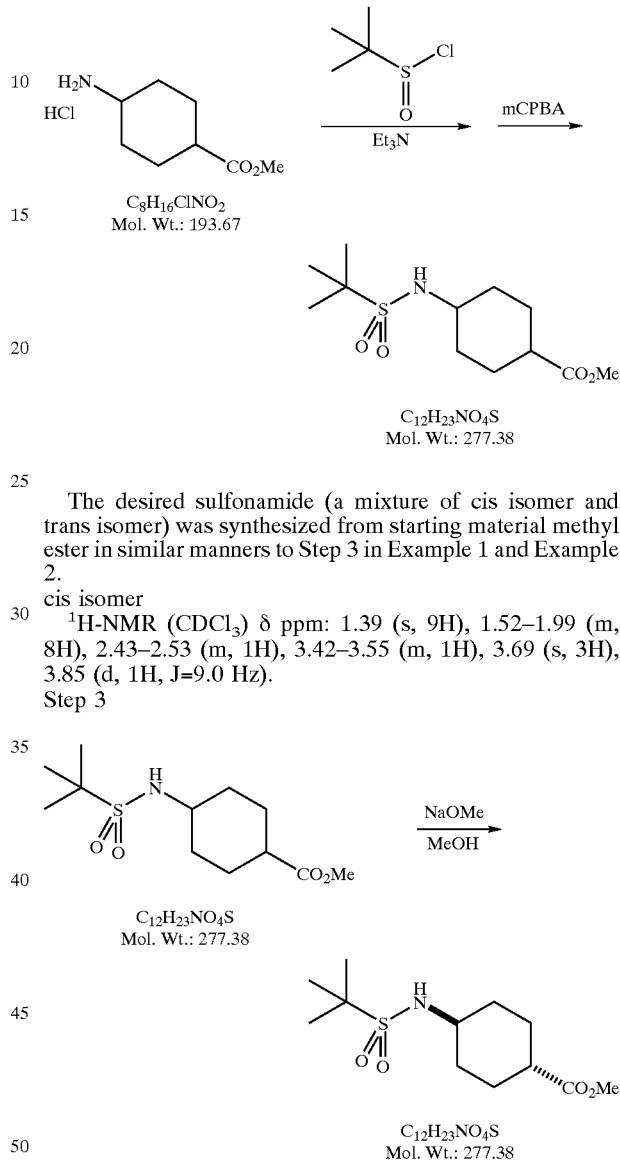

The desired sulfonamide (a mixture of cis isomer and trans isomer) was synthesized from starting material methyl ester in similar manners to Step 3 in Example 1 and Example 2.

cis isomer

¹H-NMR (CDCl₃) δ ppm: 1.39 (s, 9H), 1.52–1.99 (m, 8H), 2.43–2.53 (m, 1H), 3.42–3.55 (m, 1H), 3.69 (s, 3H), 3.85 (d, 1H, J=9.0 Hz).

Step 3

Starting material sulfonamide (19.4 g, 70.0 mmol, a mixture of cis isomer and trans isomer) was dissolved in 30 ml of methanol. To the mixture, 28% sodium methoxide (284 ml, 140.0 mmol) was added and refluxed with stirring under ice-cooling. After the solvent was removed, the residue was diluted with chloroform, and 1 mol/l HCl was added with stirring under ice-cooling until pH of an aqueous layer reached 3. The aqueous layer was extracted with chloroform and the organic layer was washed with water and dried over magnesium sulfate anhydride. The obtained crude crystals were recrystallized from hexane-ethyl acetate to give the desired sulfonamide (trans isomer, 7.75 g, 40% yield).

trans isomer

¹H-NMR (CD₃OD) δ ppm: 1.16–1.32 (m, 2H), 1.39 (s, 9H), 1.44–1.52 (m, 2H), 1.98–2.09 (m, 2H), 2.14–2.29 (m, 3H), 3.18–3.37 (m, 1H), 3.63 (d, 1H, J=9.0 Hz), 3.67 (s, 3H).

Step 4

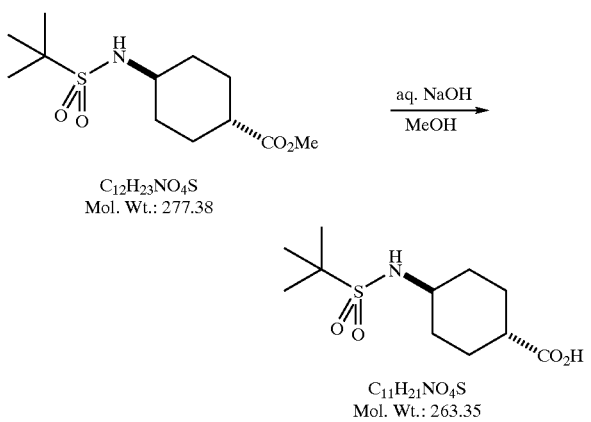

Starting material methyl ester (4.77 g, 17.2 mmol) was dissolved in 95 ml of methanol and 1 mol/l NaOH (43 ml, 43.0 mmol) was added with stirring under ice-cooling. The mixture was stirred at room temperature overnight and concentrated under reduced pressure. After 1 mol/l HCl was added with stirring until pH of the mixture reached 3 under ice-cooling, the precipitated crystals were collected by filtration, washed with water and dried. The obtained crude crystals were recrystallized from hexane-ethylacetate to give the desired carboxylic acid (4.20 g, 93% yield).

$^1$H-NMR (CDCl$_3$) δ ppm: 1.18–1.35 (m, 2H), 1.39 (s, 91), 1.46–1.63 (m, 2H), 2.01–2.14 (m, 2H), 2.14–2.32 (m, 3H), 3.18–3.35 (m, 1H), 3.80 (d, 1H, J=9.6 Hz).

Step 5

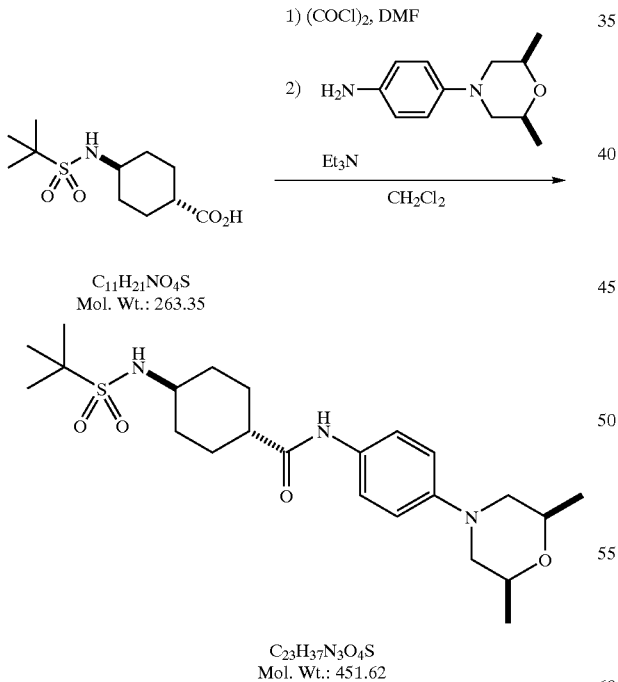

A starting material carboxylic acid (5.86 g, 22.3 mmol) was dissolved in 88 ml of dichloromethane at room temperature. To the mixture, oxalyl chloride (2.34 ml, 26.7 mmol) and catalytic amount of DMF were added under ice-cooling and stirred at room temperature for an hour. After the solvent was removed under reduced pressure, dichloromethane (115 ml), substituted aniline (5.05 g, 24.5 mmol) and triethylamine (4.65 ml, 33.4 mmol) were added. The mixture was stirred at room temperature for 2.5 hours, the ice-cooling water was poured thereto, and the mixture was extracted with chloroform. An organic layer was washed with water and dried over magnesium sulfate anhydride. The solvent was removed under reduced pressure and ethyl acetate and hexane were added to the residue. The precipitated crystals were collected with filtration to give the desired amide (7.00 g, 70% yield).

$^1$H-NMR (CDCl$_3$) δ ppm: 1.25 (d, 6H, J=6.3 Hz), 1.17–1.42 (m, 2H), 1.40 (s, 9H), 1.60–1.78 (m, 2H), 1.98–2.43 (m, 7H), 3.20–3.43 (m, 3H), 3.67 (d, 1H, J=9.6 Hz), 3.74–3.86 (m, 2H), 6.86 (d, 2H, J=9.0 Hz), 7.04 (s, 1H), 7.38 (d, 2H, J=9.0 Hz).

Example 5

Synthesis of Compound (I-2)

Step 1

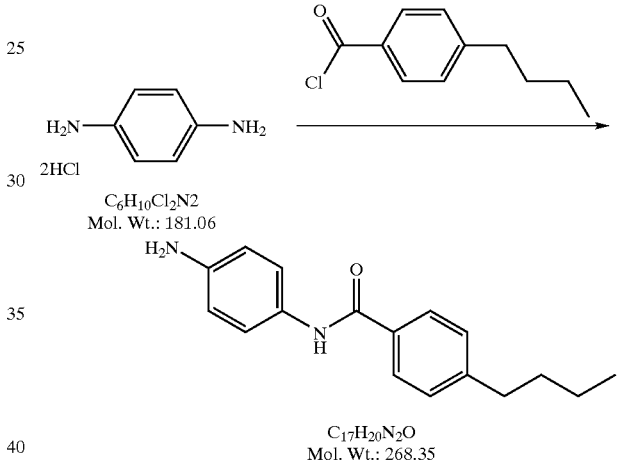

After starting material diamine (461 mg, 2.5 mmol) was suspended in dichloromethane under ice-cooling, an acid chloride (500 mg, 2.5 mmol) and triethylamine (773 mg, 7.5 mmol) were added and the mixture was reacted for 30 min. Water and dichloromethane were added to the reactant and insoluble materials were filtered off. The organic layer was washed with water and dried over magnesium sulfate anhydride. The solvent was removed under reduced pressure to give the desired compound as a residue (100 mg, 15% yield).

$^1$H-NMR (CDCl$_3$) δ ppm: 0.93 (t, 3H, J=7.2 Hz), 1.30–1.42 (m, 2H), 1.57–1.67 (m, 2H), 2.66 (t, 2H, J=7.8 Hz), 3.50 (brs, 1H), 6.57 (s, 1H), 6.68 (d, 2H, J=8.7 Hz), 7.26 (d, 2H, J=8.4 Hz), 7.39 (d, 2H, J=8.7 Hz), 7.68 (s, 1H), 7.75 (d, 2H, J=8.1 Hz).

Step 2

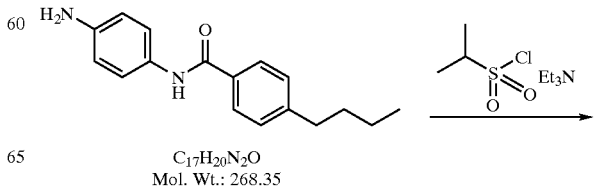

-continued

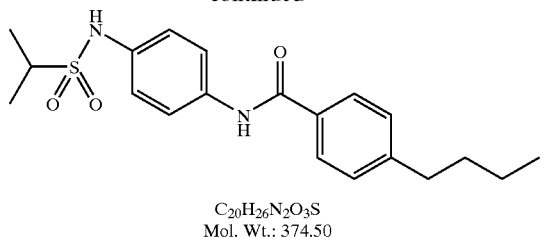

C₂₀H₂₆N₂O₃S
Mol. Wt.: 374.50

The desired compound was synthesized in a similar manner to Step 4 in Example 1.

$^1$H-NMR (CDCl₃) δ ppm: 0.94 (t, 3H, J=7.5 Hz), 1.34–1.44 (m, 2H), 1.40 (d, 6H, J=6.6 Hz), 1.59–1.68 (m, 2H), 2.69 (t, 2H, J=7.8 Hz), 3.24–3.35 (m, 1H), 6.49 (s, 1H), 7.23–7.32 (m, 4H), 7.6 (d, 2H, J=8.7 Hz), 7.79 (d, 2H, J=8.1 Hz), 7.85 (s, 1H).

Example 6

Synthesis of Compound (I-31)

Step 1

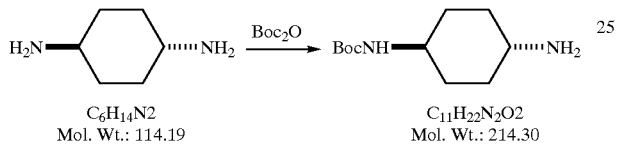

C₆H₁₄N₂
Mol. Wt.: 114.19

C₁₁H₂₂N₂O₂
Mol. Wt.: 214.30

A starting material diamine (8.37 g, 73.3 mmol) was dissolved in 30 ml of dioxane at room temperature and a solution of Boc₂O (2 g, 9.2 mmol) in dioxane (30 ml) was added. The mixture was reacted at room temperature for 3 days and the solvent was removed. Water was added to the residue and the mixture was extracted with chloroform. The organic layer was washed with water and dried over magnesium sulfate anhydride. The solvent was removed under reduced pressure to give the desired compound as a residue (1.8 g, 92% yield based on Boc₂O).

$^1$H-NMR (CDCl₃) δ ppm: 1.07–1.26 (m, 6H), 1.44 (s, 9H), 1.84–2.00 (m, 4H), 2.58–2.67 (m, 1H), 3.37 (brs, 1H), 4.43 (brs, 1H).

Step 2

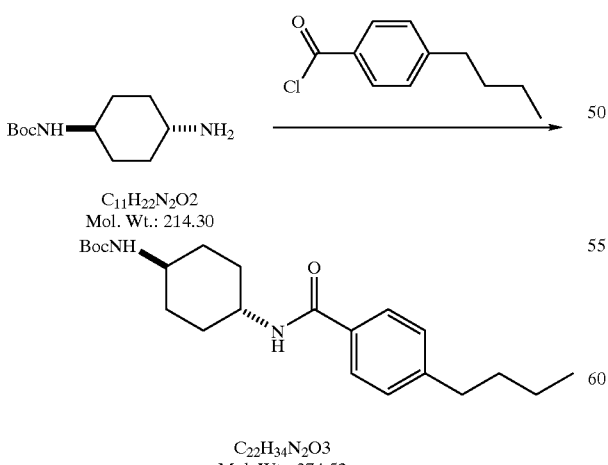

C₁₁H₂₂N₂O₂
Mol. Wt.: 214.30

C₂₂H₃₄N₂O₃
Mol. Wt.: 374.52

The desired compound was synthesized in a similar manner to Step 1 in Example 5.

$^1$H-NMR (CDCl₃) δ ppm: 0.92 (t, 3H, J=7.2 Hz), 1.26–1.42 (m, 6H), 1.45 (s, 9H), 1.54–1.68 (m, 2H), 1.99–2.12 (m, 4H), 2.64 (t, 2H, J=7.8 Hz), 3.43 (brs, 1H), 3.90–4.00 (m, 1H), 4.48 (d, 1H, J=5.7 Hz), 5.95 (d, 1H, J=8.4 Hz), 7.21 (d, 2H, J=8.4 Hz), 7.65 (d, 2H, J=8.4 Hz).

Step 3

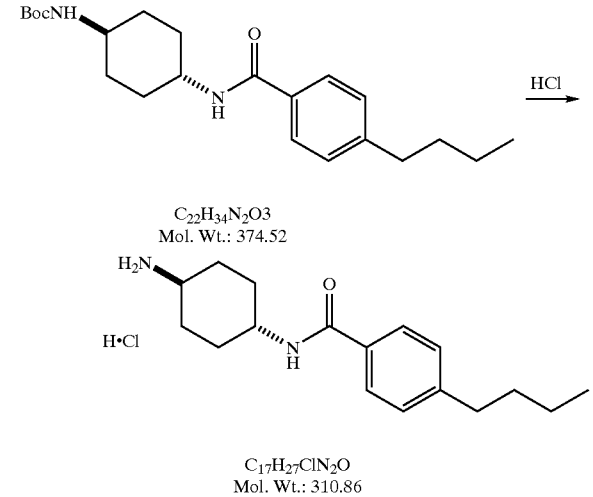

C₂₂H₃₄N₂O₃
Mol. Wt.: 374.52

C₁₇H₂₇ClN₂O
Mol. Wt.: 310.86

A starting material Boc compound (2.08 g, 5.55 mmol) was dissolved in 20 ml of ethyl acetate under ice-cooling and 20 ml of 4mol/l HCl/AcOEt was added. The mixture was reacted at room temperature for an hour and the solvent was removed under reduced pressure to give the desired compound as a residue (1.7 g, 98% yield).

$^1$H-NMR (CD₃OD) δ ppm: 0.93 (t, 3H, J=7.2 Hz), 1.29–1.41 (m, 2H), 1.50–1.66 (m, 6H), 2.02–2.18 (m, 4H), 2.66 (t, 2H, J=7.8 Hz), 3.13 (brs, 1H), 3.82–3.94 (m, 1H), 7.26 (d, 2H, J=8.7 Hz), 7.72 (d, 2H, J=8.4 Hz).

Step 4

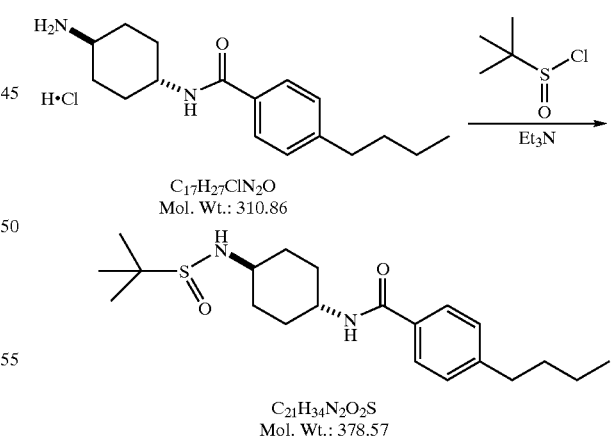

C₁₇H₂₇ClN₂O
Mol. Wt.: 310.86

C₂₁H₃₄N₂O₂S
Mol. Wt.: 378.57

The desired compound was synthesized in a similar manner to Step 4 in Example 1.

$^1$H-NMR (CDCl₃) δ ppm: 0.92 (t, 3H, J=7.5 Hz), 1.21 (s, 9H), 1.28–1.62 (m, 8H), 2.07–2.14 (m, 4H), 2.64 (t, 2H, J=7.8 Hz), 3.11 (d, 1H, J=5.1 Hz), 3.20 (brs, 1H), 3.90–4.04 (m, 1H), 6.06–6.14 (m, 1H), 7.21 (t, 2H, J=8.1 Hz), 7.67 (t, 2H, J=8.4 Hz).

Example 7

Synthesis of Compound (1–32)

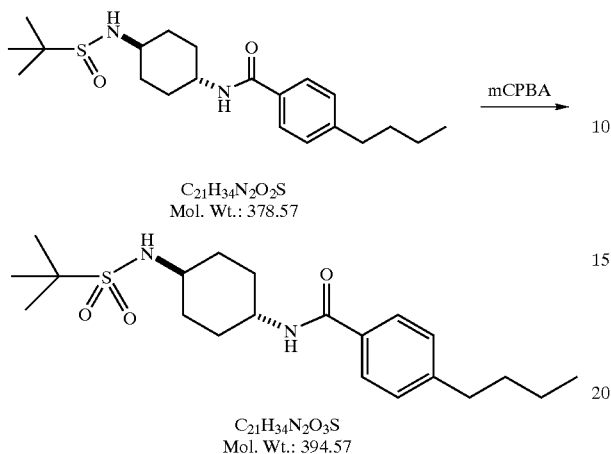

The desired compound was synthesized from the compound obtained in Example 6 in a similar manner to Example 3.

$^1$H-NMR (CDCl$_3$) δ ppm: 0.92 (t, 3H, J=7.2 Hz), 1.27–1.65 (m, 8H), 1.40 (s, 9H), 2.10–2.23 (m, 4H), 2.65 (t, 2H, J=7.5 Hz), 3.23–3.35 (m, 1H), 3.49 (s, 1H), 3.88–4.02 (m, 1H), 5.84–5.92 (m, 1H), 7.13 (t, 2H, J=8.4 Hz), 7.65 (d, 2H, J=8.1 Hz).

Example 8

Synthesis of Compound (1–5)

Step 1

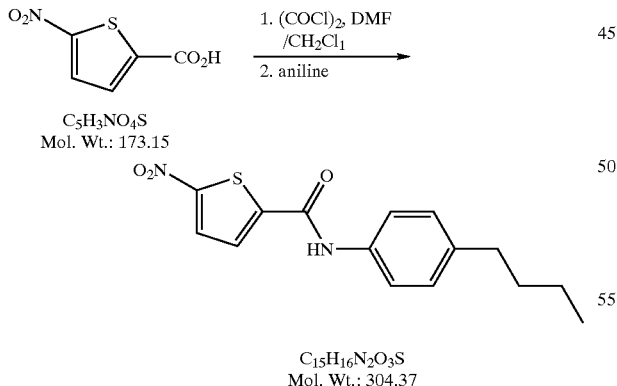

The desired compound was synthesized in a similar manner to Step 2 in Example 1.

$^1$H-NMR (CDCl$_3$) δ ppm: 0.94 (t, 3H, J=7.5 Hz), 1.30–1.42 (m, 2H), 1.50–1.65 (m, 2H), 2.61 (t, 2H, J=7.8 Hz), 7.20 (d, 2H, J=7.2 Hz), 7.48–7.51 (m, 3H), 7.72 (s, 1H), 7.88–7.90 (m, 1H).

Step 2

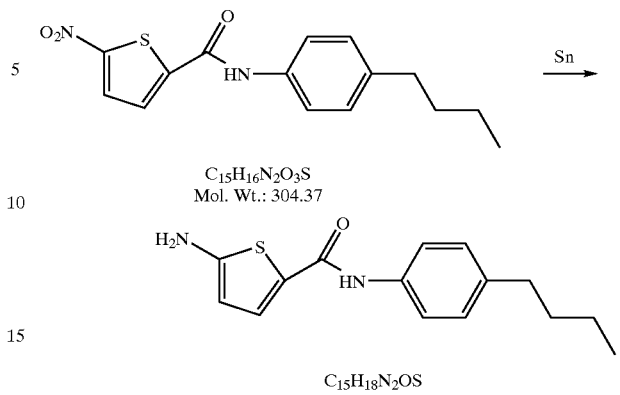

To a mixture of a starting material nitro compound (593 mg, 1.95 mmol) and tin (358 mg, 3.0 mmol), 30 ml of 6 mol/l HCl and 6 ml of THF were added and reacted at 50° C. for 3 hours. After cooling, the solvent was removed and the residue was neutralized 10% with NaOH and extracted with chloroform. The organic layer was washed with water and dried over magnesium sulfate anhydride. The solvent was removed under reduced pressure and the residue was purified by silica gel chromatography to give the desired compound (110 mg, 21% yield).

$^1$H-NMR (CDCl$_3$) δ ppm: 0.91 (t, 3H, J=7.2 Hz), 1.26–1.39 (m, 2H), 1.49–1.59 (m, 2H), 2.50 (t, 2H, J=7.8 Hz), 4.37 (s, 1H), 6.65 (d, 2H, J=8.4 Hz), 6.97 (d, 2H, J=8.4 Hz), 7.14 (d, 1H, J=8.4 Hz), 7.43 (d, 1H, J=8.7 Hz).

Step 3

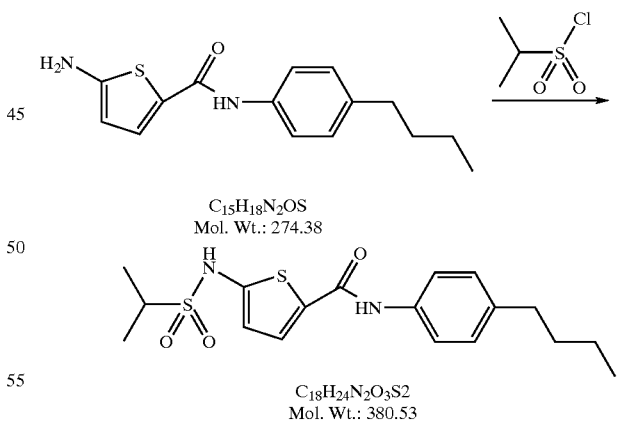

The desired compound was synthesized in a similar manner to Step 4 in Example 1.

$^1$H-NMR (CDCl$_3$) δ ppm: 0.92 (t, 3H, J=7.2 Hz), 1.28–1.41 (m, 2H), 1.46 (d, 6H, J=6.9 Hz), 1.53–1.63 (m, 2H), 2.59 (t, 2H, J=7.8 Hz), 3.35–3.44 (m, 1H), 7.15 (d, 2H, J=8.7 Hz), 7.38 (s, 1H), 7.45 (d, 2H, J=8.7 Hz), 7.57 (s, 1H).

Example 9

Synthesis of Compound (1-4)

Step 1

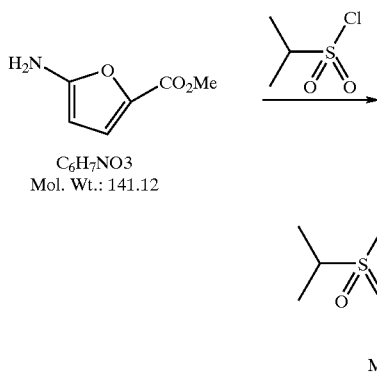

The desired compound was synthesized in a similar manner to Step 4 in Example 1.

$^1$H-NMR (CDCl$_3$) δ ppm: 1.44 (d, 6H, J=6.9 Hz), 3.33–3.43 (m, 1H), 3.88 (s, 9H), 6.24–6.26 (m, 1H), 7.11–7.14 (m, 2H).

Step 2

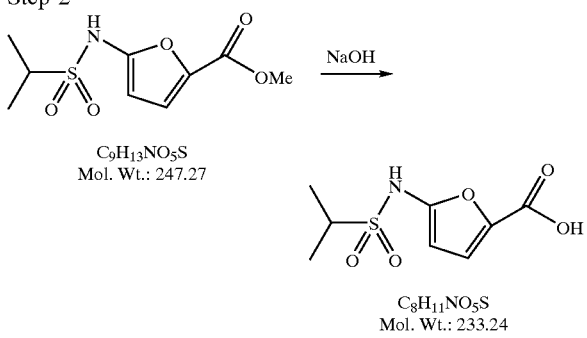

The desired compound was synthesized in a similar manner to Step 4 in Example 4. $^1$H-NMR (CDCl$_3$) δ ppm: 1.44 (d, 6H, J=6.3 Hz), 3.33–3.45 (m, 1H), 6.25–6.28 (m, 1H), 7.27–7.28 (m, 1H), 7.51 (s, 1H).

Step 3

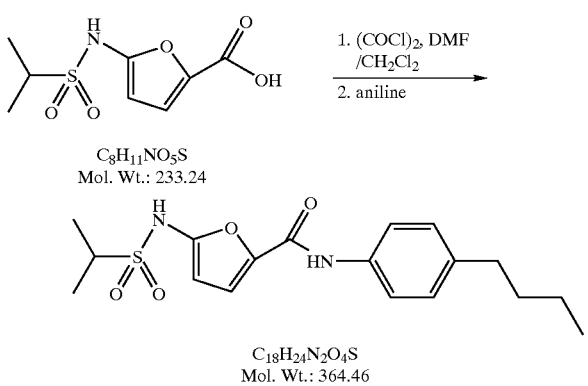

The desired compound was synthesized in a similar manner to Step 2 in Example 1.

$^1$H-NMR (CD$_3$OD) δ ppm: 0.92 (t, 3H, J=6.9 Hz), 1.28–1.41 (m, 2H), 1.46 (d, 6H, J=6.3 Hz), 1.53–1.63 (m, 2H), 2.58 (t, 2H, J=7.8 Hz), 3.33–3.43 (m, 1H), 6.27–6.29 (m, 1H), 7.14–7.16 (m, 3H), 7.50 (d, 2H, J=8.4 Hz), 7.90 (s, 1H).

Example 10

Synthesis of Compound (I-28)

Step 1

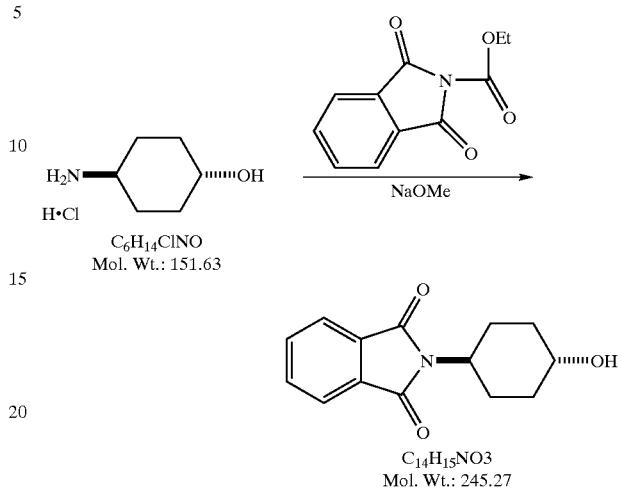

The desired compound was synthesized in a similar manner to Step 1 in Example 1.

$^1$H-NMR (CDCl$_3$) δ ppm: 1.37–1.52 (m, 3H), 1.74–1.79 (m, 2H), 2.07–2.13 (m, 2H), 2.28–2.42 (m, 2H), 3.72–3.81 (m, 1H), 4.09–4.20 (m, 1H), 7.68–7.73 (m, 2H), 7.81–7.85 (m, 2H).

Step 2

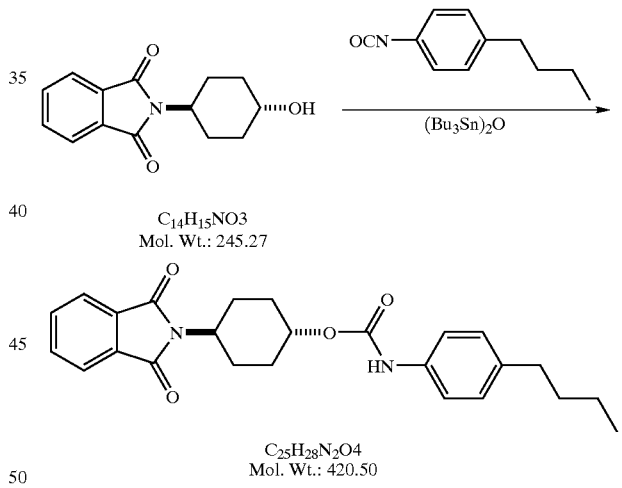

4-butylphenyl isocyanate (2.85 g, 16.3 mmol) was dissolved in 30 ml of THF, and a starting material alcohol (1.0 g, 4.08 mmol) and bis(tributyltin)oxide (972 mg, 1.63 mmol) were added. After the mixture was stirred overnight, the solvent was removed, water was added and the solution was extracted with chloroform. The organic layer was washed with water and dried over magnesium sulfate anhydride. The solvent was removed under reduced pressure and the residue was purified by silica gel chromatography to give the desired compound (332 mg, 19% yield).

$^1$H-NMR (CDCl$_3$) δ ppm: 0.92 (t, 3H, J=6.9 Hz), 1.30–1.40 (m, 2H), 1.48–1.62 (m, 4H), 1.79–1.83 (m, 2H), 2.21–2.25 (m, 2H), 2.37–2.50 (m, 2H), 2.57 (t, 2H, J=7.8 Hz), 4.11–4.22 (m, 1H), 4.77–4.87 (m, 1H), 6.49 (s, 1H), 7.11 (d, 2H, J=8.7 Hz), 7.28 (d, 2H, J=8.7 Hz), 7.69–7.73 (m, 2H), 7.80–7.84 (m, 2H).

Step 3
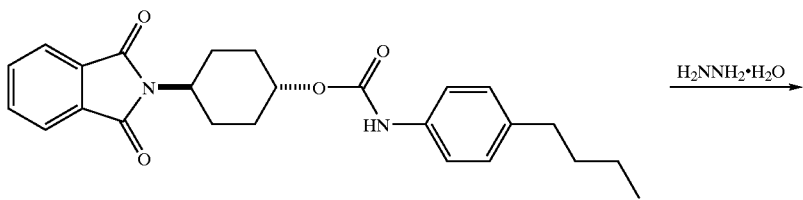
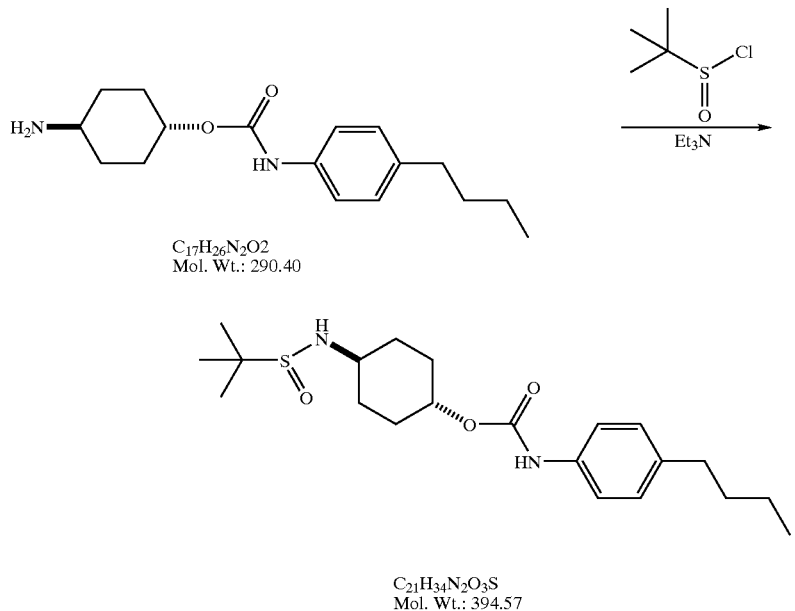
The desired compound was synthesized in similar manners to Step 3 in Example 1 and Example 2.
$^1$H-NMR (CDCl$_3$) δ ppm: 0.91 (t, 3H, J=7.2 Hz), 1.21 (s, 9H), 1.30–1.62 (m, 8H), 2.08 (d, 4H, J=11.1 Hz), 2.56 (t, 2H, J=7.8 Hz), 3.04 (d, 1H, J=4.8 Hz), 3.20–3.30 (m, 1H), 4.65–4.76 (m, 1H), 6.57 (s, 1H), 7.10 (d, 2H, J=8.7 Hz), 7.26 (d, 2H, J=8.1 Hz).
Example 11
Synthesis of Compound (I-29)
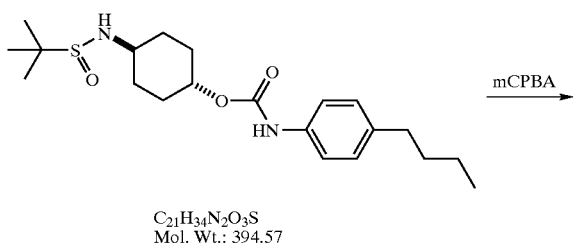
-continued
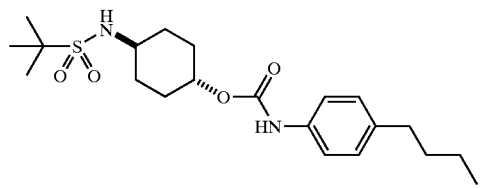
The desired compound was synthesized in a similar manner to Example 3.
$^1$H-NMR (CDCl$_3$) δ ppm: 0.91 (t, 3H, J=7.2 Hz), 1.23–1.62 (m, 8H), 1.40 (s, 9H), 2.12 (d, 4H, J=14.4 Hz), 2.56 (t, 2H, J=7.8 Hz), 3.28–3.40 (m, 1H), 3.90 (s, 1H), 4.60–4.73 (m, 1H), 6.57 (s, 1H), 7.10 (d, 2H, J=8.4 Hz), 7.25 (d, 2H, J=8.4 Hz).

Example 12

Synthesis of Compound (I-114)

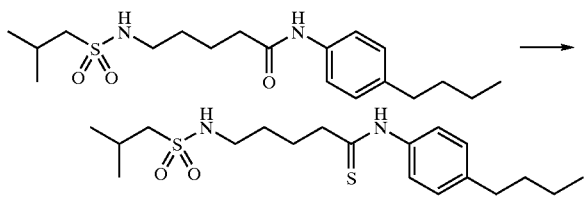

Lawesson's reagent [2,4-bis(4-methoxyphenyl)-1,3-dithia-2,4-diphosphetane-2,4-disulfide] (132 mg) was added to a solution of 100 mg of Compound (I-110) synthesized in a similar manner to Example 1 in toluene (2.7 ml) and the mixture was stirred at 80° C. for 3 hours. The reactant was concentrated under reduced pressure and the residue was purified by silica gel chromatography (ethyl acetate:n-hexane=1:1) to give pale yellow crystals (82.3 mg, 79%). The crystals were recrystallized from methylene chloride-diisopropyl ether to give the desired compound as colorless needles (50.5 mg, 48%).

Example 13

Synthesis of Compound (1–120)

Step 1

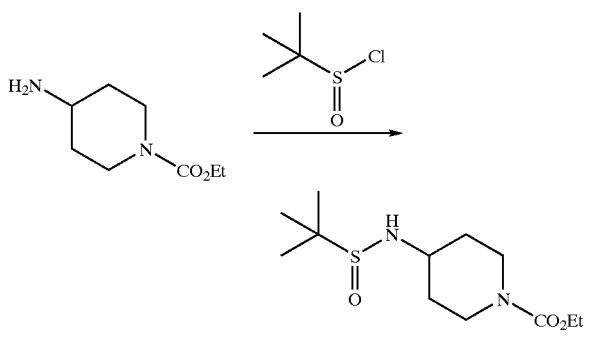

Ethyl 4-amino-1-piperidinecarboxylate (300 mg) and triethylamine (258 mg) were dissolved in 5 ml of dichloromethane. To the mixture, 2 ml of solution of t-butylsulfinyl chloride (222 mg) in dichloromethane was added and the mixture was stirred at room temperature for 4 hours. The solution was partitioned into an aqueous solution of potassium hydrogen sulfate and ethyl acetate. The organic layer was washed with brine and dried over magnesium sulfate anhydride. The solvent was removed under reduced pressure and the residue was purified by silica gel chromatography to give 378 mg of 4-t-butylsulfiny amino-1-ethoxycarbonyl piperidine.

Step 2

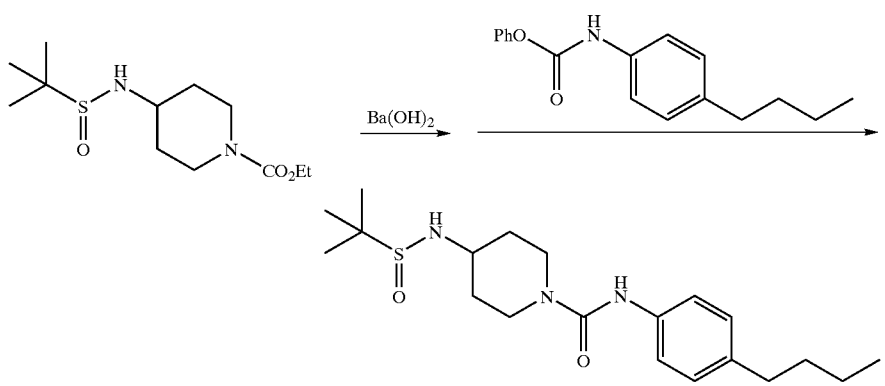

In a mixture of 5 ml of 2-propanol and 5 ml of water, 378 mg of 4-t-butylsulfinylamino-1-ethoxycarbonyl piperidine was suspended and 1.77 g of barium hydroxide was added. The mixture was refluxed with stirring and heating for 4 hours. The mixture was diluted with methanol and the insoluble material was filtered off. The solvent was removed under reduced pressure to give 4-t-butylsulfinylaminopiperidine. Without purification, the obtained material was dissolved in 5 ml of THF, and 984 mg of N-phenoxycarbonyl-4-butyl aniline and 236 mg of diisopropyl ethylamine were added, followed by stirring at room temperature overnight. An aqueous solution of potassium hydrogen sulfate was added to the mixture and the mixture was extracted with ethyl acetate. The organic layer was washed with brine and dried over magnesium sulfate anhydride. The solvent was removed under reduced pressure and the residue was purified by silica gel chromatography to give 291 mg of 4-t-butylsulfinylaminopiperidine-1-carboxlic acid(4-t-butylphenyl)amide.

$^1$H-NMR (CDCl$_3$) δ ppm: 0.89 (t, 3H, J=7.3 Hz), 1.19 (s, 9H), 1.25–1.38 (m, 4H), 1.40–1.60 (m, 4H), 1.89–2.03 (m, 3H), 2.52 (t, 2H, J=7.7 Hz), 2.89–3.04 (m, 2H), 3.14 (d, 1H, J=5.2 Hz), 3.37 (m, 1H), 3.96 (m, 2H), 6.67 (s, 1H), 7.05 (d, 2H, J=8.5 Hz), 7.22 (d, 2H, J=8.5 Hz).

Step 3

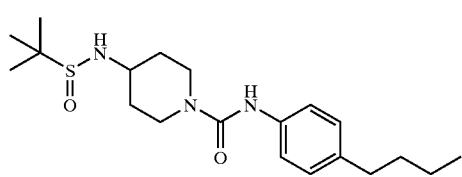
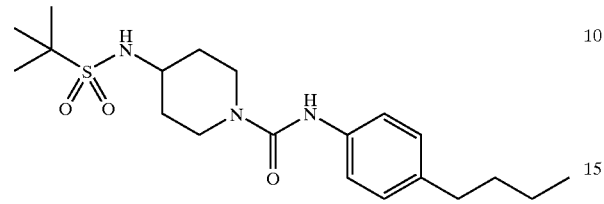

→ MMPP

I-5

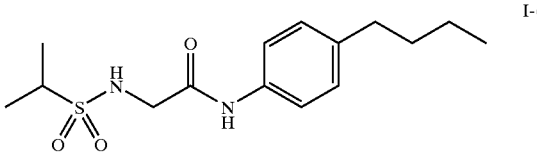
I-6

In a mixture of 2 ml of methanol and 2 ml of methylene chloride, 291 mg of 4-t-butylsulfinyl aminopiperidine-1-carboxlic acid(4-t-butylphenyl)amide was dissolved. To the mixture, 570 mg of 80%-MMPP (magnesium monoperoxyphthalate hexahydrate) was added and the mixture was stirred at room temperature for 2 hours. The solution was diluted with water and extracted with ethyl acetate. The organic layer was washed with brine and dried over magnesium sulfate anhydride. The solvent was removed under reduced pressure and the residue was purified by silica gel chromatography to give 130 mg of 4-t-butylsulfonylaminopiperidine-1-carboxylic acid(4-butylphenyl)amide (I-120).

Other Compounds (I) are synthesized by the similar methods. The structures and physical properties are shown below.

I-1
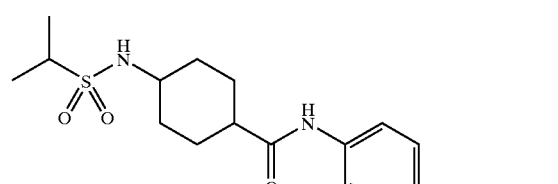

I-7
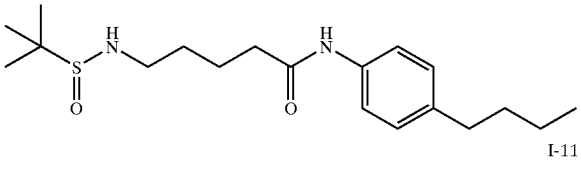

I-2
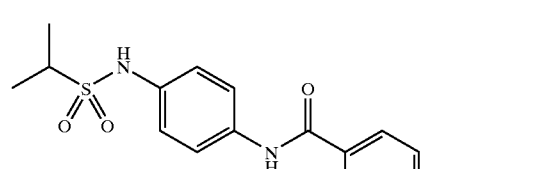

I-8
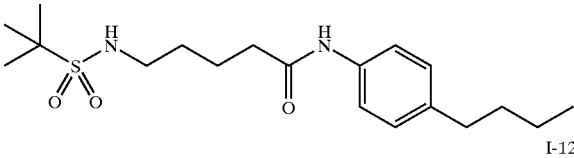

I-3
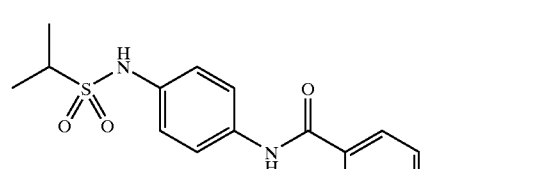

I-9
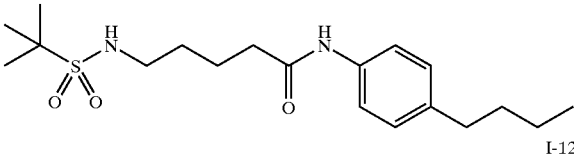

I-4
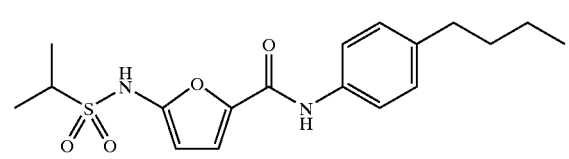

I-10
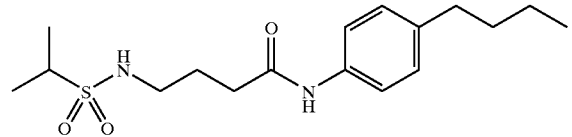

I-11
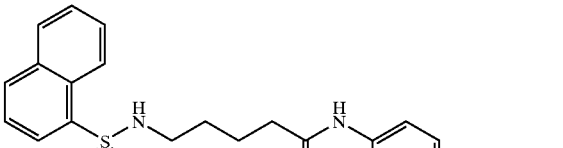

I-12
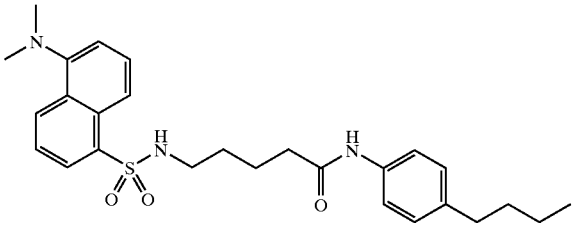

I-13

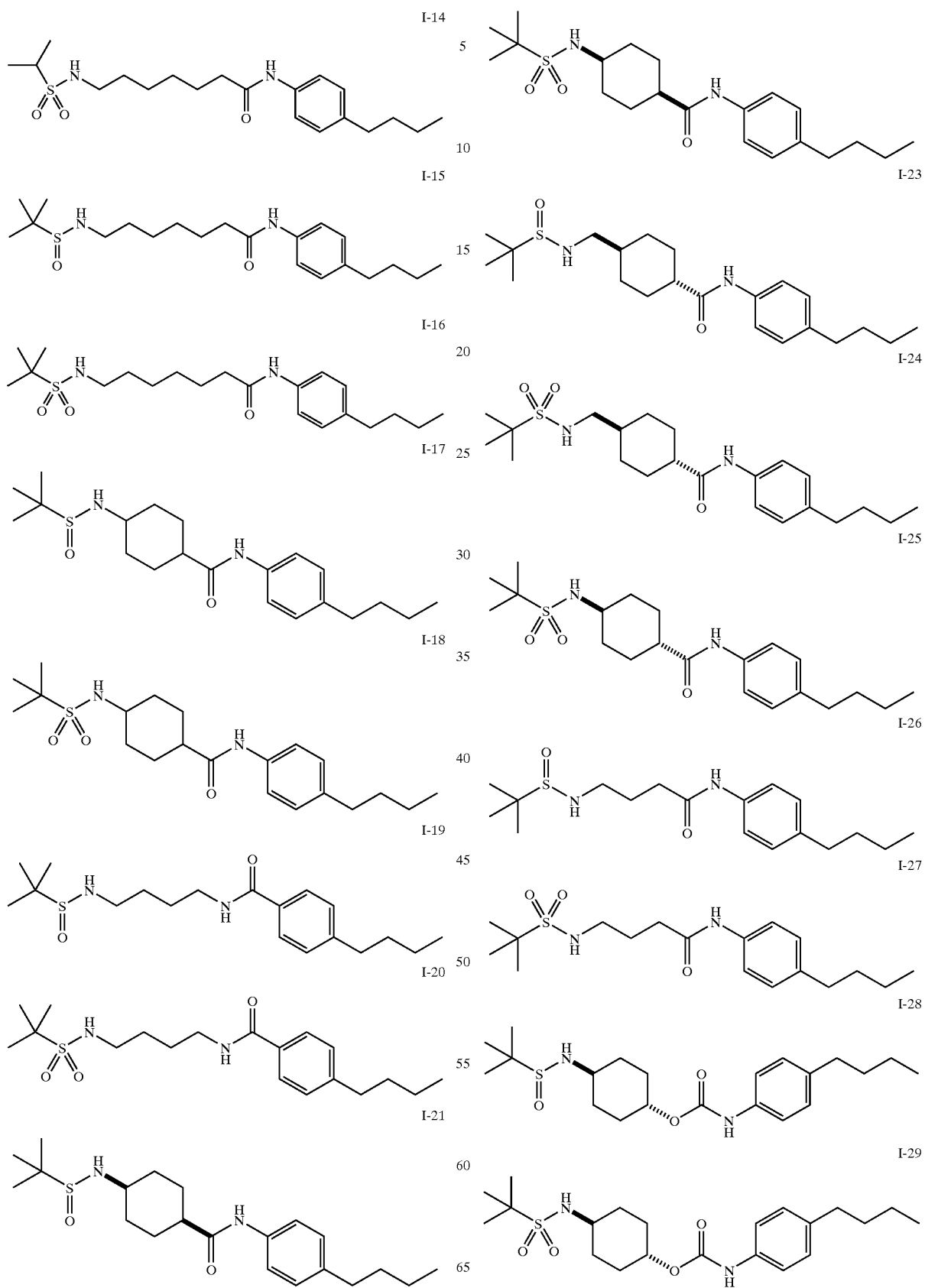

I-30
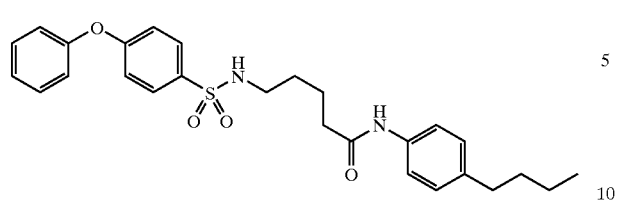
I-31
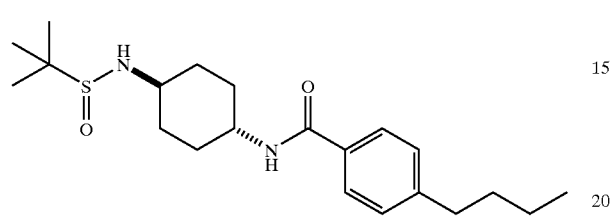
I-32
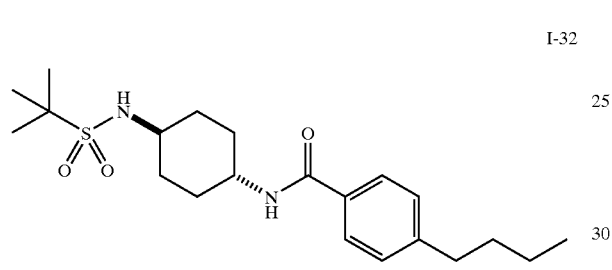
I-33
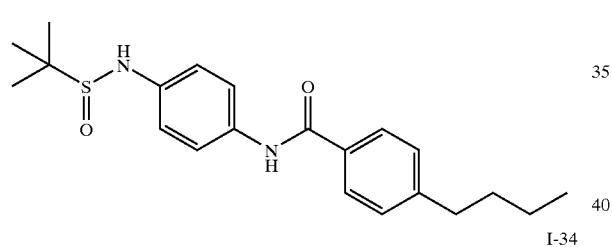
I-34
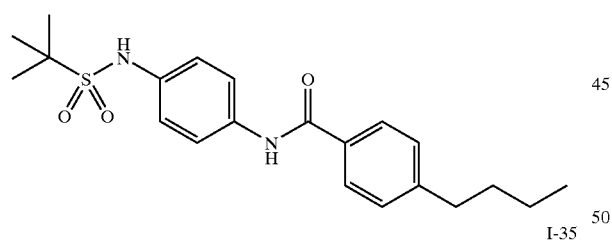
I-35
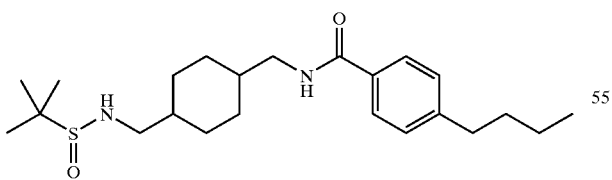
I-36
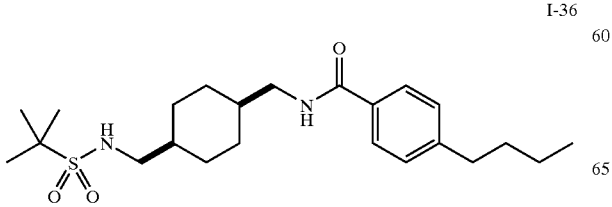
I-37
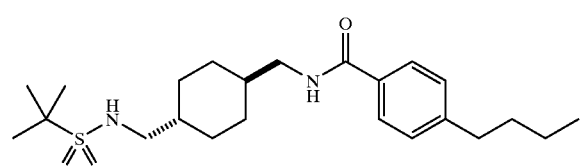
I-38
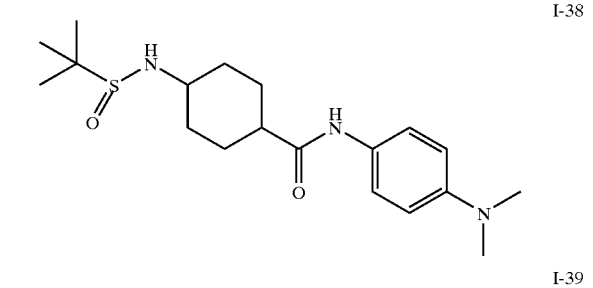
I-39
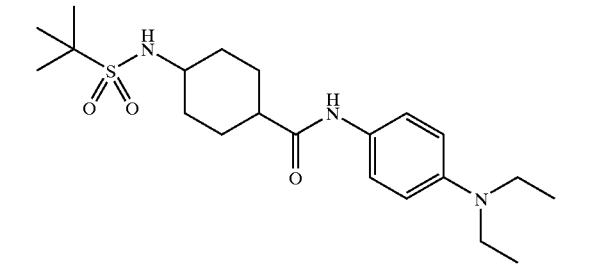
I-40
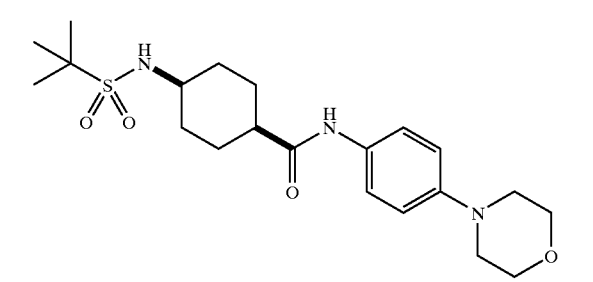
I-41
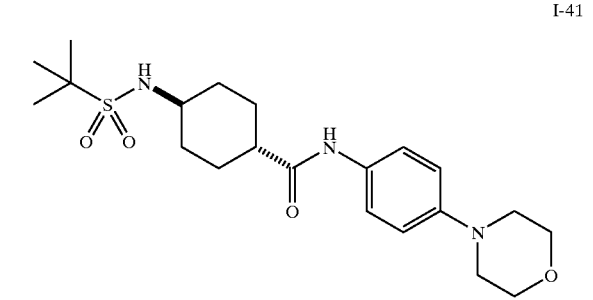
I-42

I-43
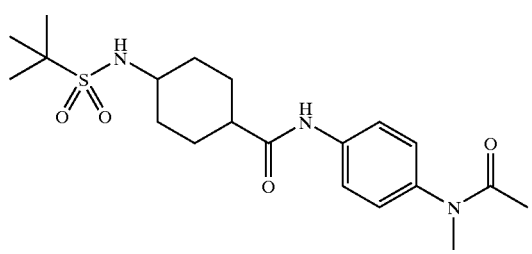
I-44
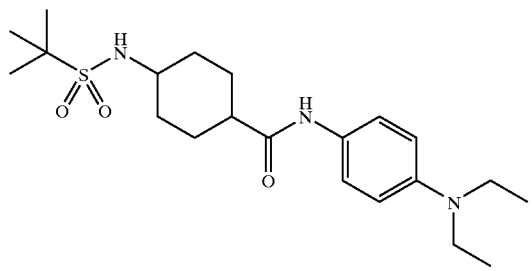
I-45
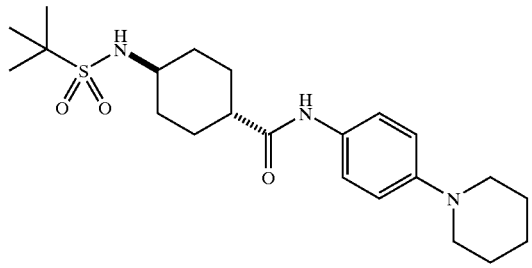
I-46
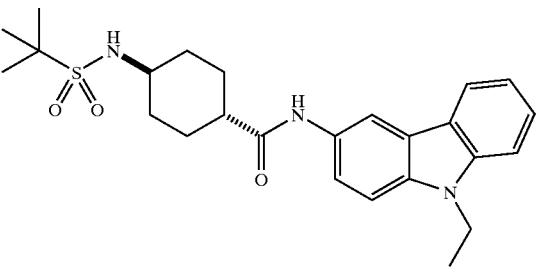
I-47
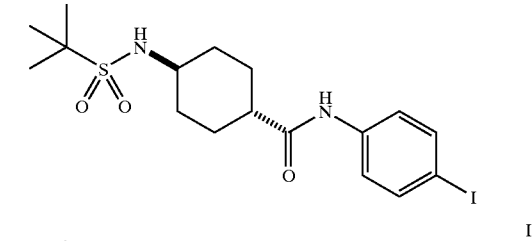
I-48
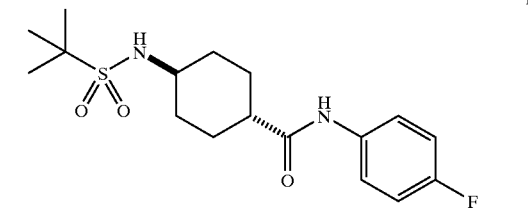
I-49
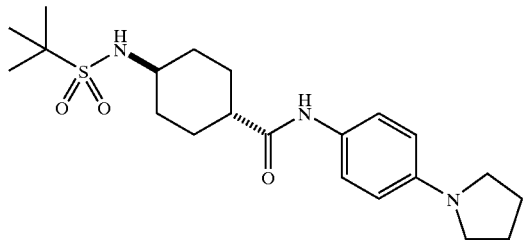
I-50
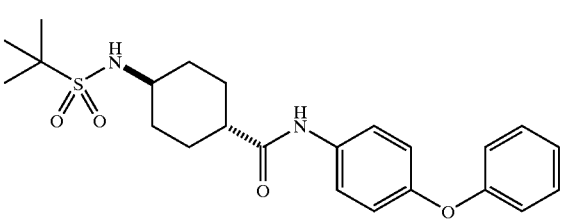
I-51
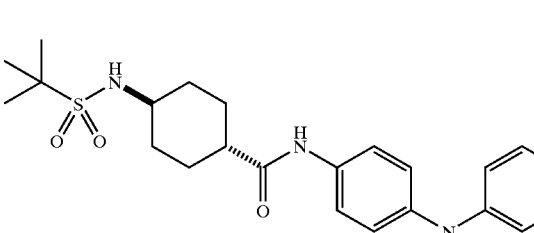
I-52
I-53
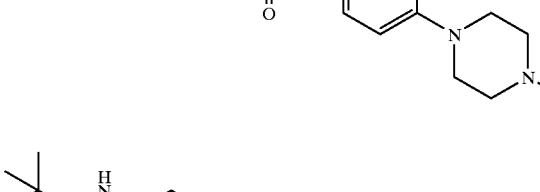

I-54
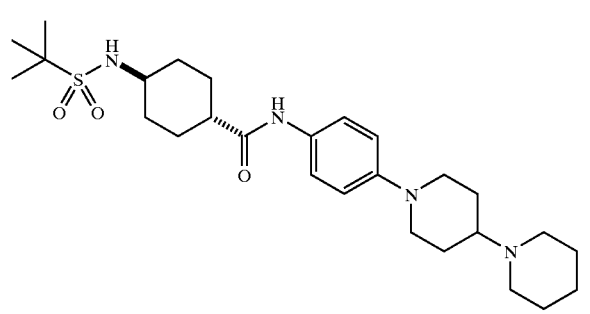
I-55
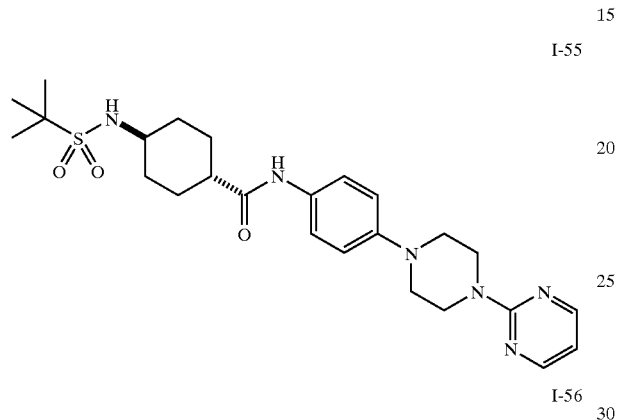
I-56
I-57
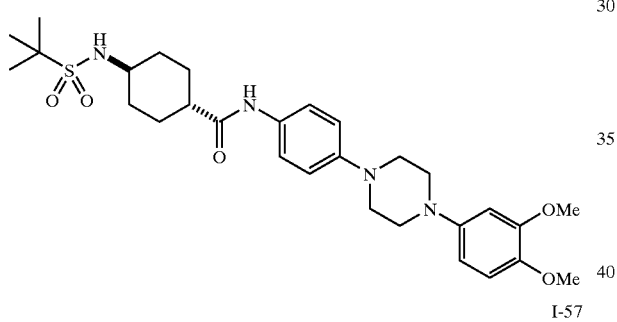
I-58
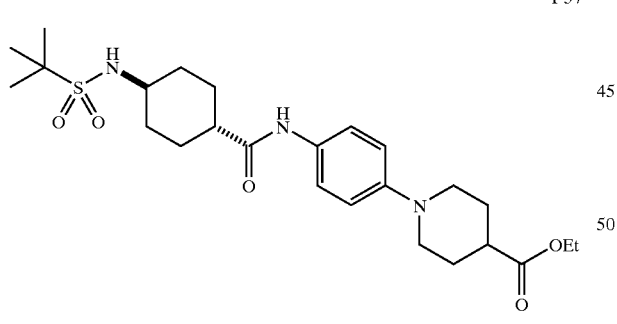
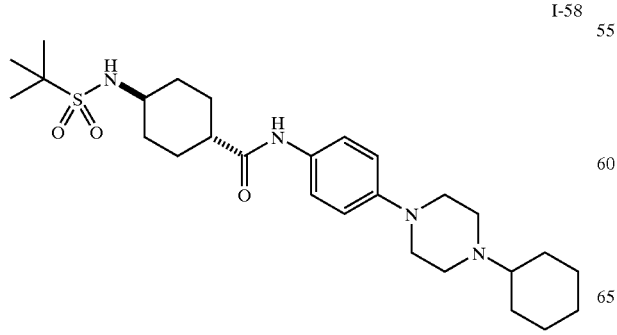
I-59
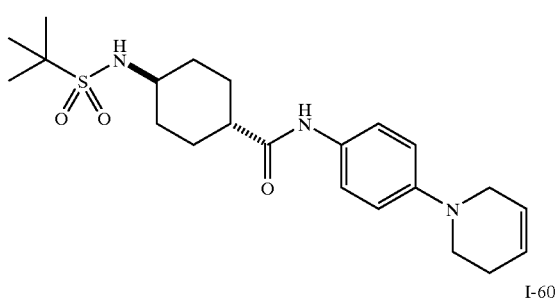
I-60
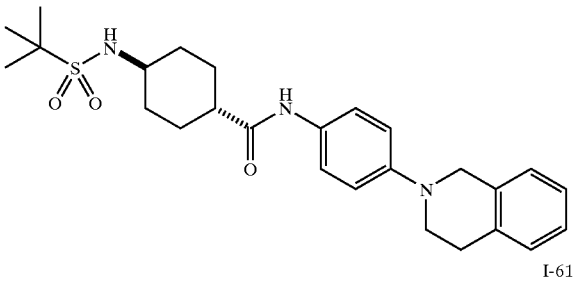
I-61
I-62
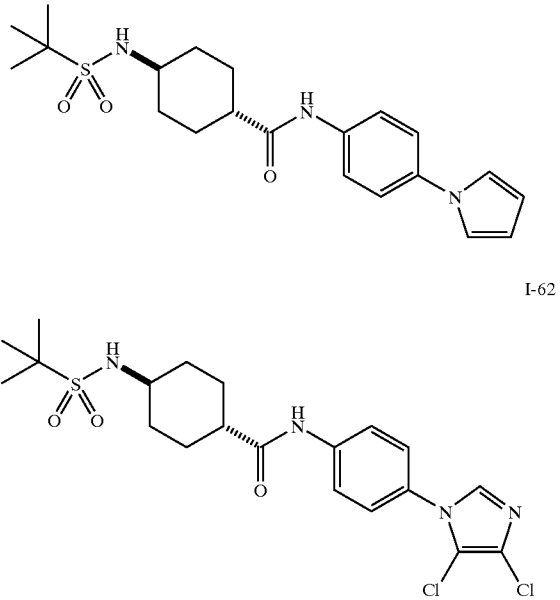
I-63
I-64
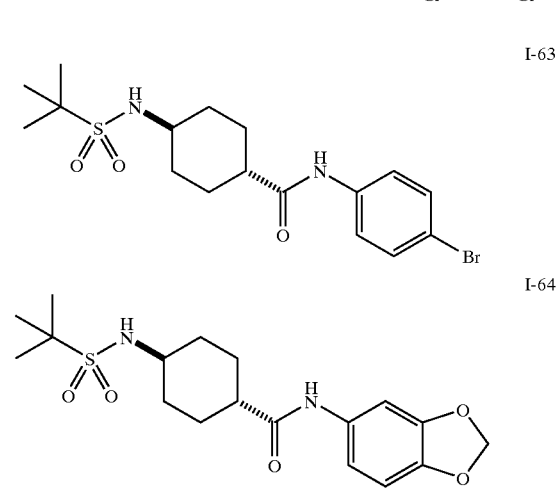

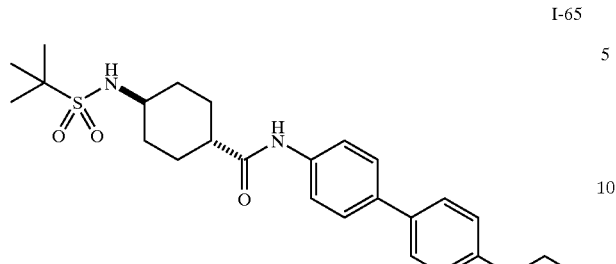
I-65
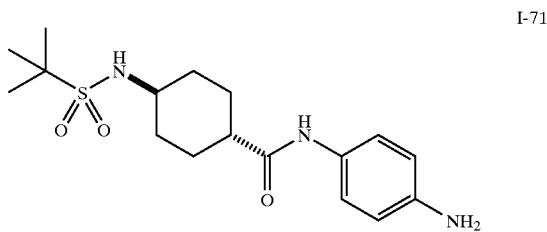
I-71
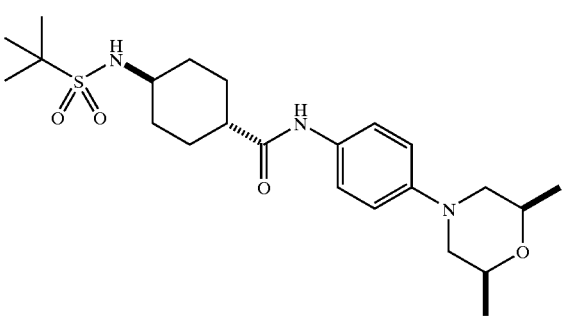
I-72
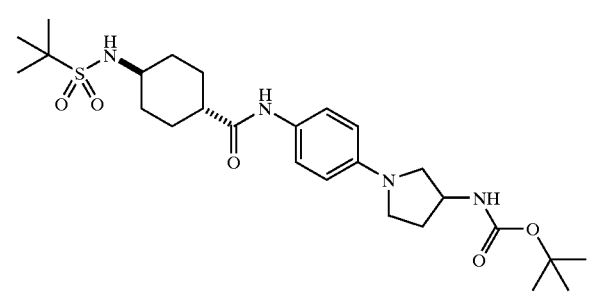
I-73
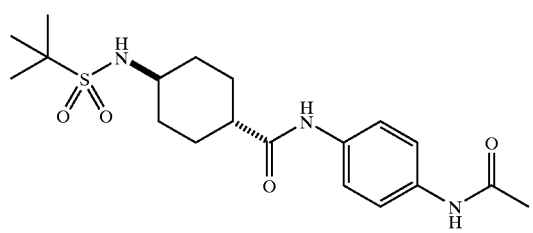
I-66
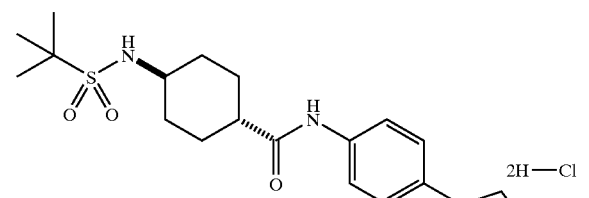
I-74
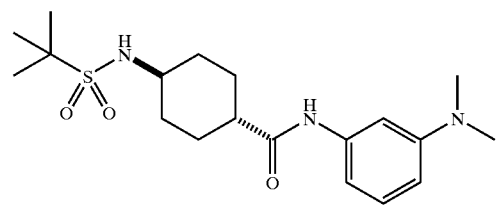
I-67
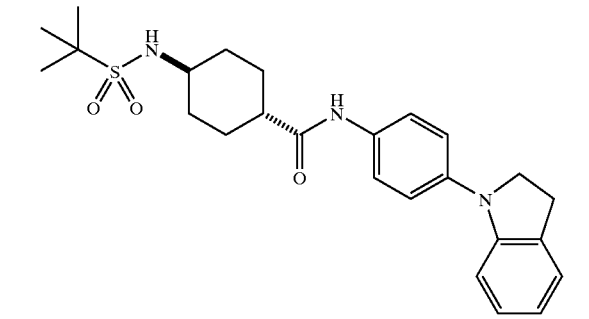
I-75
I-68
I-69
I-70

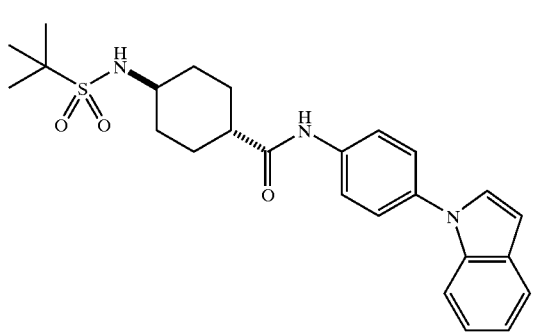
I-76
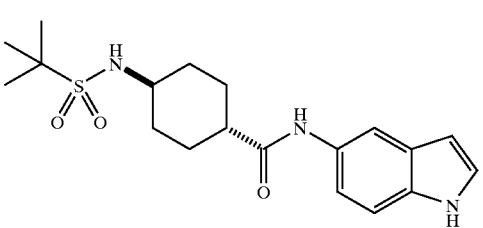
I-81
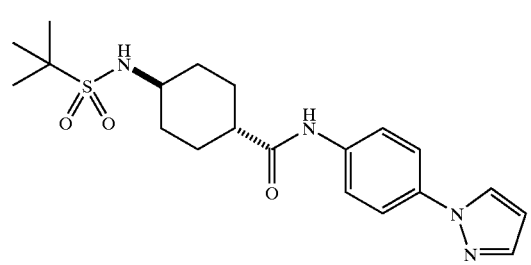
I-77
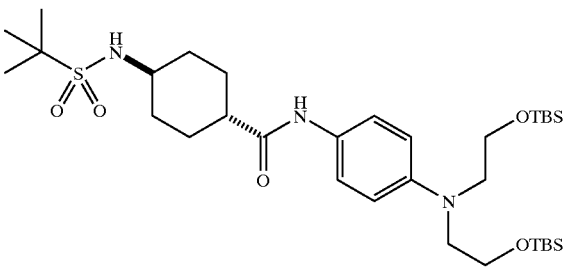
I-82
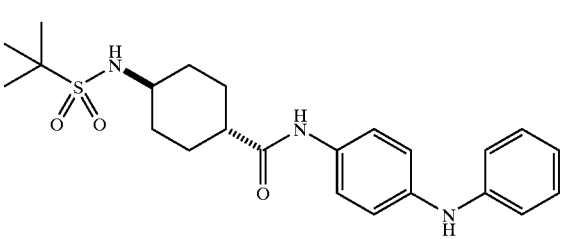
I-83
I-78
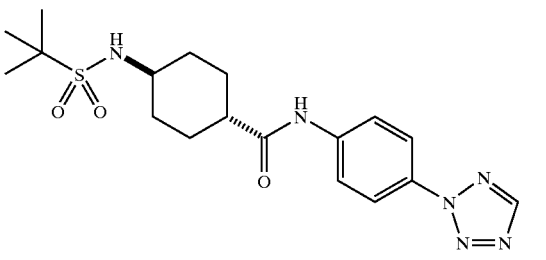
I-84
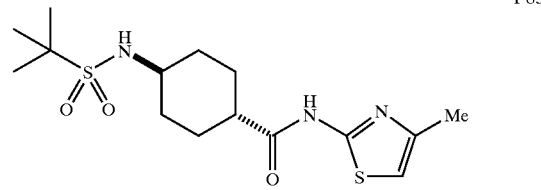
I-79
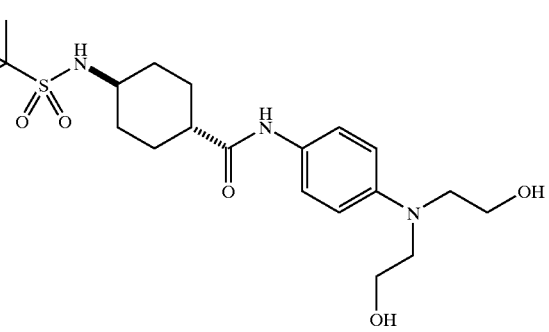
I-85
I-86
I-80


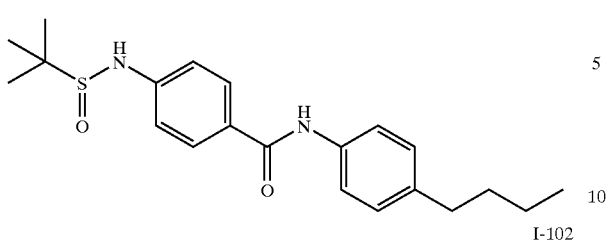
I-101
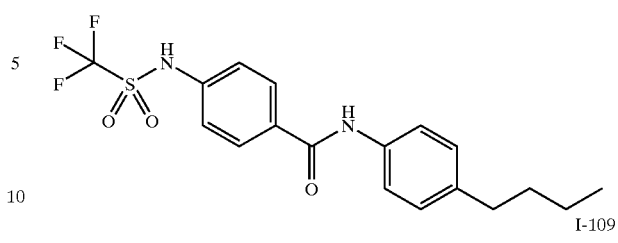
I-108
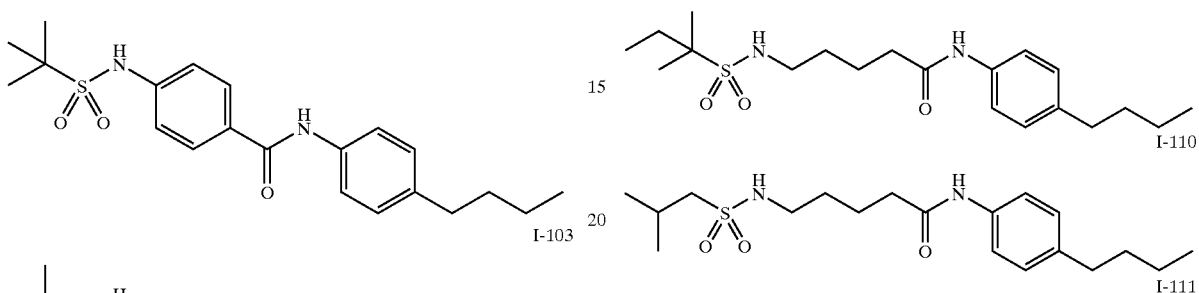
I-102
I-109
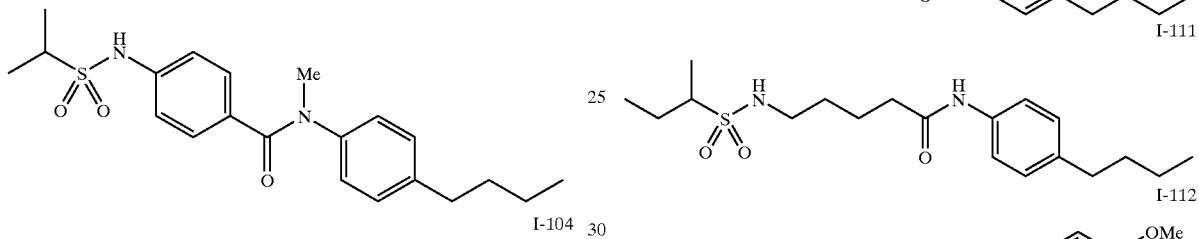
I-103
I-110
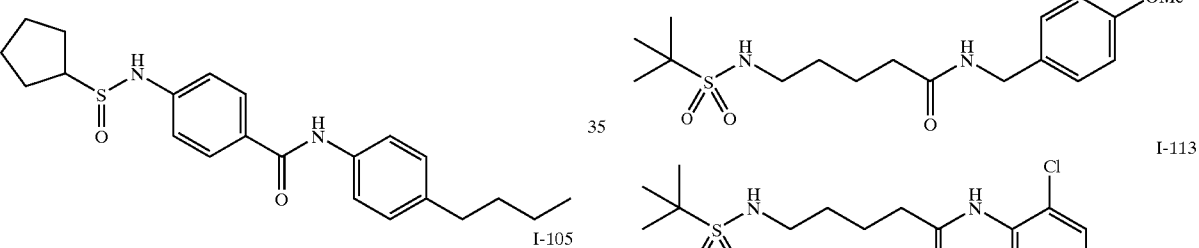
I-104
I-111
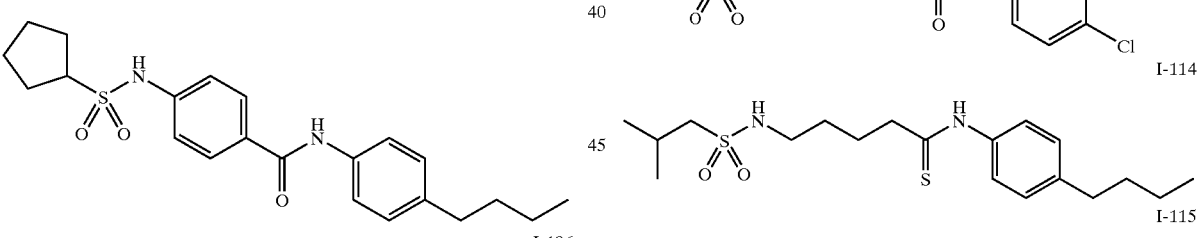
I-105
I-112
I-113
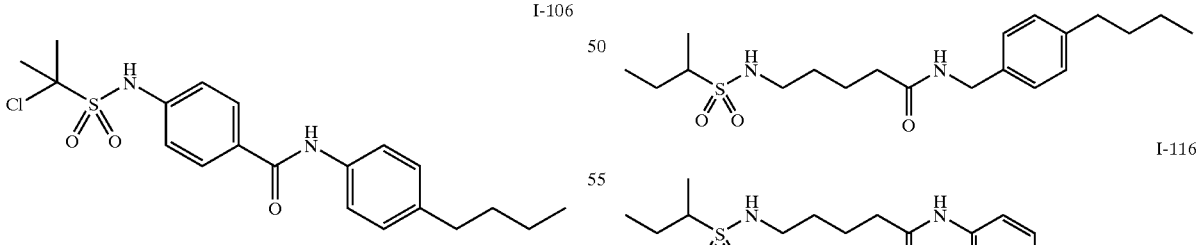
I-106
I-114
I-115
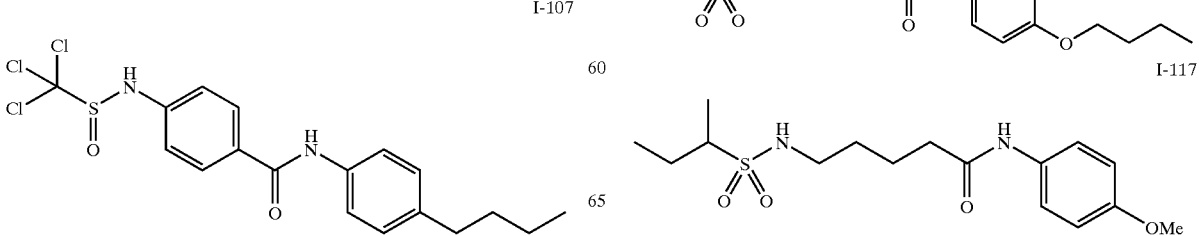
I-107
I-116
I-117

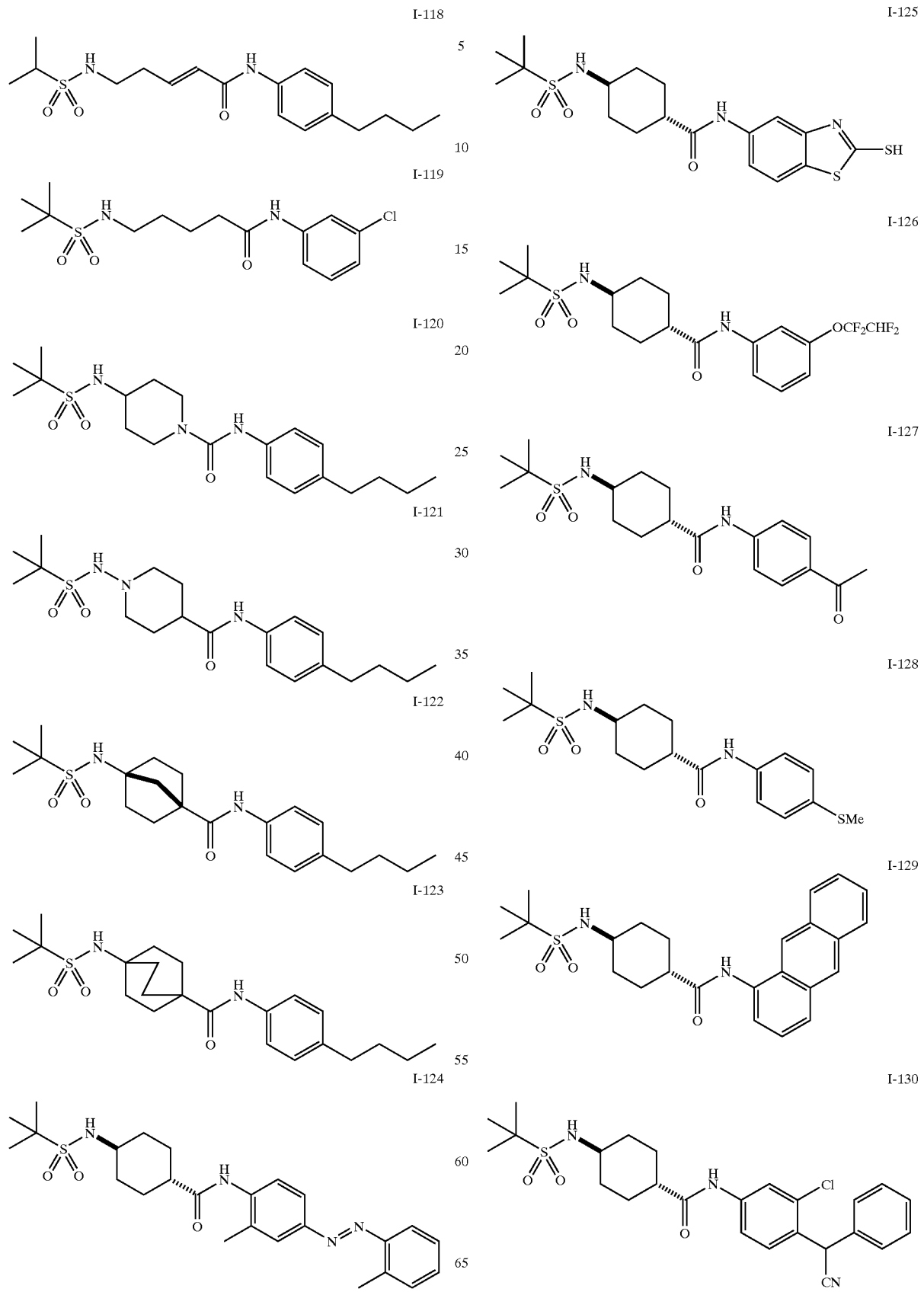

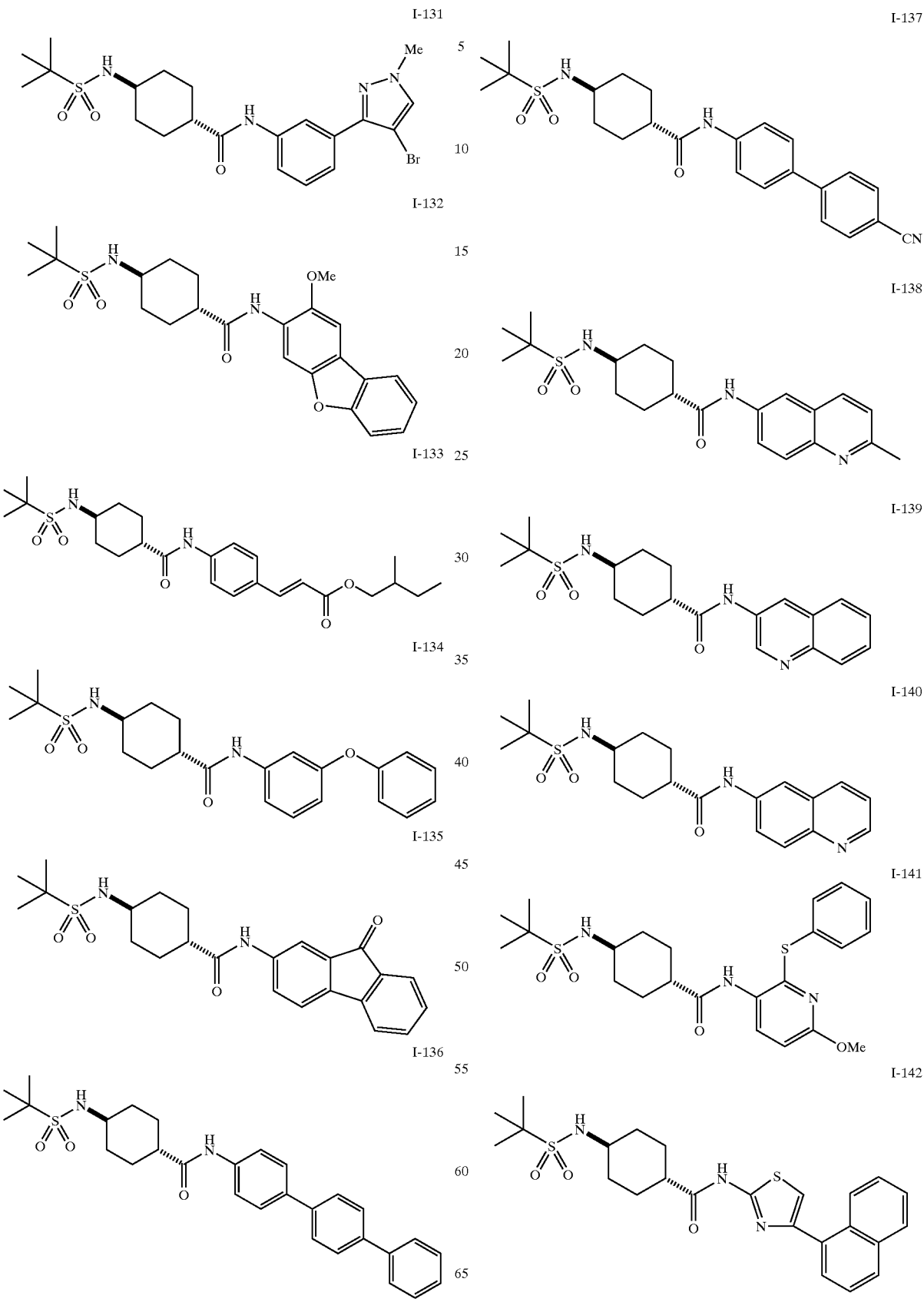

I-143
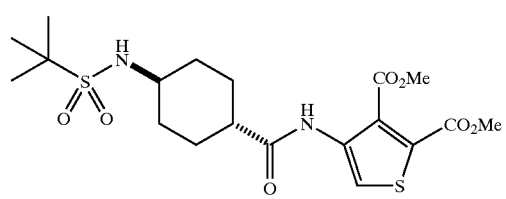
I-144
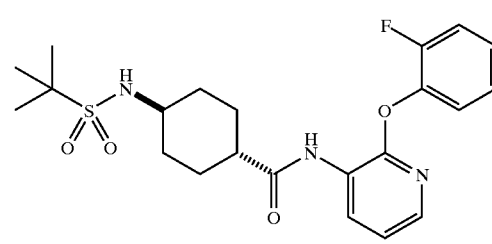
I-145
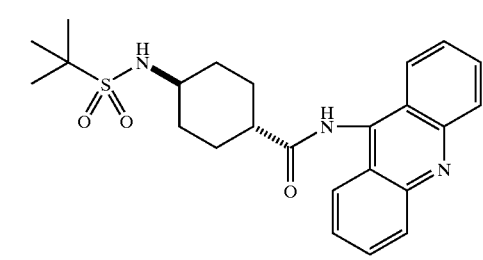
I-146
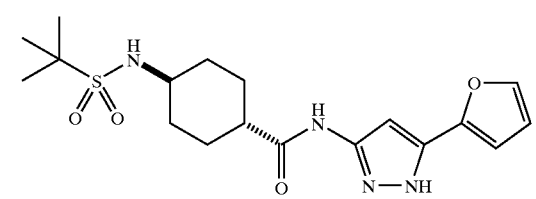
I-147
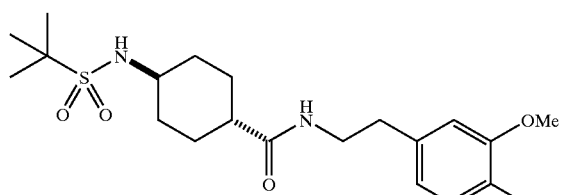
I-148
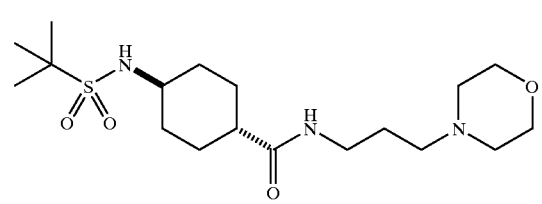
I-149
I-150
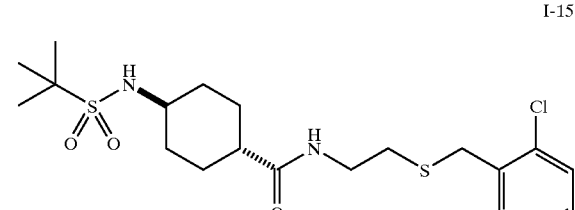
I-151
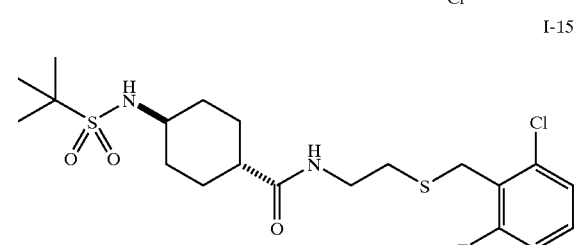
I-152
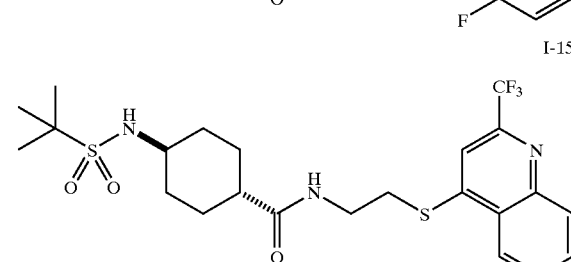
I-153
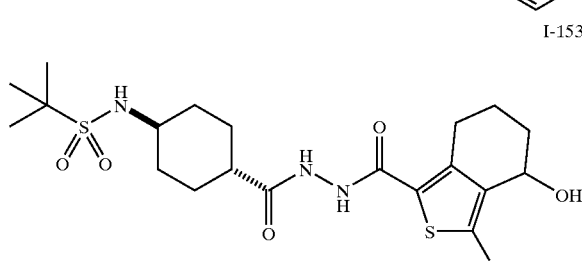
I-154
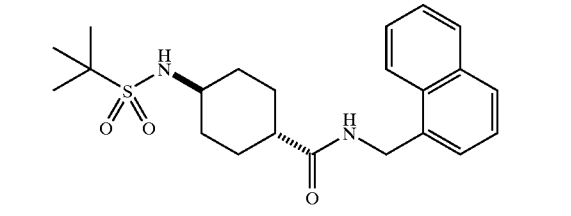
I-155
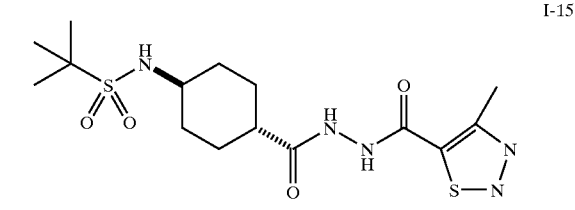
I-156

I-157
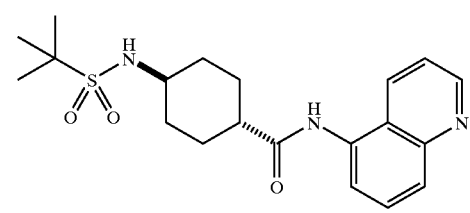
I-158
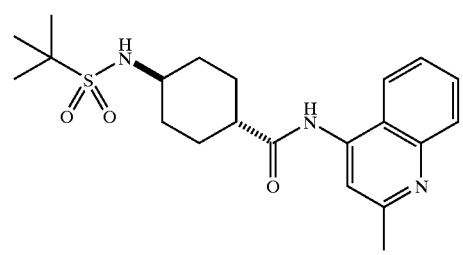
I-159
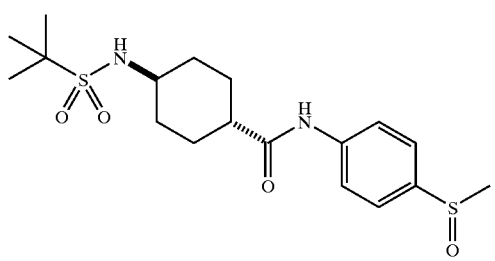
I-160
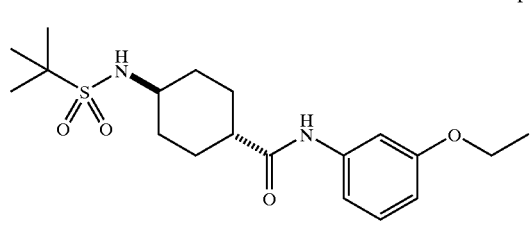
I-161
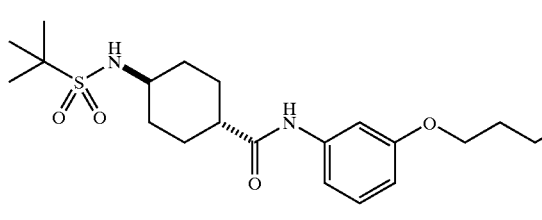
I-162
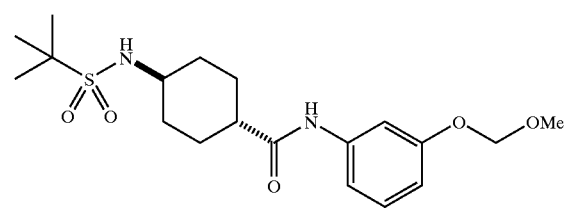
I-163
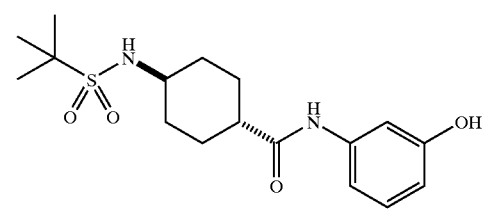
I-164
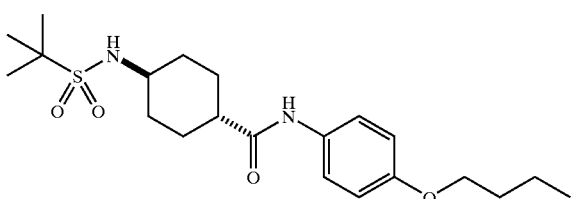
I-165
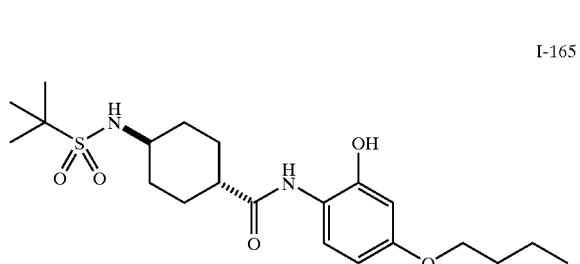
I-166
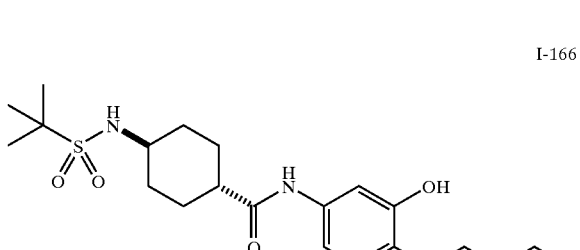
I-167
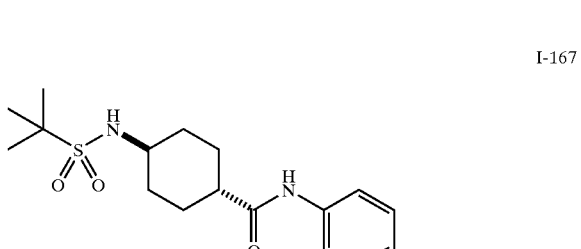
I-168
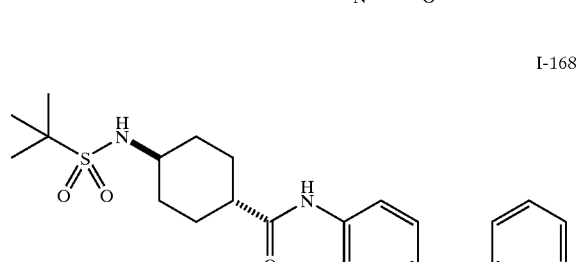
I-169
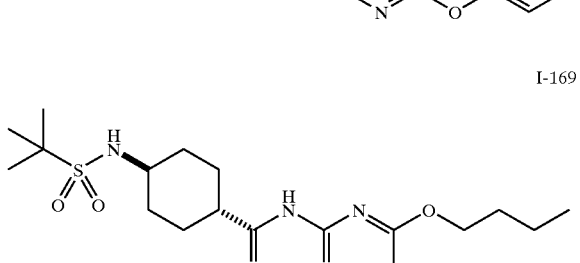

-continued
I-170
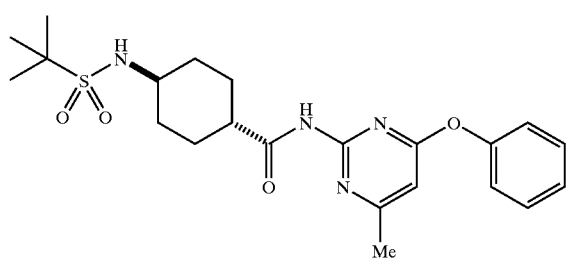
I-177
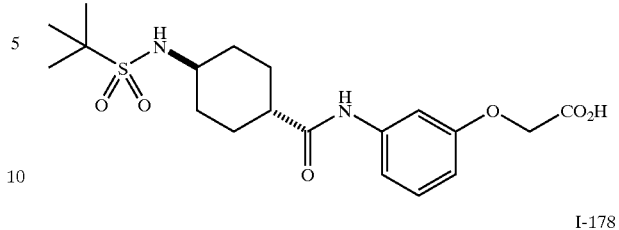
I-171
I-178

I-172
I-179

I-173
I-180
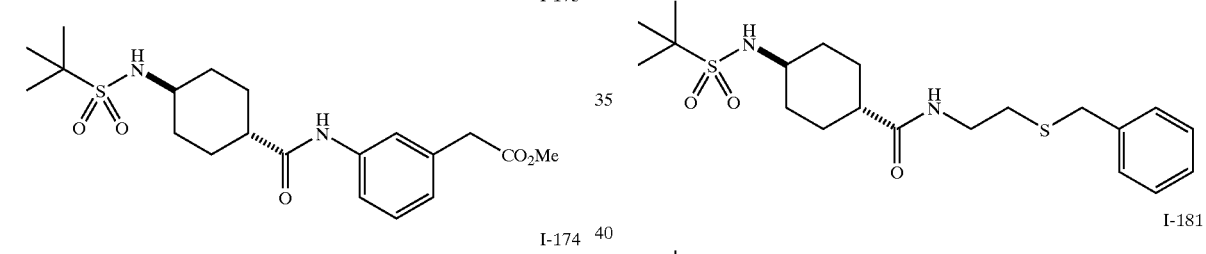
I-174
I-181

I-175
I-182
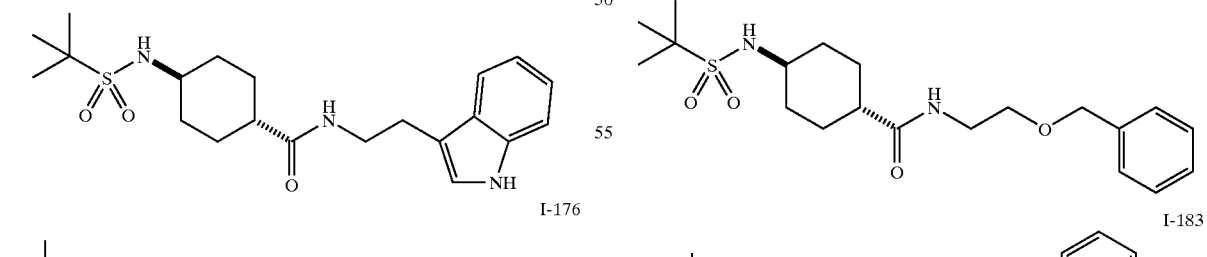
I-176
I-183
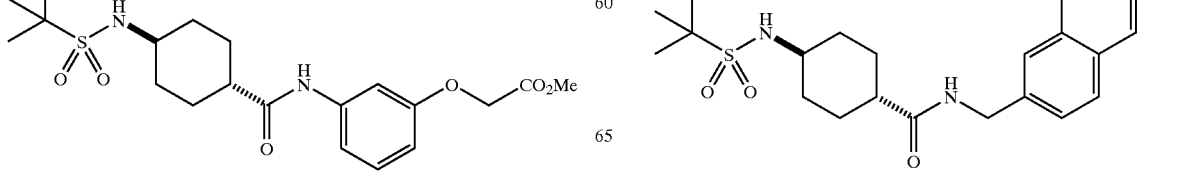

I-184 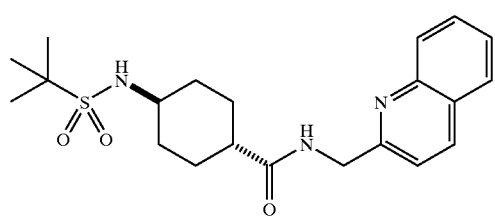
I-185 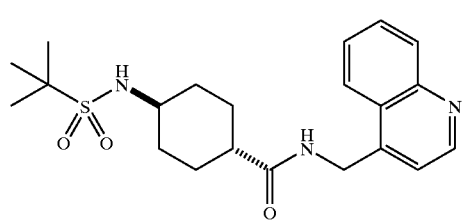
I-186 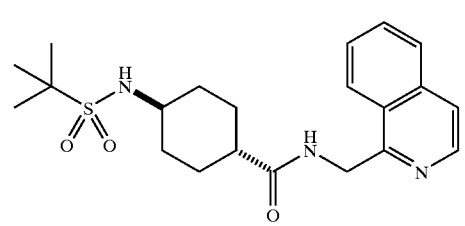
I-187 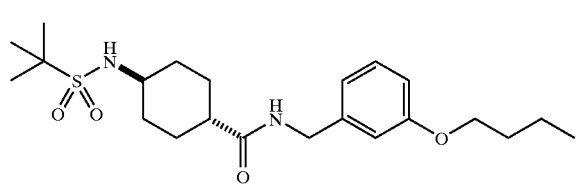
I-188 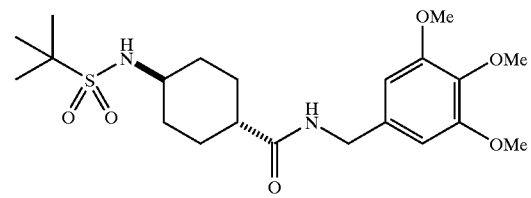
I-189 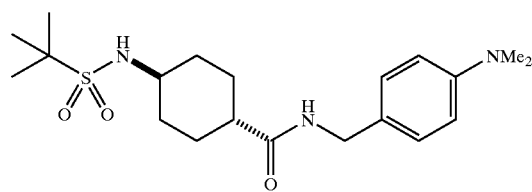
I-190 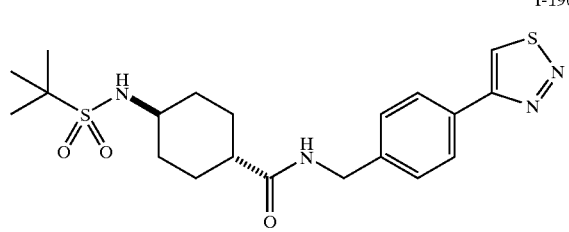
I-191 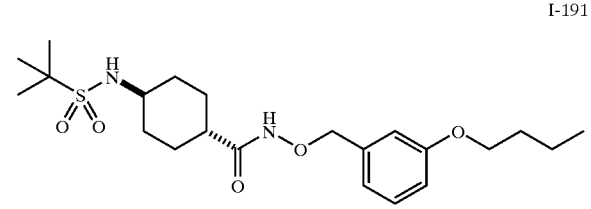
I-192 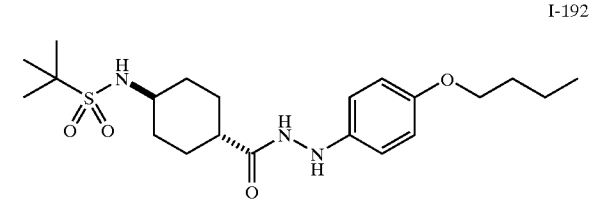
I-193 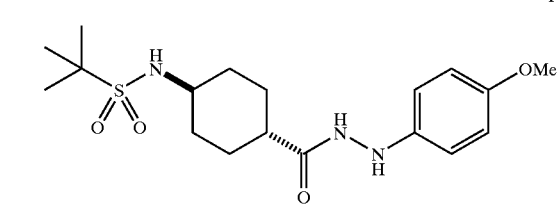
I-194 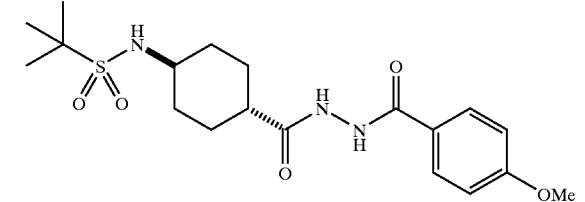
I-195 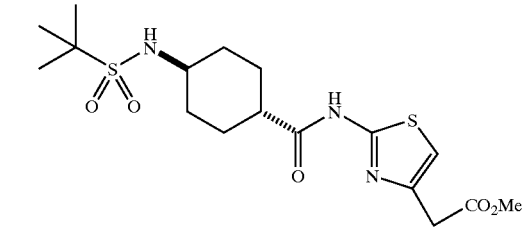
I-196 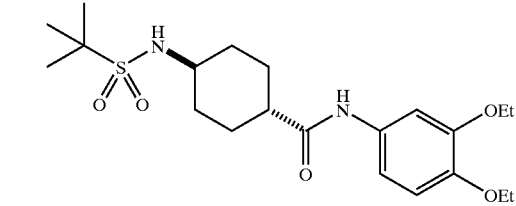
I-197 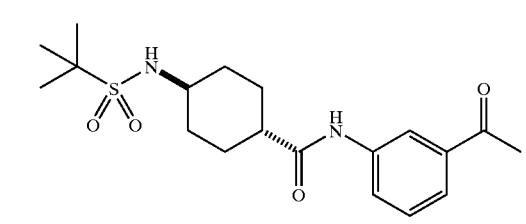

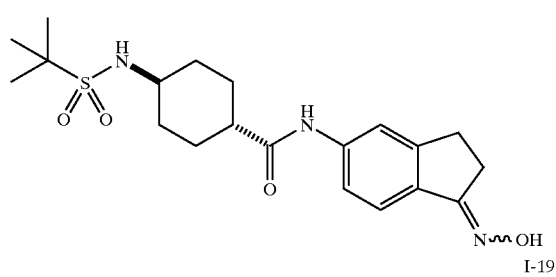
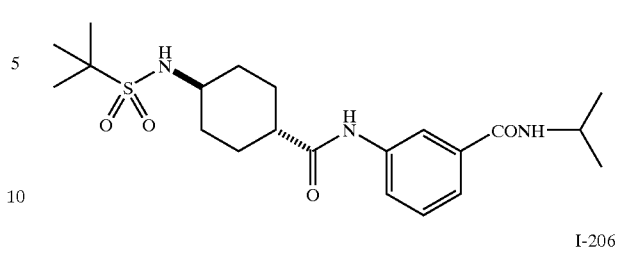
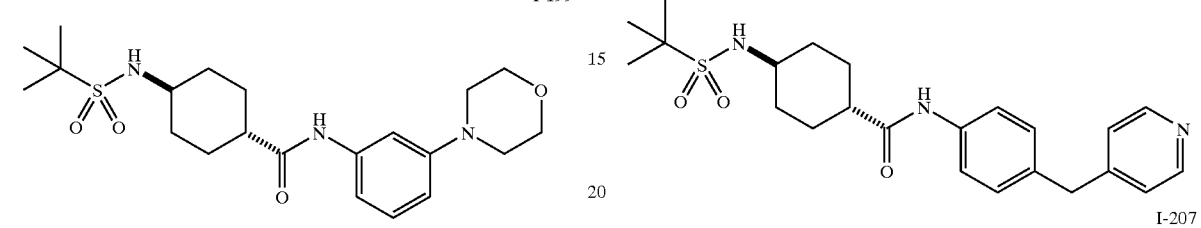

I-212
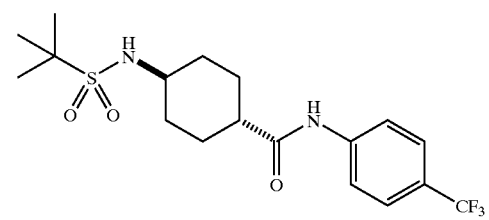
I-213
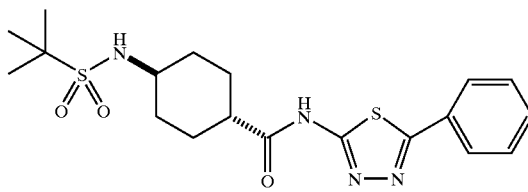
I-214
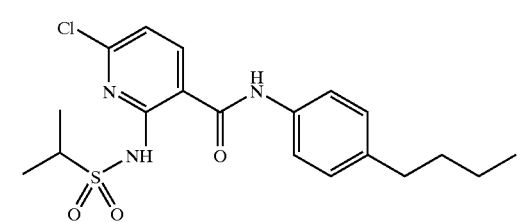
I-215
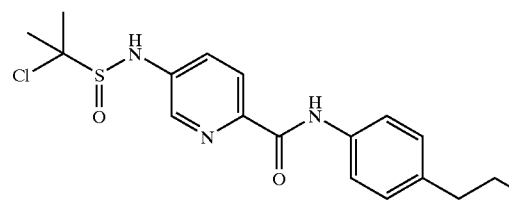
I-216
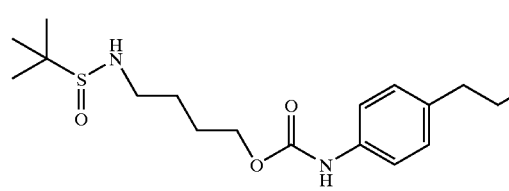
I-217
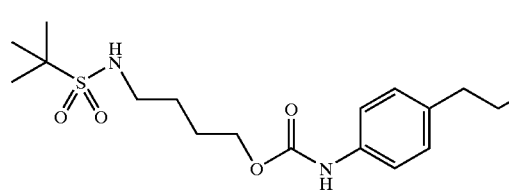
I-218
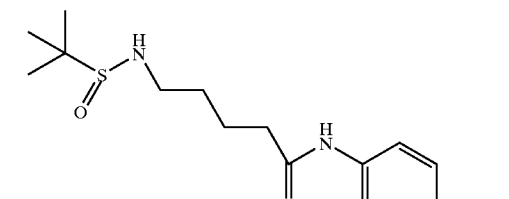
I-219
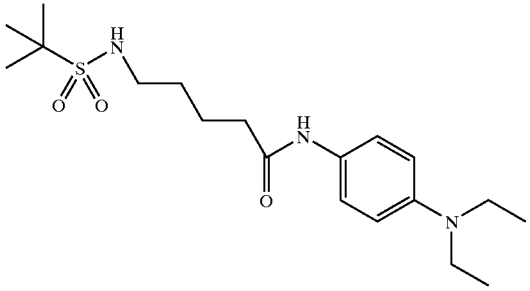
I-220
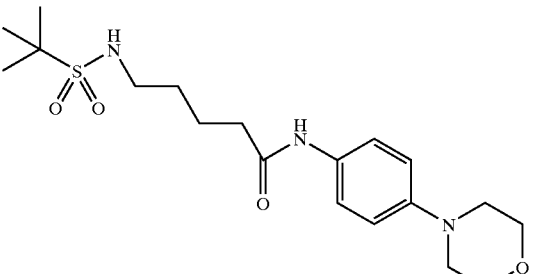
I-221
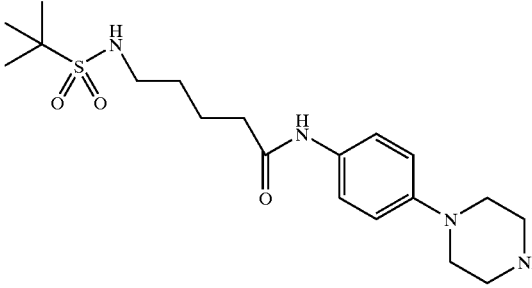
I-222
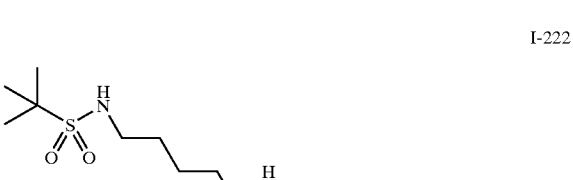
I-223
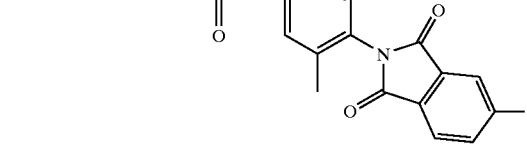
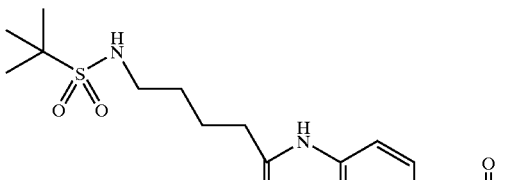

I-224
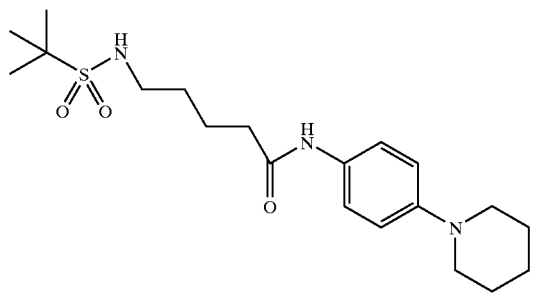
I-225
I-226
I-227
I-228
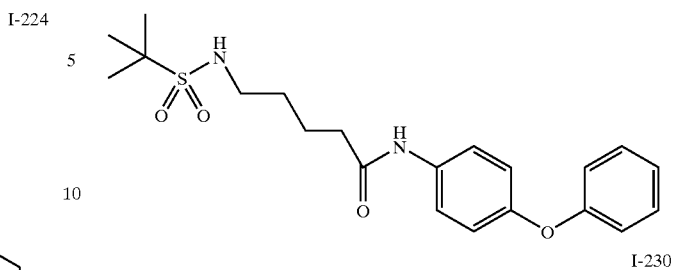
I-229
I-230
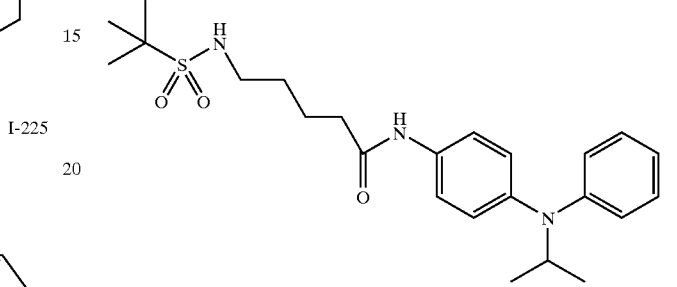
I-231
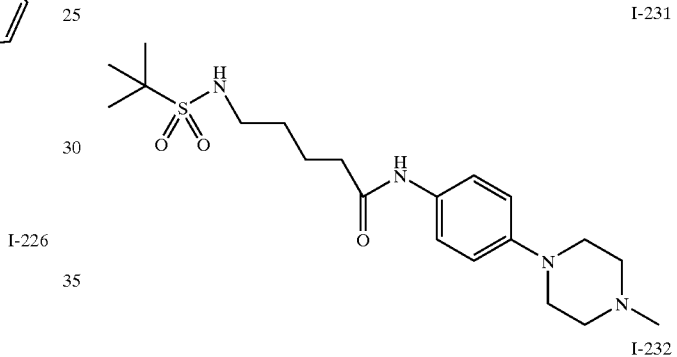
I-232
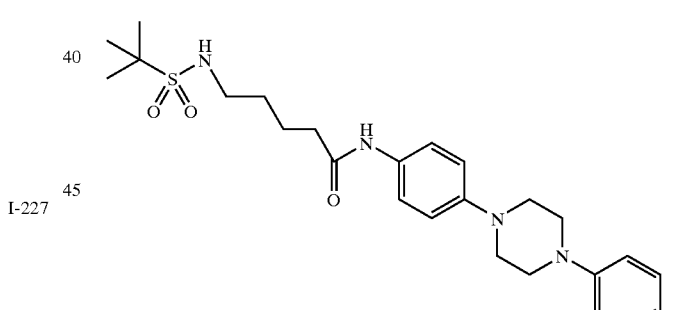
I-233
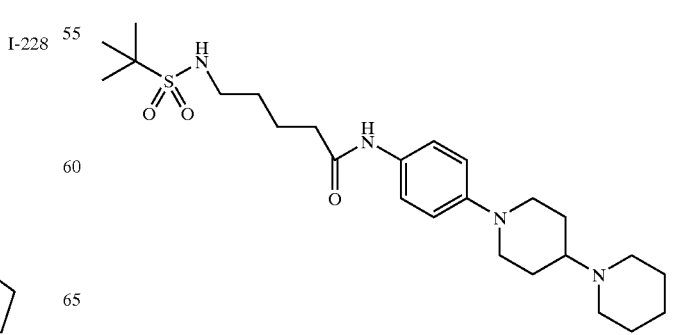

-continued
I-234
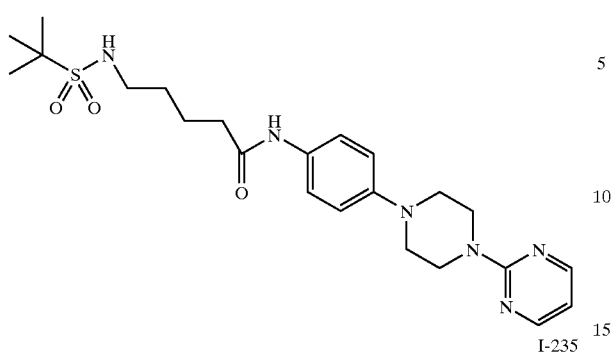
I-235
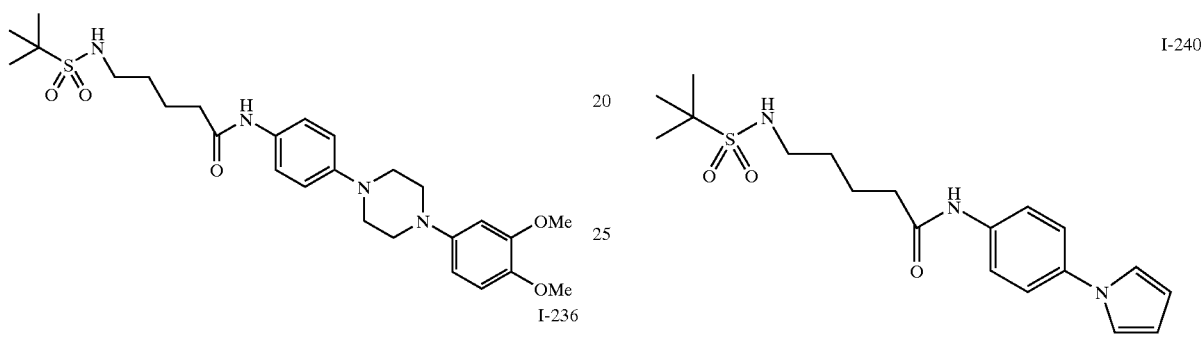
I-236
I-237
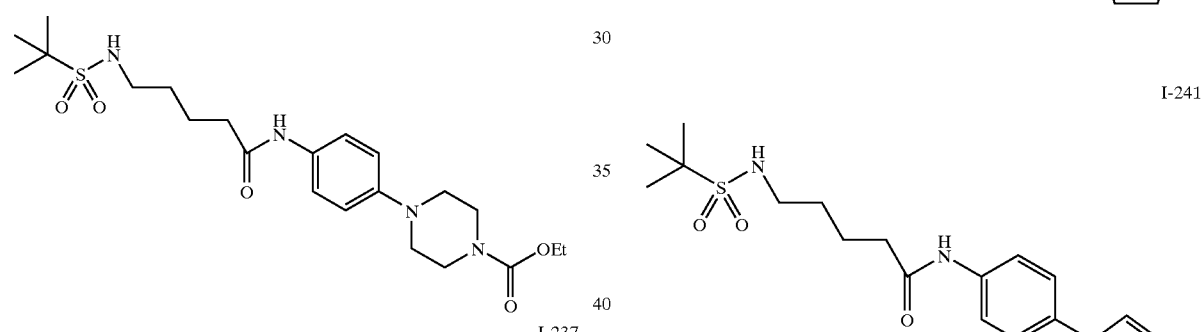
I-238
-continued
I-239
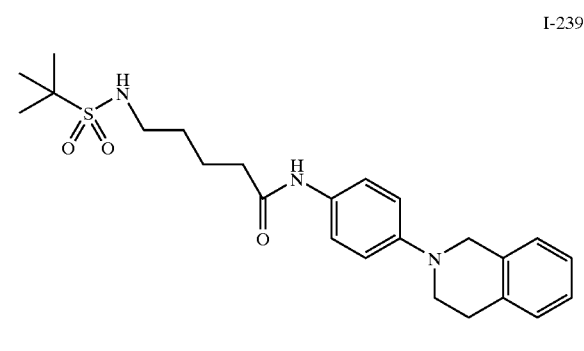
I-240
I-241
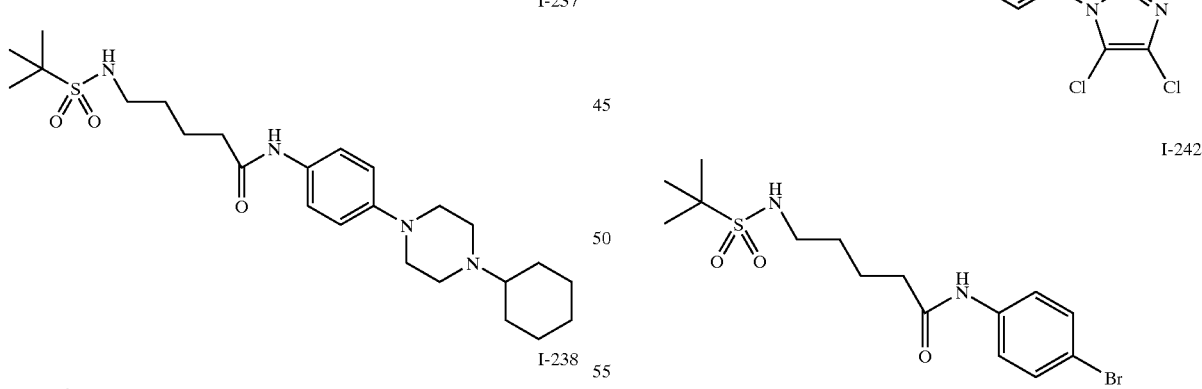
I-242
I-243
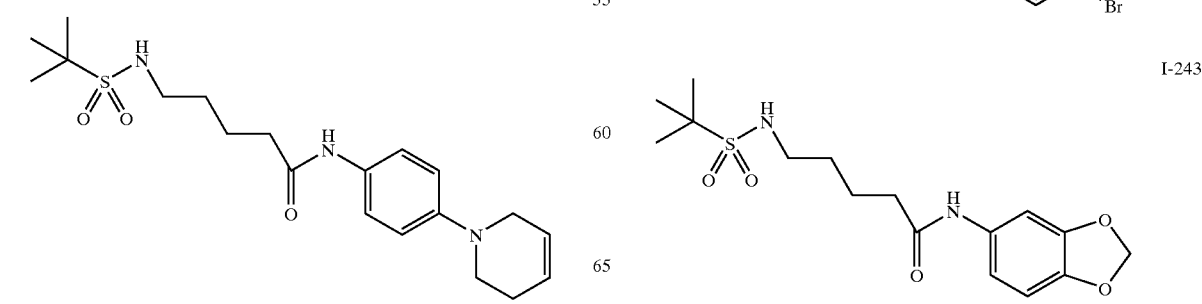

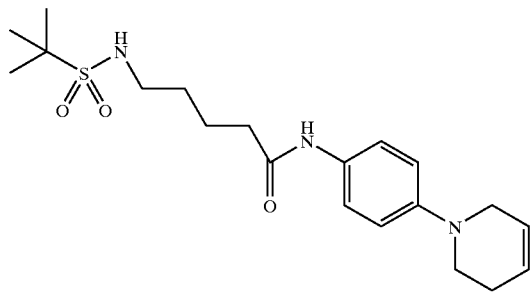
I-238
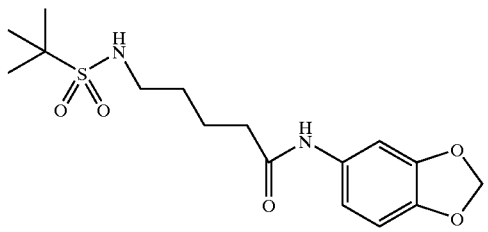
I-243
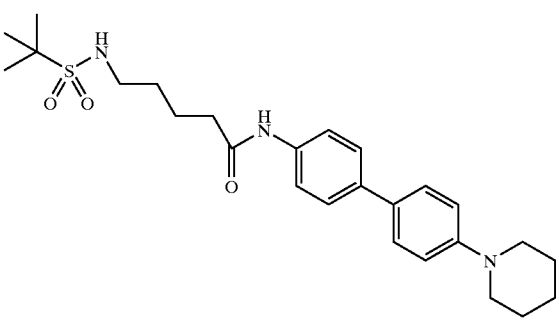
I-239
I-244
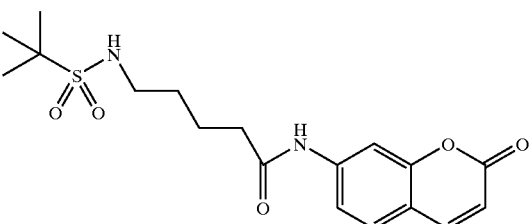
I-240
I-245
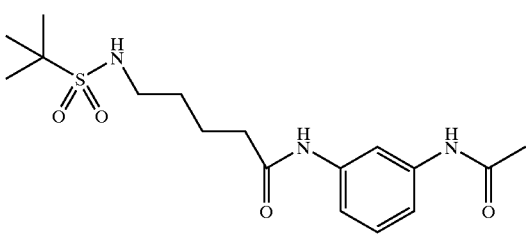
I-241
I-246
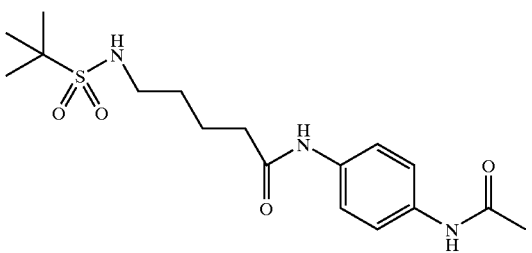
I-242
I-247
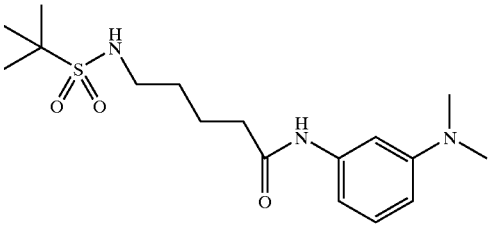
I-248

I-249
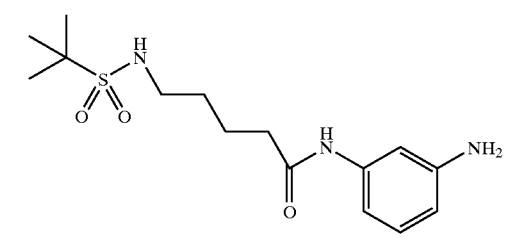
I-250
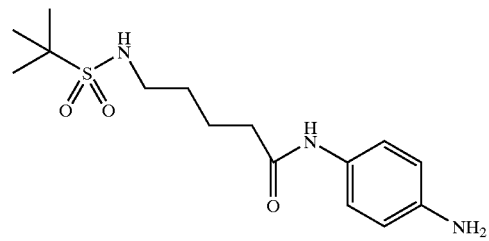
I-251
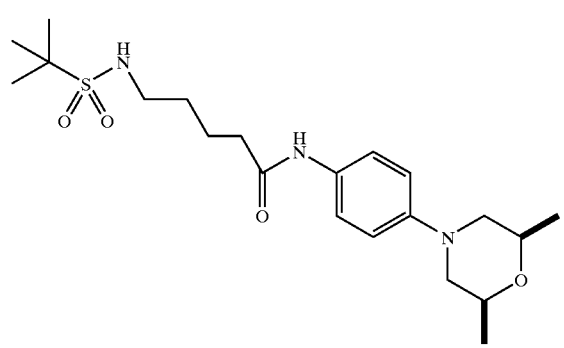
I-252
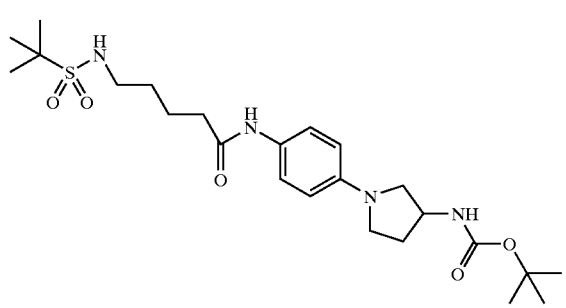
I-253
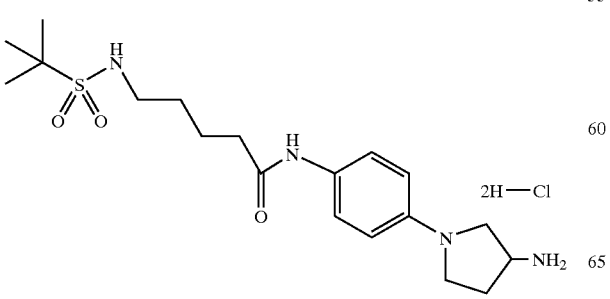
I-254
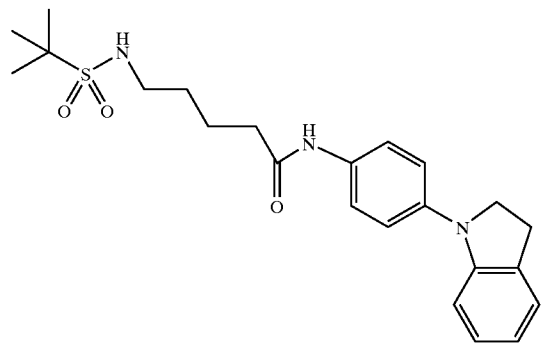
I-255
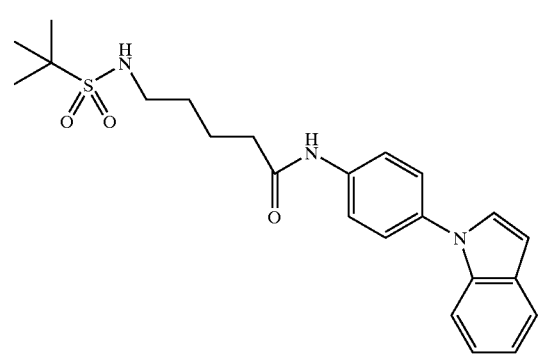
I-256
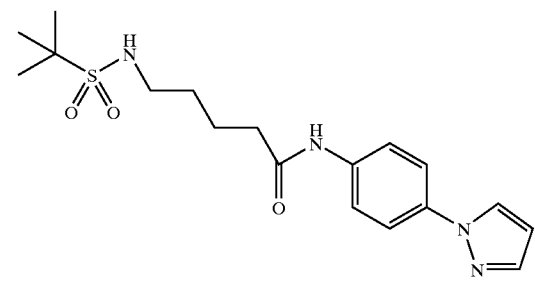
I-257
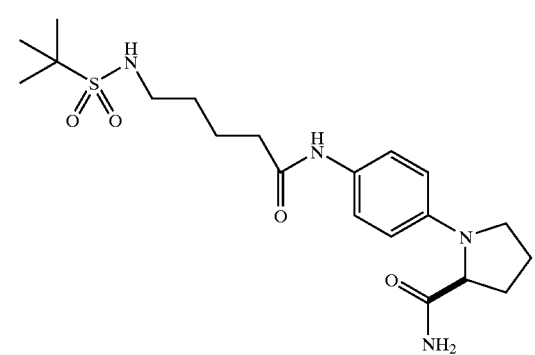

I-258
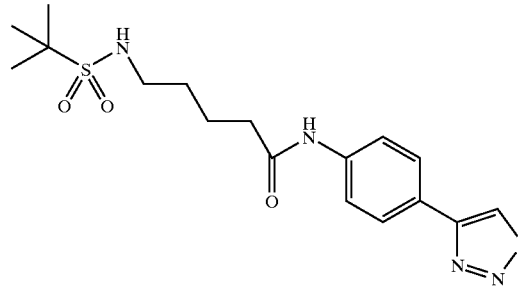
I-259
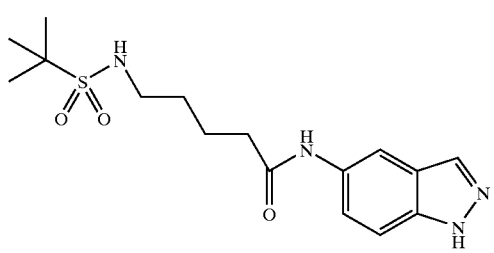
I-260
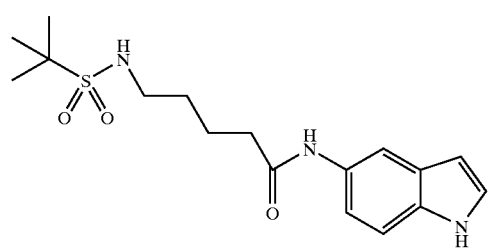
I-261
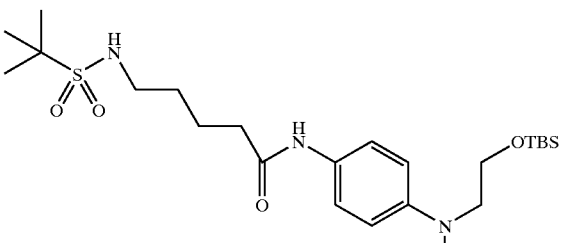
I-262
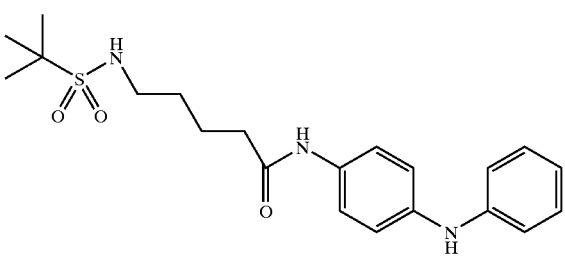
I-263
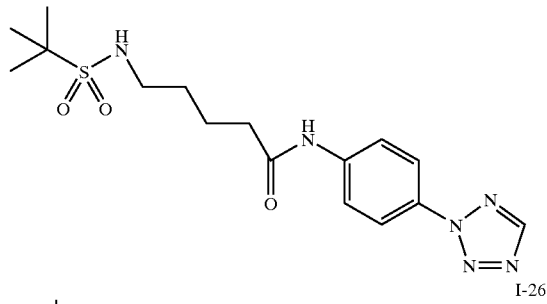
I-264
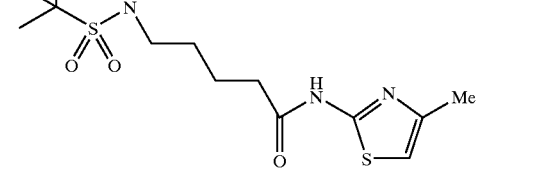
I-265
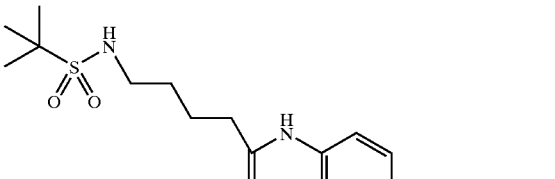
I-266
I-267
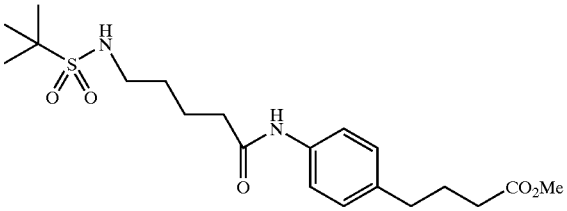
I-268
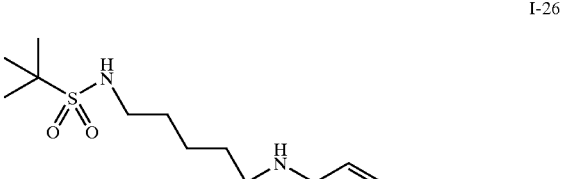
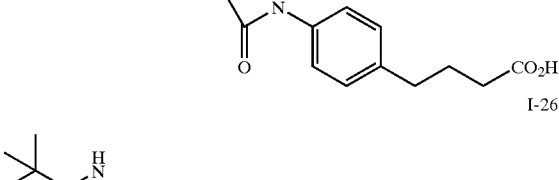
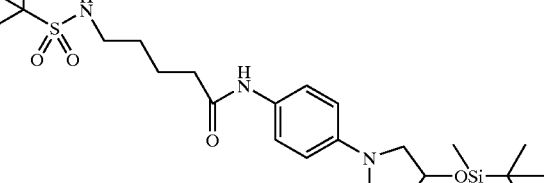

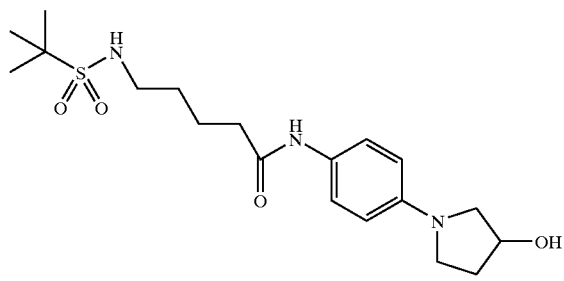
I-269
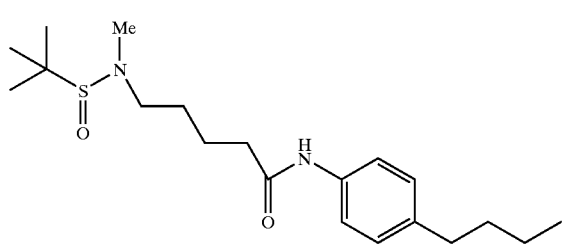
I-270
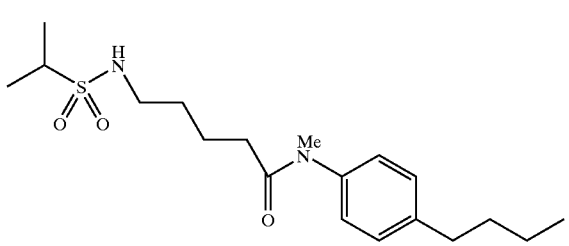
I-271
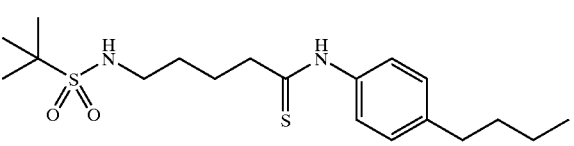
I-272
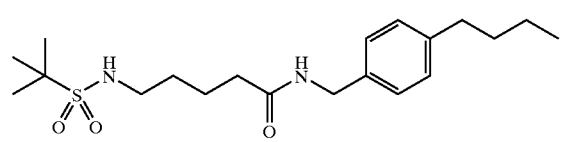
I-273
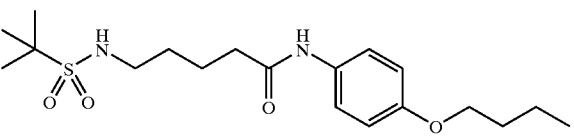
I-274
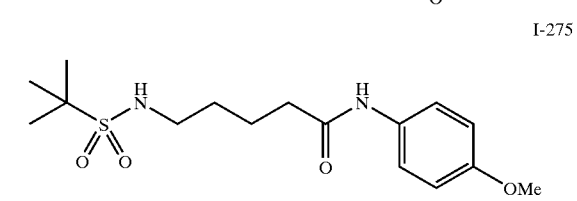
I-275
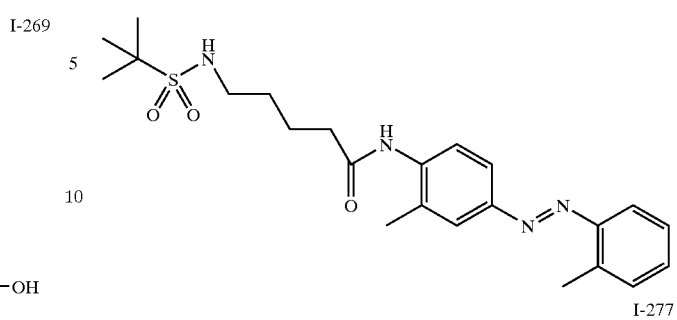
I-276
I-277
I-278
I-279
I-280
I-281

I-282
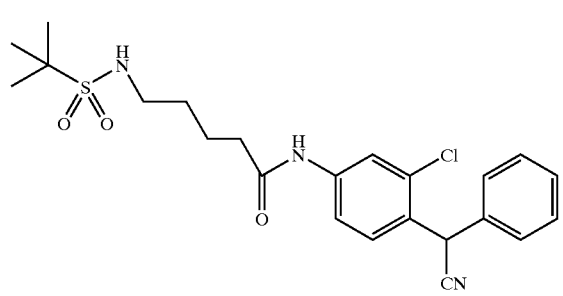
I-283
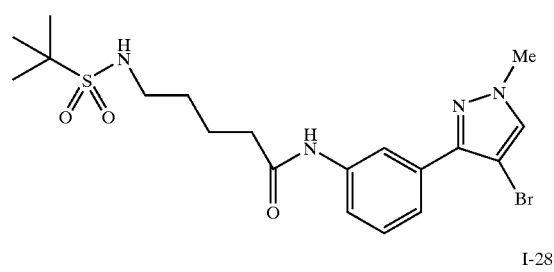
I-284
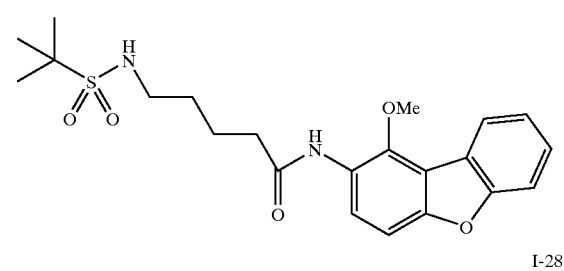
I-285
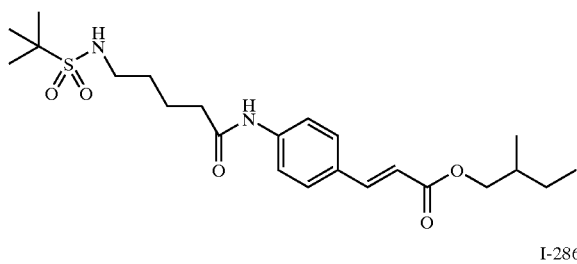
I-286
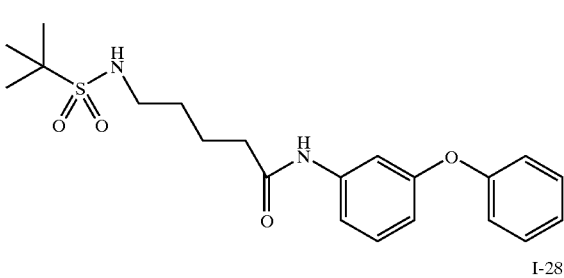
I-287
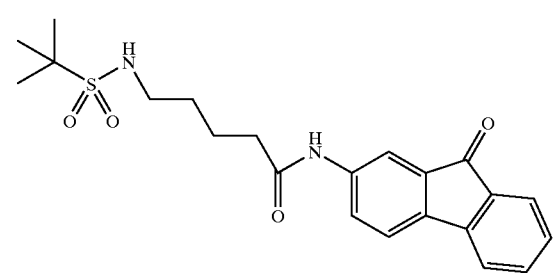
I-288
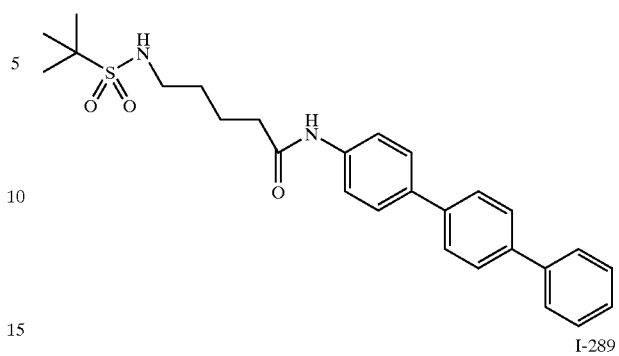
I-289
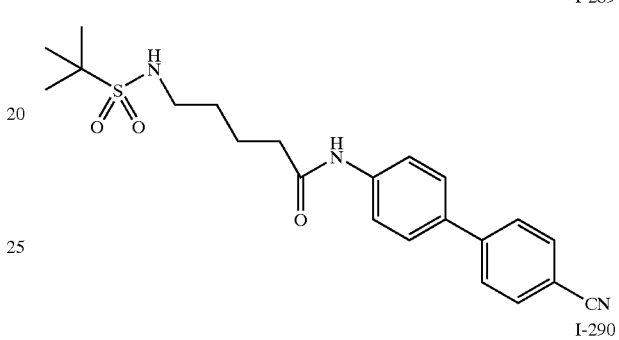
I-290
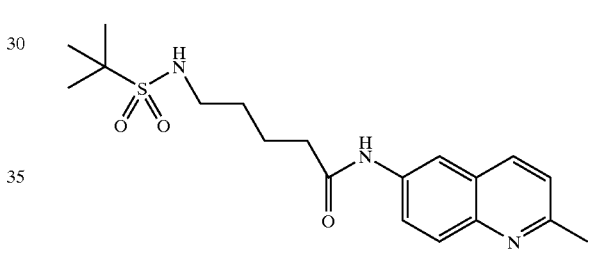
I-291
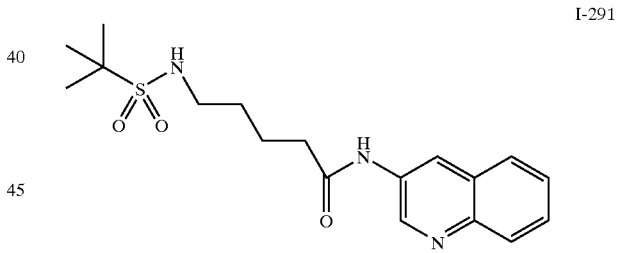
I-292
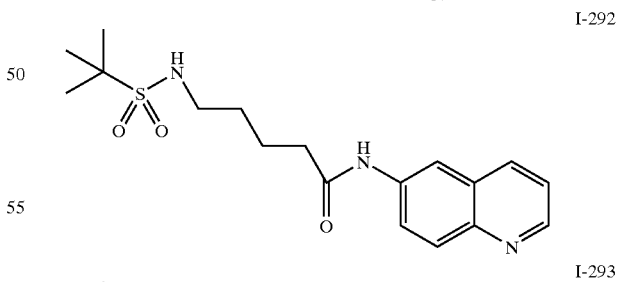
I-293
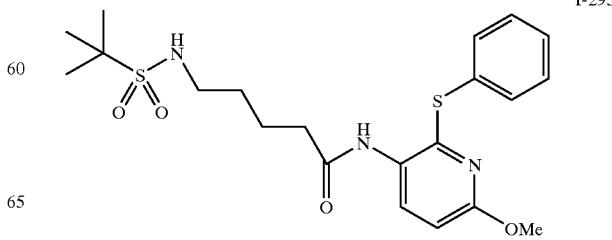

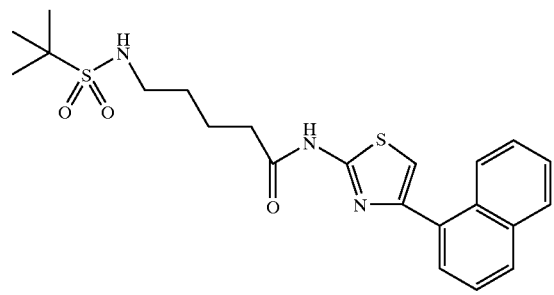

I-306
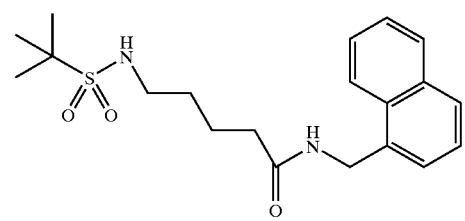
I-307
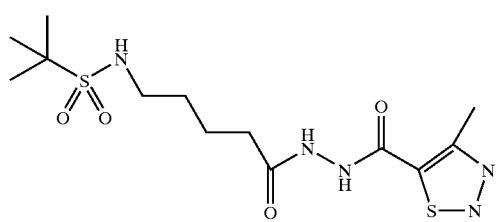
I-308
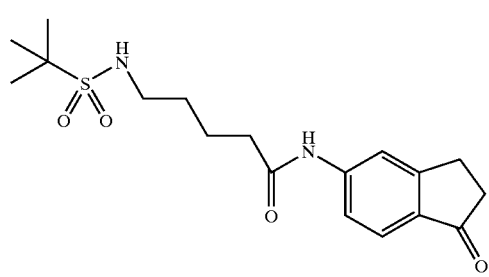
I-309
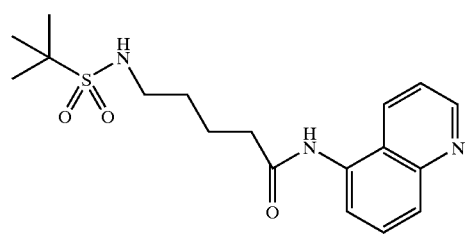
I-310
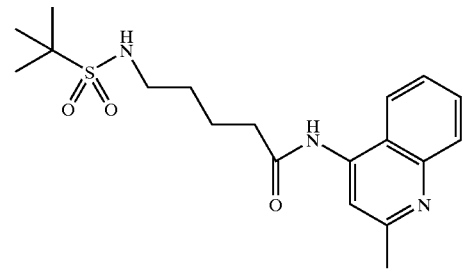
I-311
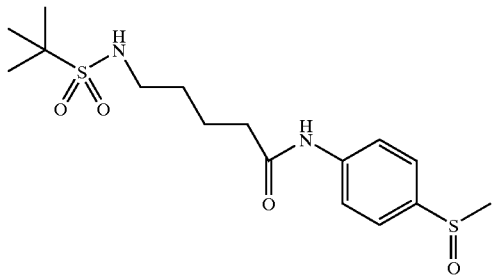
I-312
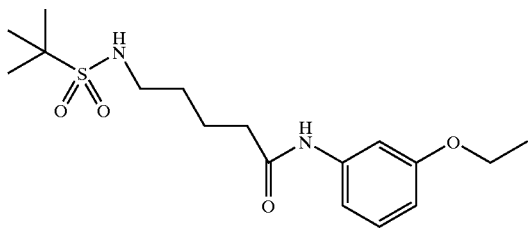
I-313
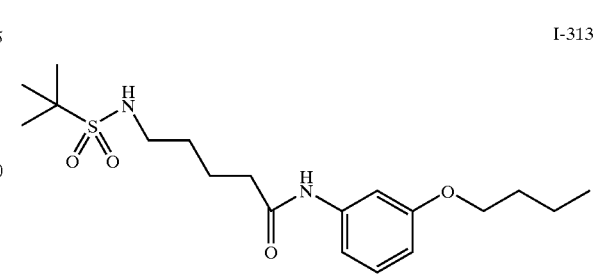
I-314
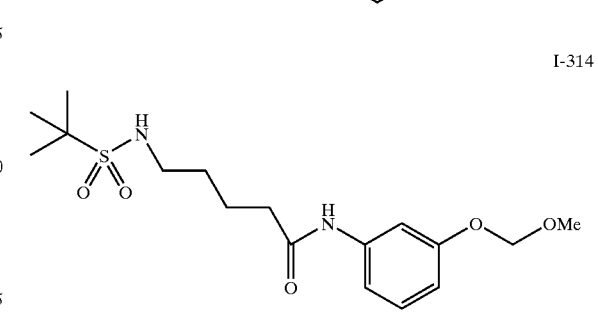
I-315
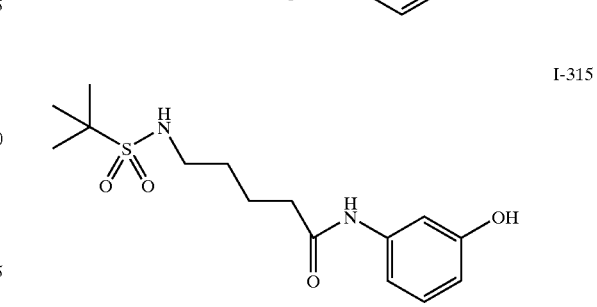
I-316
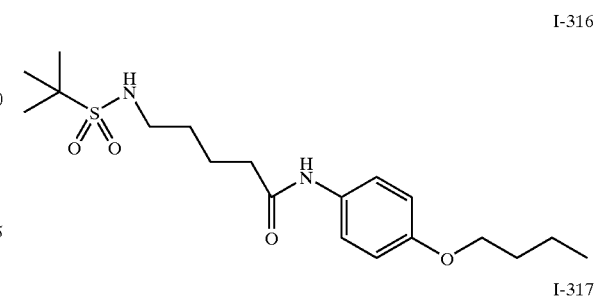
I-317
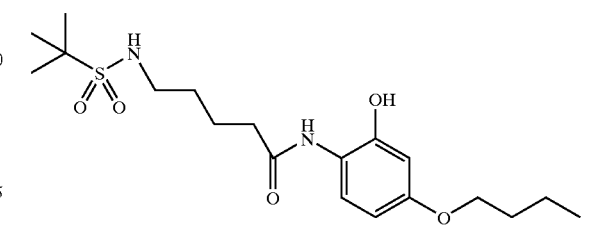

I-318
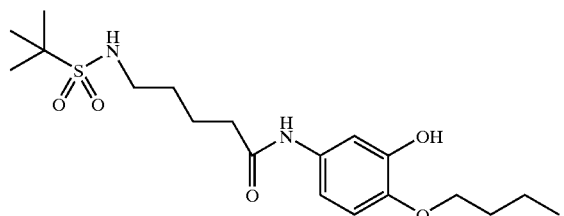
I-319
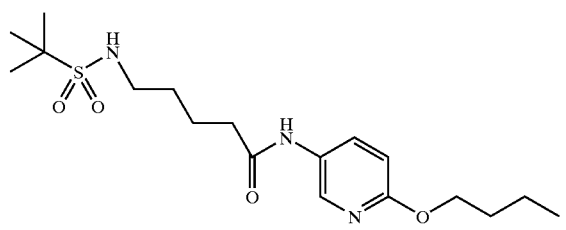
I-320
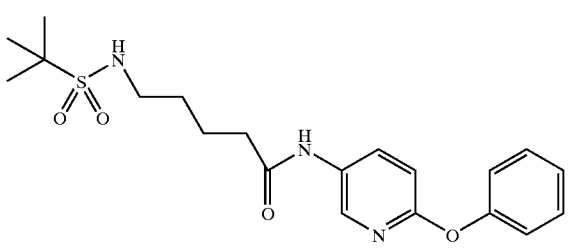
I-321
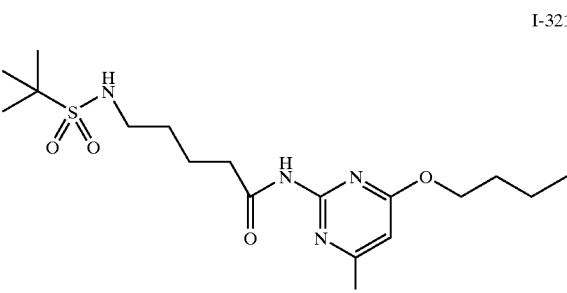
I-322
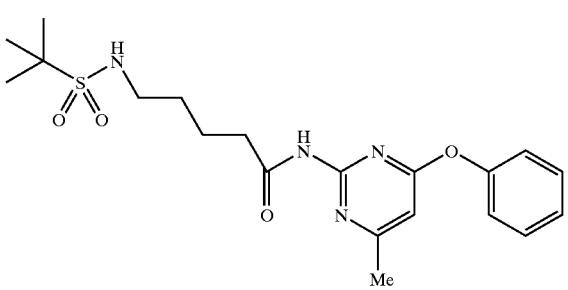
I-323
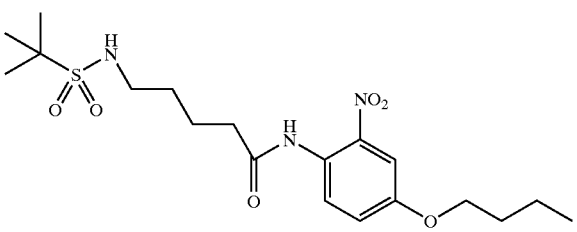
I-324
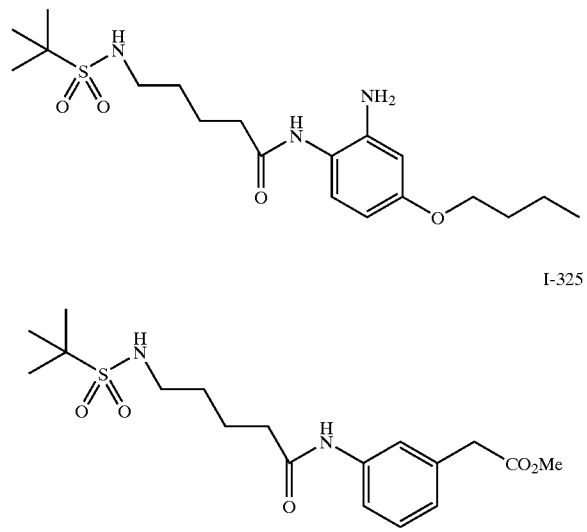
I-325
I-326
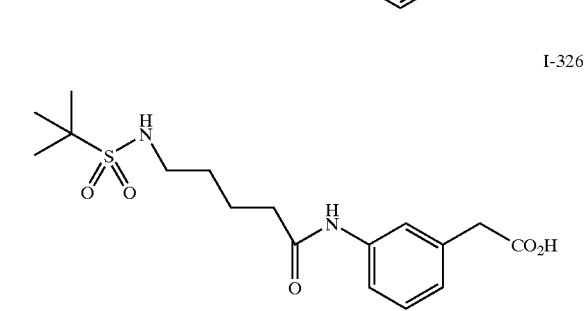
I-327
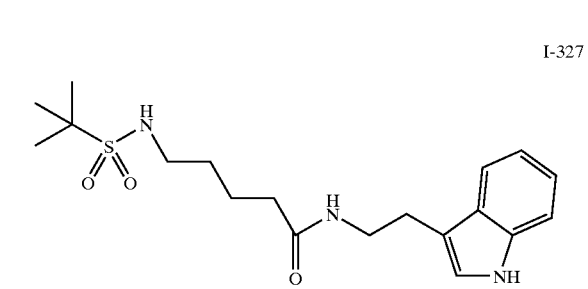
I-328
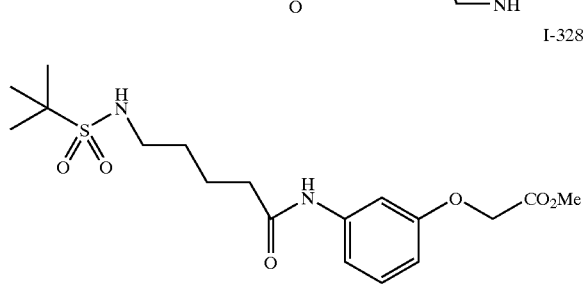
I-329
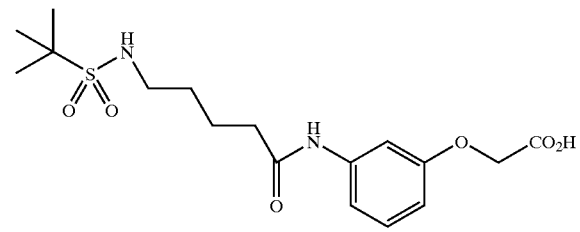

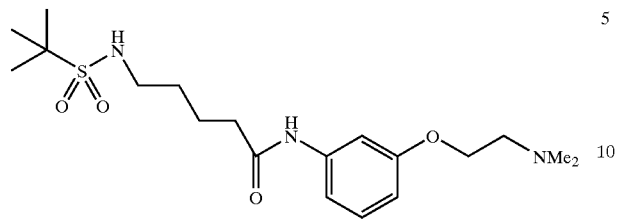
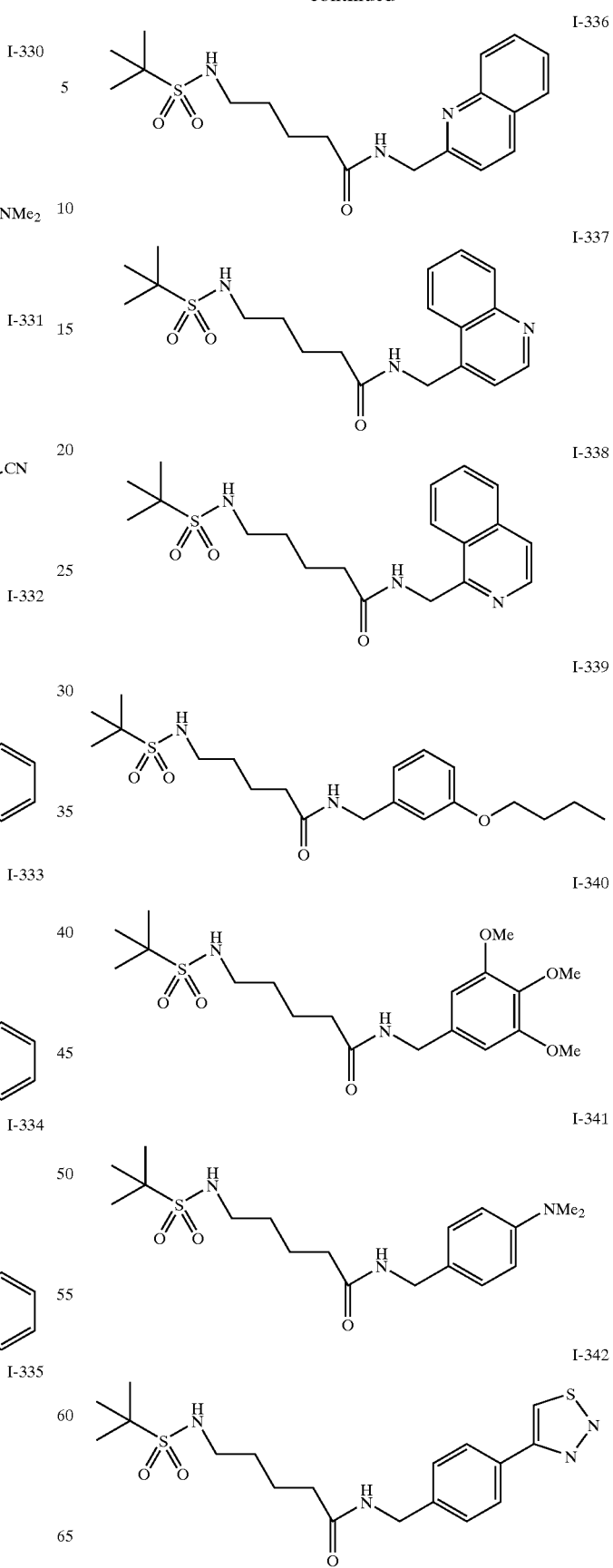

I-343
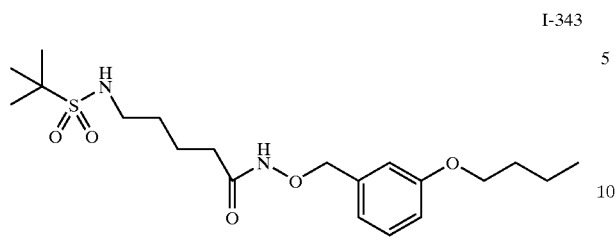
I-349
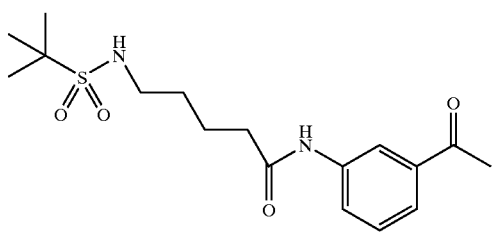
I-344
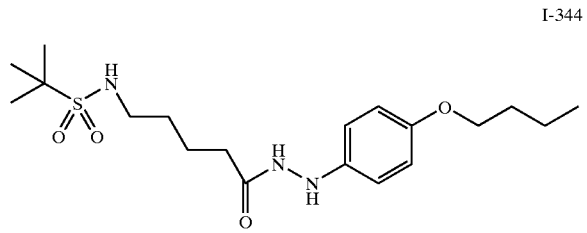
I-350
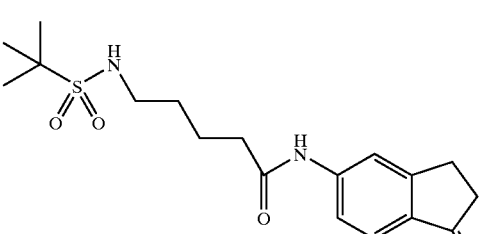
I-345
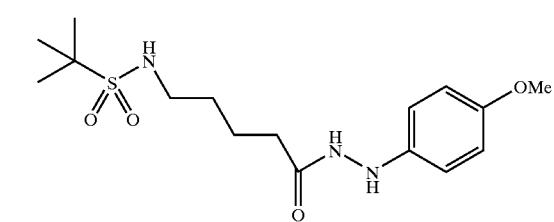
I-351
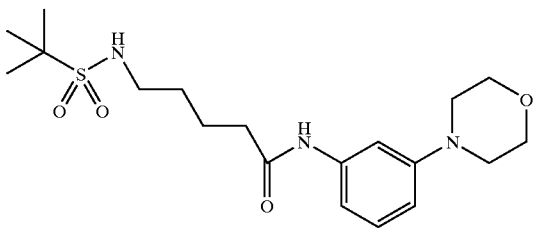
I-346
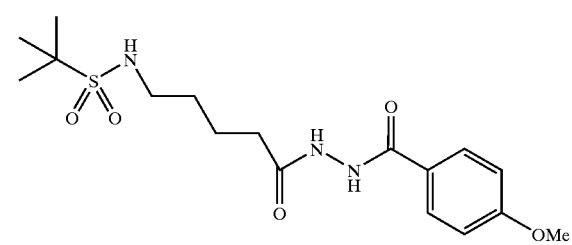
I-352
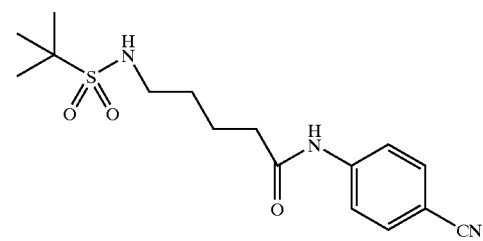
I-347
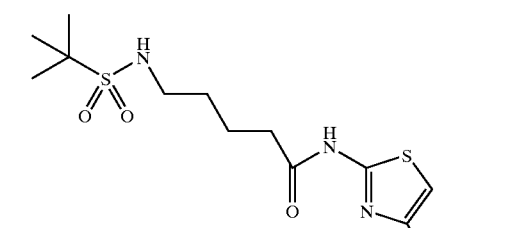
I-353
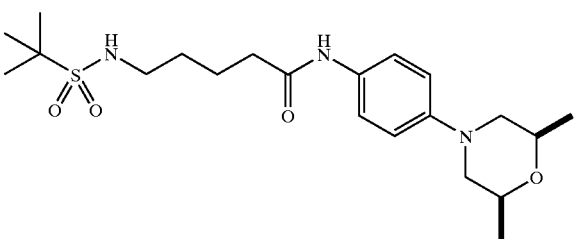
I-348
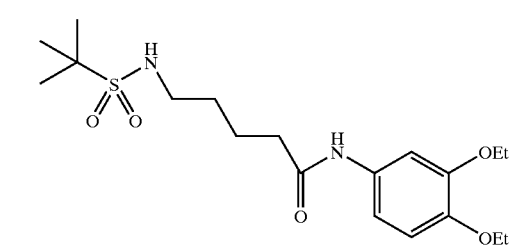
I-354
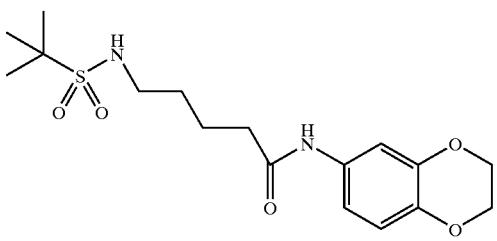

-continued

I-384

I-385

I-386

I-387

I-388

I-389

I-390

I-391

I-392

I-393

I-394

I-395

I-396

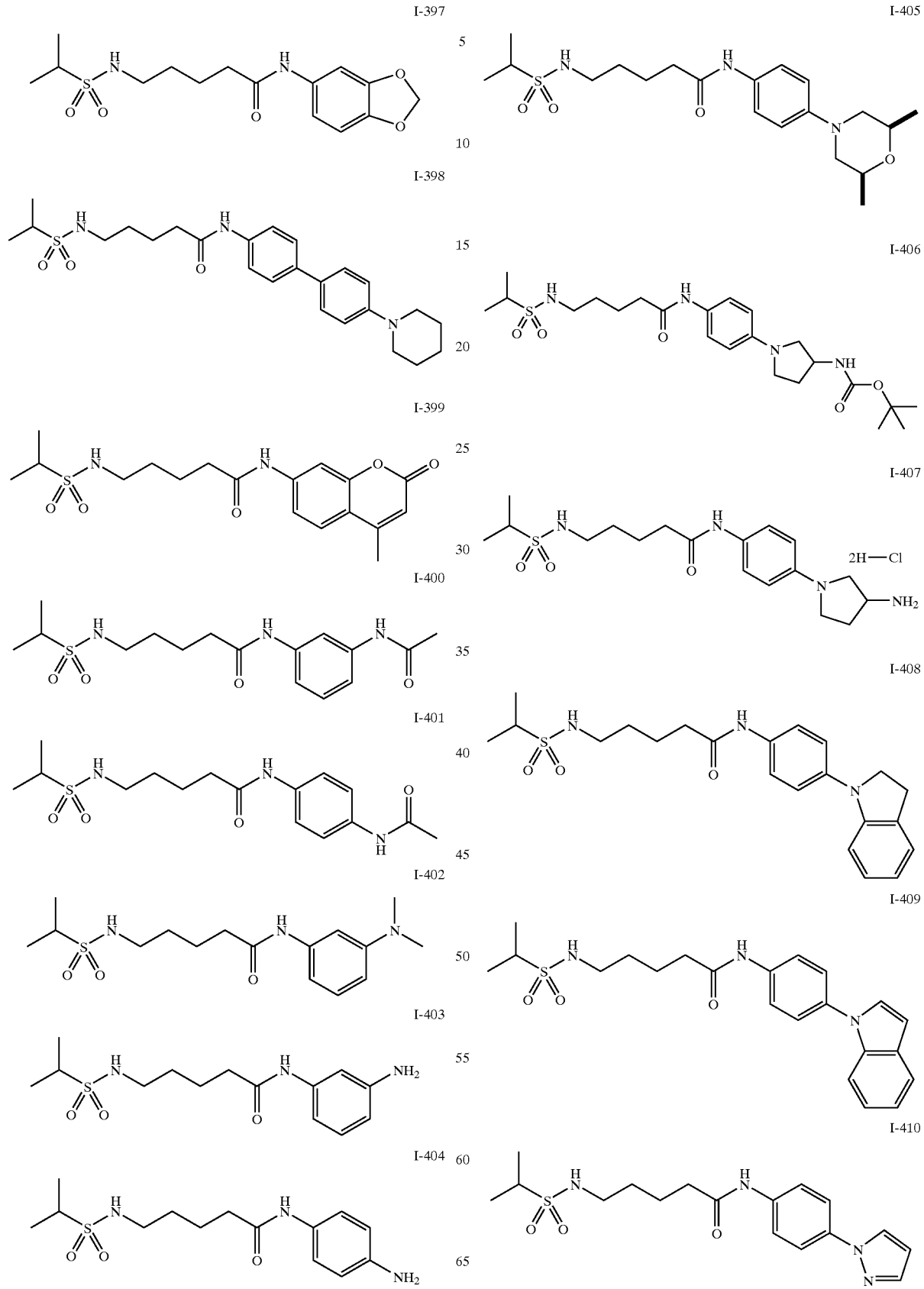

I-411
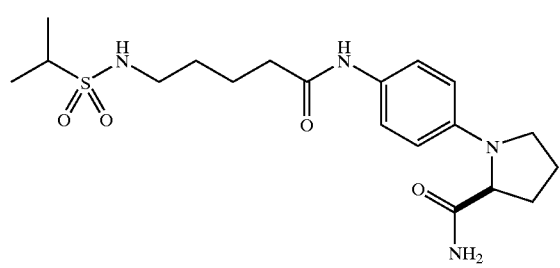
I-419
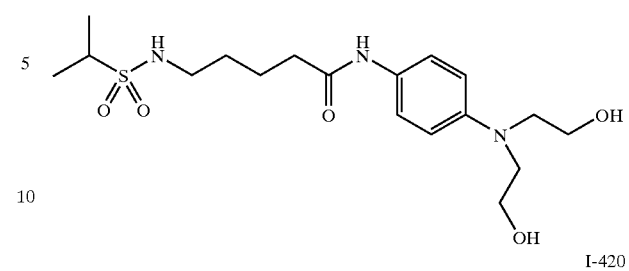
I-412
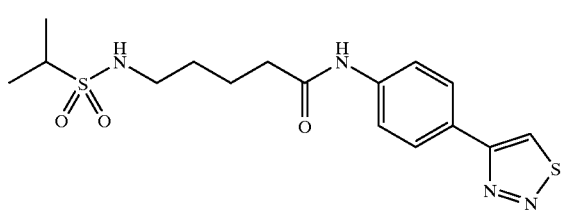
I-420
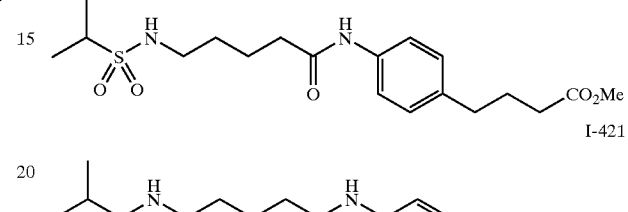
I-413
I-421
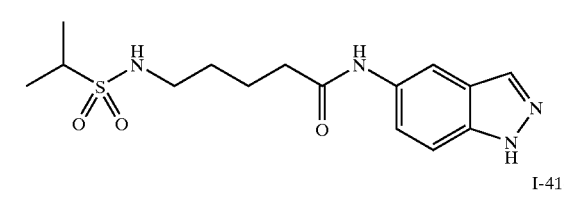
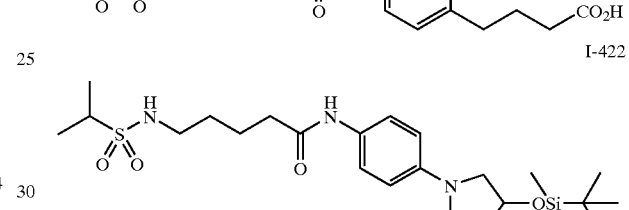
I-414
I-422
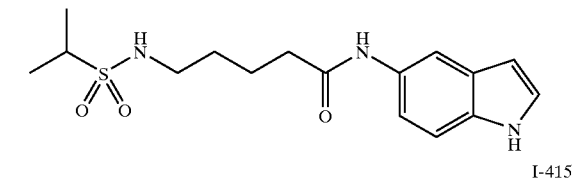
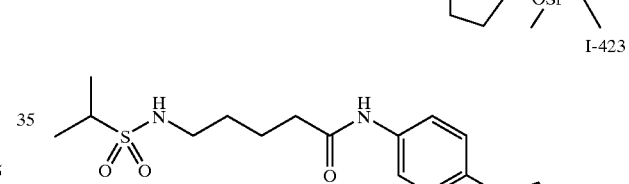
I-415
I-423
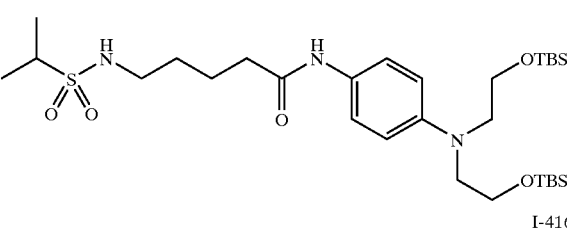
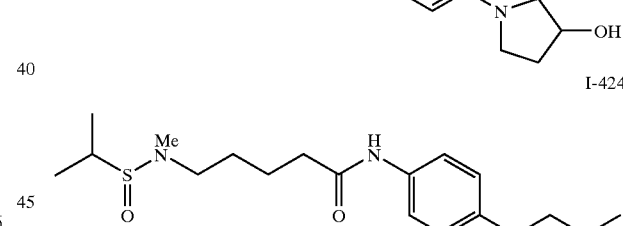
I-416
I-424
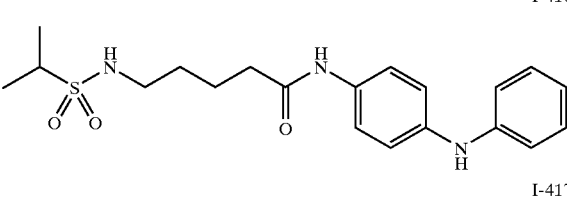
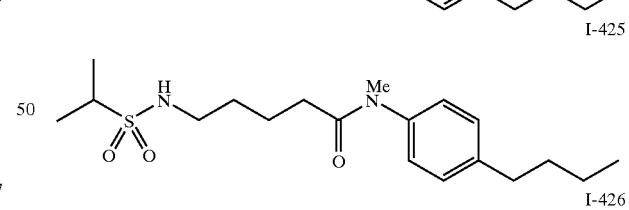
I-417
I-425
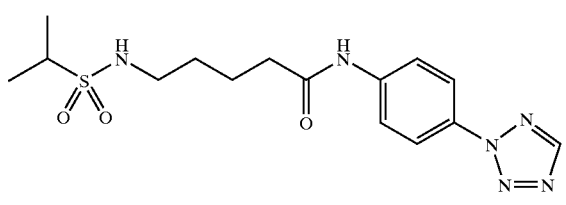
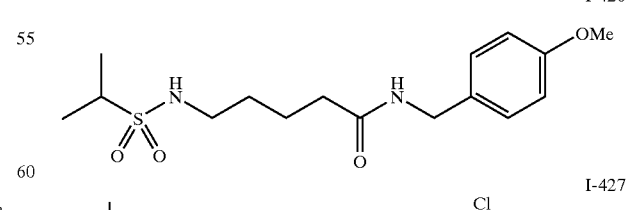
I-418
I-426
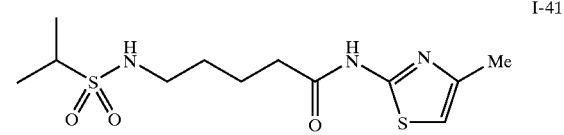
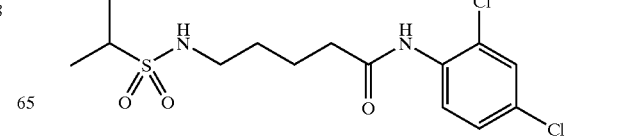
I-427

105 -continued

I-428, I-429, I-430, I-431, I-432, I-433, I-434, I-435, I-436

106 -continued

I-437, I-438, I-439, I-440, I-441, I-442, I-443, I-444

I-445
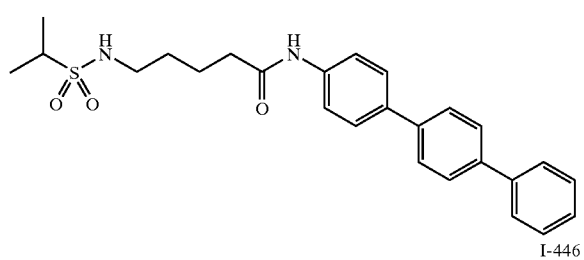
I-446
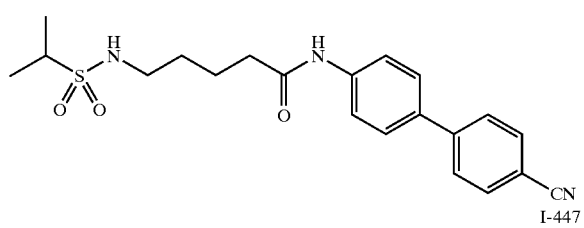
I-447
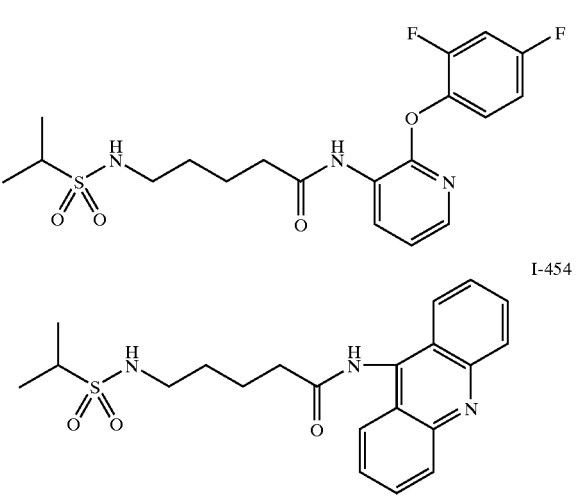
I-448
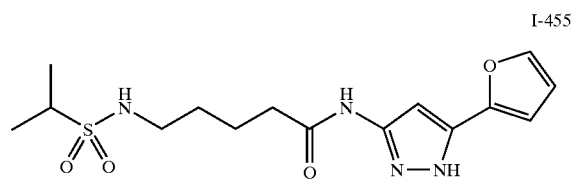
I-449

I-450

I-451

I-452
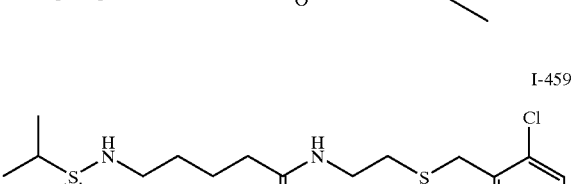
I-453
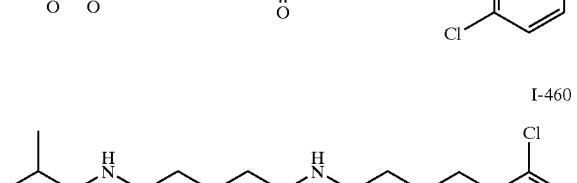
I-454
I-455
I-456
I-457
I-458
I-459
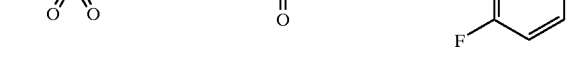
I-460

I-461
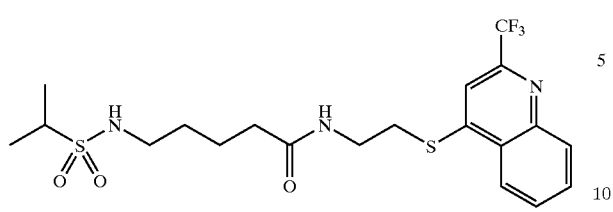
I-462
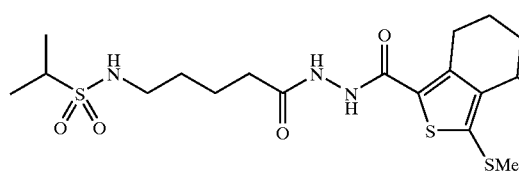
I-463
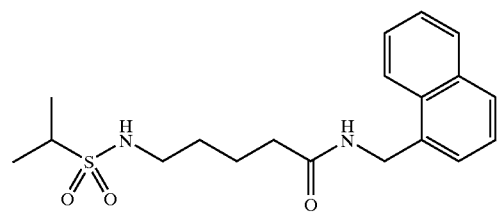
I-464
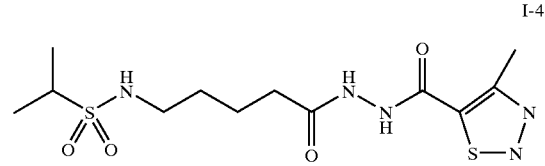
I-465
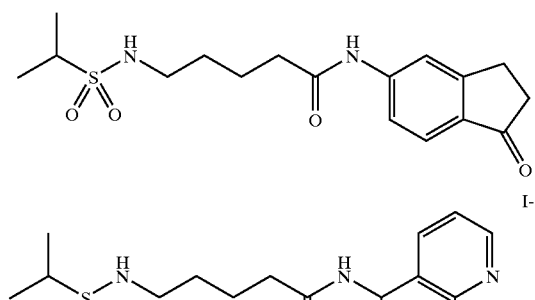
I-466
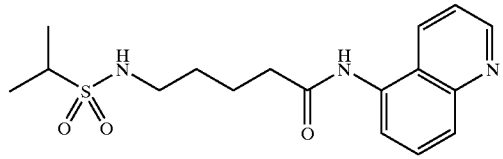
I-467
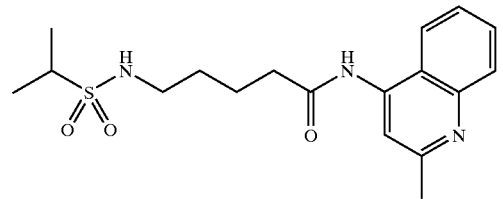
I-468
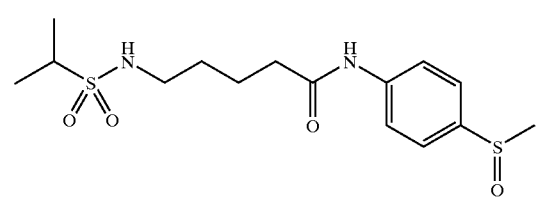
I-469
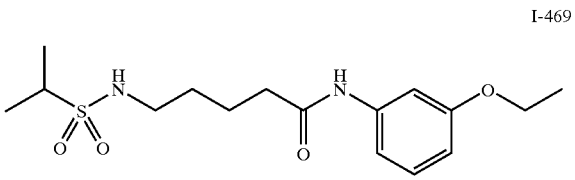
I-470
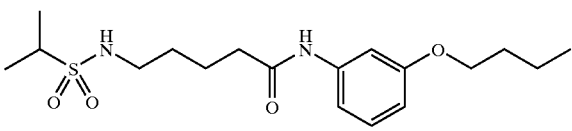
I-471
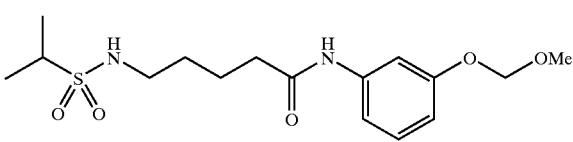
I-472
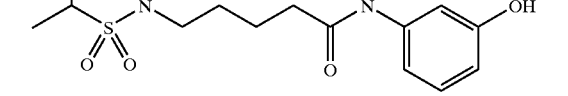
I-473
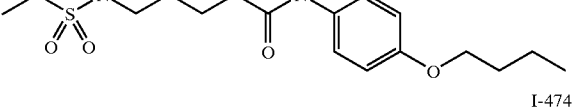
I-474
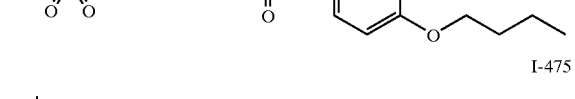
I-475
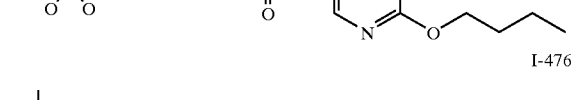
I-476
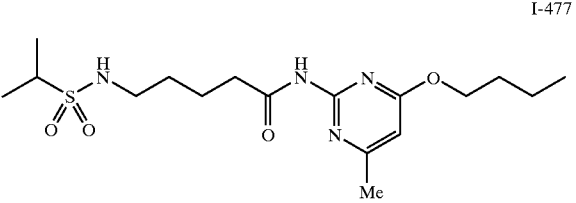
I-477

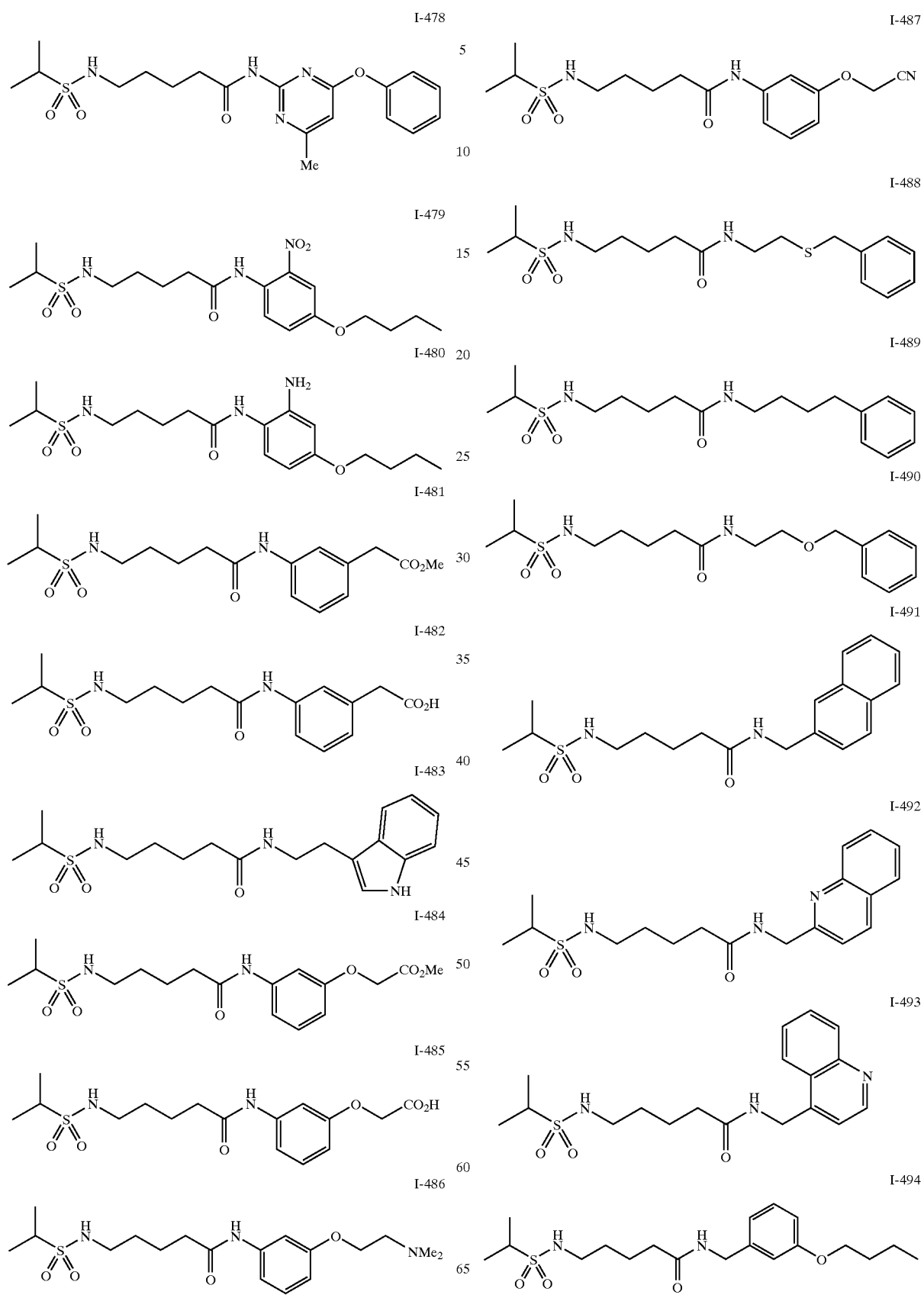

I-495
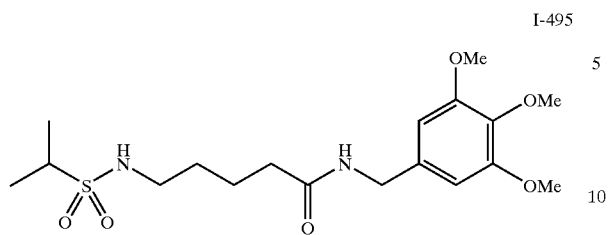
I-503
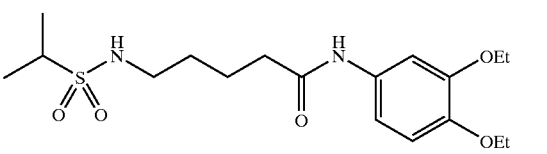
I-496
I-504
I-497
I-505
I-498
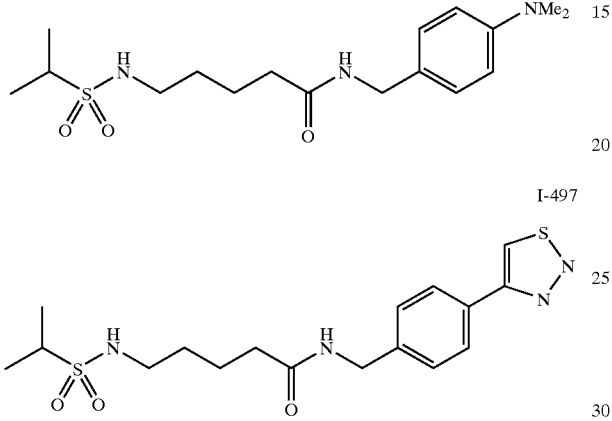
I-506
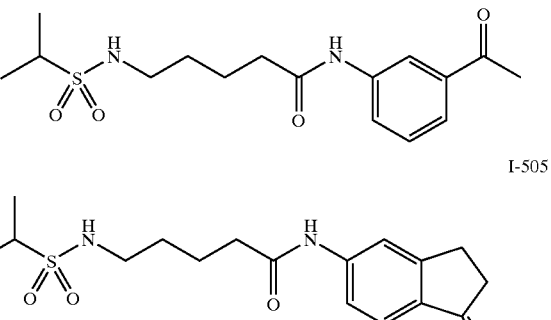
I-499
I-507
I-500
I-508
I-501
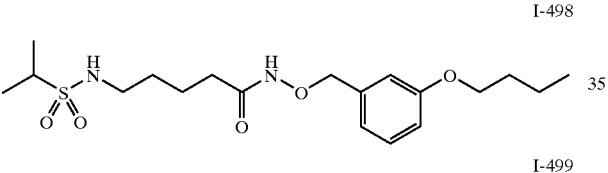
I-509
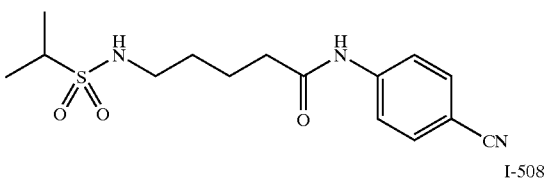
I-502
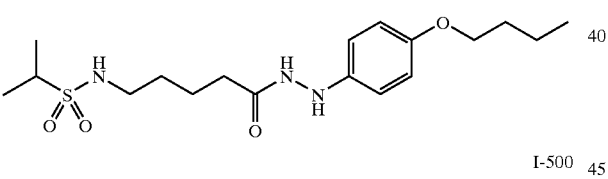
I-510
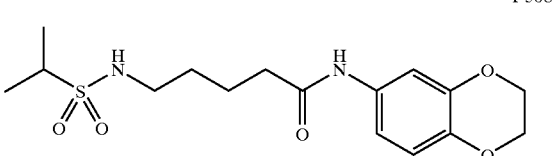
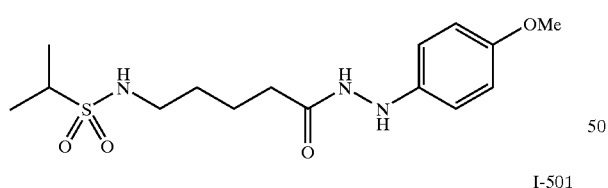
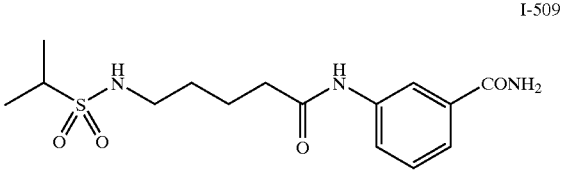
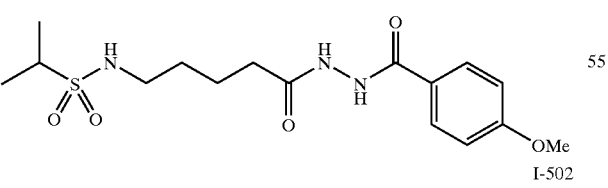
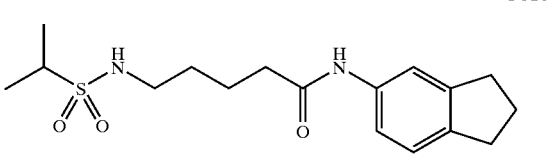
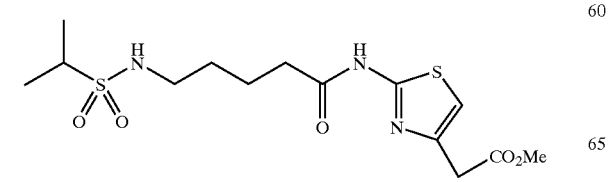
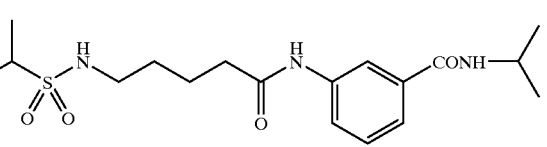

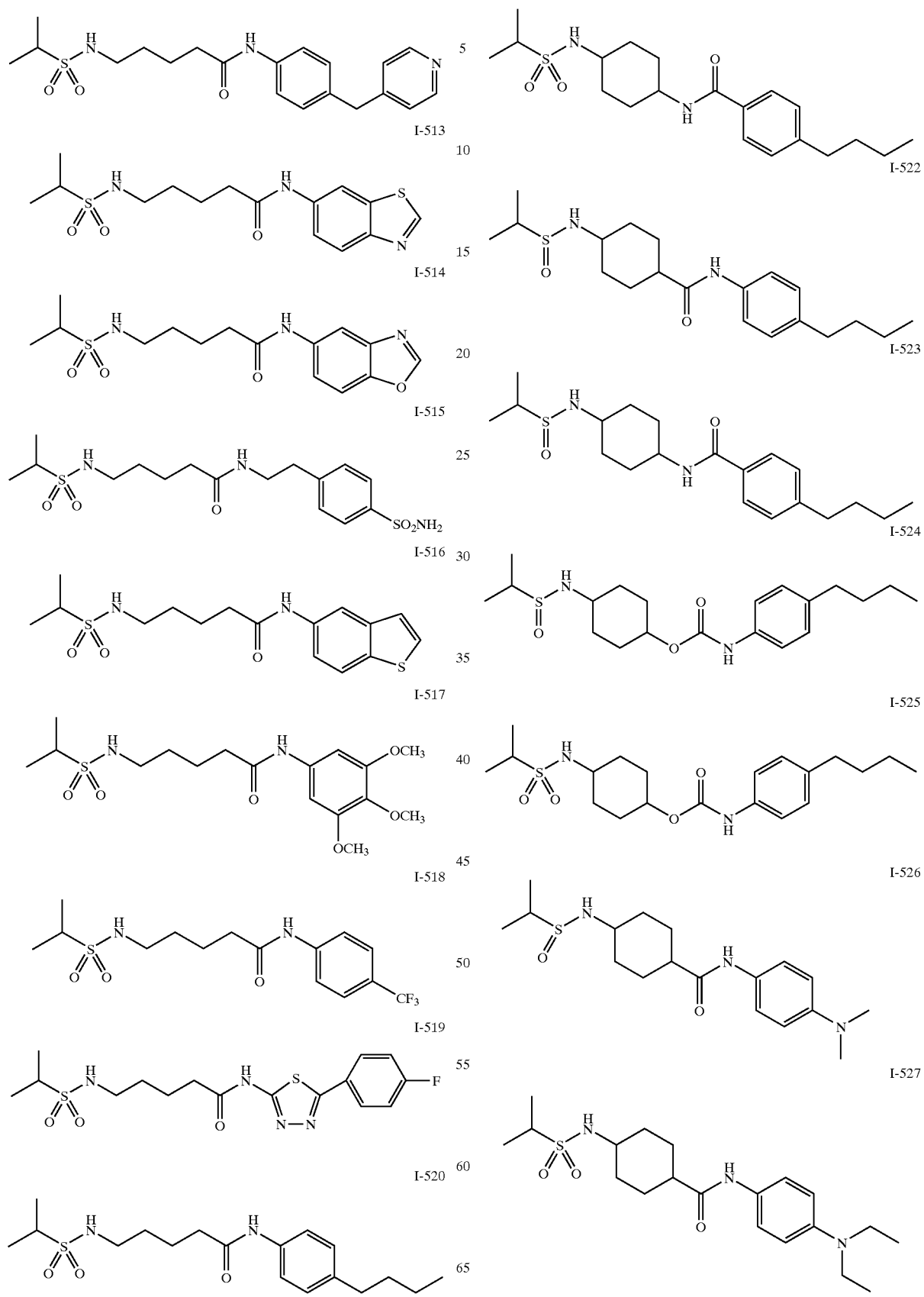

I-528
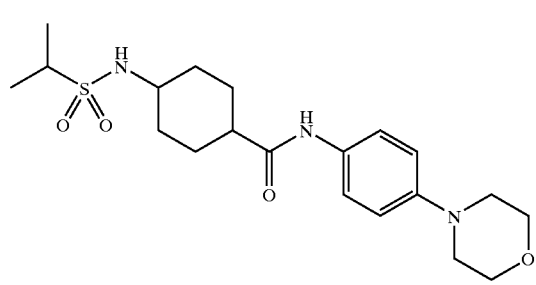
I-529
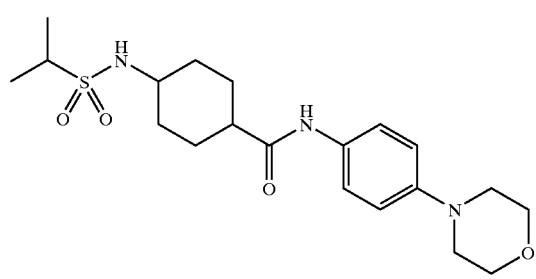
I-530
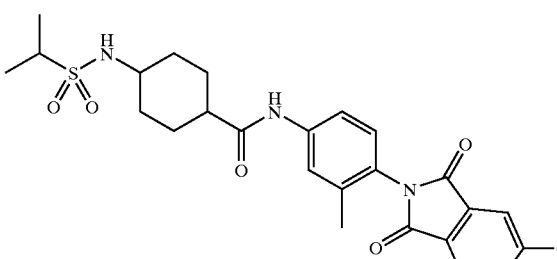
I-531
I-532
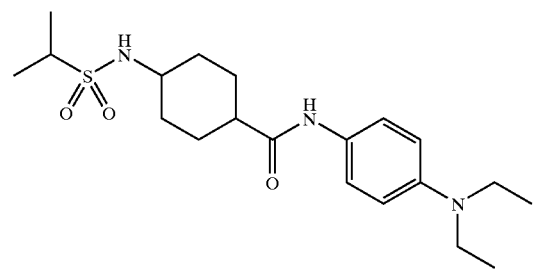
I-533
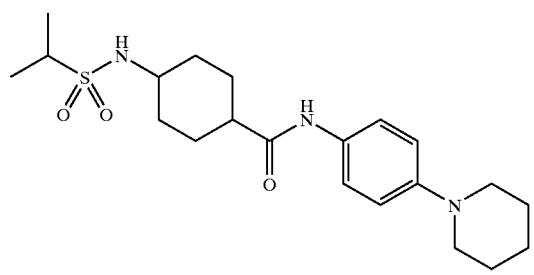
I-534
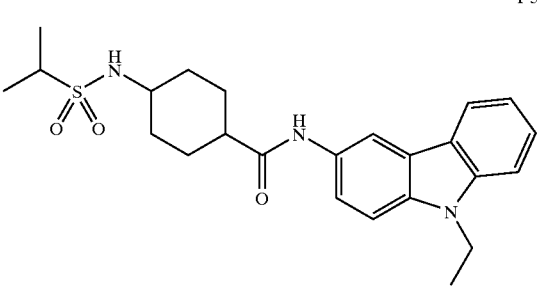
I-535
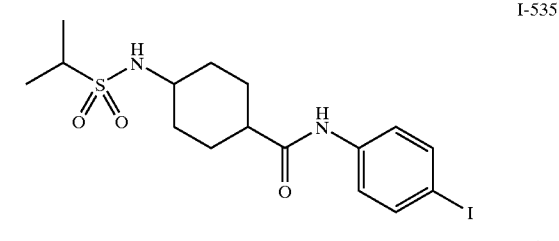
I-536
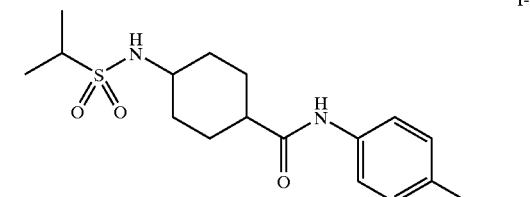
I-537
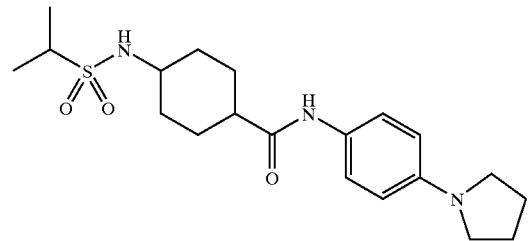
I-538
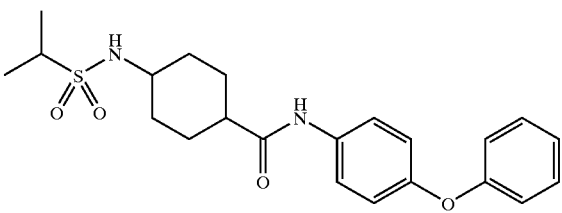

I-539
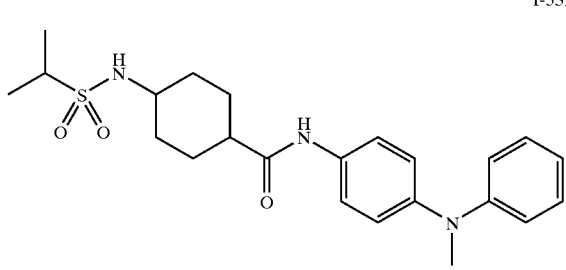
I-544
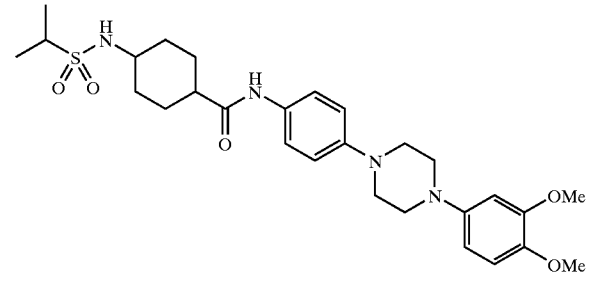
I-540
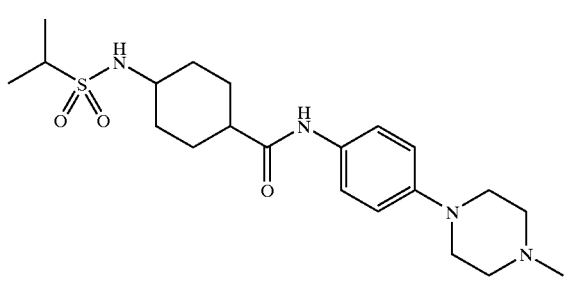
I-545
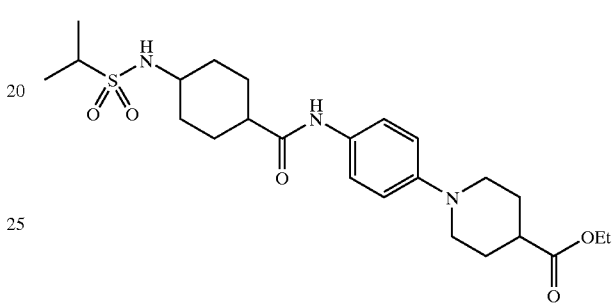
I-541
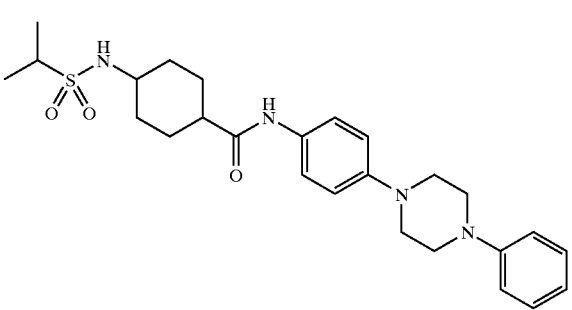
I-546
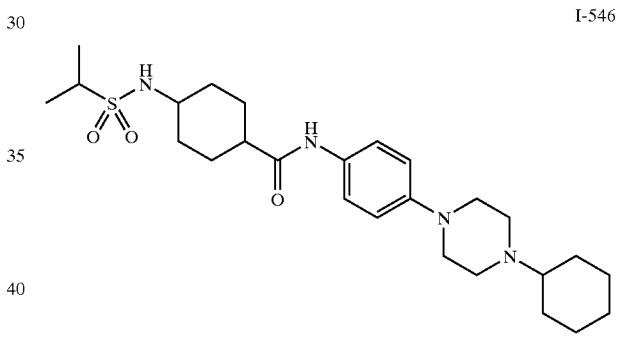
I-542
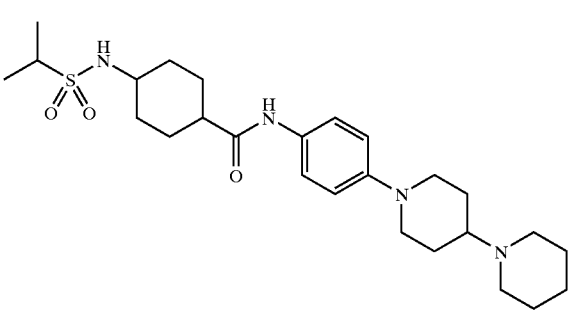
I-547
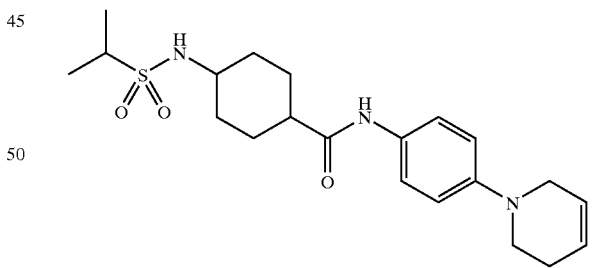
I-543
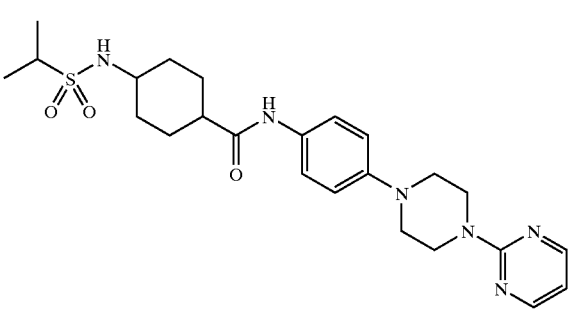
I-548
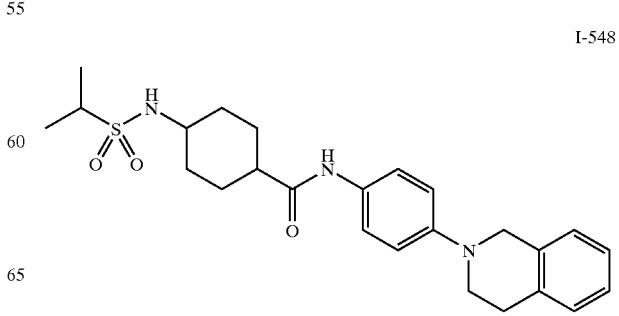

I-549
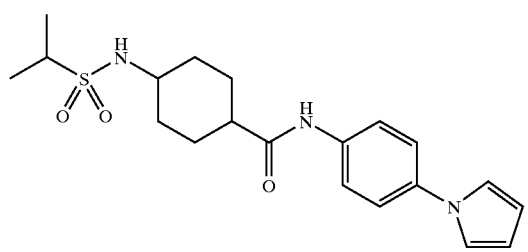
I-550
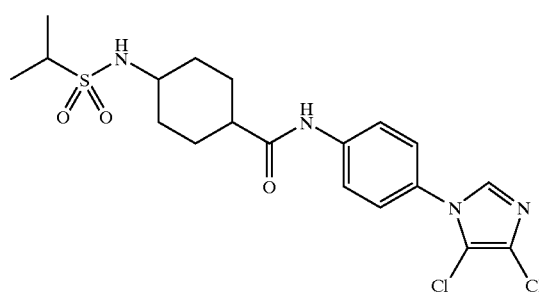
I-551
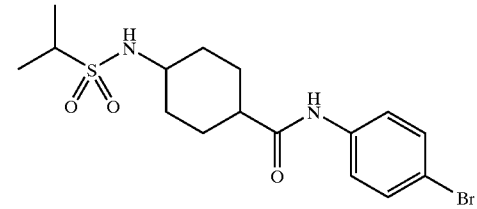
I-552
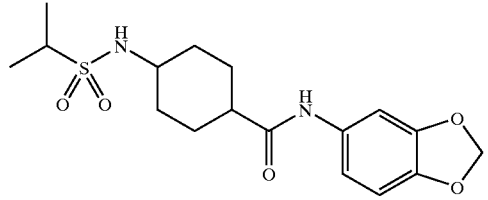
I-553
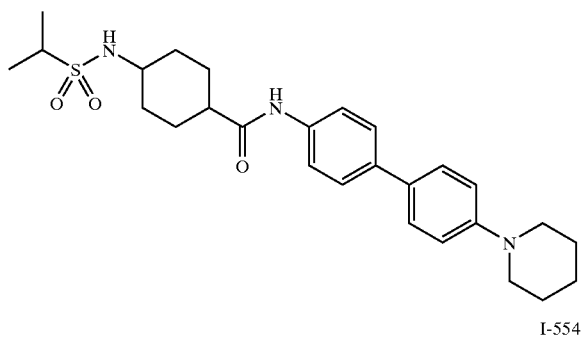
I-554
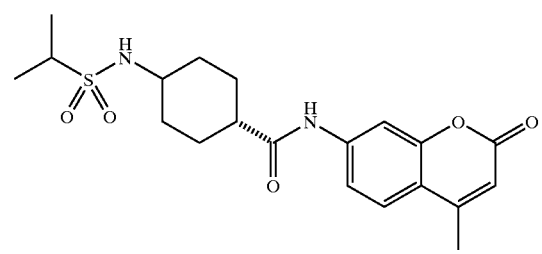
I-555
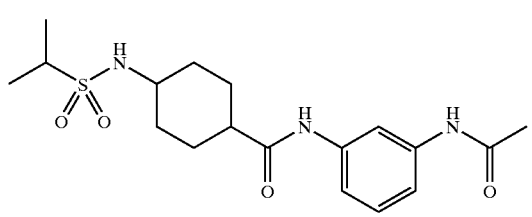
I-556
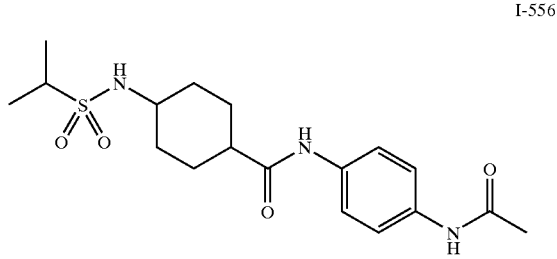
I-557
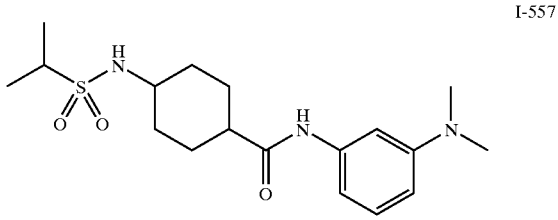
I-558
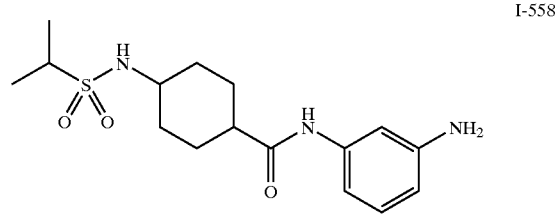
I-559
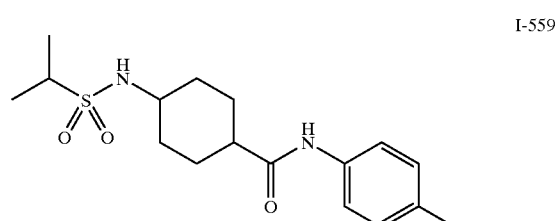
I-560
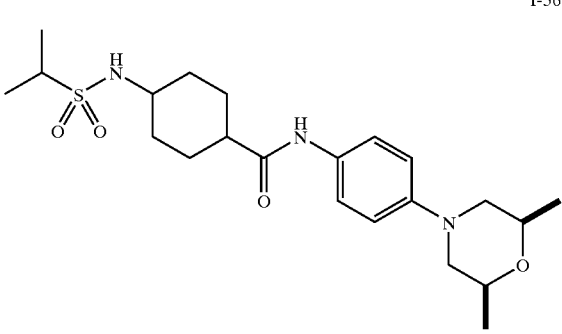

123
-continued
I-561
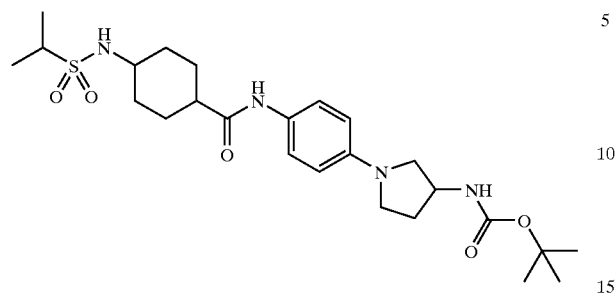
I-562
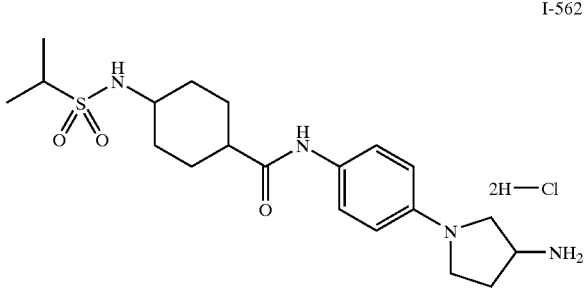
2H—Cl
I-563
I-564
I-565
124
-continued
I-566
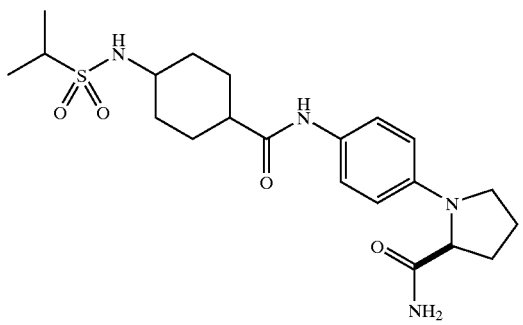
I-567
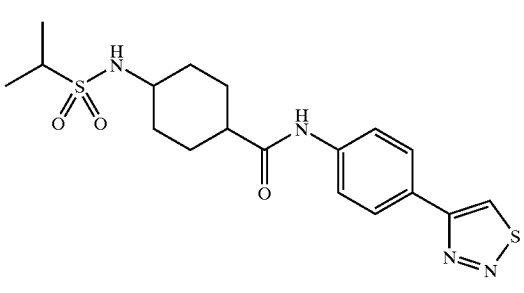
I-568
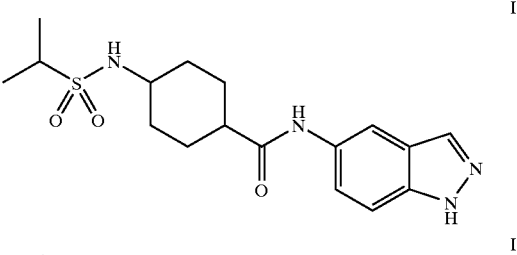
I-569
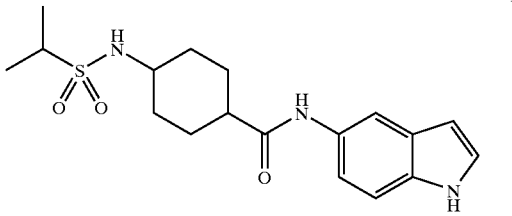
I-570
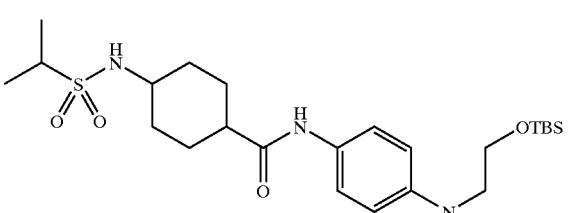
I-571
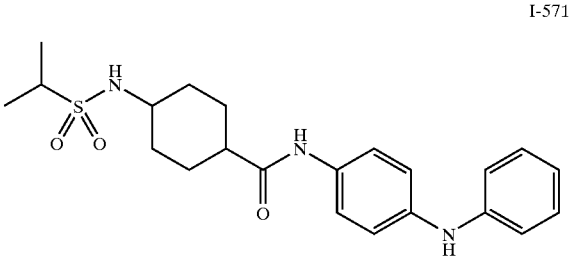

-continued
I-572
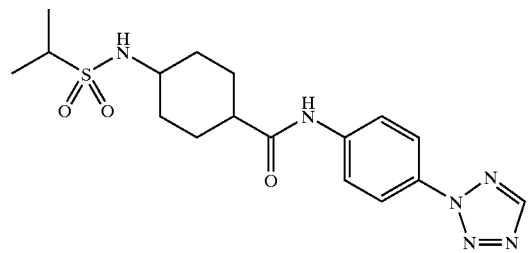
I-573
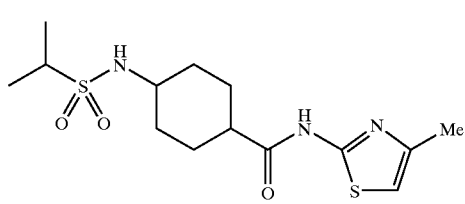
I-574
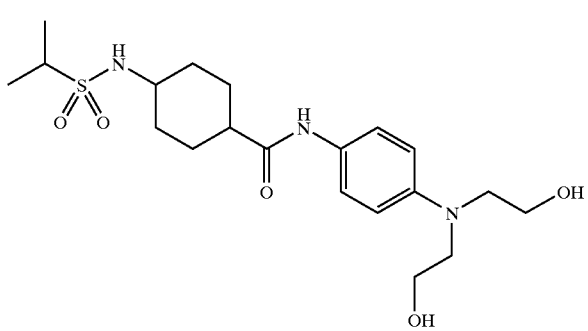
I-575
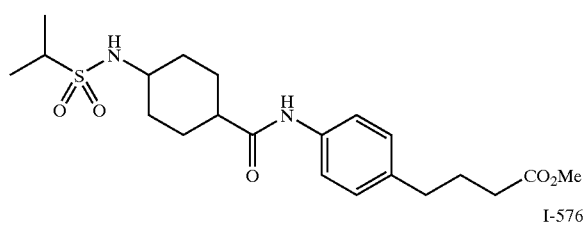
I-576
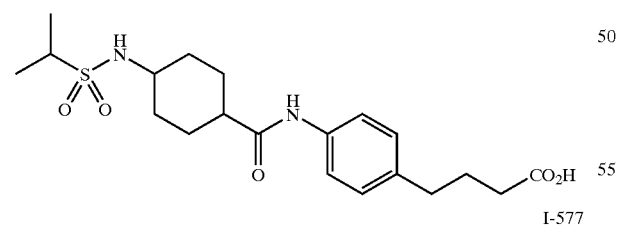
I-577
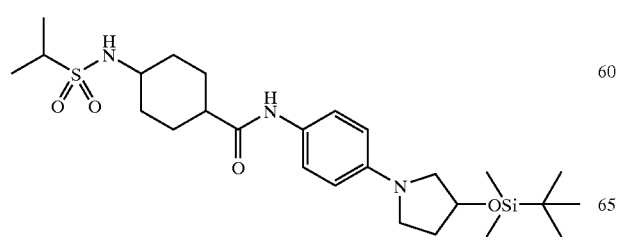
-continued
I-578
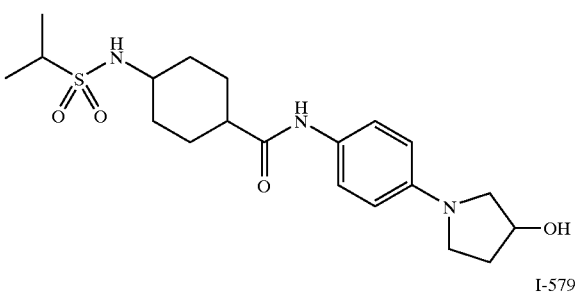
I-579
I-580
I-581
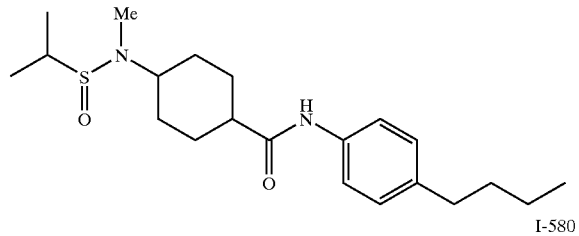
I-582
I-583
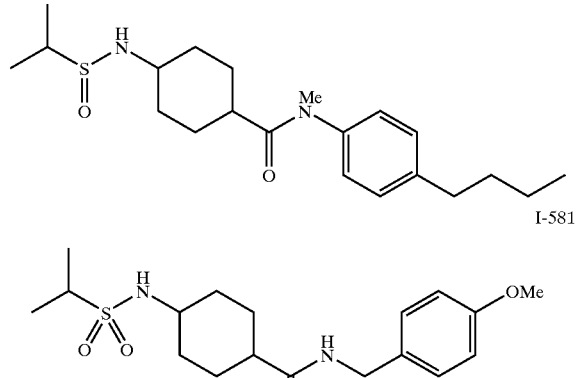
I-584
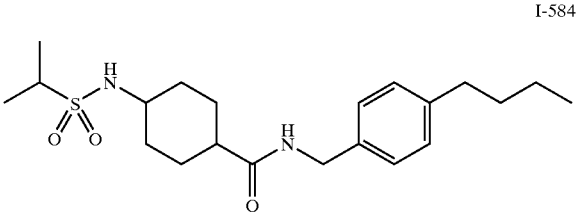

I-585
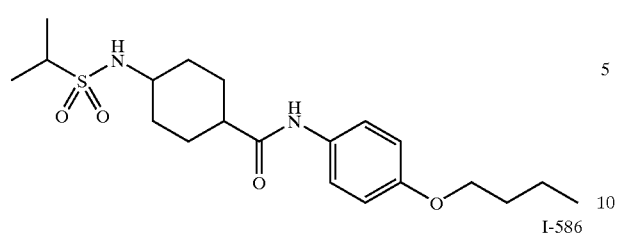
I-586
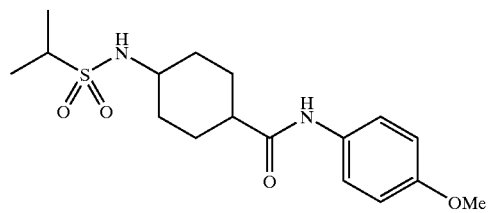
I-587
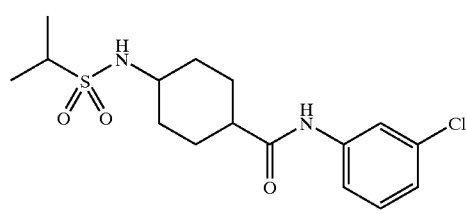
I-589
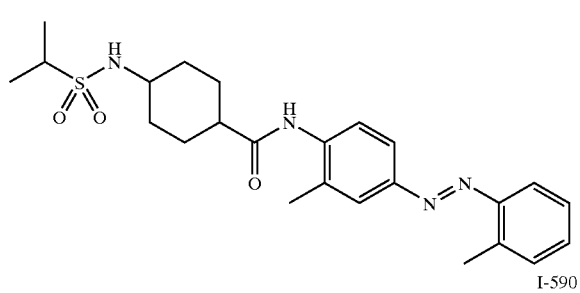
I-590
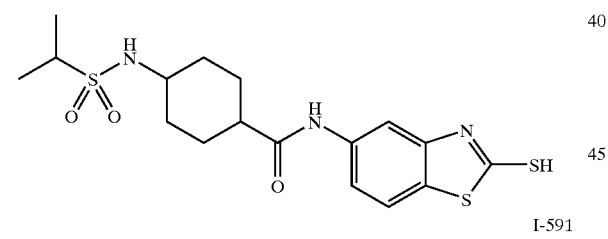
I-591
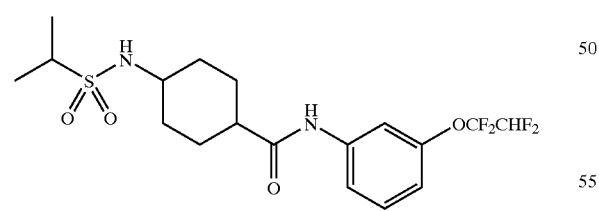
I-592
I-593
I-594
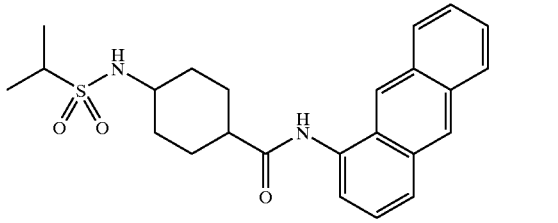
I-595
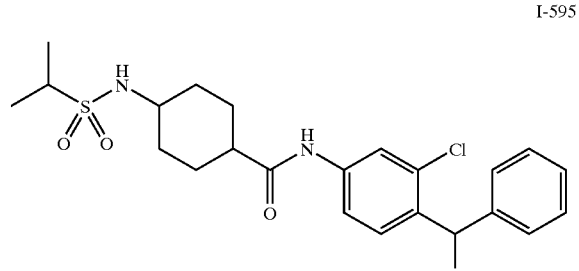
I-596
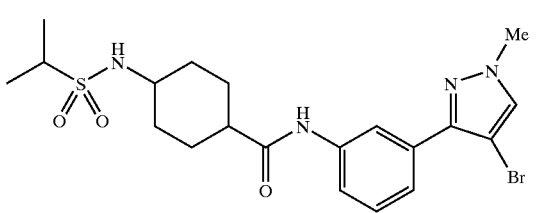
I-597
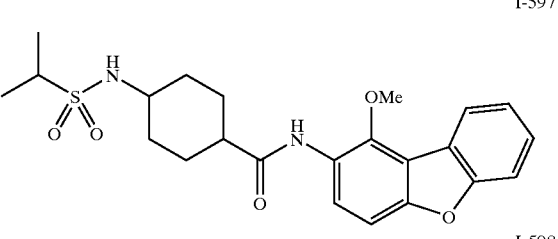
I-598
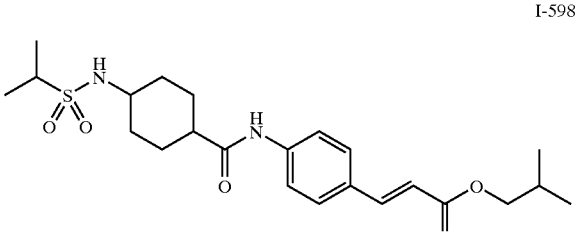
I-599
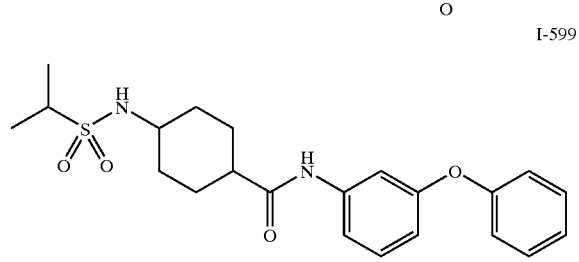

I-600
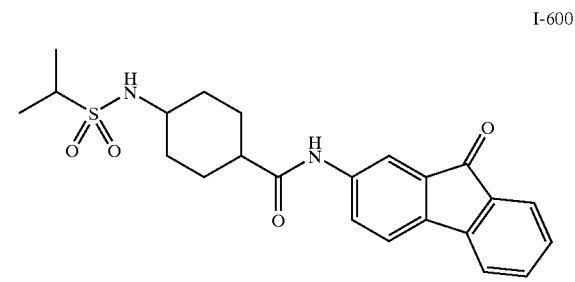
I-601
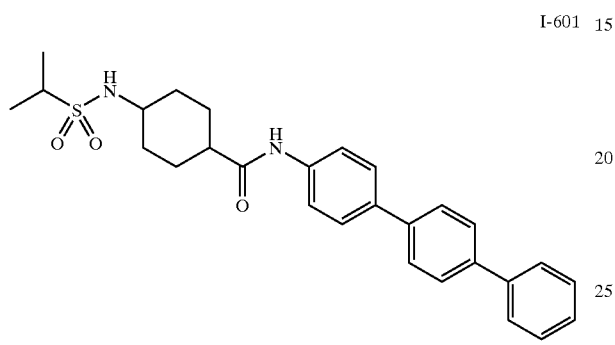
I-602
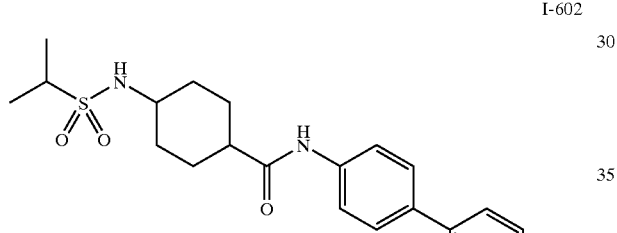
I-603
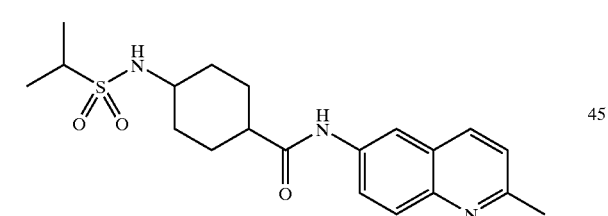
I-604
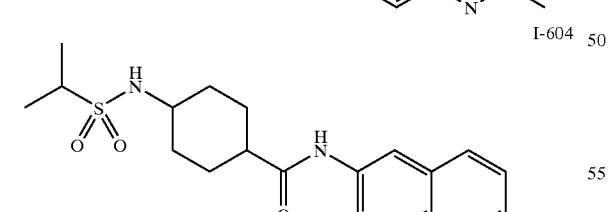
I-605
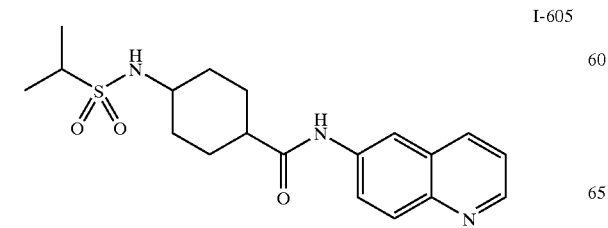
I-606
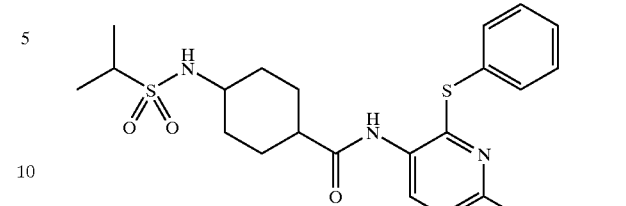
I-607
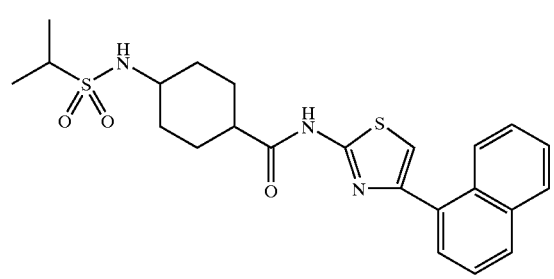
I-608
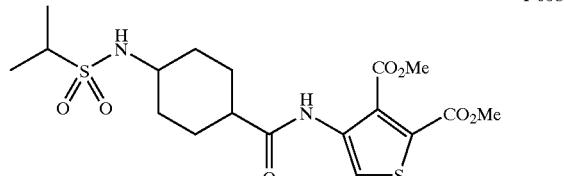
I-609
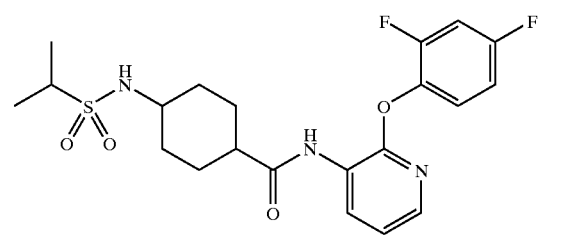
I-610
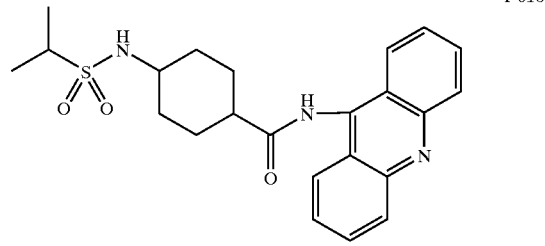
I-611
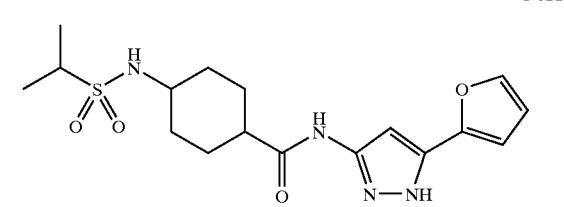

-continued
I-612
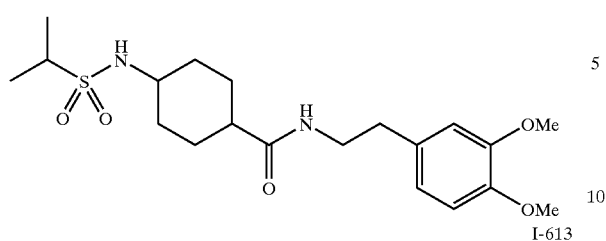
I-613
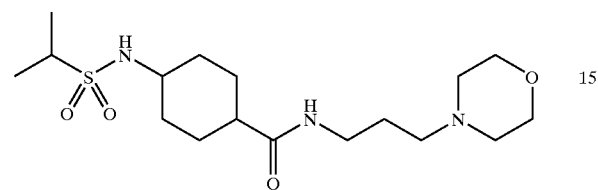
614
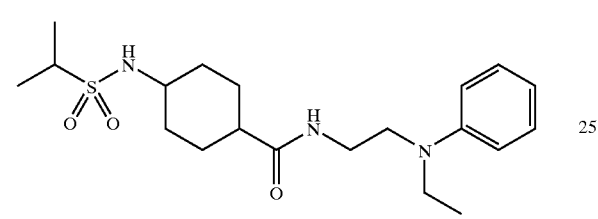
I-615
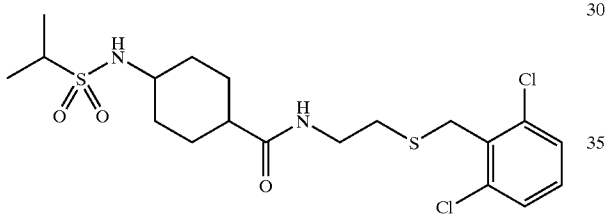
I-616
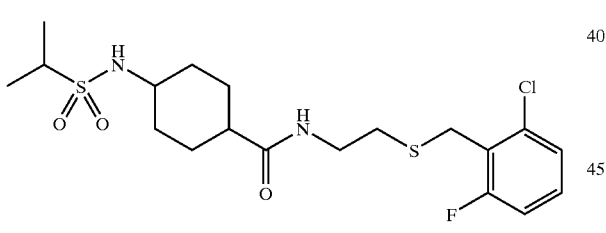
I-617
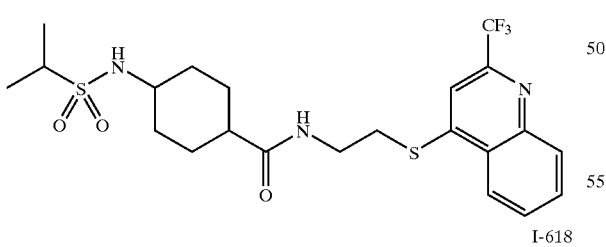
I-618
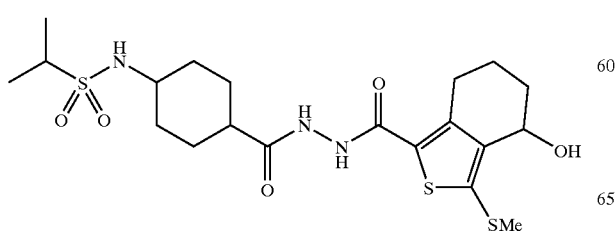
-continued
I-619
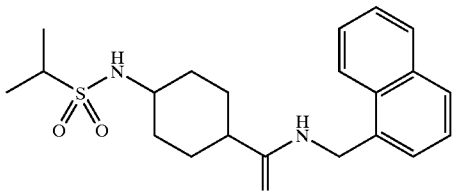
I-620
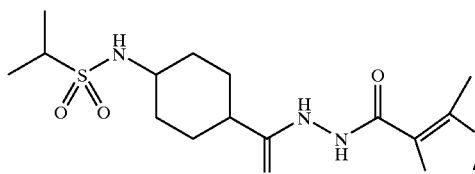
I-621
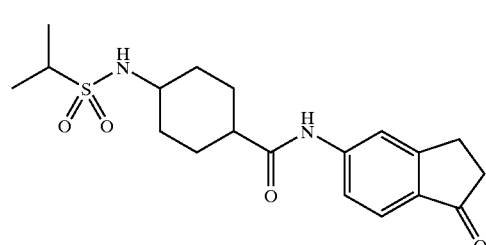
I-622
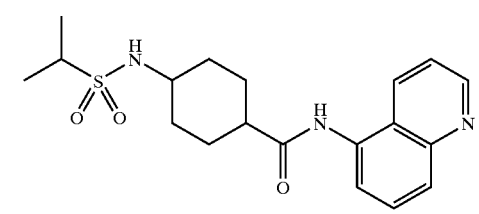
I-623
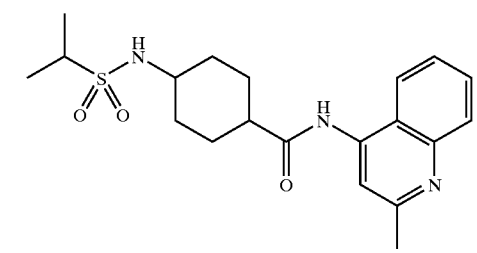
I-624
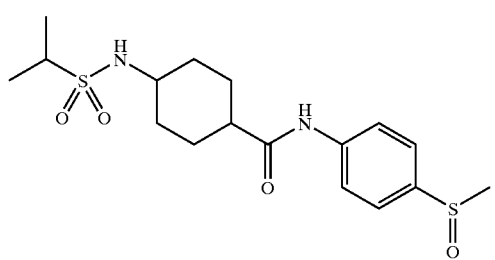
I-625

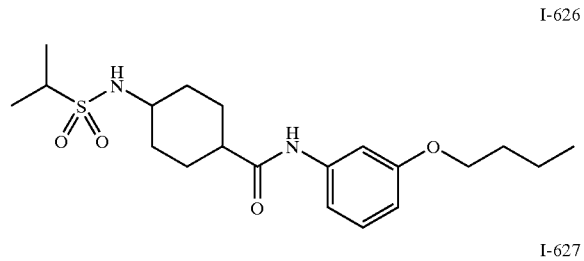
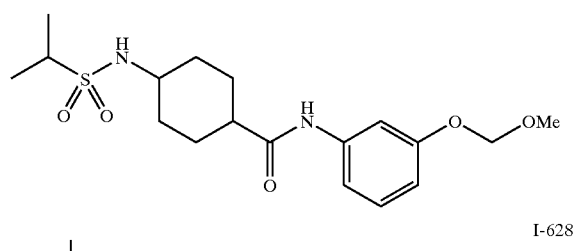
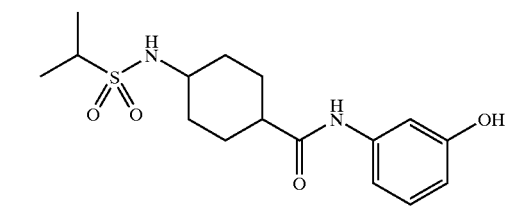
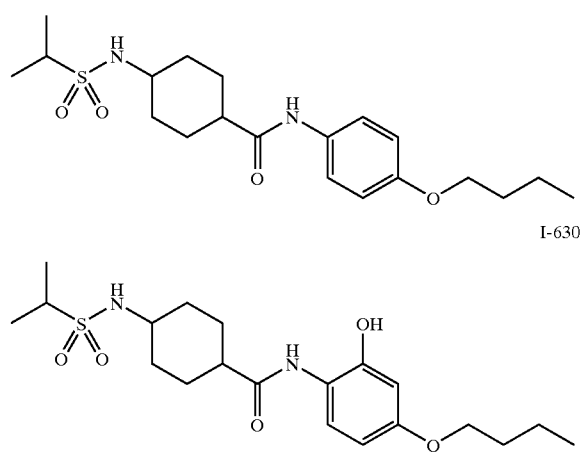
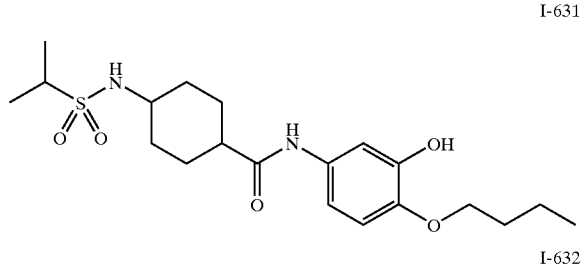
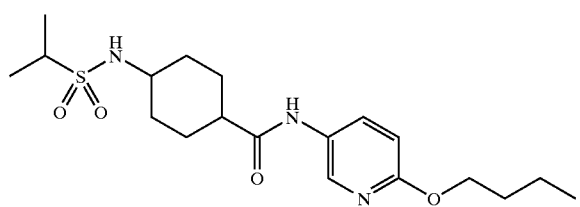
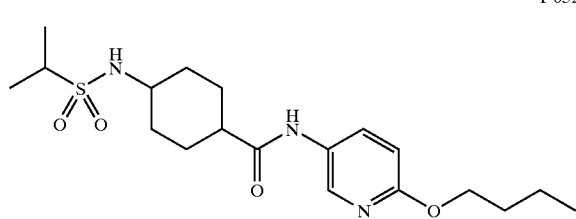

I-639
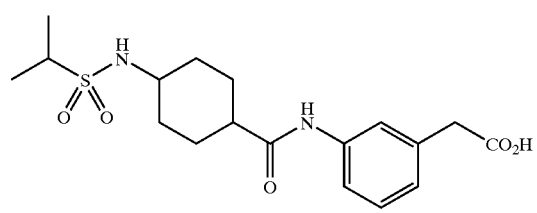
I-640
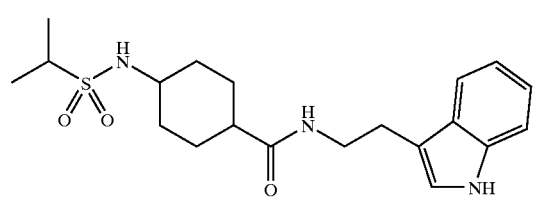
I-641
I-642
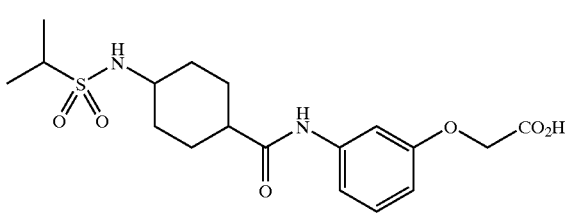
I-643
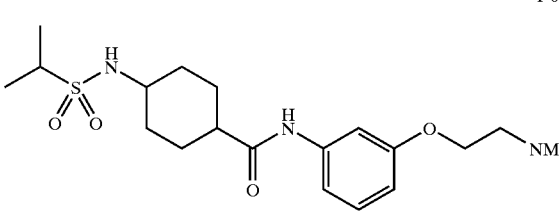
I-644
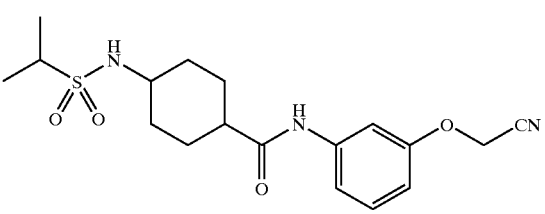
I-645
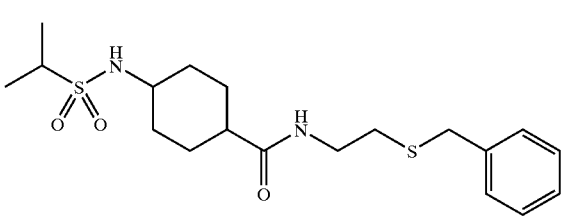
I-646
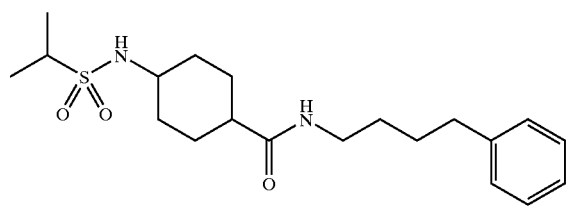
I-647
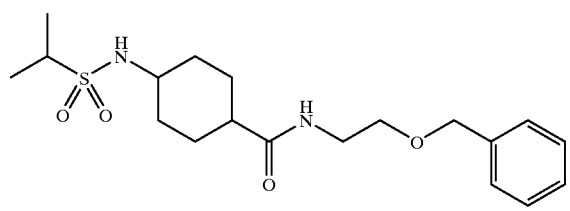
I-648
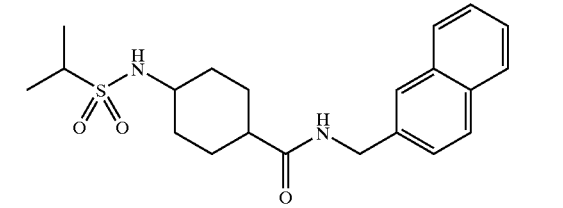
I-649
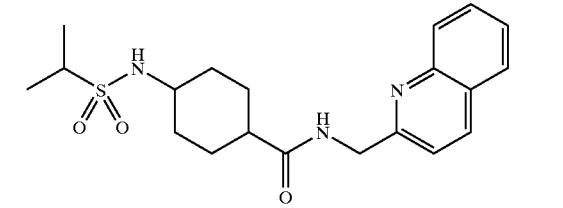
I-650
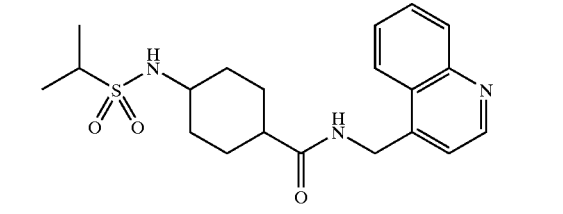
I-651
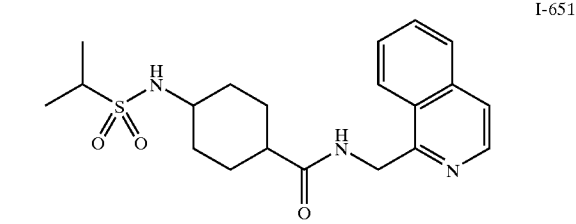
I-652
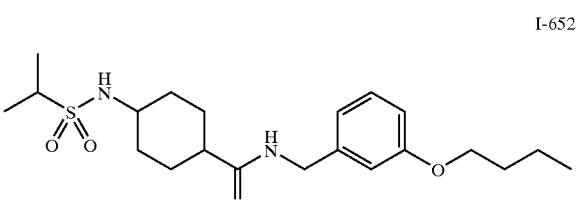

I-653
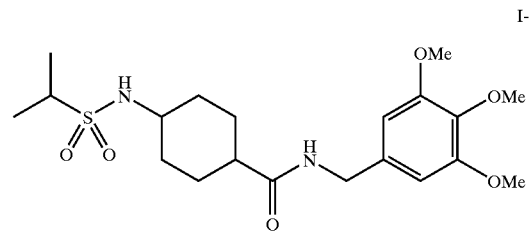
I-654
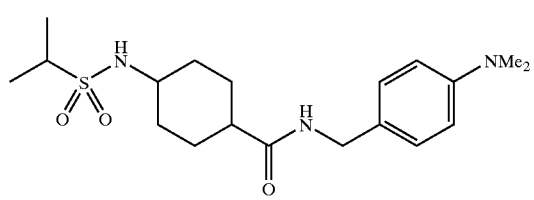
I-655
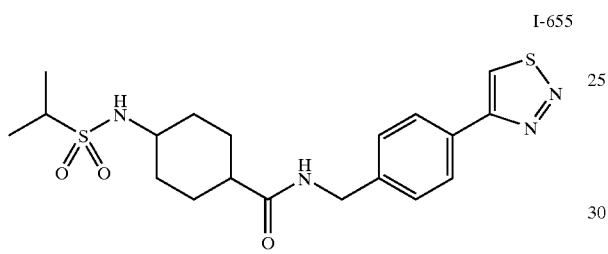
I-656
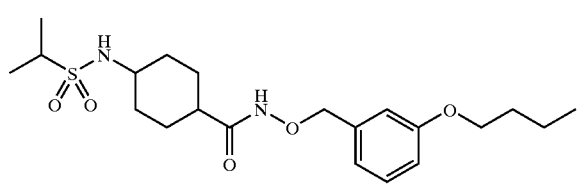
I-657
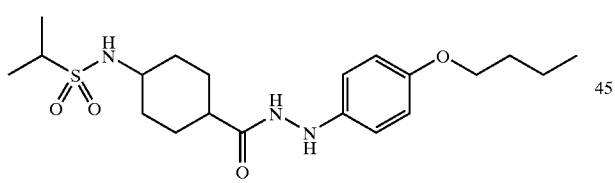
I-658
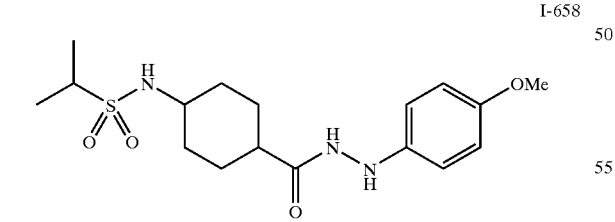
I-659
I-660
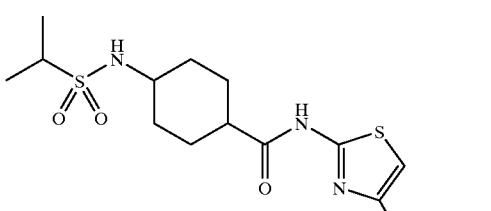
I-661
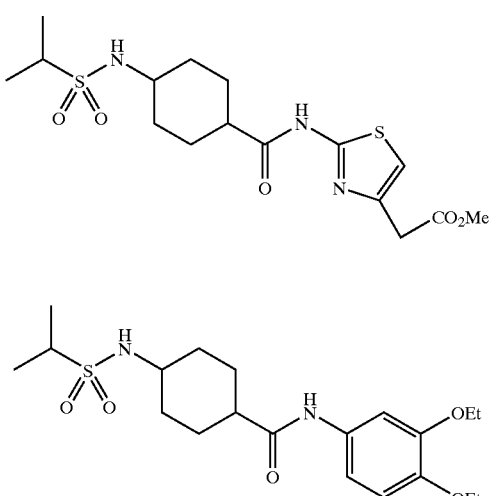
I-662
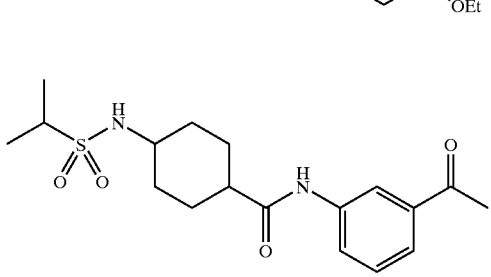
I-663
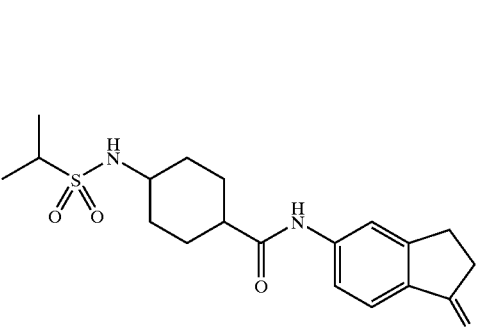
I-664
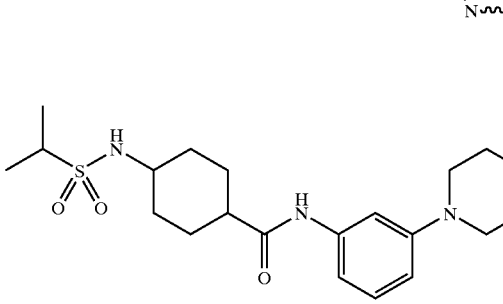
I-665
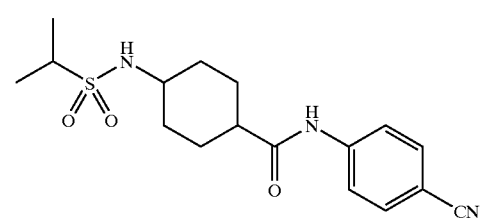

-continued
I-666
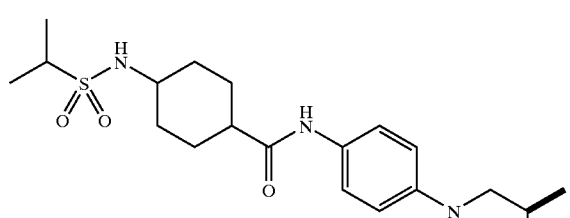
I-667
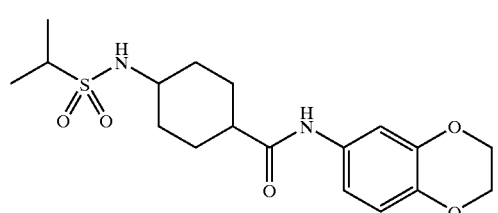
I-668
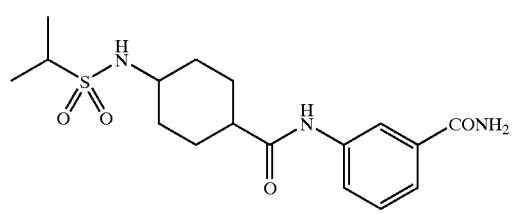
I-669
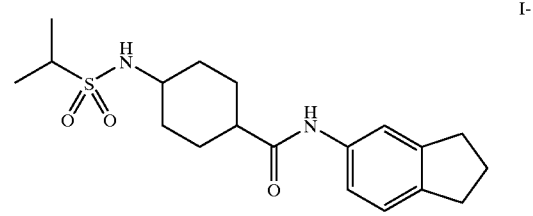
I-670
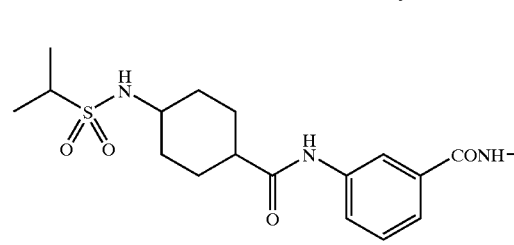
I-671
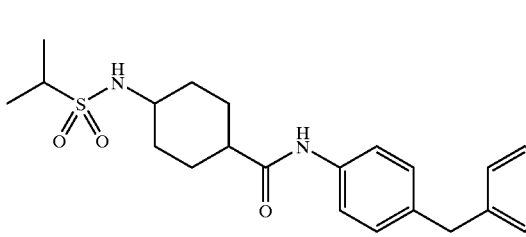
I-672
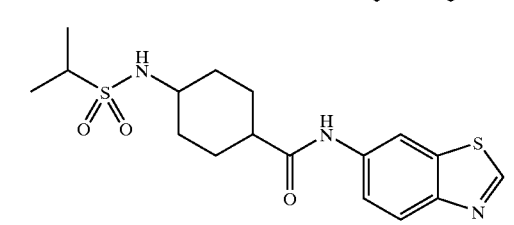
-continued
I-673
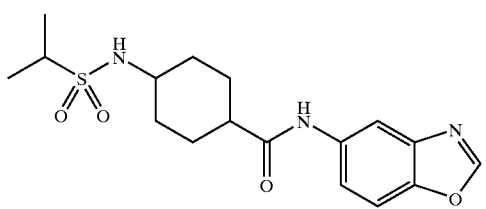
I-674
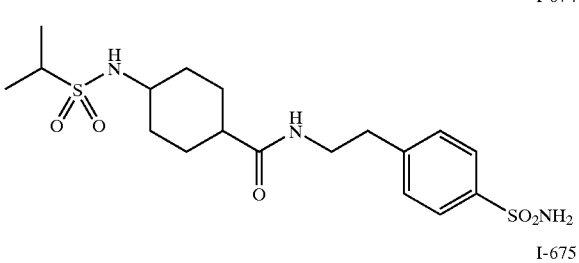
I-675
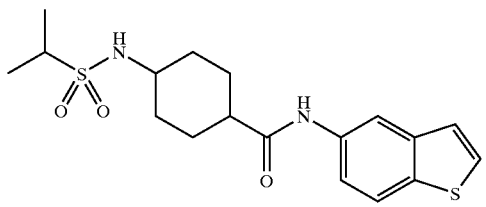
I-676
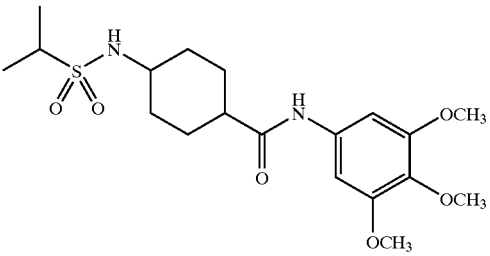
I-677
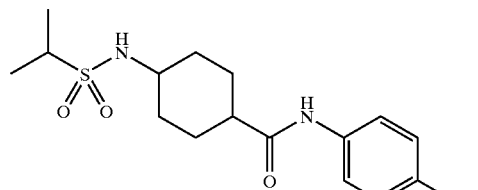
I-678
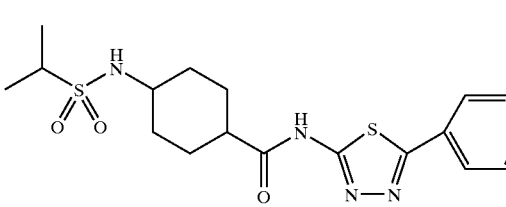
I-679
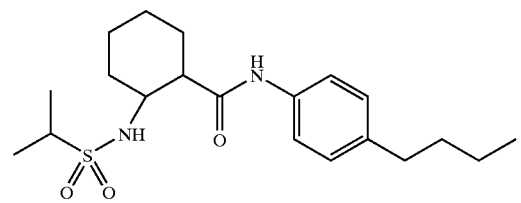

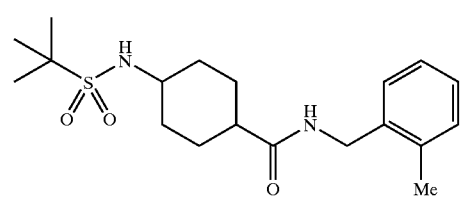
I-680
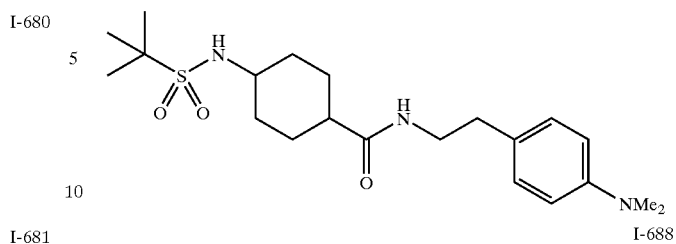
I-687
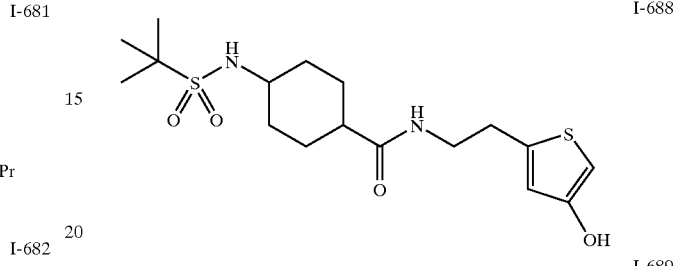
I-681
I-688
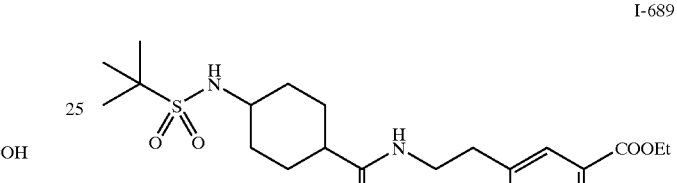
I-682
I-689
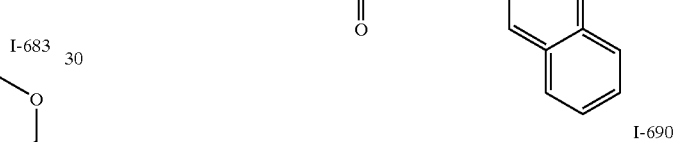
I-683
I-690
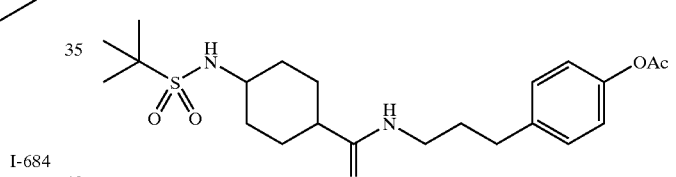
I-684
I-691
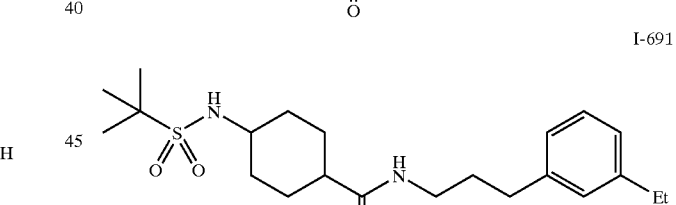
I-685
I-692
I-686
I-693

-continued
I-694
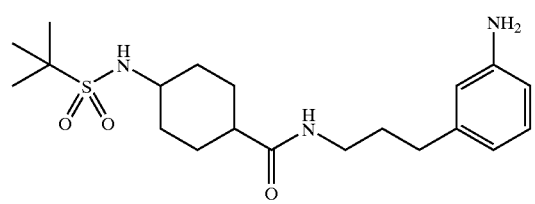
I-695
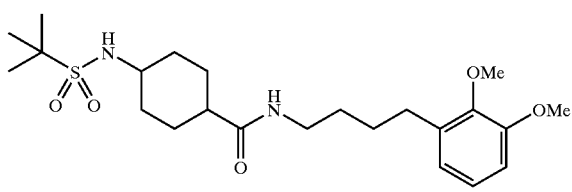
I-696
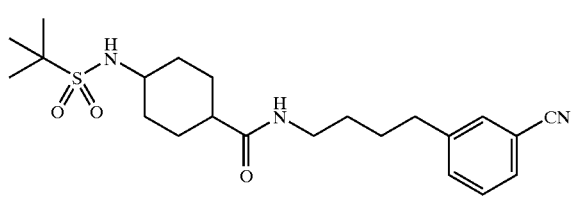
I-697
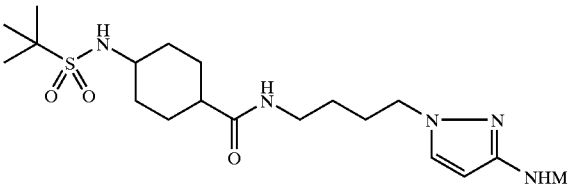
I-698
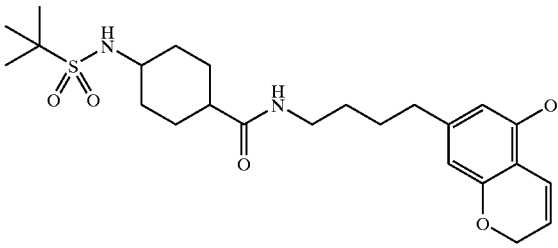
I-699
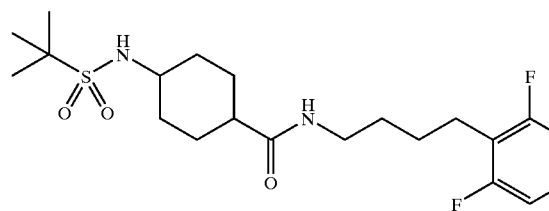
I-700
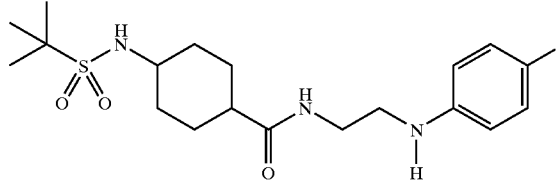
-continued
I-701
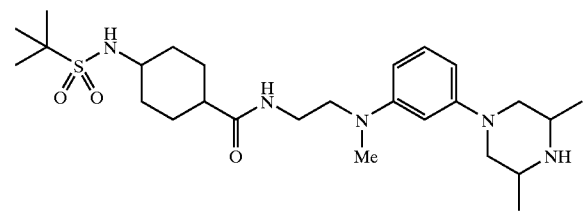
I-702
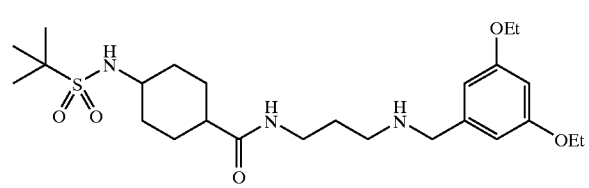
I-703
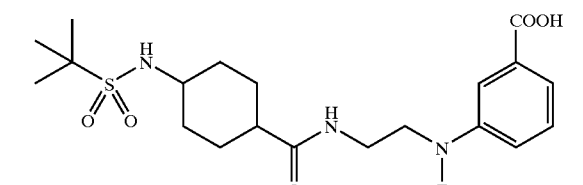
I-704
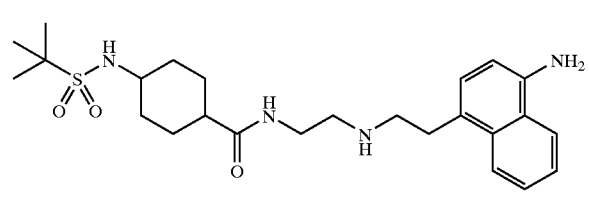
I-705
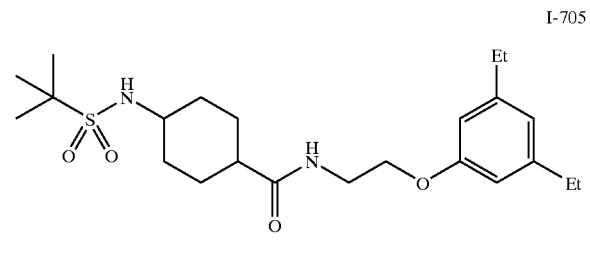
I-706
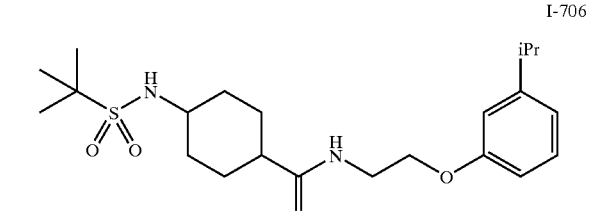
I-707
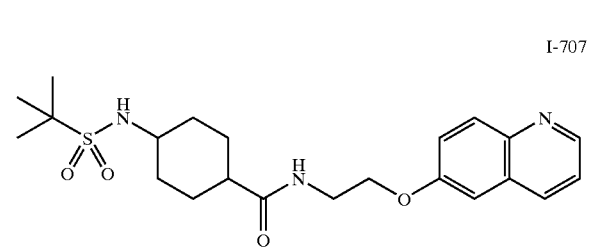

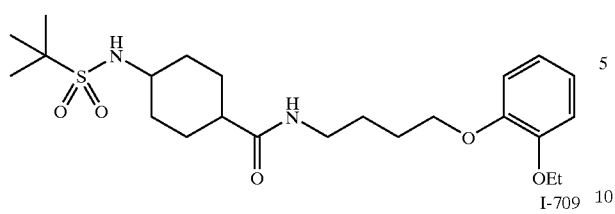
I-708
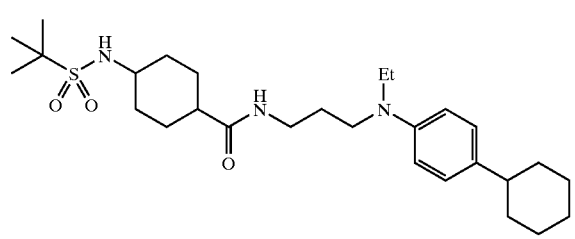
I-716
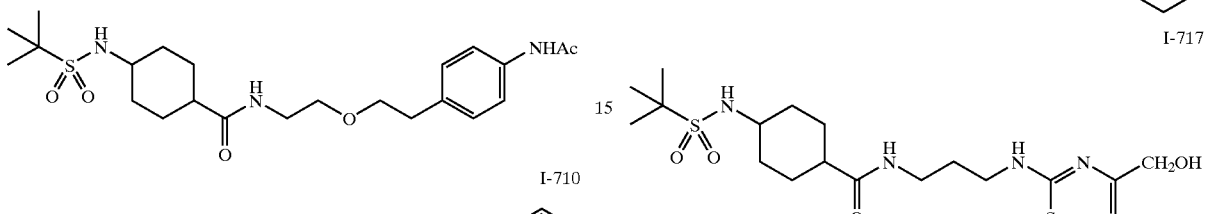
I-709
I-717

I-710
I-718
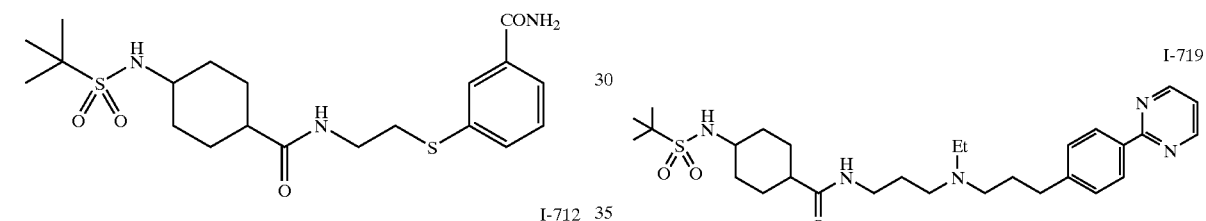
I-711
I-719
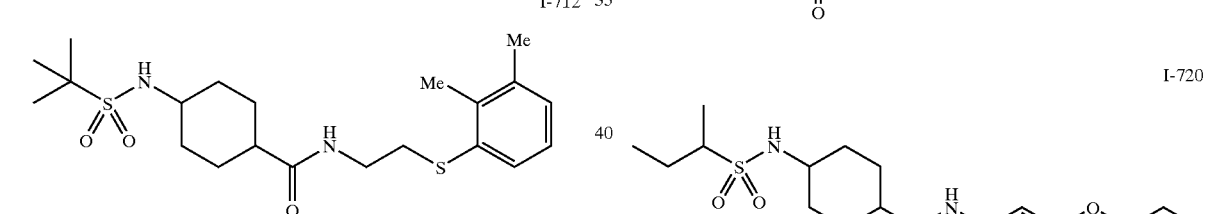
I-712
I-720
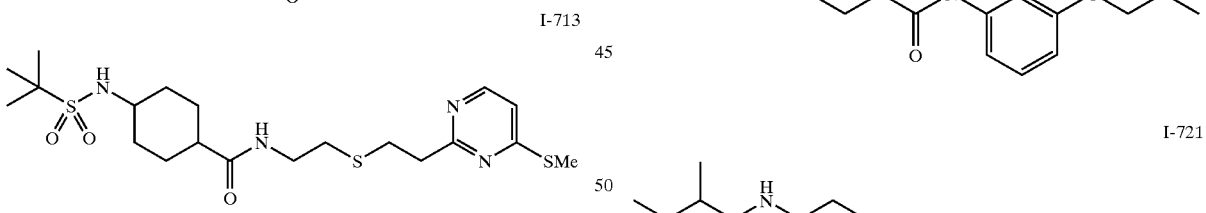
I-713
I-721

I-714
I-722
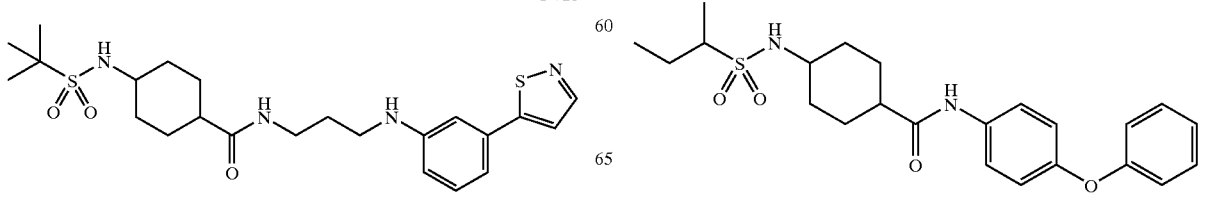
I-715

147
-continued
I-723
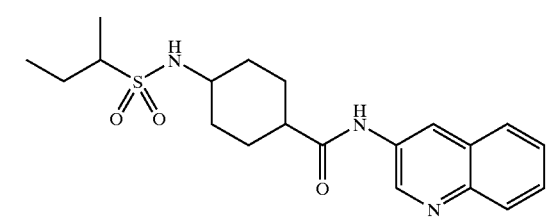
I-724
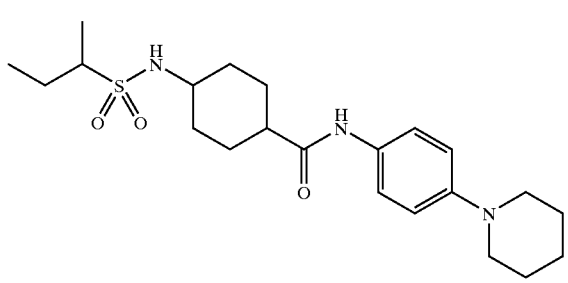
I-725
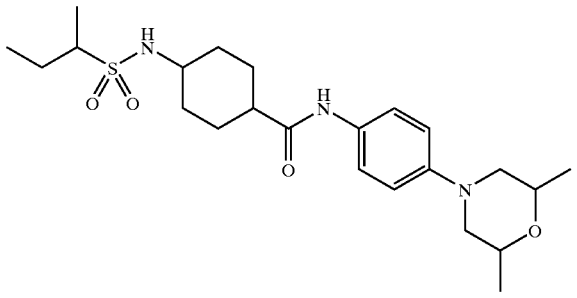
I-726
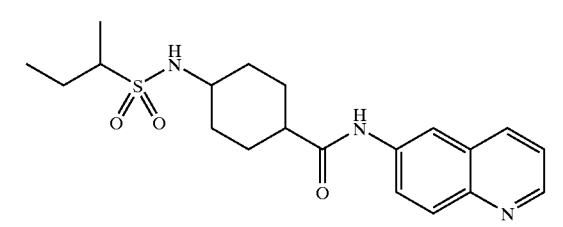
I-727
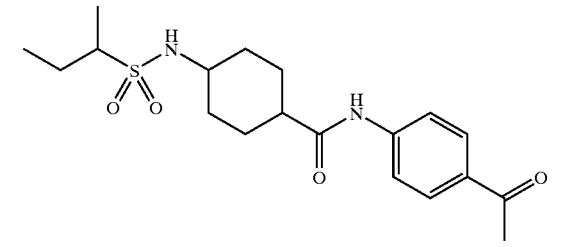
I-728
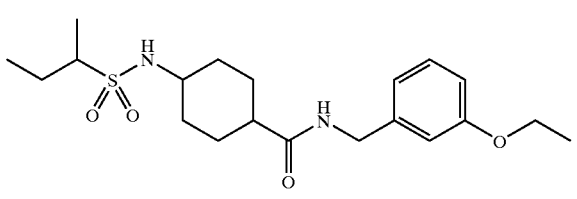
148
-continued
I-729
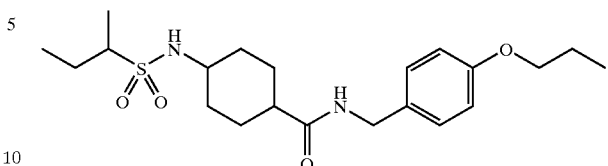
I-730
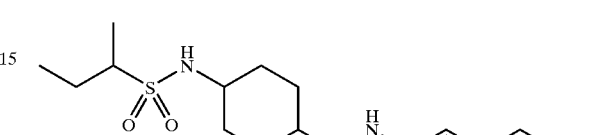
I-731
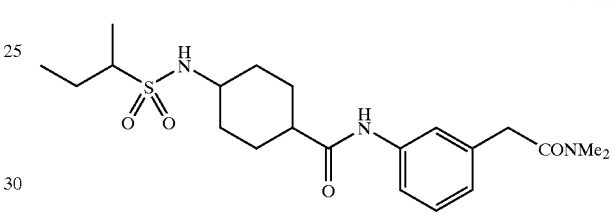
I-732
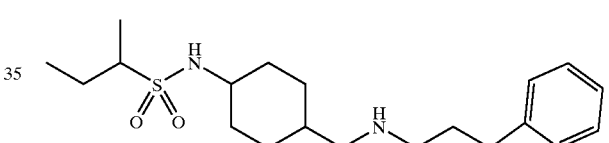
I-733
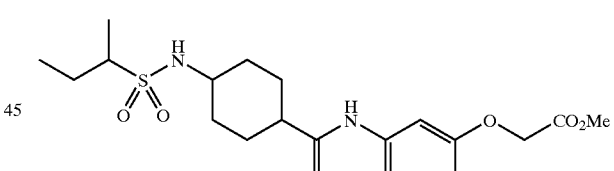
I-734

I-735

I-736 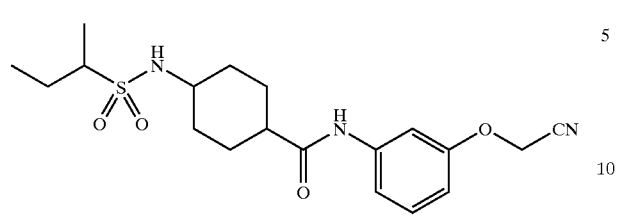
I-737 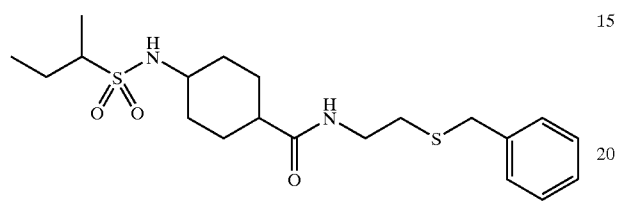
I-738 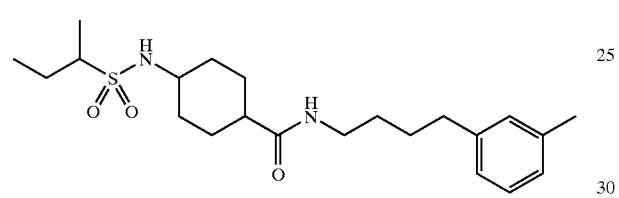
I-739 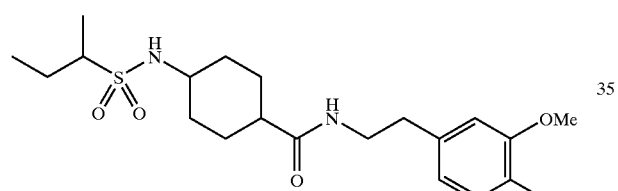
I-740
I-741 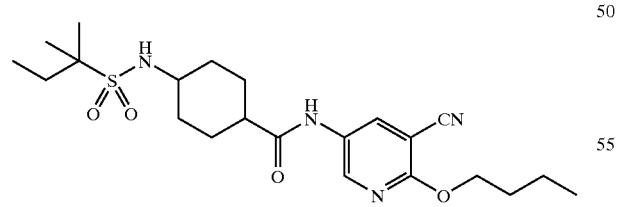
I-742 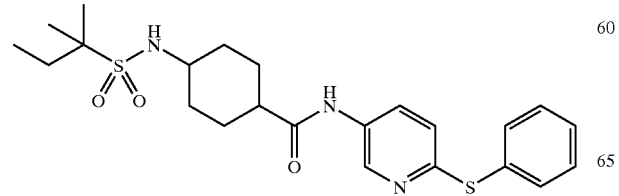
I-743 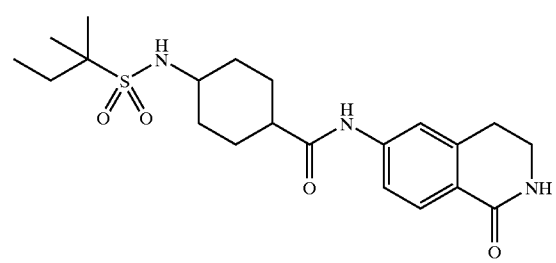
I-744
I-745 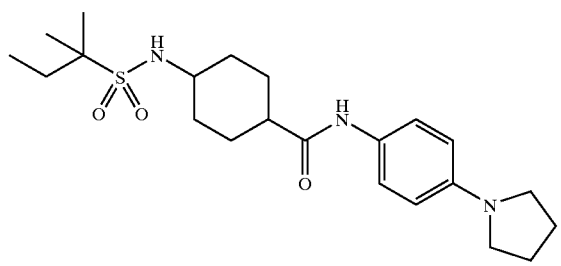
I-746 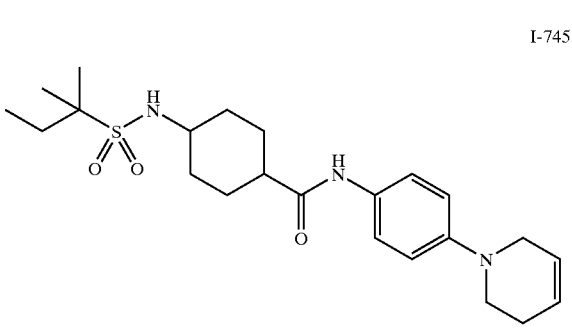
I-747 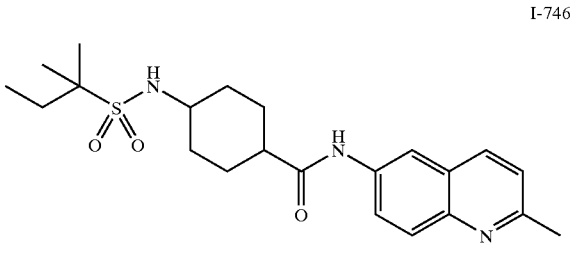
I-748 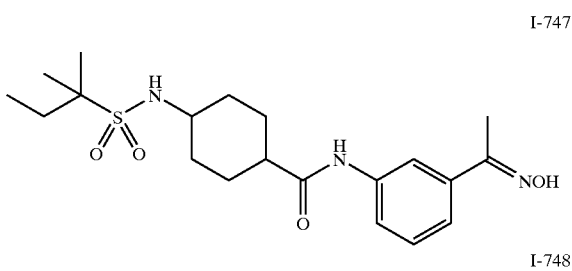

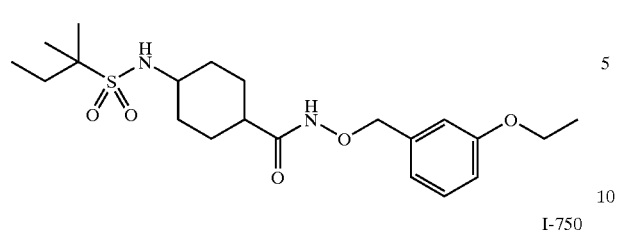
I-749
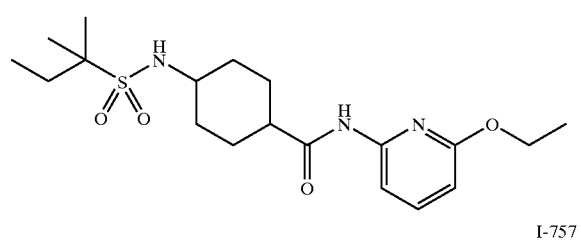
I-756
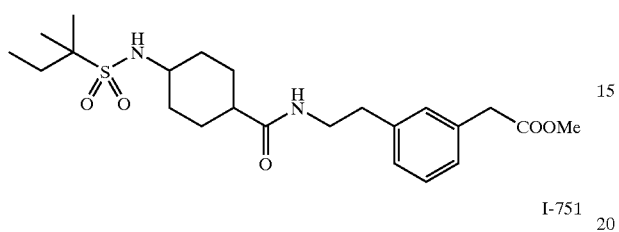
I-750
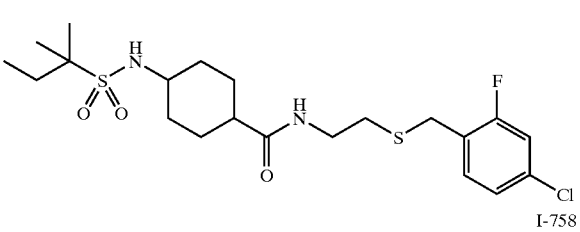
I-757
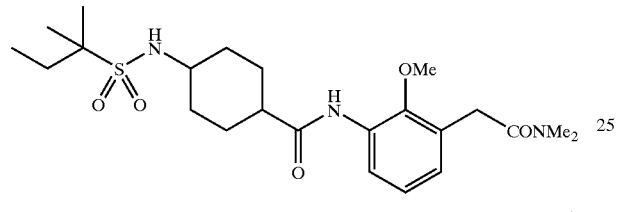
I-751
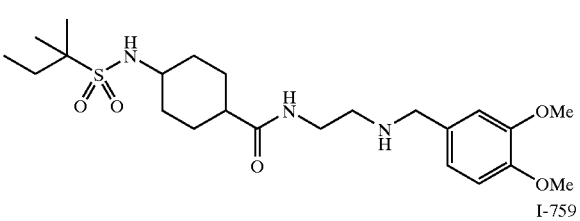
I-758
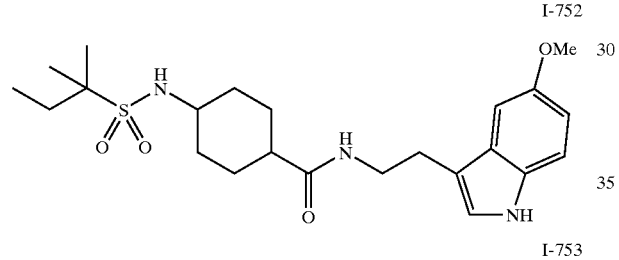
I-752
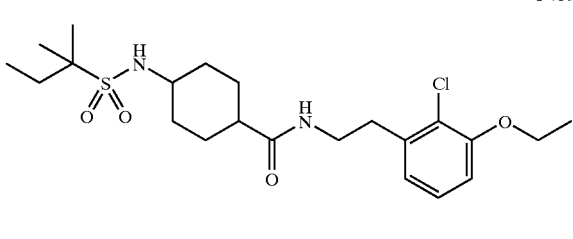
I-759
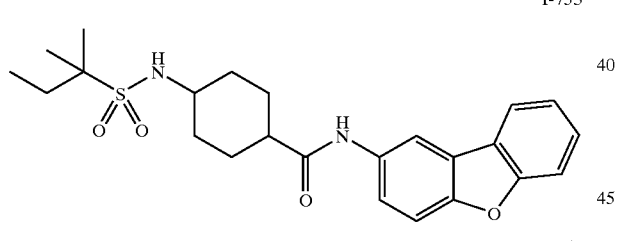
I-753
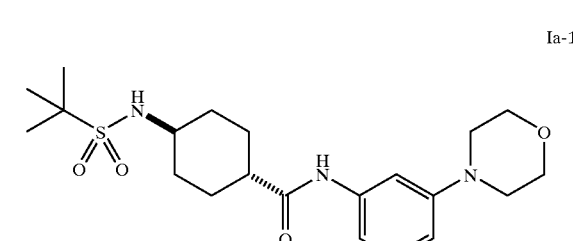
Ia-1
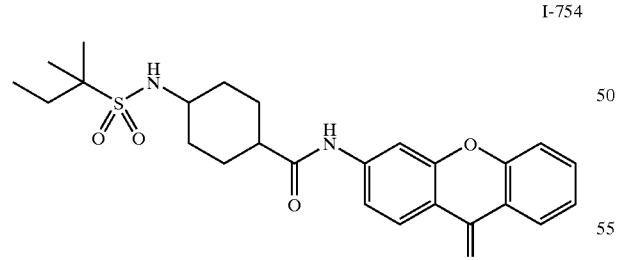
I-754
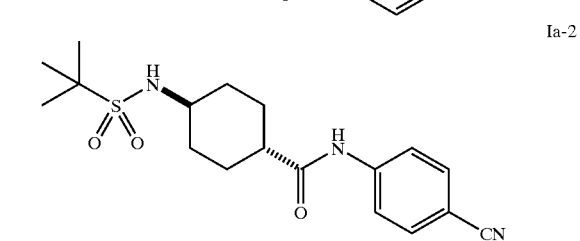
Ia-2
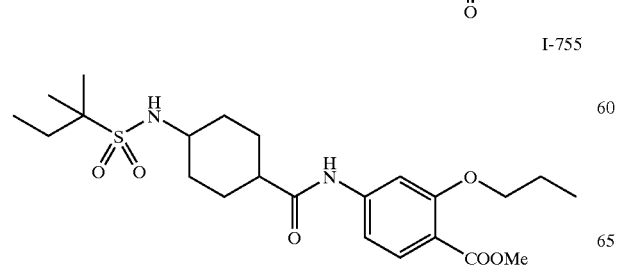
I-755
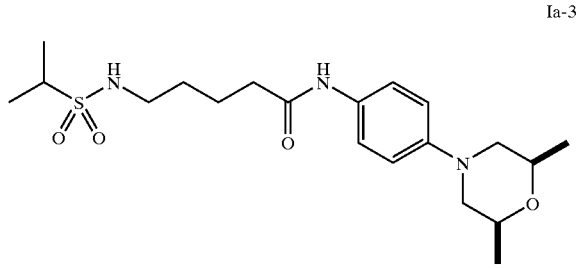
Ia-3

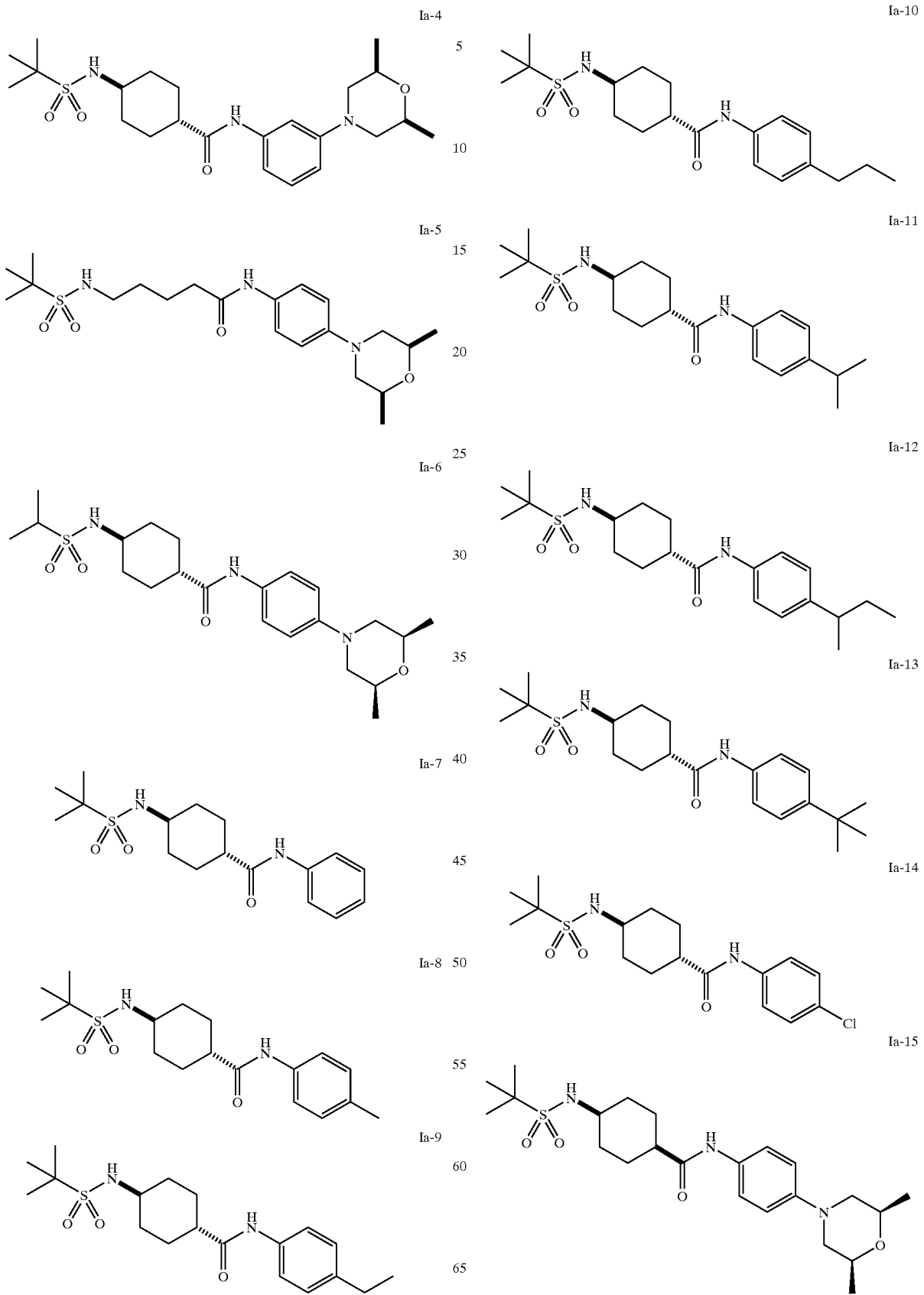

Ia-16
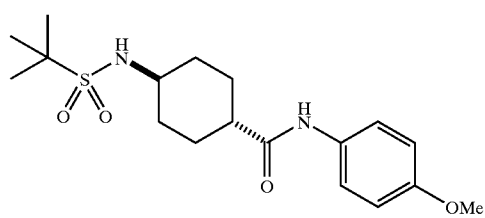
Ia-17
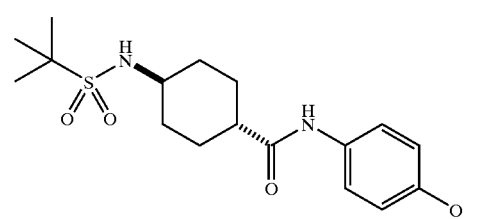
Ia-18
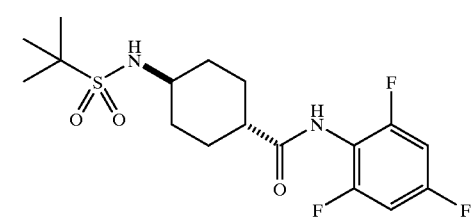
Ia-19
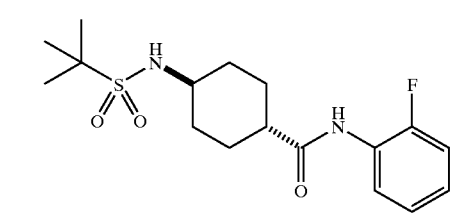
Ia-20
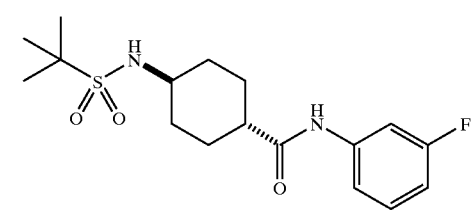
Ia-21
Ia-22
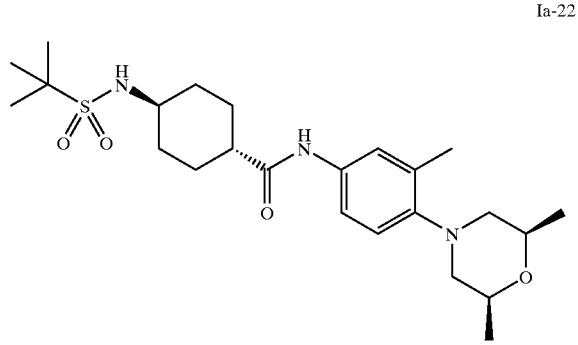
Ia-23
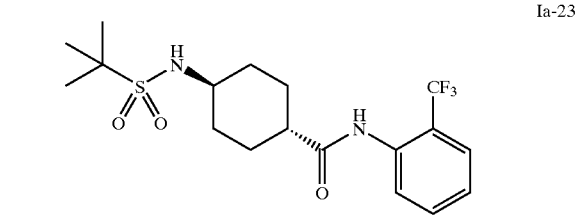
Ia-24
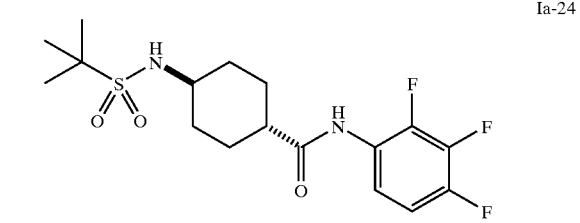
Ia-25
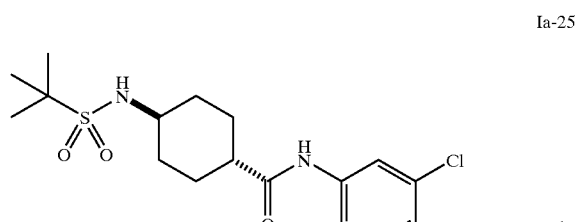
Ia-26
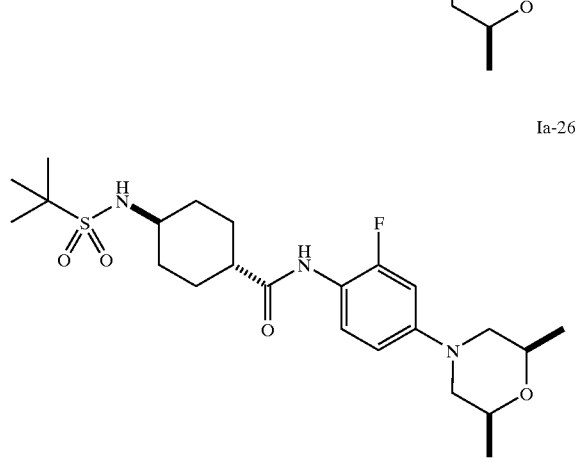

Ia-27
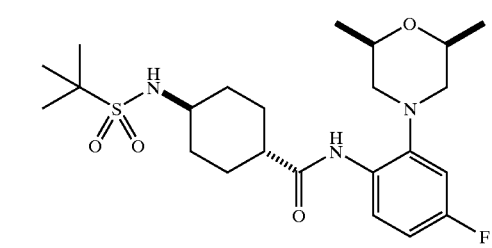
Ia-28
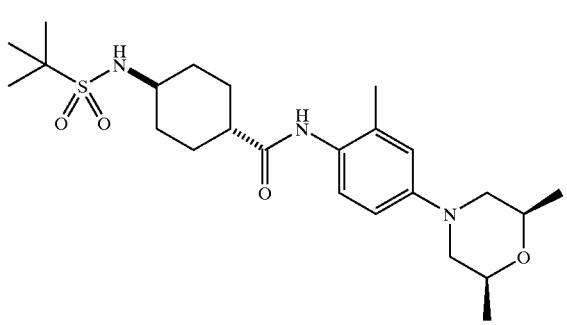
Ia-29
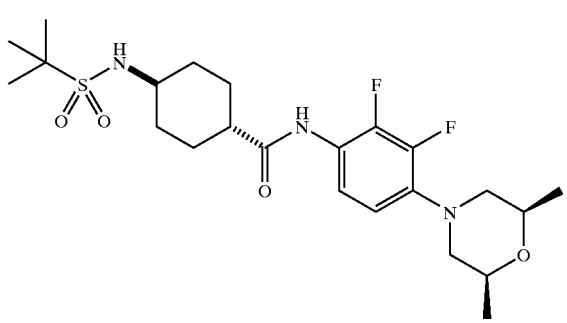
Ia-30
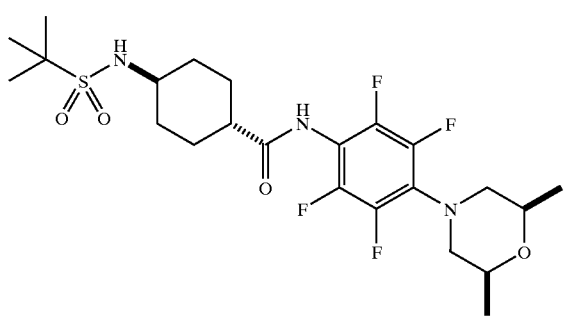
Ia-31
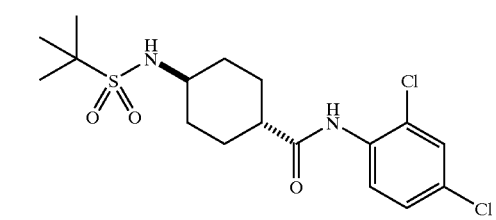
Ia-32
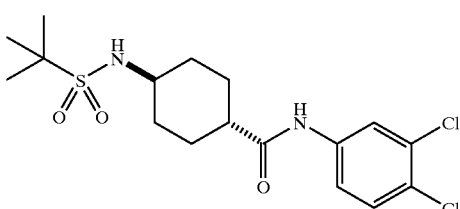
Ia-33
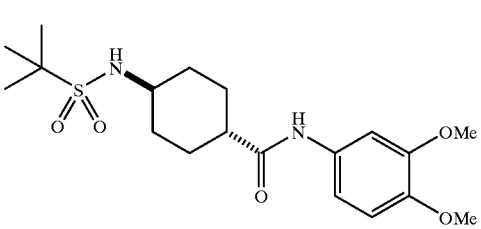
Ia-35
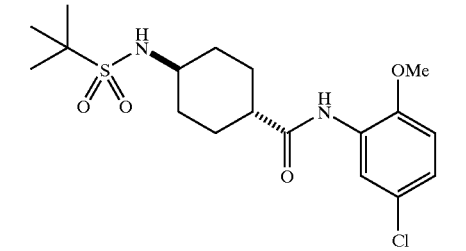
Ia-36
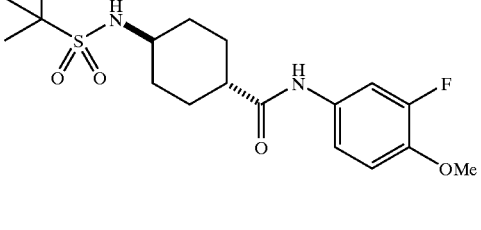
Ia-37
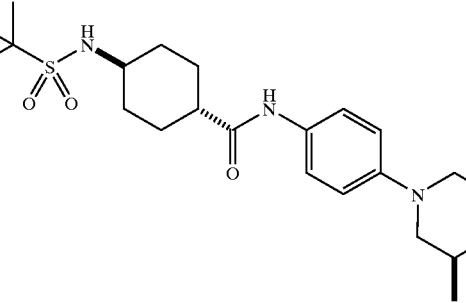
Ia-38
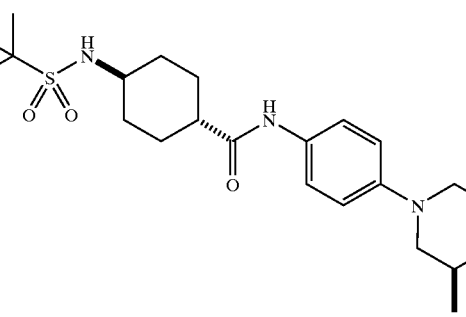

Ia-39 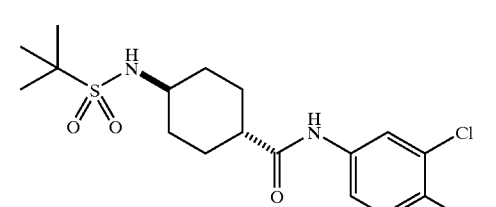
Ia-40 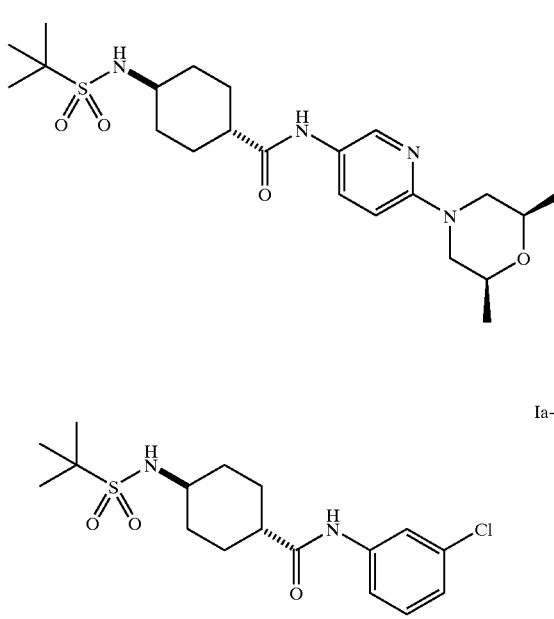
Ia-41 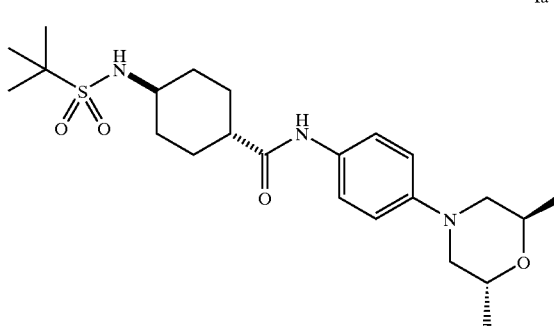
Ia-42 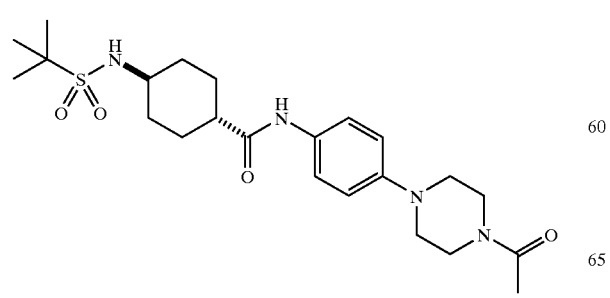
Ia-43
Ia-44 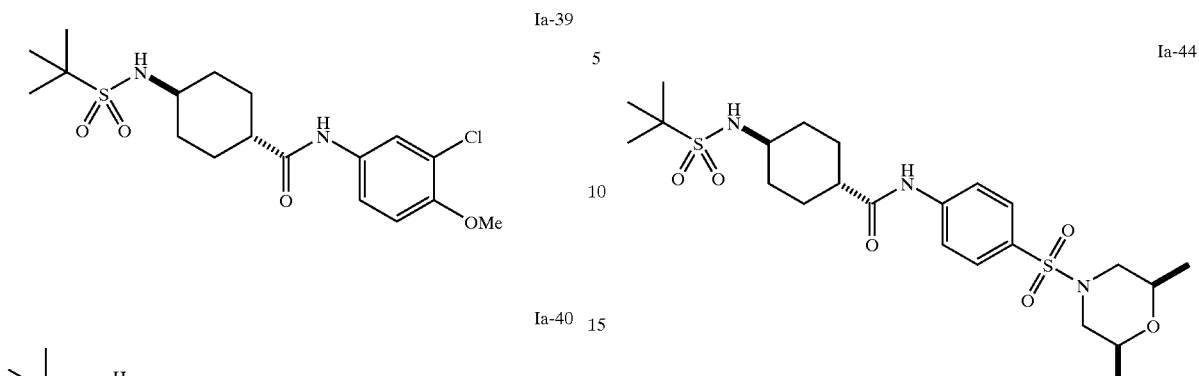
Ia-45 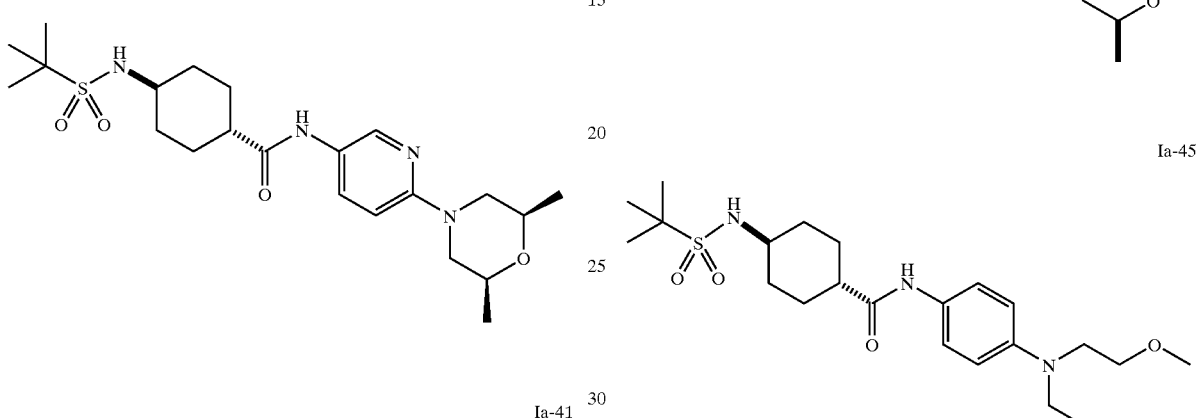
Ia-46 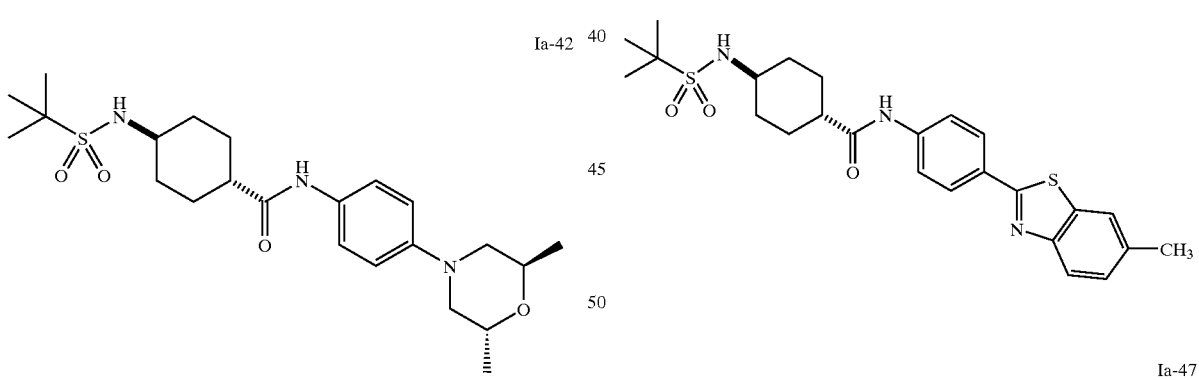
Ia-47 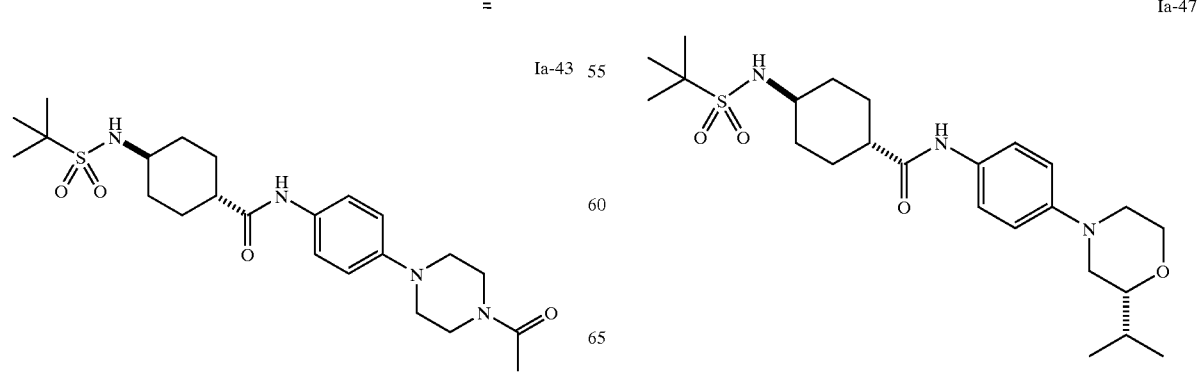

-continued
Ia-48
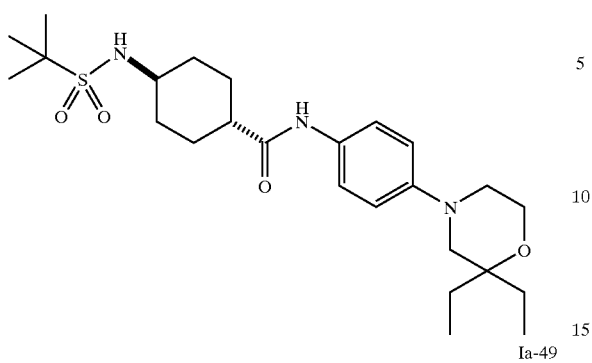
Ia-49
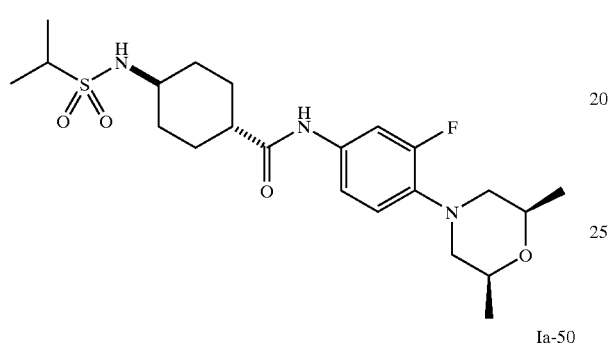
Ia-50
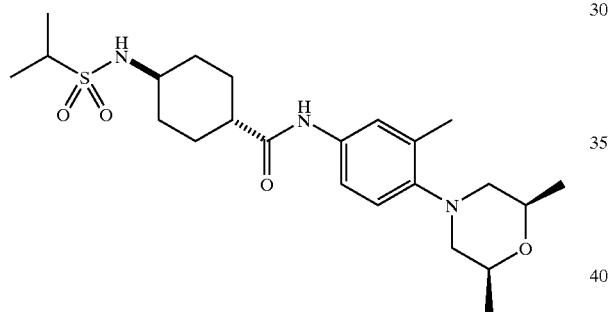
Ia-51
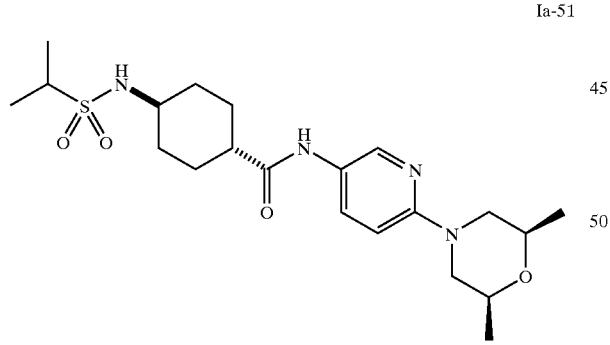
Ia-52
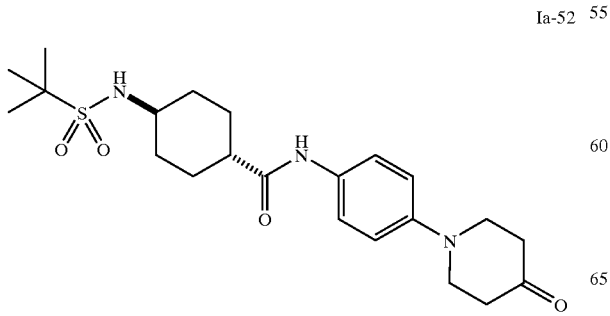
-continued
Ia-53
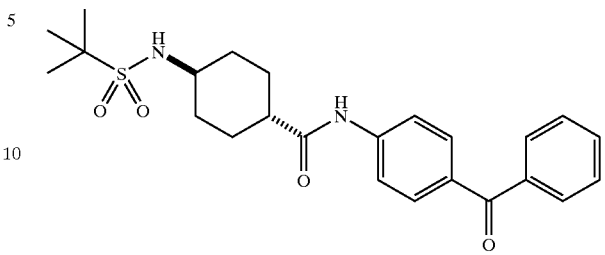
Ia-54
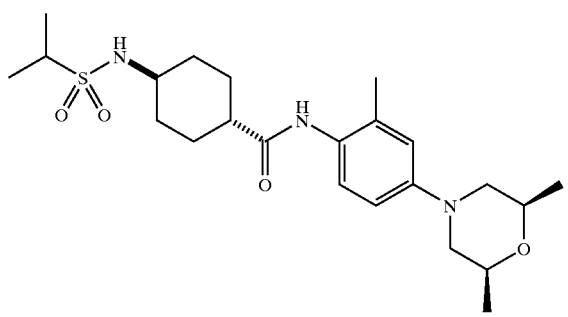
Ia-55
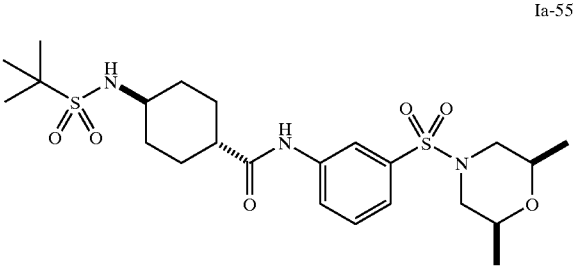
Ia-56
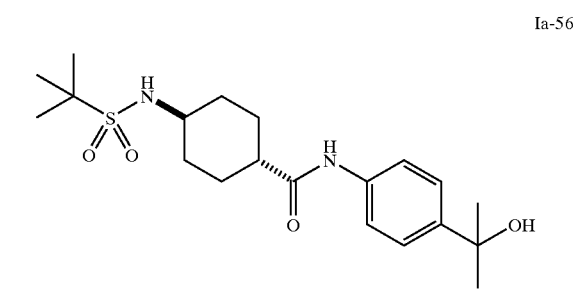
Ia-57
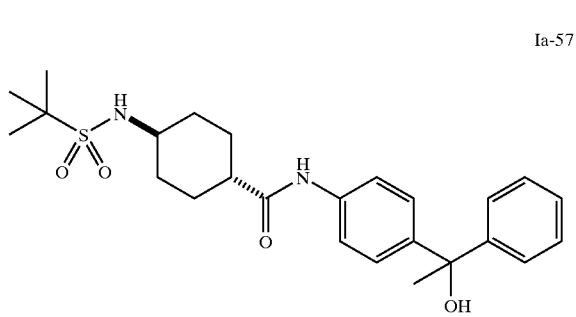

Ia-58
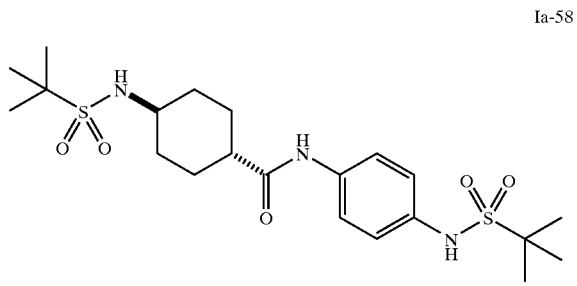
Ia-59
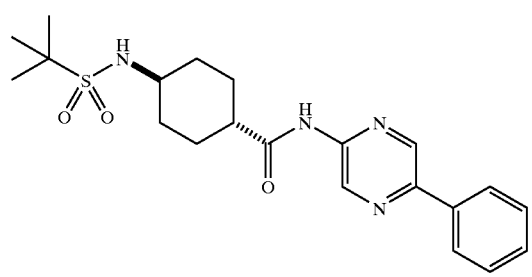
Ia-60
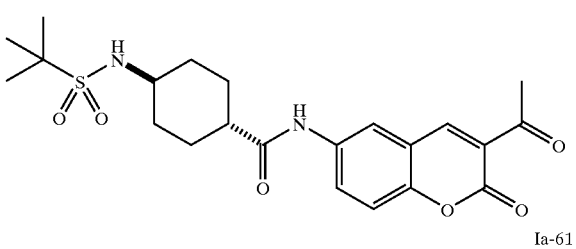
Ia-61
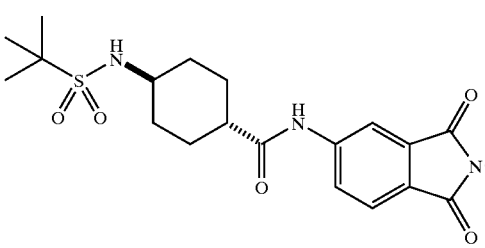
Ia-62
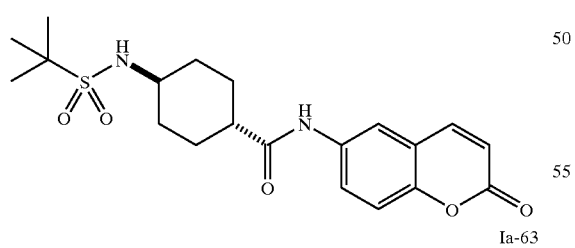
Ia-63
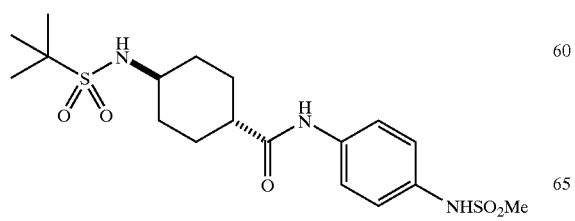
Ia-64
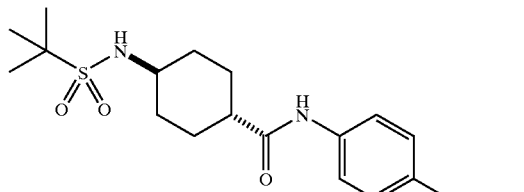
Ia-65
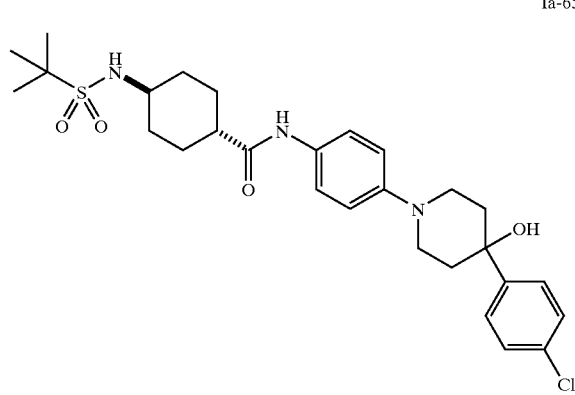
Ia-66
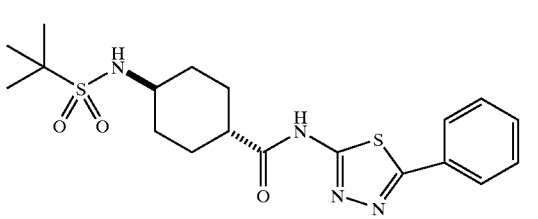
Ia-67
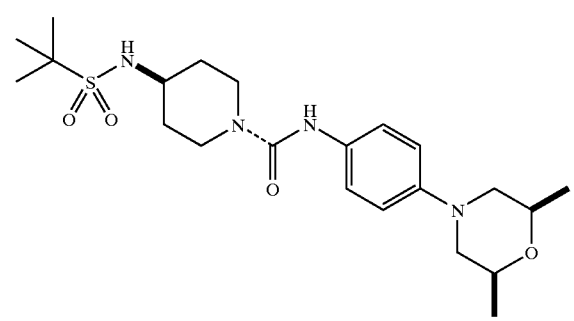
Ia-68
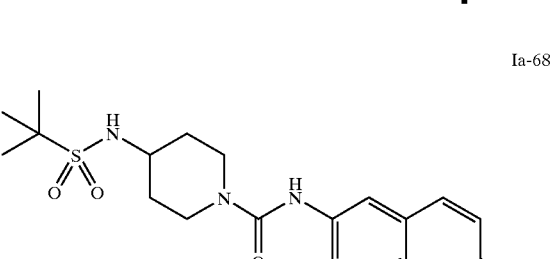

Ia-69
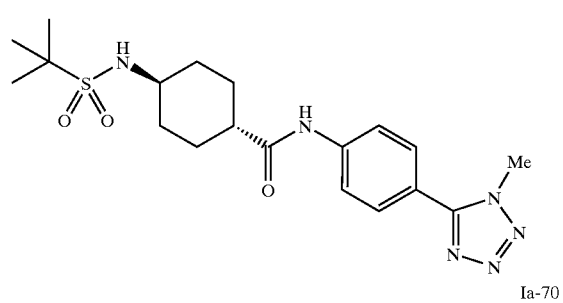
Ia-70
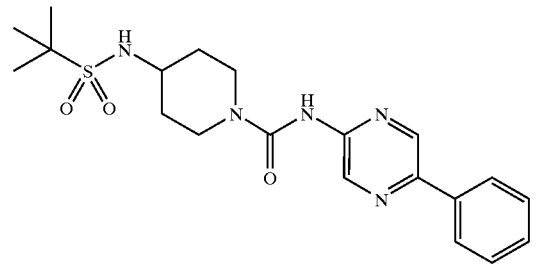
Ia-71
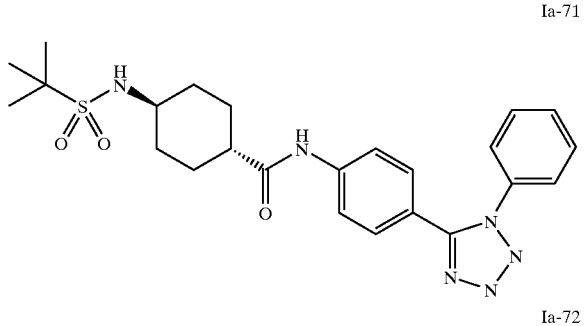
Ia-72
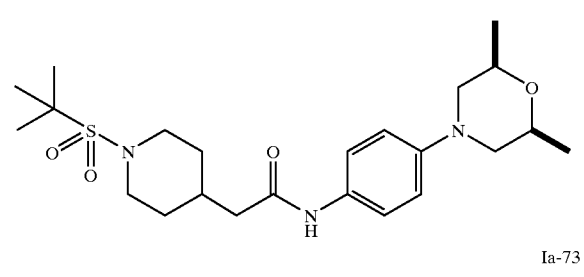
Ia-73
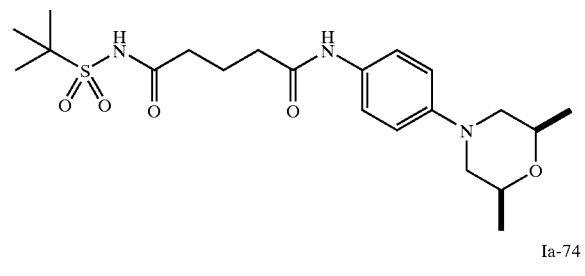
Ia-74
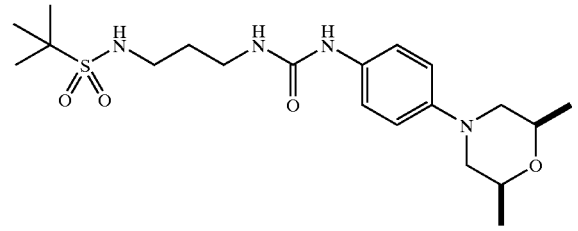
Ia-75

Ia-76
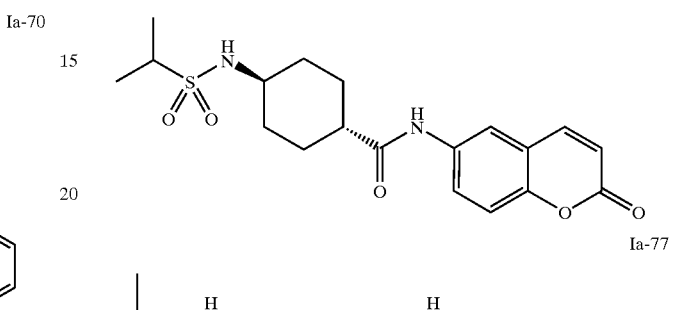
Ia-77
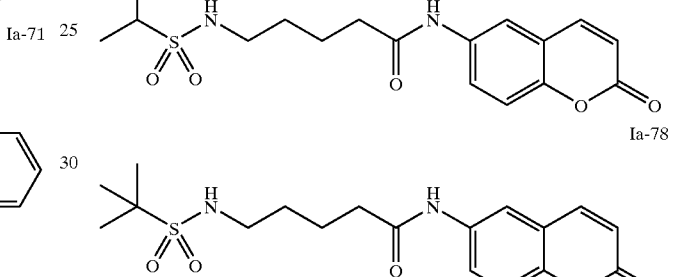
Ia-78
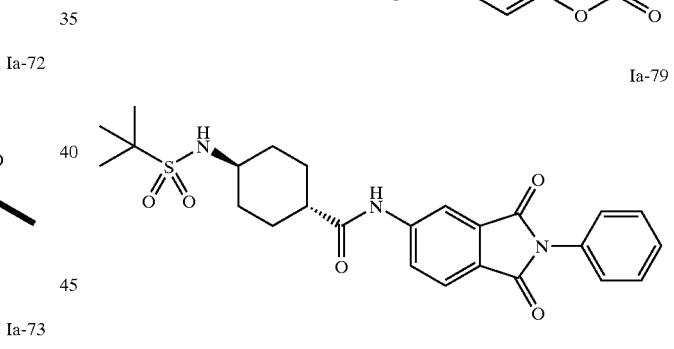
Ia-79
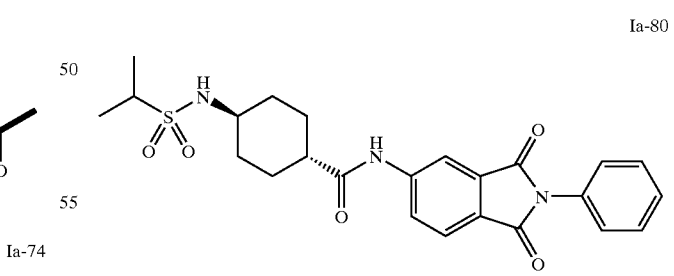
Ia-80
Ia-81
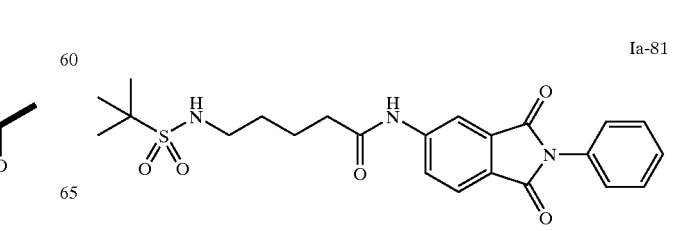

Ia-82
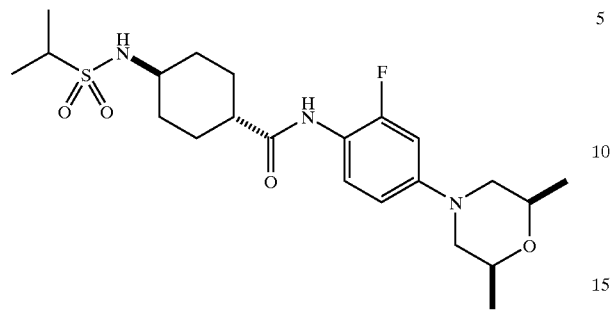
Ia-83
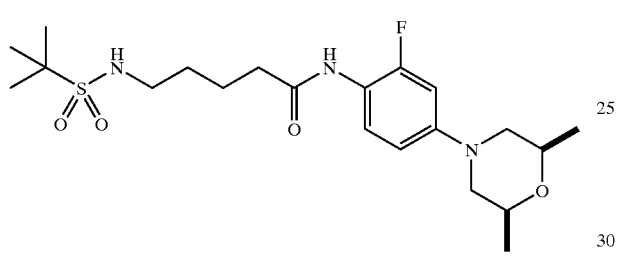
Ia-84
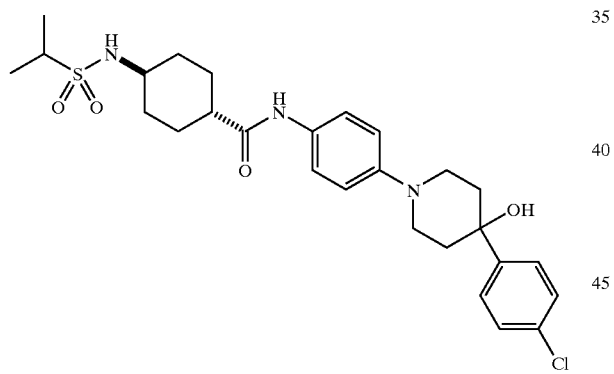
Ia-85
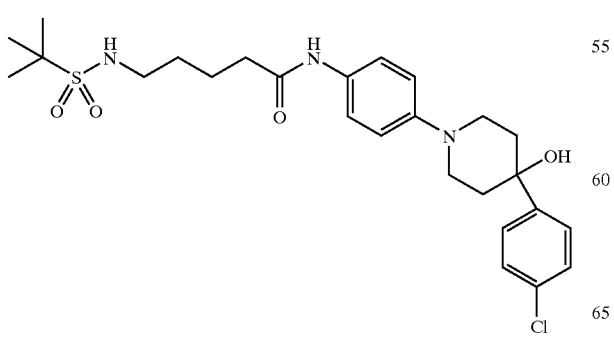
Ia-86
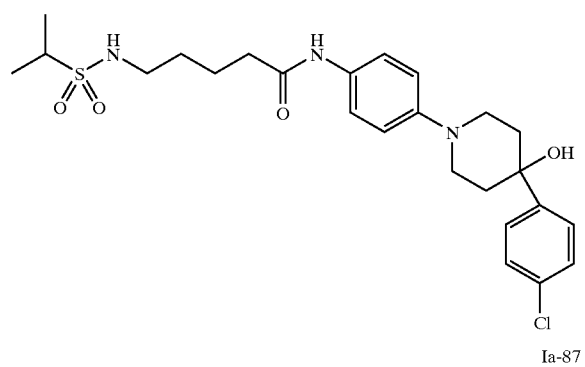
Ia-87
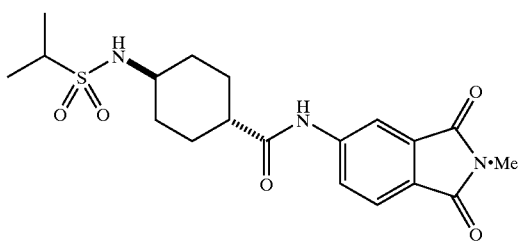
Ia-88
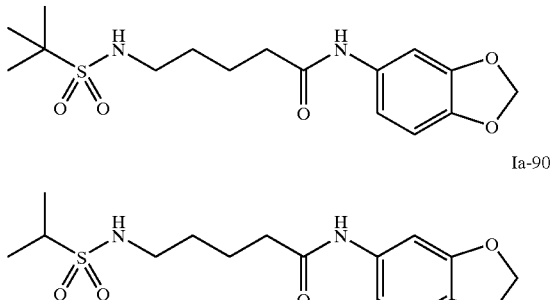
Ia-89
Ia-90
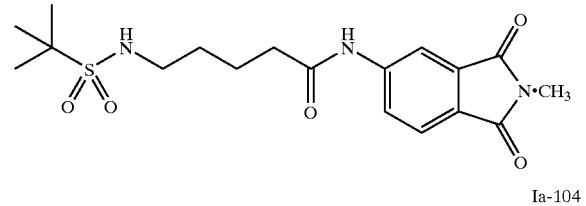
Ia-91
Ia-104
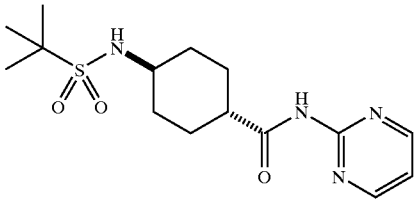

Ia-105
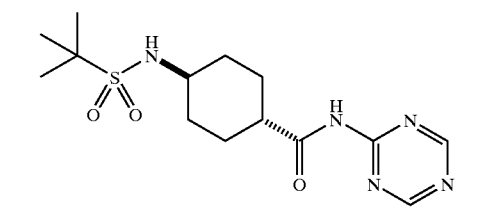
Ia-106
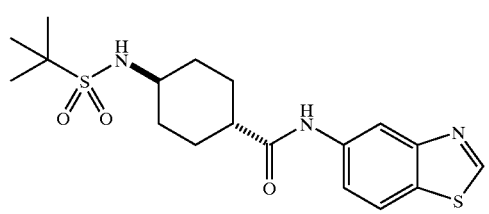
Ia-107
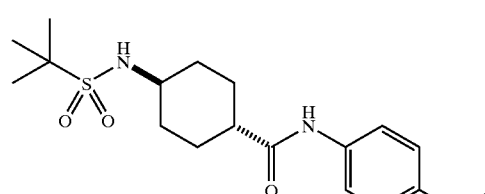
Ia-108
Ia-109
Ia-110
Ia-111
Ia-122
Ia-123
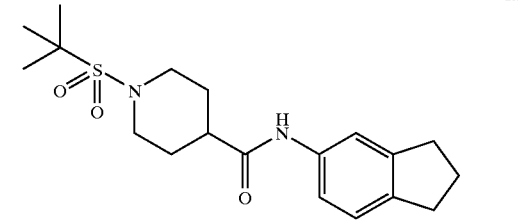
Ia-124
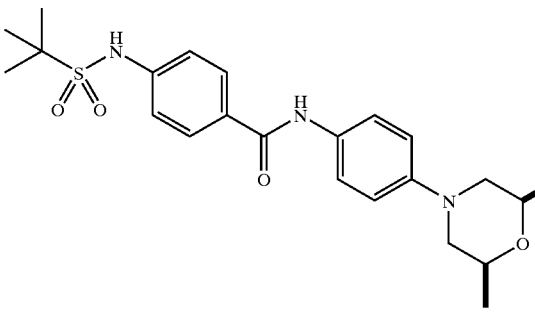
Ia-125
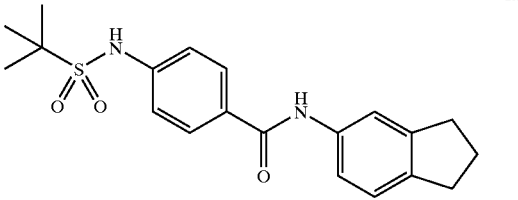
Ia-126
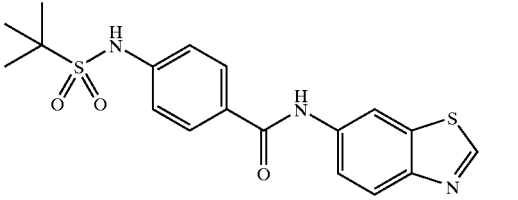
Ia-127
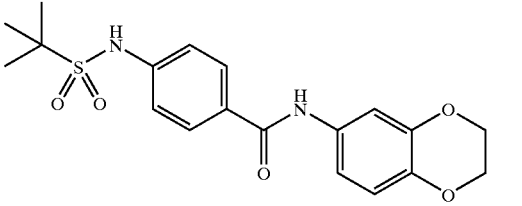

Ia-128
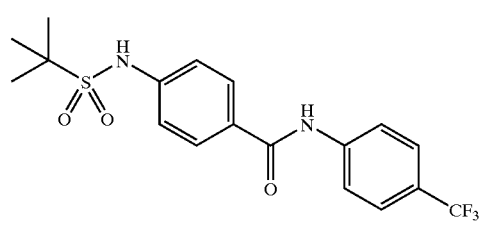
Ia-129
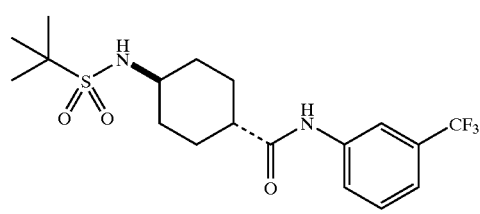
Ia-130
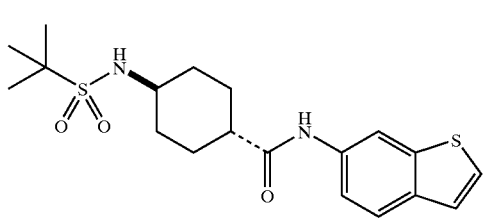
Ia-131
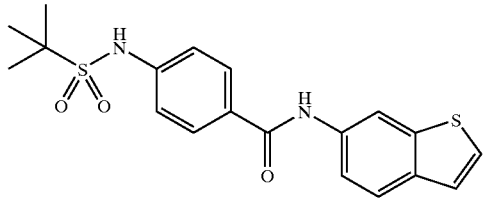
Ia-132
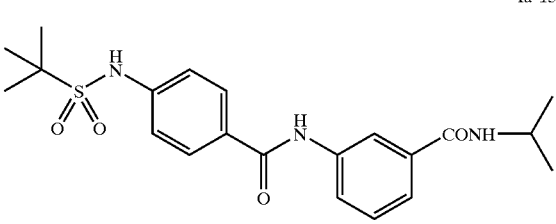
Ia-133
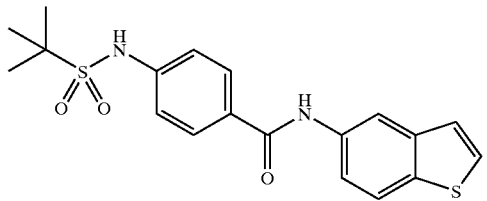
Ia-134
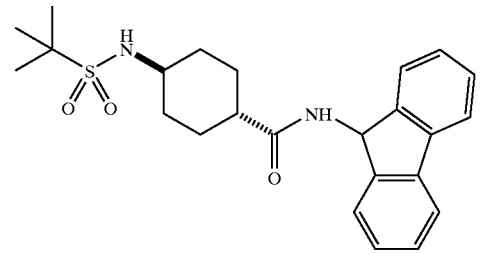
Ia-135
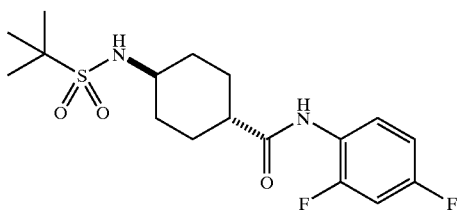
Ia-136
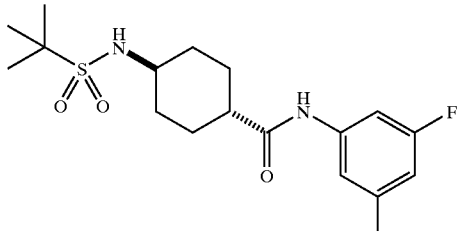
Ia-137
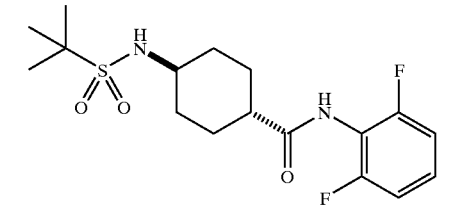
Ia-138
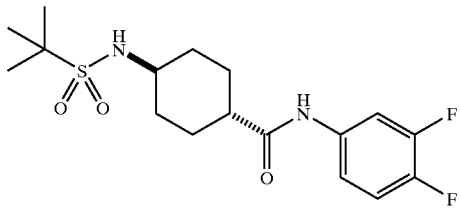
Ia-139
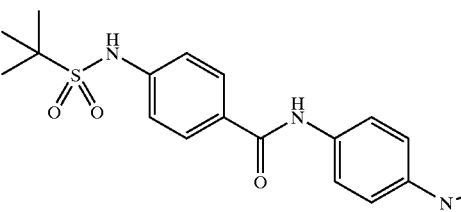
Ia-140
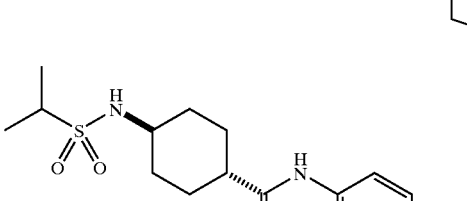
Ia-141
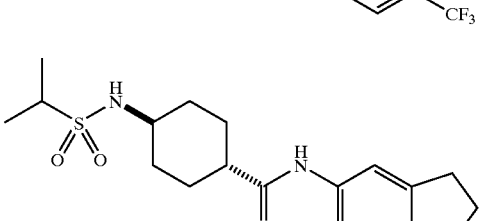

Ia-142
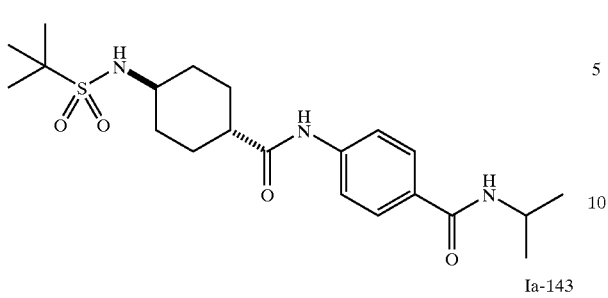
Ia-143
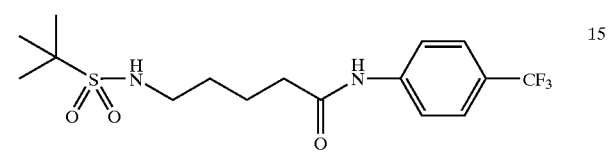
Ia-144
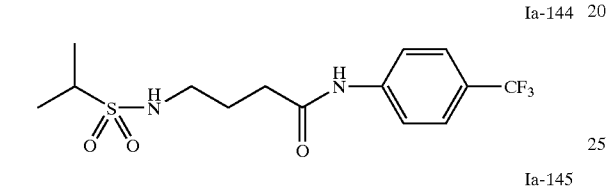
Ia-145
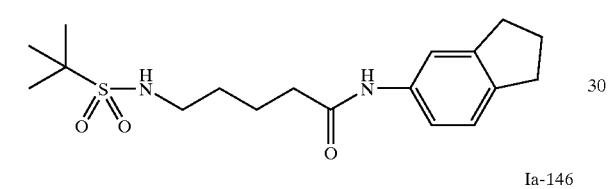
Ia-146
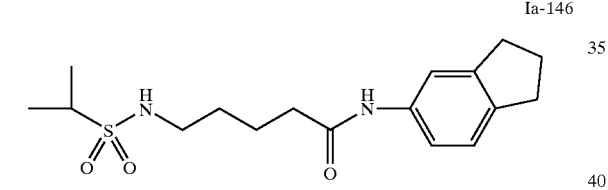
Ia-147
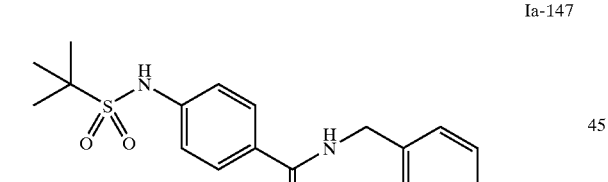
Ia-148
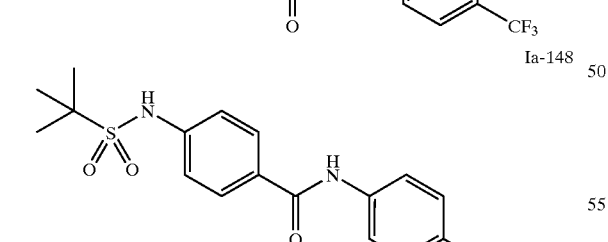
Ia-149
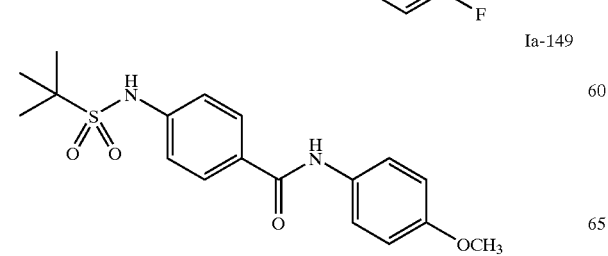
Ia-150
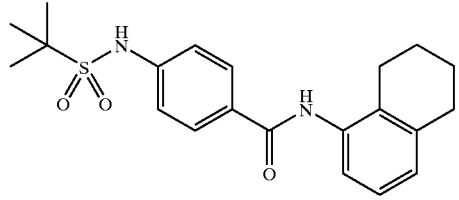
Ia-151
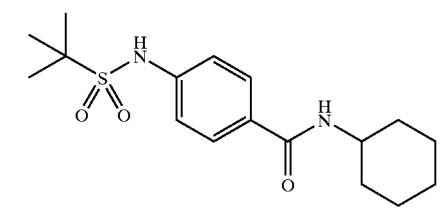
Ia-152
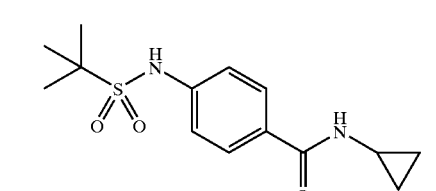
Ia-153
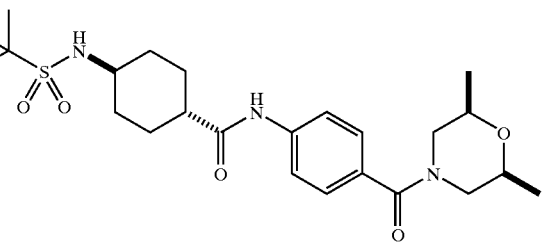
Ia-154
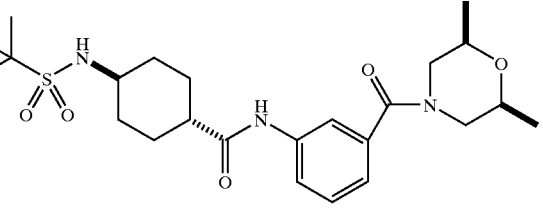
Ia-155
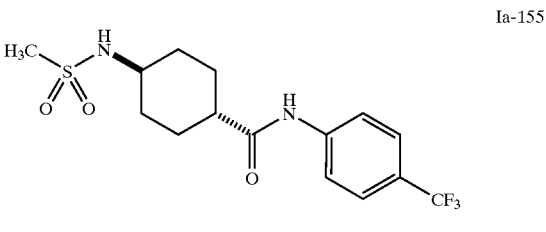
Ia-156

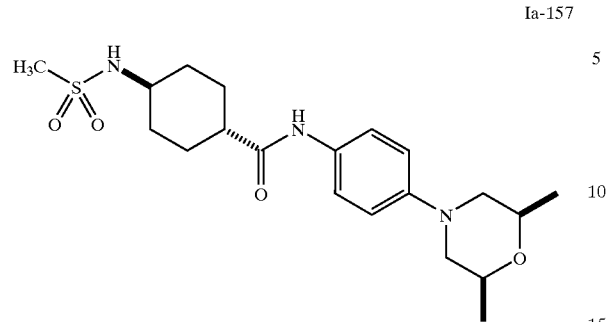
Ia-157
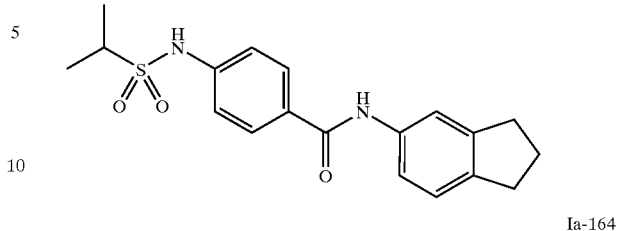
Ia-163
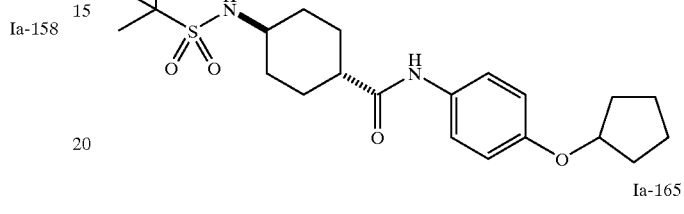
Ia-158
Ia-164
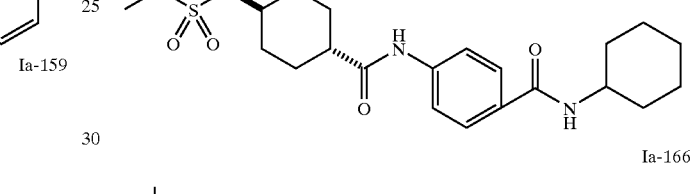
Ia-159
Ia-165
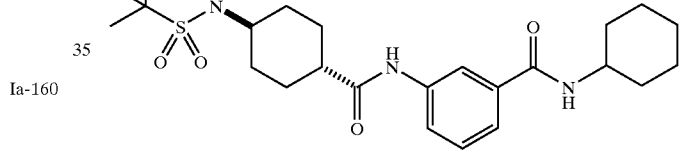
Ia-160
Ia-166
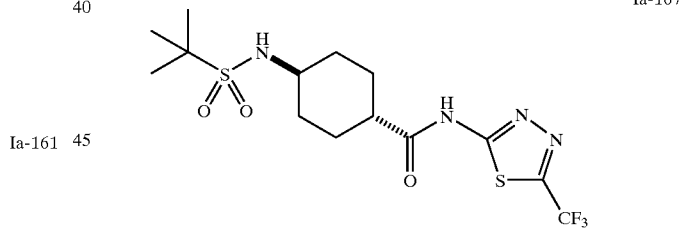
Ia-161
Ia-167
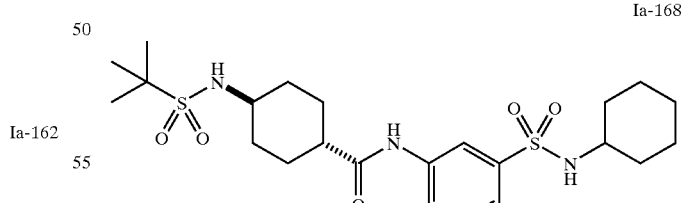
Ia-162
Ia-168
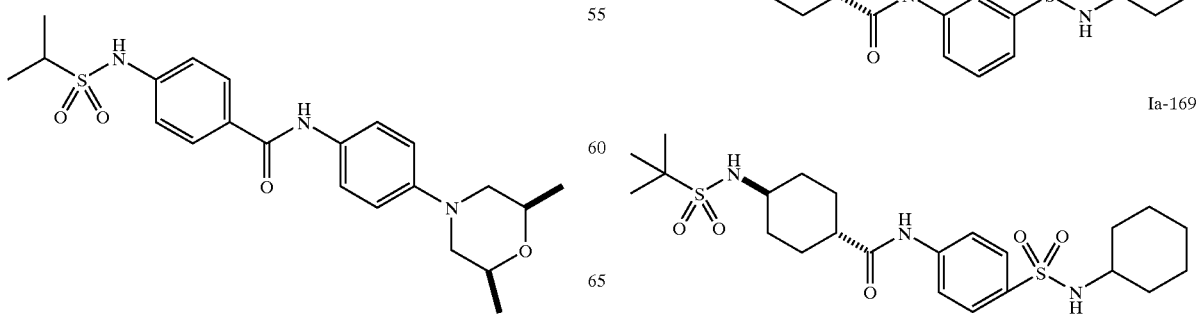
Ia-169

Ia-171
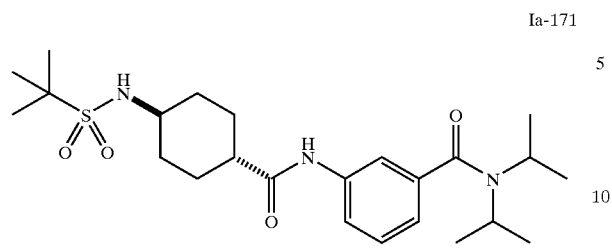
Ia-172
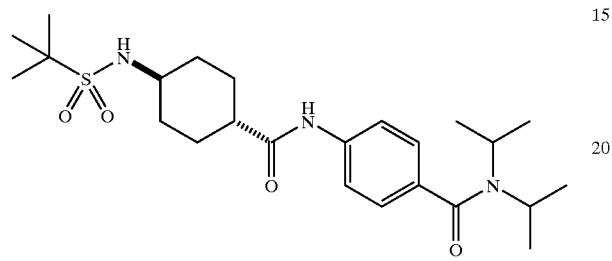
Ia-173
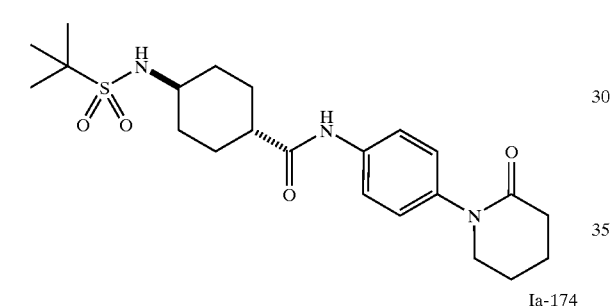
Ia-174
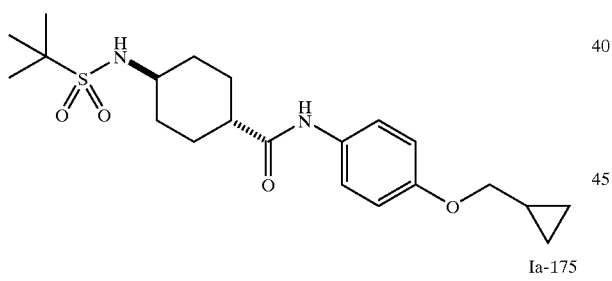
Ia-175
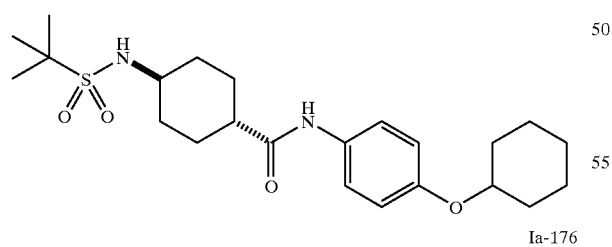
Ia-176
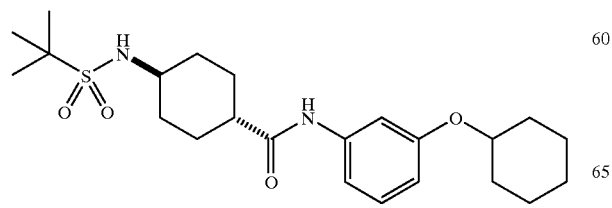
Ia-177
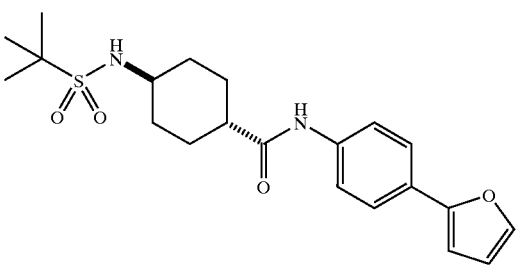
Ia-178
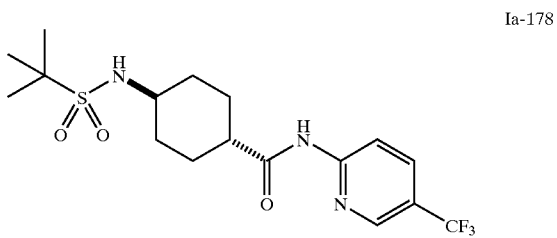
Ia-179
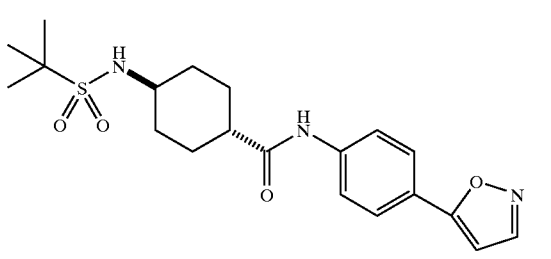
Ia-180
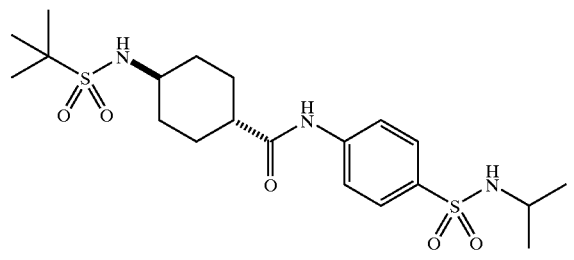
Ia-181
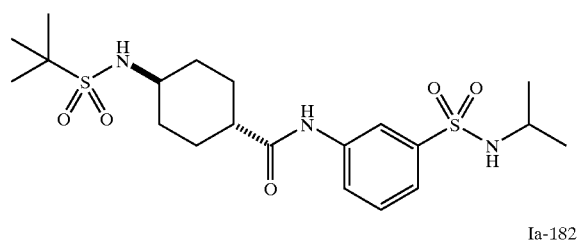
Ia-182
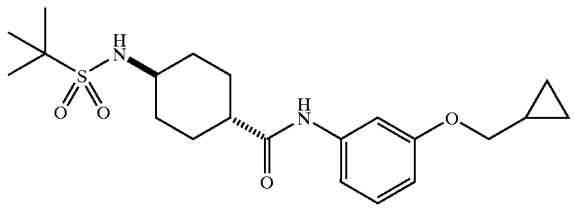

Ia-183
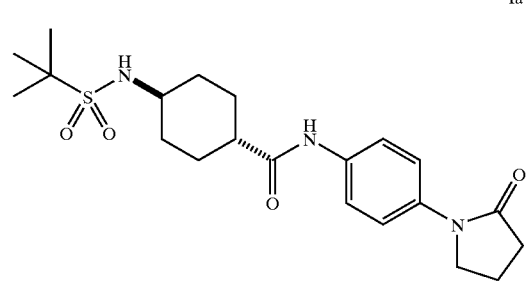
Ia-184
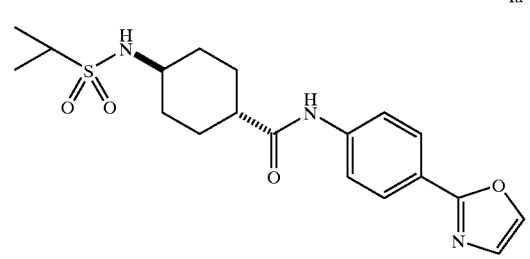
Ia-185
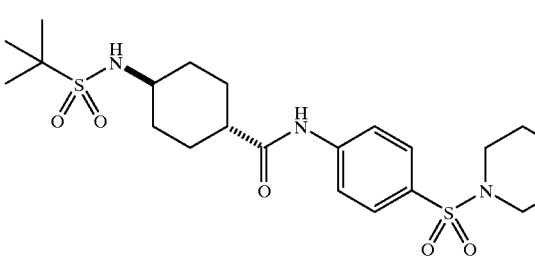
Ia-186
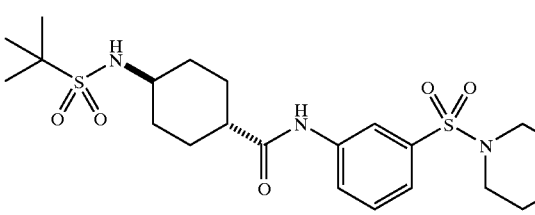
Ia-187
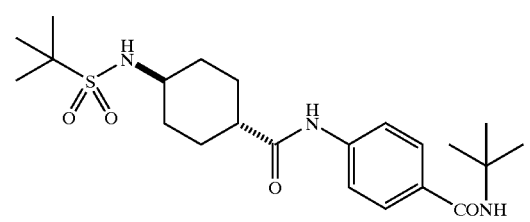
Ia-188
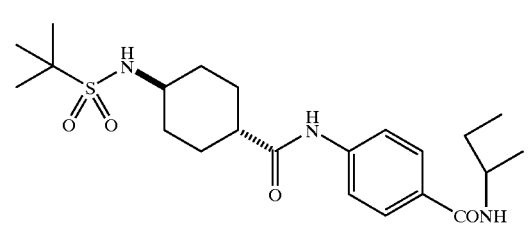
Ia-189
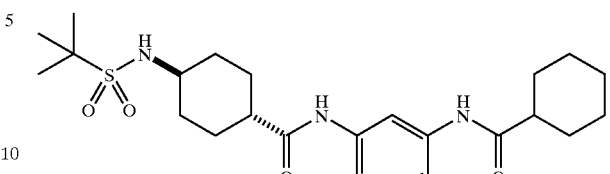
Ia-190
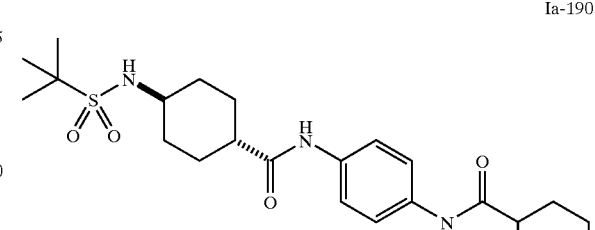
Ia-191
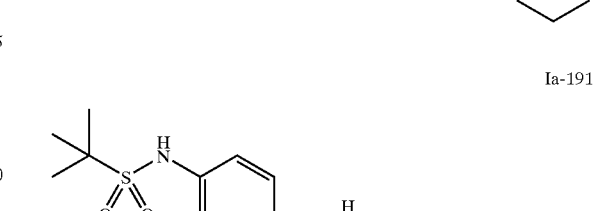
Ia-192
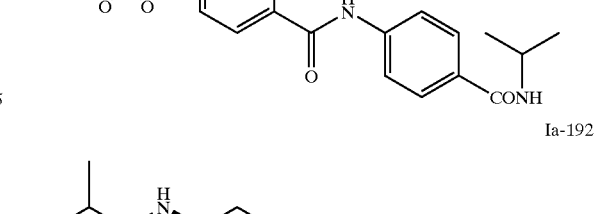
Ia-193
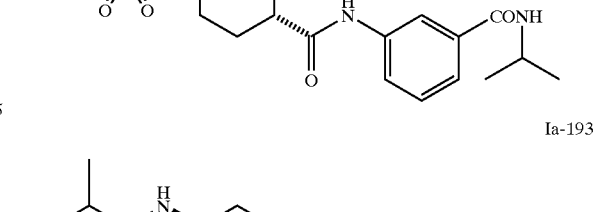
Ia-194
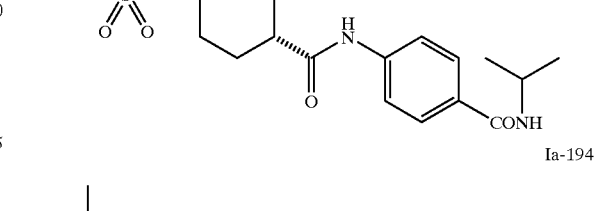

Ia-195
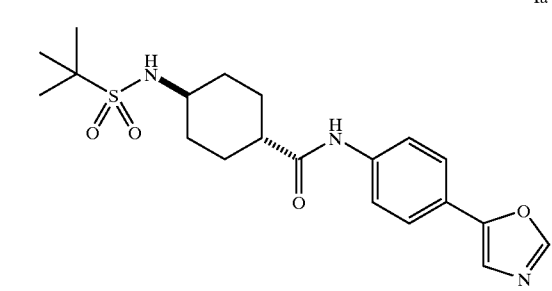
Ia-196
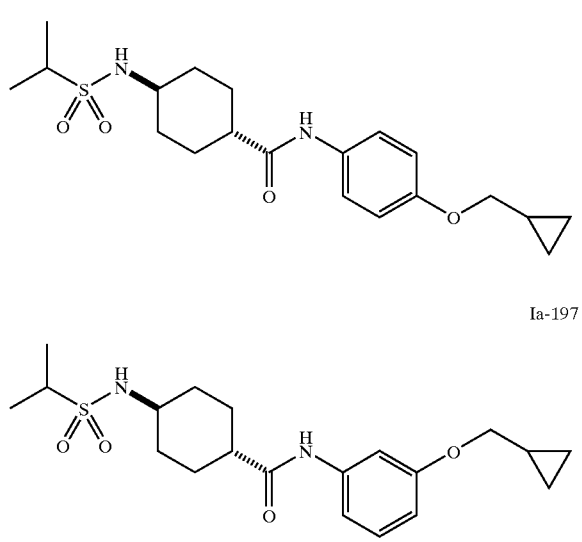
Ia-197
Ia-198
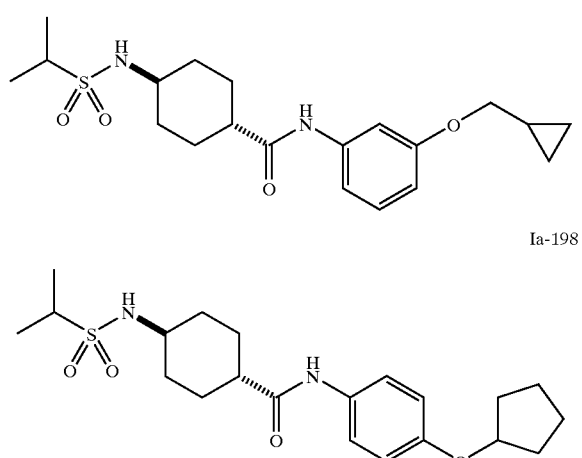
Ia-199
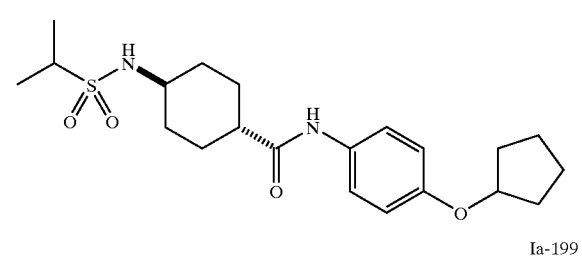
Ia-200
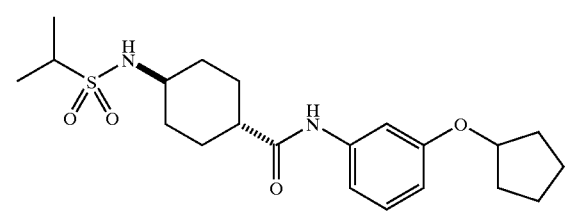
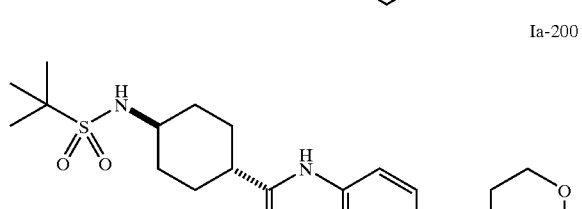
Ia-201
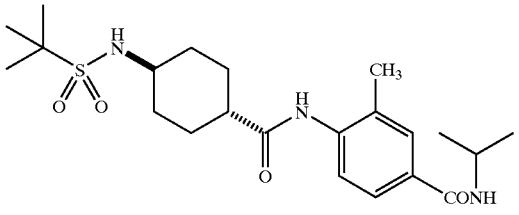
Ia-202
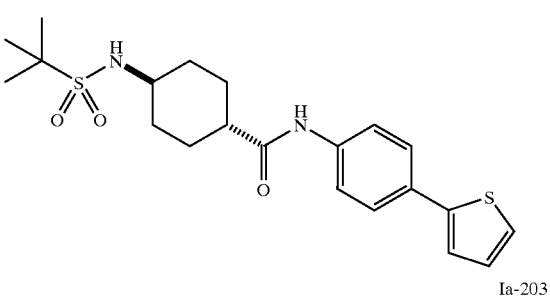
Ia-203
Ia-204
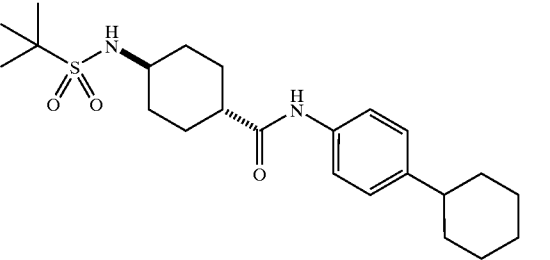
Ia-205
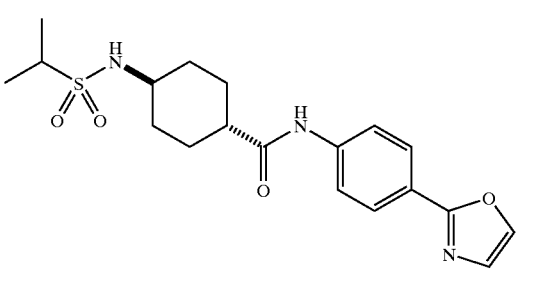
Ia-206
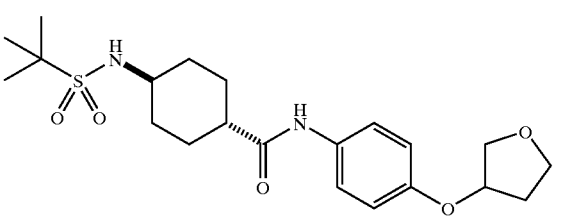
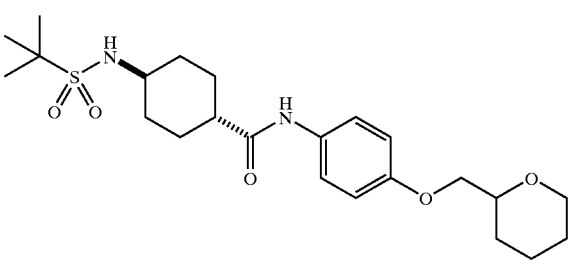

Ia-207
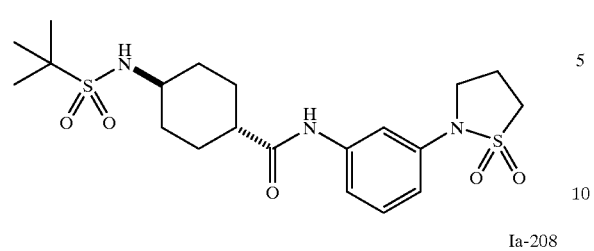
Ia-208
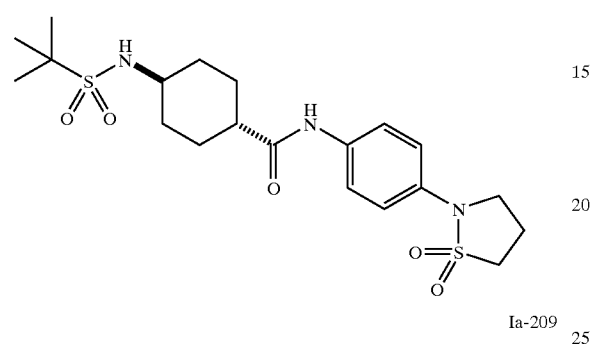
Ia-209
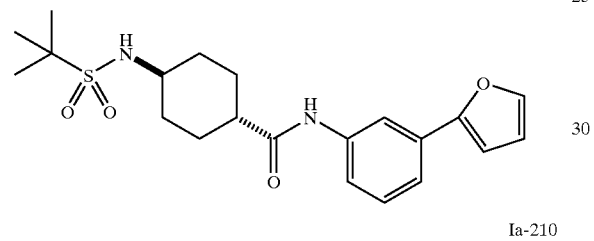
Ia-210
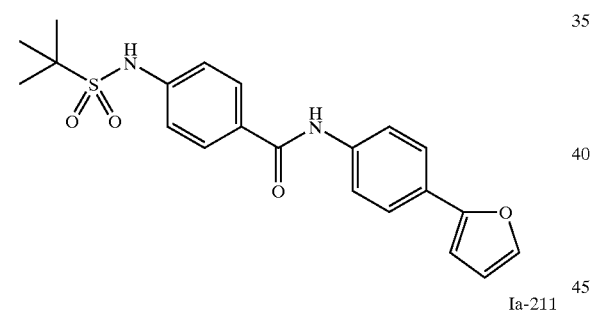
Ia-211
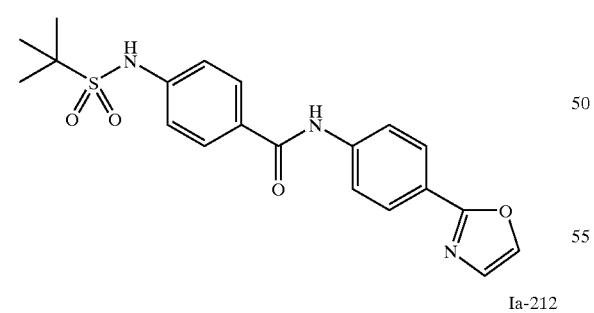
Ia-212
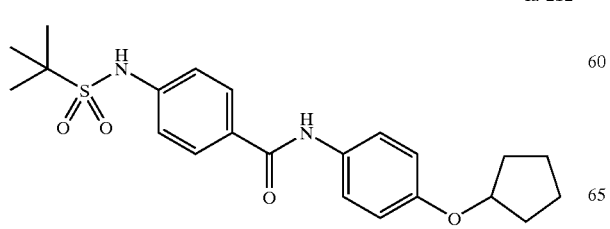
Ia-213
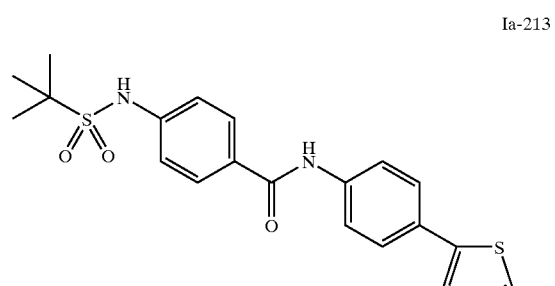
Ia-214
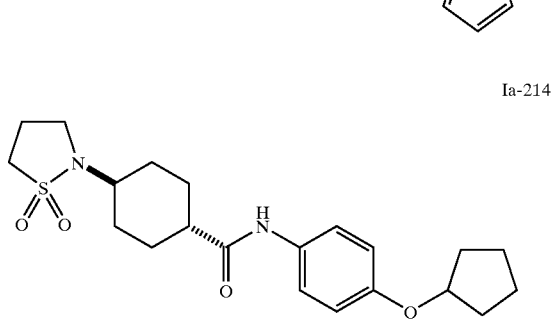
Ia-215
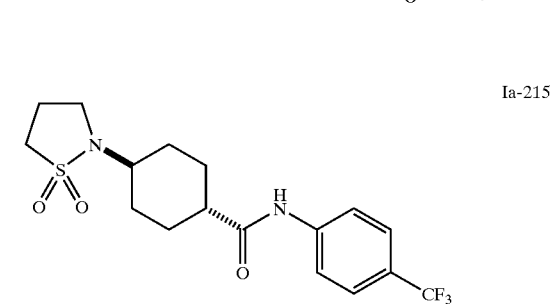
Ia-216
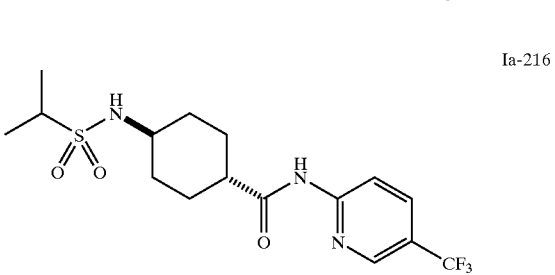
Ia-219
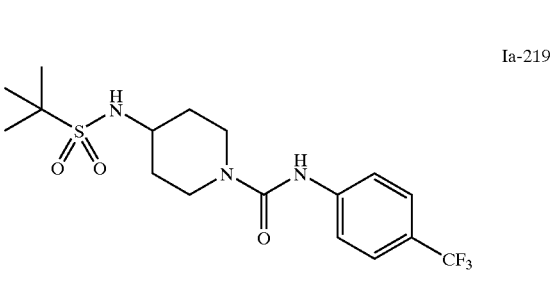
Ia-220
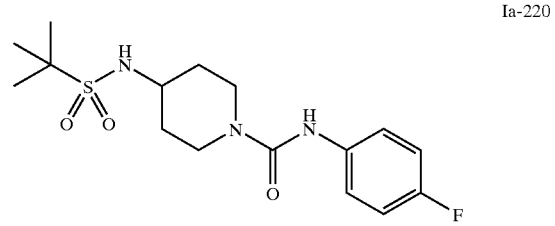

Ia-221
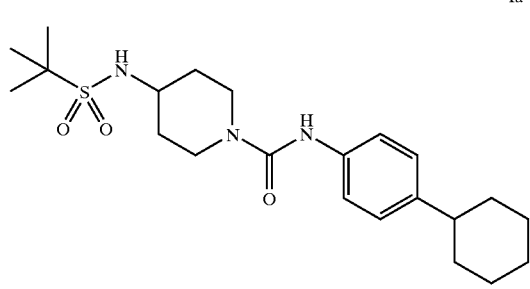
Ia-222
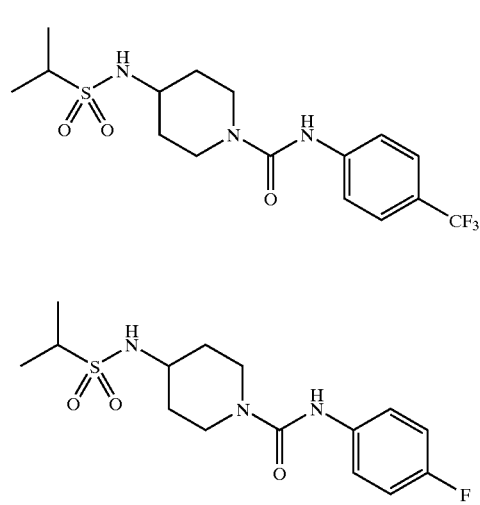
Ia-223
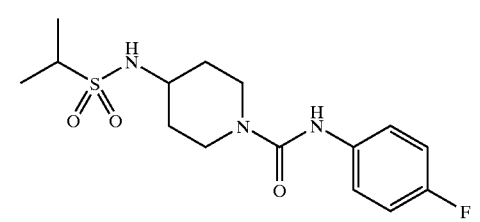
Ia-224
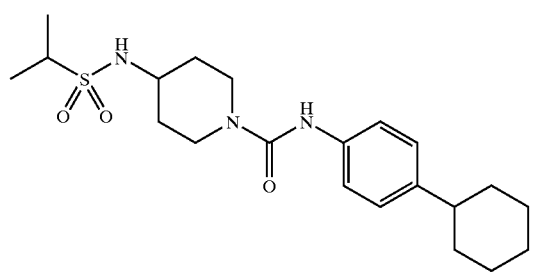
Ia-225
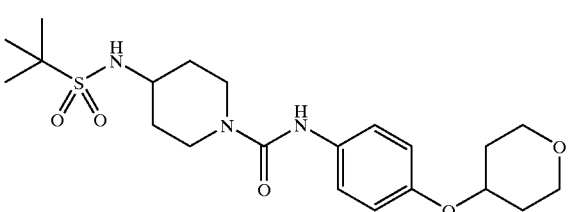
Ia-226
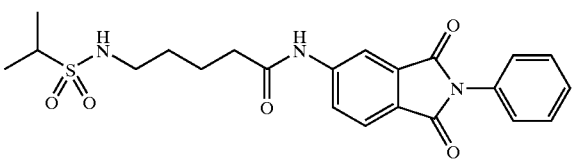
Ia-227
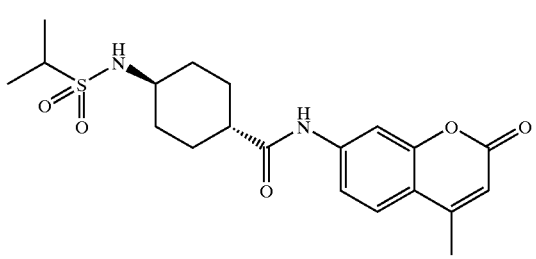
Ia-228
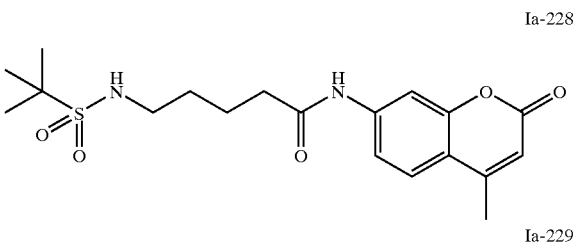
Ia-229
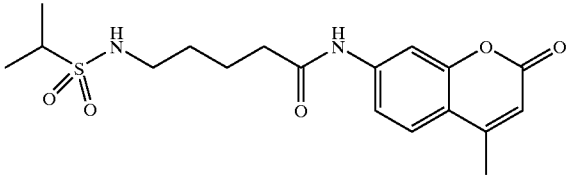
Ia-230
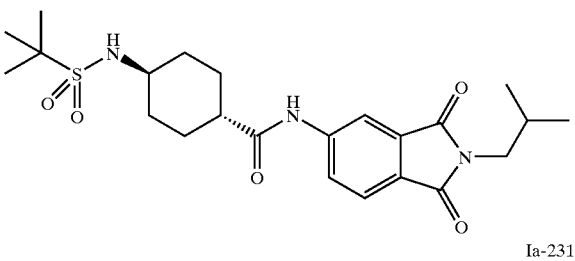
Ia-231
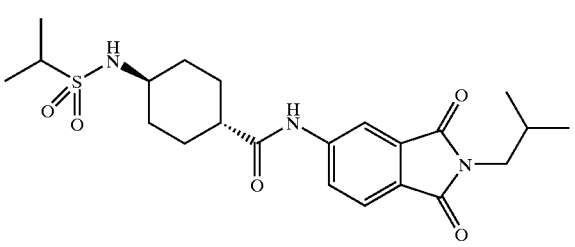
Ia-232
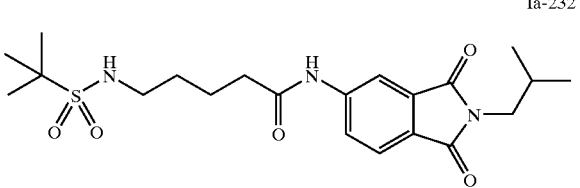
Ia-233
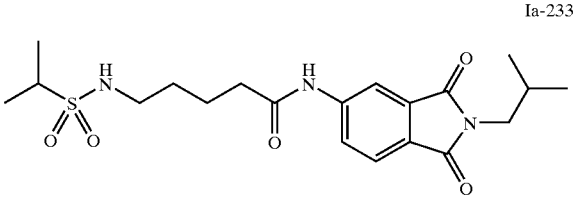

187
-continued
Ia-234

Ia-235
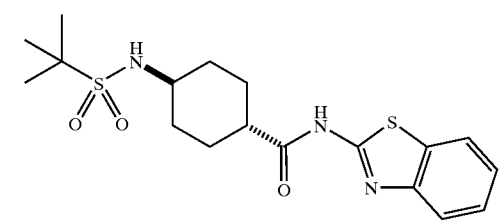
Ia-236

Ia-237
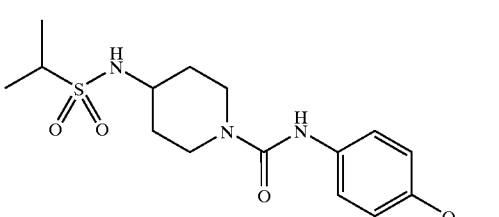
Ia-238
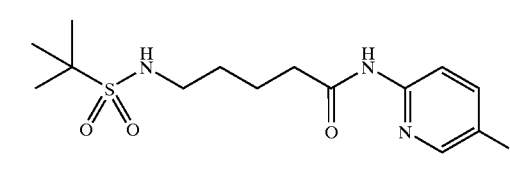
Ia-239
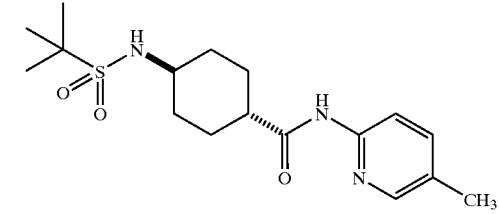
188
-continued
Ia-240
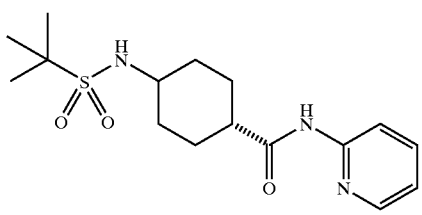
Ia-241
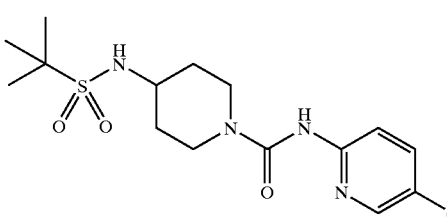
Ia-242
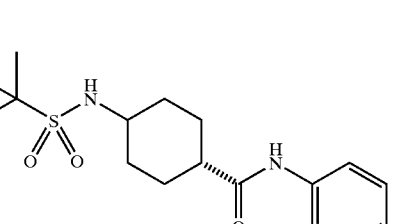
Ia-243
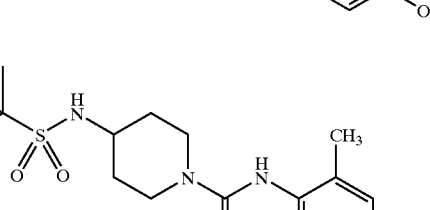
Ia-244
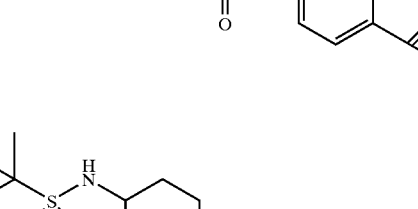
Ia-245
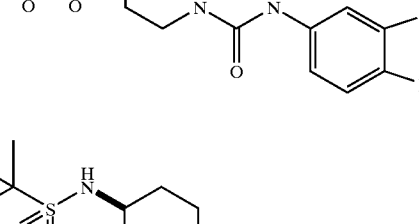
Ia-246
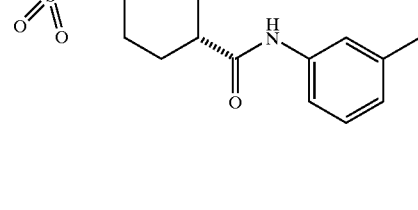

Ia-247
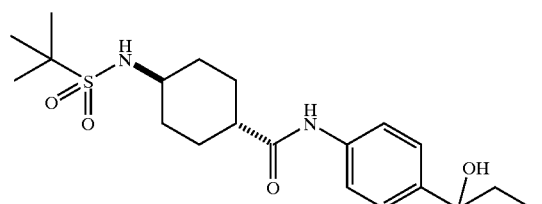
Ia-248
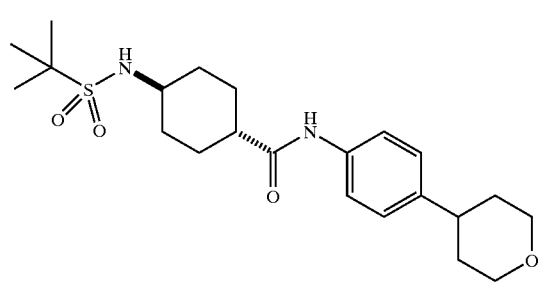
Ia-249
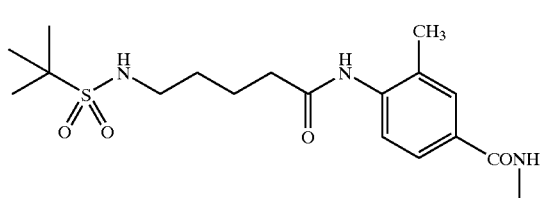
Ia-250
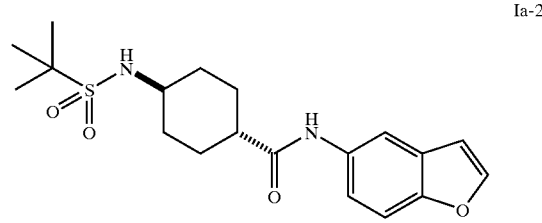
Ia-252
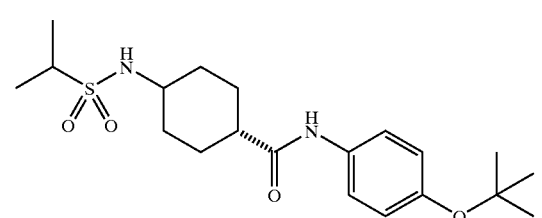
Ia-253
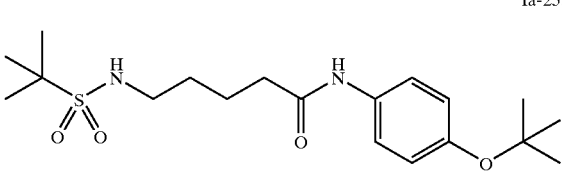
Ia-254
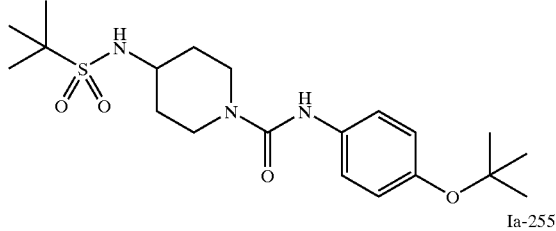
Ia-255
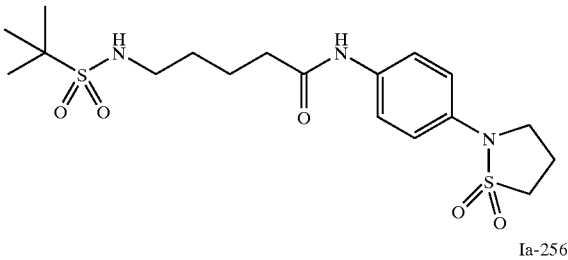
Ia-256
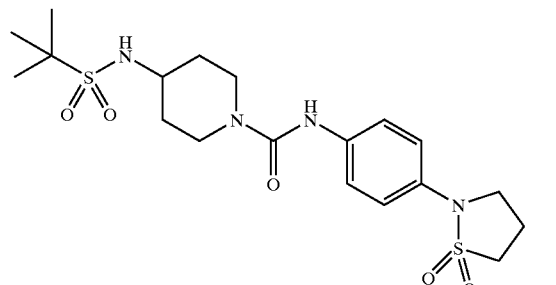
Ia-257
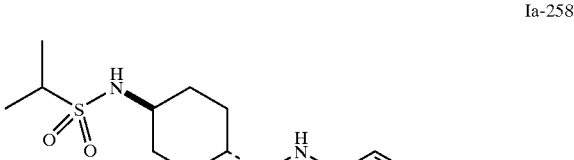
Ia-258
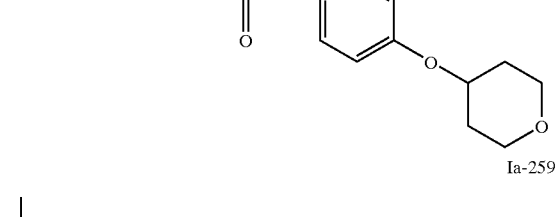
Ia-259
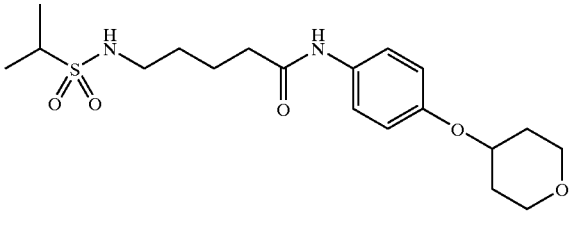

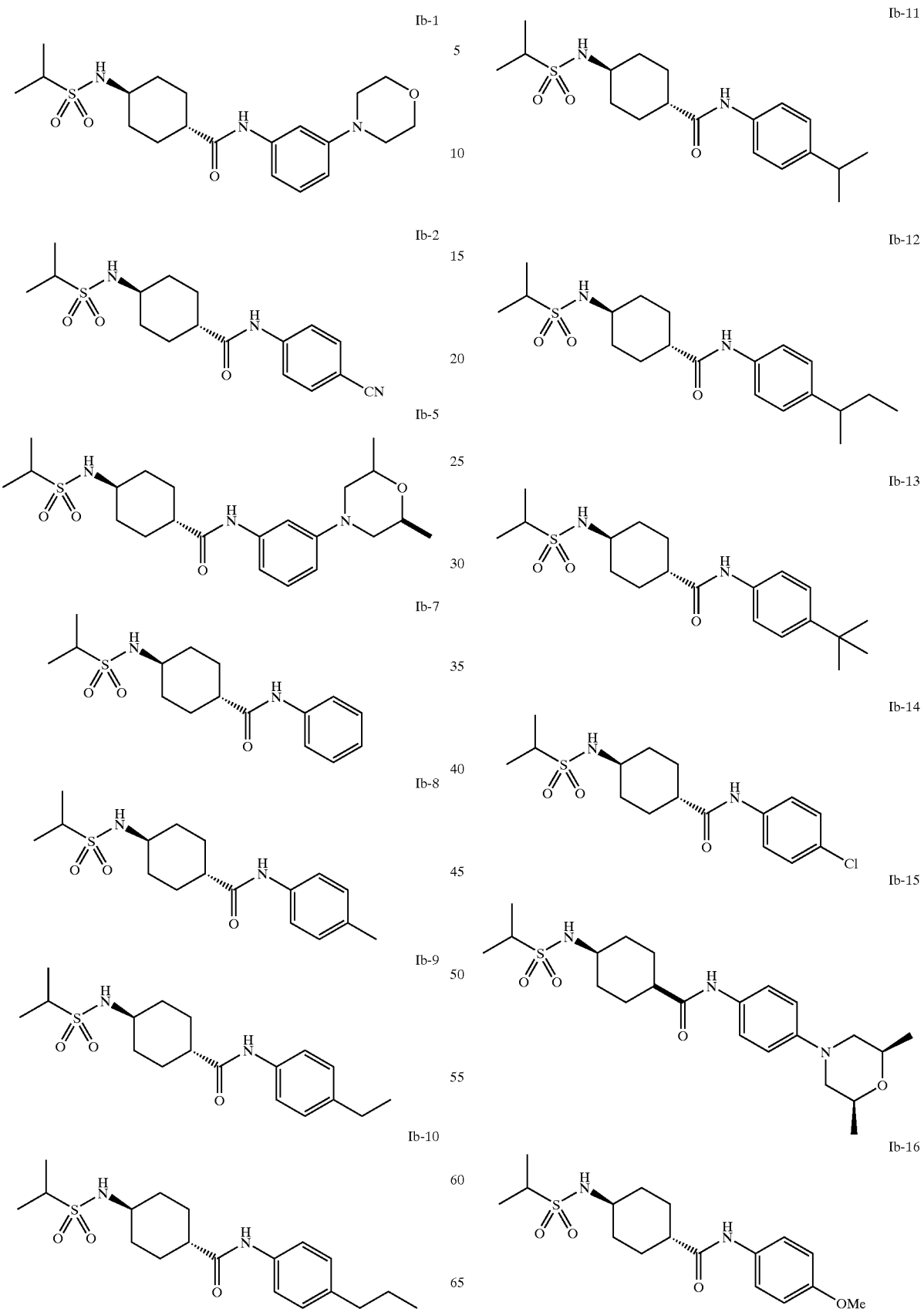

Ib-17
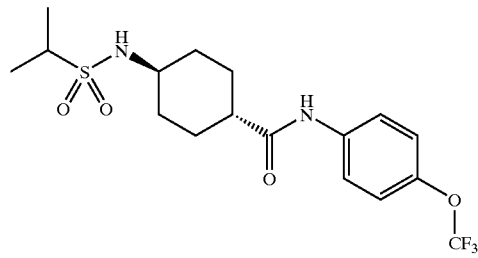
Ib-18
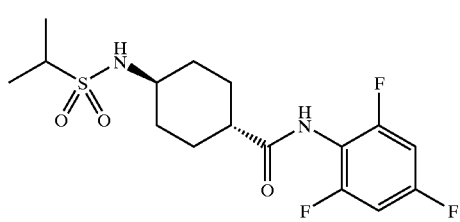
Ib-19
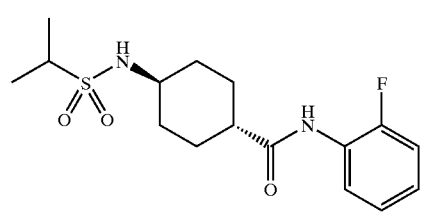
Ib-20
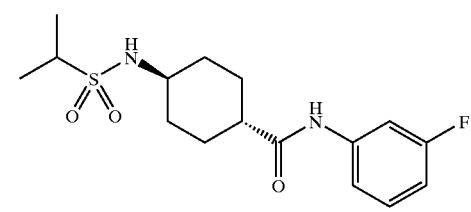
Ib-21
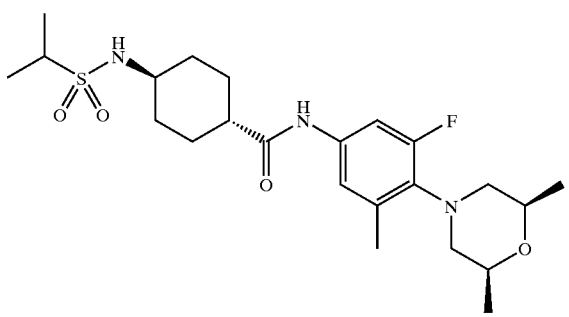
Ib-22
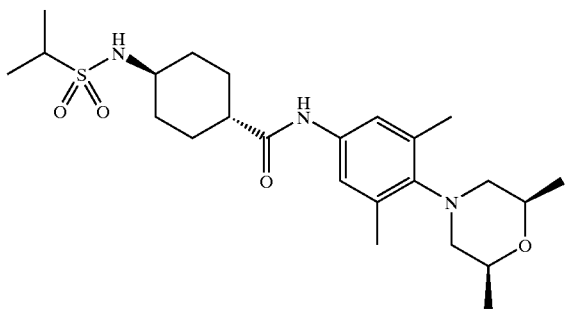
Ib-23
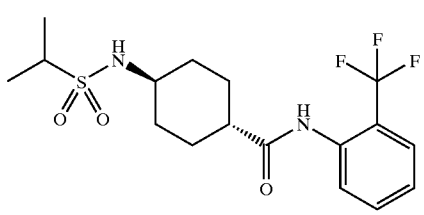
Ib-24
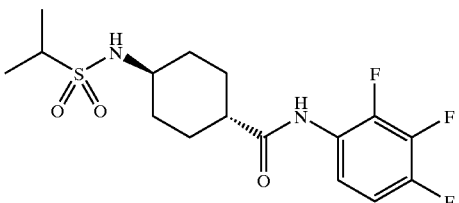
Ib-25
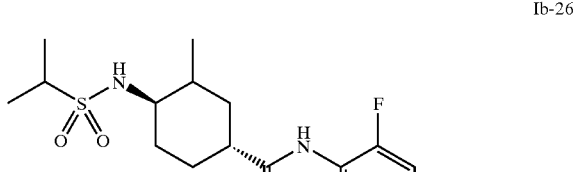
Ib-26
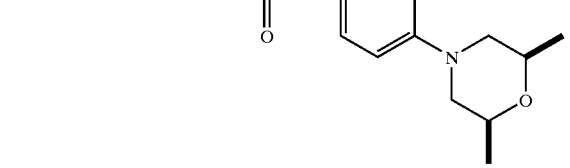
Ib-27
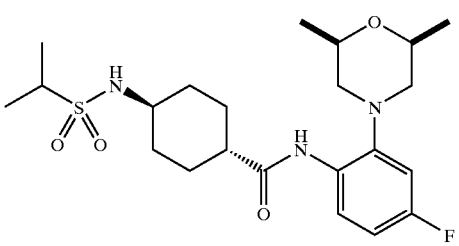

-continued
Ib-28
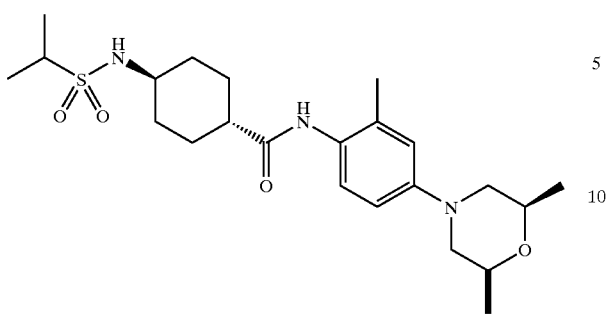
Ib-29
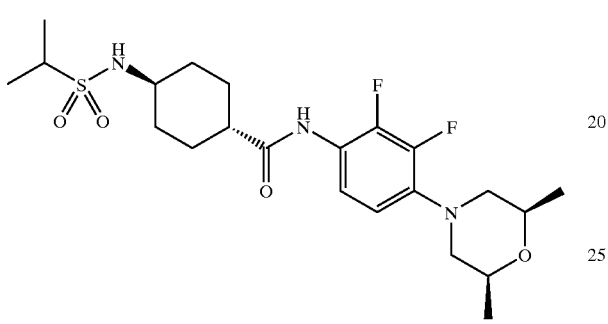
Ib-30
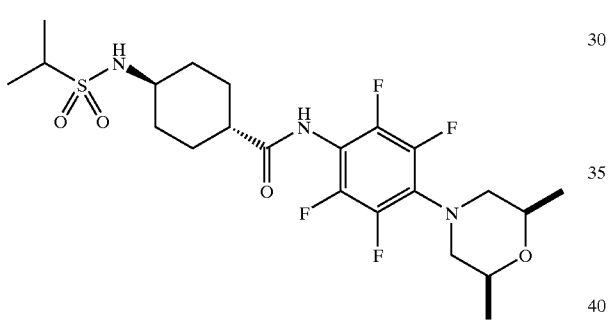
Ib-31
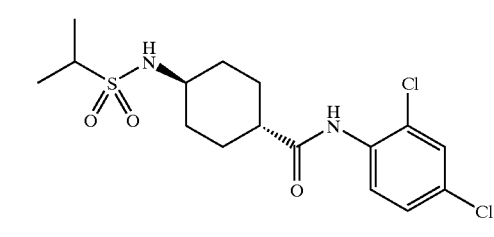
Ib-32
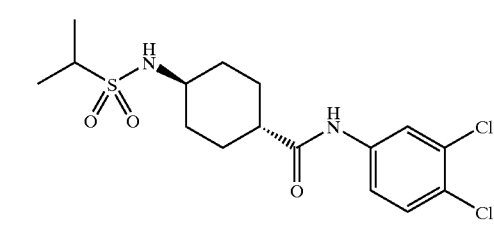
Ib-33
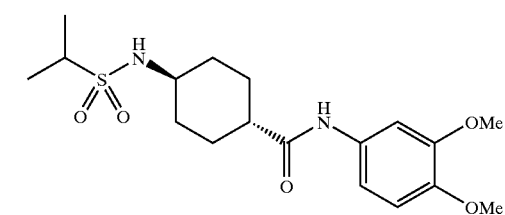
-continued
Ib-34
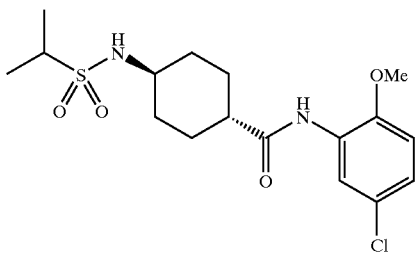
Ib-36
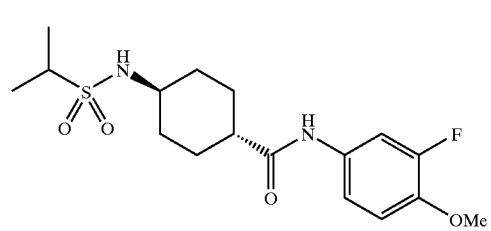
Ib-37
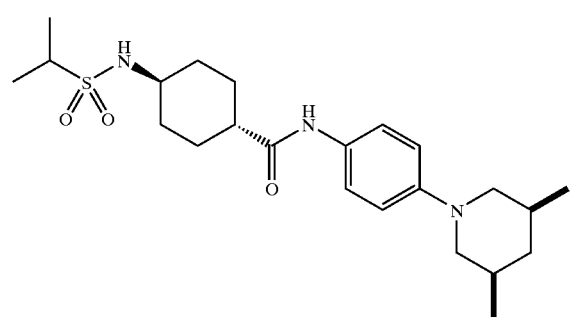
Ib-38
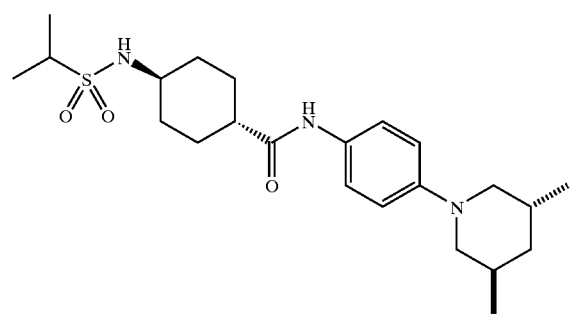
Ib-39
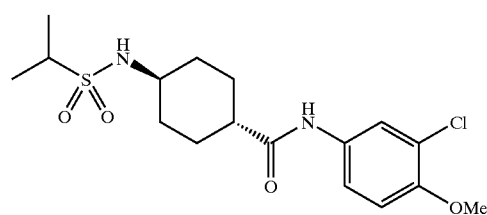

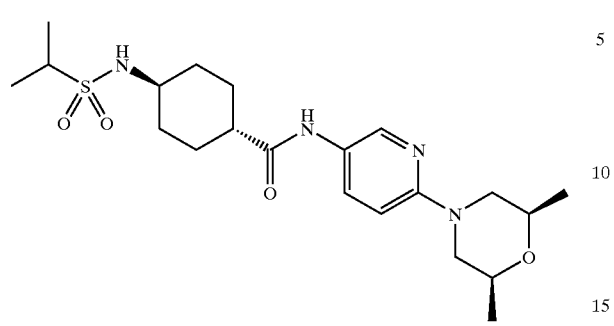
Ib-40
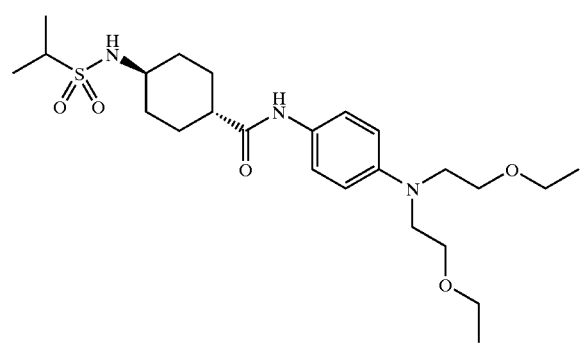
Ib-45
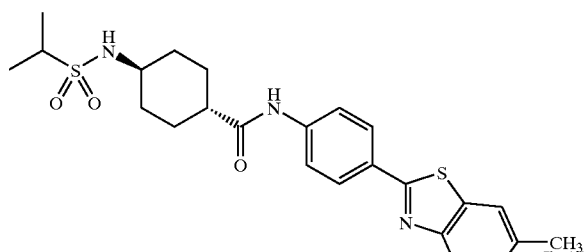
Ib-41
Ib-46
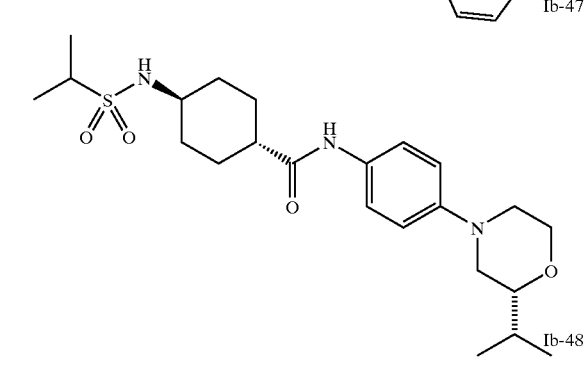
Ib-42
Ib-47
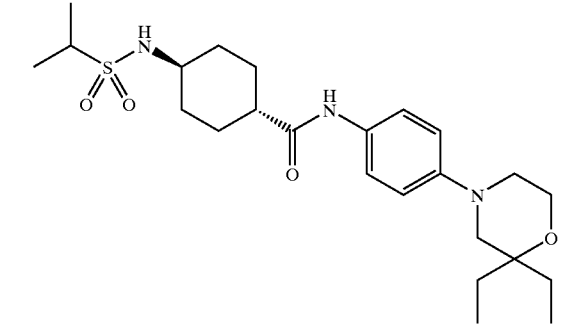
Ib-43
Ib-48
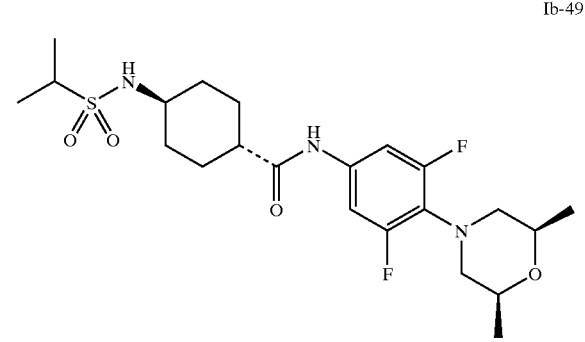
Ib-44
Ib-49

Ib-50
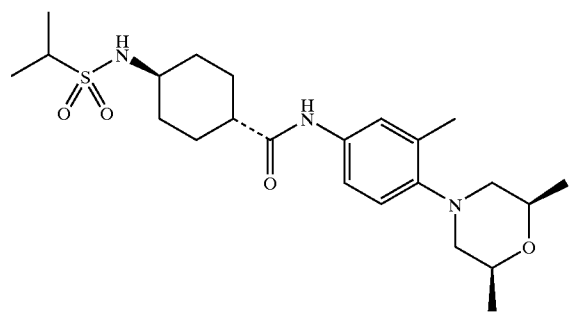
Ib-51
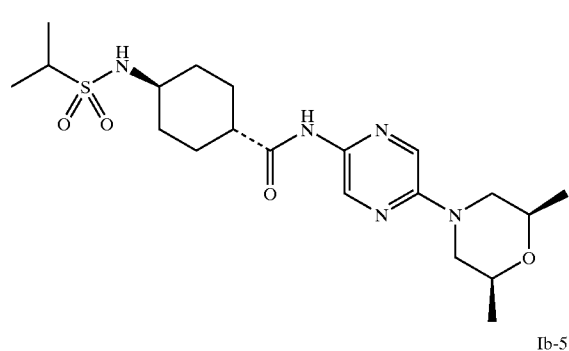
Ib-52
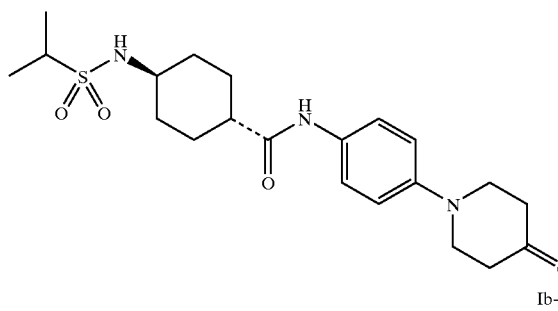
Ib-53
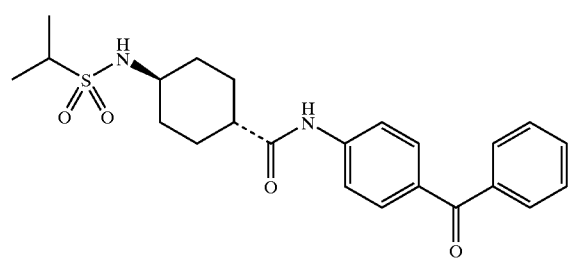
Ib-54
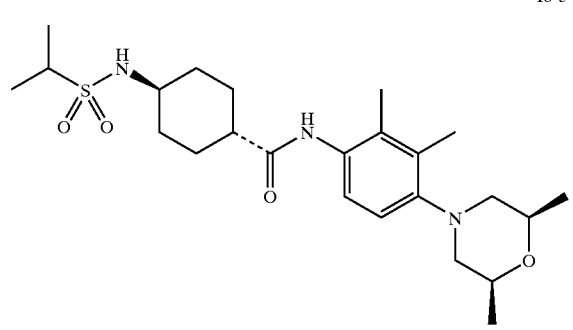
Ib-55
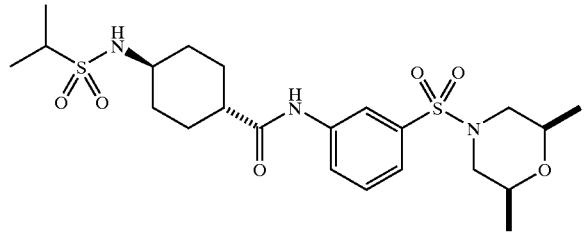
Ib-56
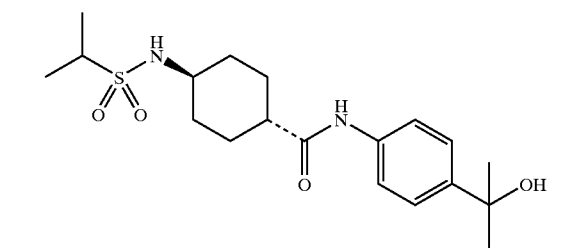
Ib-57
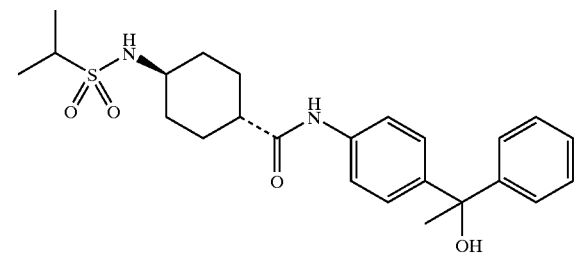
Ib-58
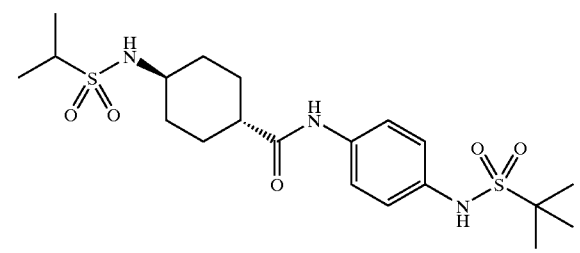
Ib-59
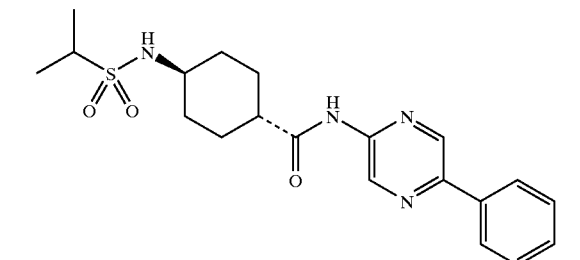
Ib-60

Ib-61
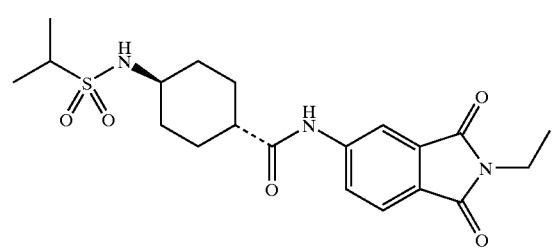
Ib-62
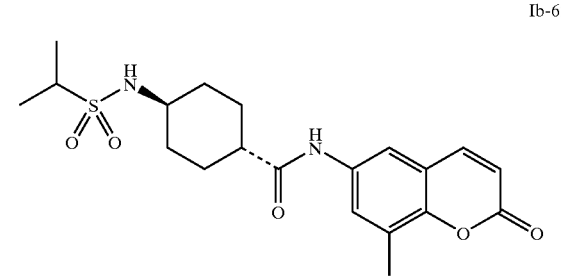
Ib-63
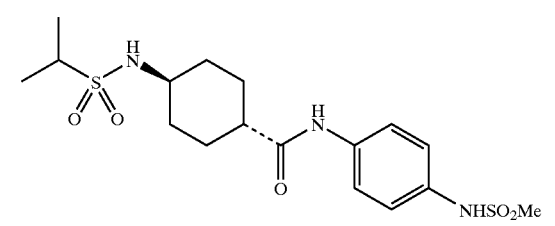
Ib-64
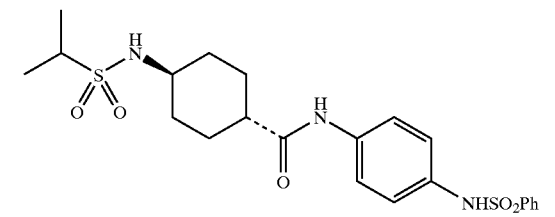
Ib-65
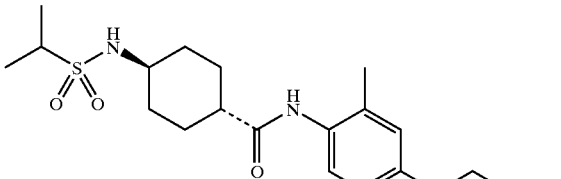
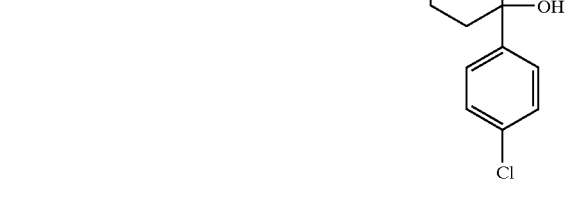
Ib-66
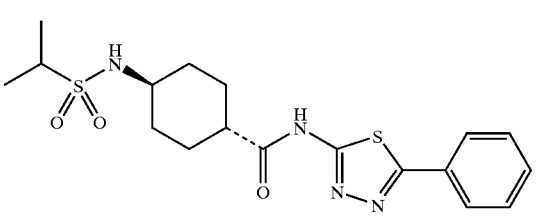
Ib-68
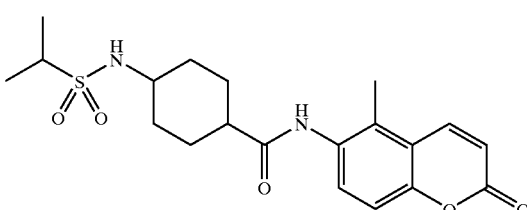
Ib-69
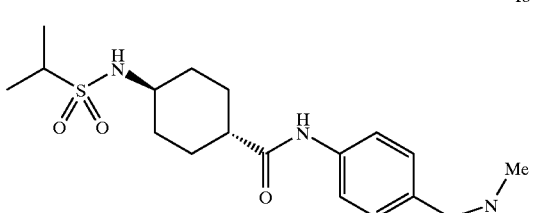
Ib-70
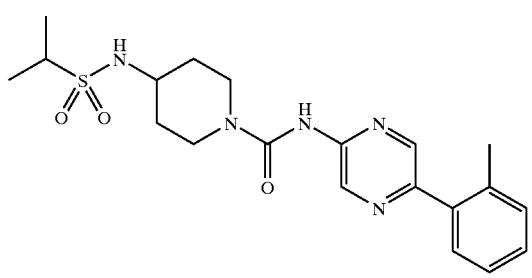
Ib-71
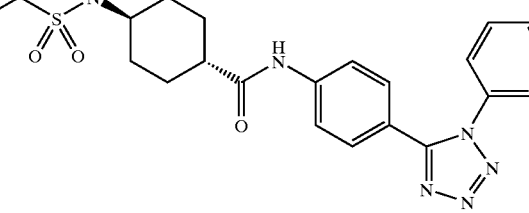
Ib-72
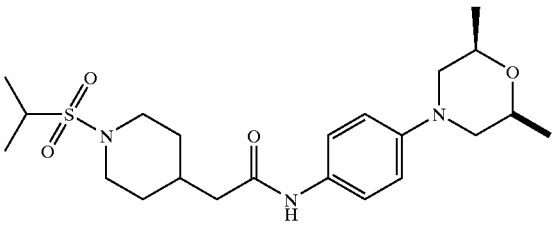

Ib-73
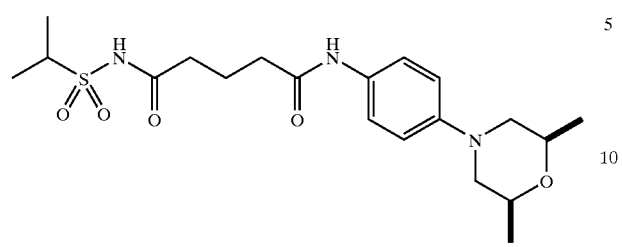
Ib-79
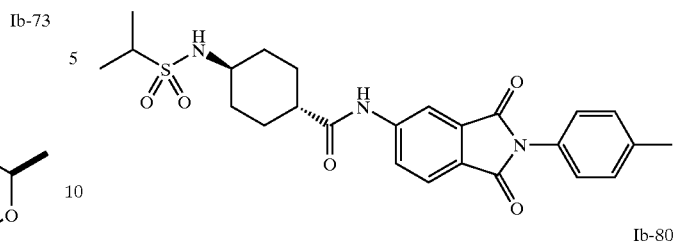
Ib-74
Ib-80
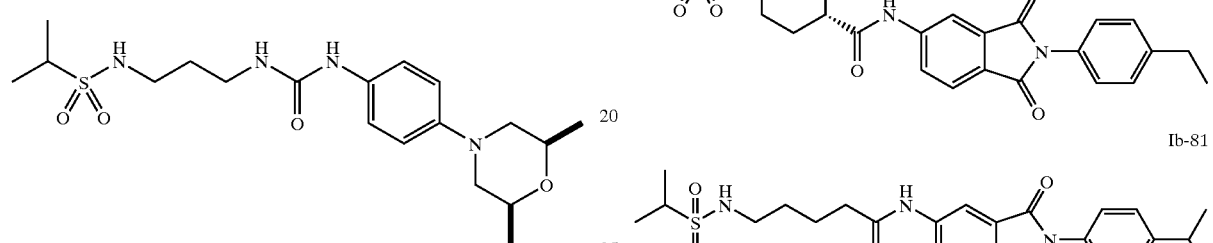
Ib-75
Ib-81
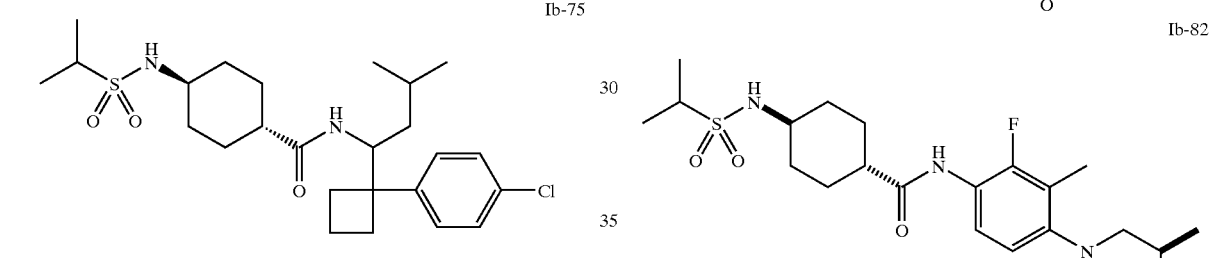
Ib-76
Ib-82
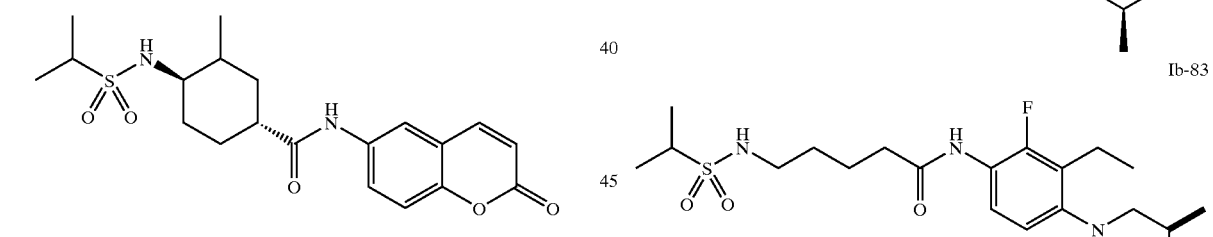
Ib-77
Ib-83
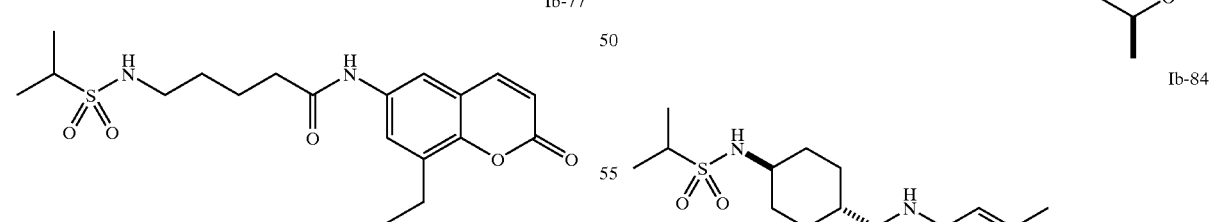
Ib-78
Ib-84
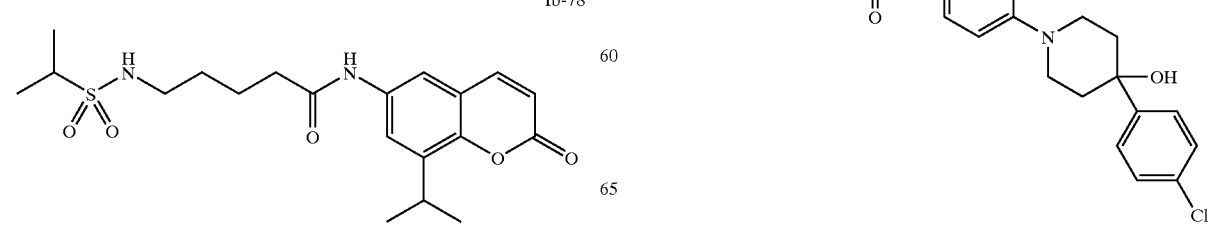

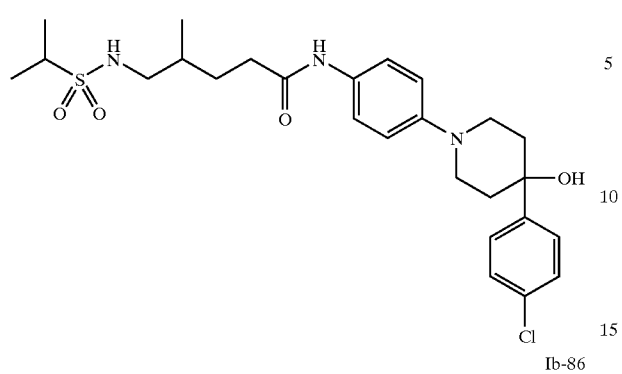
Ib-85
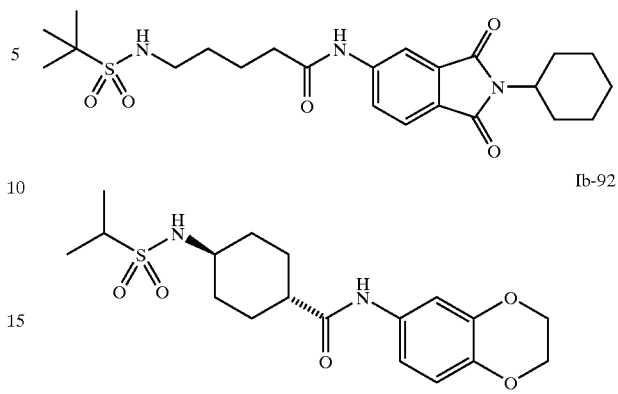
Ib-91
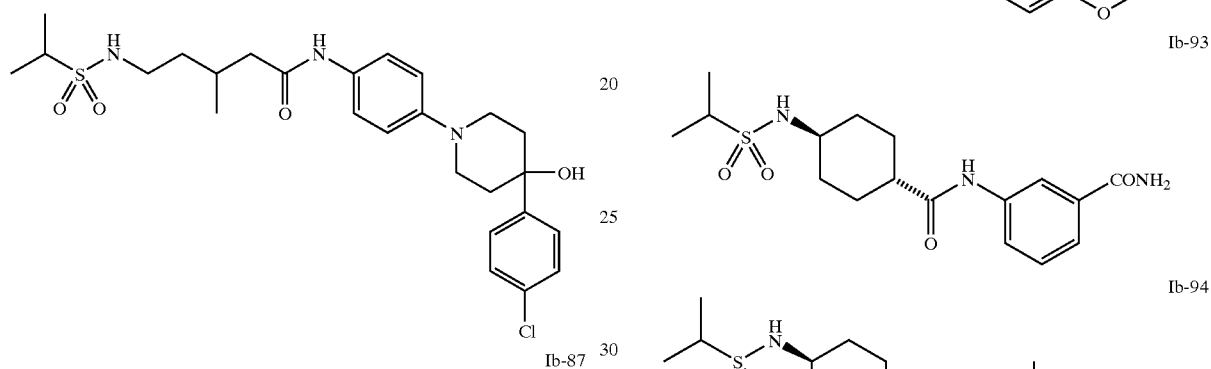
Ib-86 / Ib-92
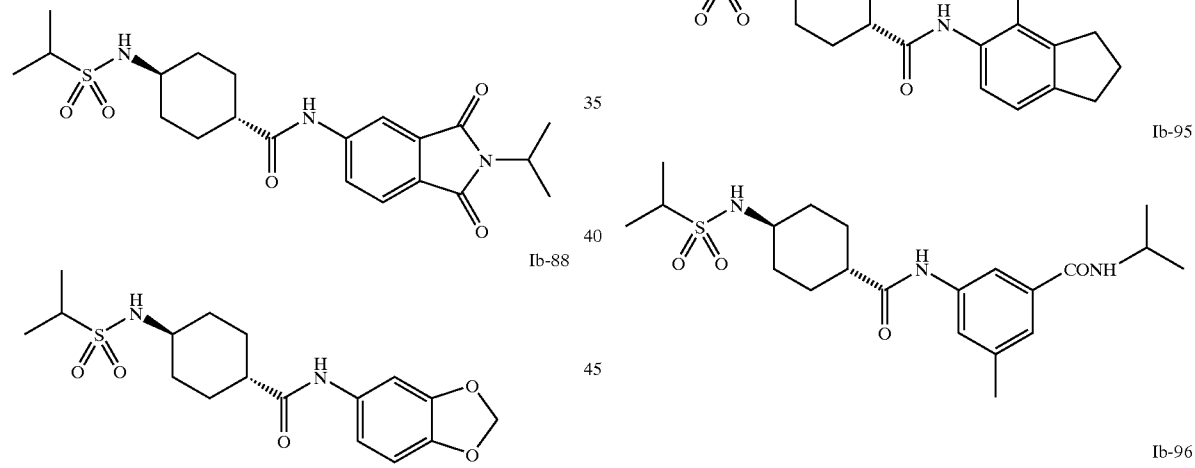
Ib-87 / Ib-93 / Ib-94
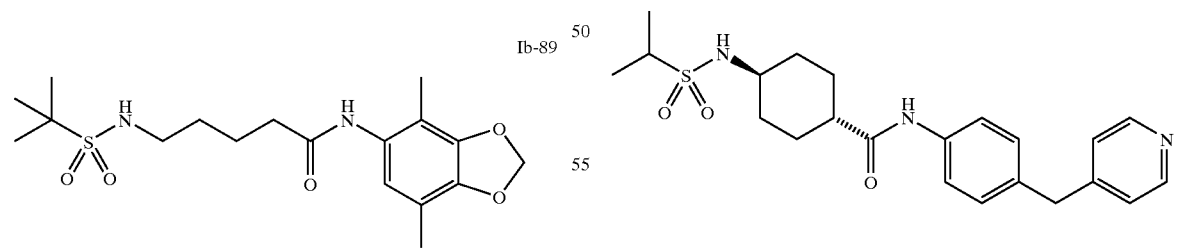
Ib-89 / Ib-95
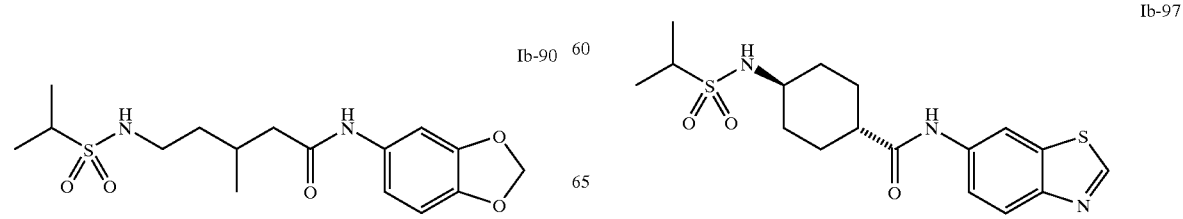
Ib-90 / Ib-96 / Ib-97

-continued
Ib-98
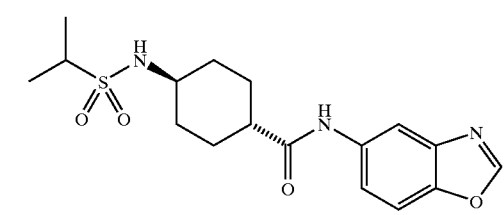
Ib-99
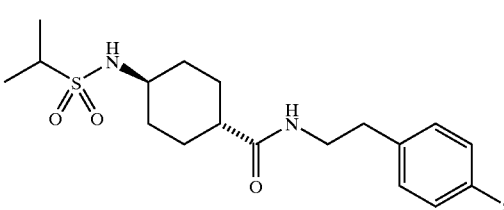
Ib-100
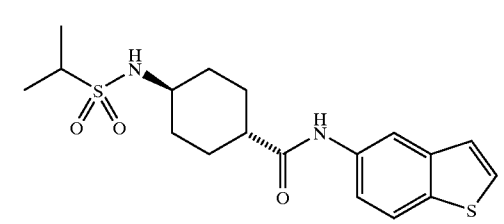
Ib-101
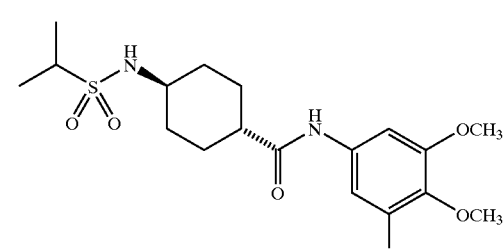
Ib-102
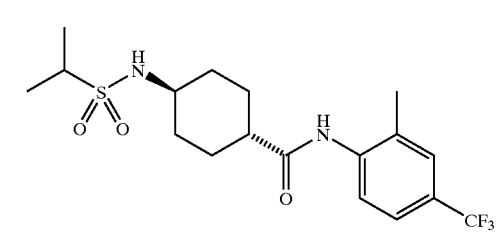
Ib-103
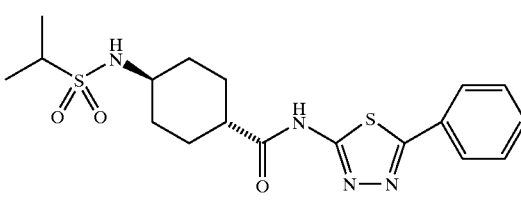
Ib-104
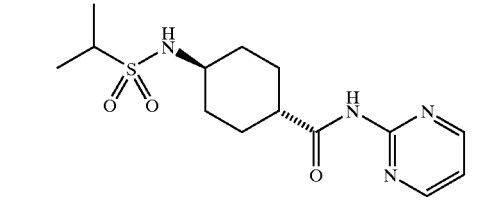
-continued
Ib-105
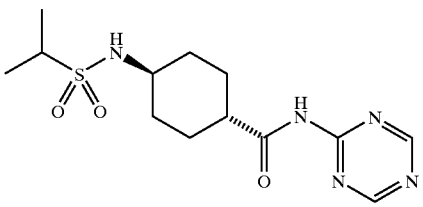
Ib-106
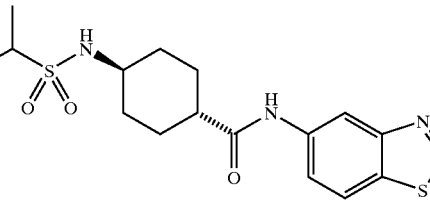
Ib-107
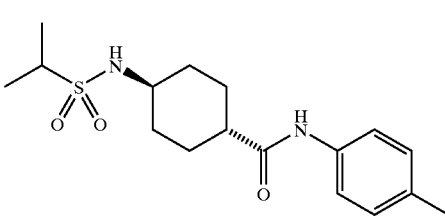
Ib-108
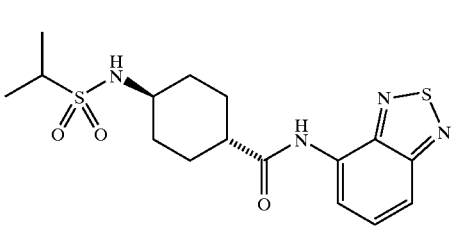
Ib-109
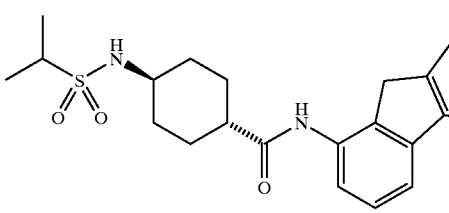
Ib-110
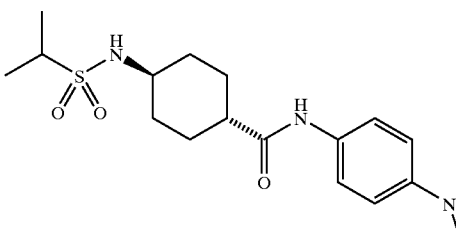
Ib-111
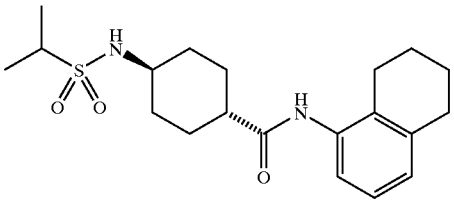

Ib-112
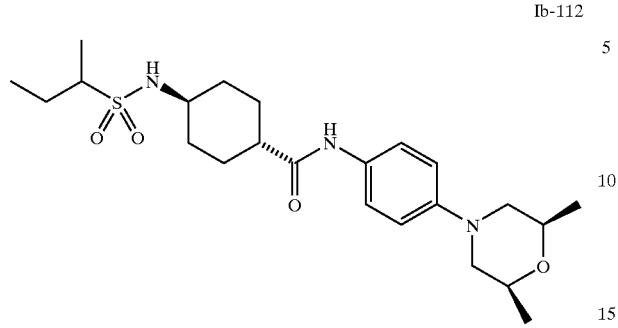
Ib-118
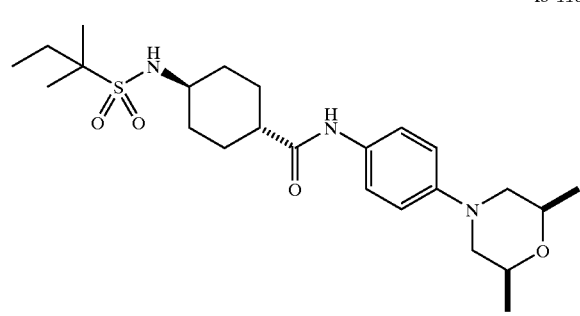
Ib-113
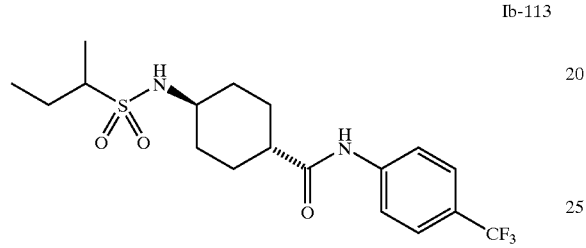
Ib-119
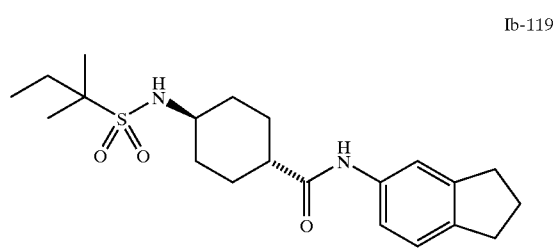
Ib-114
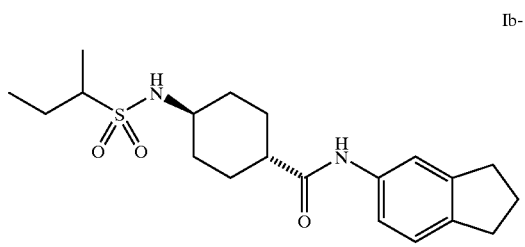
Ib-120
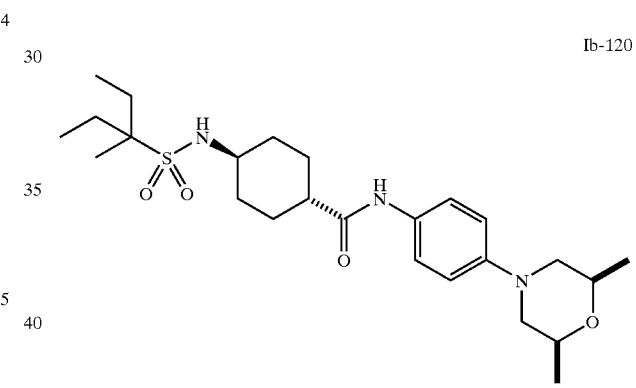
Ib-115
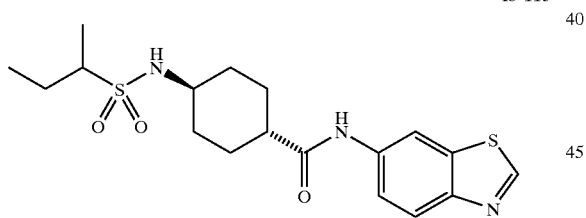
Ib-121
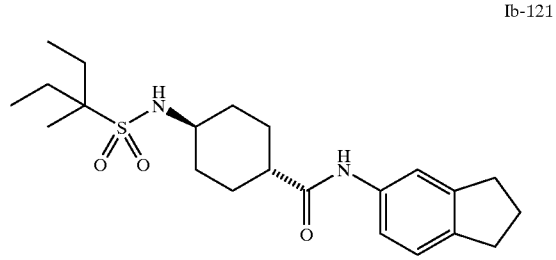
Ib-116
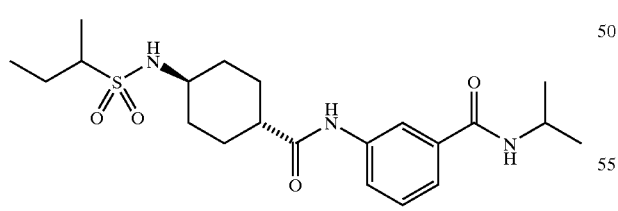
Ib-122
Ib-117
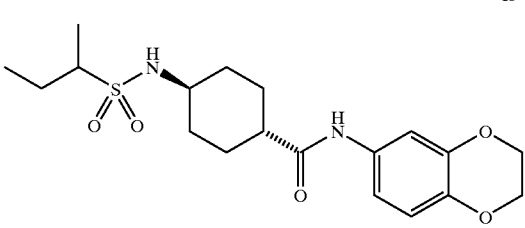

-continued
Ib-123
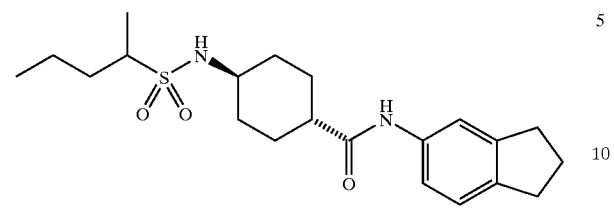
Ib-124
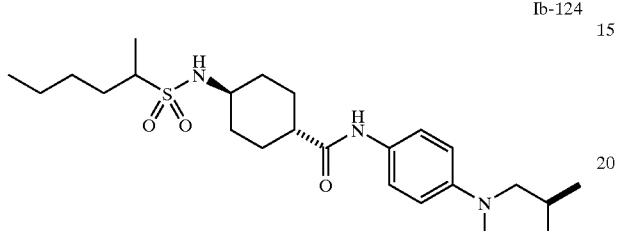
Ib-125
Ib-126
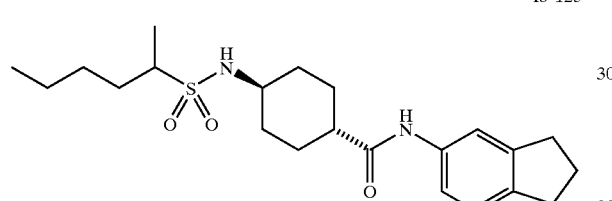
Ib-127
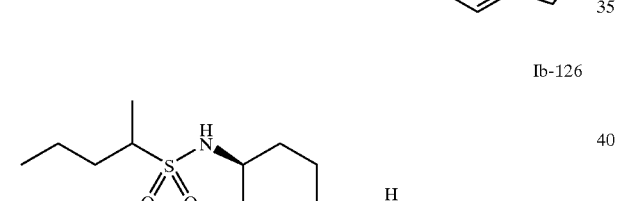
Ib-128
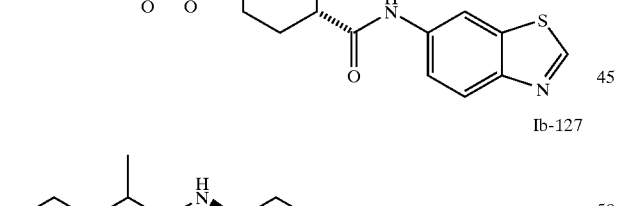
Ib-129
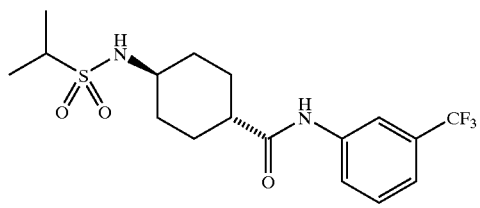
Ib-130
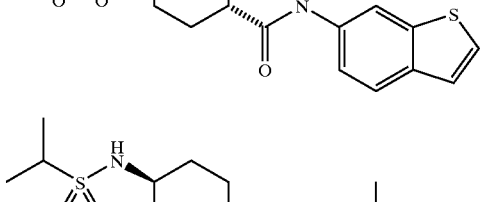
Ib-131
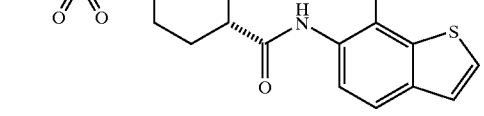
Ib-132
Ib-133
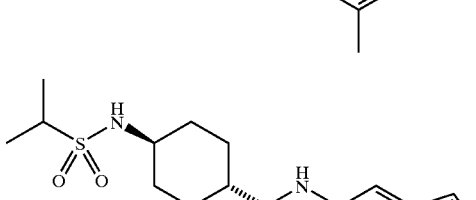
Ib-134
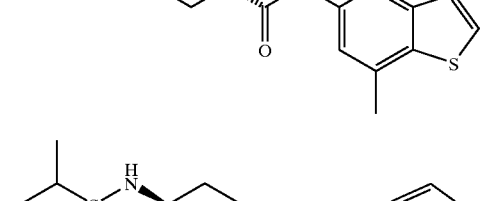
Ib-135
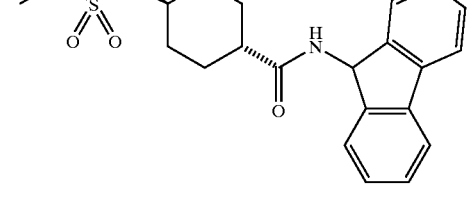
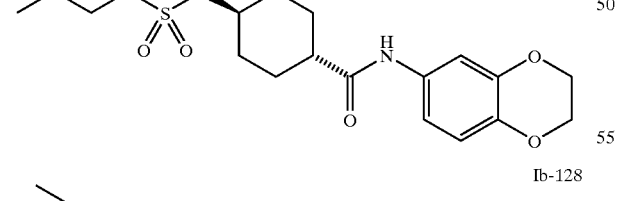
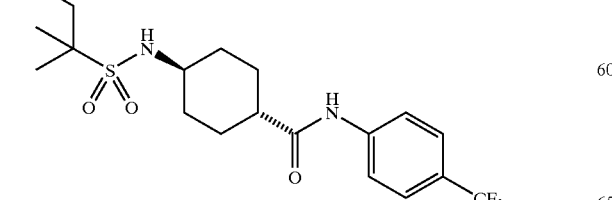
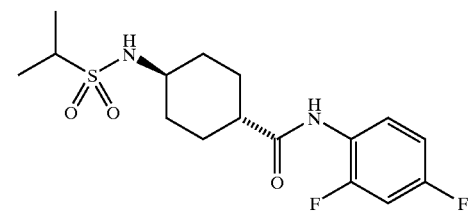

Ib-136
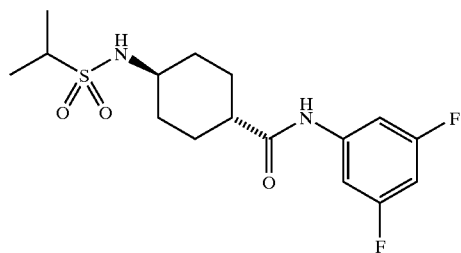
Ib-137
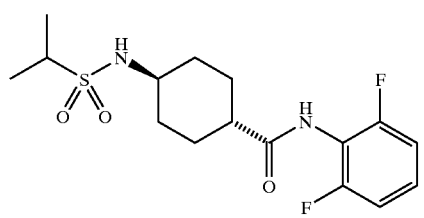
Ib-138
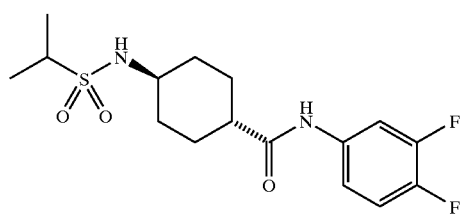
Ib-139
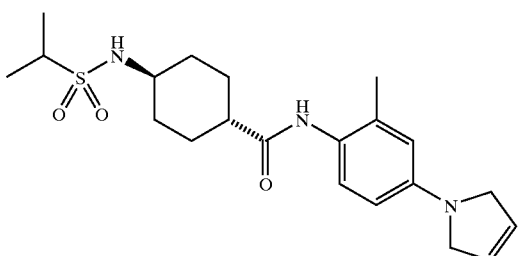
Ib-140
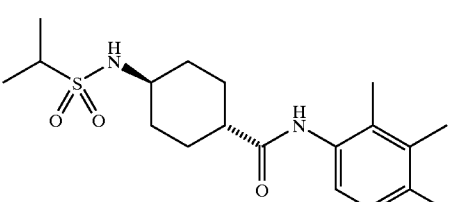
Ib-141
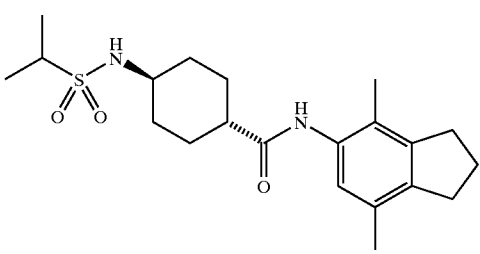
Ib-142
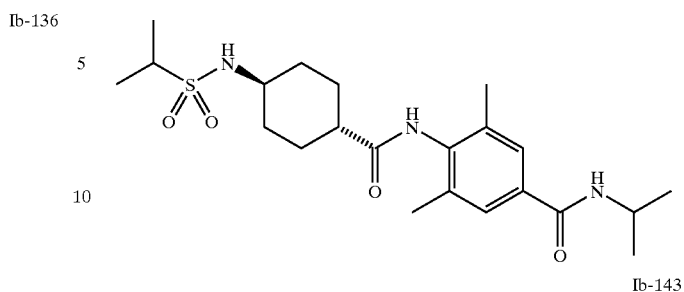
Ib-143
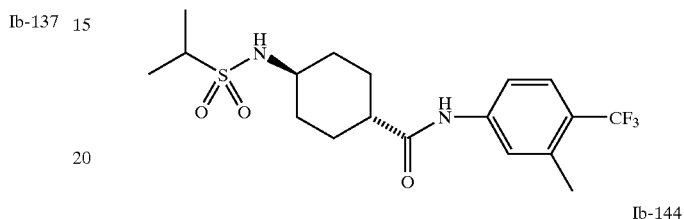
Ib-144
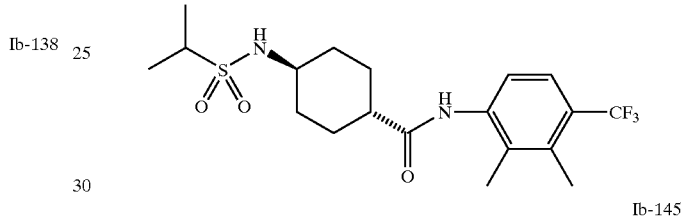
Ib-145
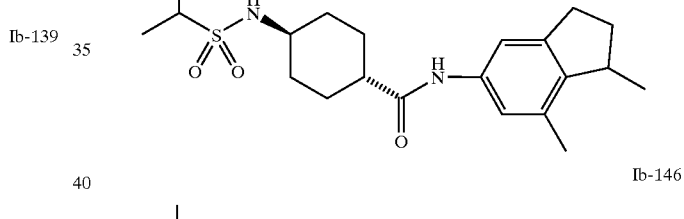
Ib-146
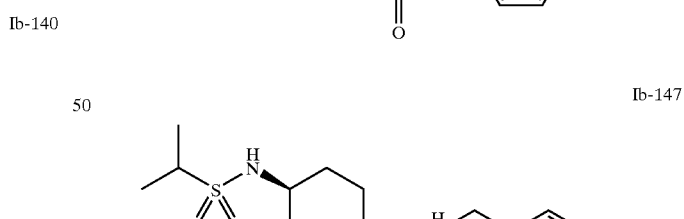
Ib-147
Ib-148
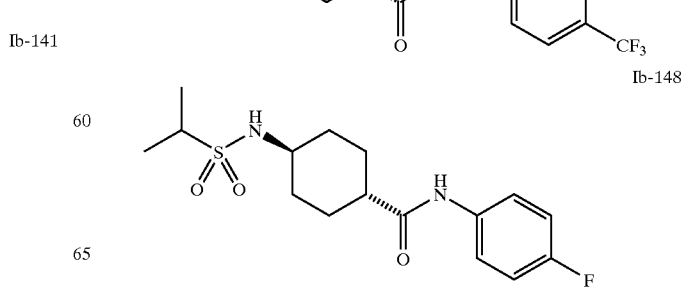

-continued
Ib-149
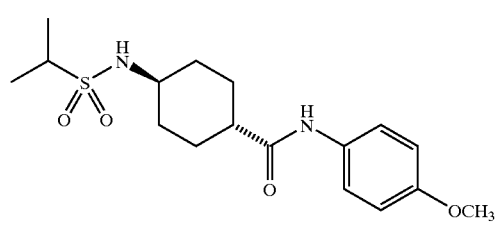
Ib-150
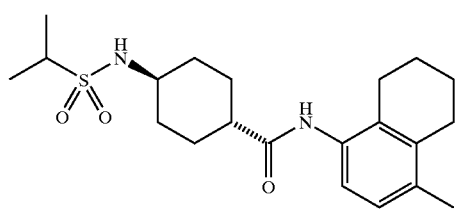
Ib-151
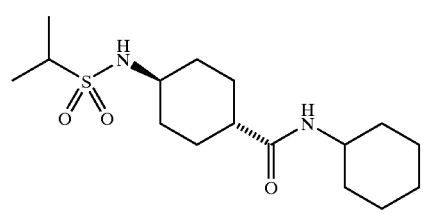
Ib-152
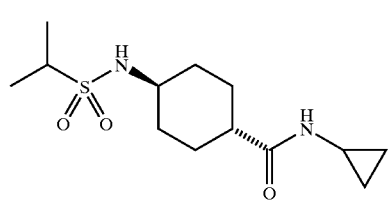
Ib-153
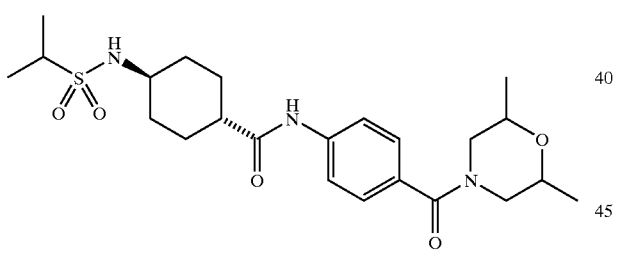
Ib-154
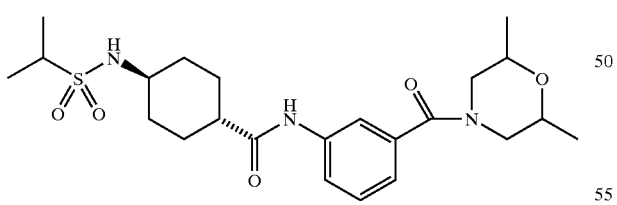
Ib-155
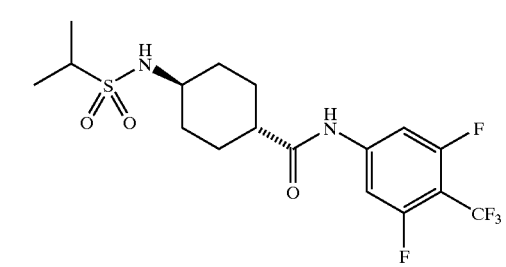
-continued
Ib-156
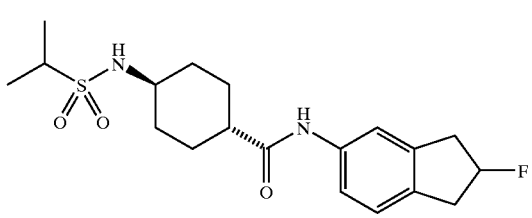
Ib-157
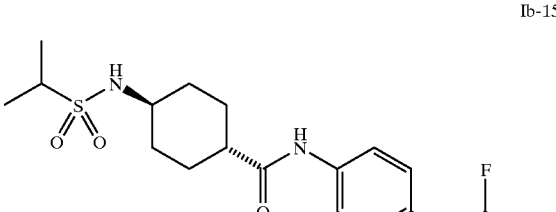
Ib-158
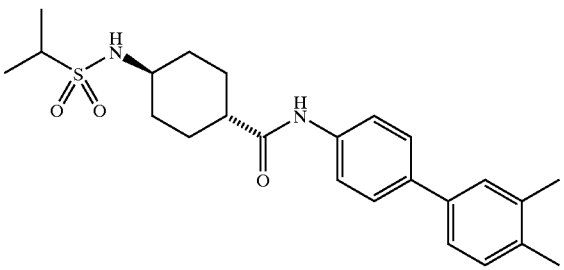
Ib-159
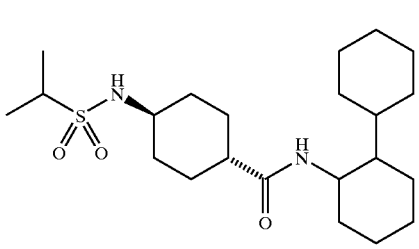
Ib-160
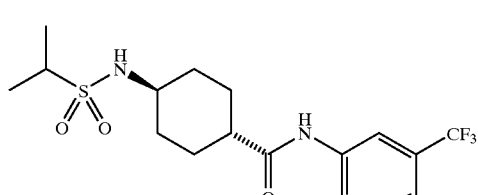
Ib-161
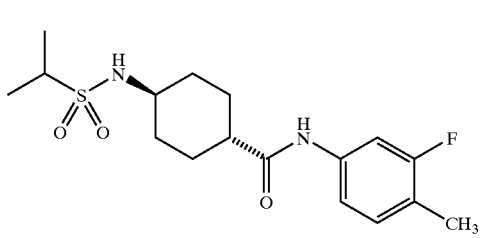

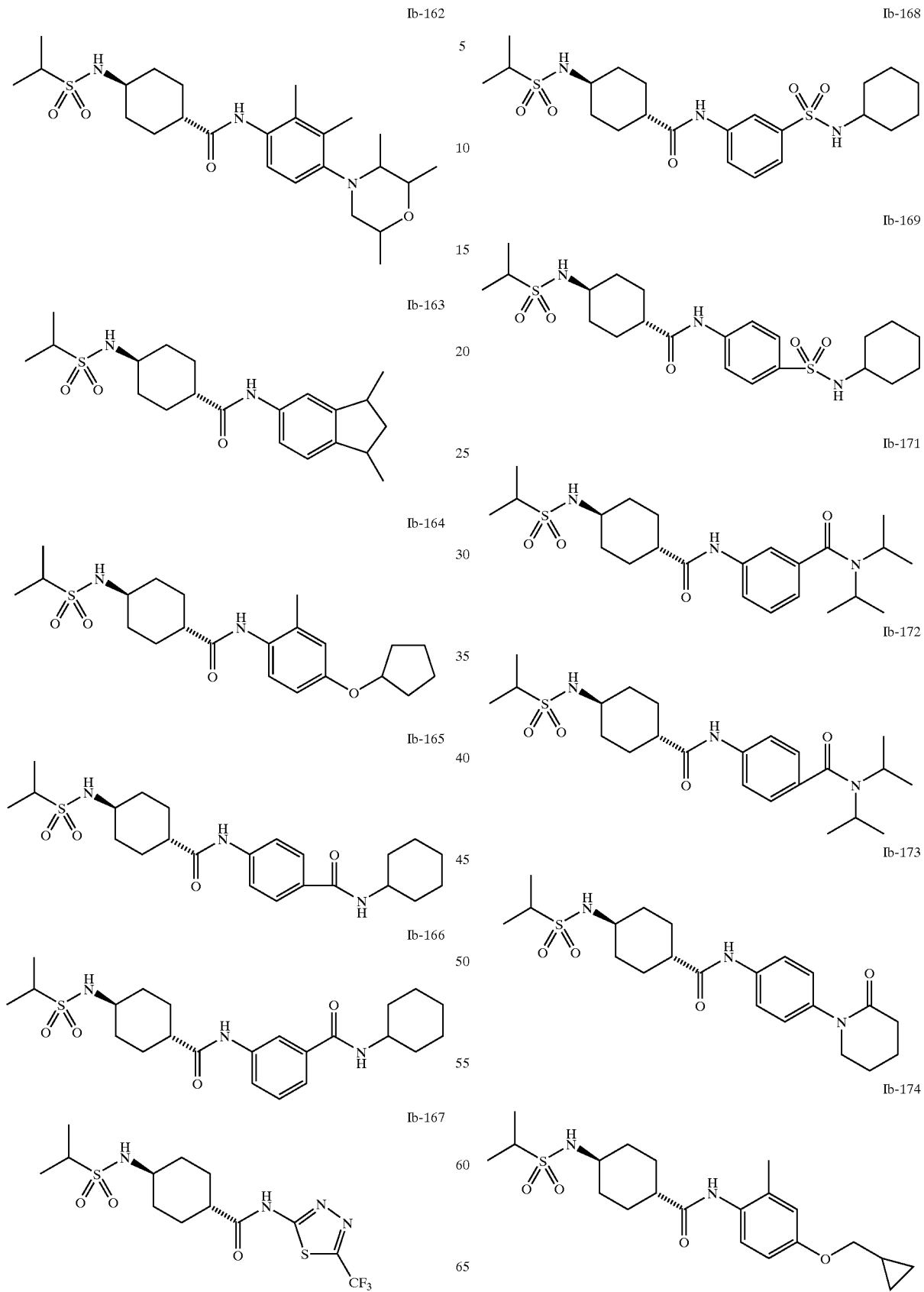

Ib-175
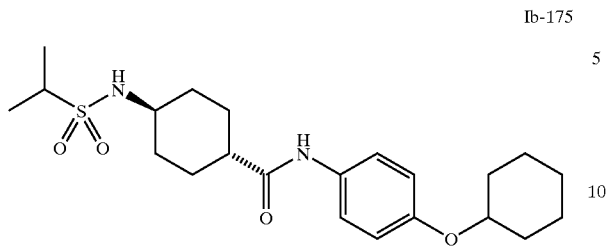
Ib-181
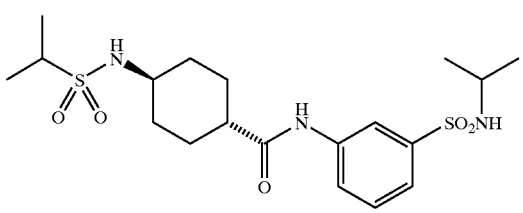
Ib-176
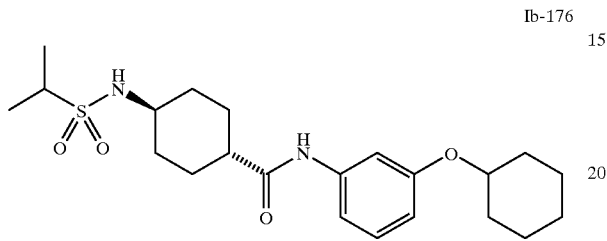
Ib-182
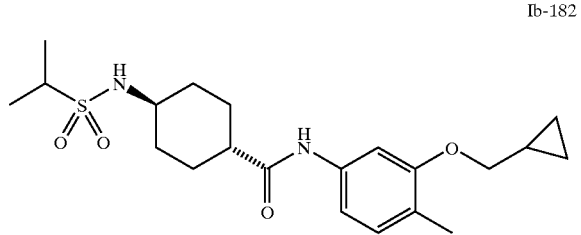
Ib-177
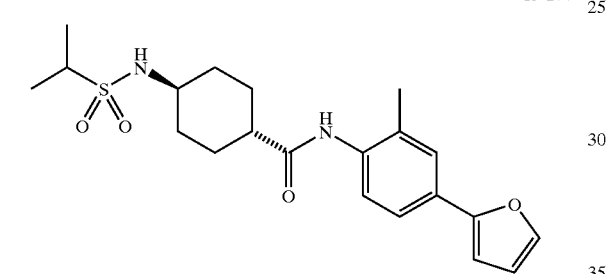
Ib-183
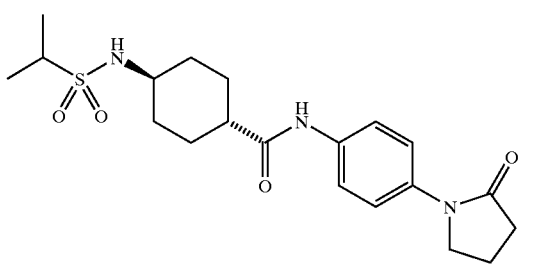
Ib-178
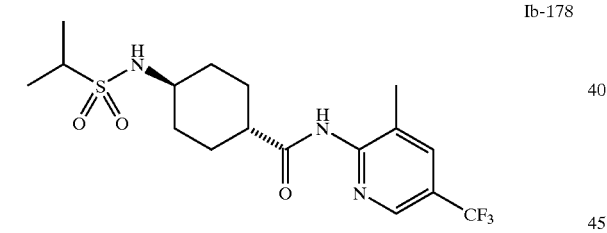
Ib-184
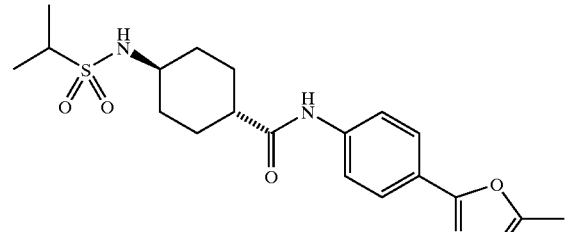
Ib-179
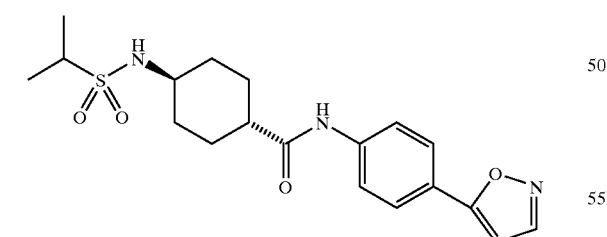
Ib-185
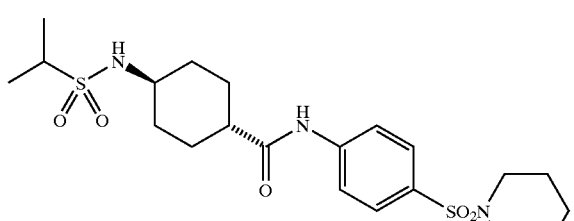
Ib-180
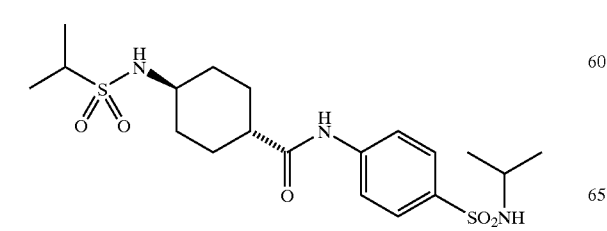
Ib-186
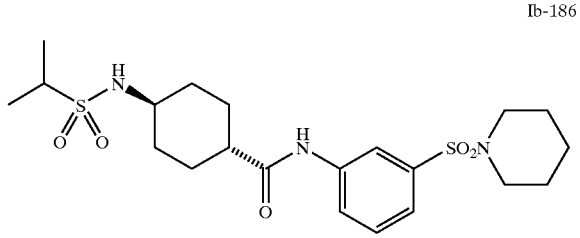

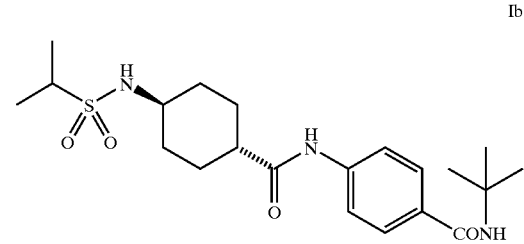
Ib-187
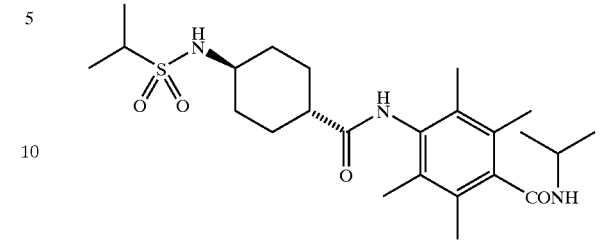
Ib-193
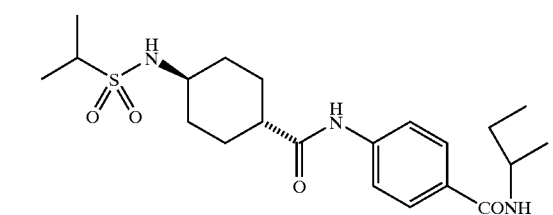
Ib-188
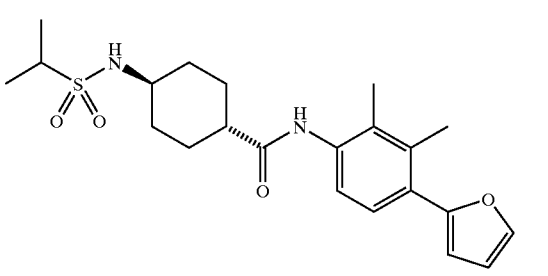
Ib-194
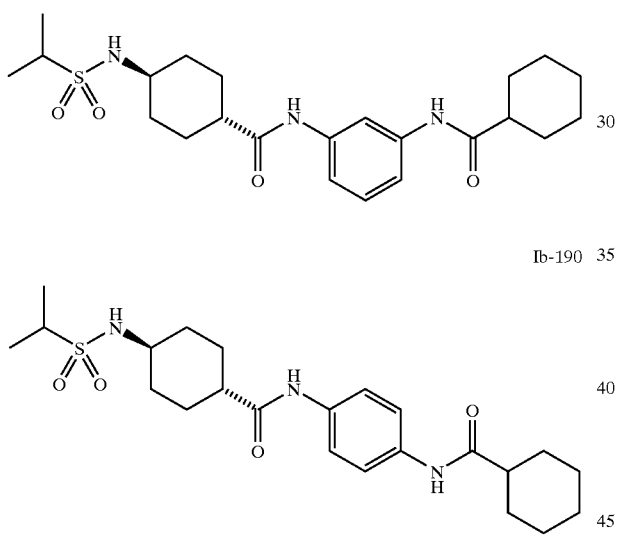
Ib-189
Ib-190
Ib-191
Ib-192
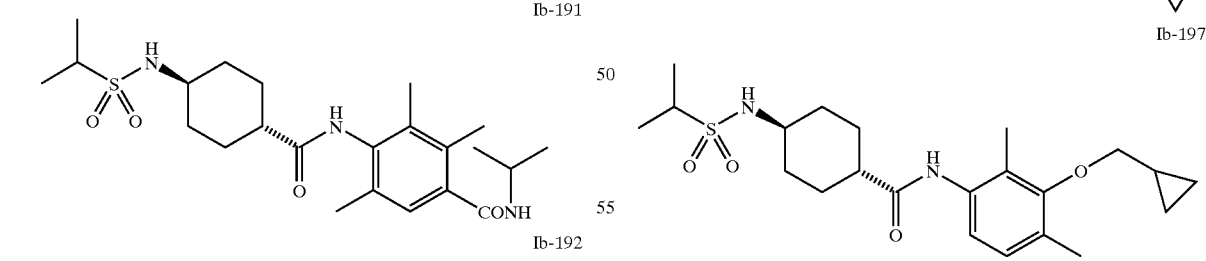
Ib-195
Ib-196
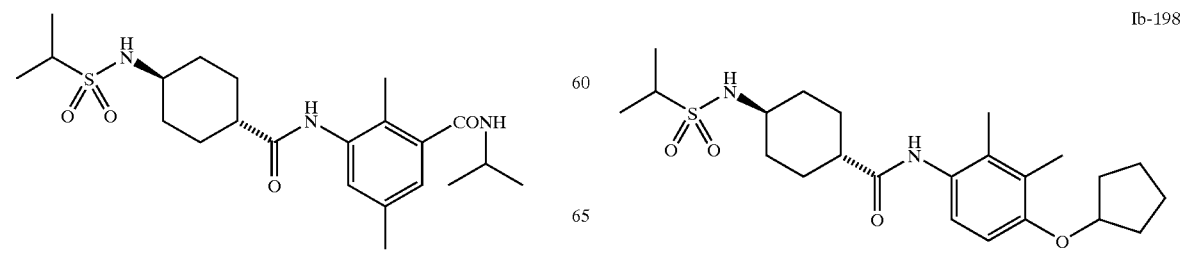
Ib-197
Ib-198

-continued
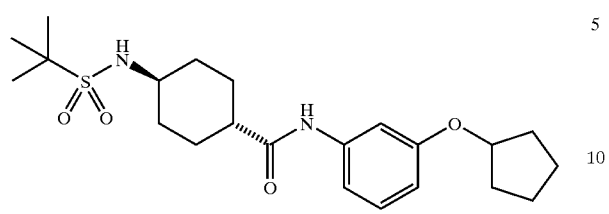
Ib-199
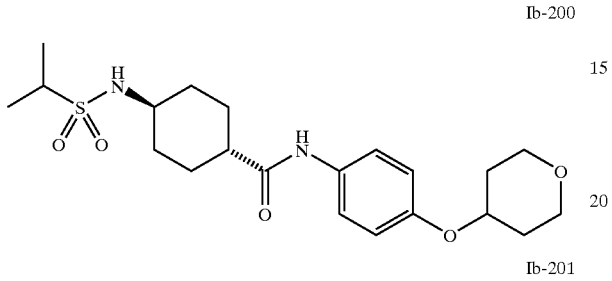
Ib-200
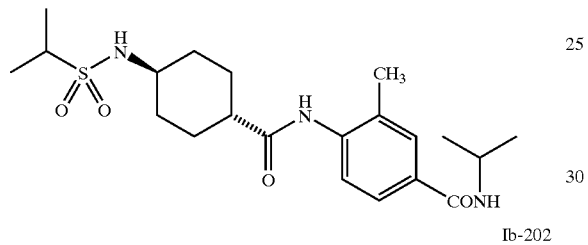
Ib-201
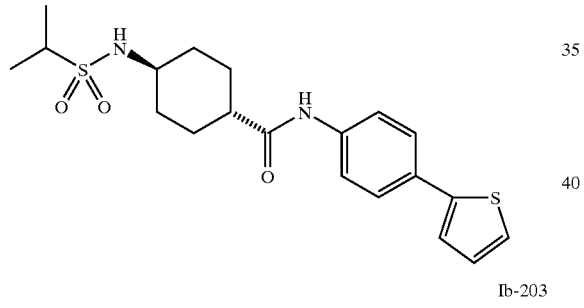
Ib-202
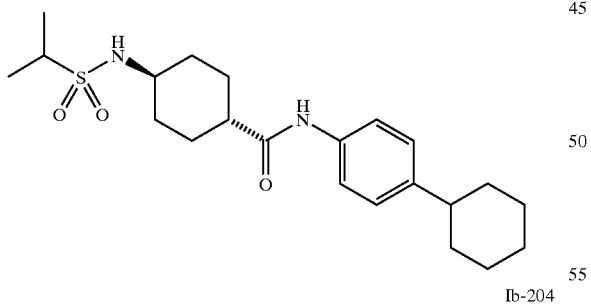
Ib-203
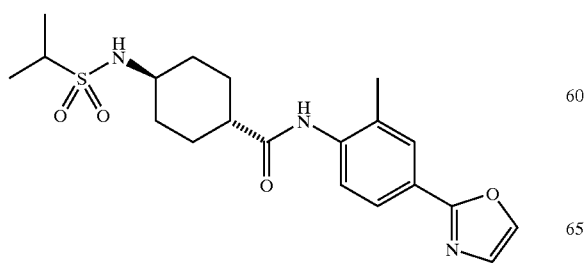
Ib-204
-continued
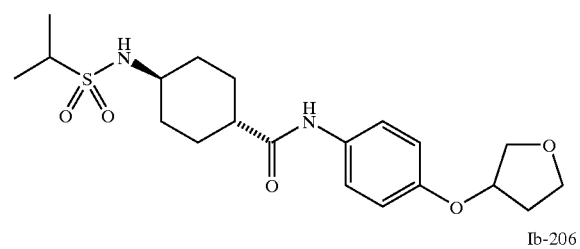
Ib-205
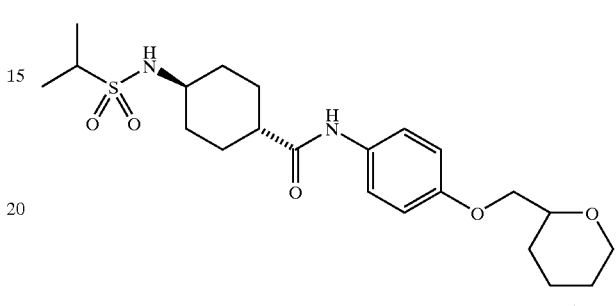
Ib-206
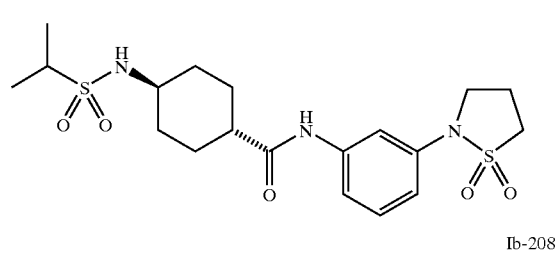
Ib-207
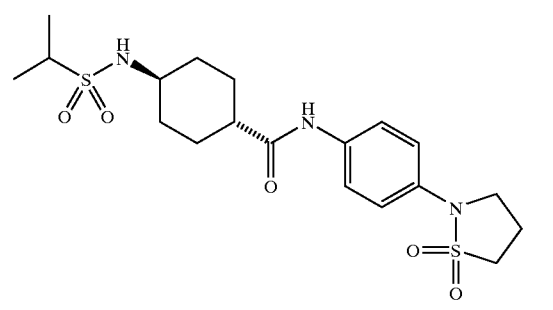
Ib-208
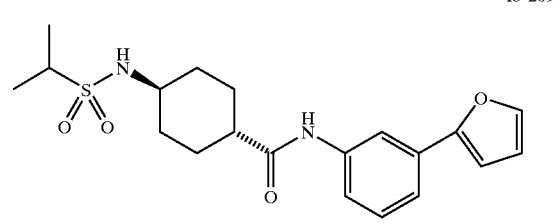
Ib-209
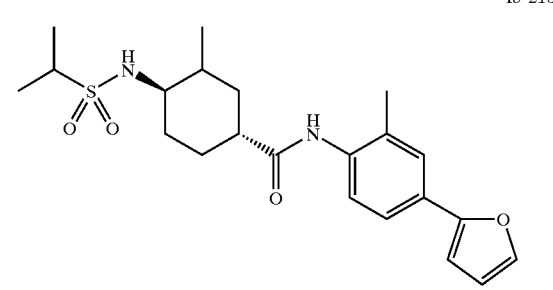
Ib-210

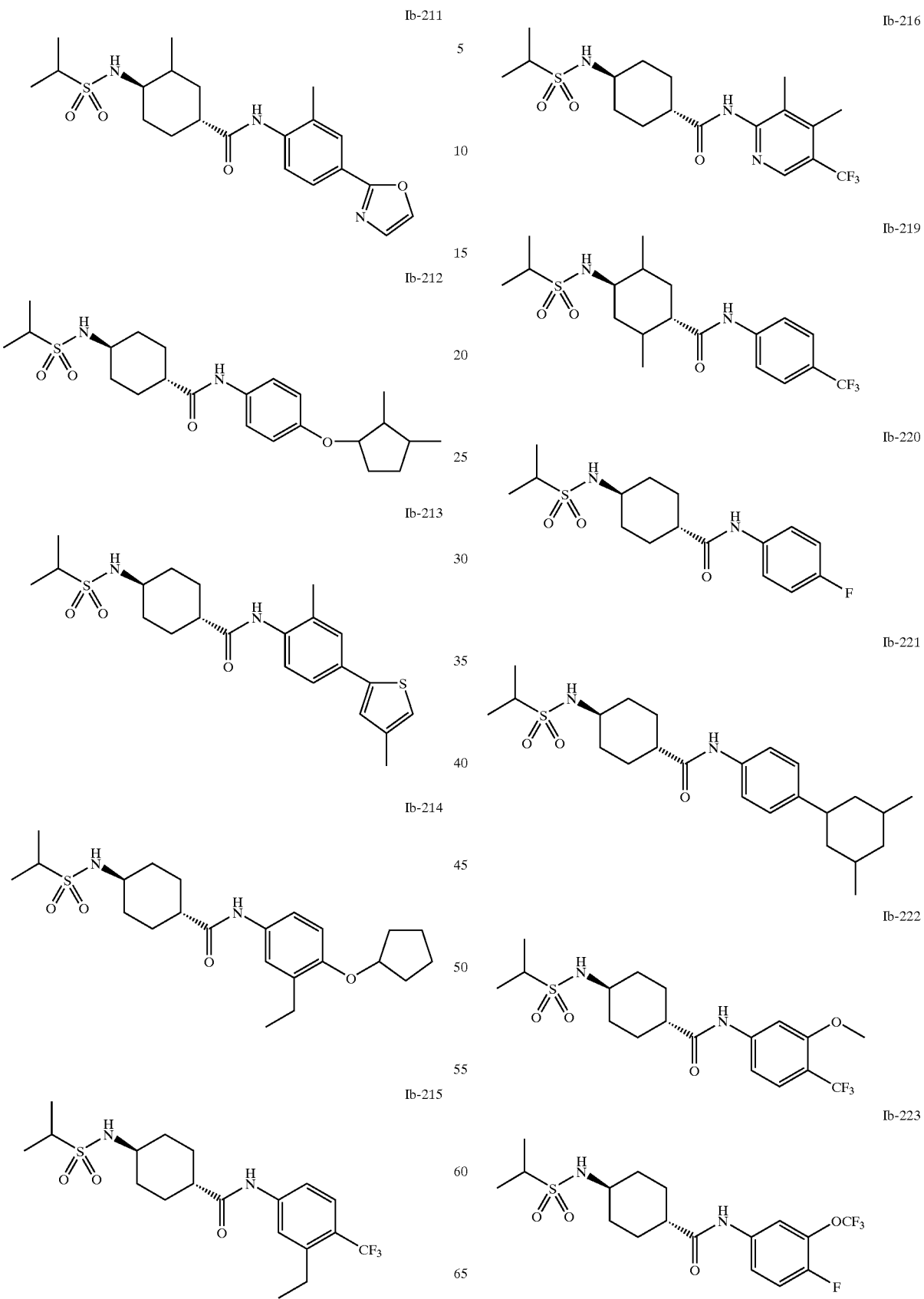

Ib-224
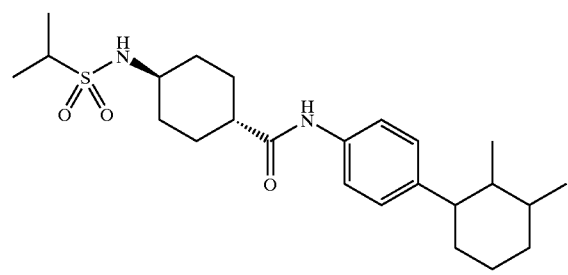
Ib-225
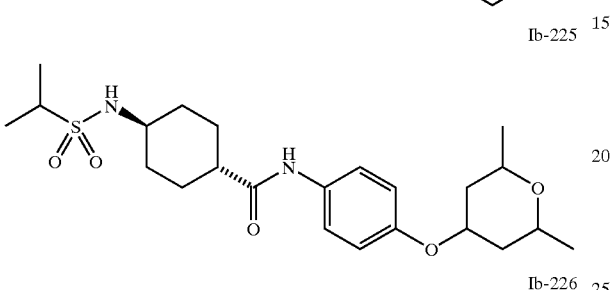
Ib-226
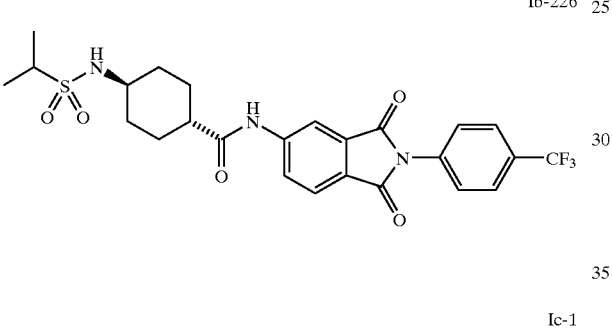
Ic-1
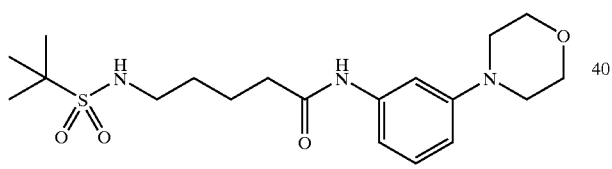
Ic-2
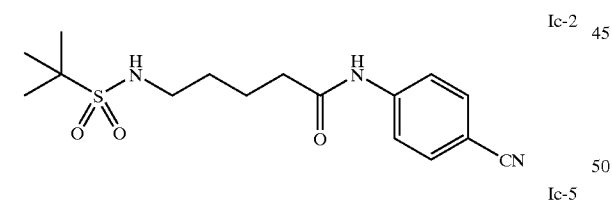
Ic-5
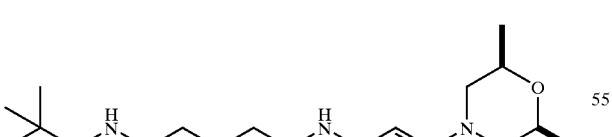
Ic-7
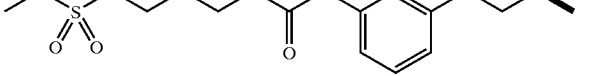
-continued
Ic-8
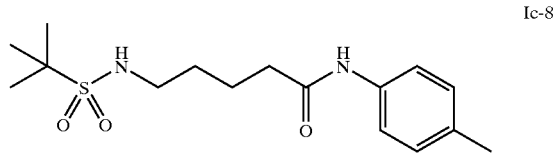
Ic-9
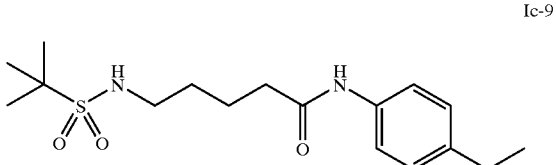
Ic-10
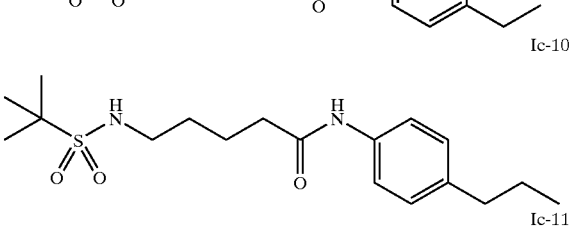
Ic-11
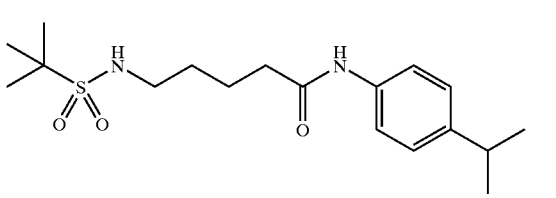
Ic-12
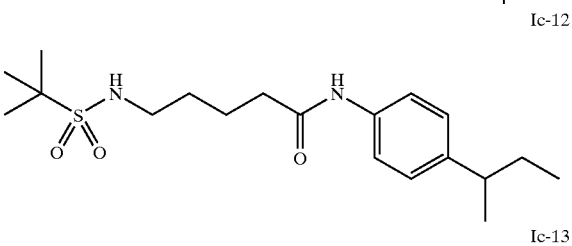
Ic-13
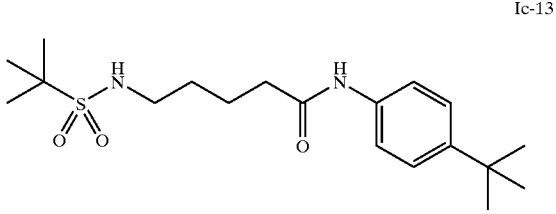
Ic-14
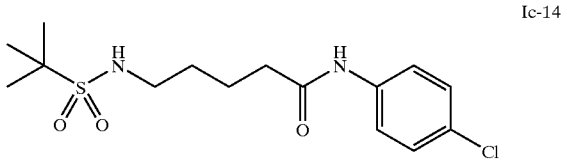
Ic-16
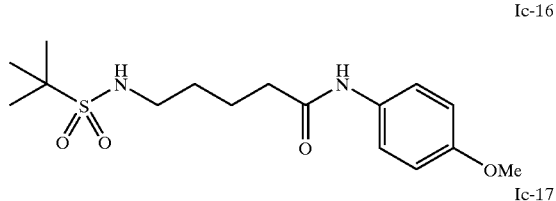
Ic-17
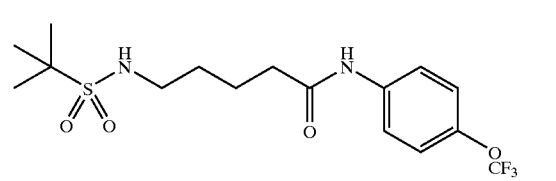

Ic-18
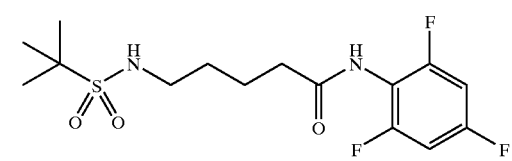
Ic-19
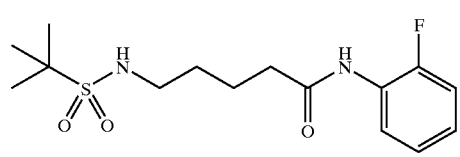
Ic-20
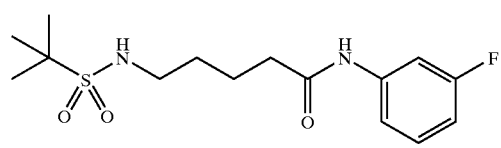
Ic-21
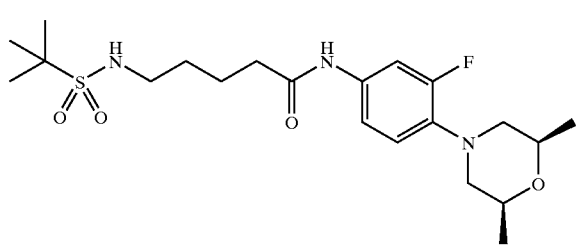
Ic-22
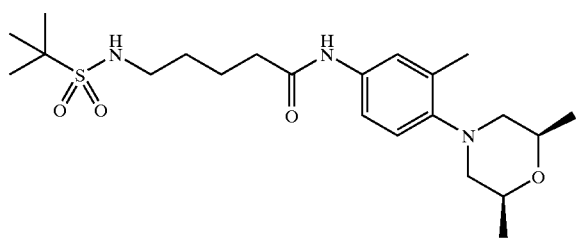
Ic-23
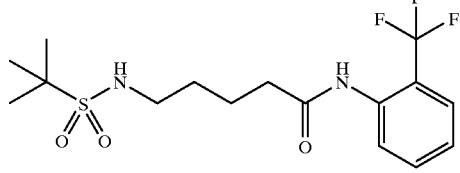
Ic-24
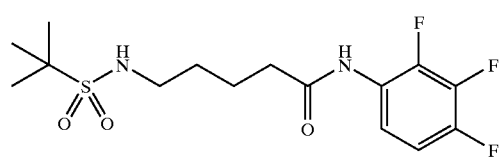
Ic-25
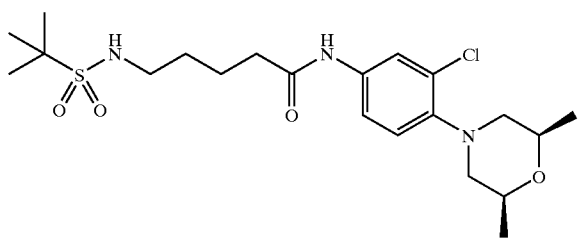
Ic-26
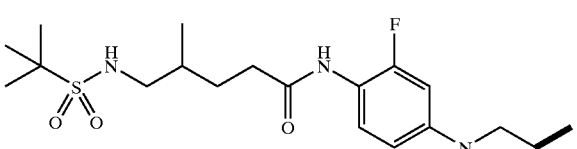
Ic-27
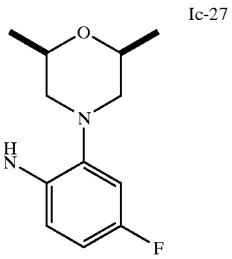
Ic-28
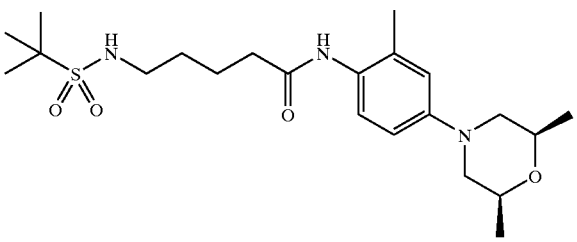
Ic-29
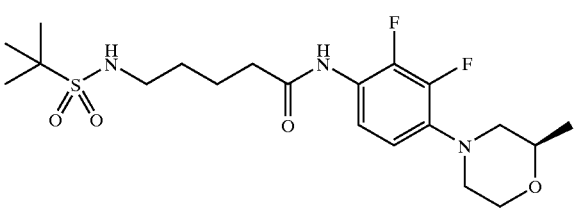
Ic-30
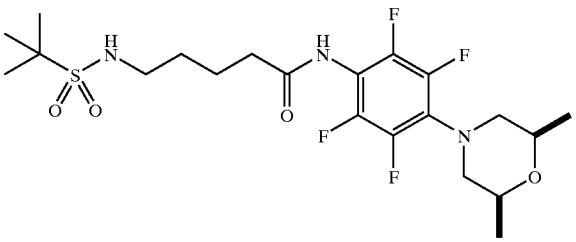
Ic-31
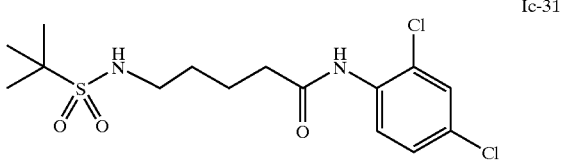
Ic-32
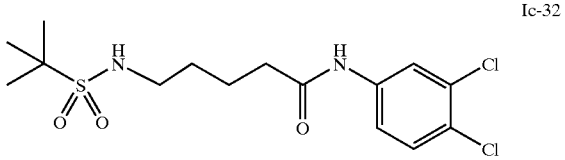

Ic-33
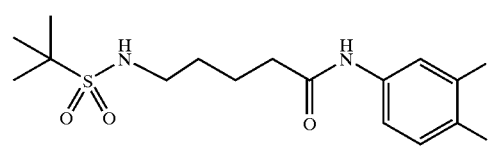
Ic-35
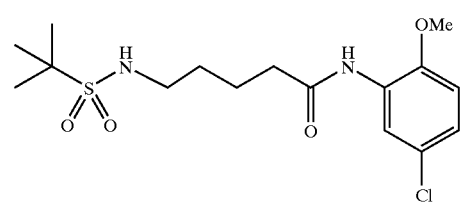
Ic-36
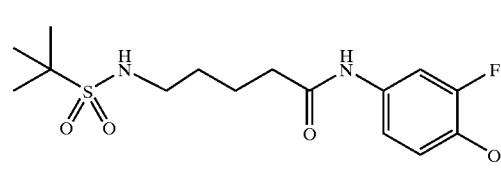
Ic-37
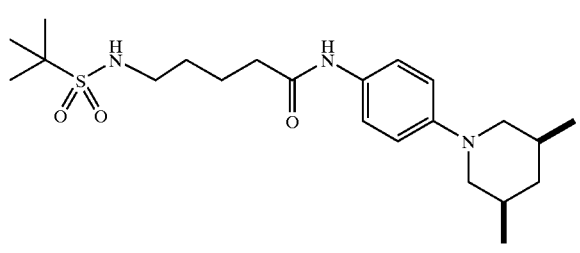
Ic-38
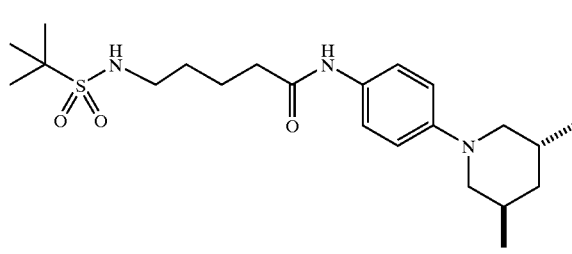
Ic-39
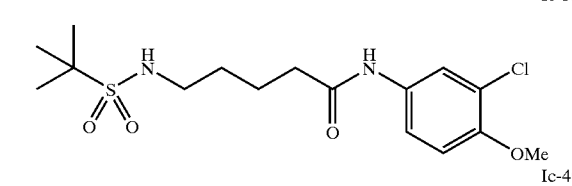
Ic-40
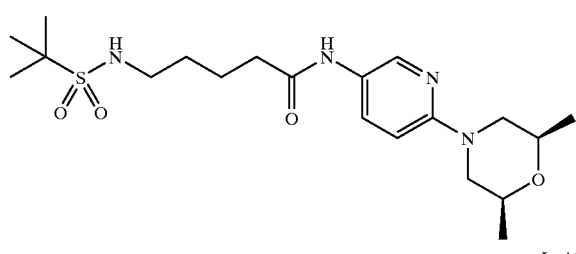
Ic-41
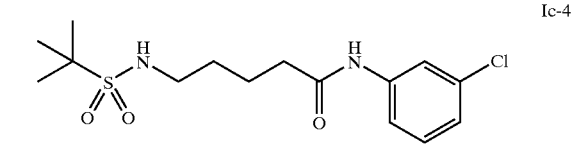
Ic-42
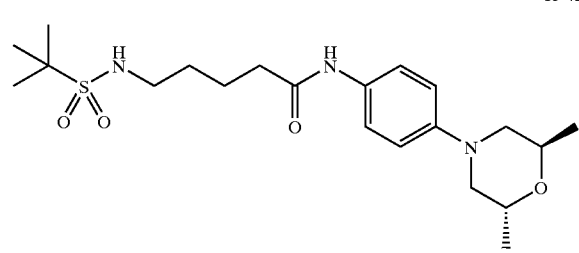
Ic-43
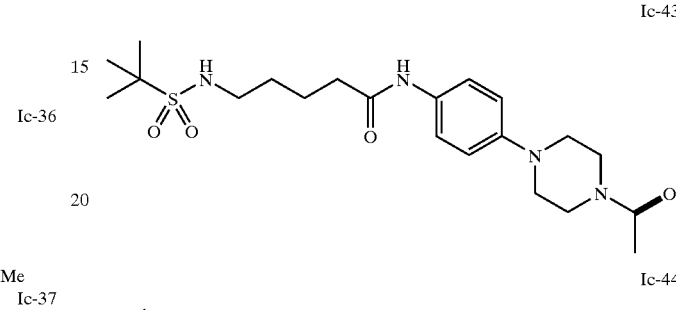
Ic-44
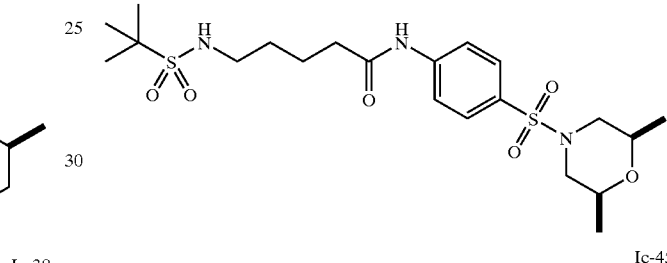
Ic-45
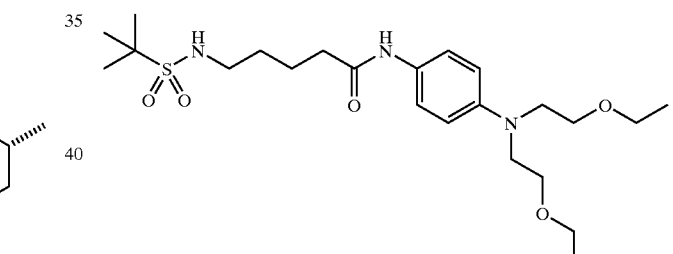
Ic-46
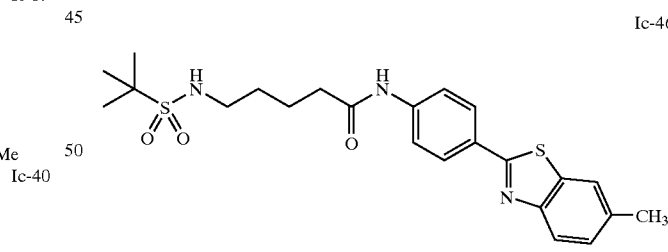
Ic-47
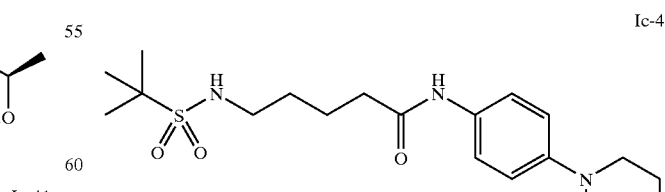

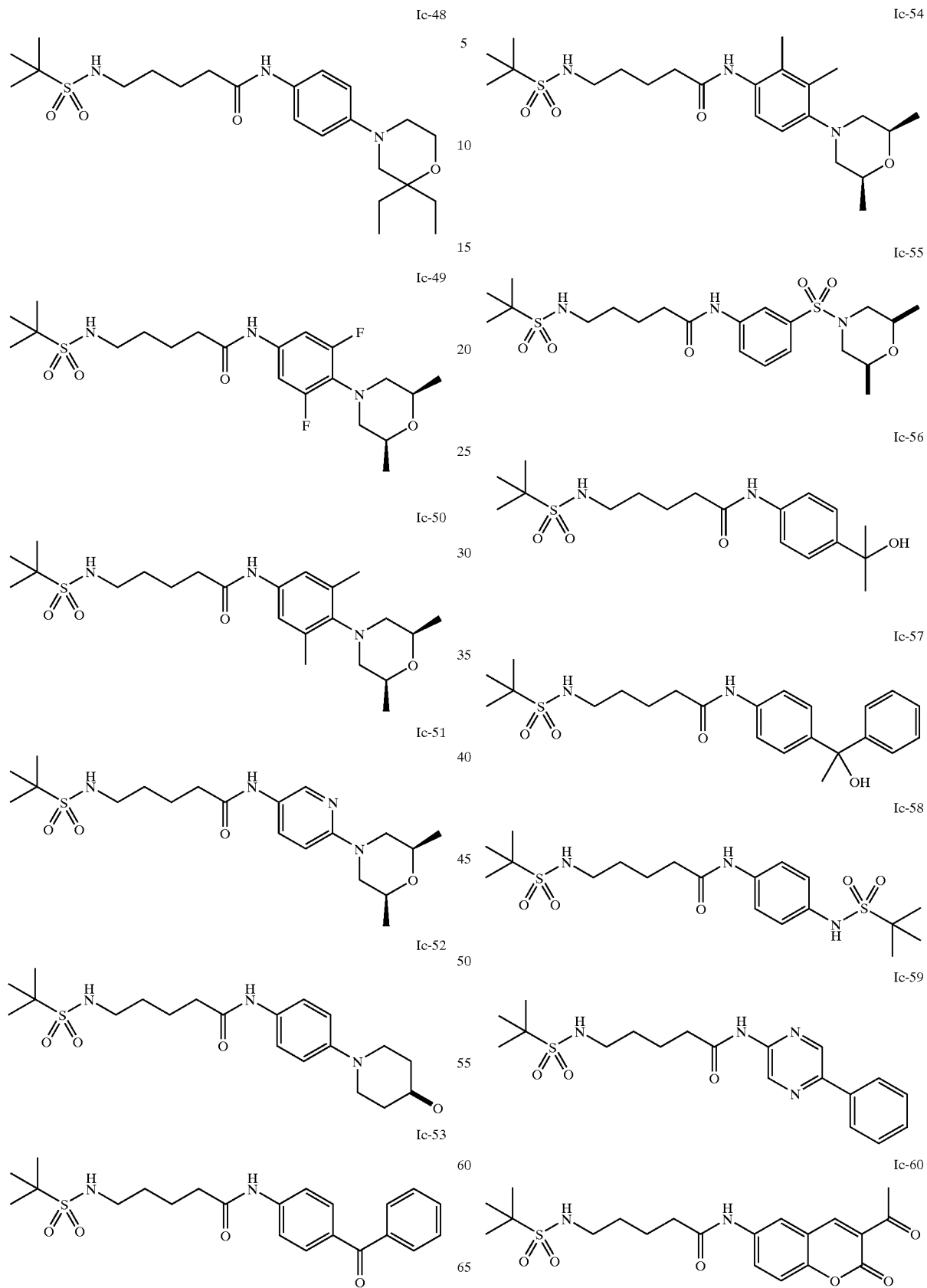

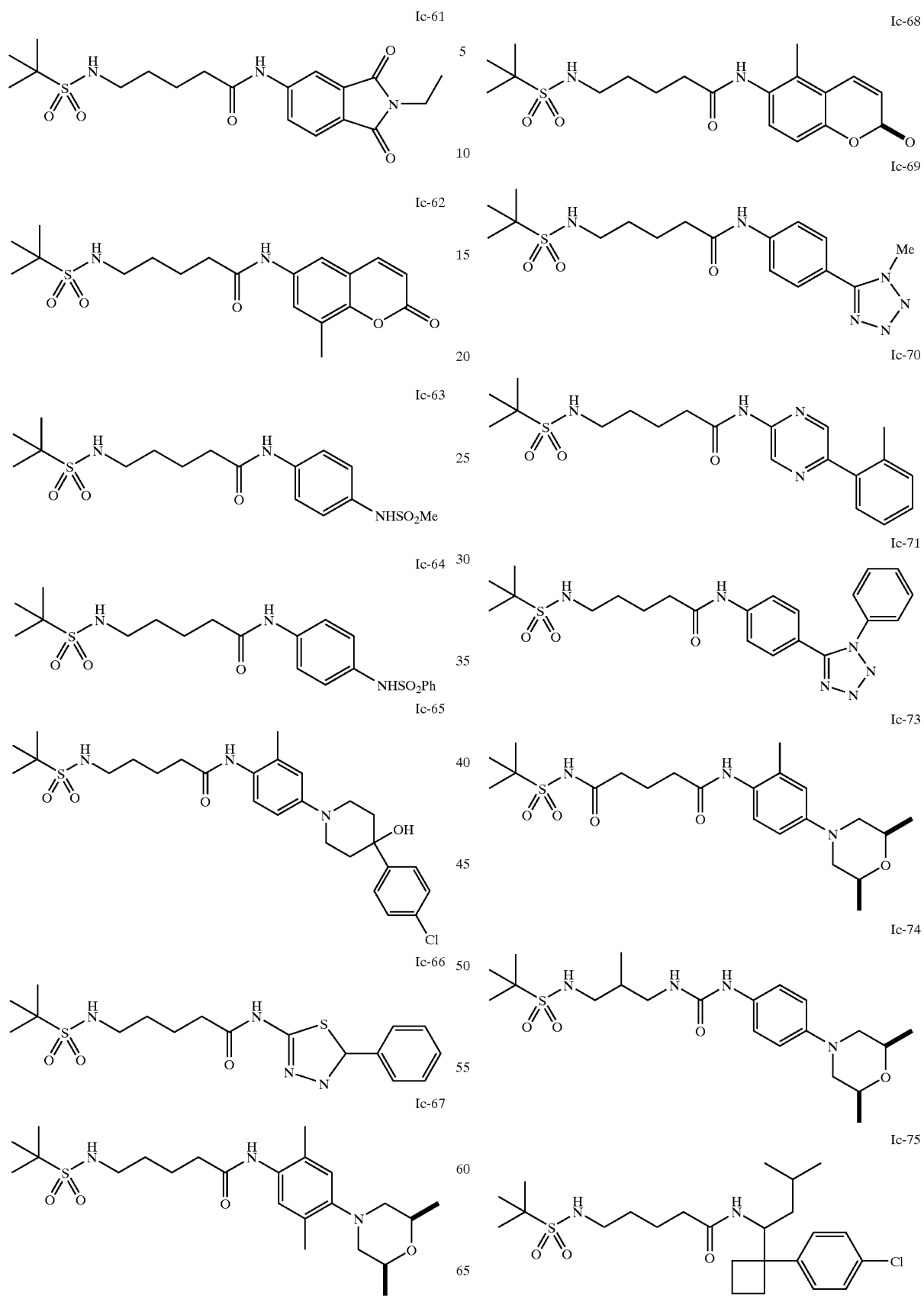

Ic-76
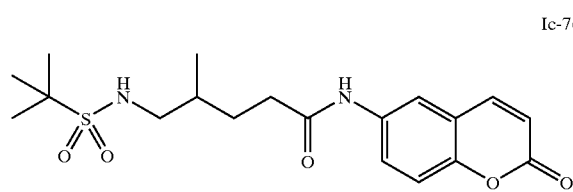
Ic-77
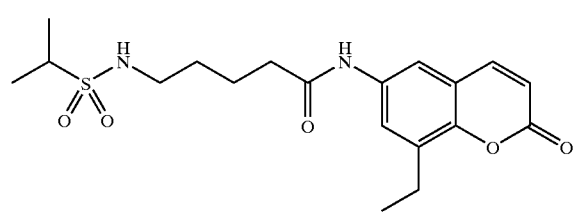
Ic-78
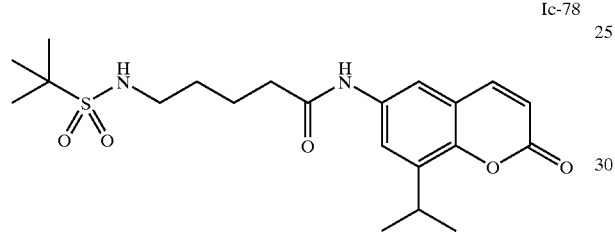
Ic-79
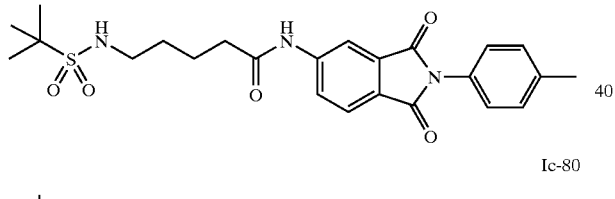
Ic-80
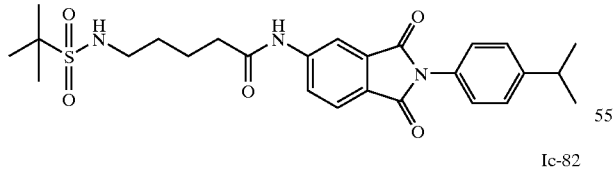
Ic-81
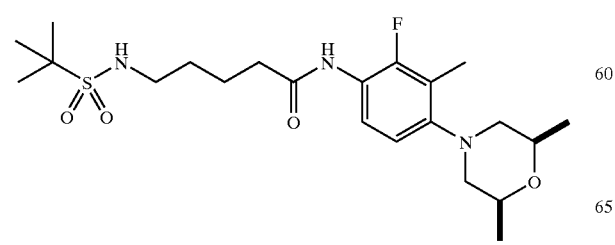
Ic-82
Ic-83
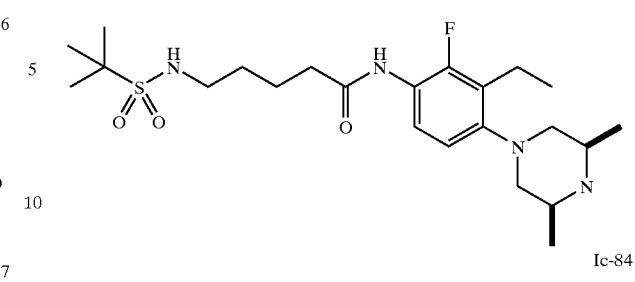
Ic-84
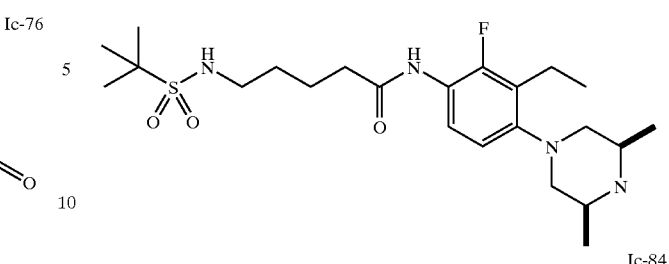
Ic-85
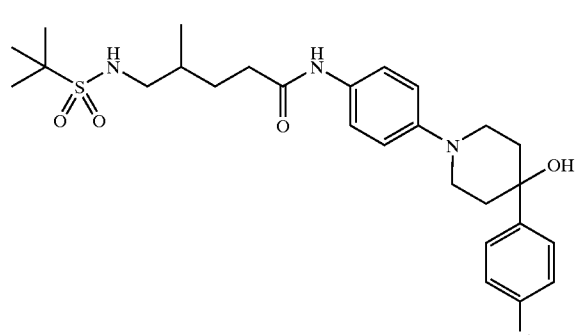
Ic-86
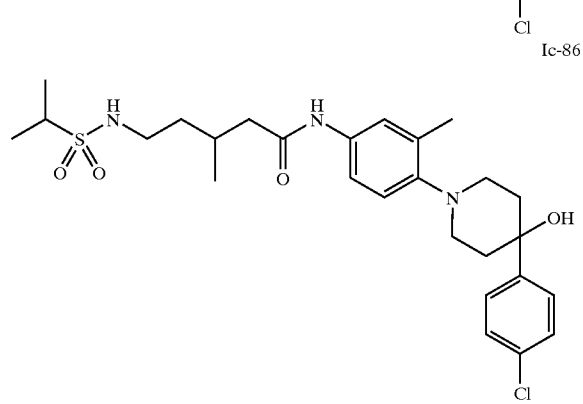
Ic-87
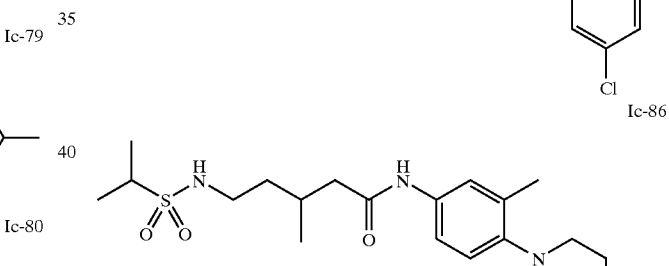
Ic-88

Ic-89
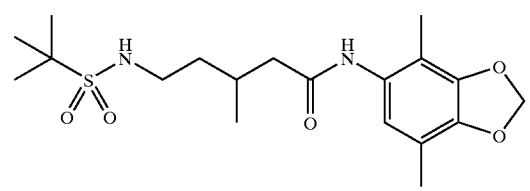
Ic-90
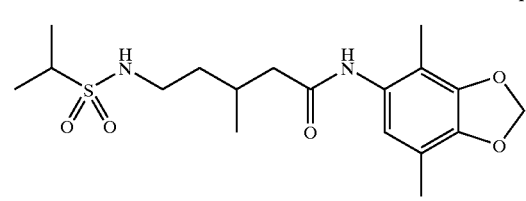
Ic-91
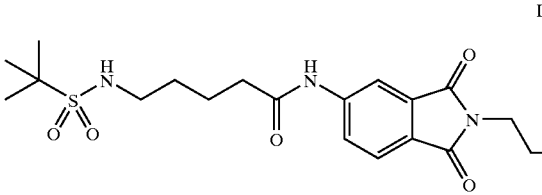
Ic-92
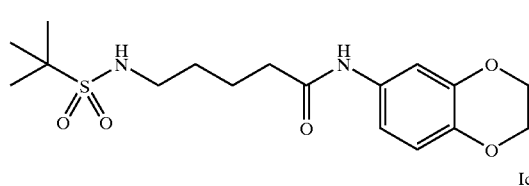
Ic-93
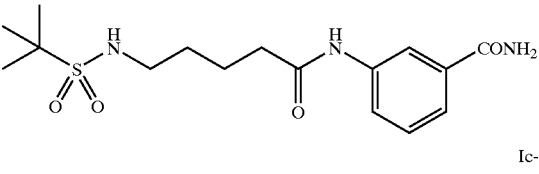
Ic-94
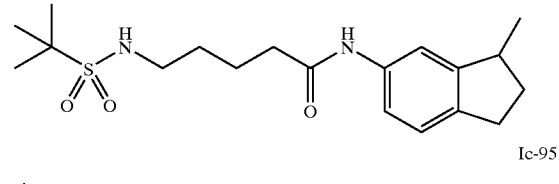
Ic-95
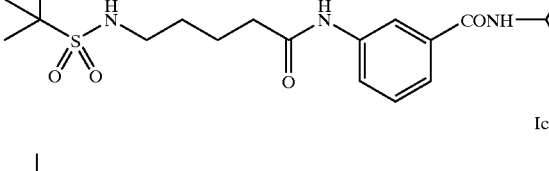
Ic-96
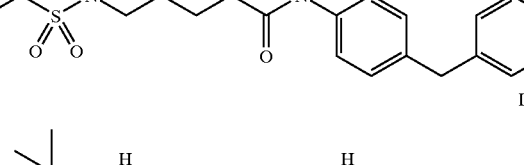
Ic-97
Ic-98
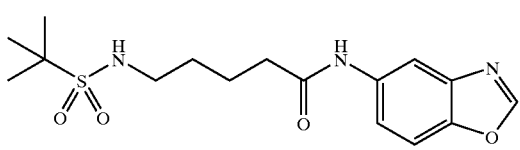
Ic-99
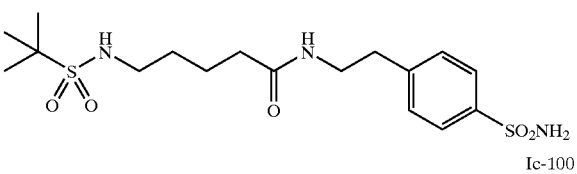
Ic-100
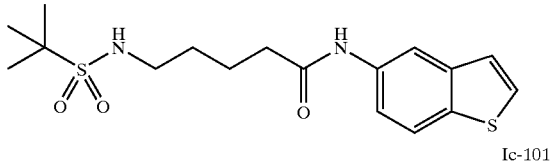
Ic-101
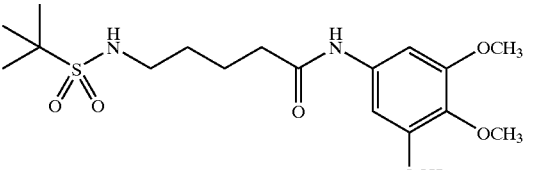
Ic-102
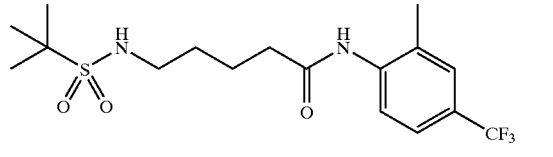
Ic-103
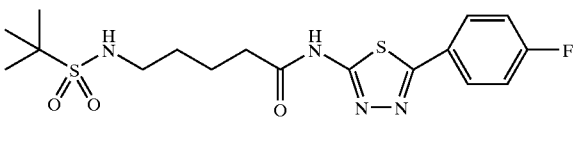
Ic-104
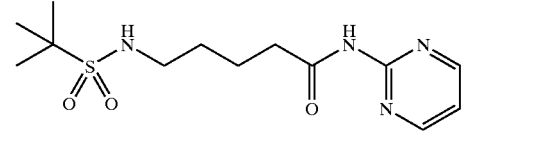
Ic-105
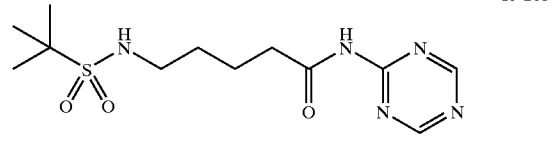
Ic-106

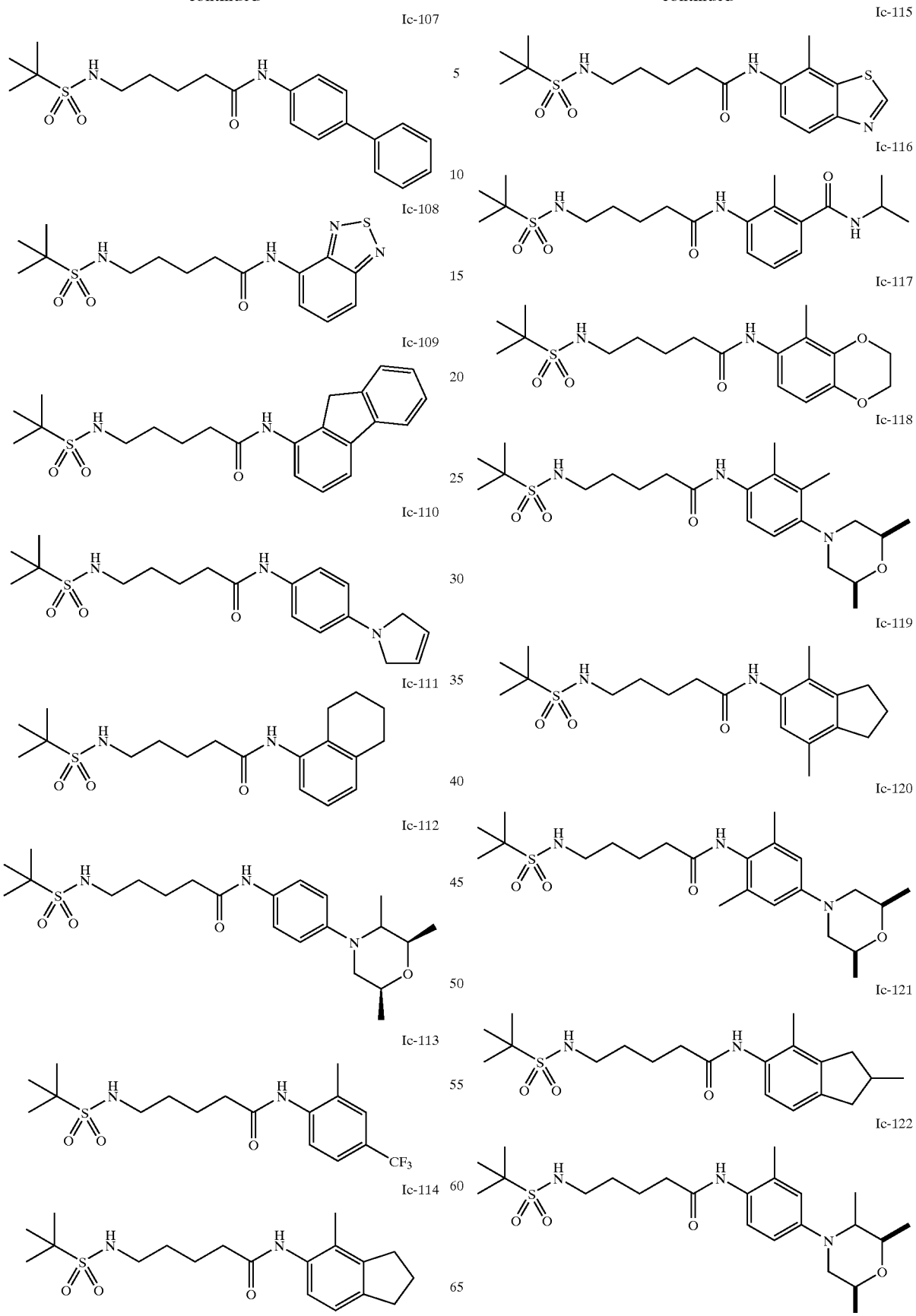

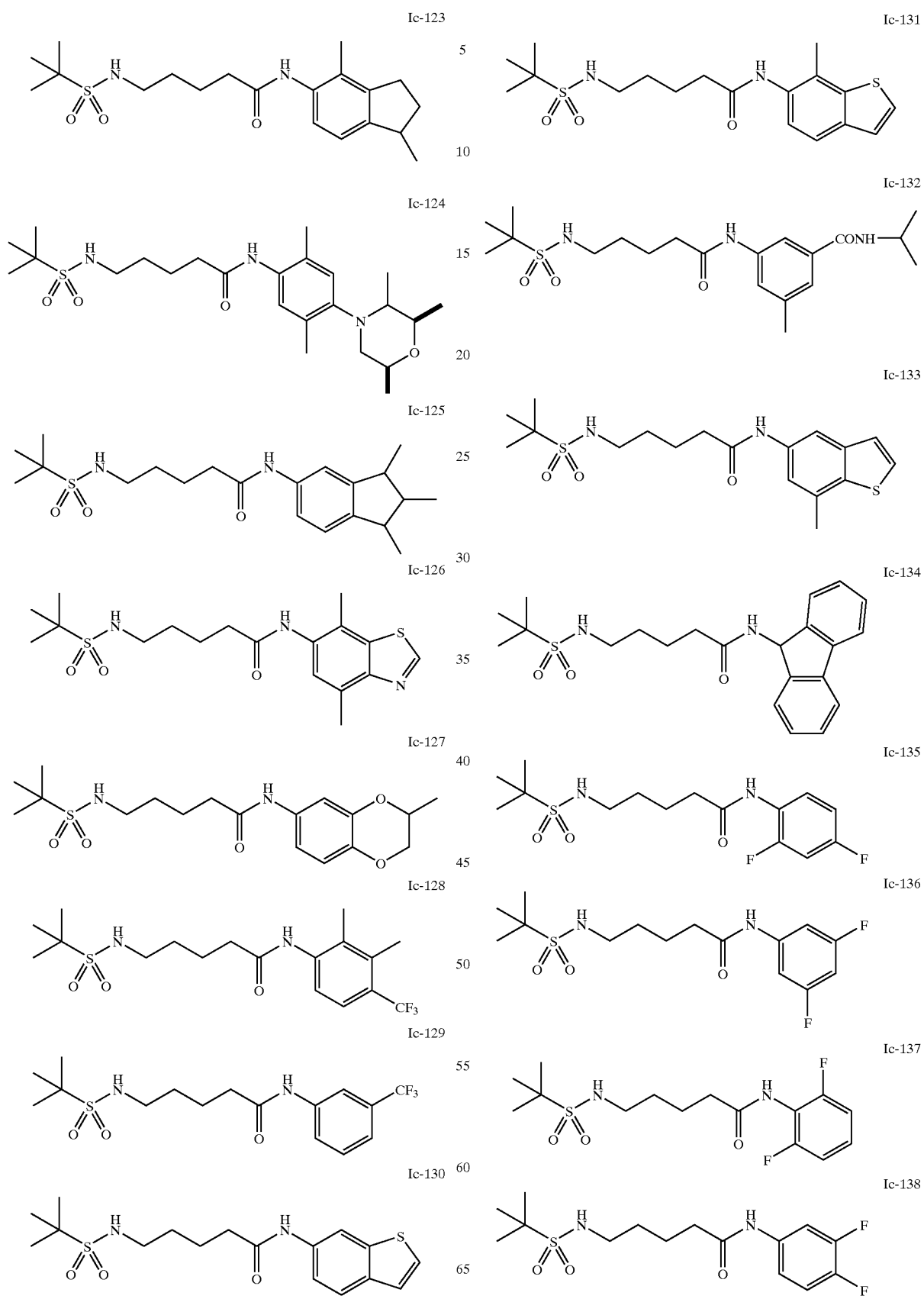

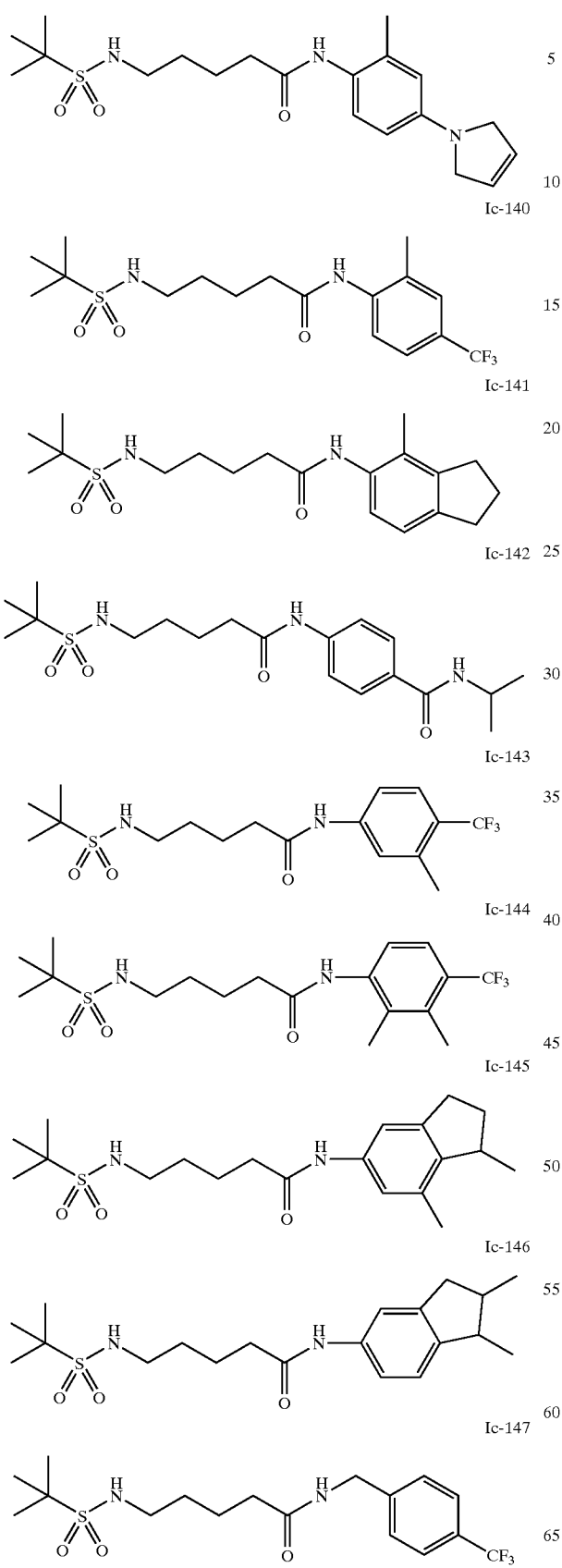

Ic-157
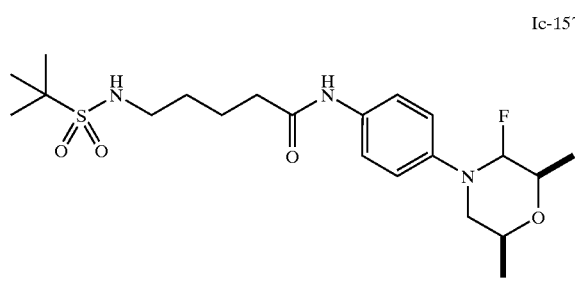
Ic-158
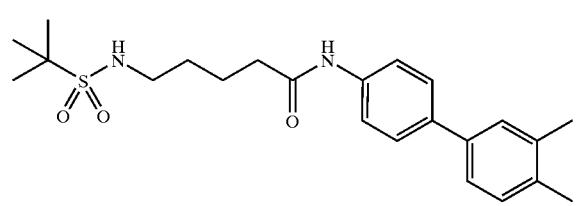
Ic-159
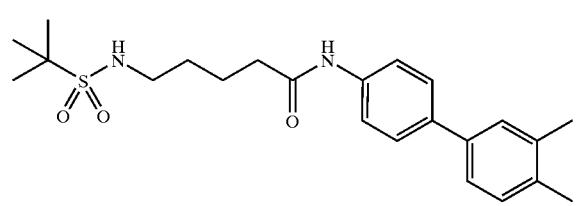
Ic-160
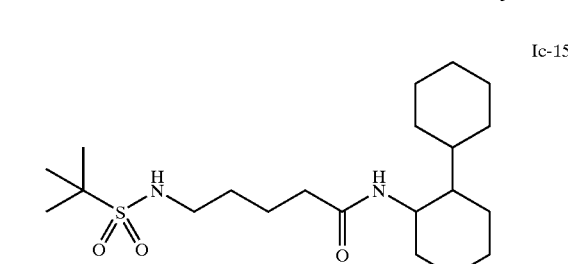
Ic-161
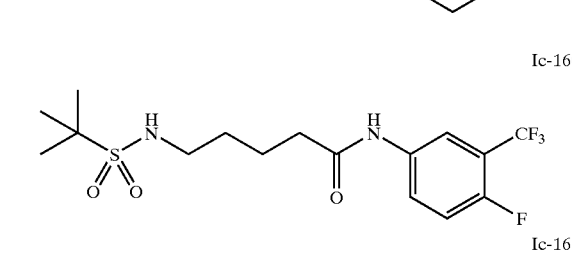
Ic-162
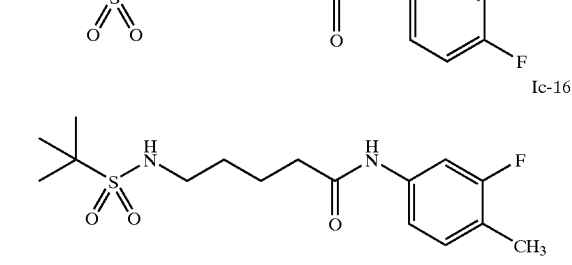
Ic-163
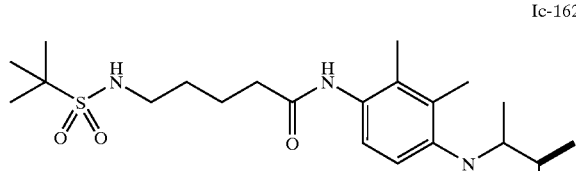
Ic-164
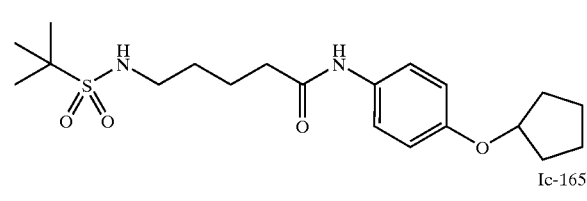
Ic-165
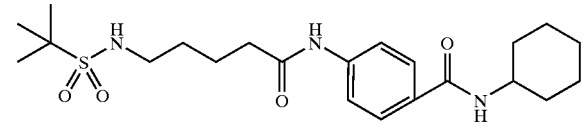
Ic-166
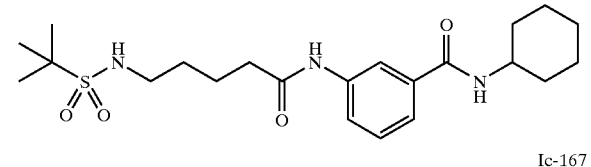
Ic-167
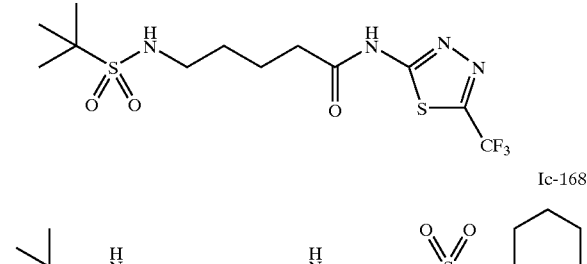
Ic-168
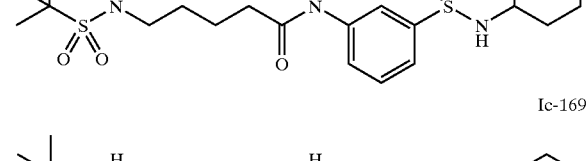
Ic-169
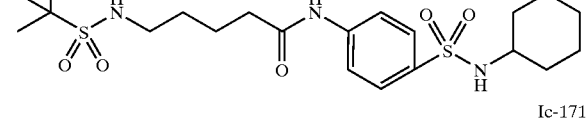
Ic-171
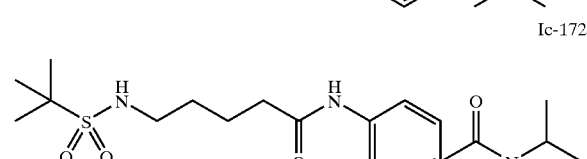
Ic-172
Ic-173
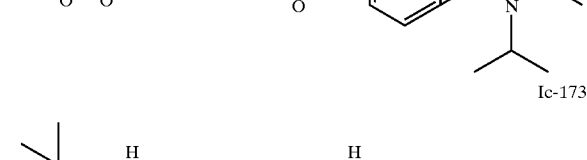

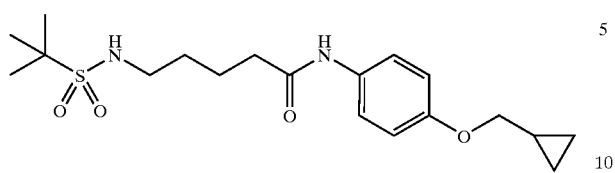
Ic-174
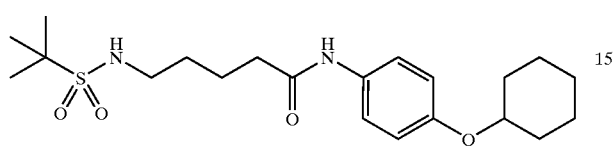
Ic-175
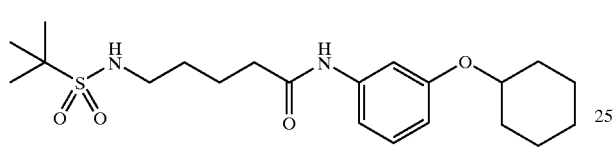
Ic-176
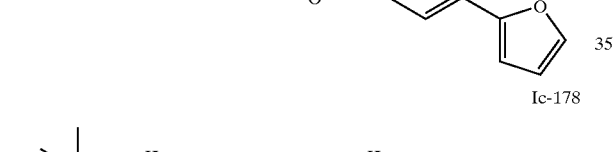
Ic-177
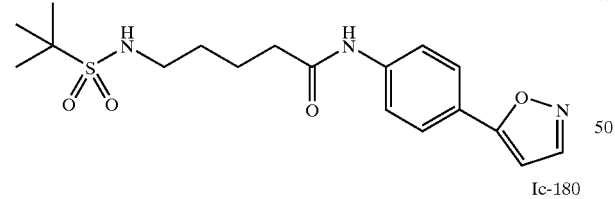
Ic-178
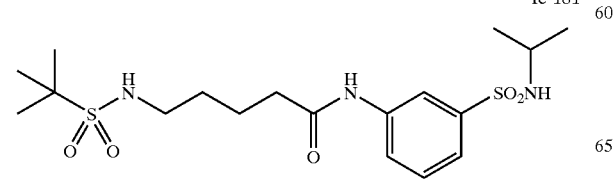
Ic-179
Ic-180
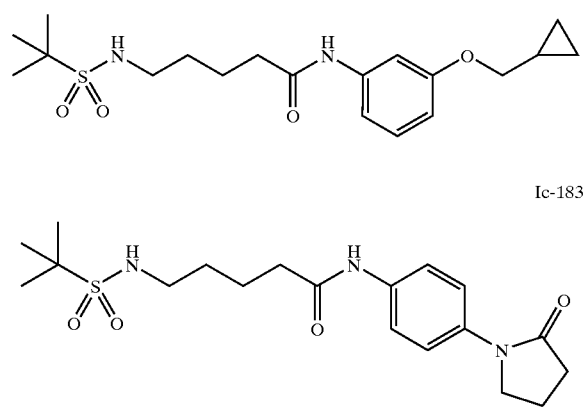
Ic-182
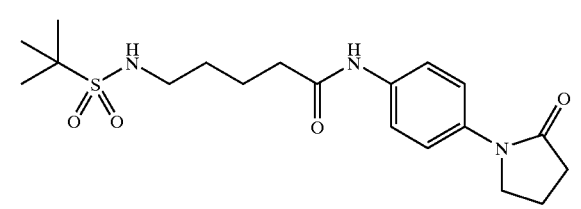
Ic-183
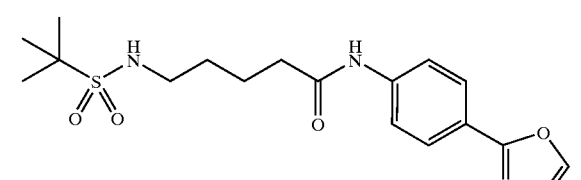
Ic-184
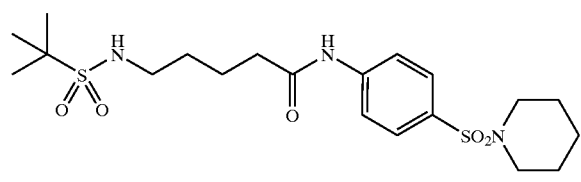
Ic-185
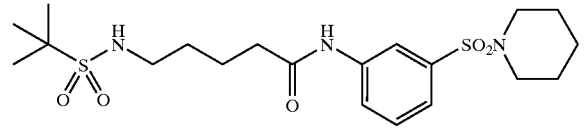
Ic-186
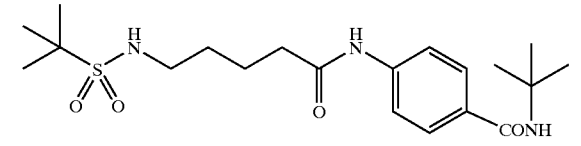
Ic-187
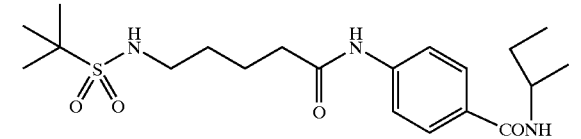
Ic-188
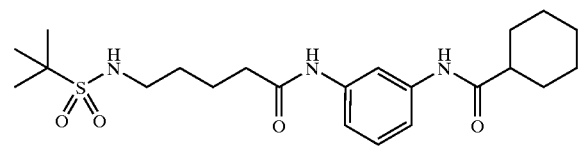
Ic-189

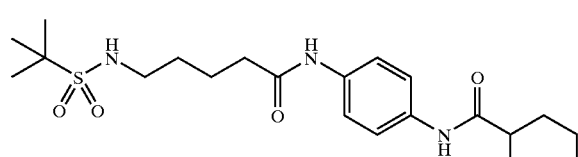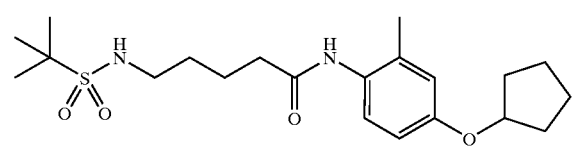

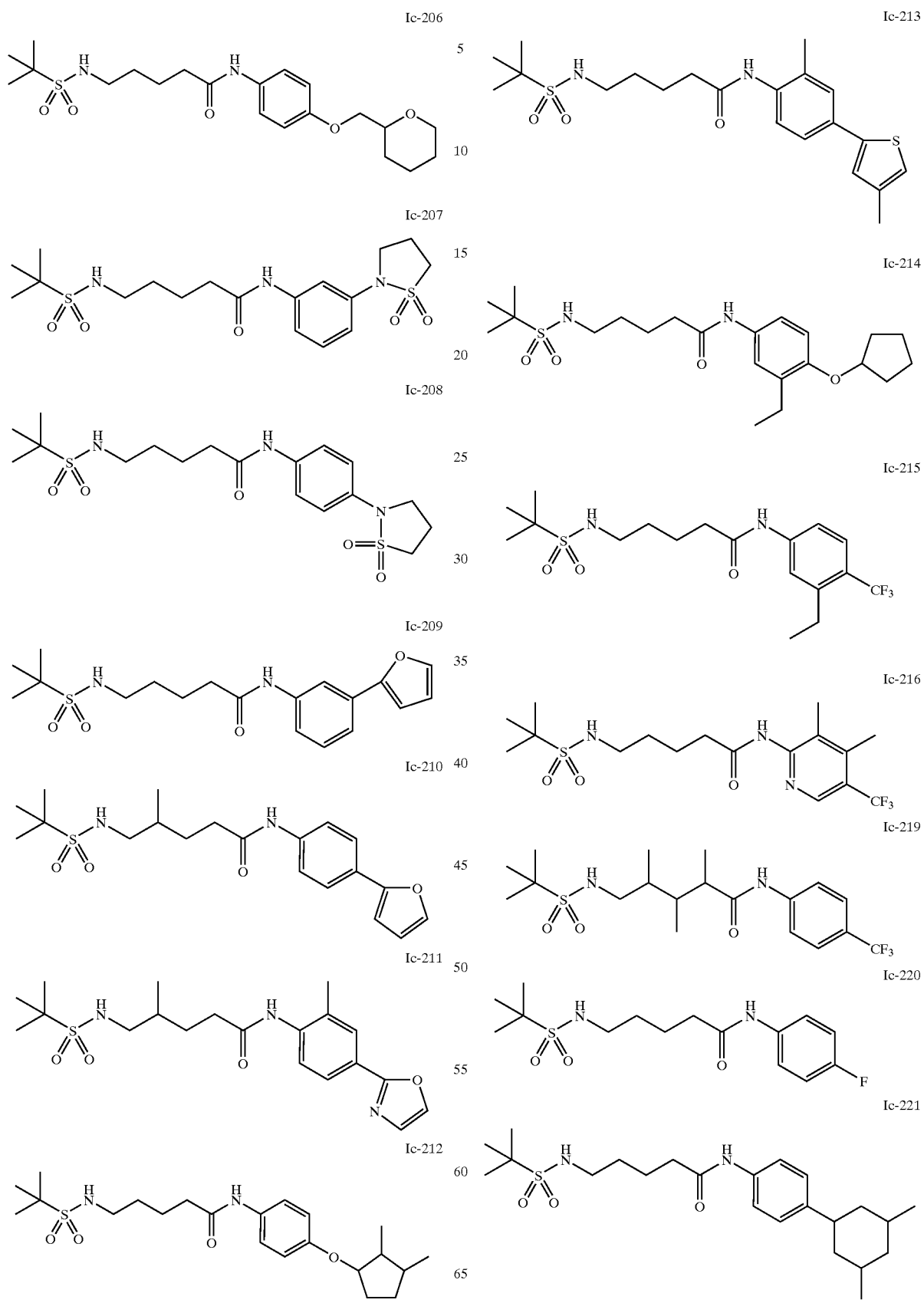

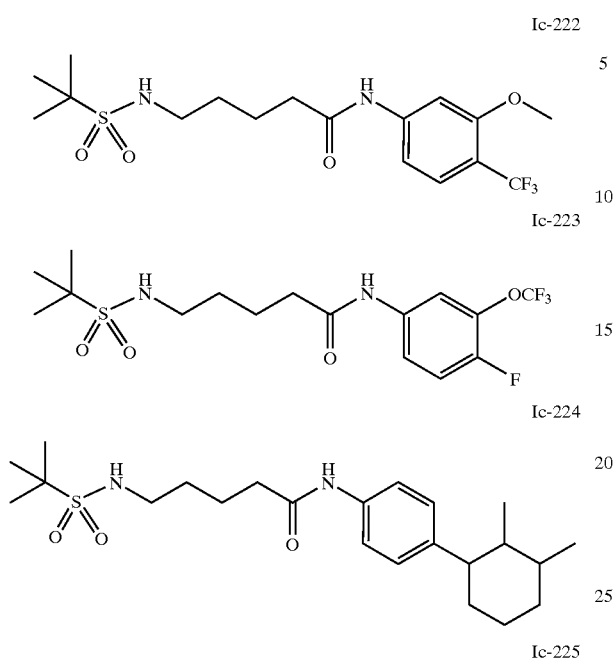
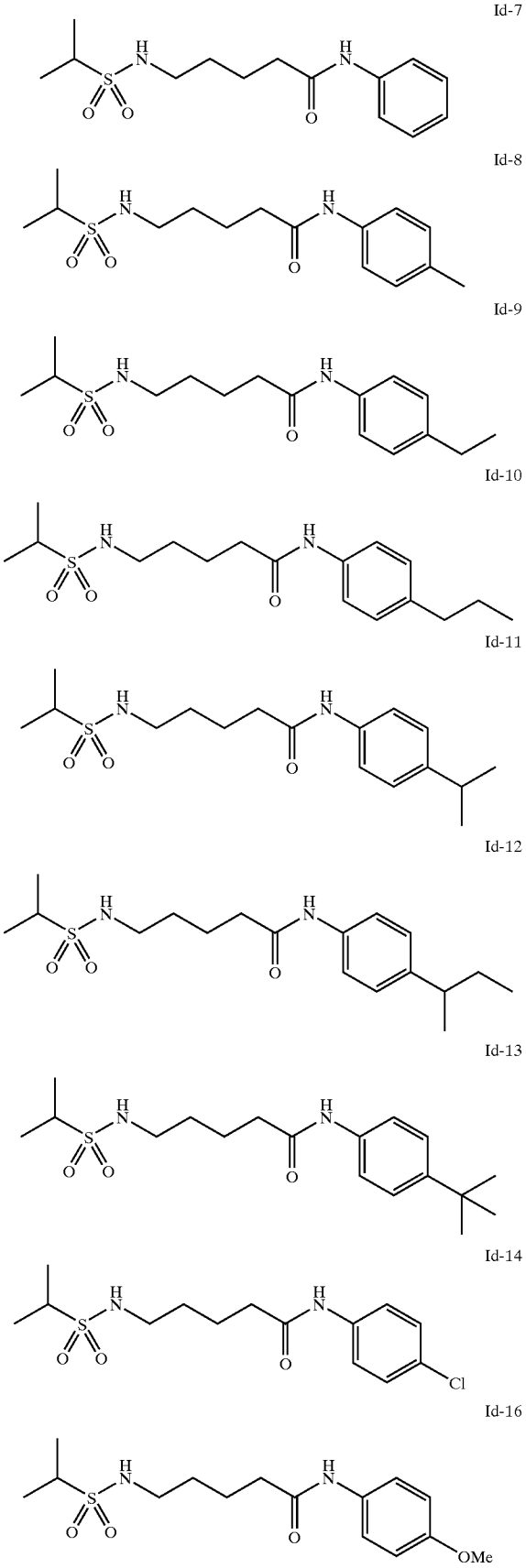

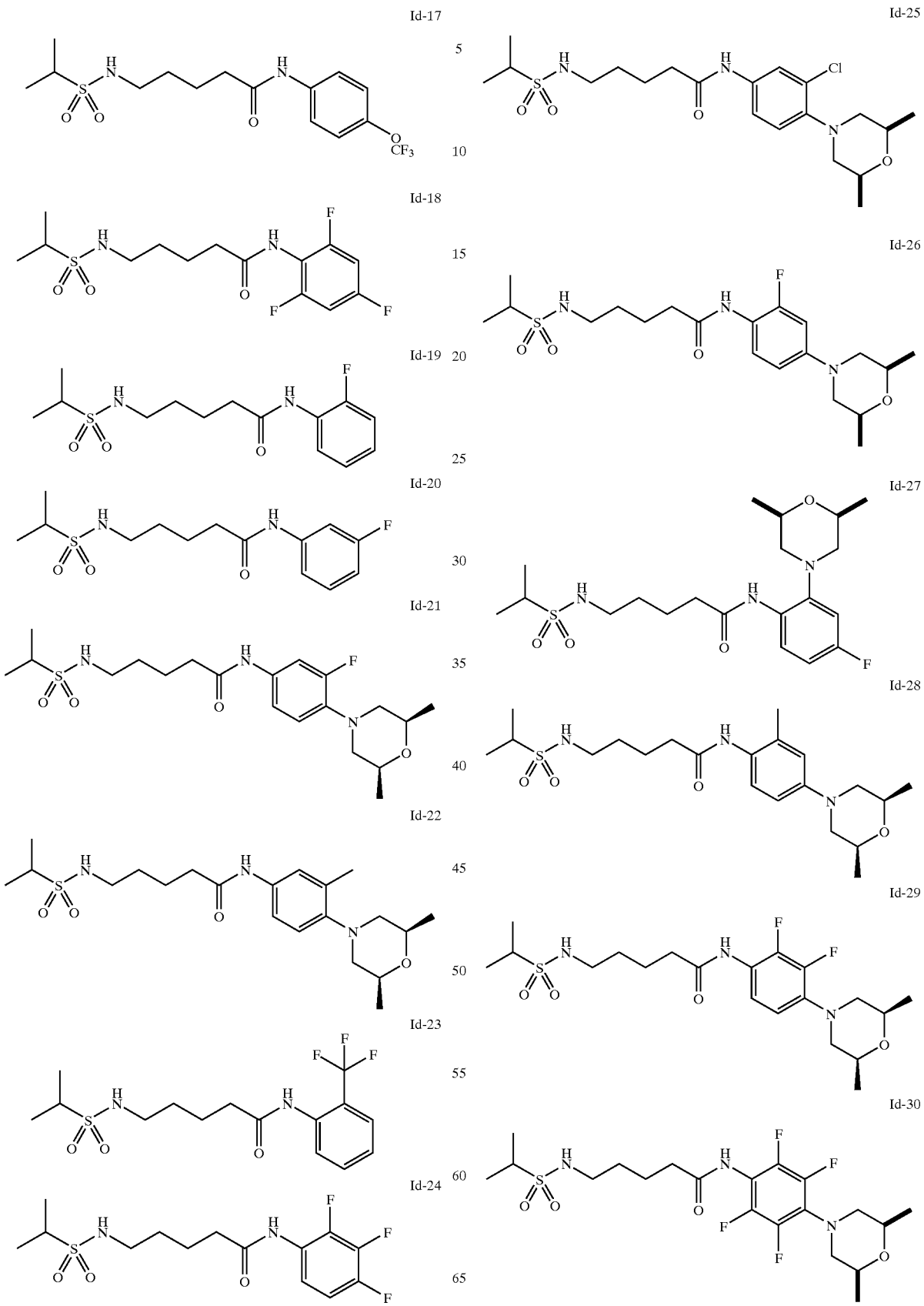

Id-31
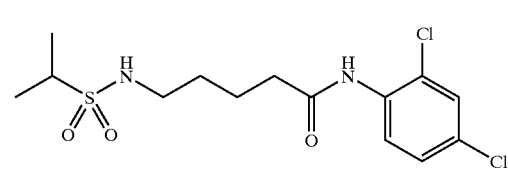
Id-32
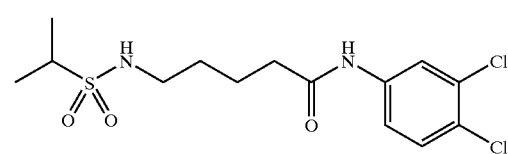
Id-33
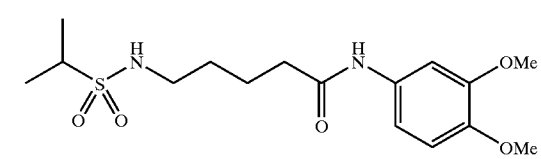
Id-35
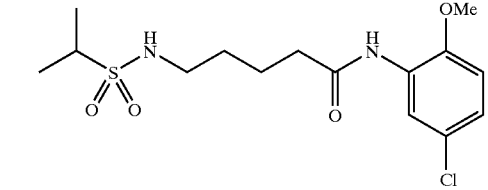
Id-36
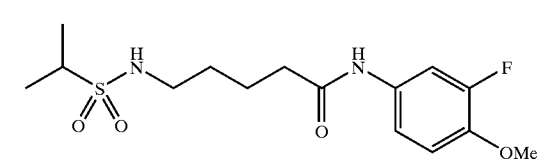
Id-37
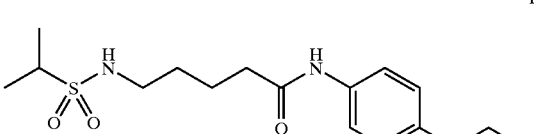
Id-38
Id-39
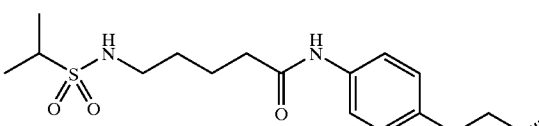
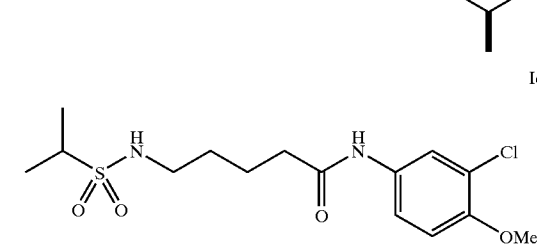
Id-40
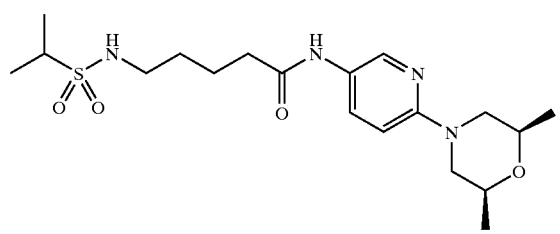
Id-41
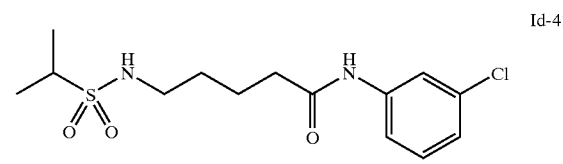
Id-42
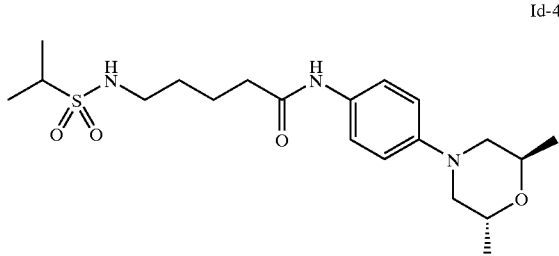
Id-43
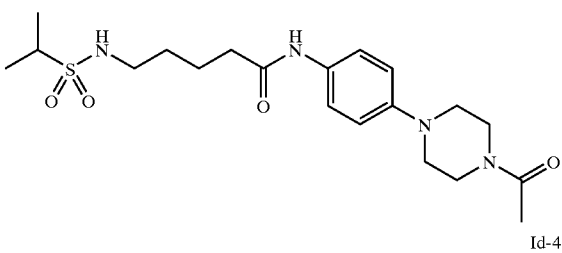
Id-44
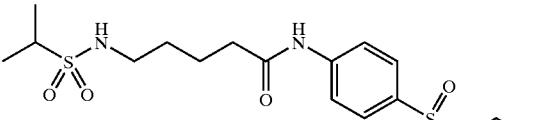
Id-45
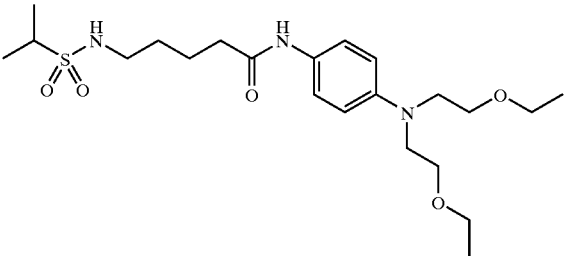

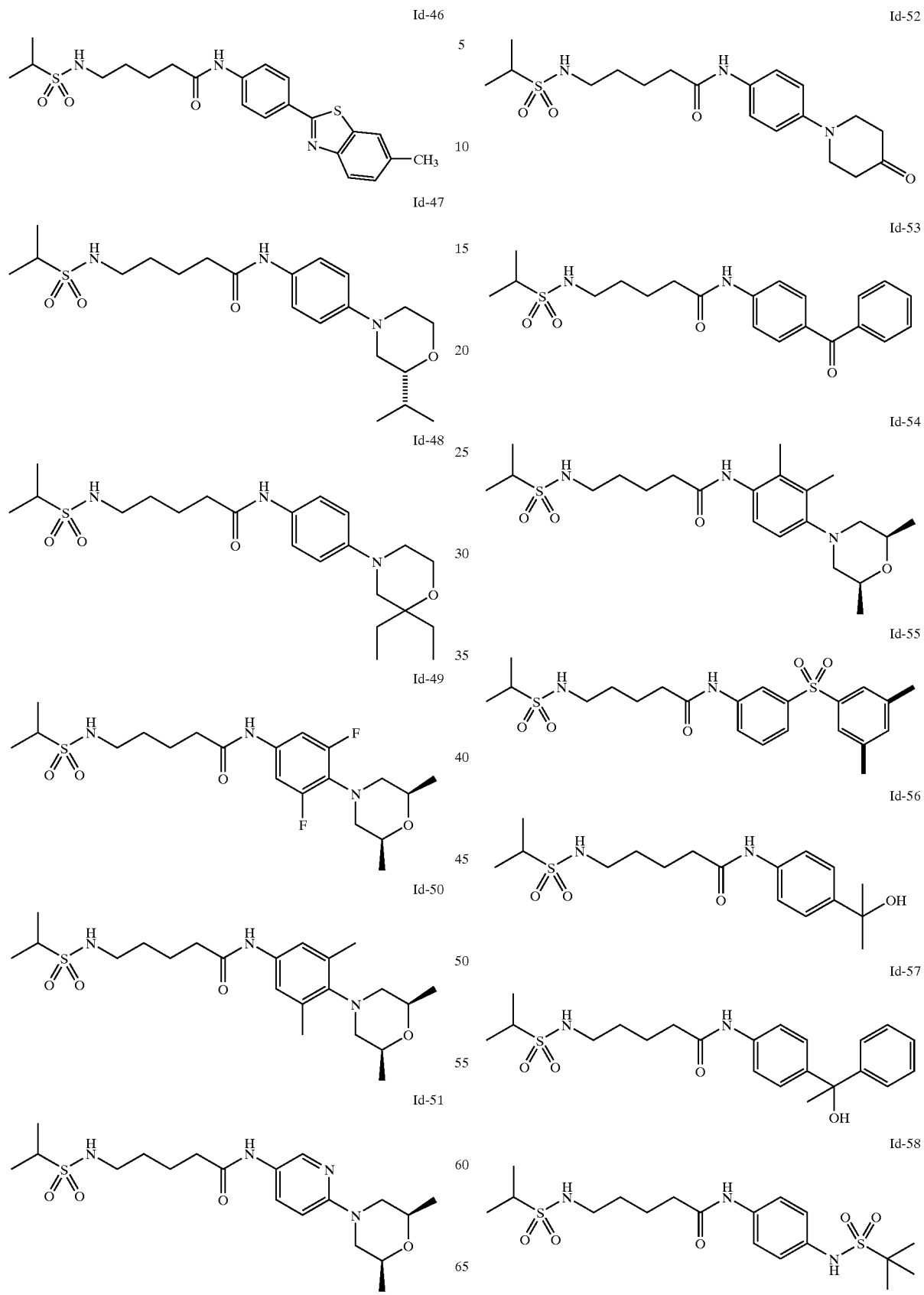

-continued
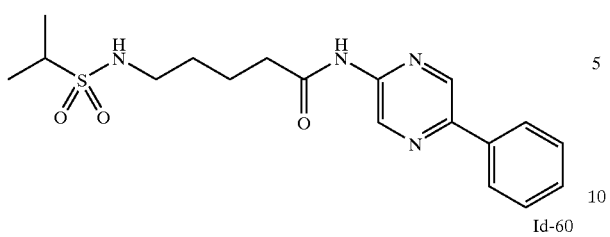
Id-59
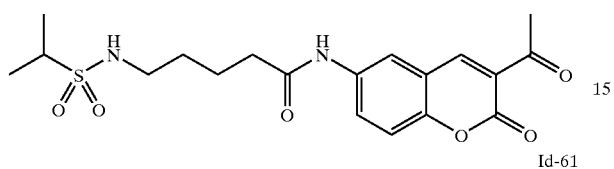
Id-60
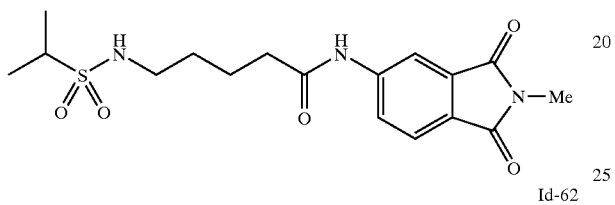
Id-61
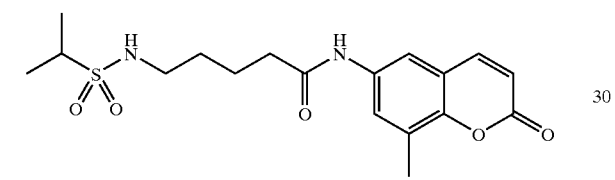
Id-62
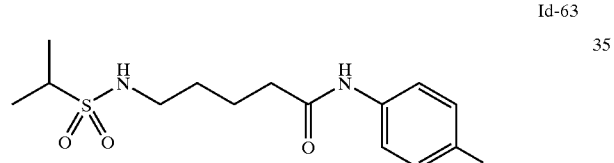
Id-63
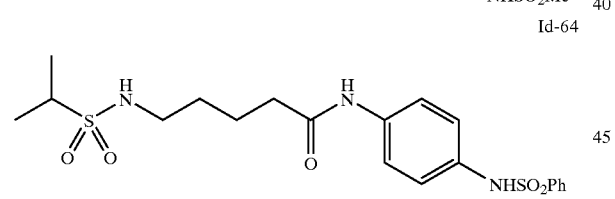
Id-64
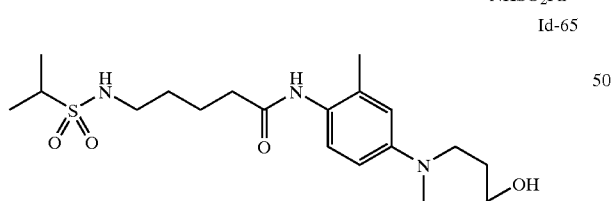
Id-65
Id-66
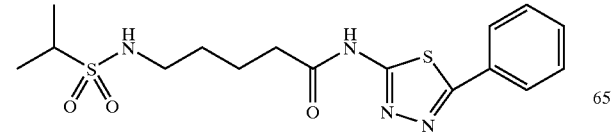
-continued
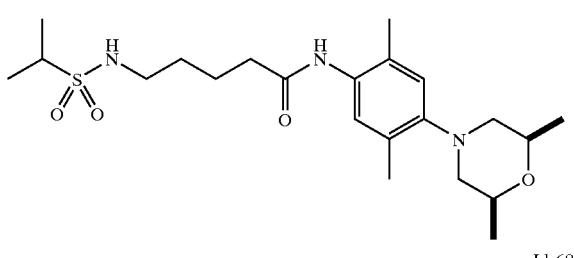
Id-67
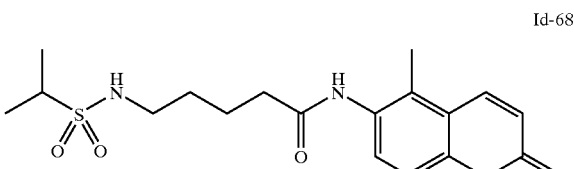
Id-68
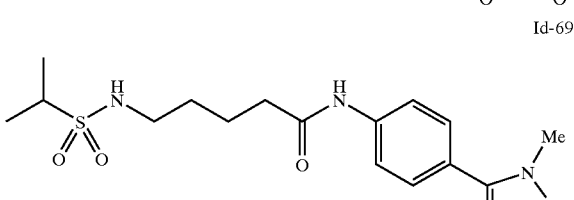
Id-69
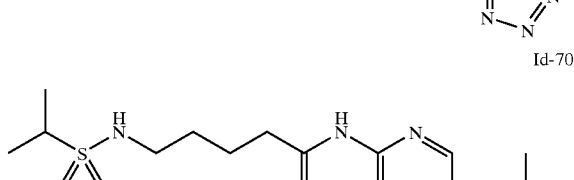
Id-70
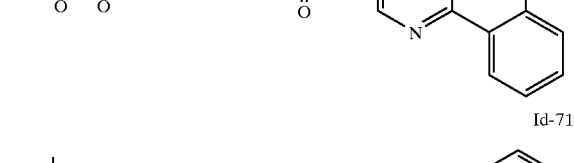
Id-71
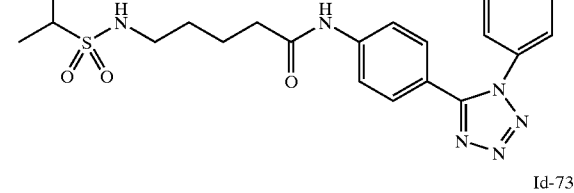
Id-72
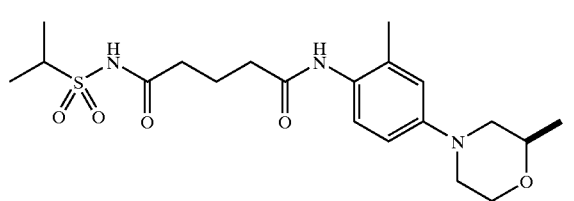
Id-73
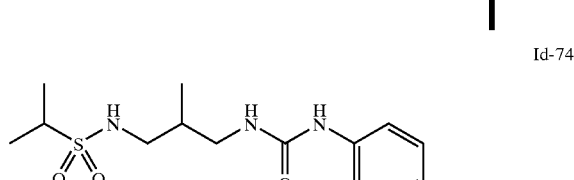
Id-74

Id-75
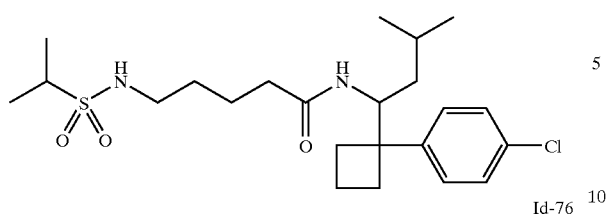
Id-76
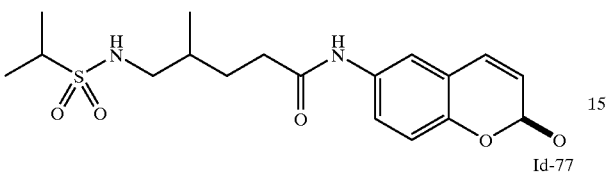
Id-77
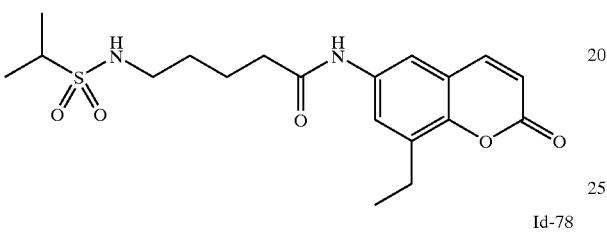
Id-78
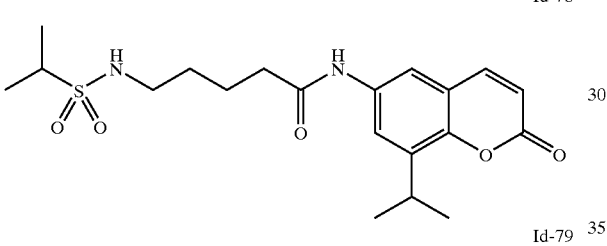
Id-79
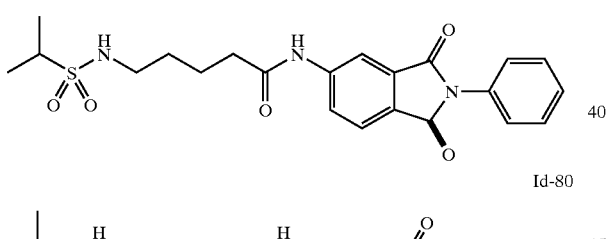
Id-80
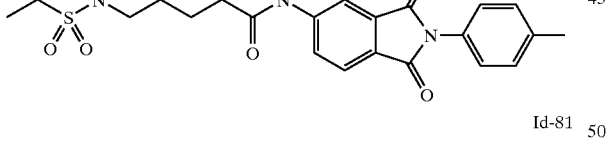
Id-81
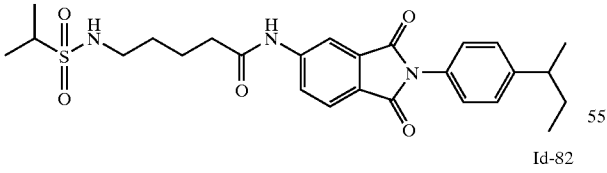
Id-82
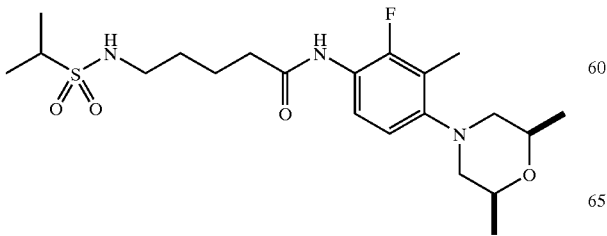
Id-83
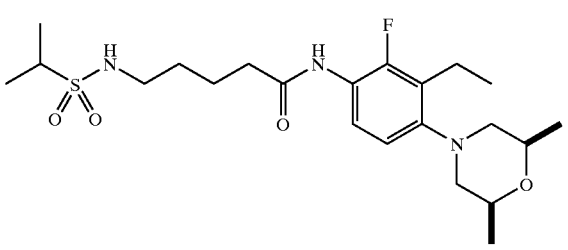
Id-84
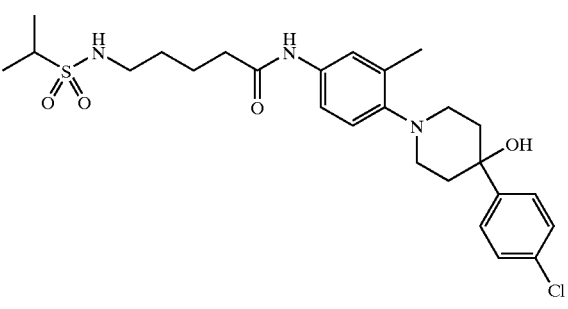
Id-85
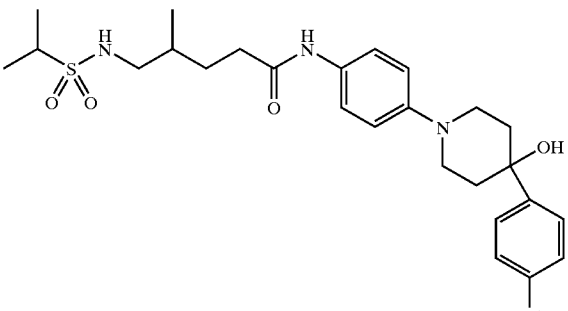
Id-86
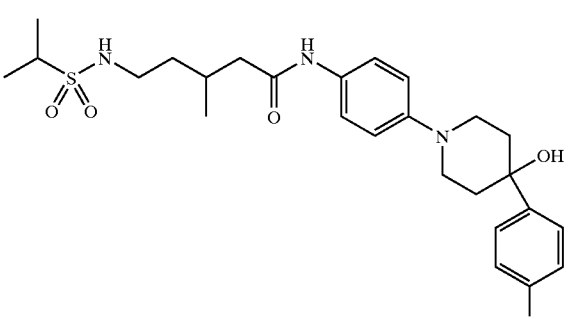
Id-87
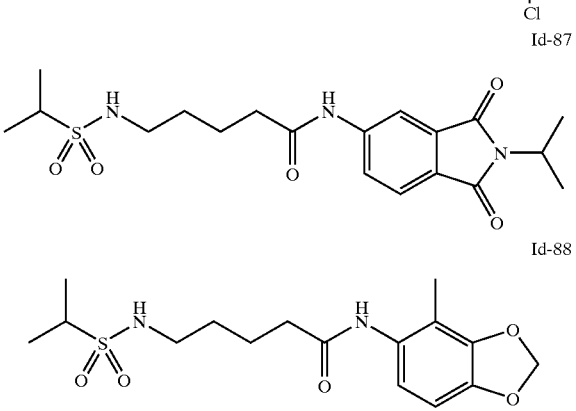
Id-88

Id-89
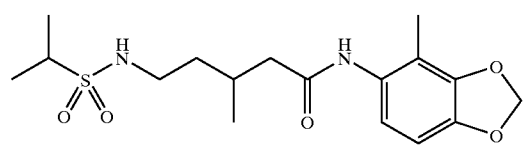
Id-90
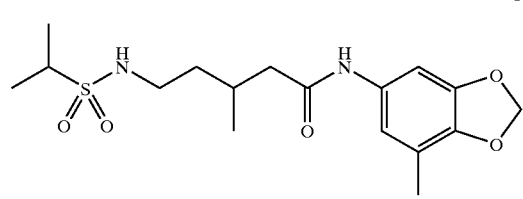
Id-91
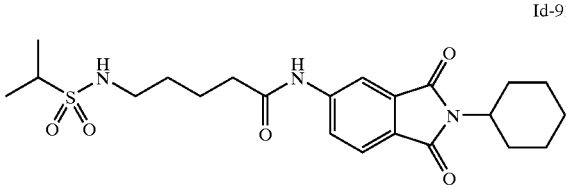
Id-92
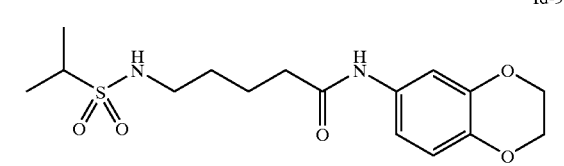
Id-93
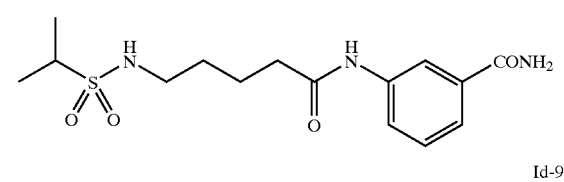
Id-94
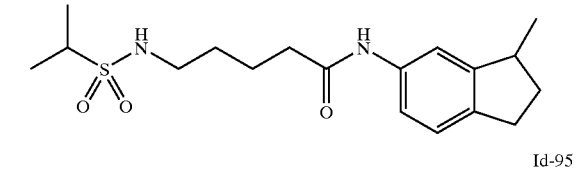
Id-95
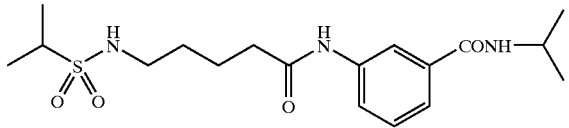
Id-96
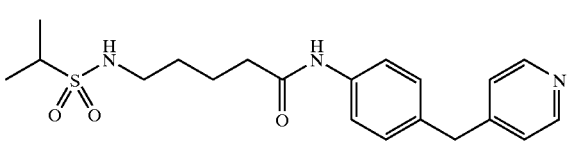
Id-97
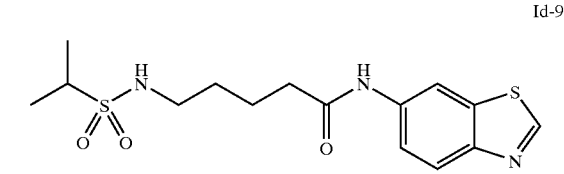
Id-98
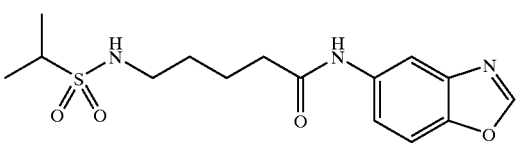
Id-99
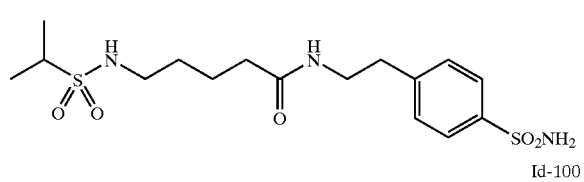
Id-100
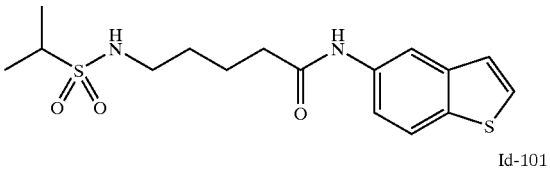
Id-101
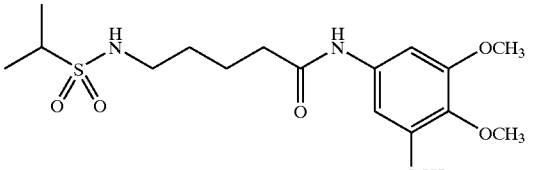
Id-102
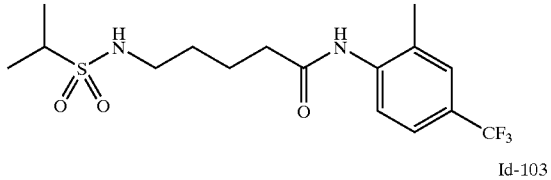
Id-103
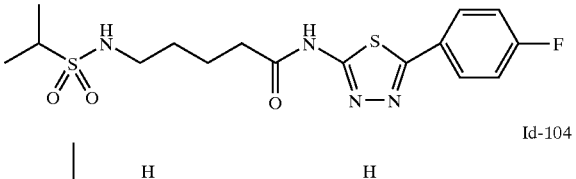
Id-104
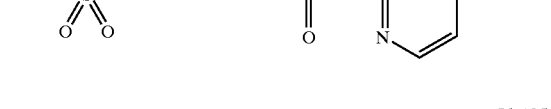
Id-105
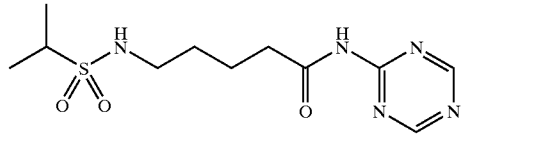
Id-106

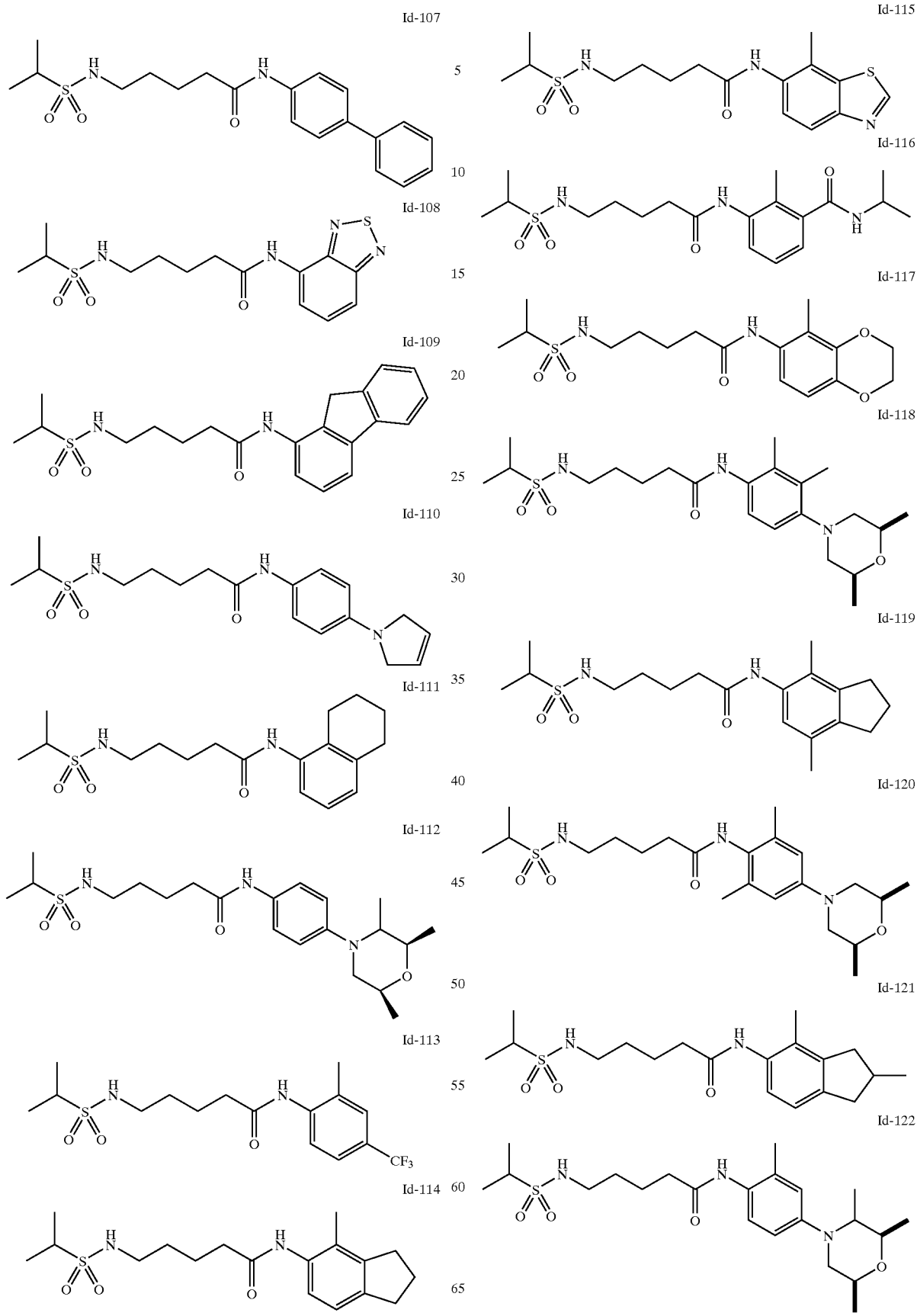

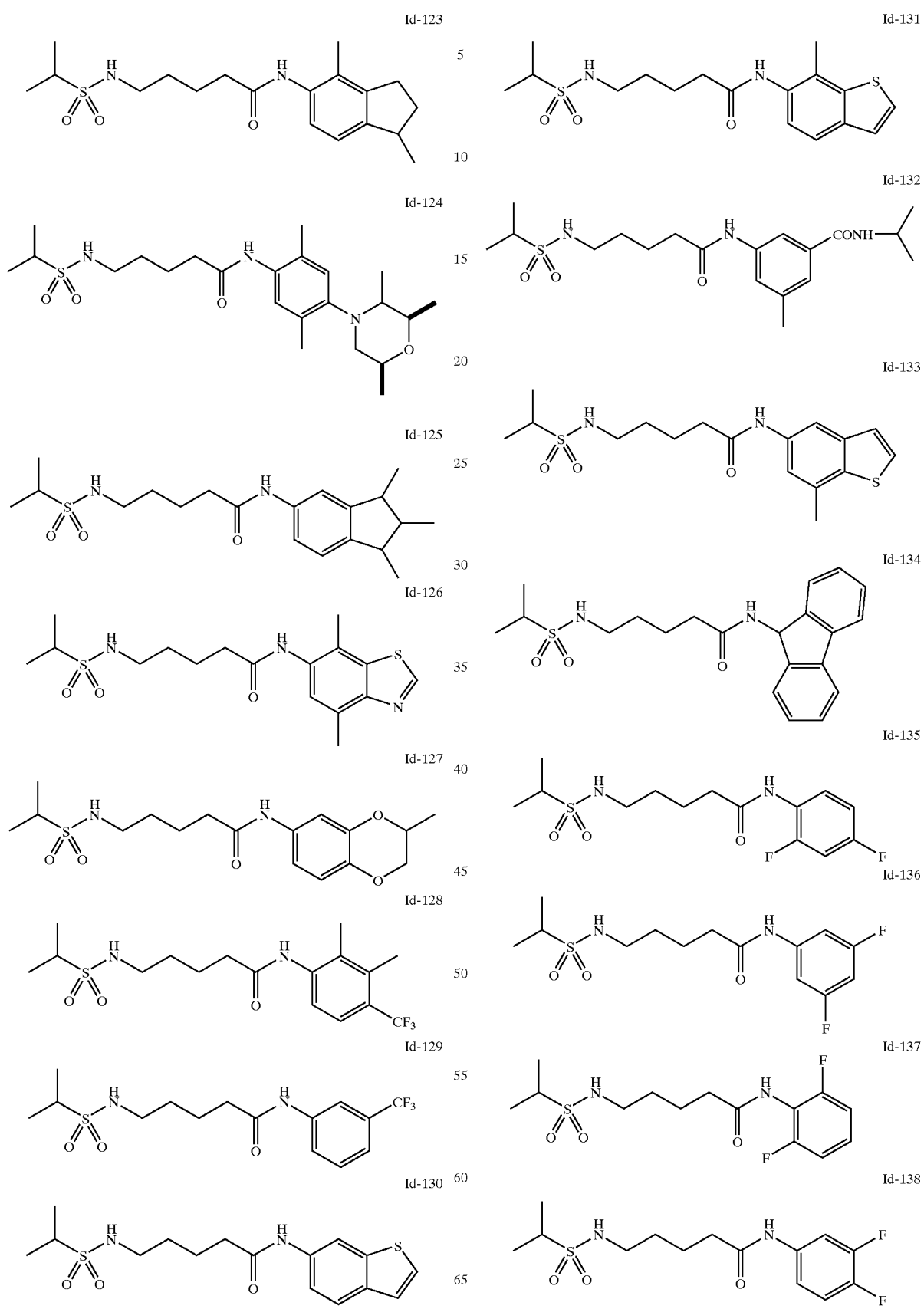

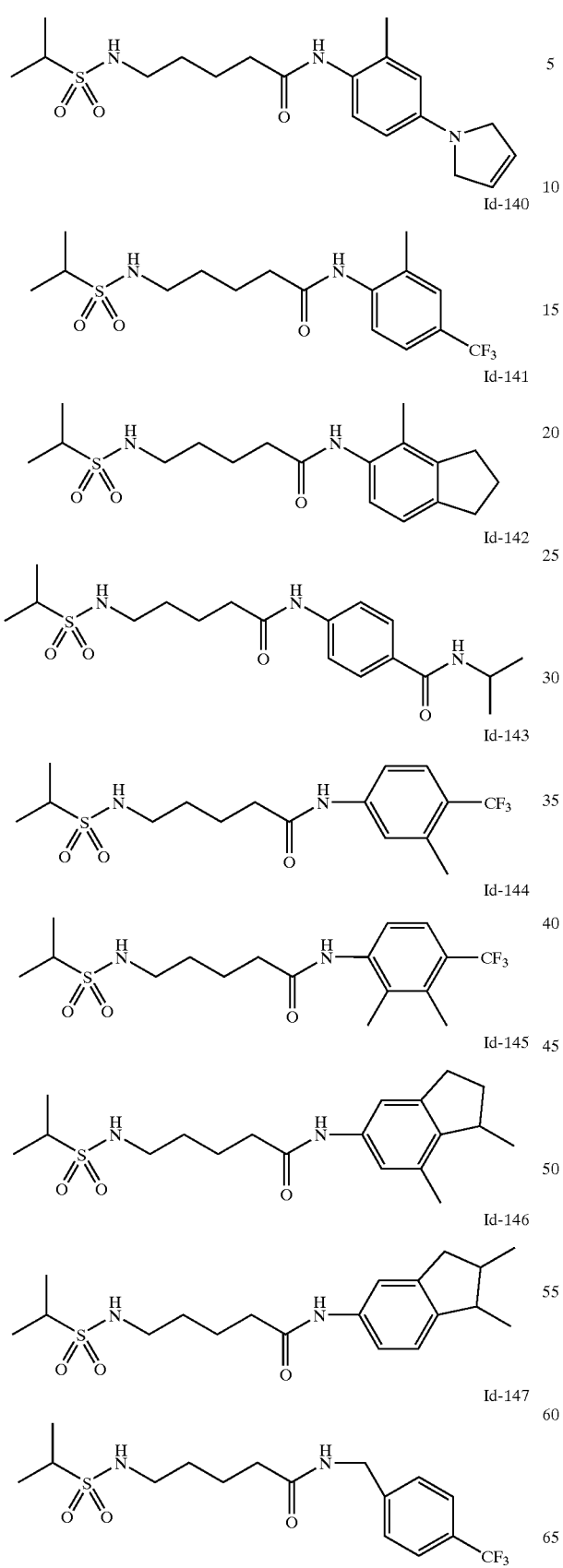
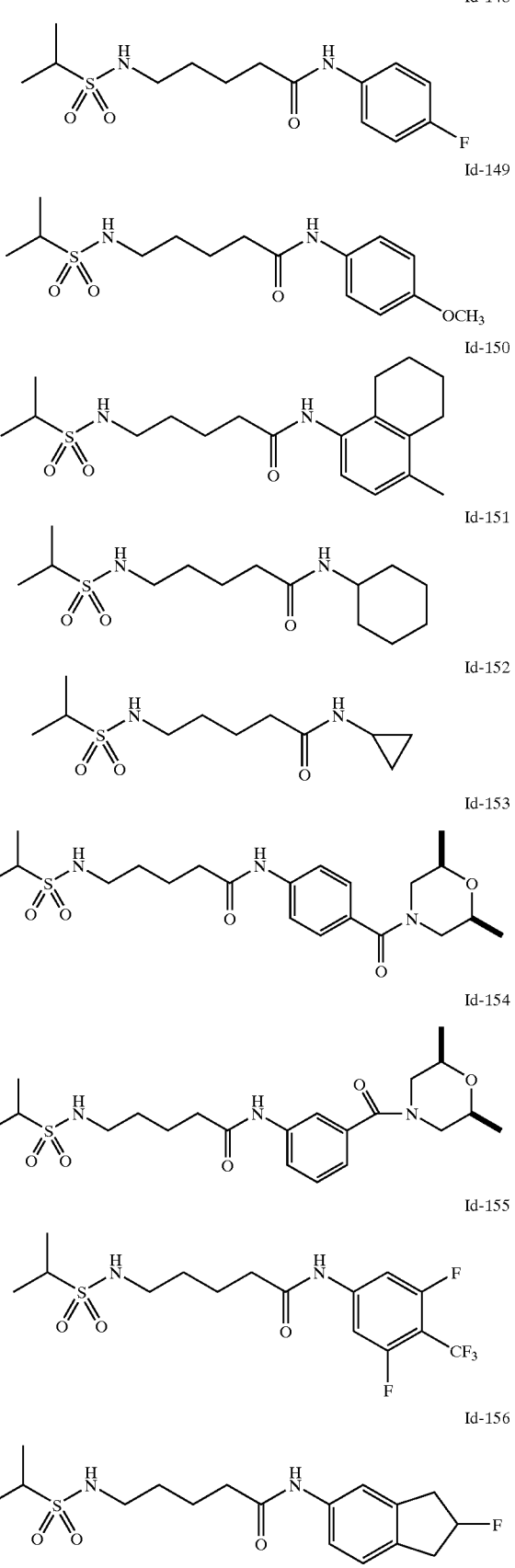

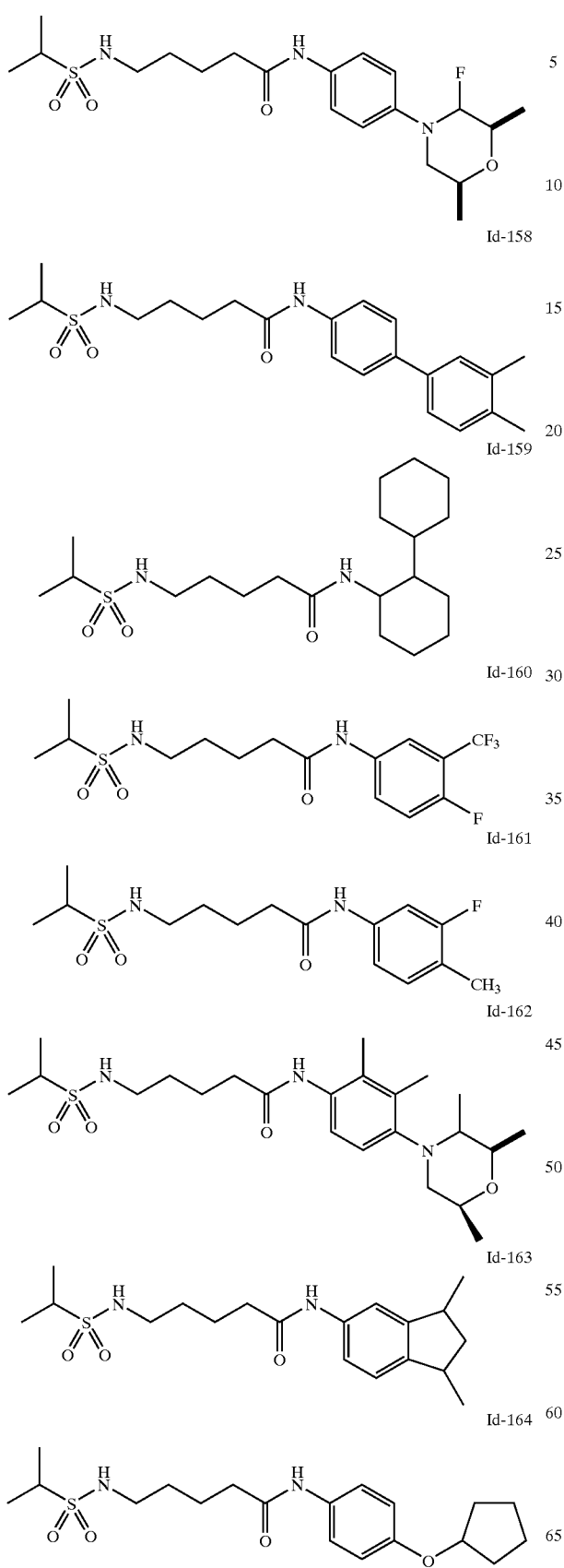
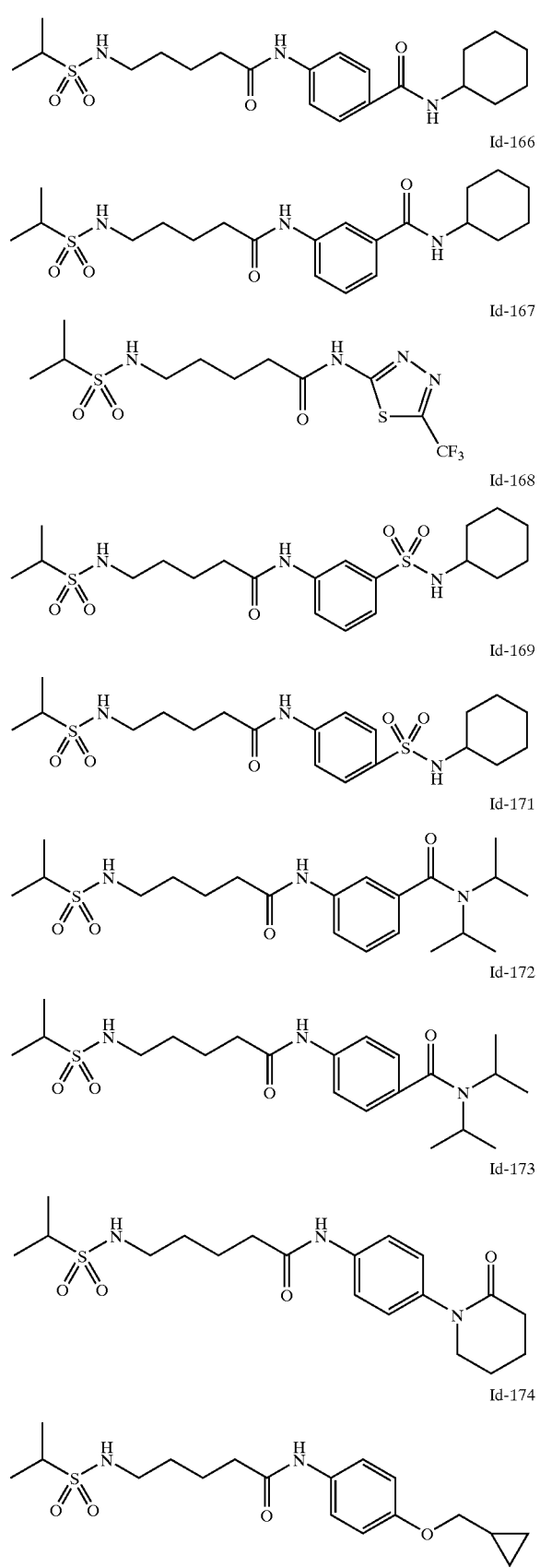

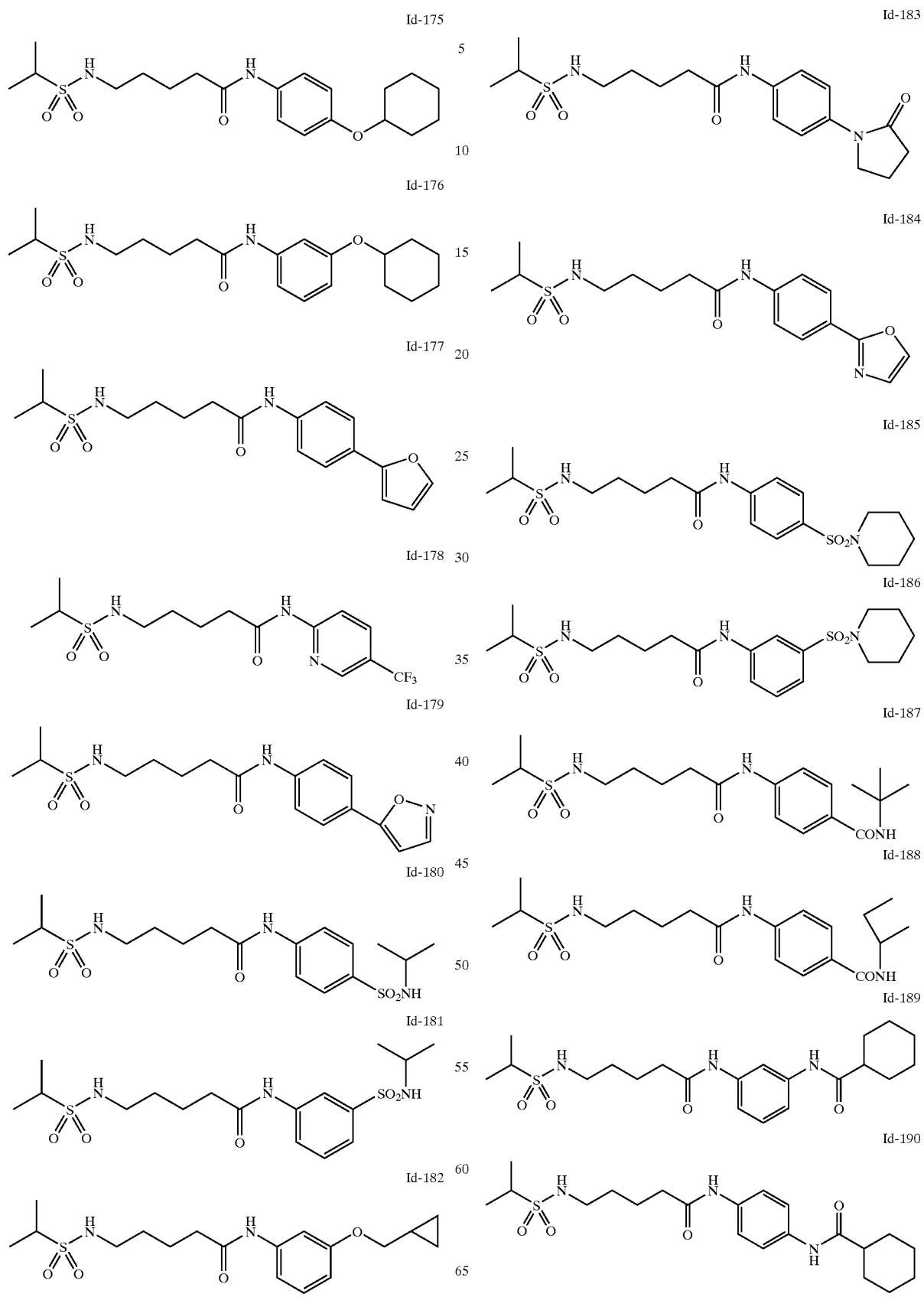

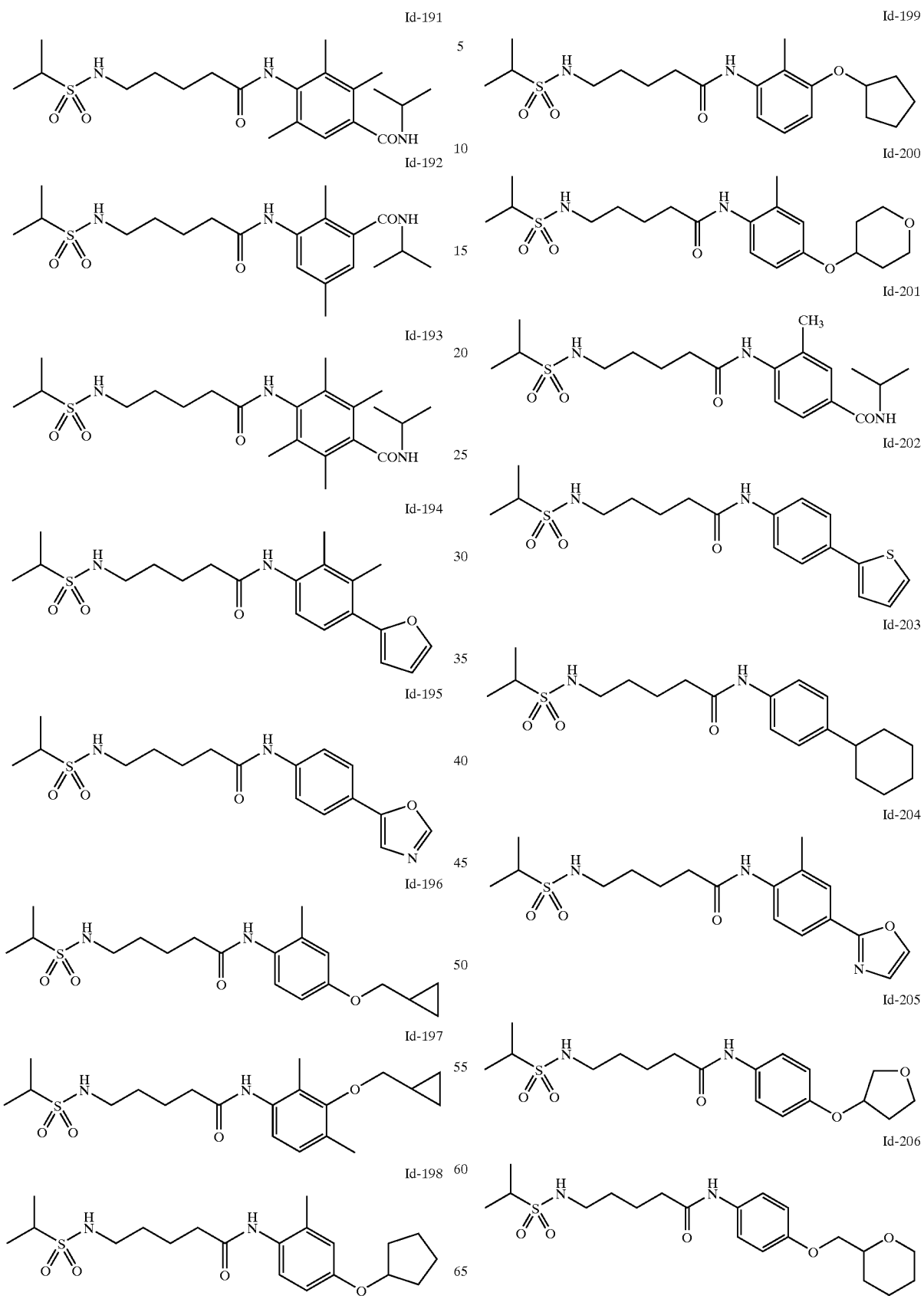

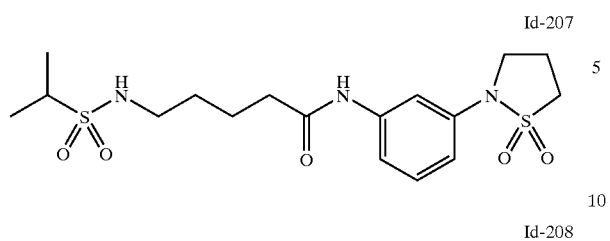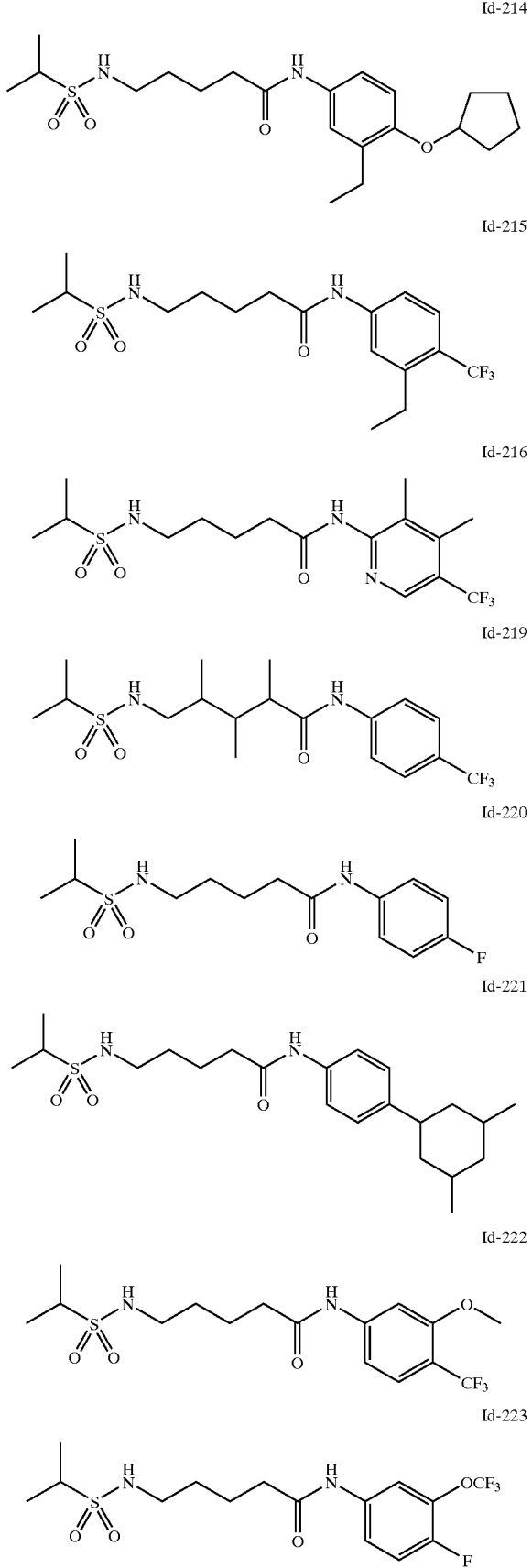

-continued

Id-224

Id-225

Id-226

Ie-1

Ie-2

Ie-4

Ie-7

-continued

Ie-8

Ie-9

Ie-10

Ie-11

Ie-12

Ie-13

Ie-14

Ie-16
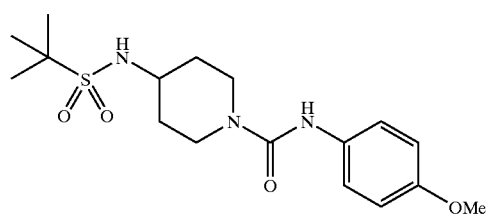
Ie-17
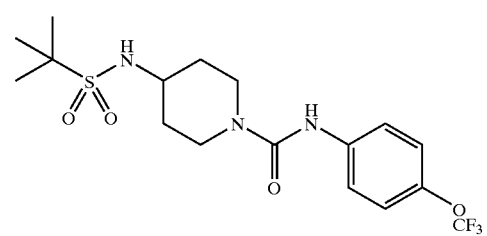
Ie-18
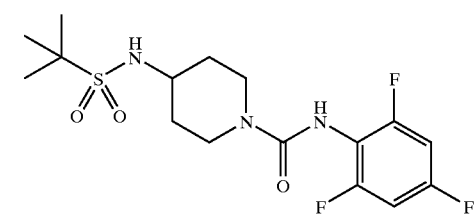
Ie-19
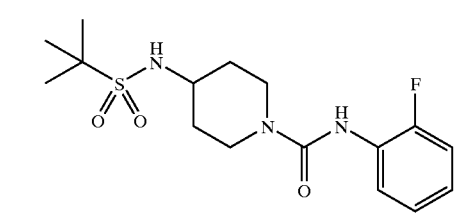
Ie-20
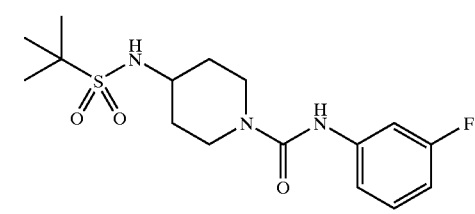
Ie-21
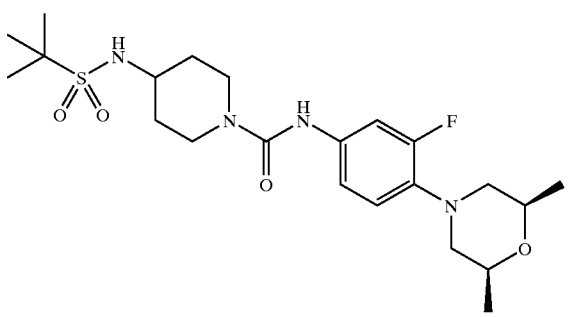
Ie-22
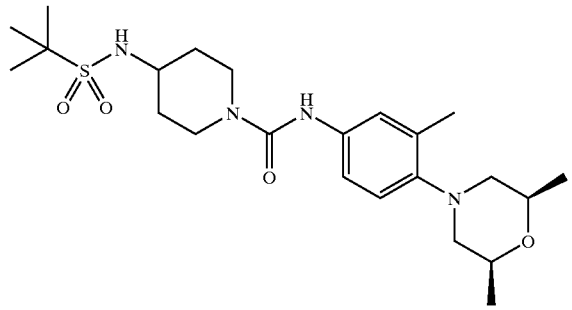
Ie-23
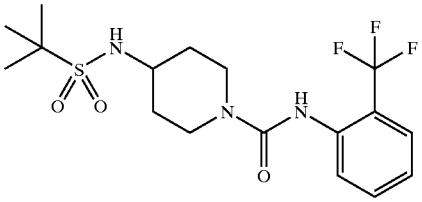
Ie-24
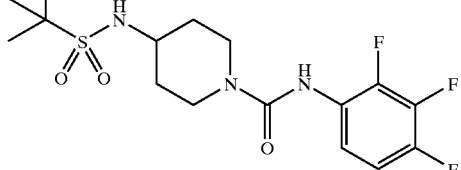
Ie-25
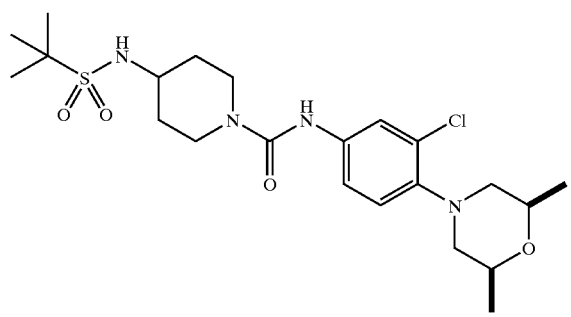
Ie-26
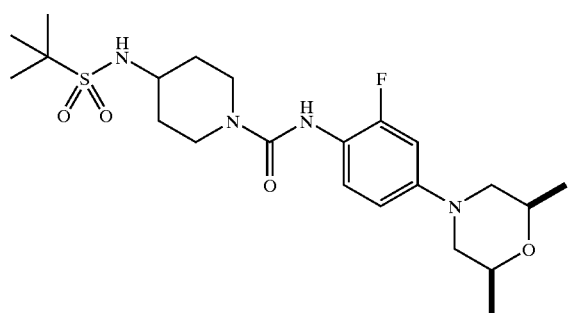

287
-continued
Ie-27
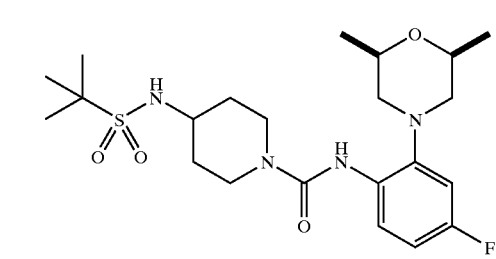
Ie-28
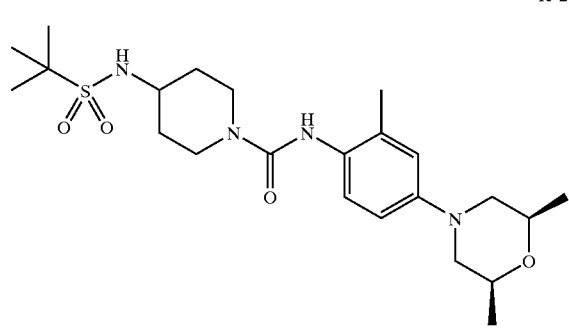
Ie-29
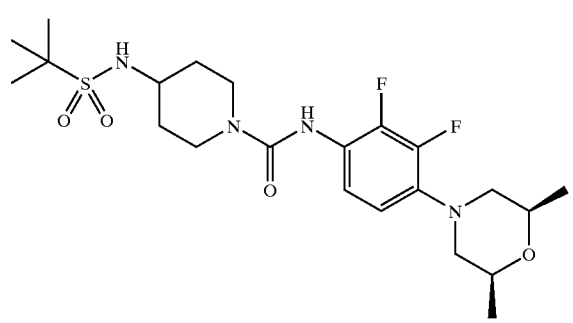
Ie-30
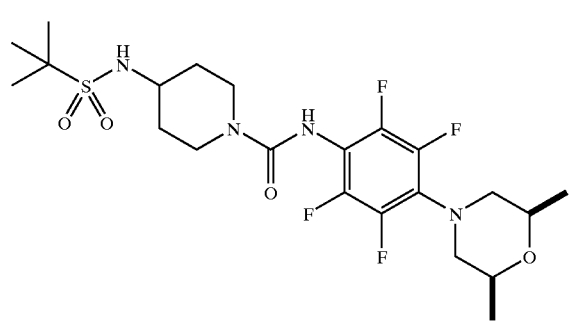
Ie-31
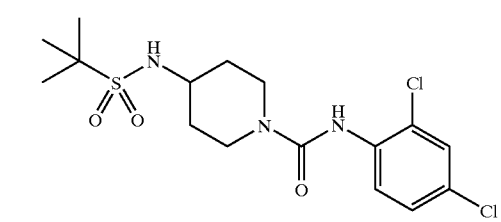
288
-continued
Ie-32
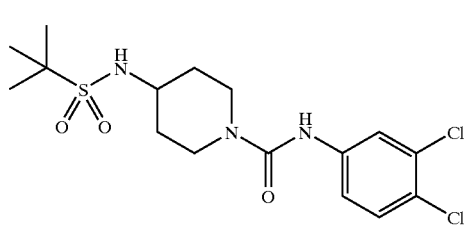
Ie-33
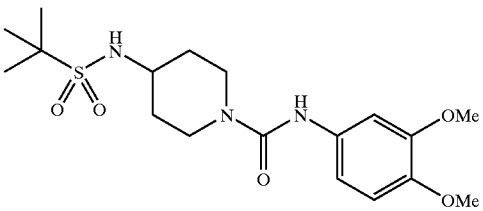
Ie-34
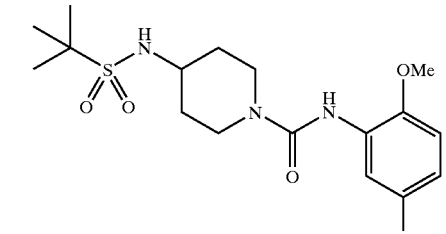
Ie-35
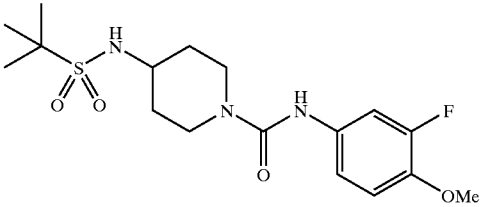
Ie-36
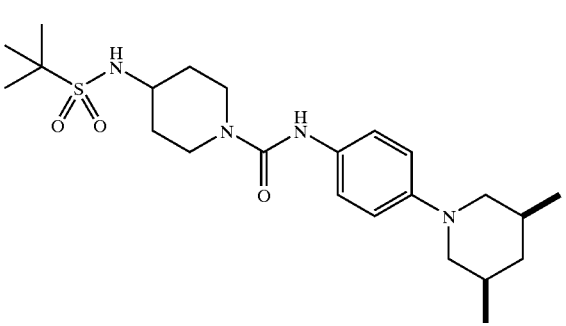
Ie-37
Ie-38
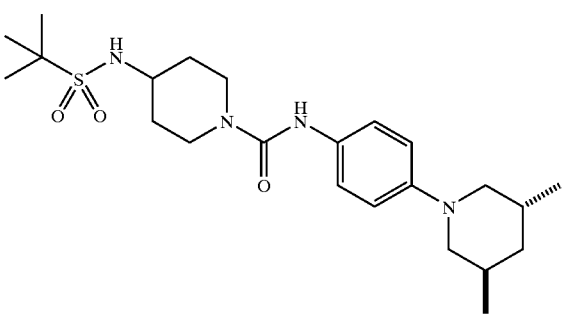

Ie-39
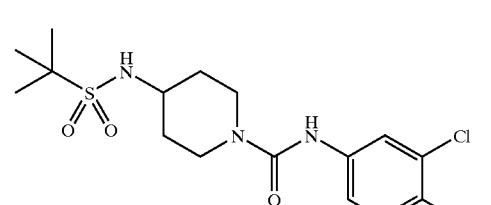
Ie-40
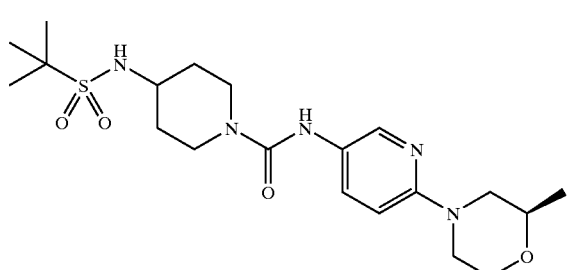
Ie-41
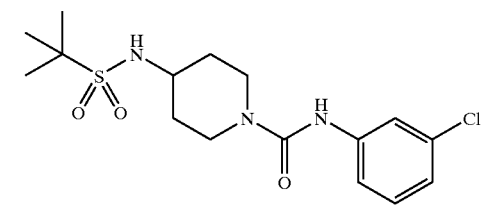
Ie-42
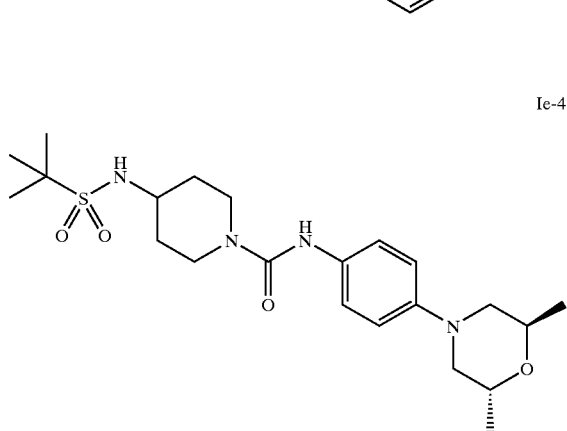
Ie-43
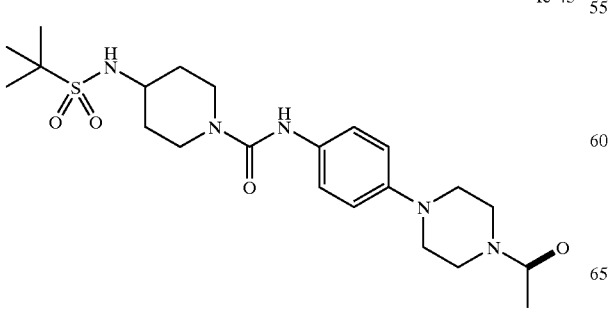
Ie-44
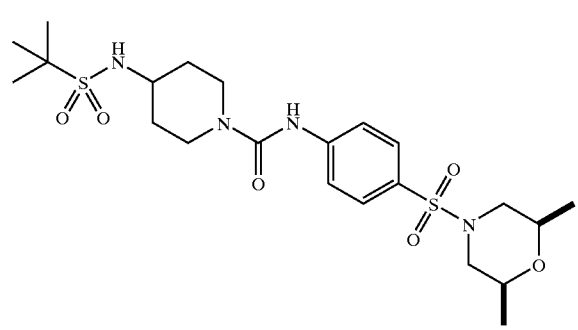
Ie-45
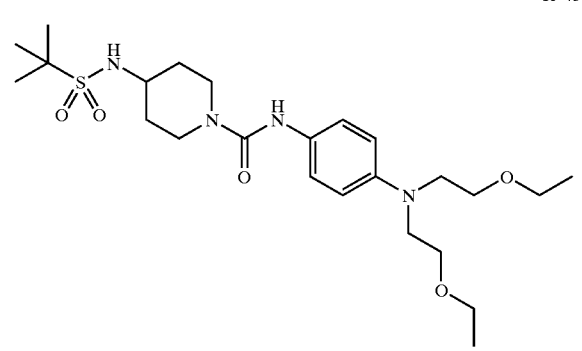
Ie-46
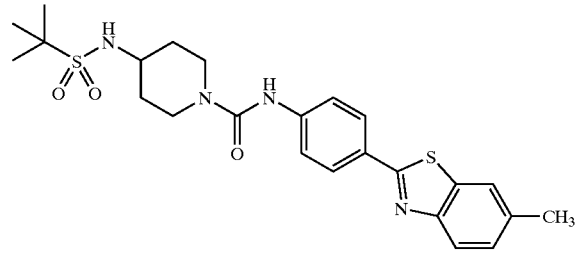
Ie-47
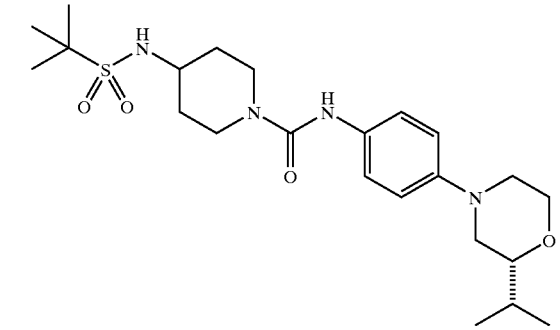

Ie-48
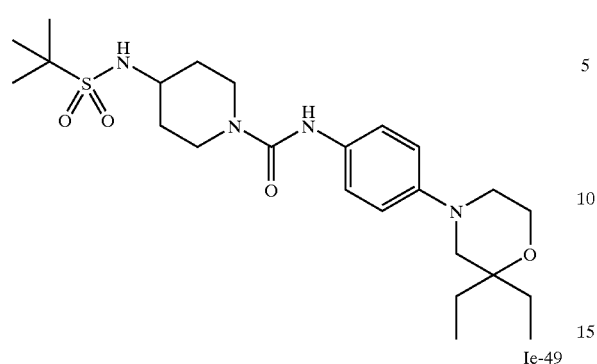
Ie-53
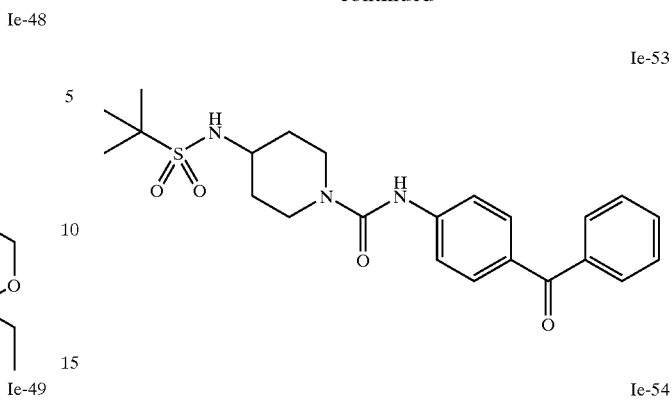
Ie-49
Ie-54
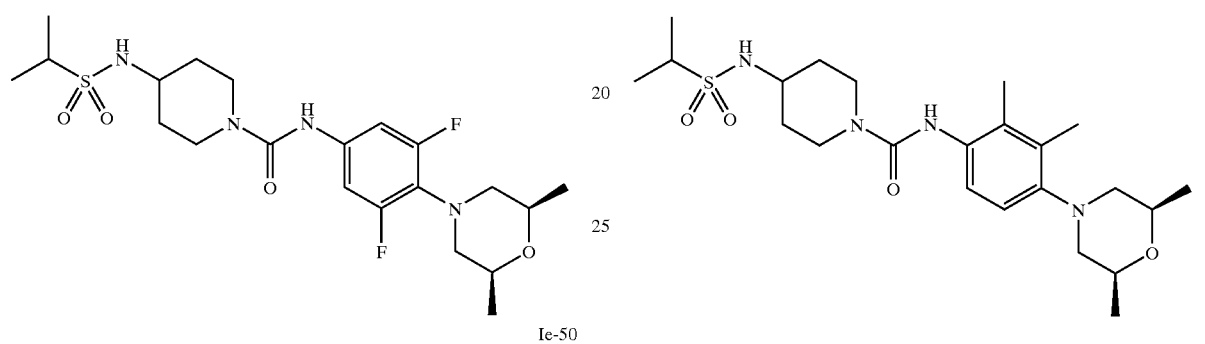
Ie-50
Ie-55
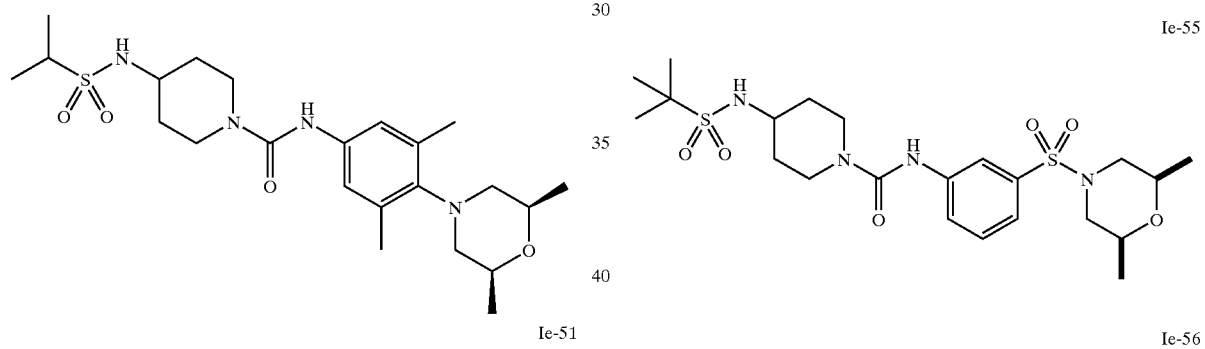
Ie-51
Ie-56
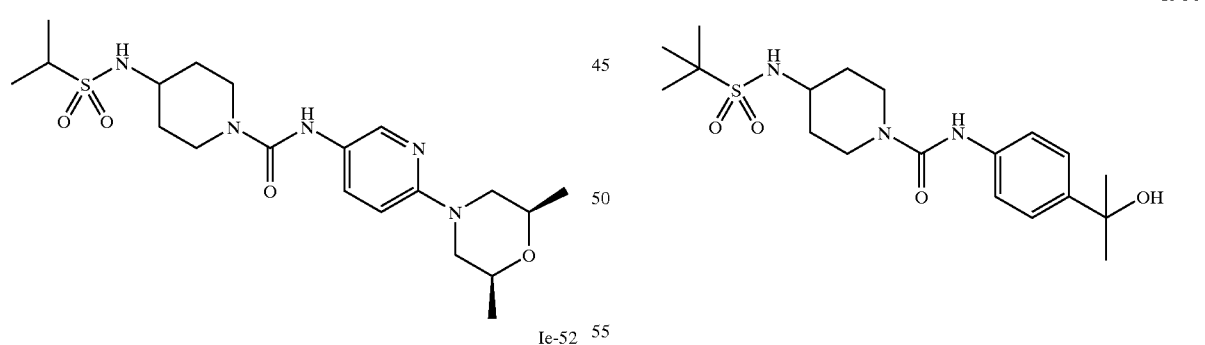
Ie-52
Ie-57
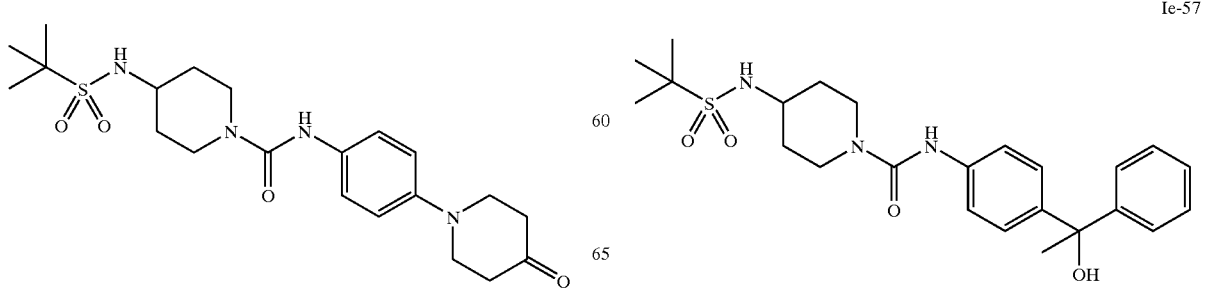

Ie-58
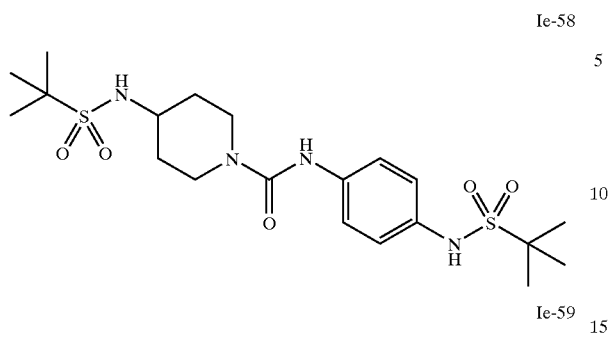
Ie-59
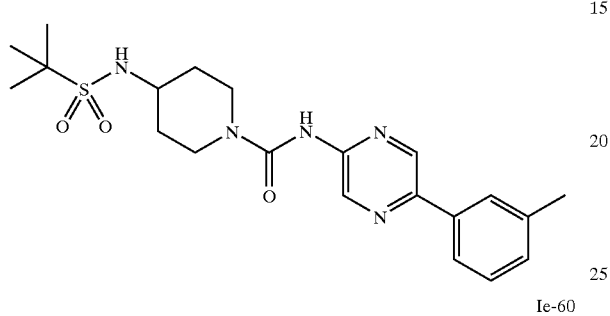
Ie-60
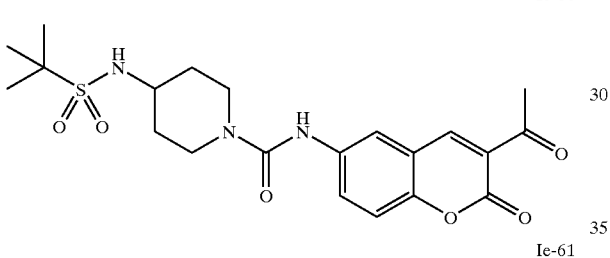
Ie-61
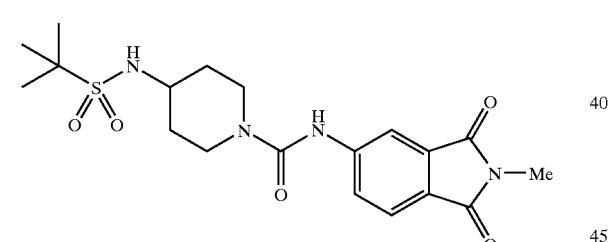
Ie-62
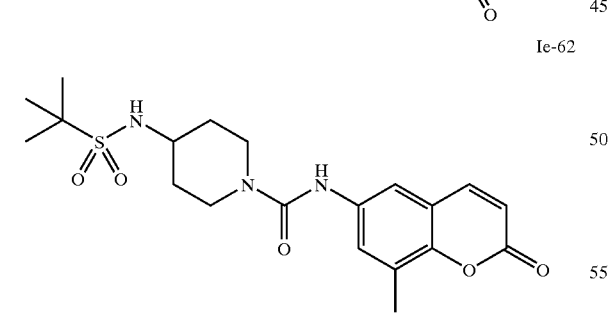
Ie-63
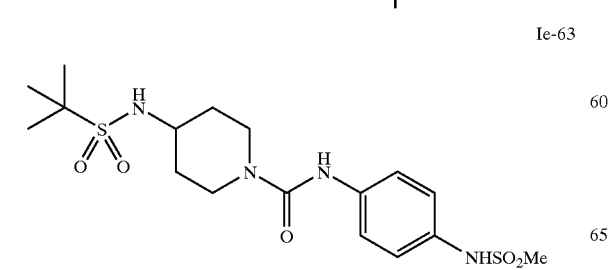
Ie-64
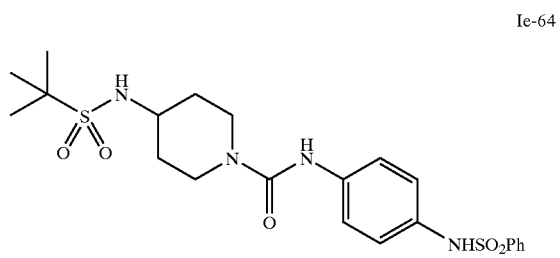
Ie-65
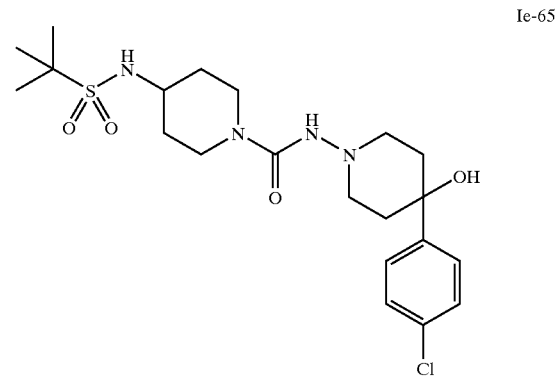
Ie-66
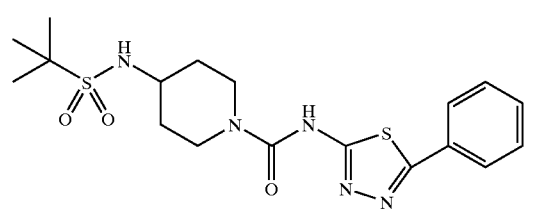
Ie-67
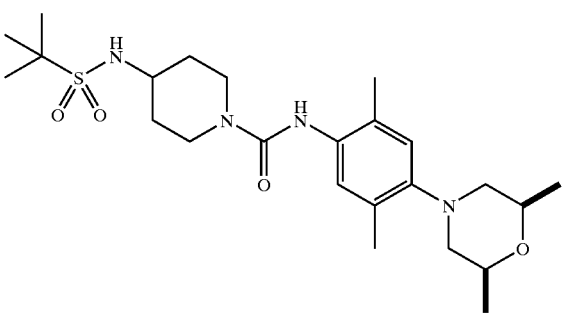
Ie-68
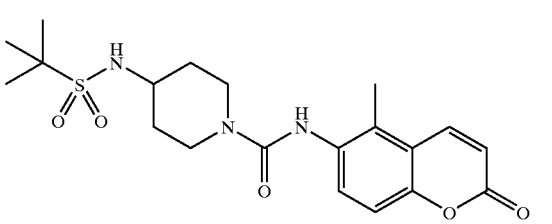

Ie-69
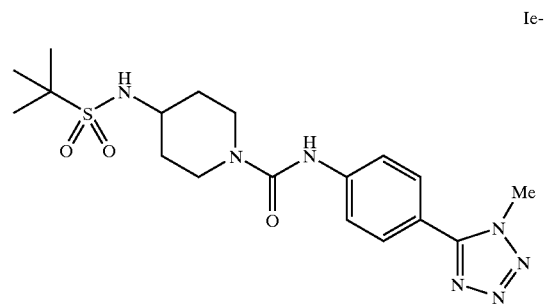
Ie-70
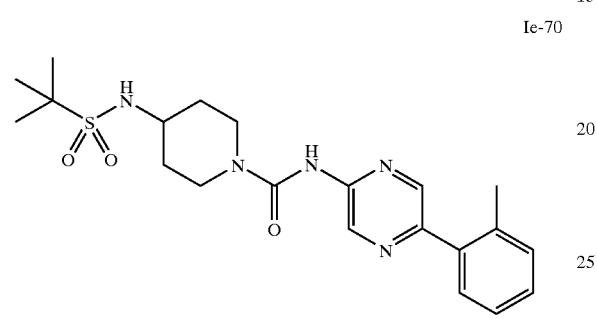
Ie-71
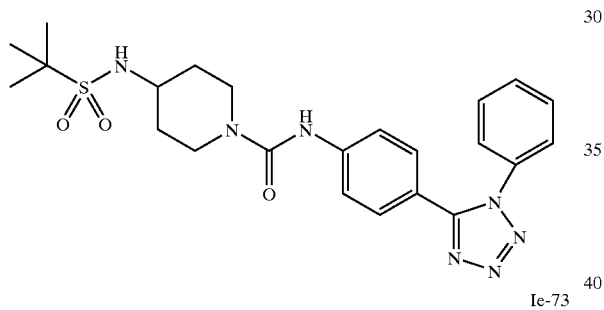
Ie-73
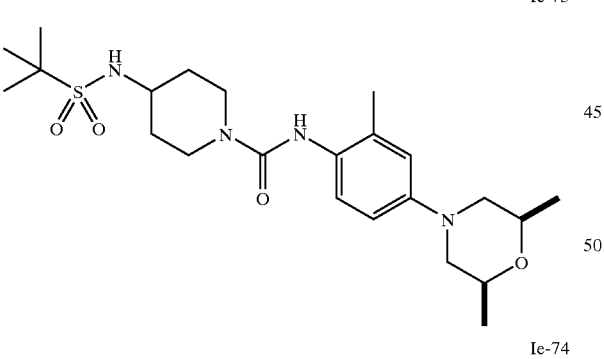
Ie-74
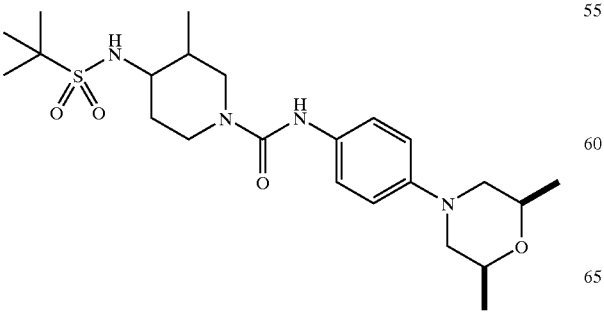
Ie-75
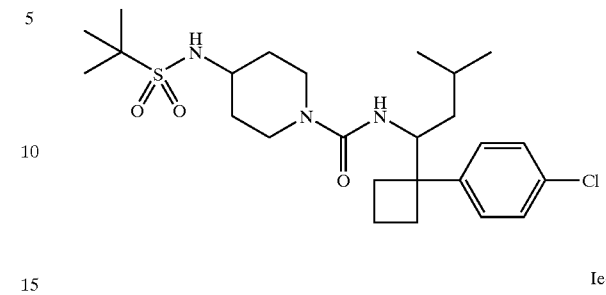
Ie-76
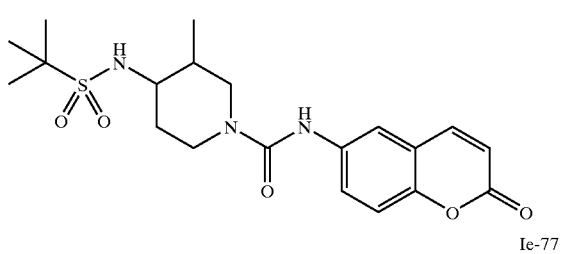
Ie-77
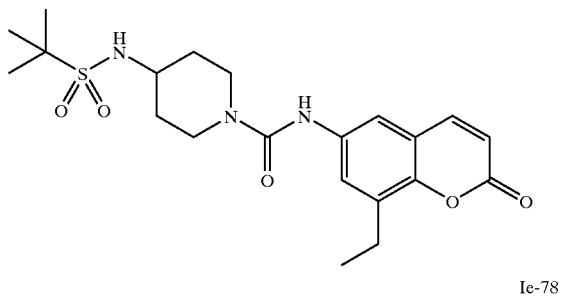
Ie-78
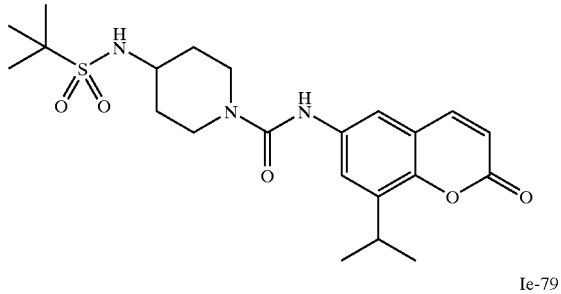
Ie-79
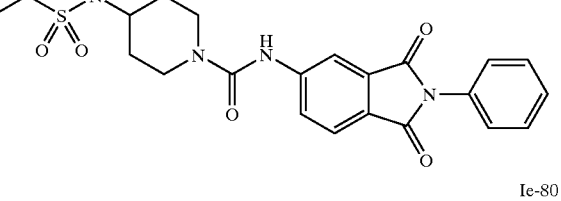
Ie-80
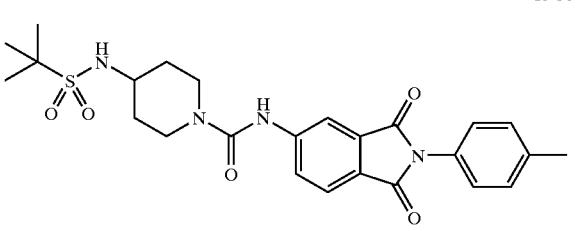

Ie-81
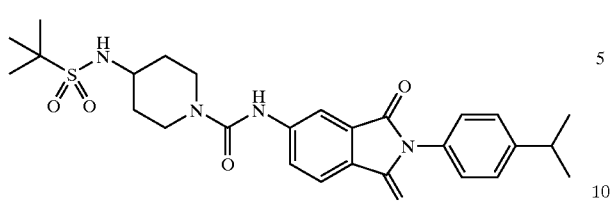
Ie-82
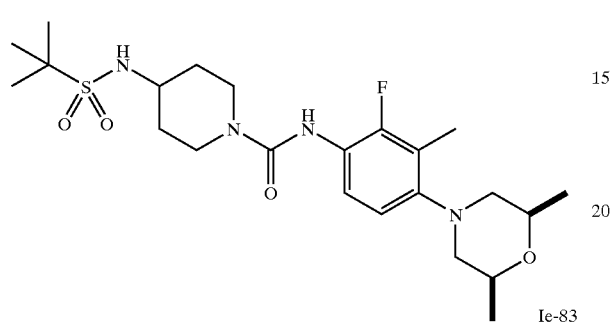
Ie-83
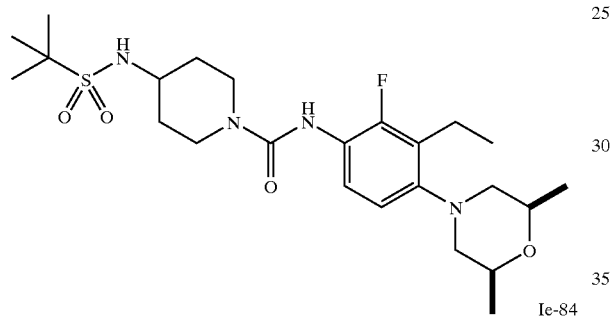
Ie-84
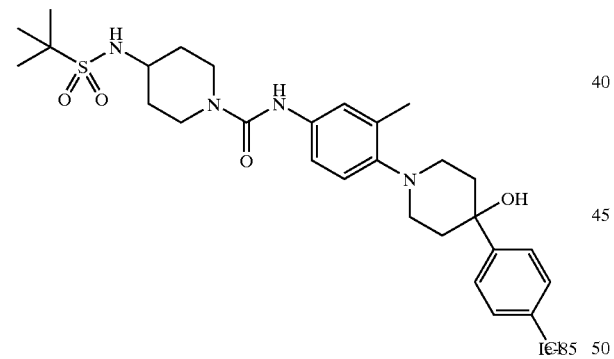
Ie-85
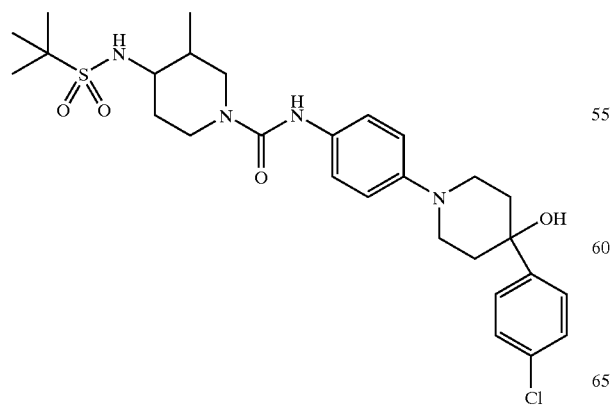
Ie-86
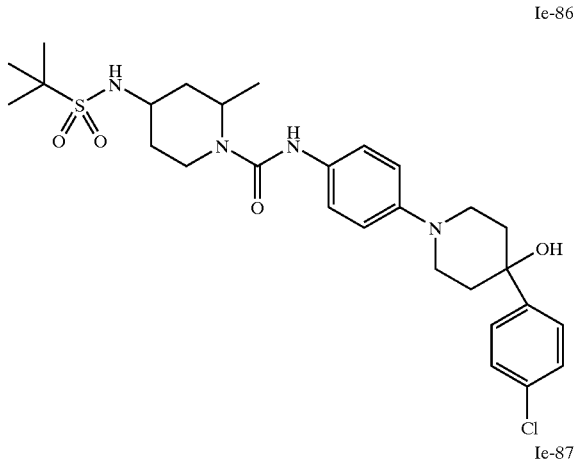
Ie-87
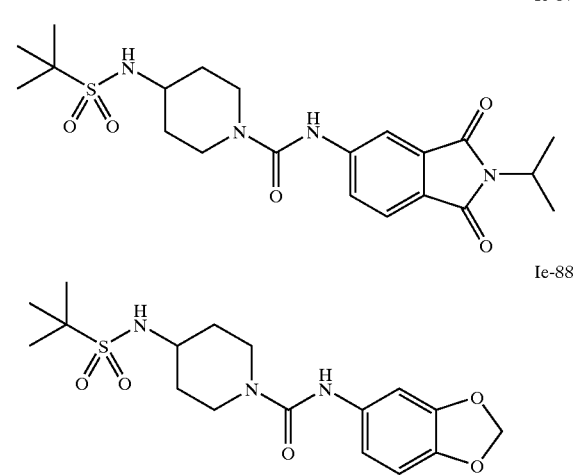
Ie-88
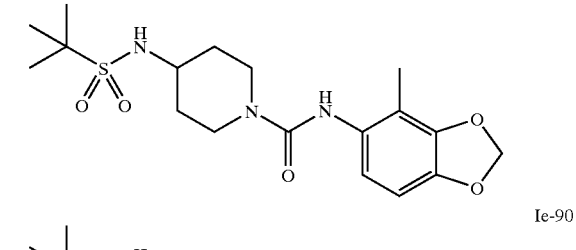
Ie-89
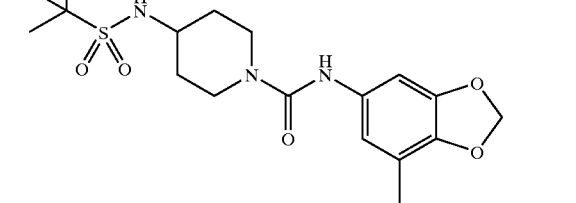
Ie-90
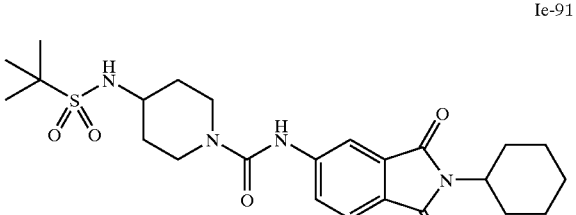
Ie-91

Ie-92 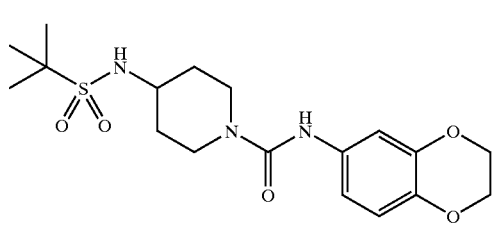
Ie-93 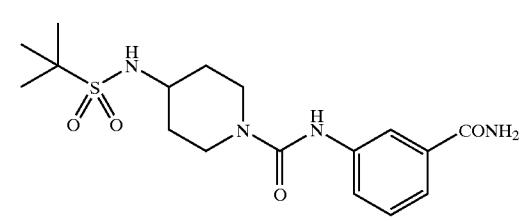
Ie-94 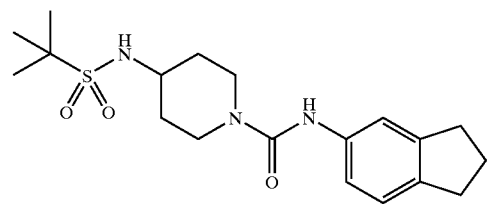
Ie-95 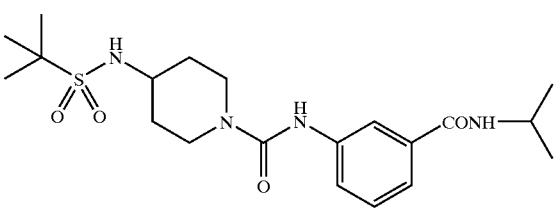
Ie-96 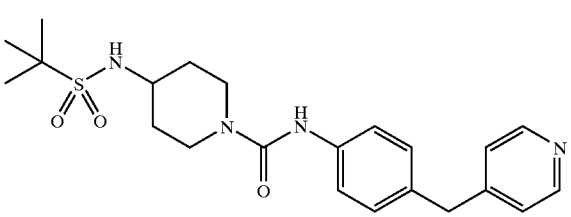
Ie-97 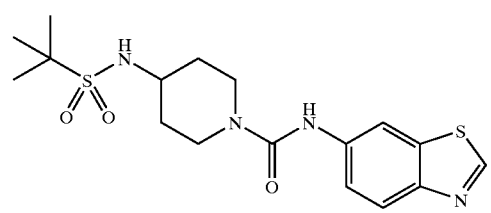
Ie-98 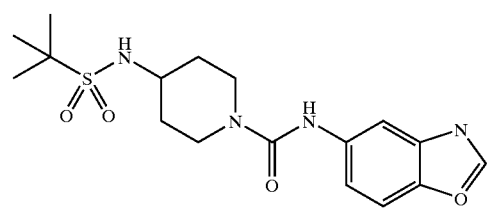
Ie-99 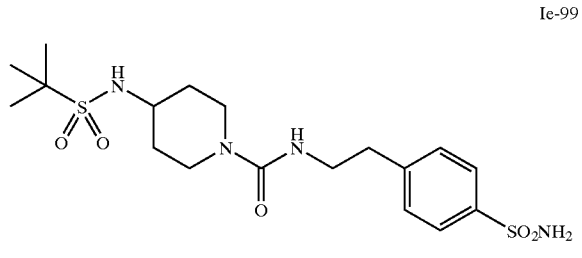
Ie-100 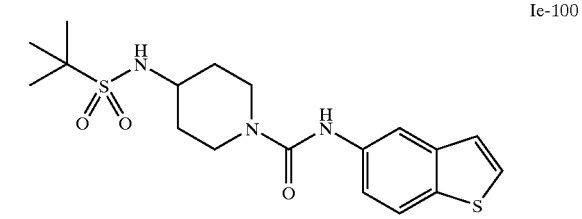
Ie-101 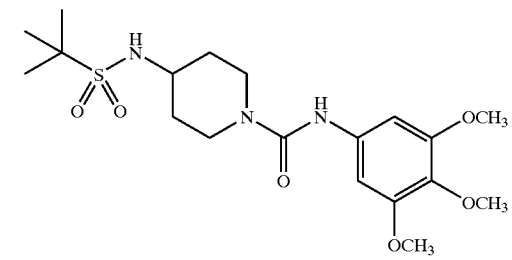
Ie-102 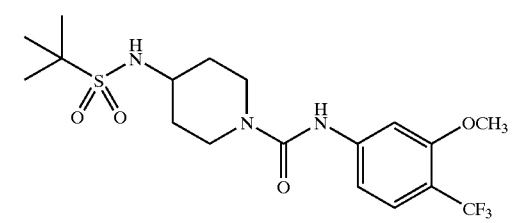
Ie-103 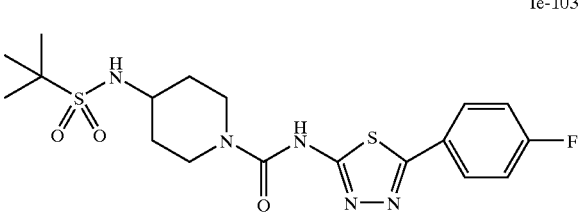
Ie-104 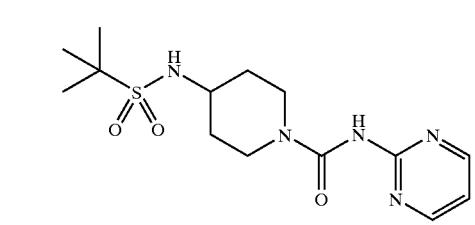
Ie-105 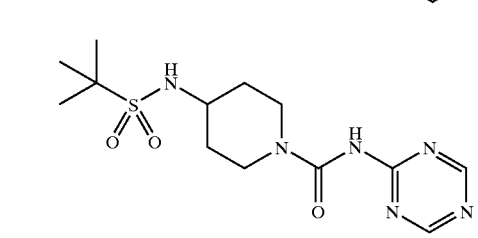

Ie-106 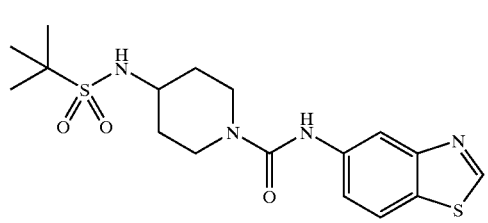
Ie-107 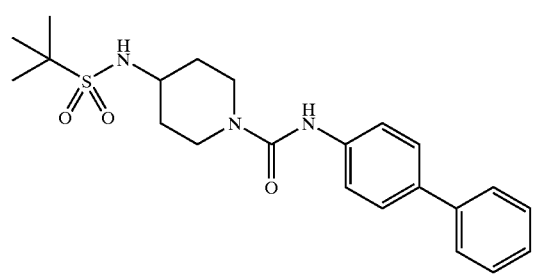
Ie-108 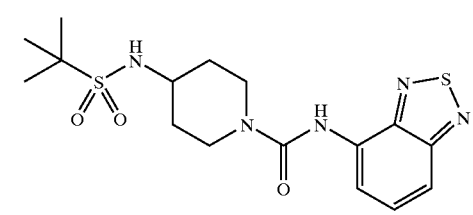
Ie-109 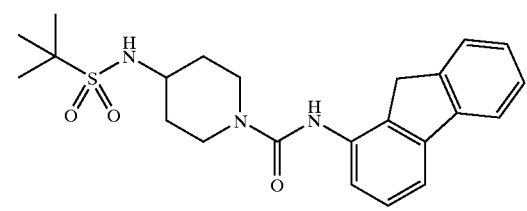
Ie-110 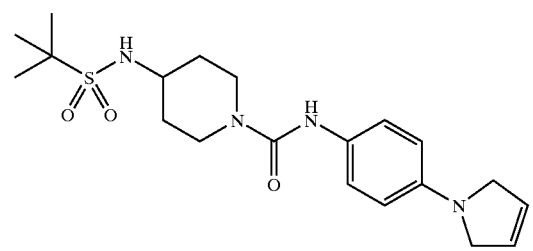
Ie-111 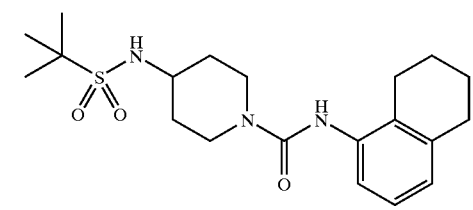
Ie-112 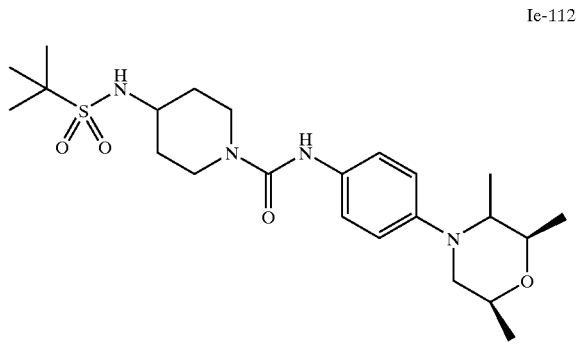
Ie-113 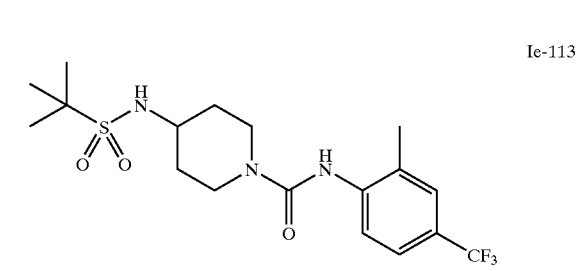
Ie-114 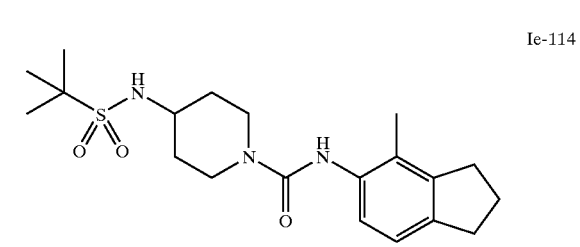
Ie-115 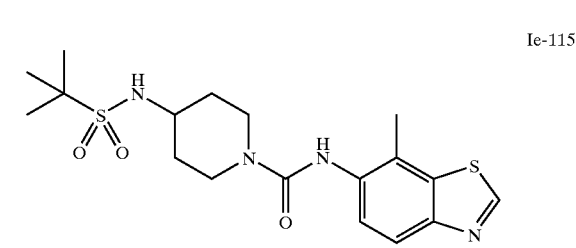
Ie-116 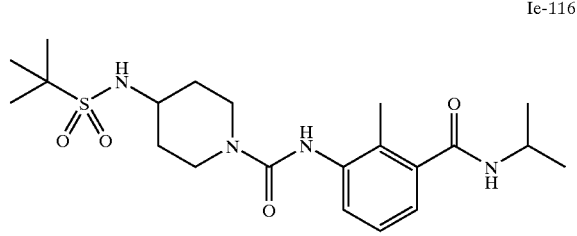
Ie-117 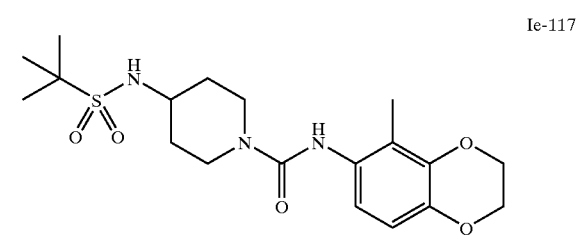

Ie-118
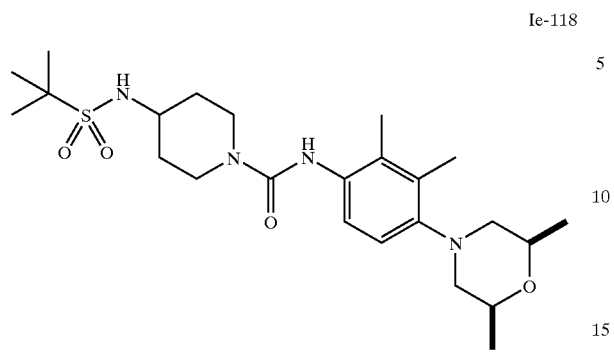
Ie-119
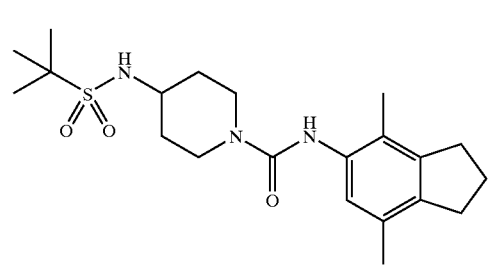
Ie-120
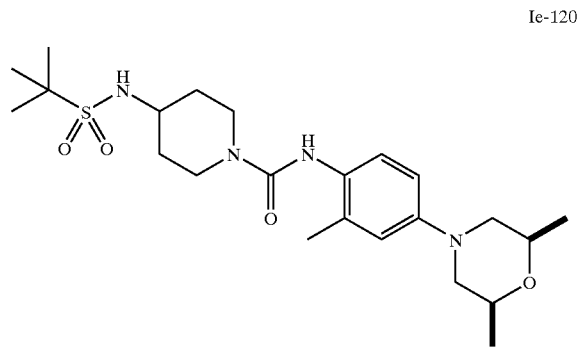
Ie-121
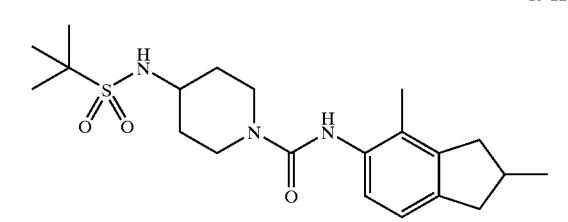
Ie-122
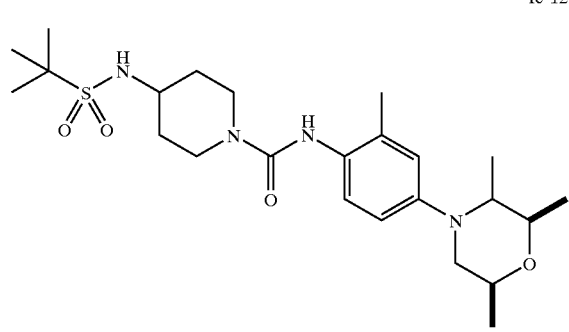
Ie-123
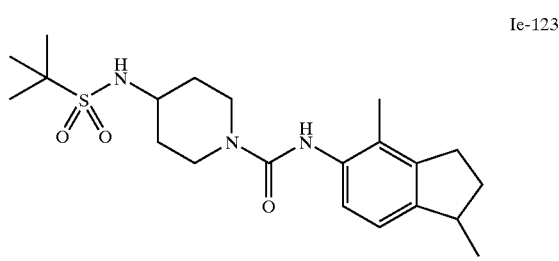
Ie-124
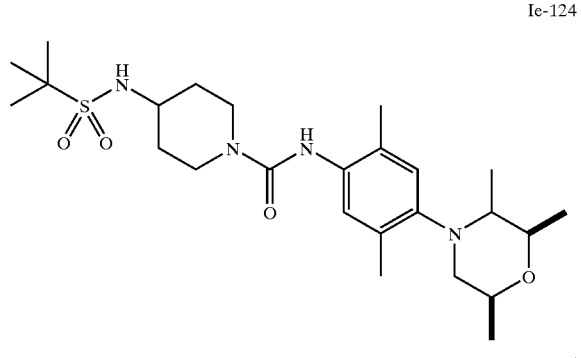
Ie-125
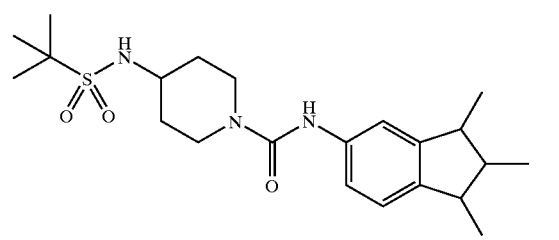
Ie-126
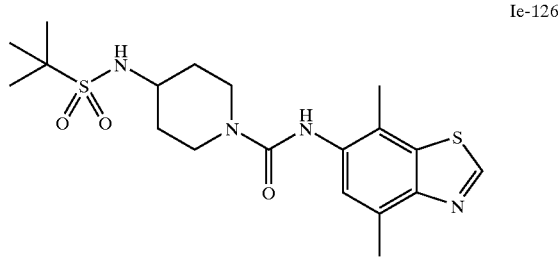
Ie-127
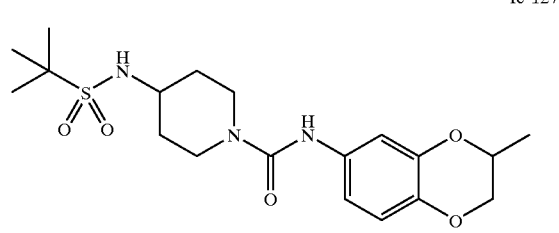
Ie-128
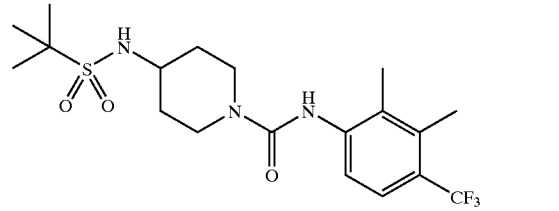

Ie-129
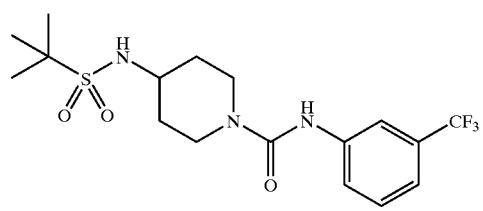
Ie-130
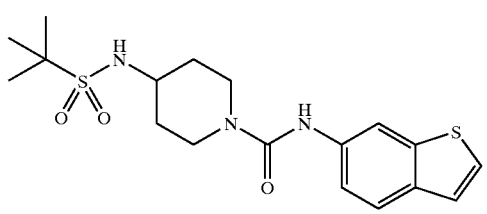
Ie-131
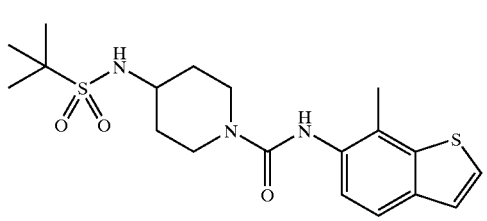
Ie-132
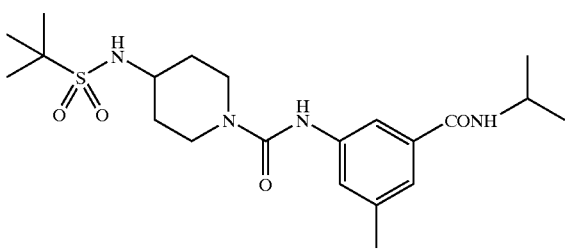
Ie-133
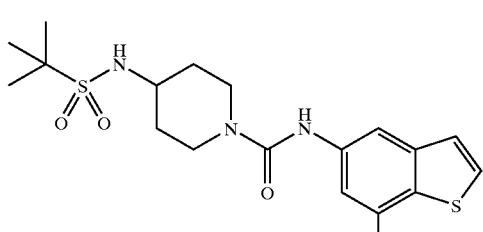
Ie-134
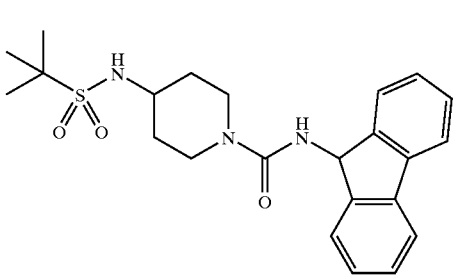
Ie-135
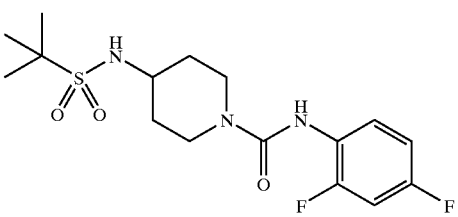
Ie-136
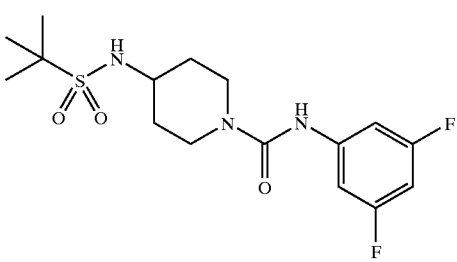
Ie-137
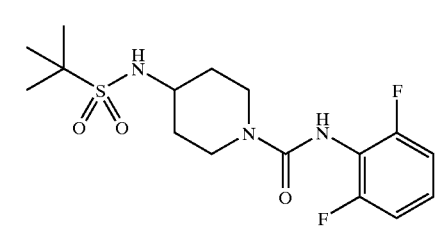
Ie-138
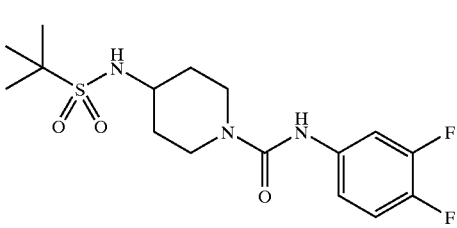
Ie-139
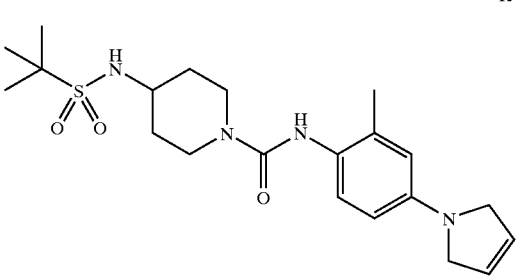
Ie-140
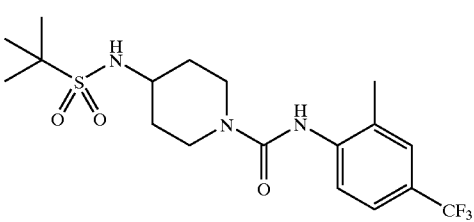
Ie-141
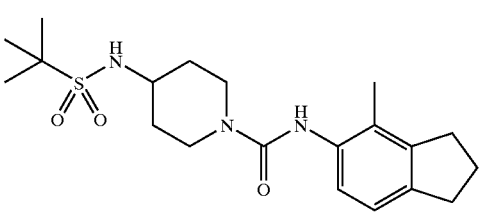

-continued
Ie-142
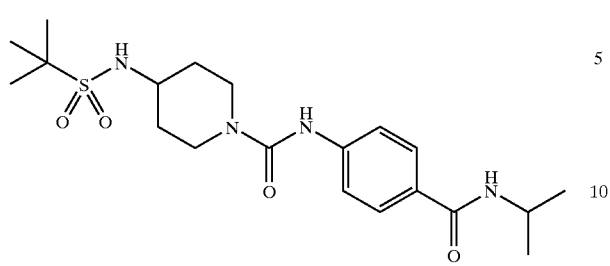
Ie-143
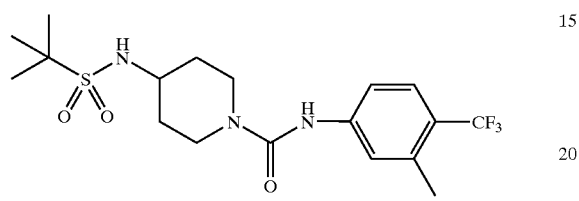
Ie-144
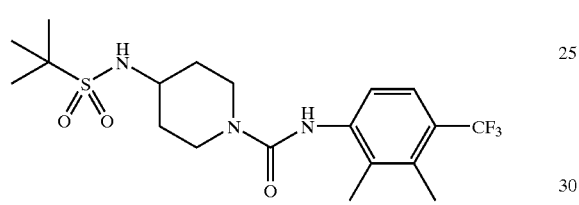
Ie-145
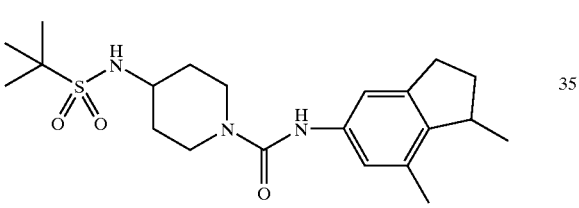
Ie-146
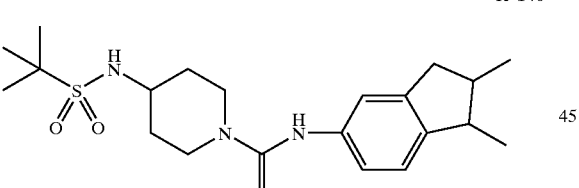
Ie-147
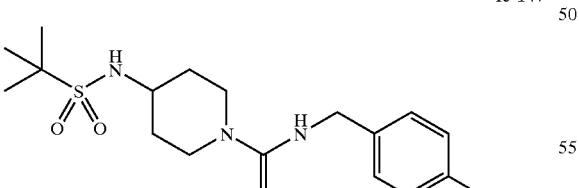
Ie-148
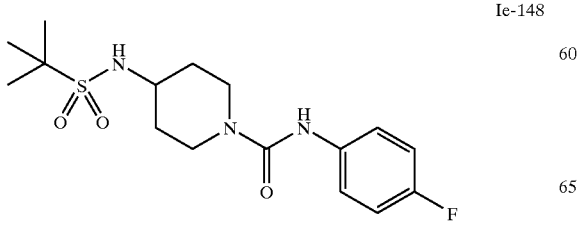
-continued
Ie-149
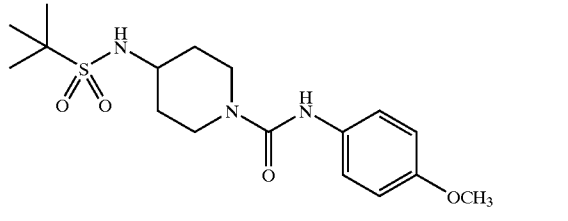
Ie-150
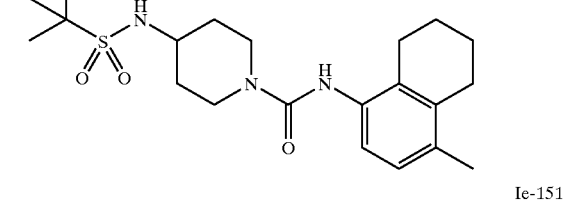
Ie-151
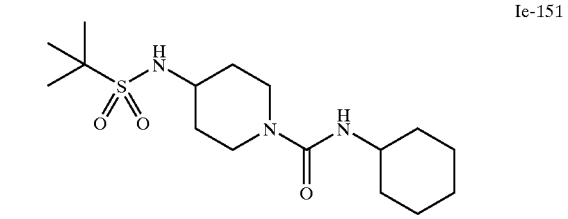
Ie-152
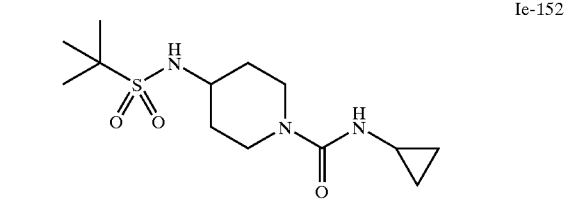
Ie-153
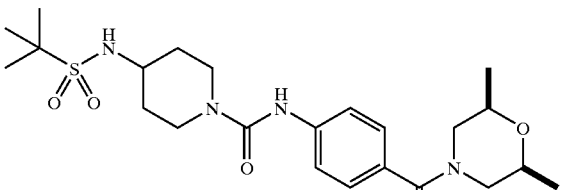
Ie-154
Ie-155
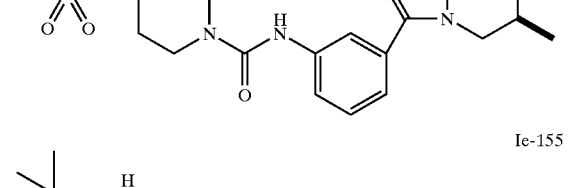
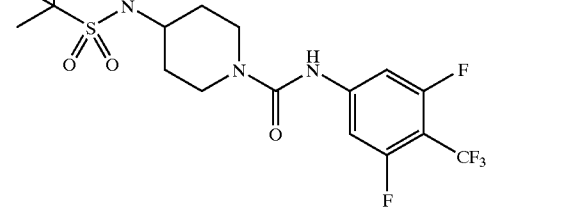

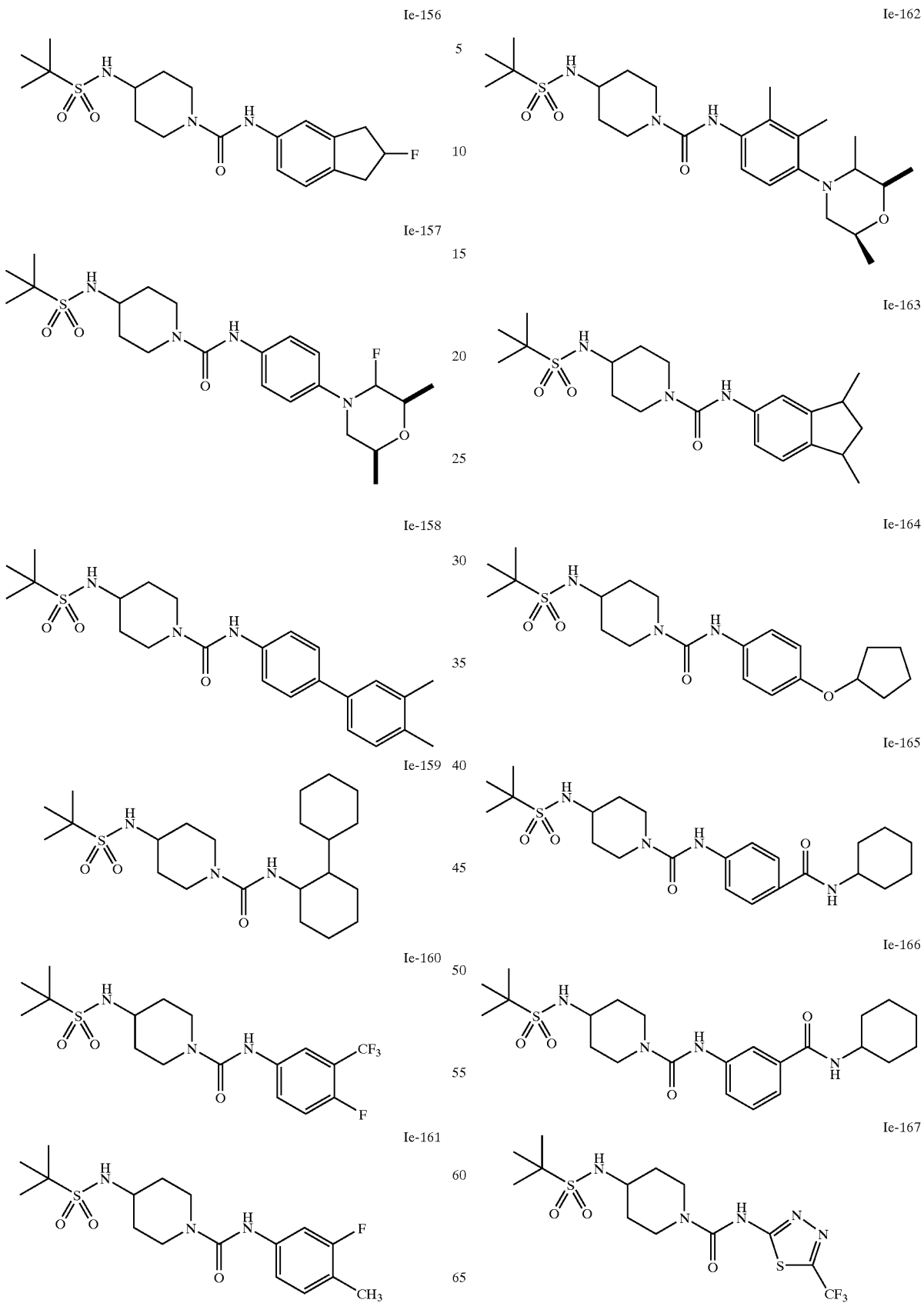

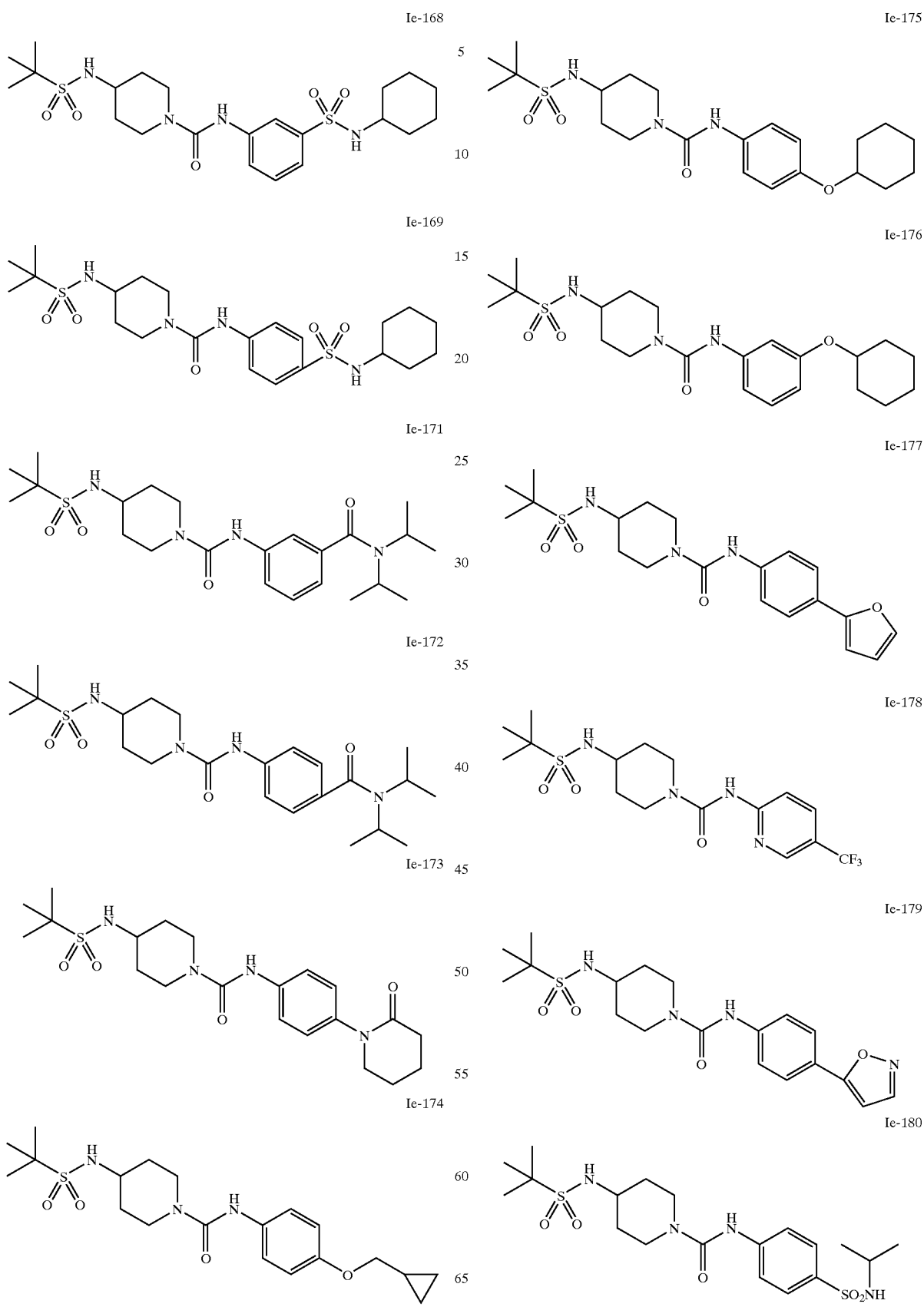

Ie-181
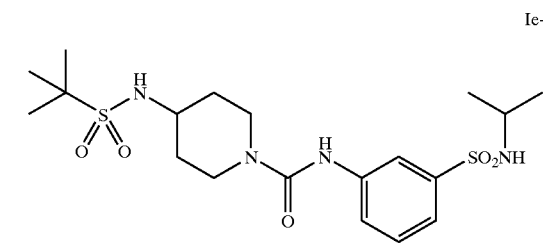
Ie-182
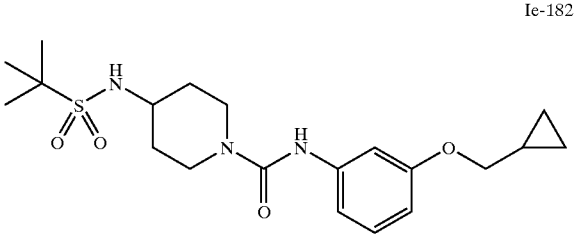
Ie-183
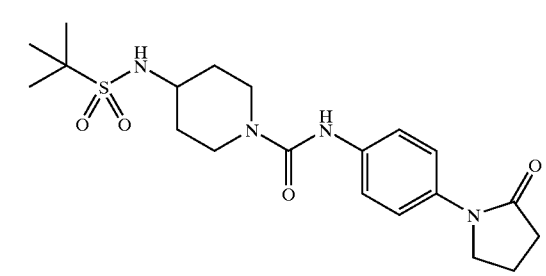
Ie-184
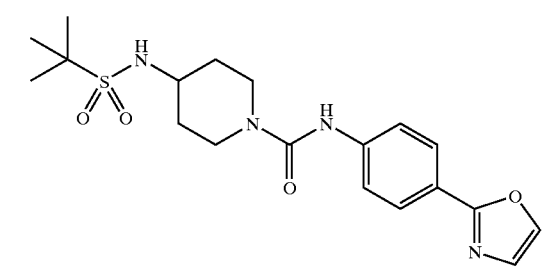
Ie-185
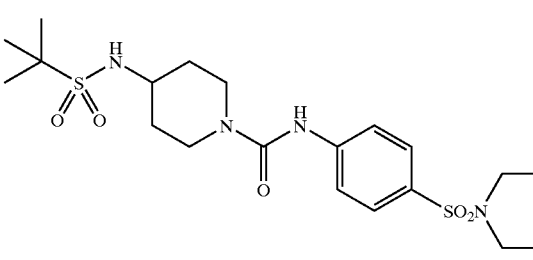
Ie-186
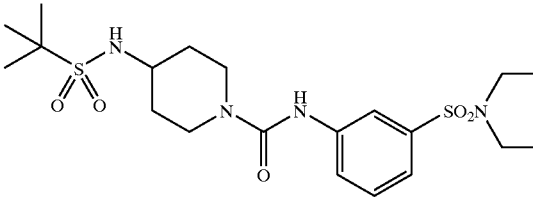
Ie-187
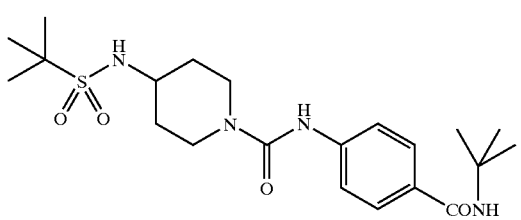
Ie-188
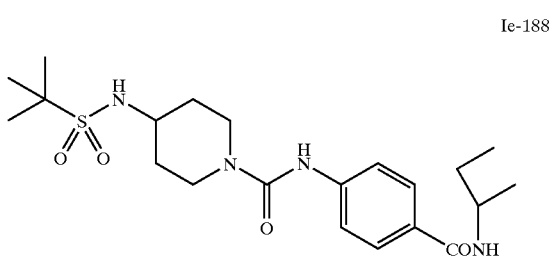
Ie-189
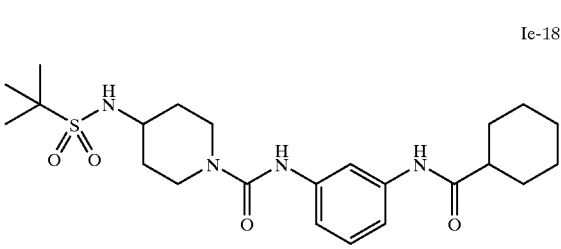
Ie-190
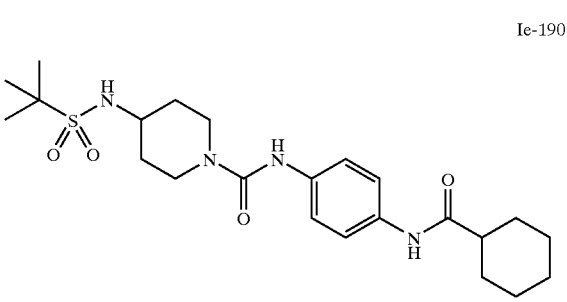
Ie-191
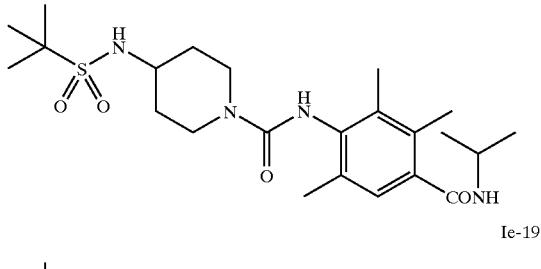
Ie-192
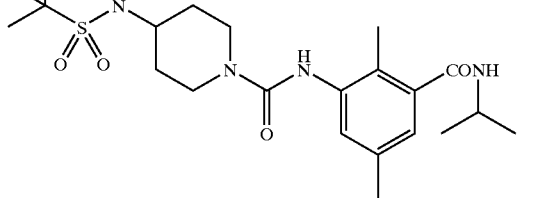

Ie-193
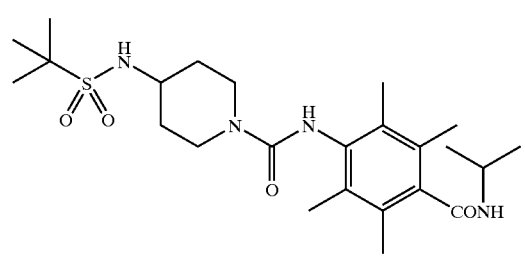
Ie-194
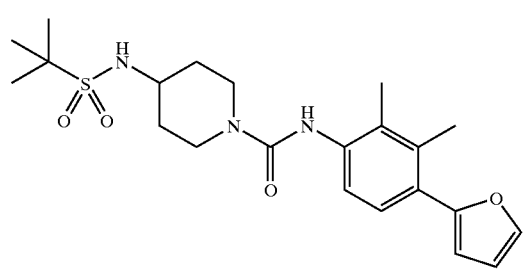
Ie-195
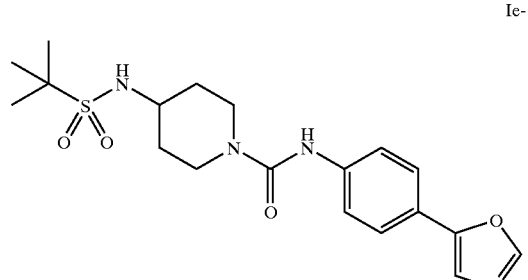
Ie-196
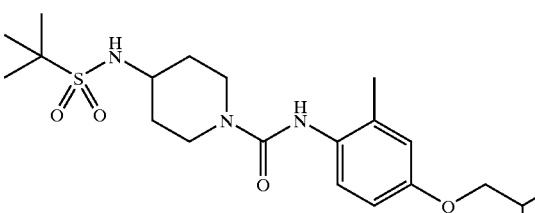
Ie-197
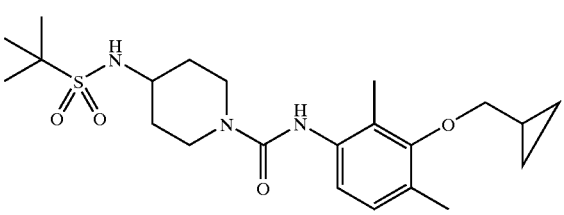
Ie-198
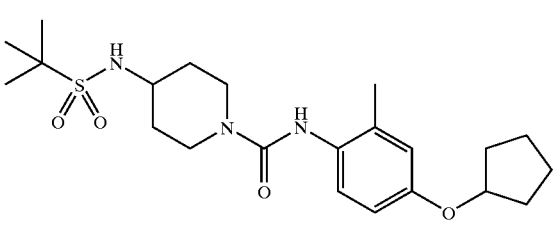
Ie-199
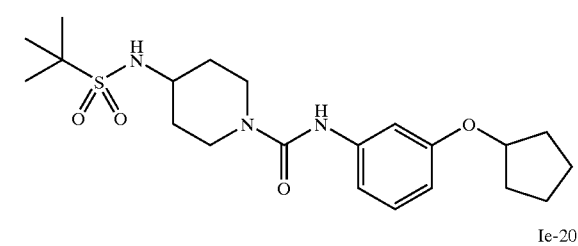
Ie-200
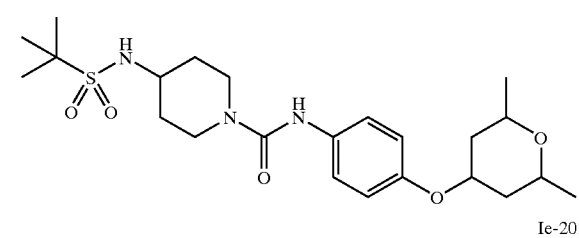
Ie-201
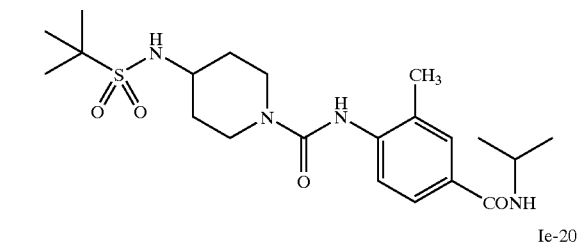
Ie-202
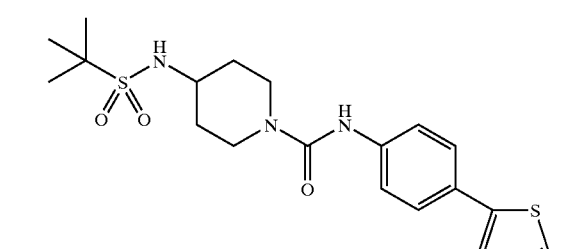
Ie-203
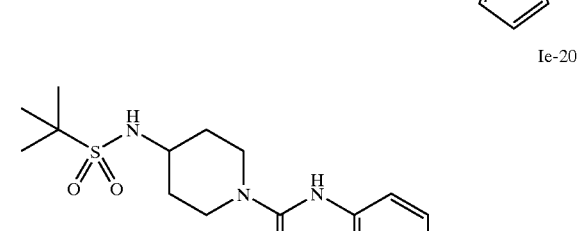
Ie-204
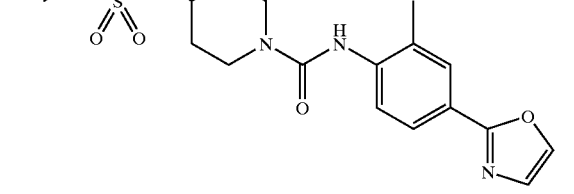

Ie-205
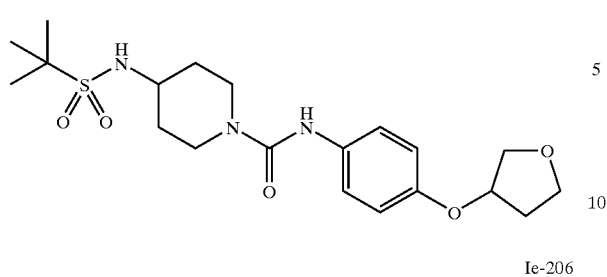
Ie-206
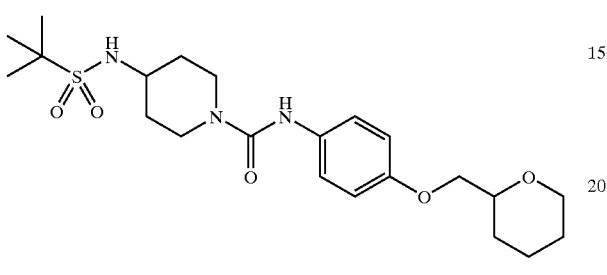
Ie-207
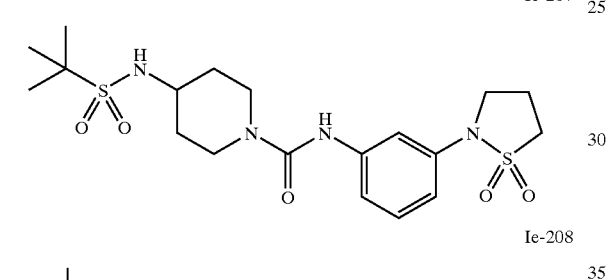
Ie-208
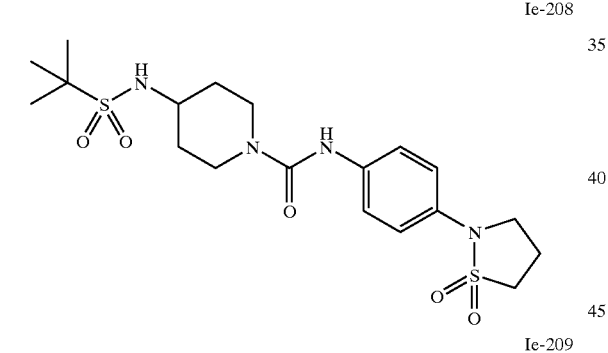
Ie-209
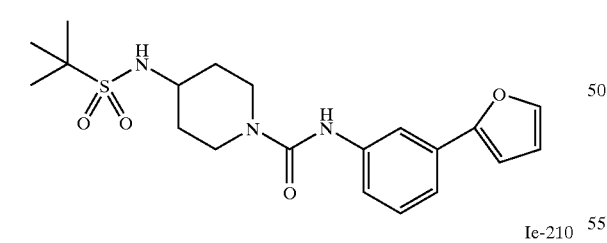
Ie-210
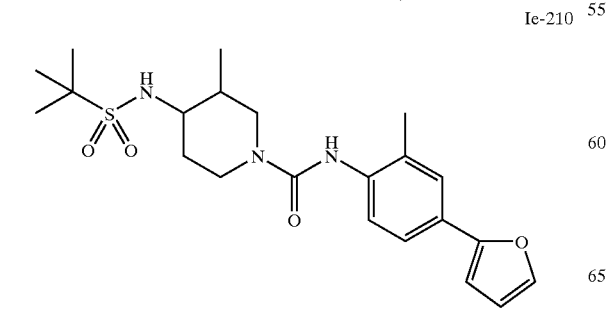
Ie-211
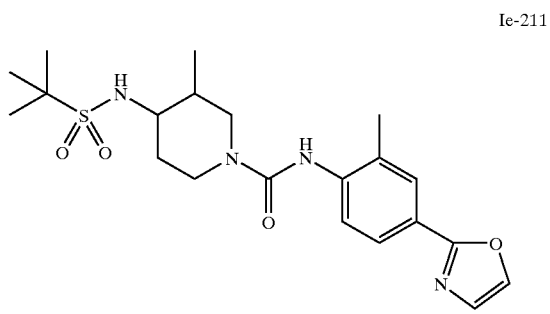
Ie-212
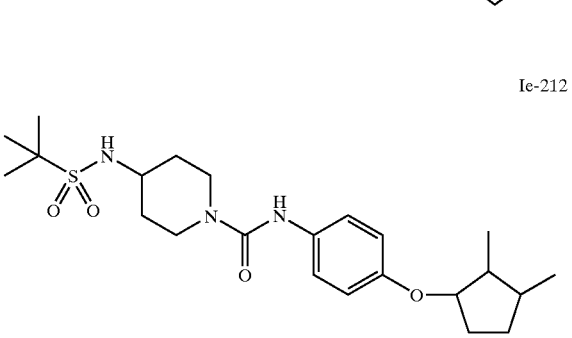
Ie-213
Ie-214
Ie-215
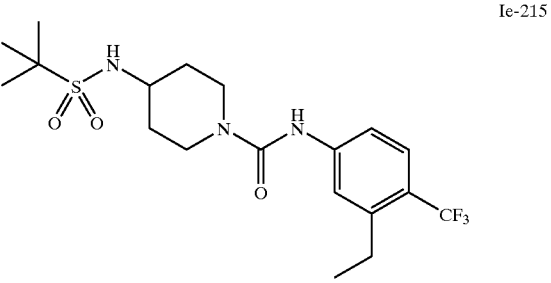

Ie-216
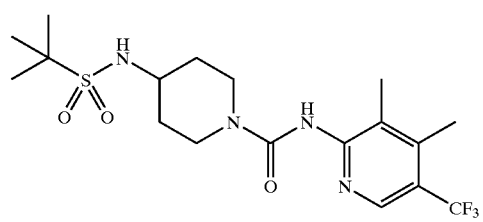
Ie-219
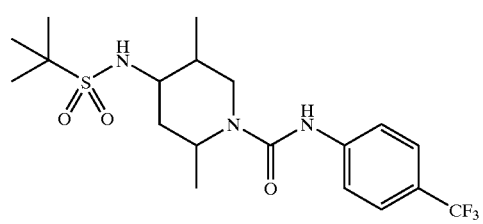
Ie-220
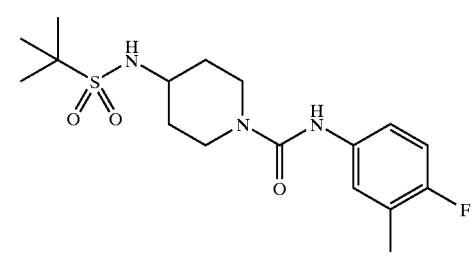
Ie-221
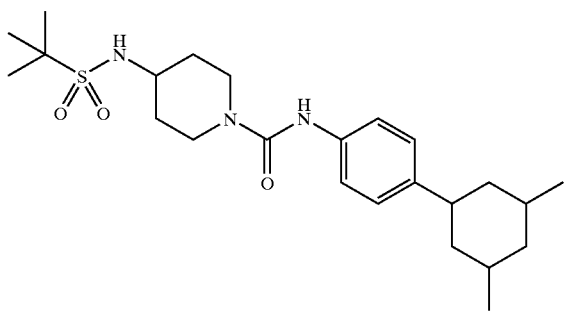
Ie-222
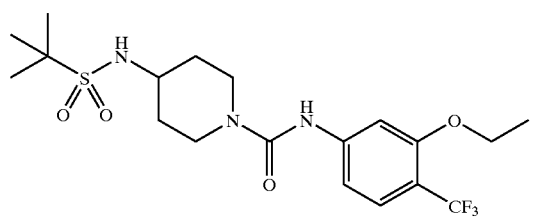
Ie-223
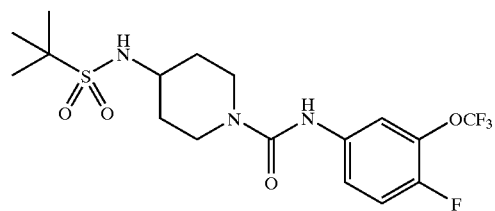
Ie-224
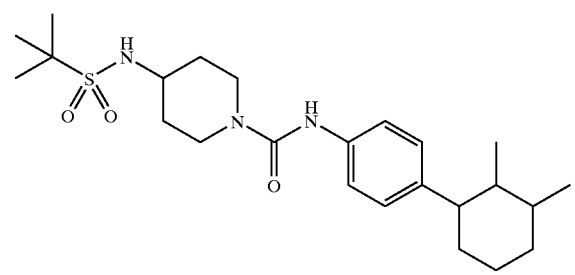
Ie-225
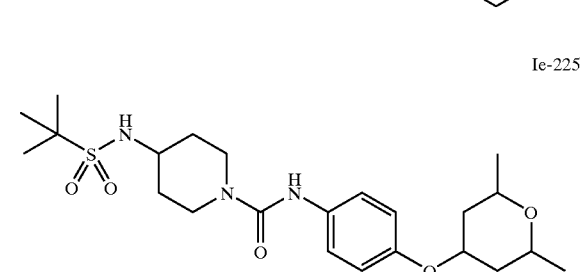
Ie-226
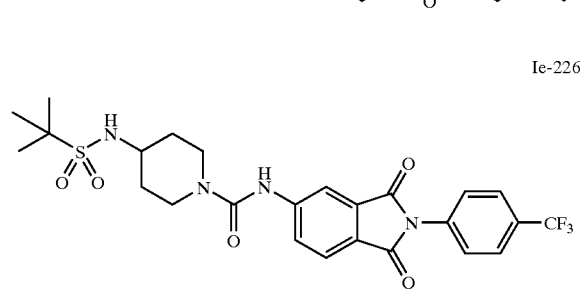
If-1
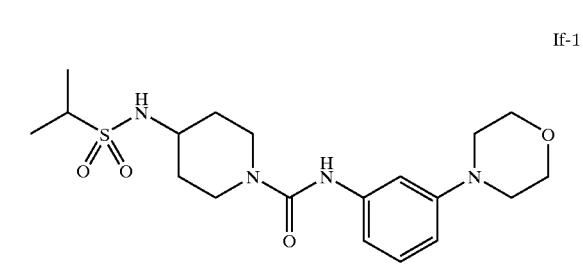
If-2
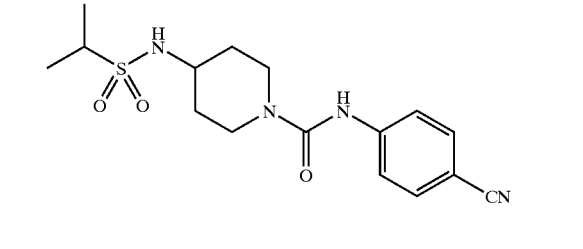
If-4
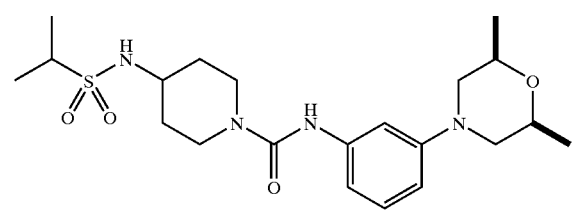

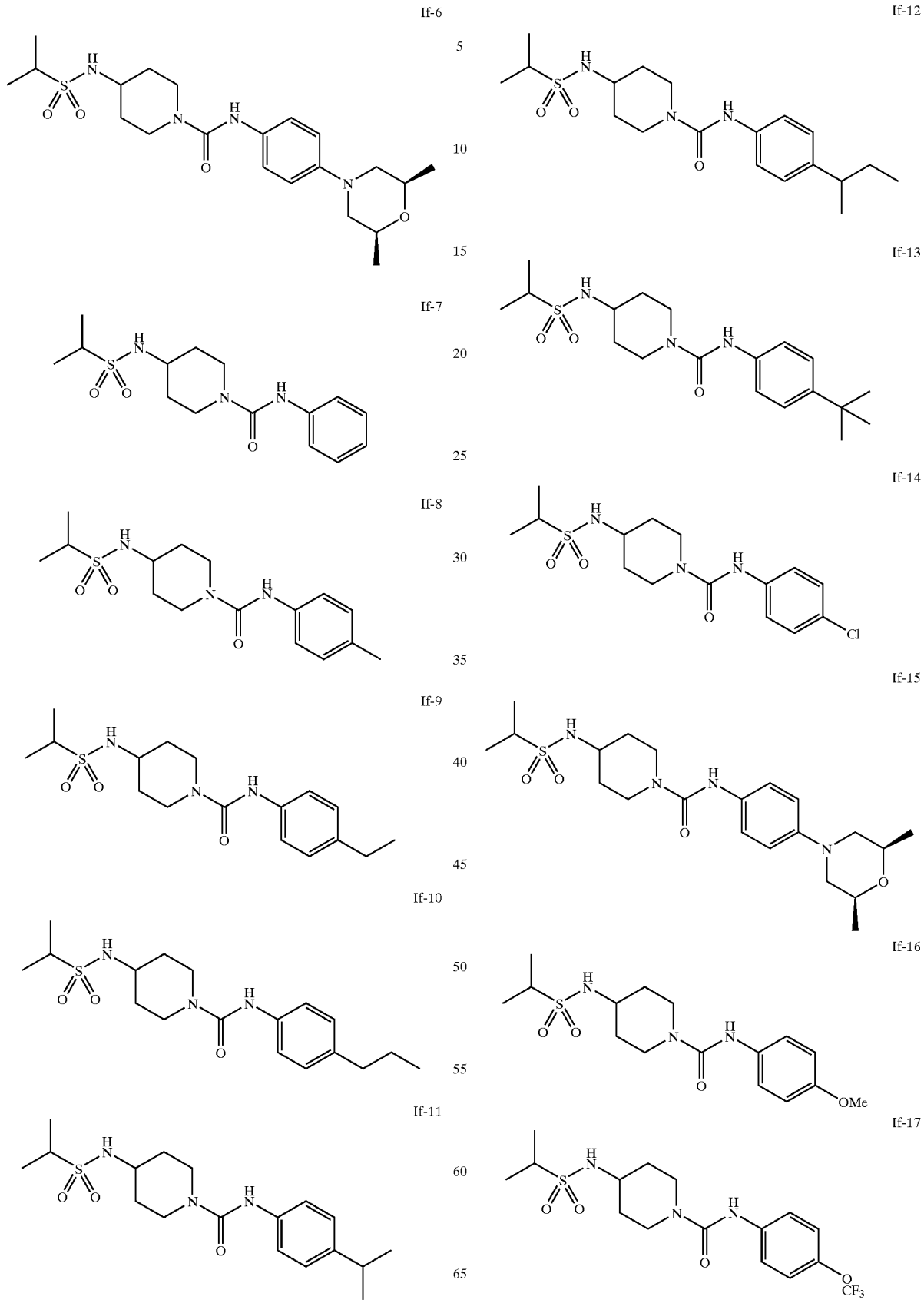

If-18
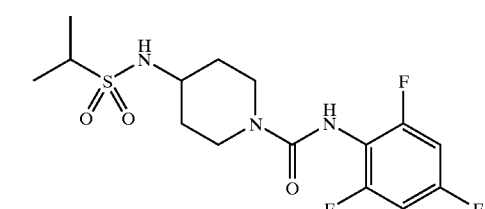
If-19
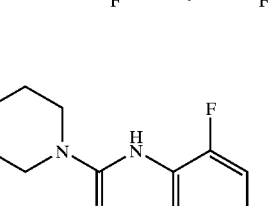
If-20
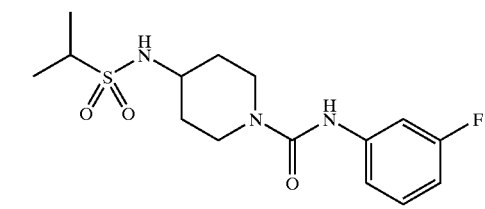
If-21
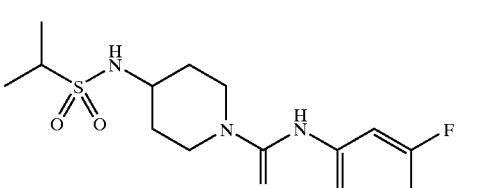
If-22
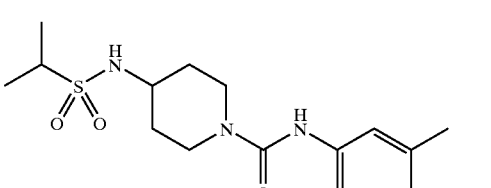
If-1
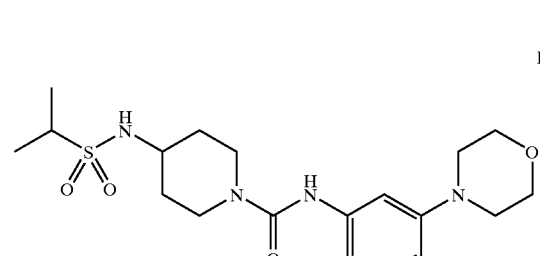
If-2
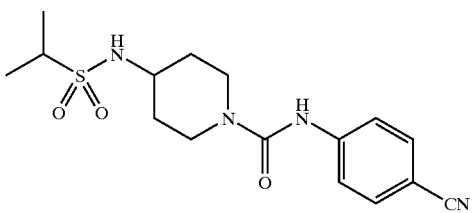
If-4
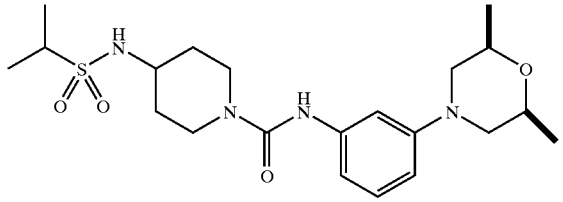
If-6
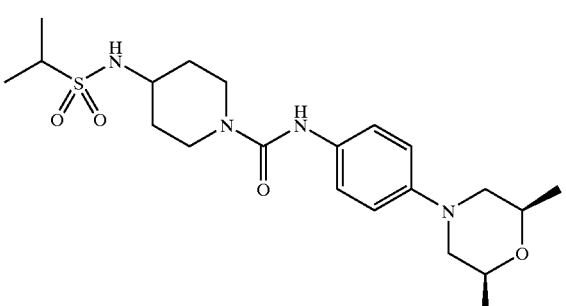
If-7
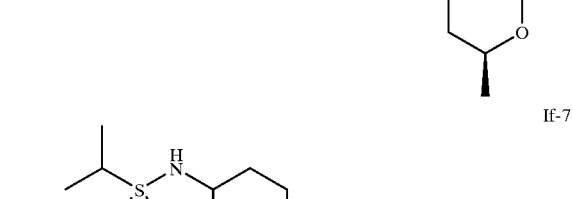
If-8
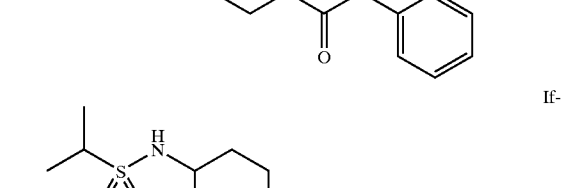
If-9
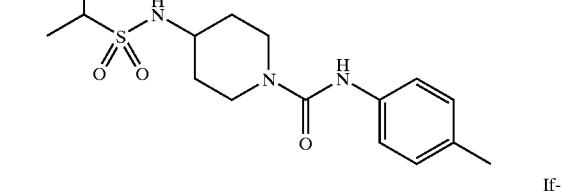
If-10
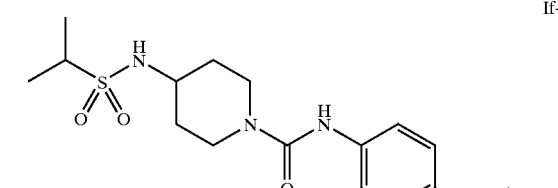
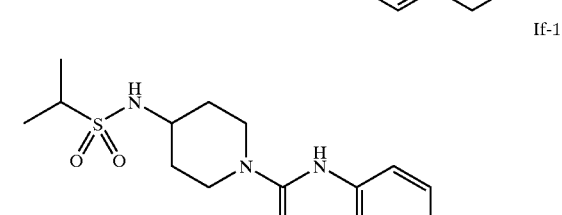
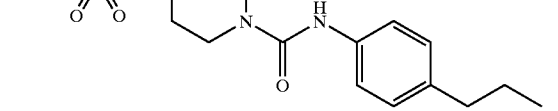

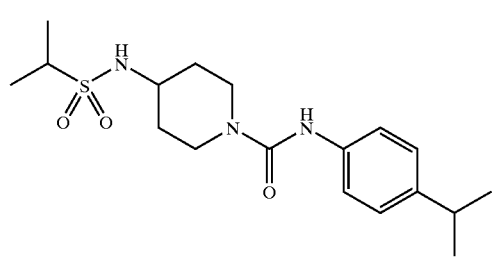
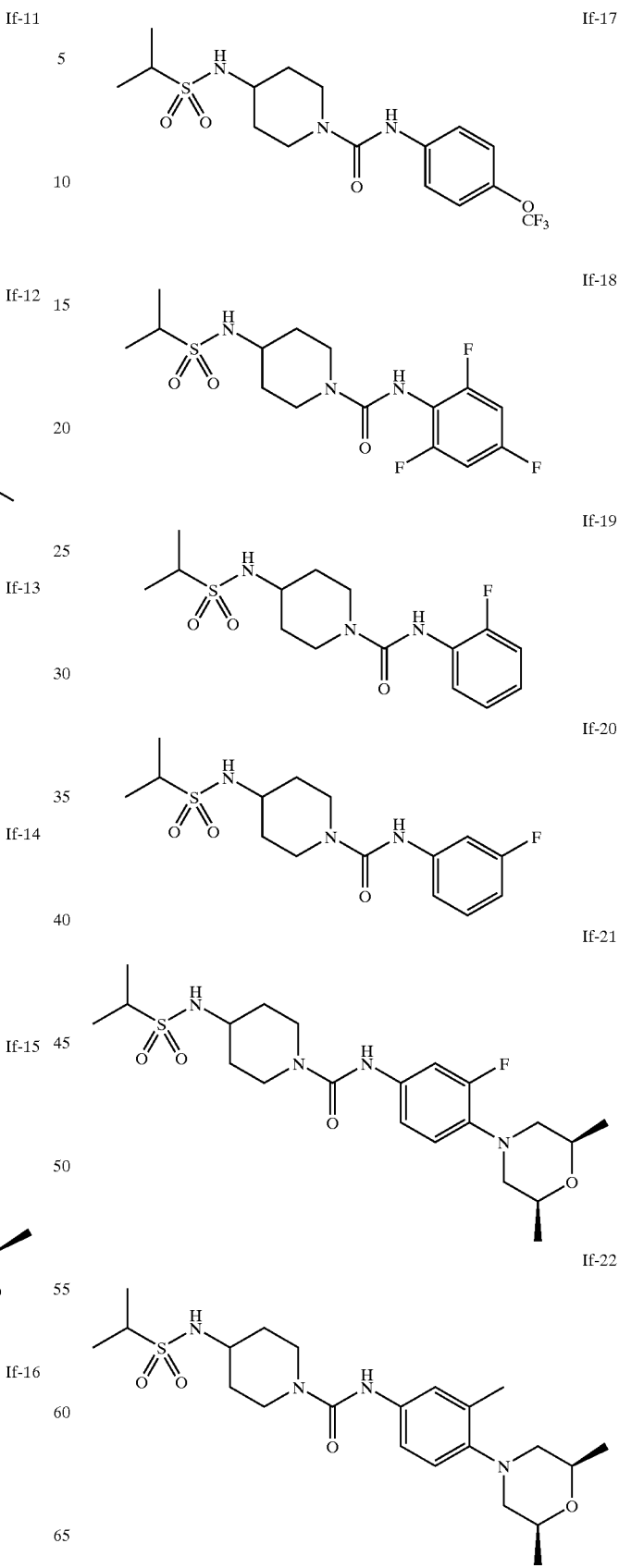

-continued
If-23
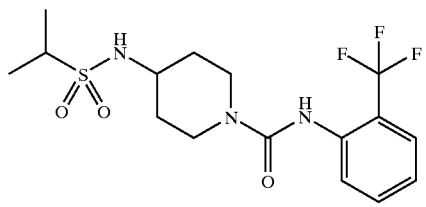
If-24
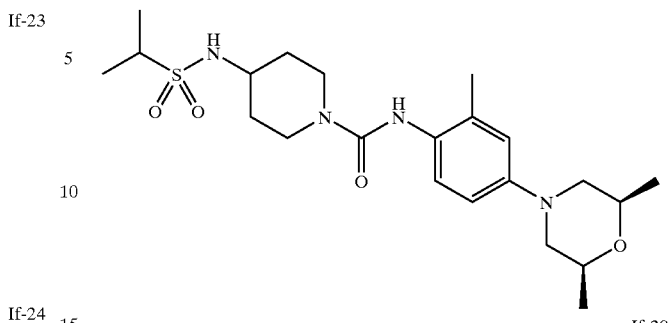
If-25
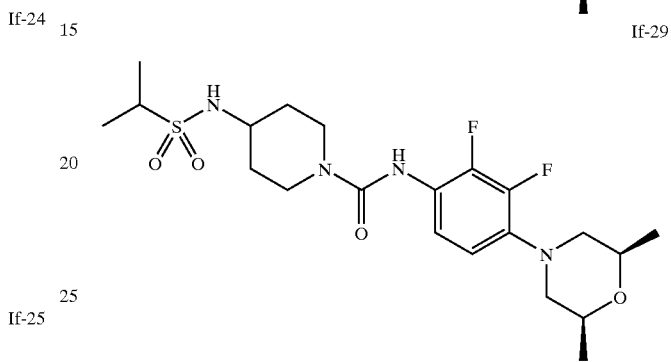
If-26
If-27
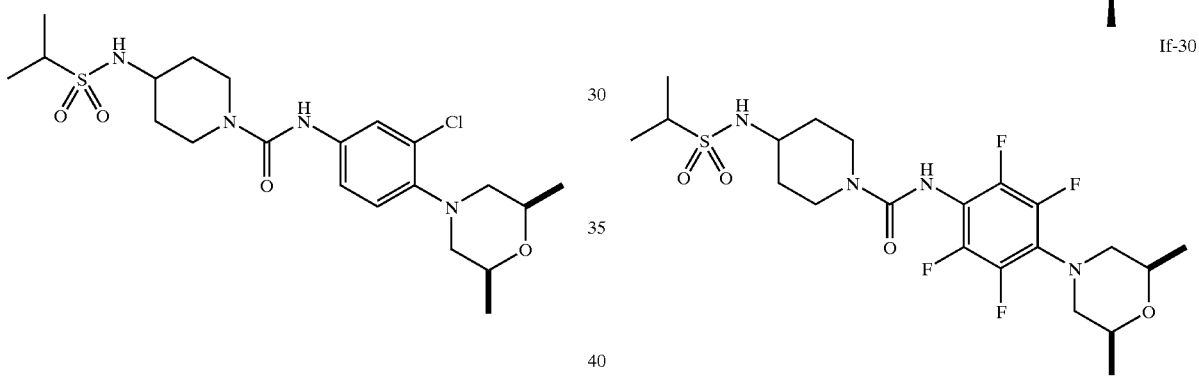
-continued
If-28
If-29
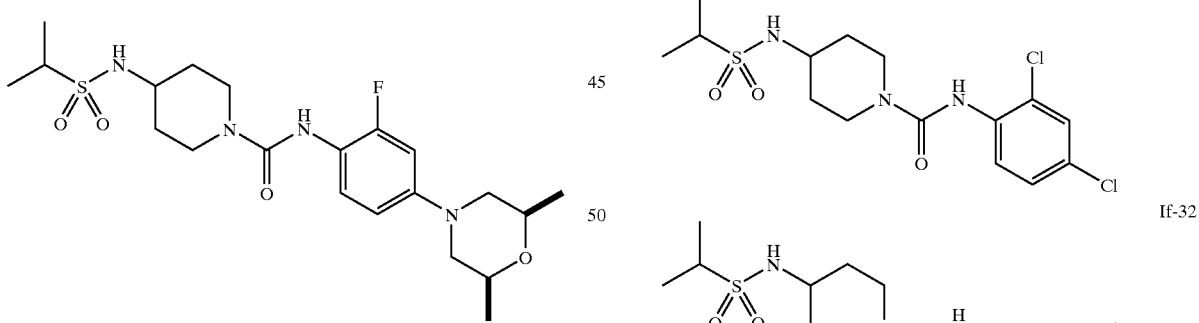
If-30
If-31
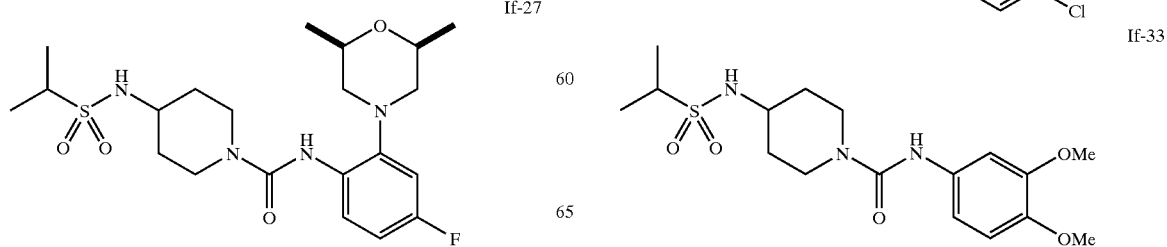
If-32
If-33

If-35
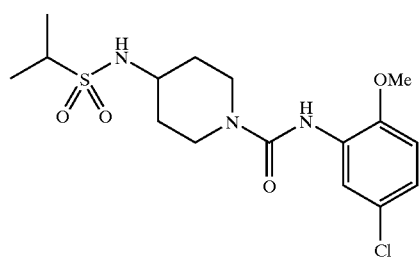
If-36
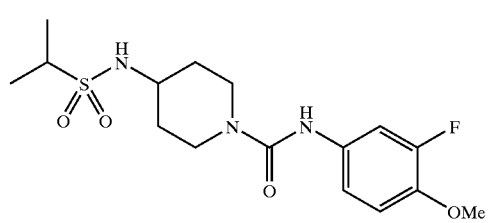
If-37
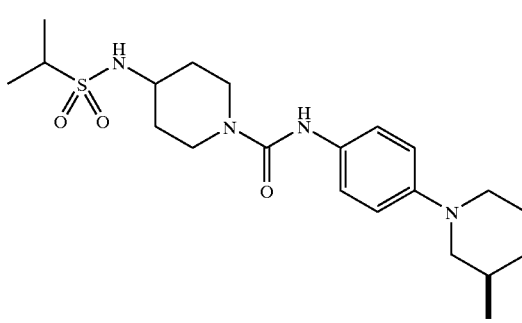
If-38
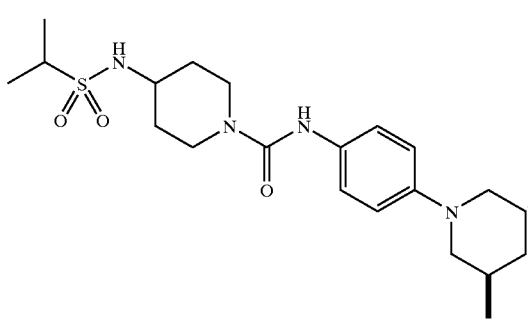
If-39
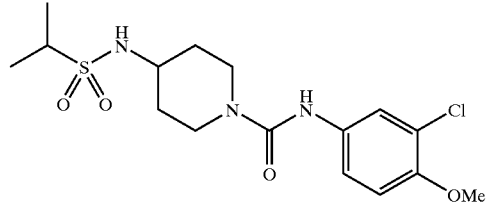
If-40
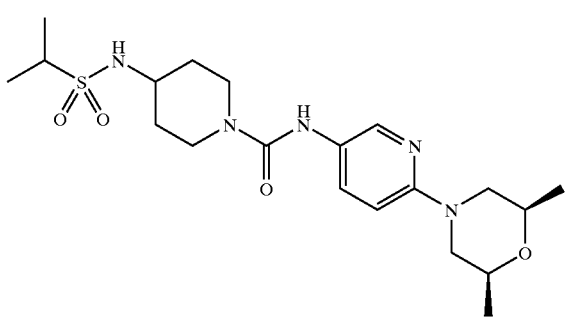
If-41
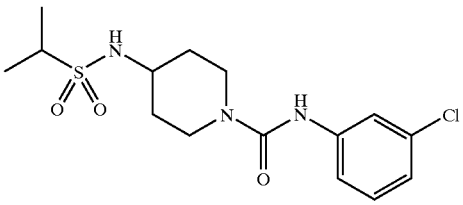
If-42
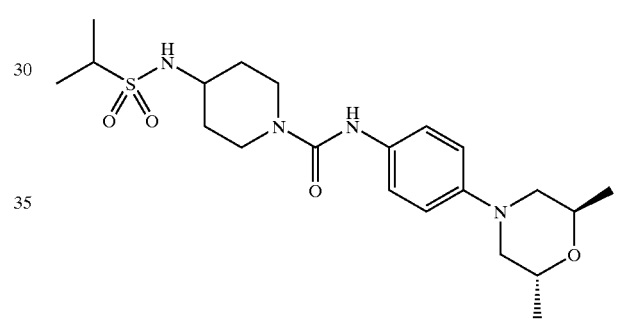
If-43
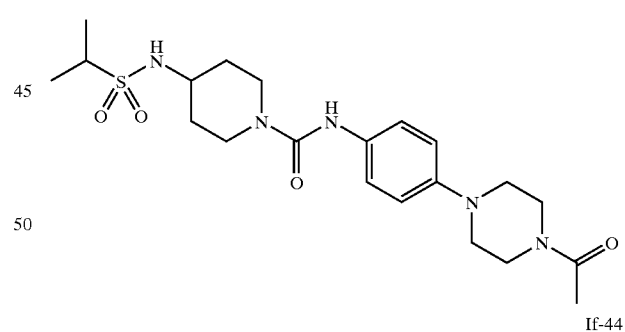
If-44

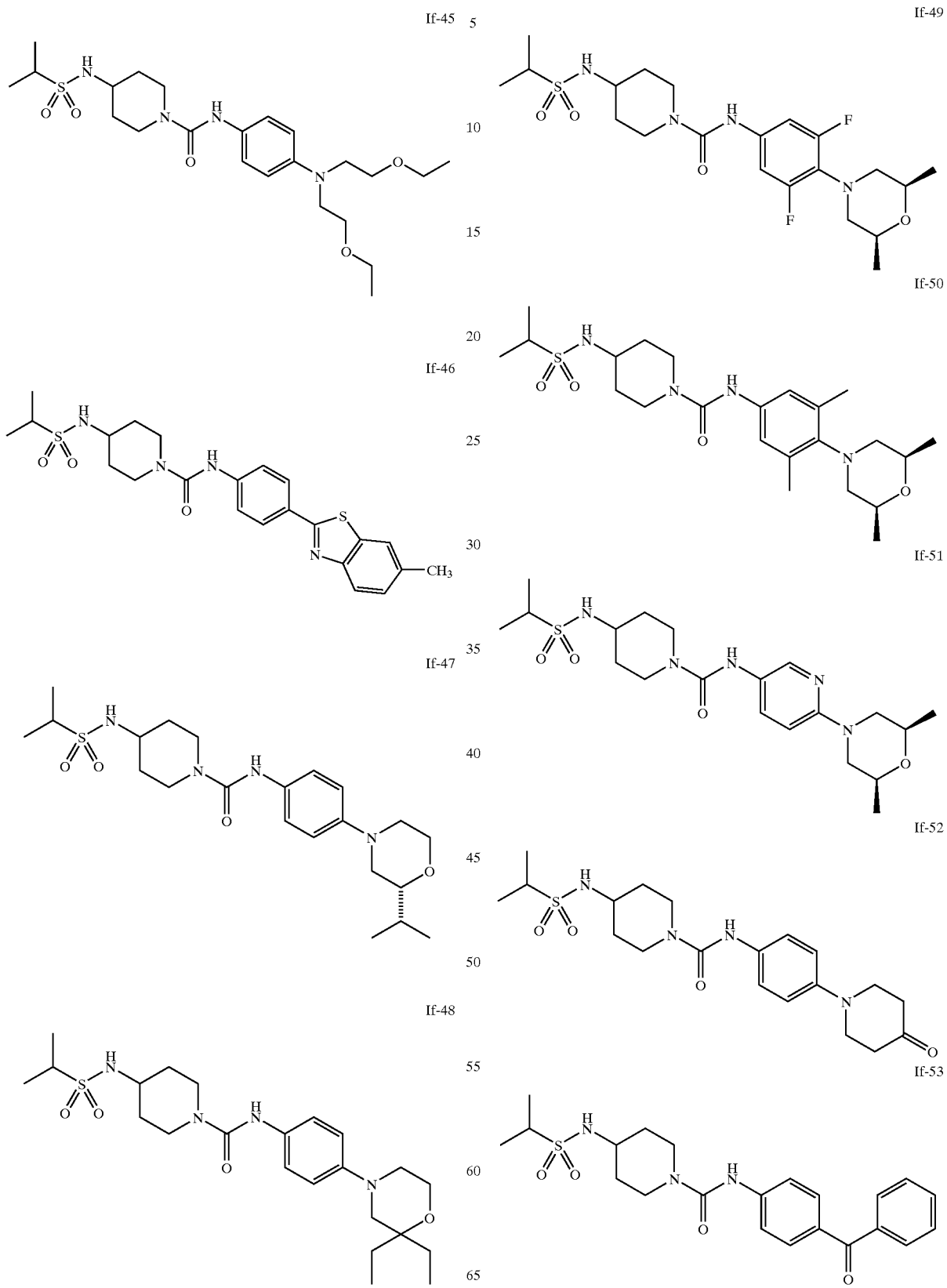

If-54
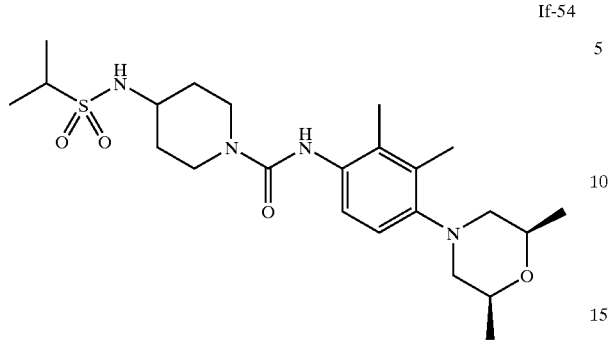
If-59
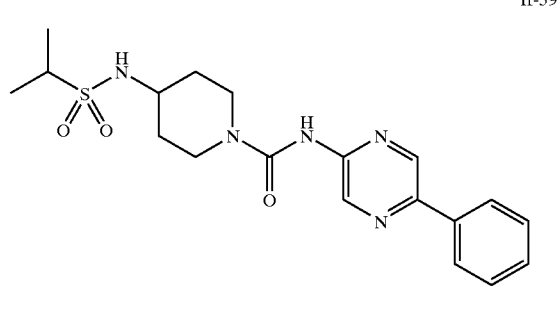
If-55
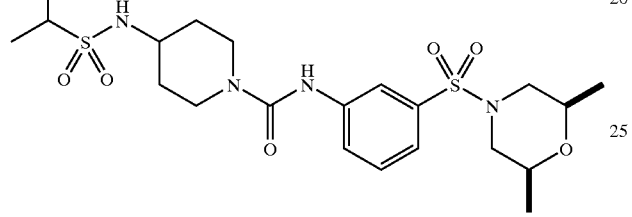
If-60
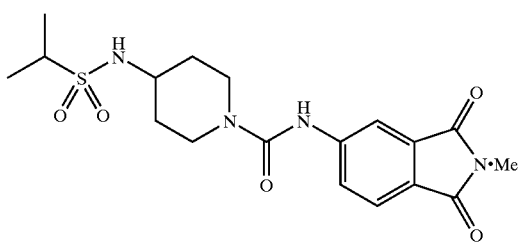
If-56
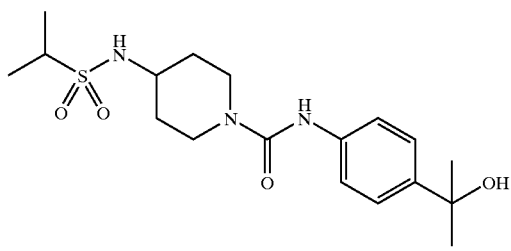
If-61
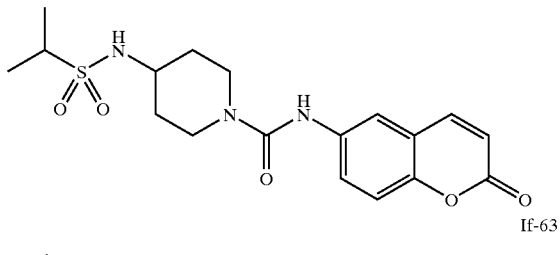
If-57
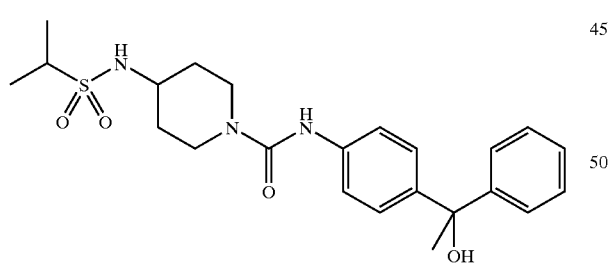
If-62
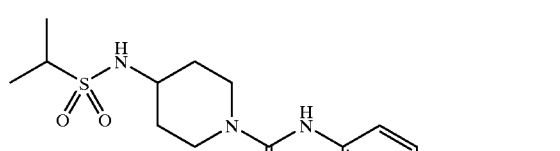
If-58
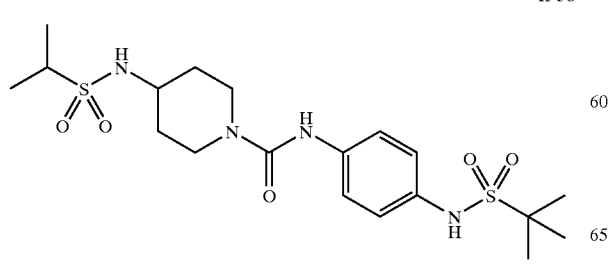
If-63
If-64
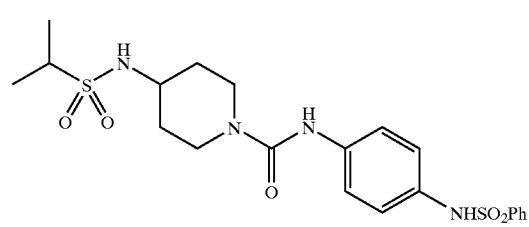

If-65
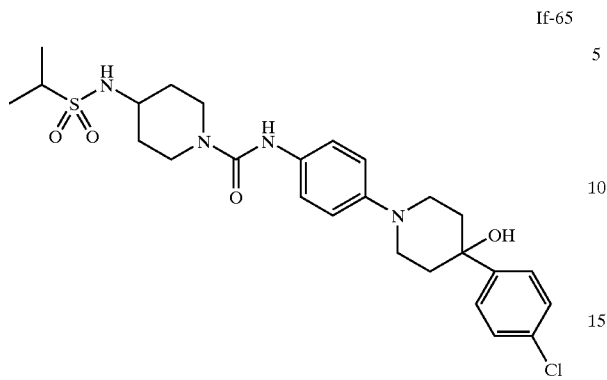
If-70
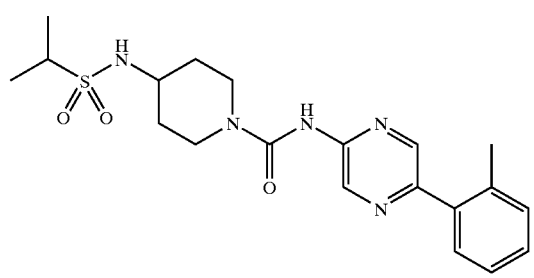
If-66
If-71
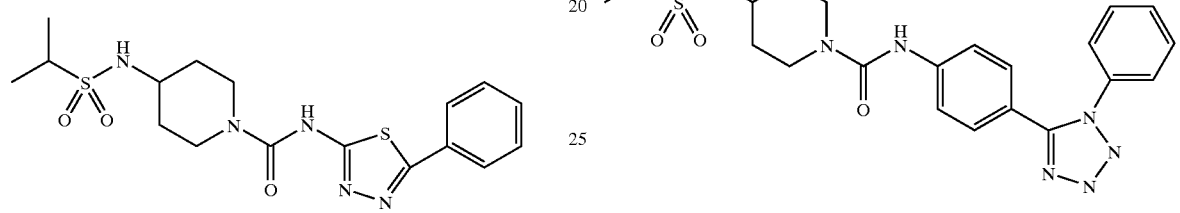
If-67
If-74
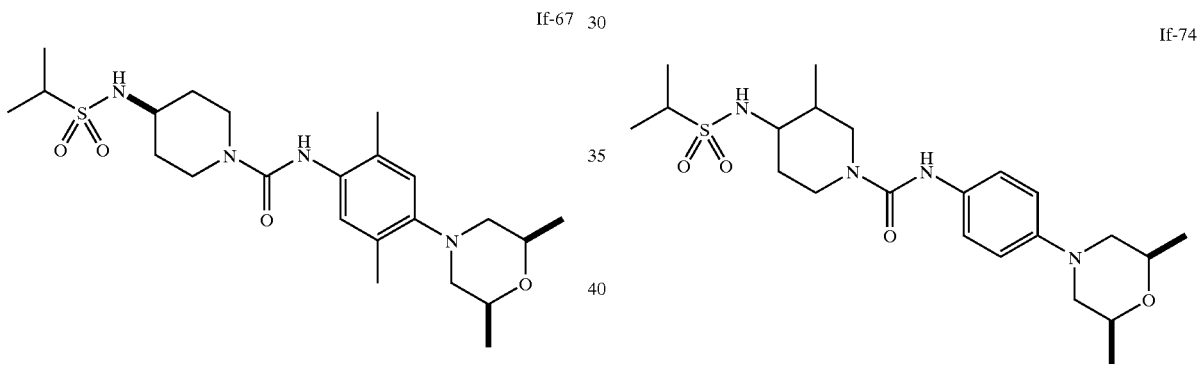
If-68
If-75
If-69
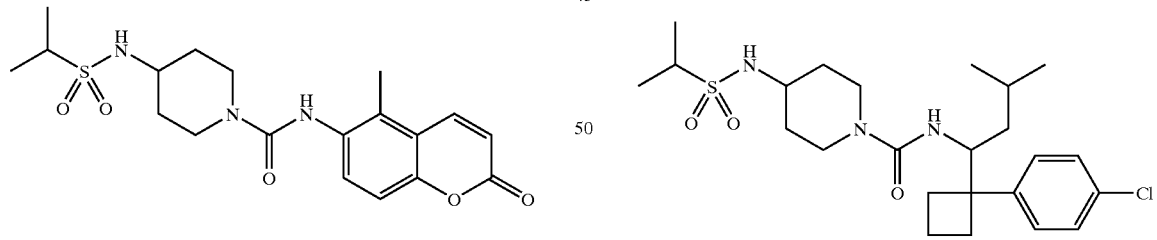
If-76
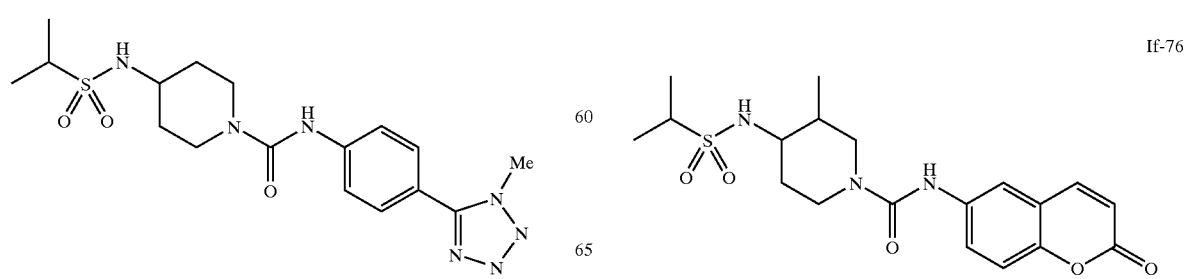

If-77
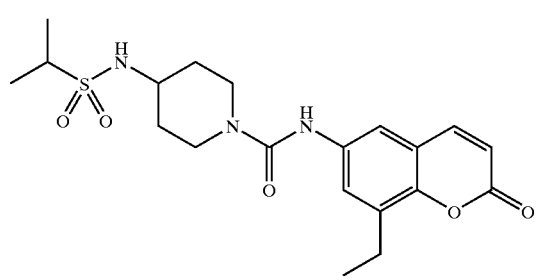
If-78
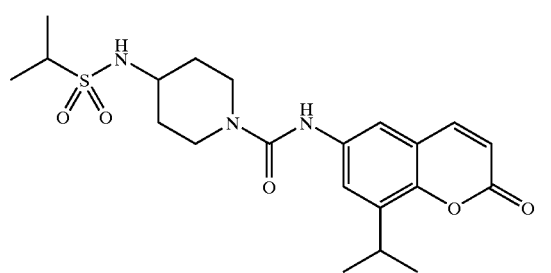
If-79
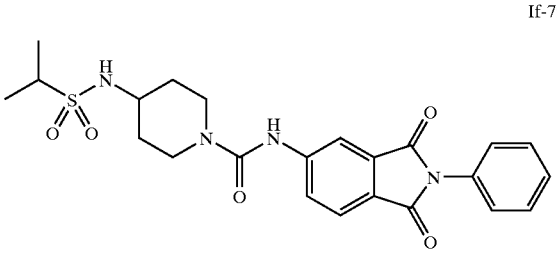
If-80
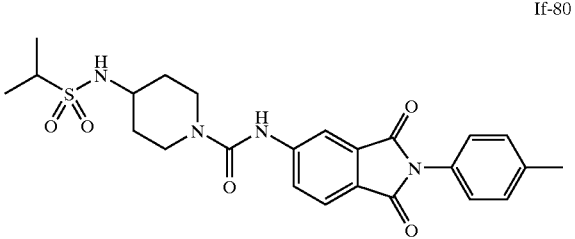
If-81
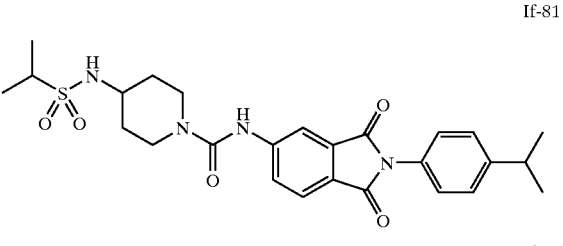
If-82
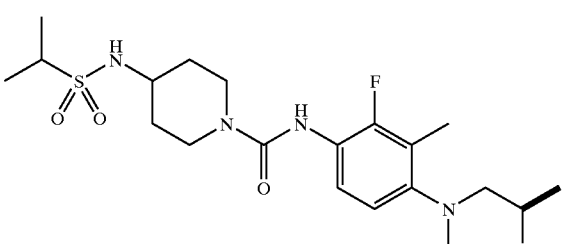
If-83
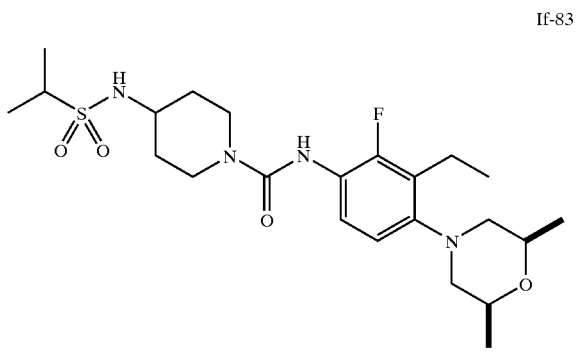
If-84
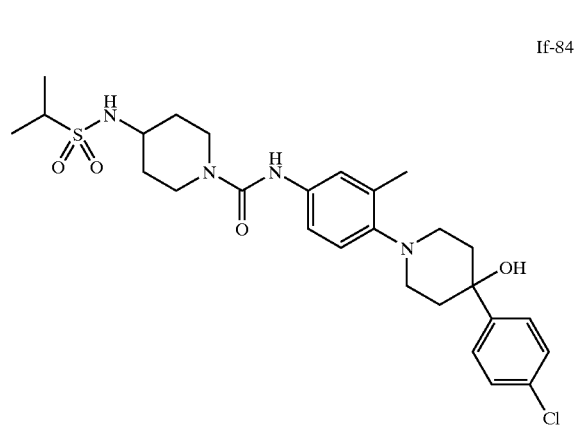
If-85
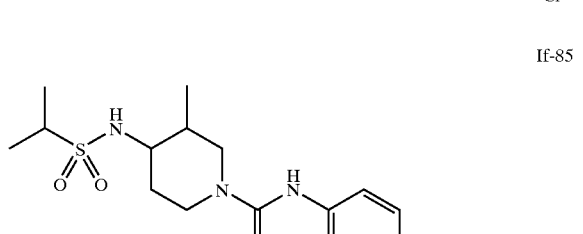
If-86
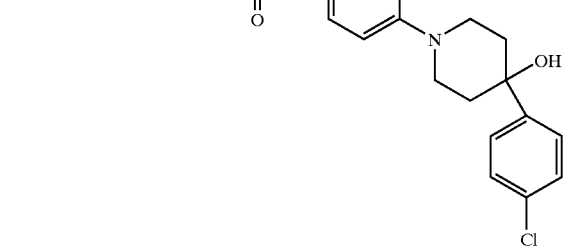

If-87
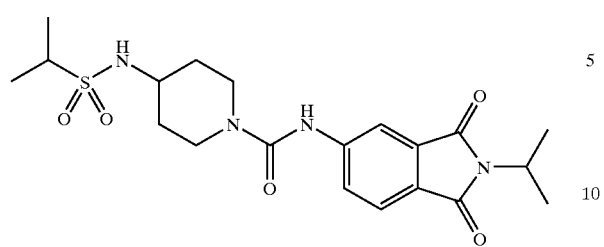
If-88
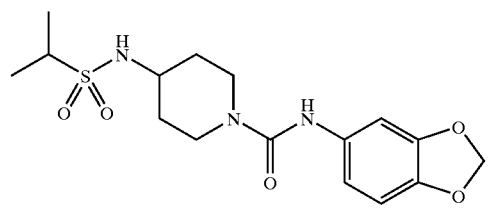
If-89
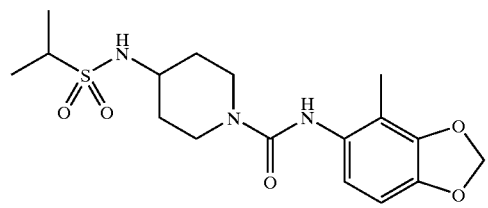
If-90
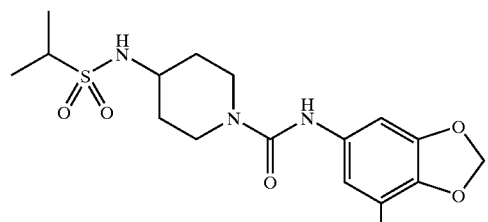
If-91
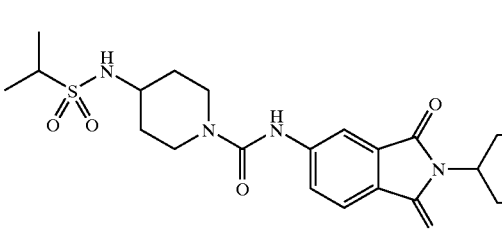
If-92
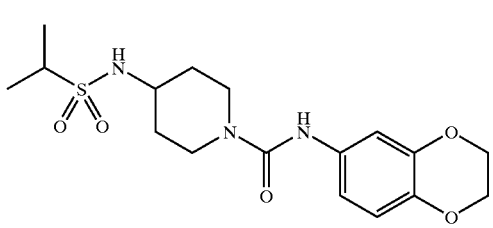
If-93
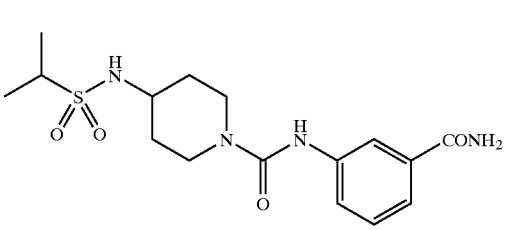
If-94
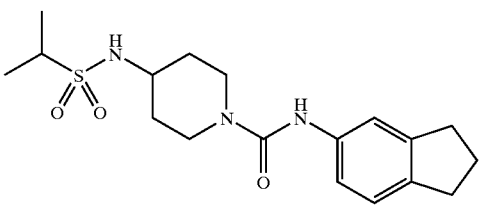
If-95
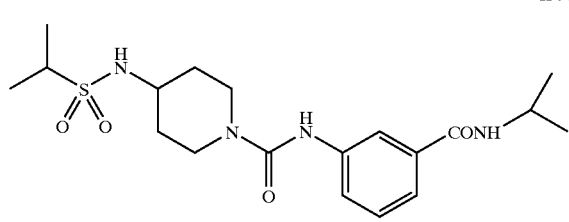
If-96
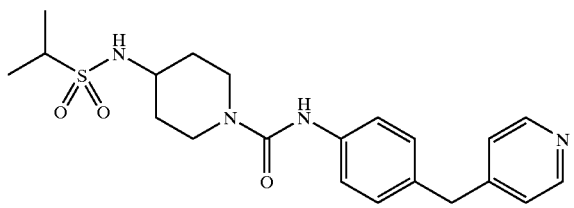
If-97
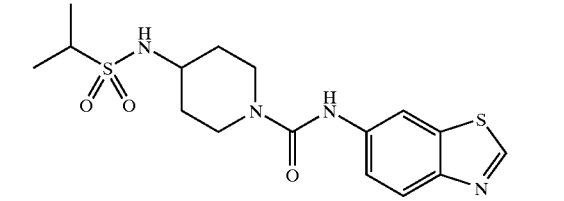
If-98
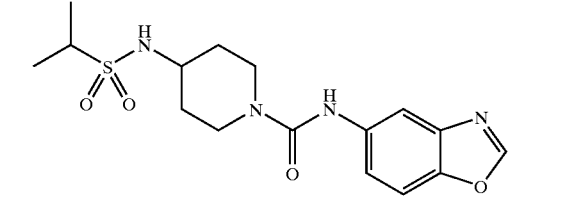
If-99
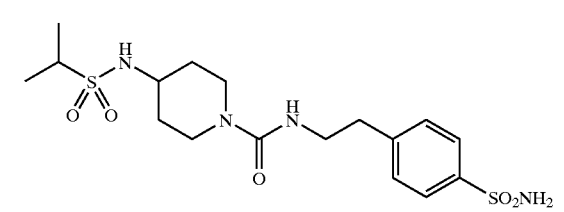
If-100
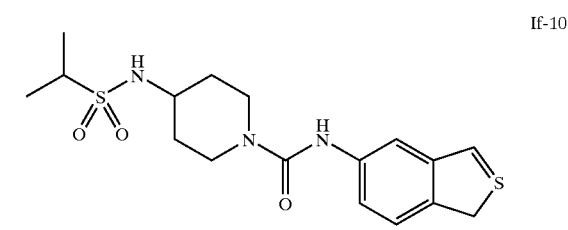

If-101
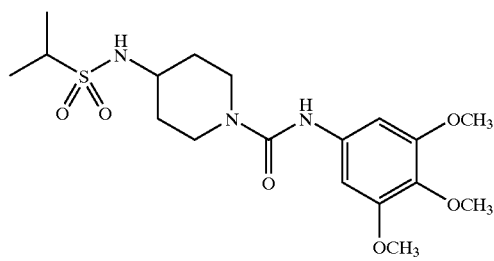
If-102
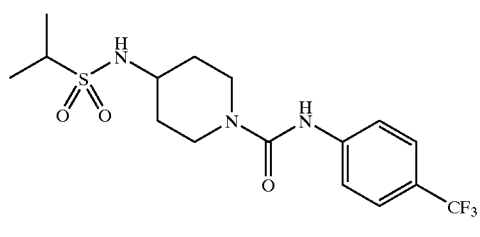
If-103
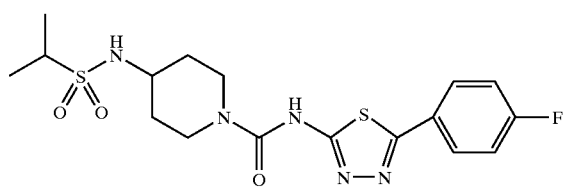
If-104
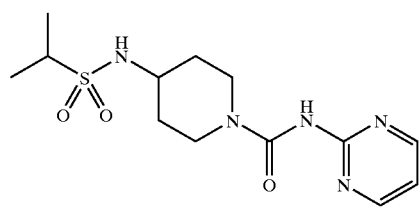
If-105
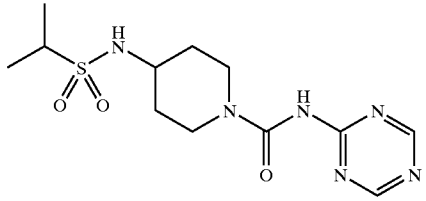
If-106
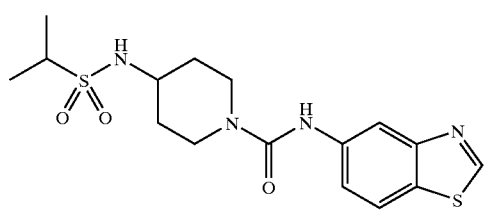
If-107
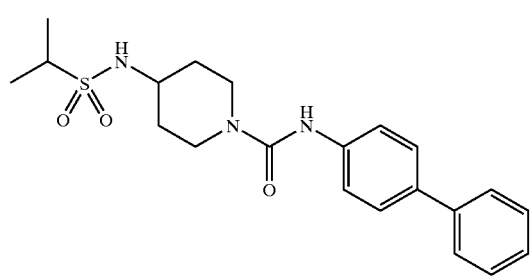
If-108
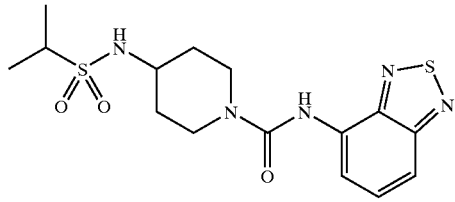
If-109
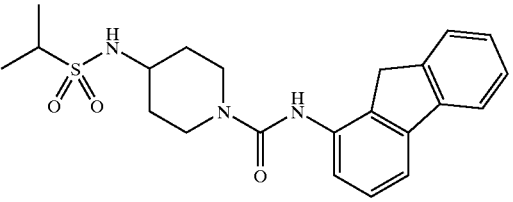
If-110
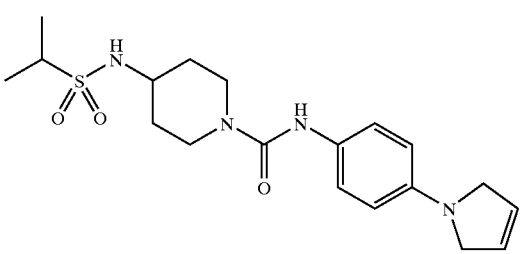
If-111
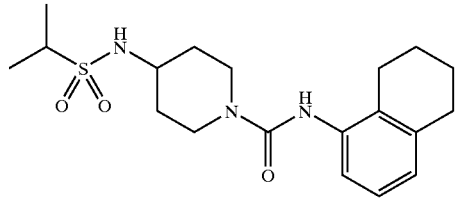
If-112
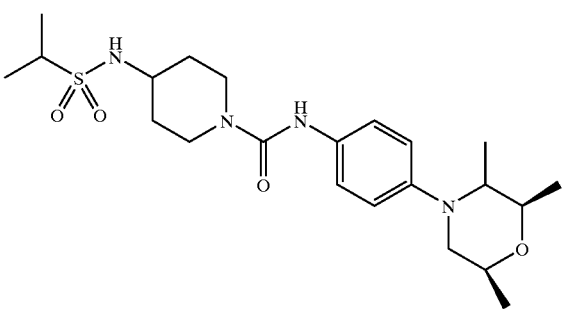
If-113
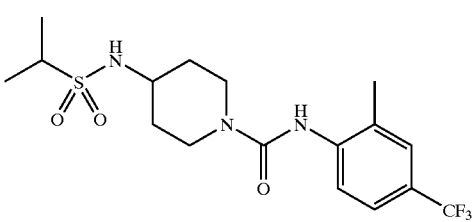

If-114
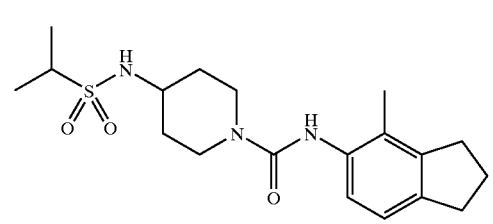
If-115
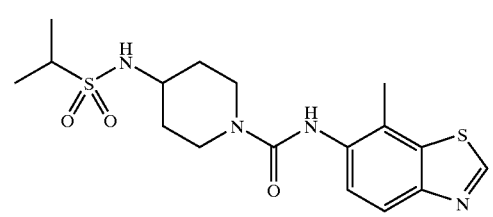
If-116
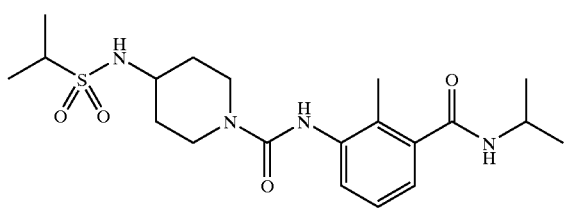
If-117
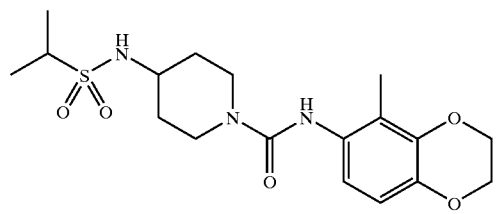
If-118
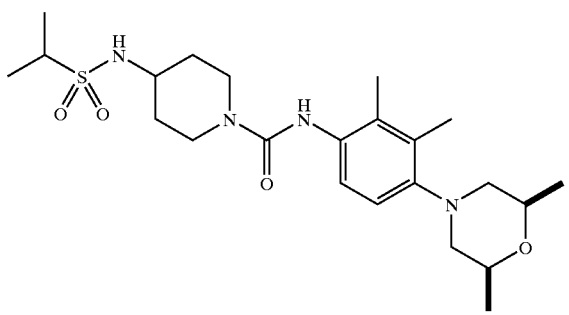
If-119
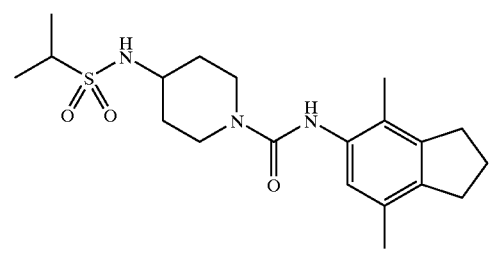
If-120
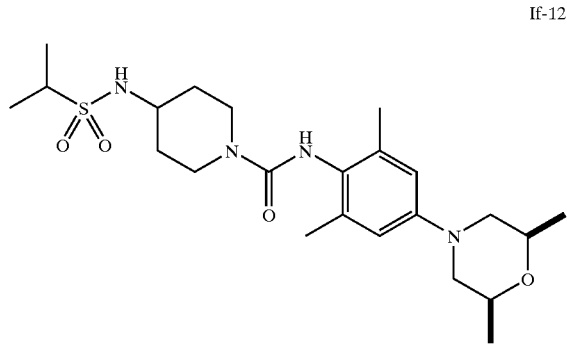
If-121
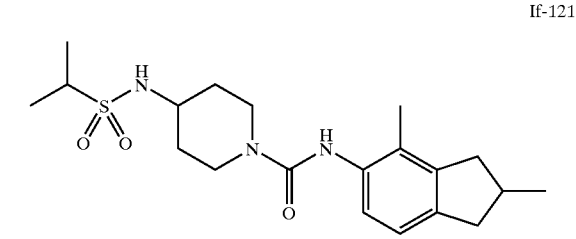
If-122
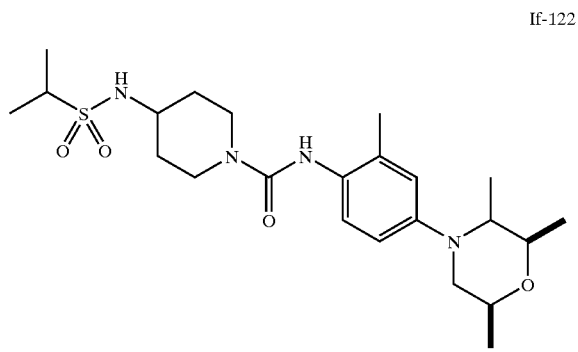
If-123
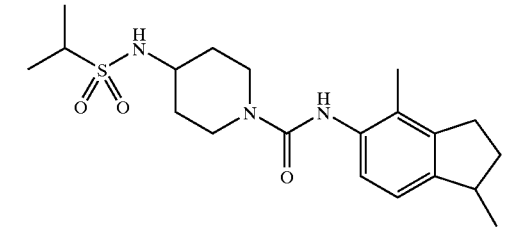
If-124
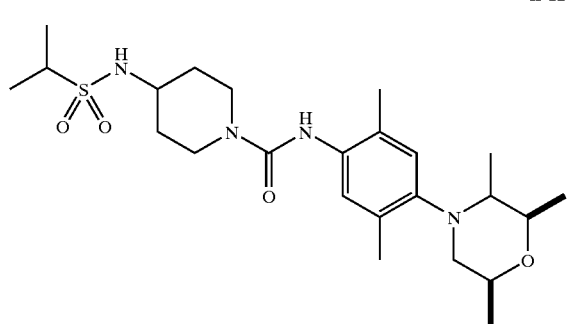

If-125
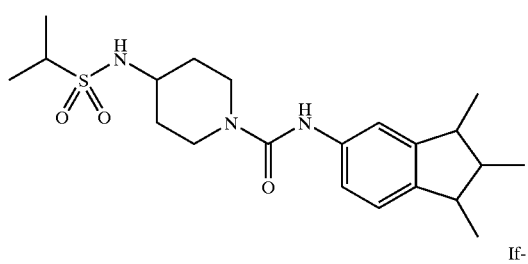
If-126
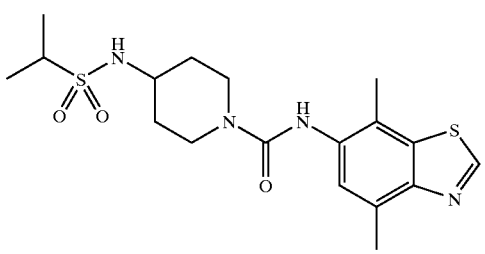
If-127
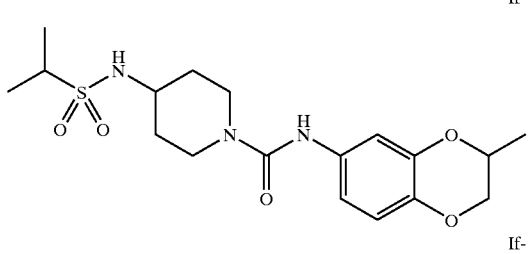
If-128
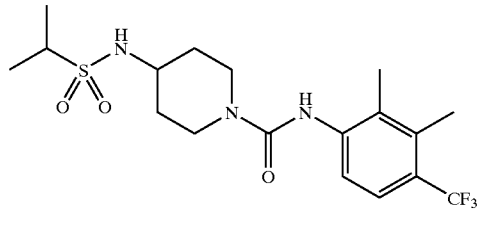
If-129
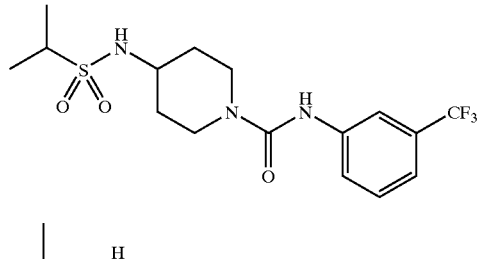
If-130
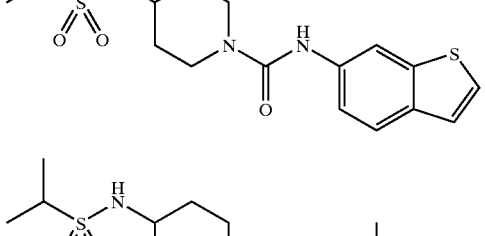
If-131
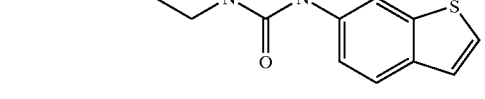
If-132
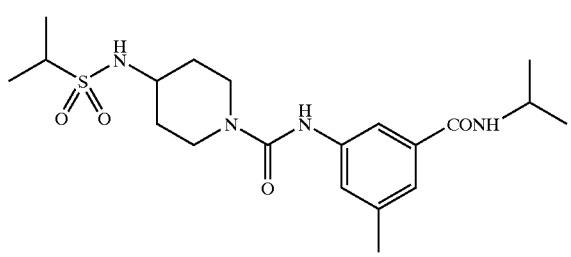
If-133
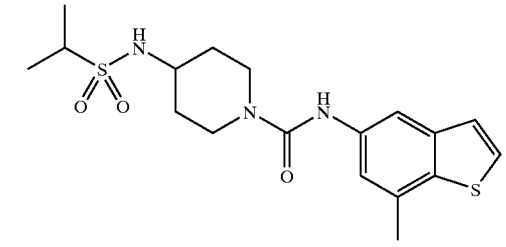
If-134
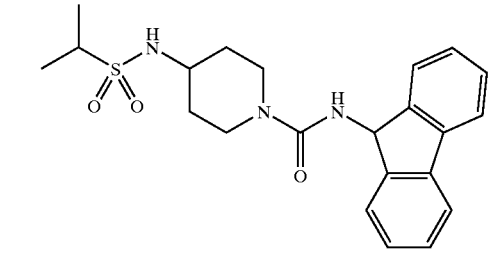
If-135
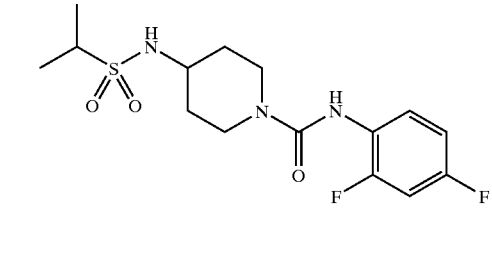
If-136
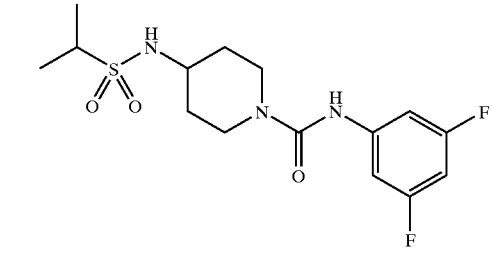
If-137
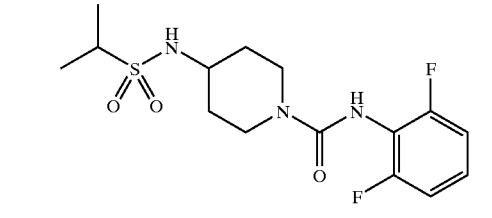

If-138
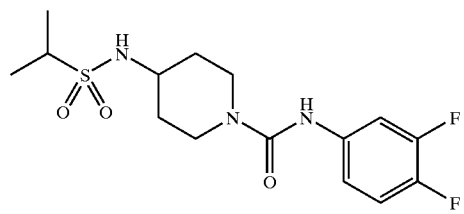
If-139
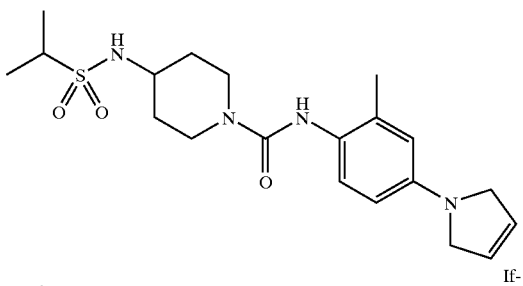
If-140
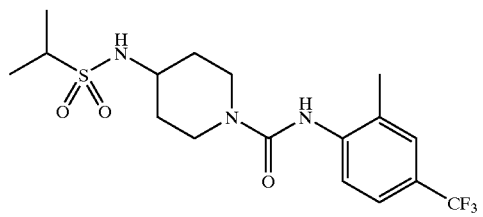
If-141
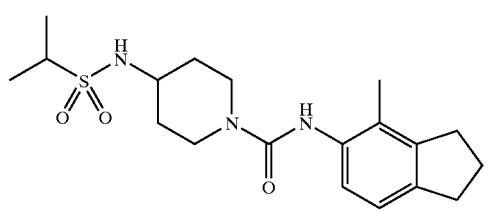
If-142
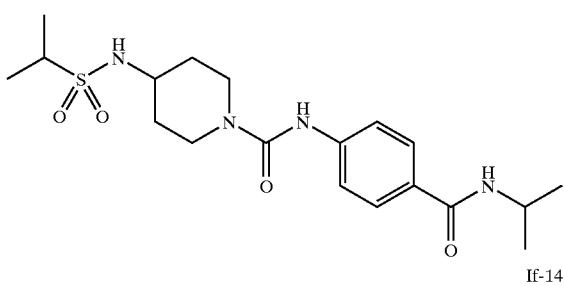
If-143
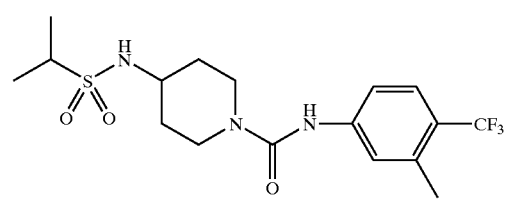
If-144
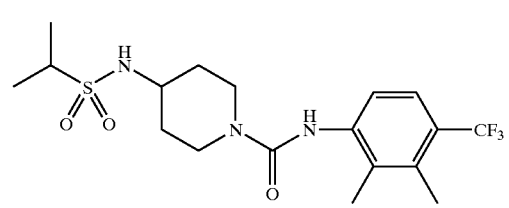
If-145
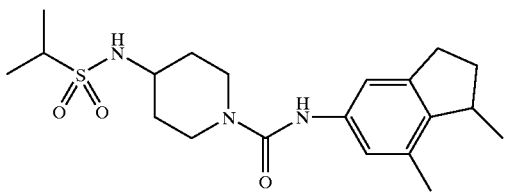
If-146
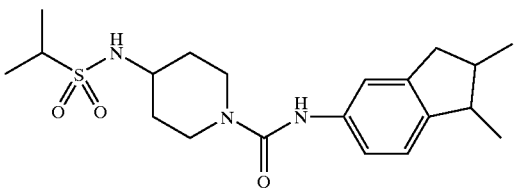
If-147
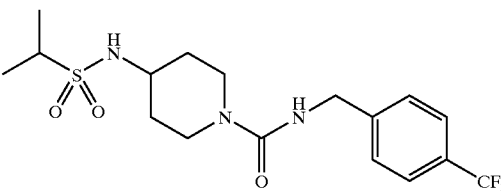
If-148
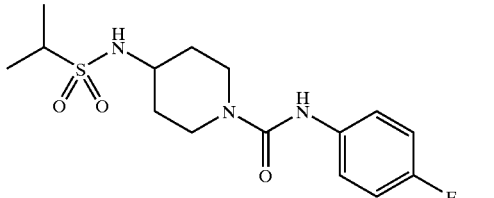
If-149
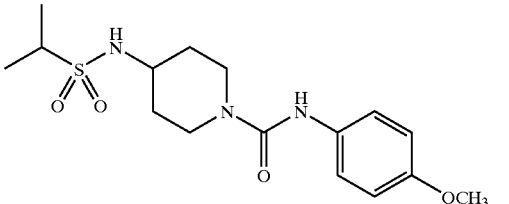
If-150
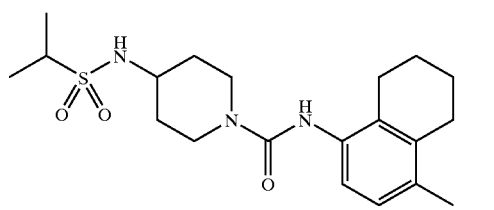
If-151
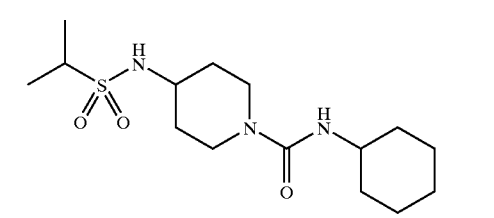

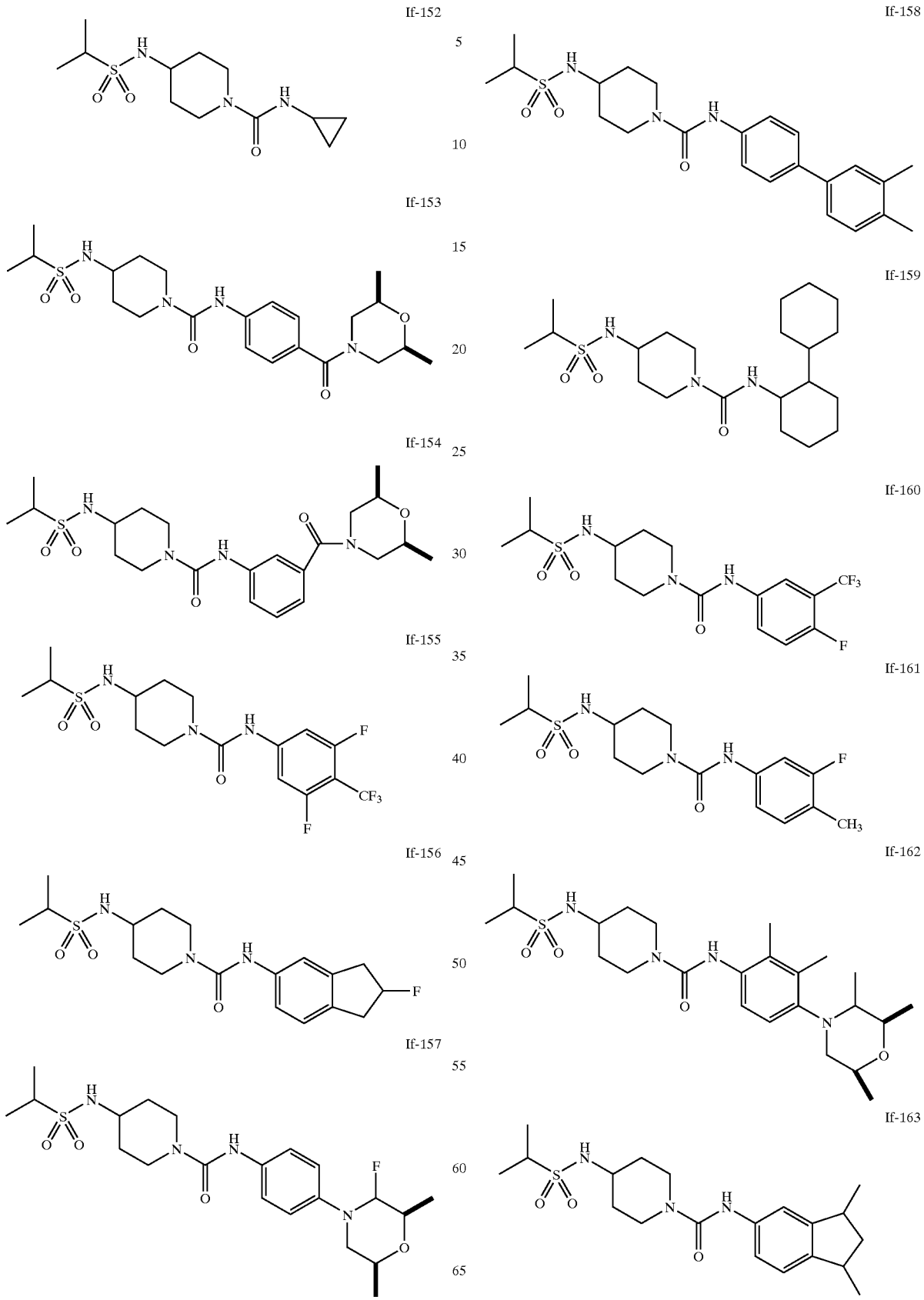

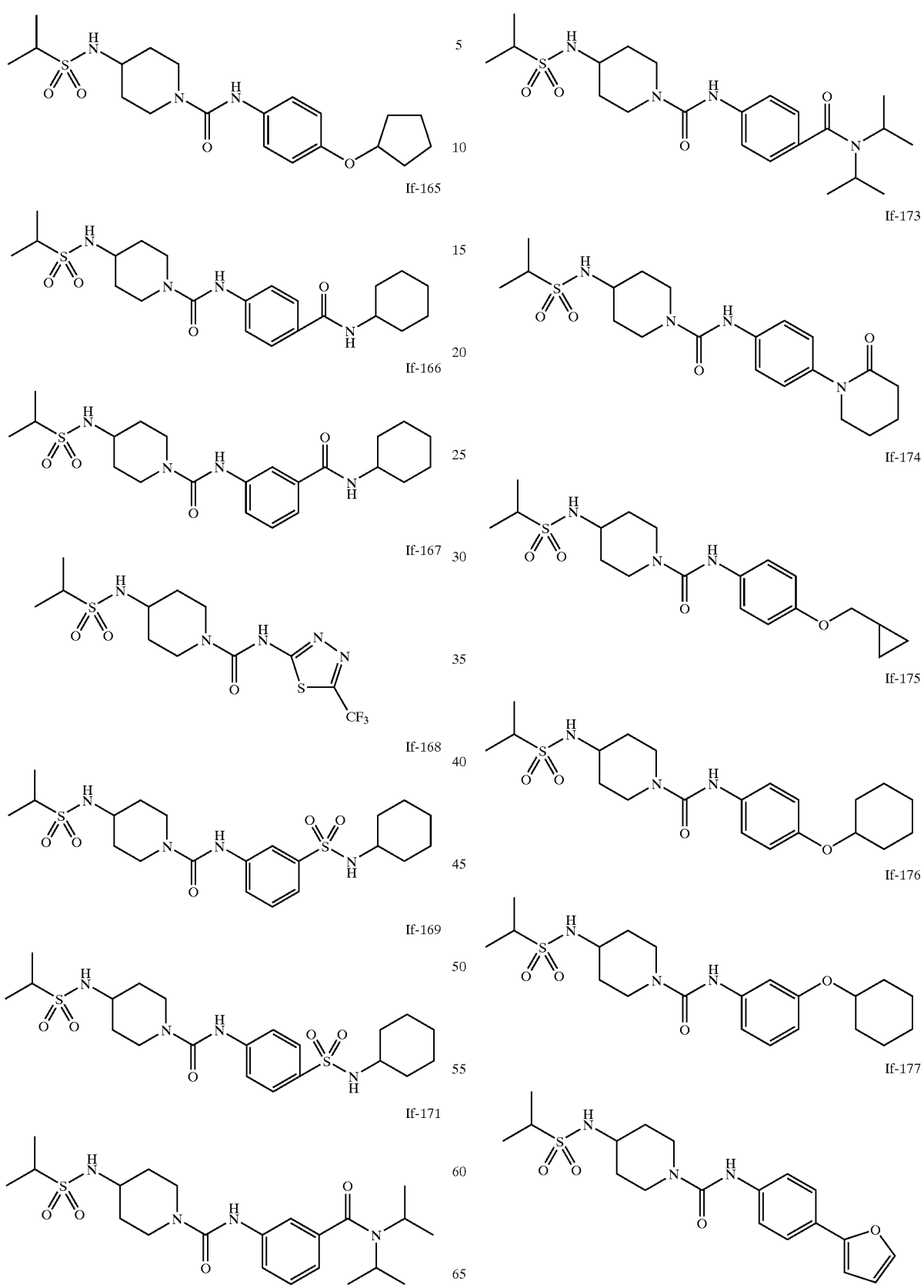

353
-continued
If-178
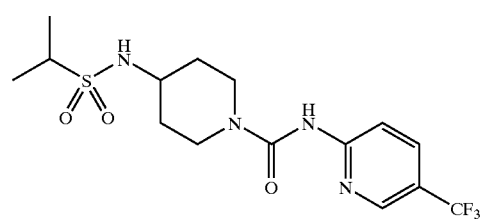
If-179
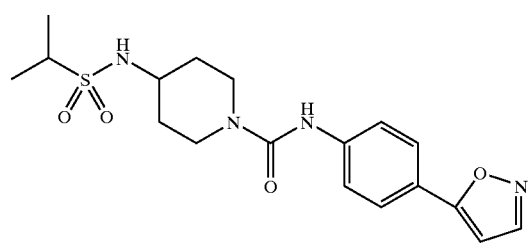
If-180
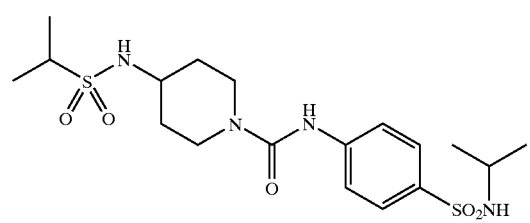
If-181
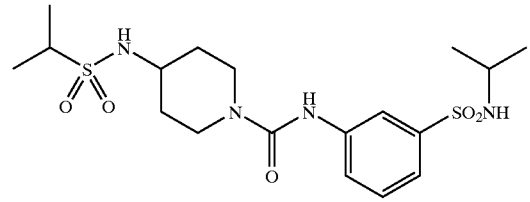
If-182
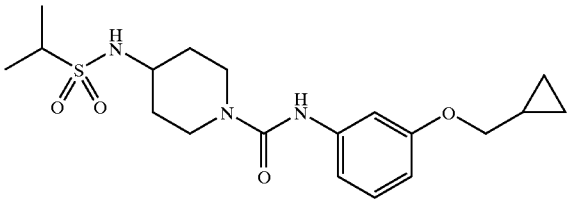
If-183
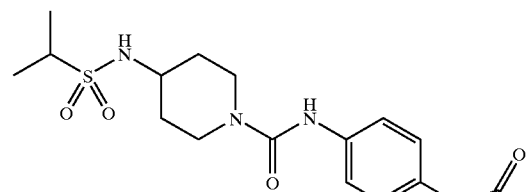
354
-continued
If-184
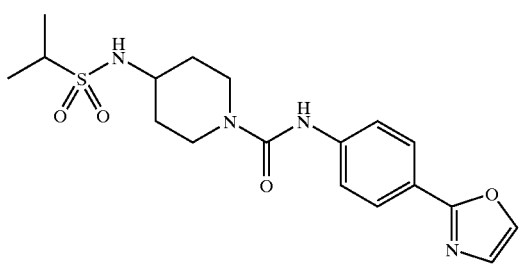
If-185
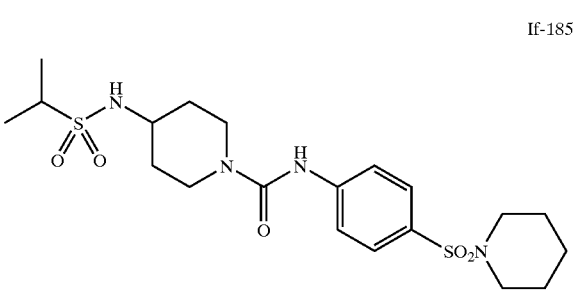
If-186
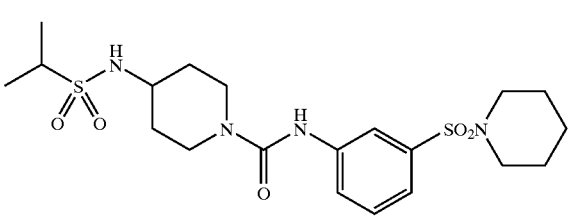
If-187
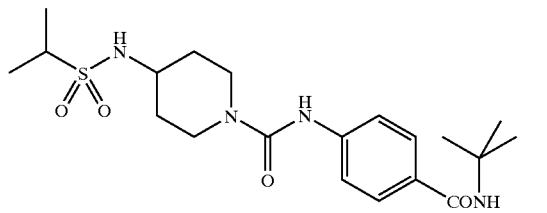
If-188
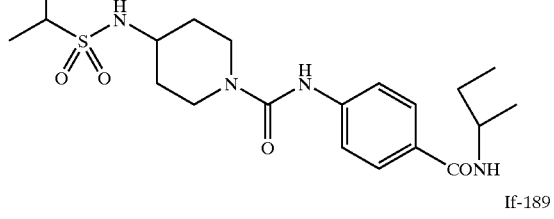
If-189
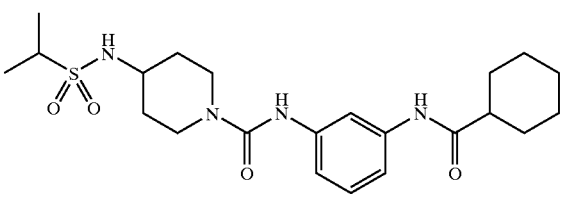

If-190
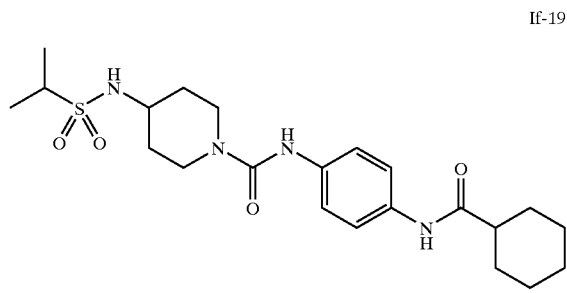
If-196
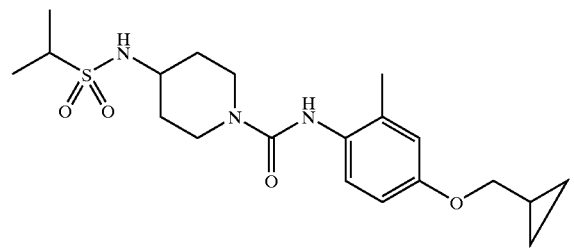
If-191
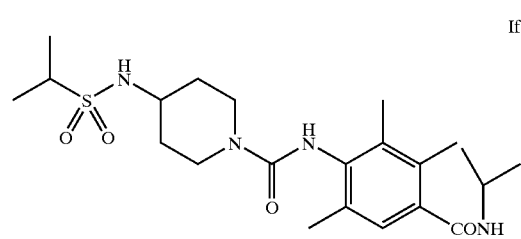
If-197
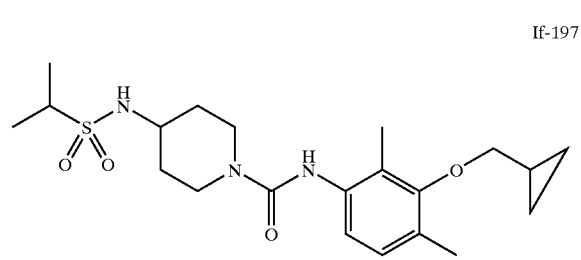
If-192
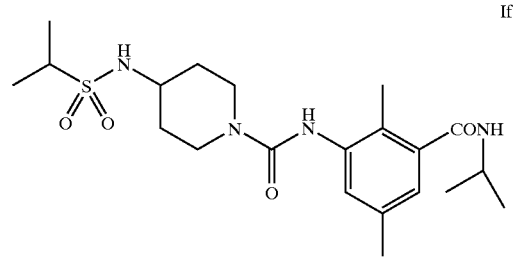
If-198
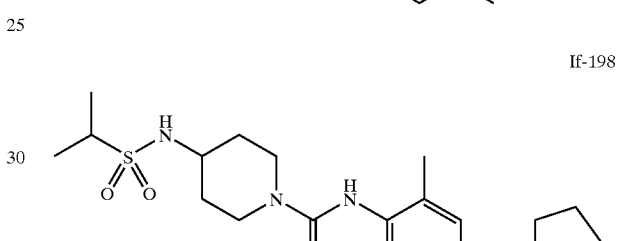
If-193
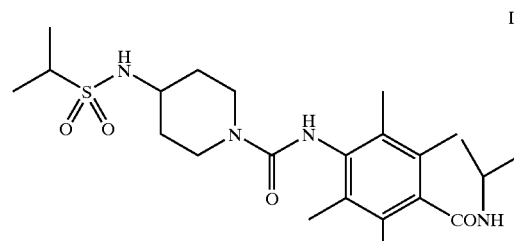
If-199
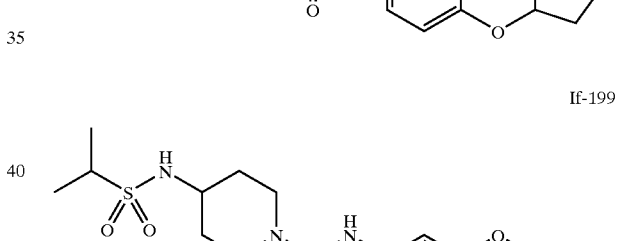
If-194
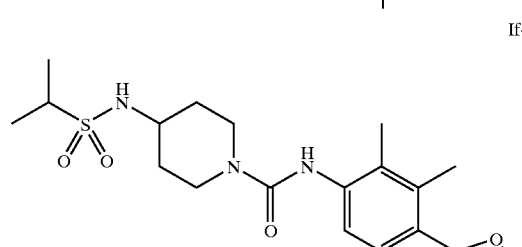
If-200
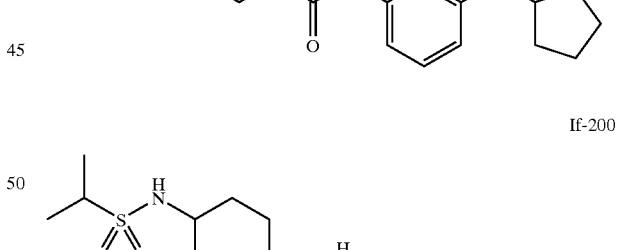
If-195
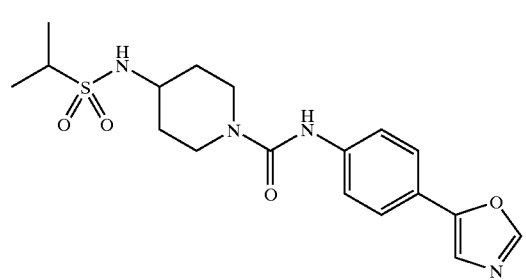
If-201
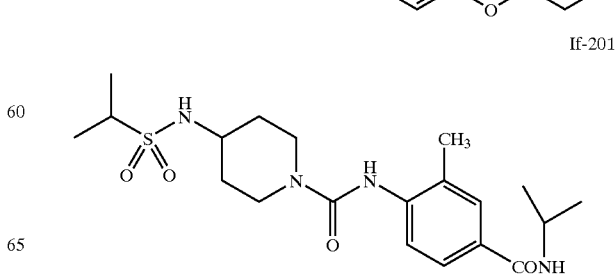

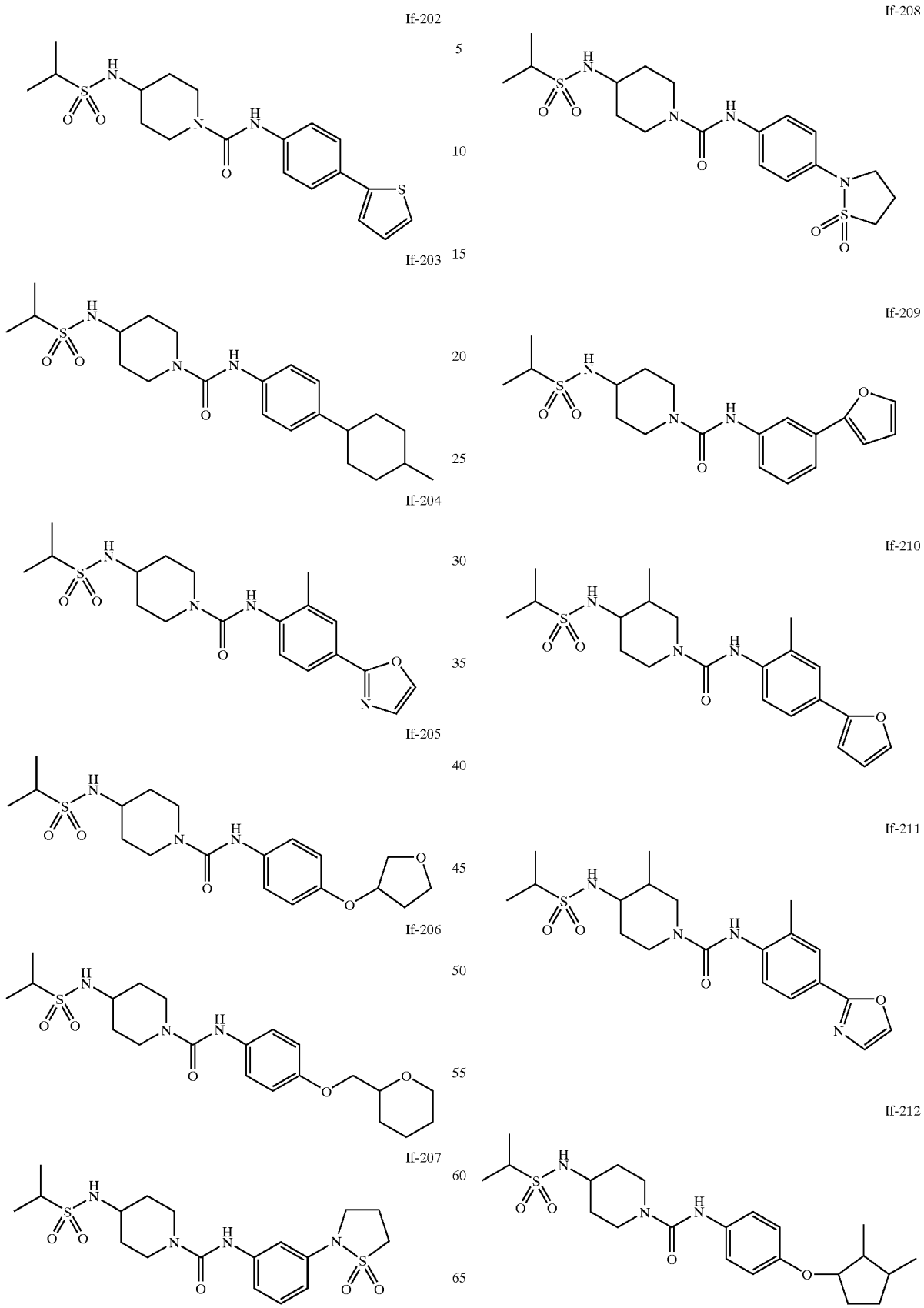

If-213
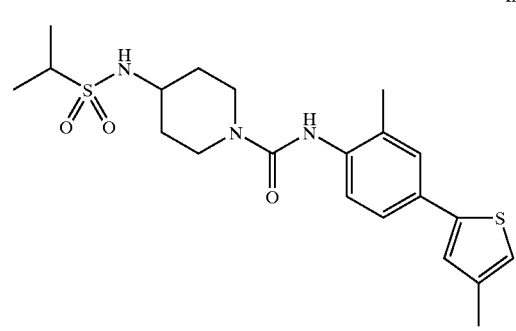
If-221
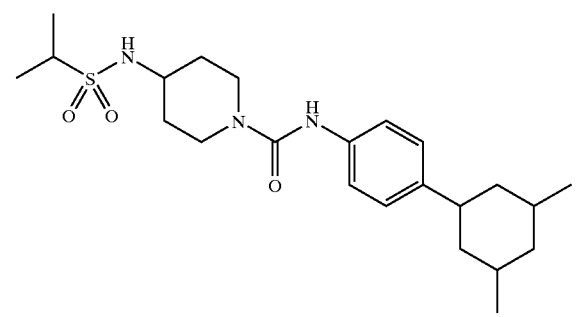
If-214
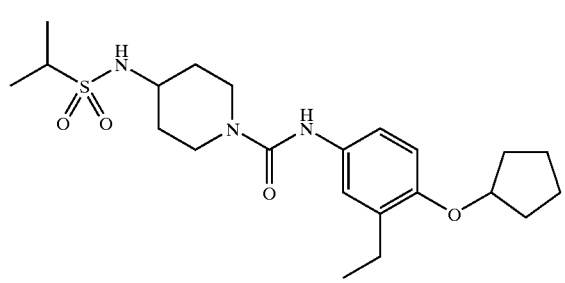
If-222
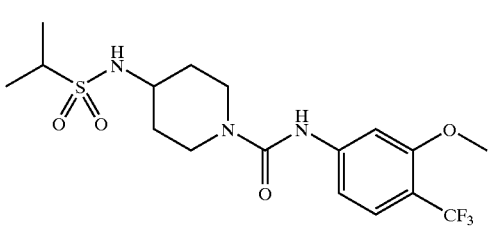
If-215
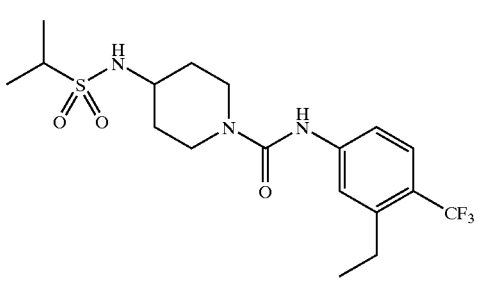
If-223
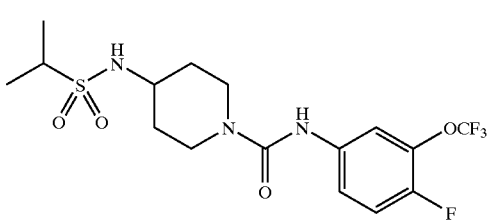
If-216
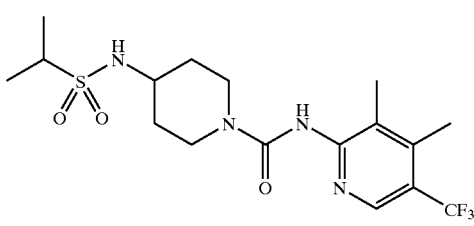
If-224
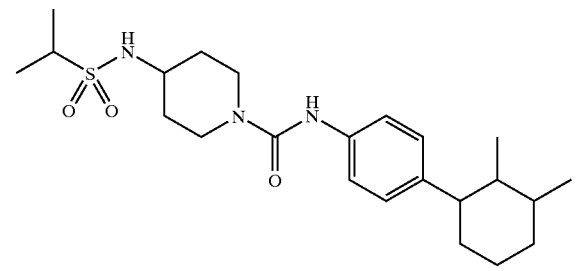
If-219
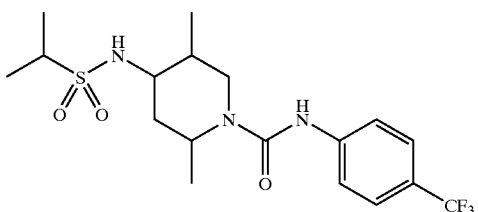
If-225
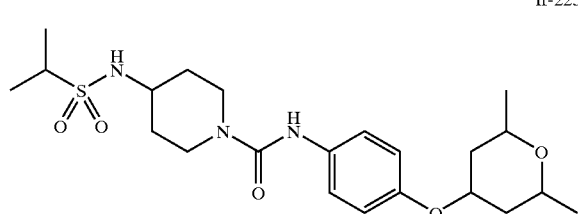
If-220
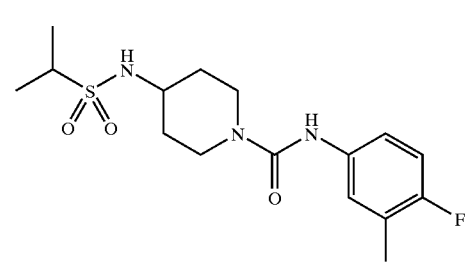
If-226
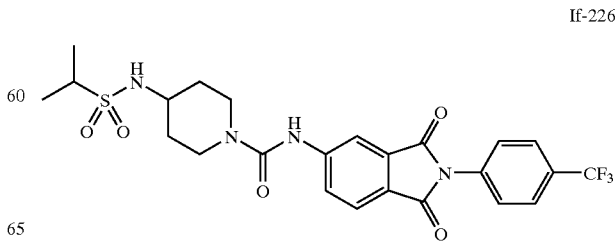

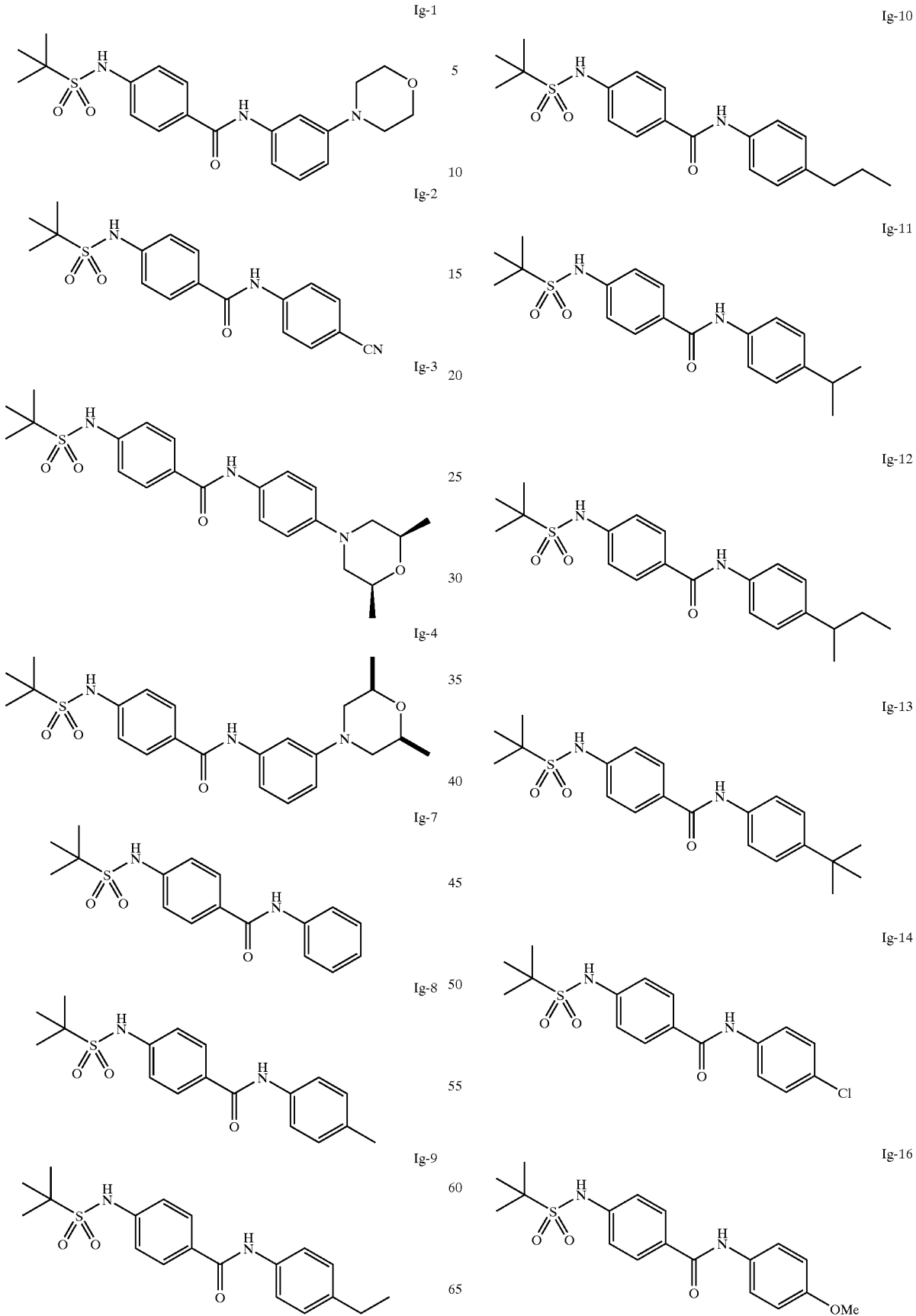

Ig-17
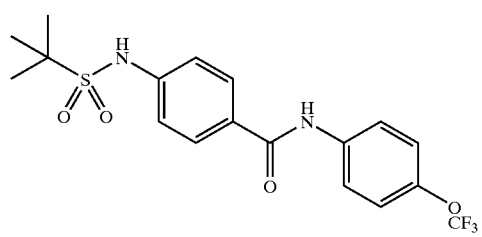
Ig-18
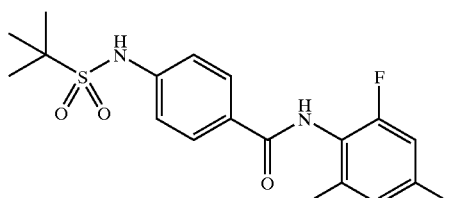
Ig-19
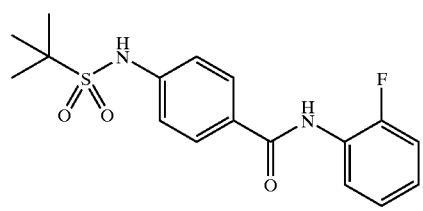
Ig-20
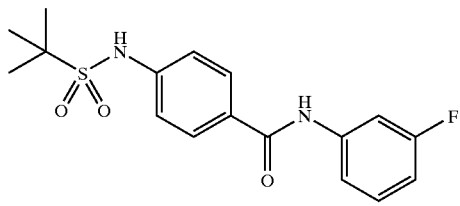
Ig-21
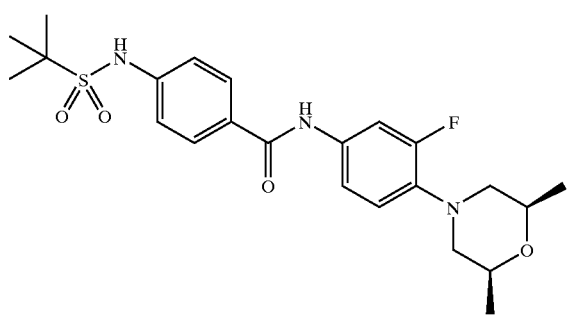
Ig-22
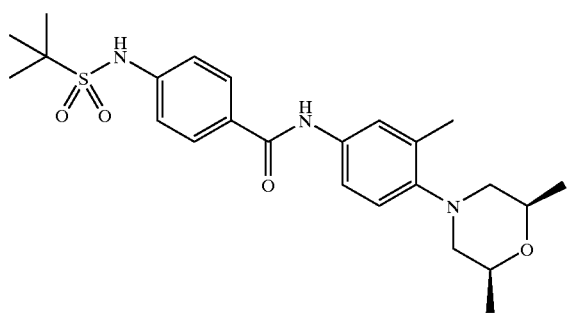
Ig-23
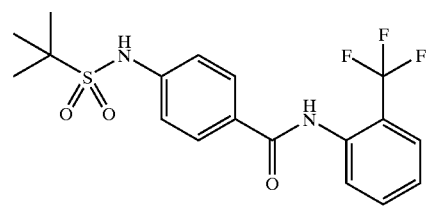
Ig-24
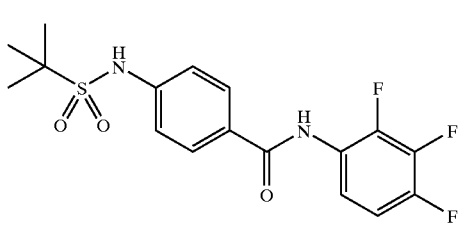
Ig-25
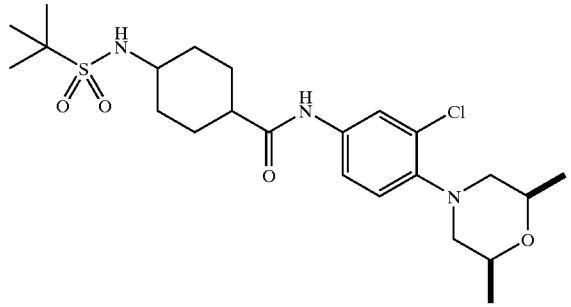
Ig-26
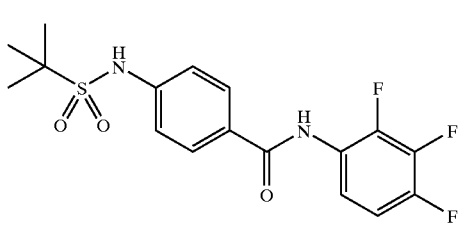
Ig-27

Ig-28
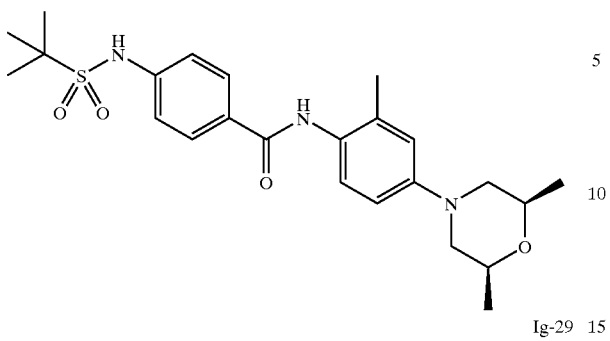
Ig-29
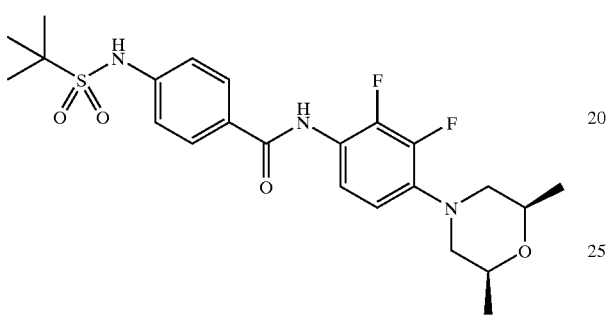
Ig-30
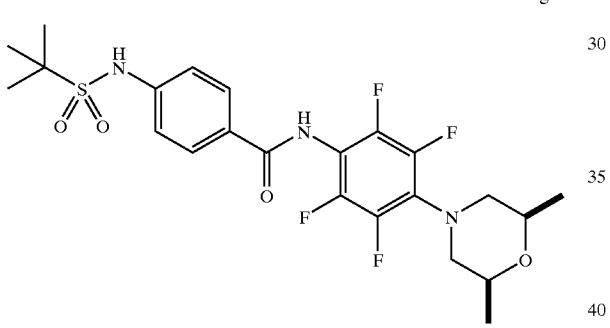
Ig-31
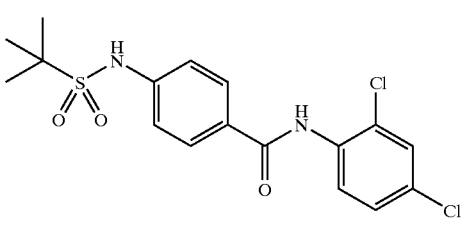
Ig-32
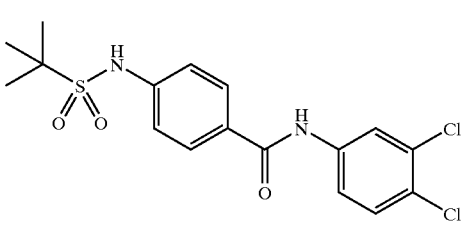
Ig-33
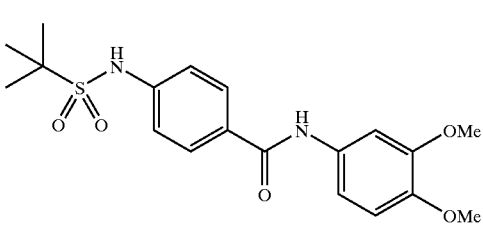
Ig-35
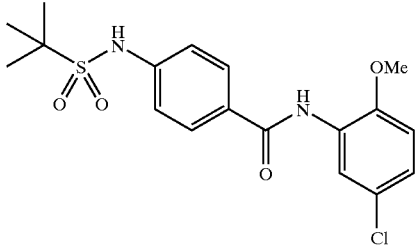
Ig-36
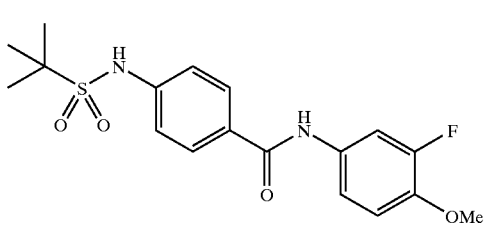
Ig-37
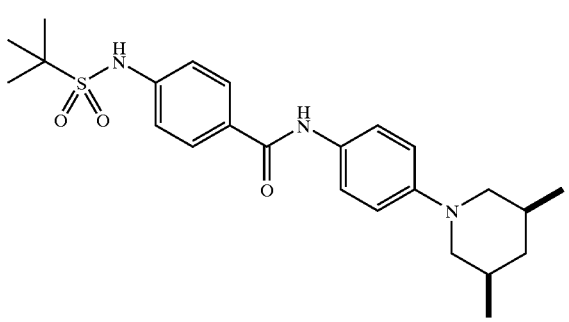
Ig-38
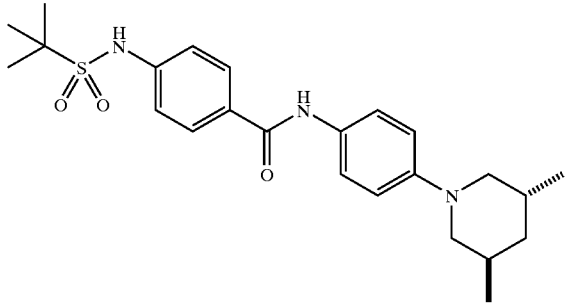
Ig-39
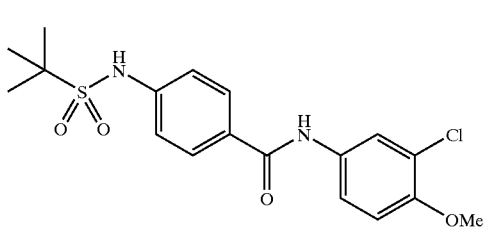

Ig-40
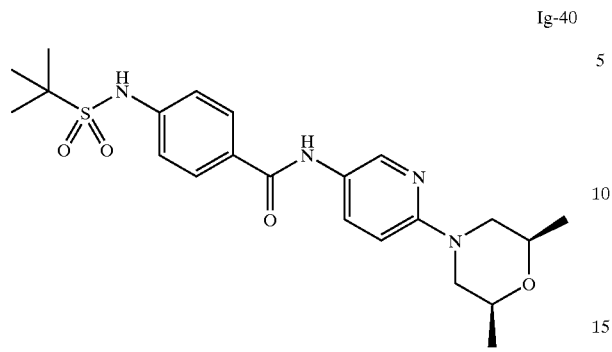
Ig-45
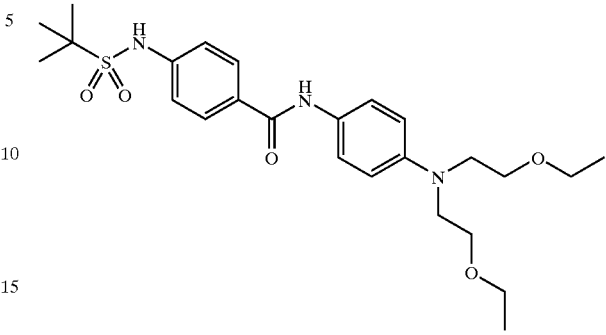
Ig-41
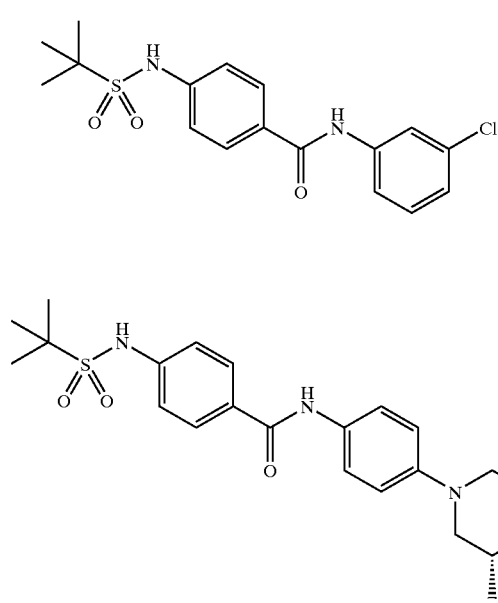
Ig-46
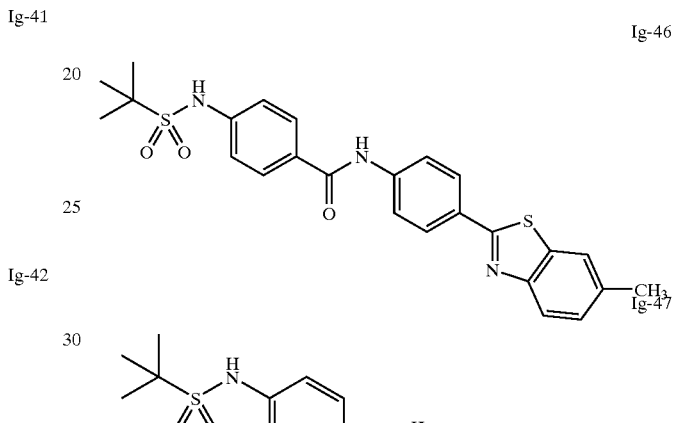
Ig-42
Ig-47
Ig-43
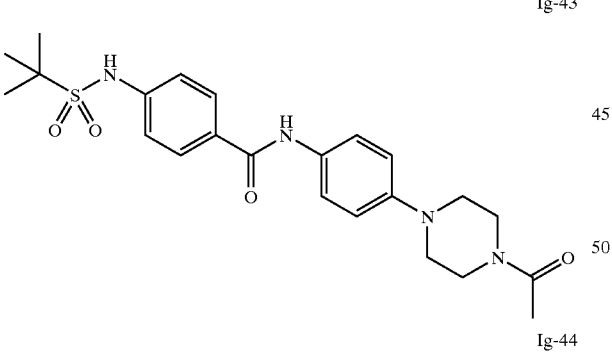
Ig-48
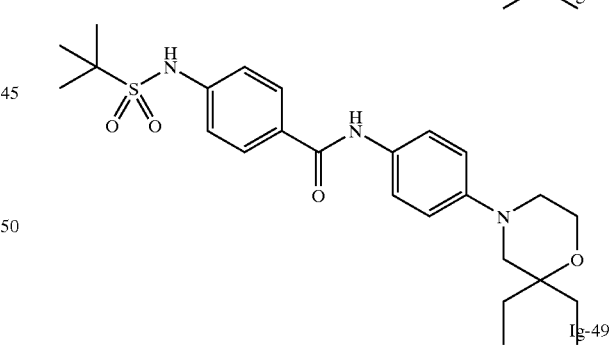
Ig-44
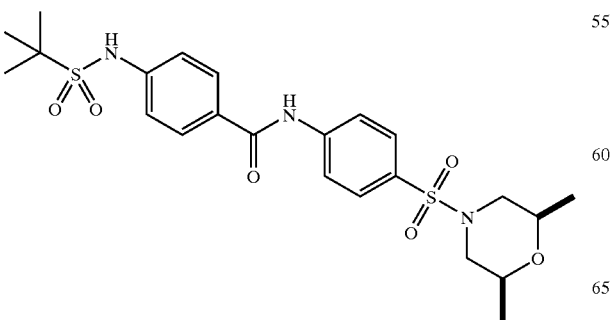
Ig-49
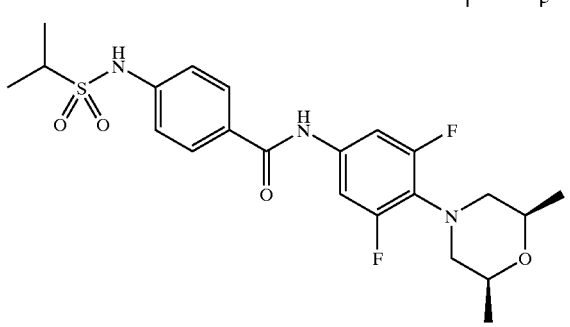

369
-continued
Ig-50
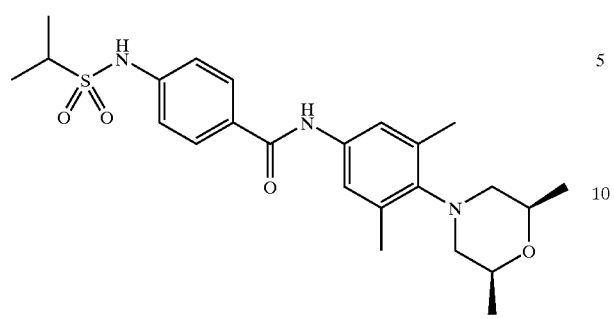
Ig-51
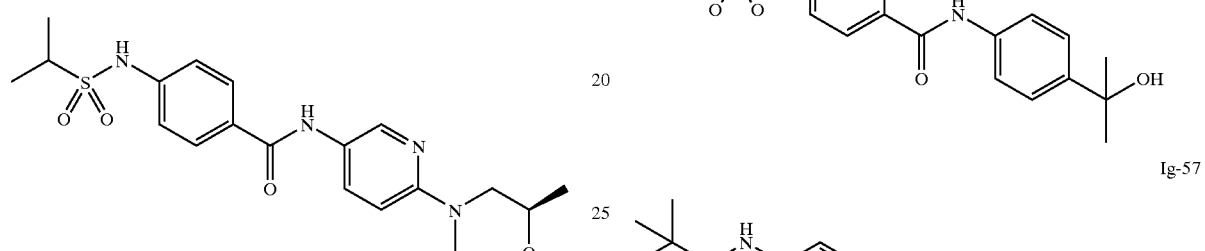
Ig-52
Ig-53
Ig-54
370
-continued
Ig-55
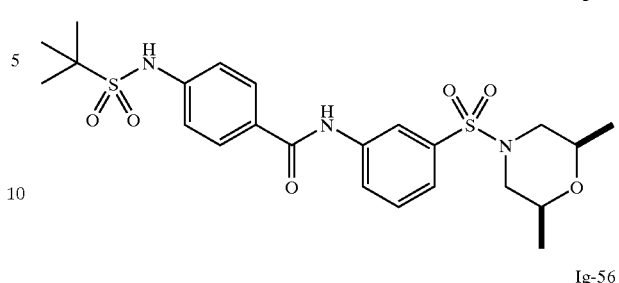
Ig-56
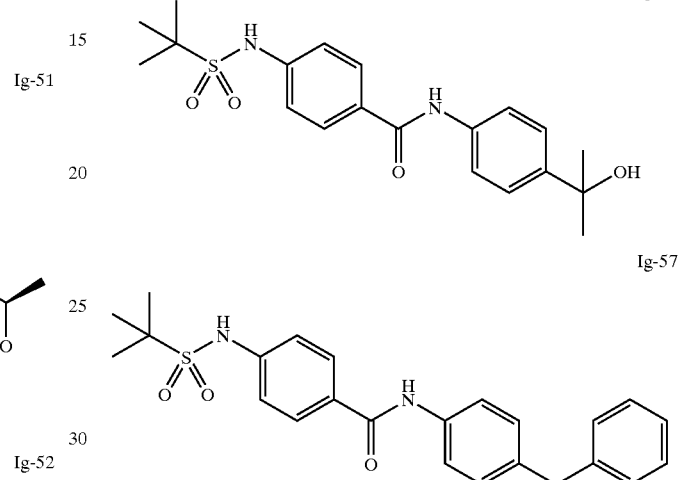
Ig-57
Ig-58
Ig-59
Ig-60

Ig-61
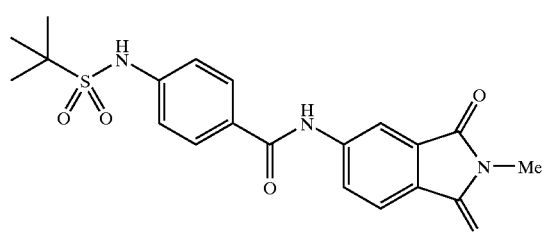
Ig-62
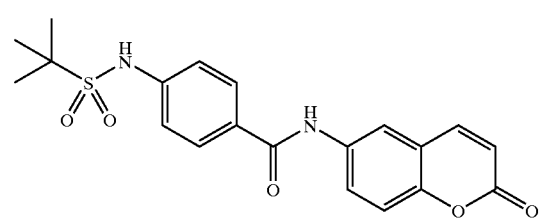
Ig-63
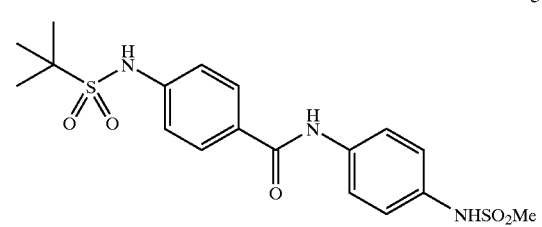
Ig-64
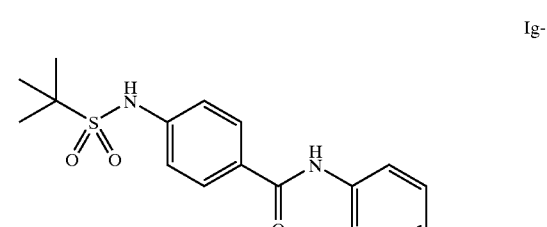
Ig-65
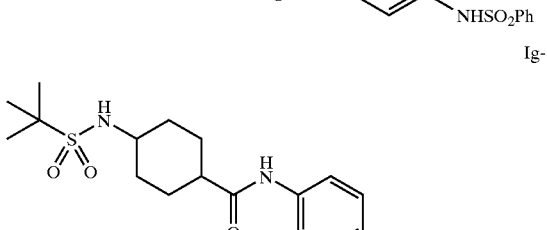
Ig-66
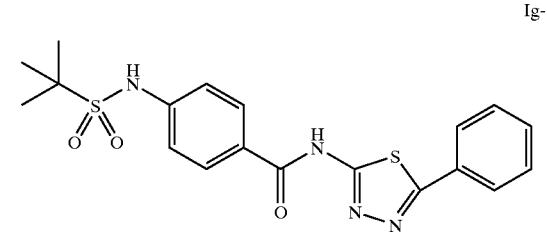
Ig-67
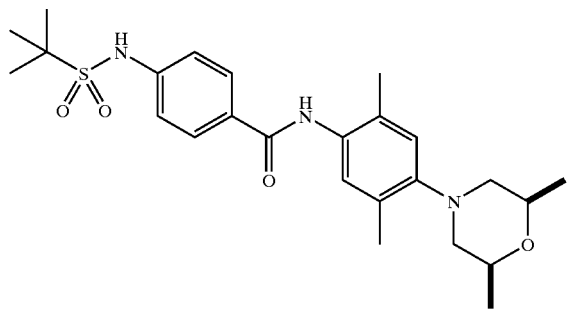
Ig-68
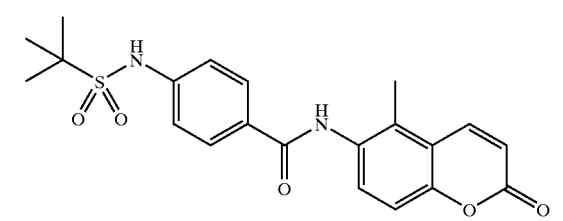
Ig-69
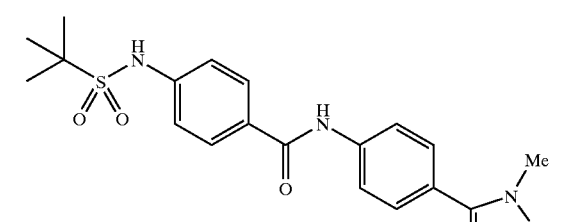
Ig-70
Ig-71
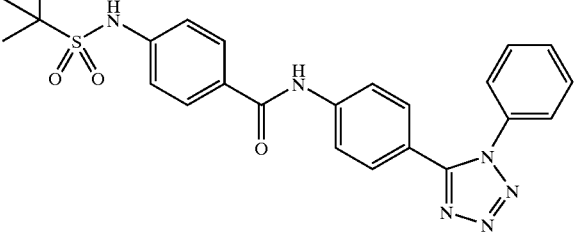

373
-continued
Ig-74
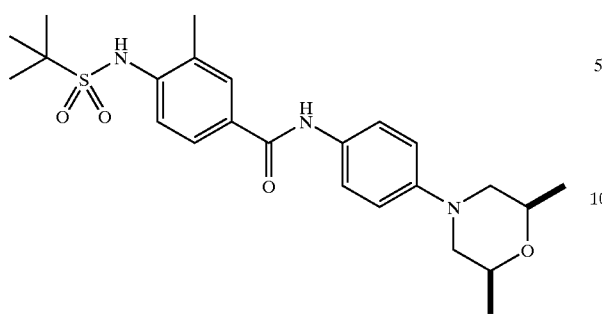
Ig-75
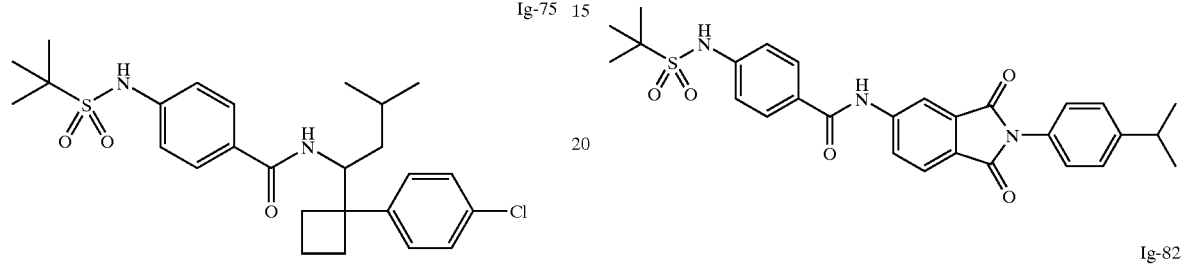
Ig-76
Ig-77
Ig-78
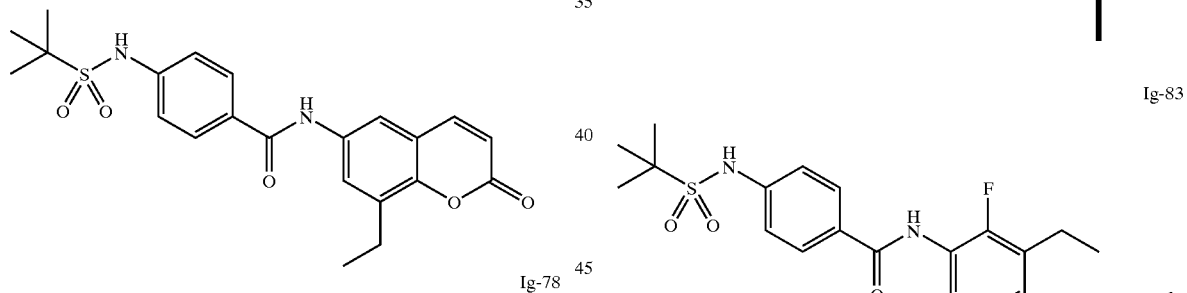
Ig-79
374
-continued
Ig-80
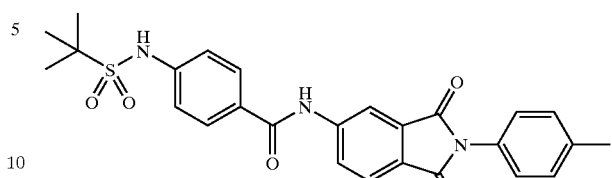
Ig-81
Ig-82
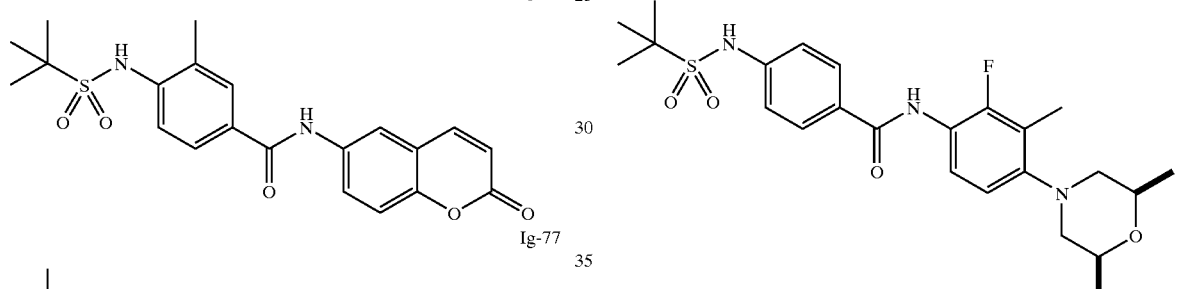
Ig-83
Ig-84
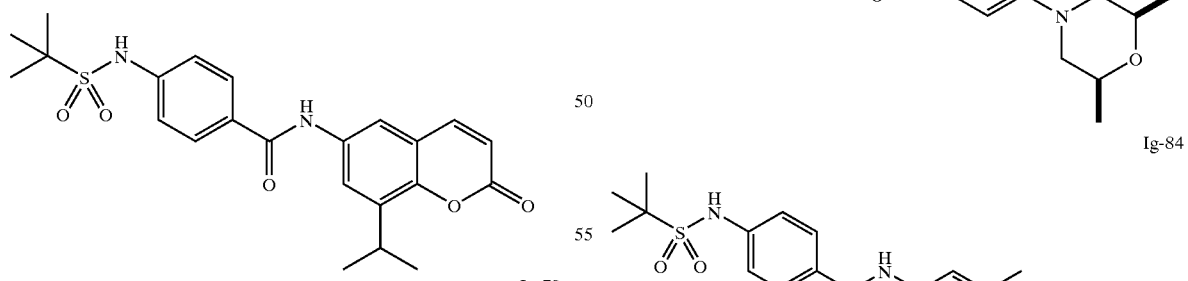
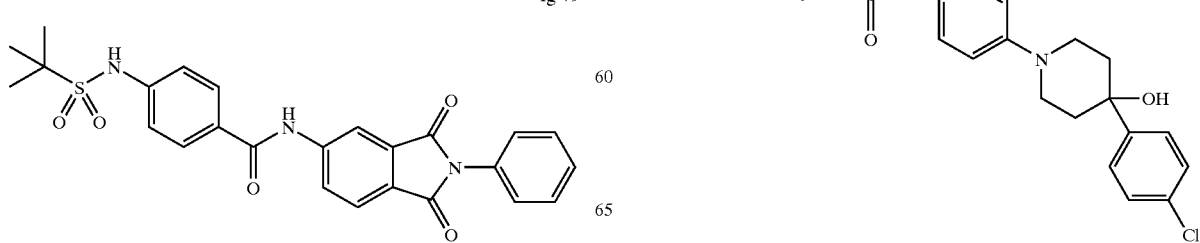

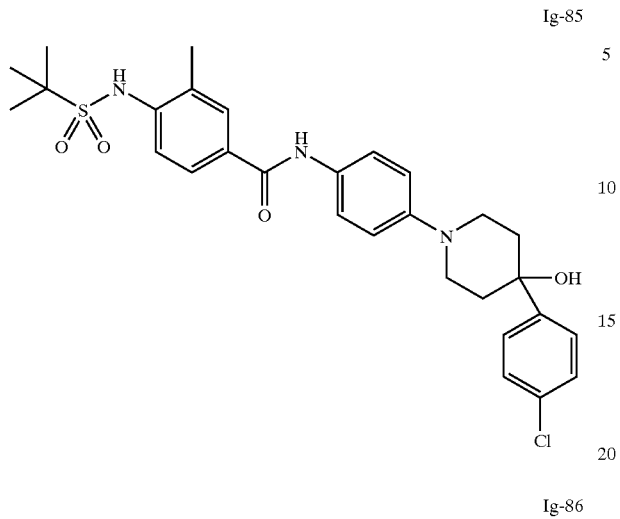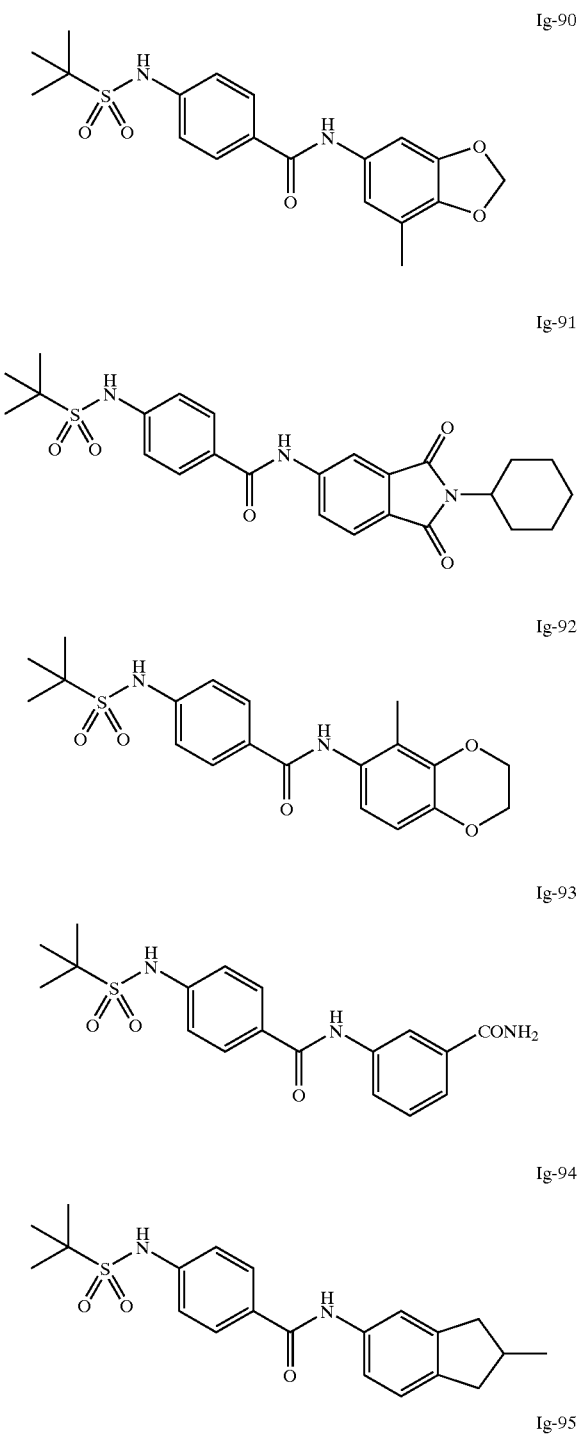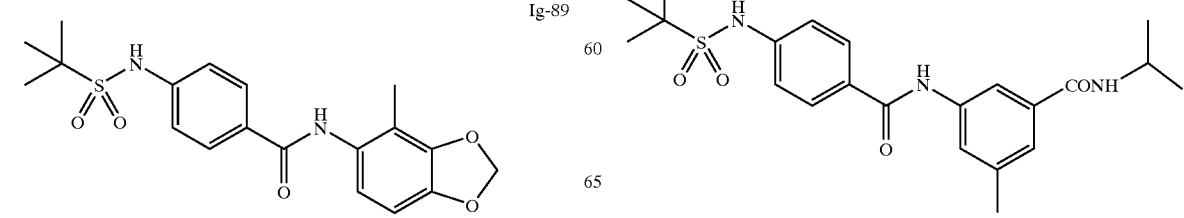

Ig-96
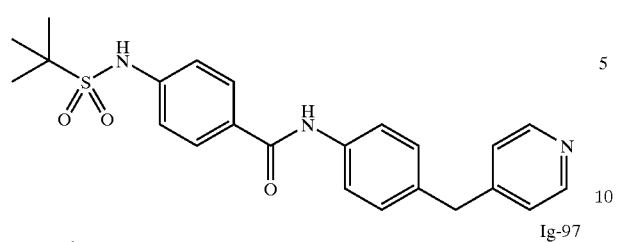
Ig-97
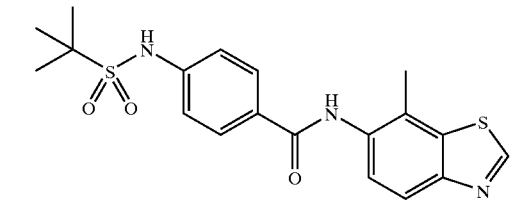
Ig-98
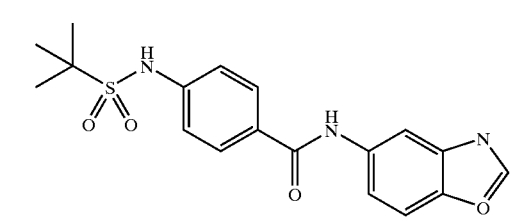
Ig-99
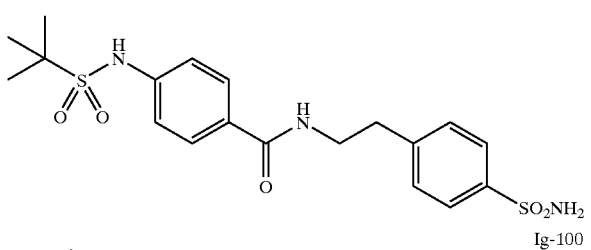
Ig-100
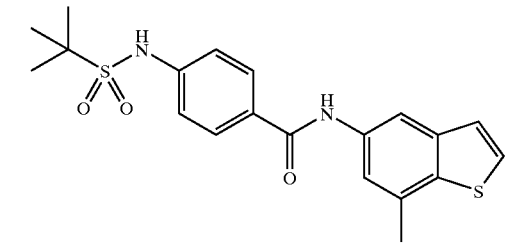
Ig-101
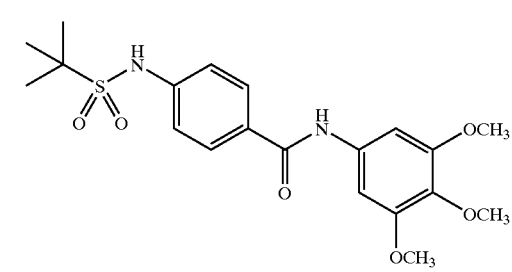
Ig-102
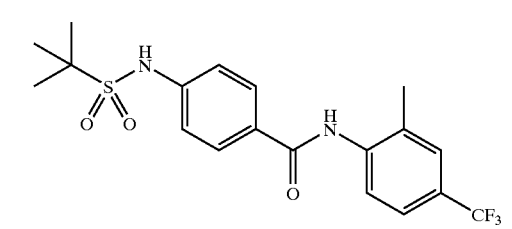
Ig-103
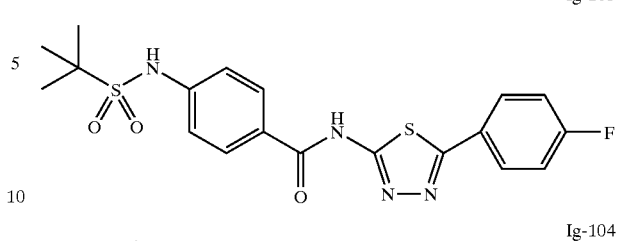
Ig-104
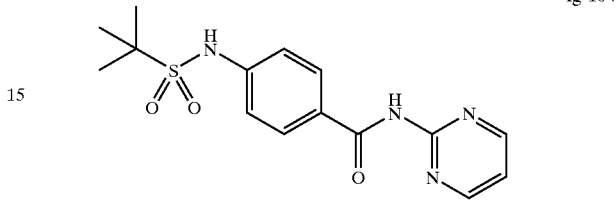
Ig-105
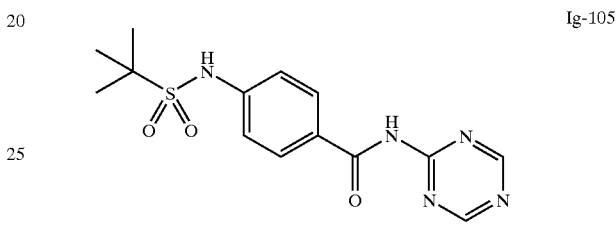
Ig-106
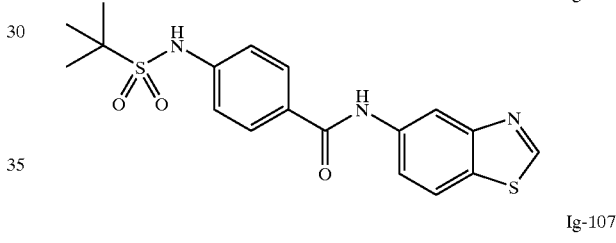
Ig-107
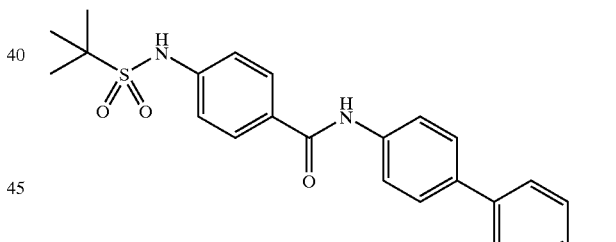
Ig-108
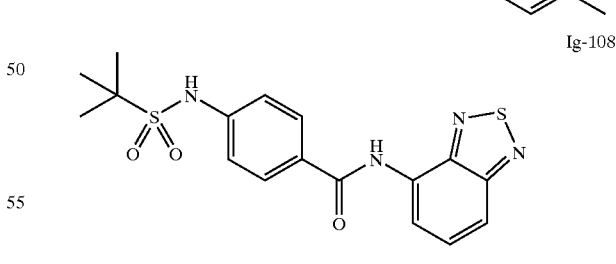
Ig-109
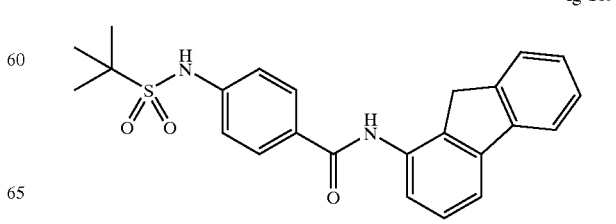

Ig-110
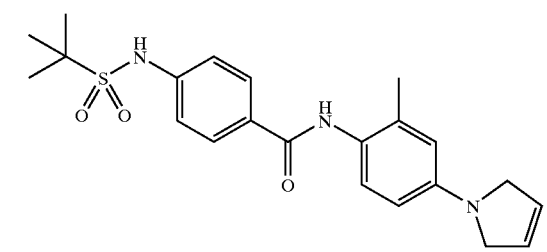
Ig-111
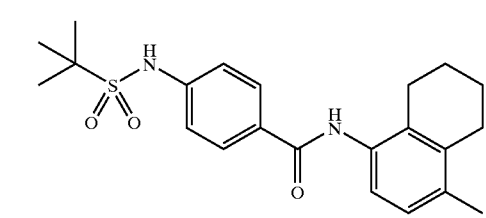
Ig-112
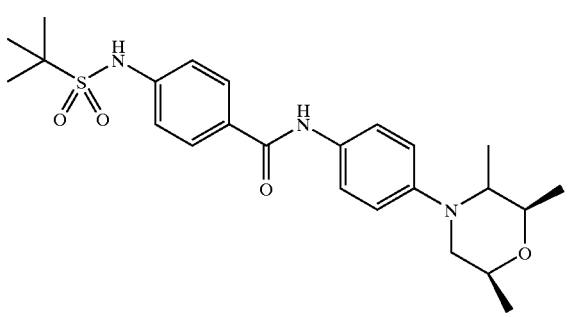
Ig-113
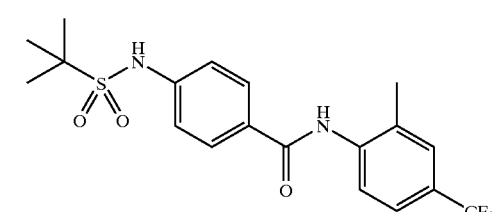
Ig-114
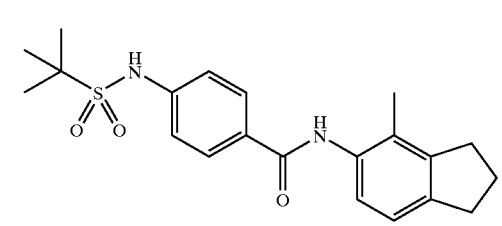
Ig-115
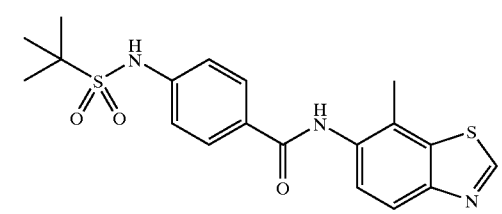
Ig-116
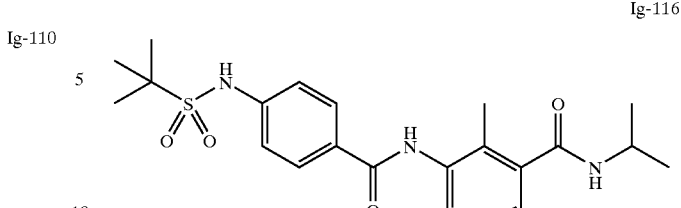
Ig-117
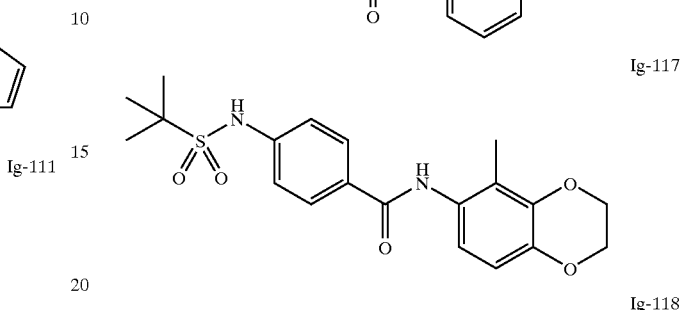
Ig-118
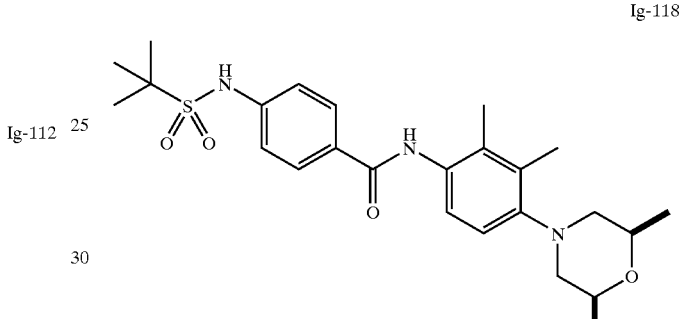
Ig-119
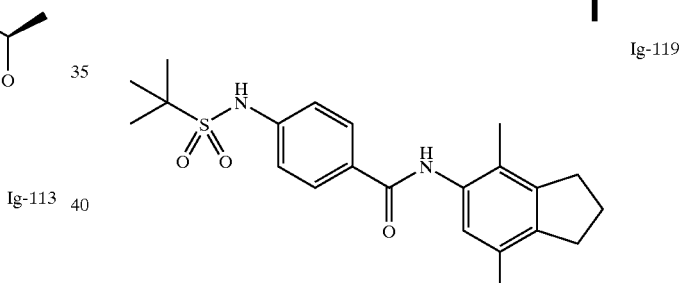
Ig-120
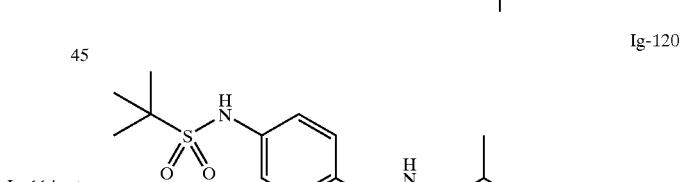
Ig-121
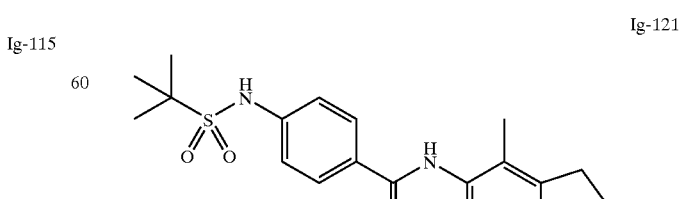

-continued
Ig-122
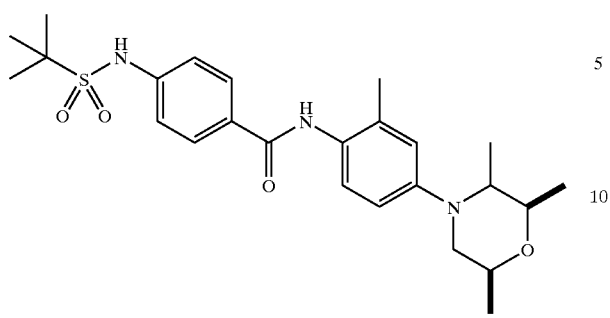
Ig-123
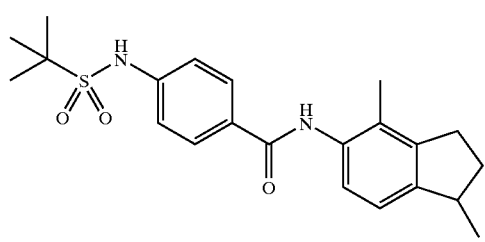
Ig-124
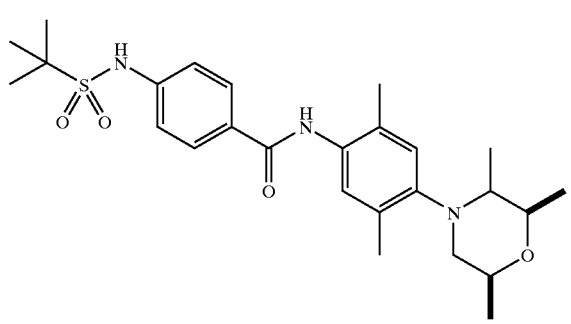
Ig-125
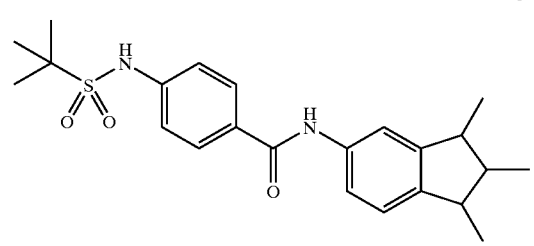
Ig-126
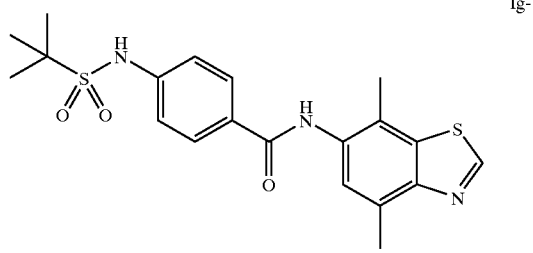
Ig-127
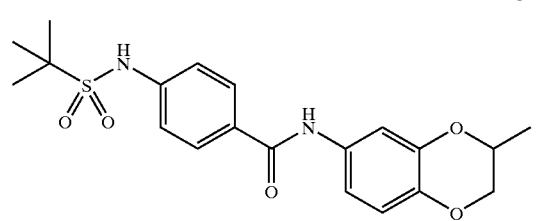
-continued
Ig-128
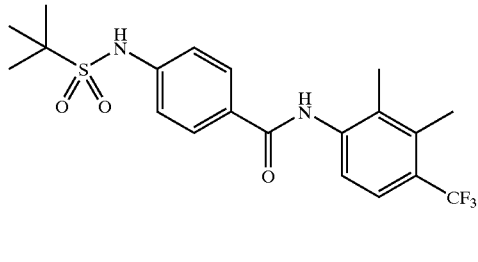
Ig-129
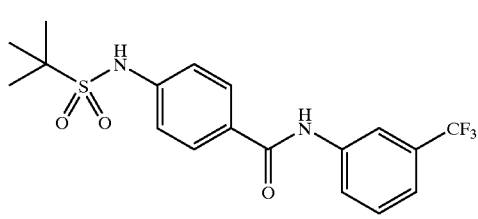
Ig-130
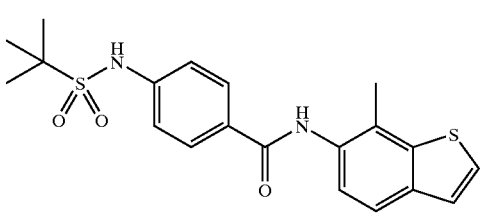
Ig-131
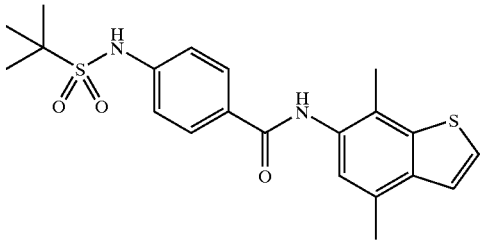
Ig-132
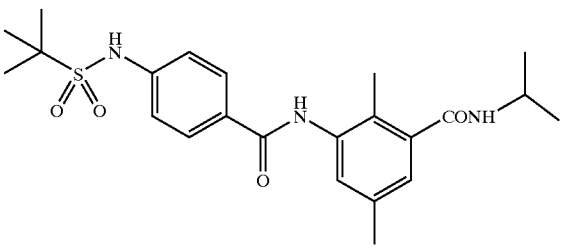
Ig-133
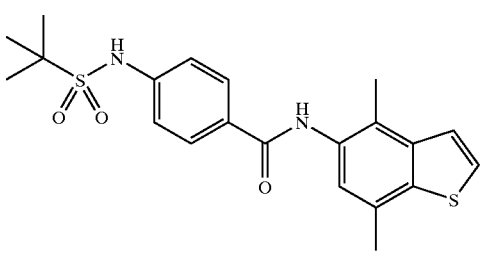

Ig-134
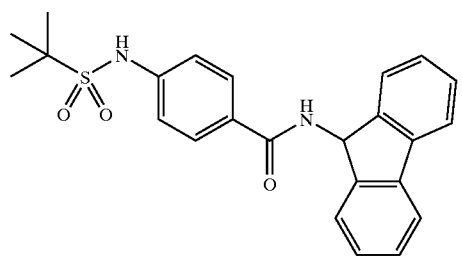
Ig-135
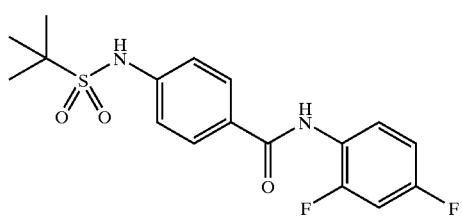
Ig-136
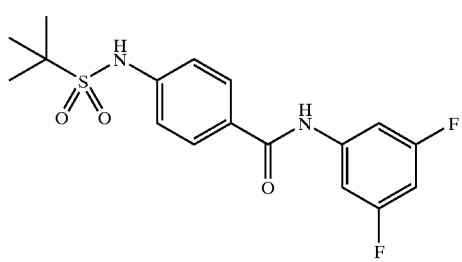
Ig-137
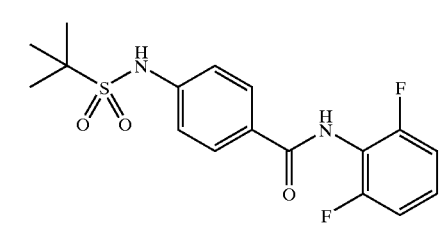
Ig-138
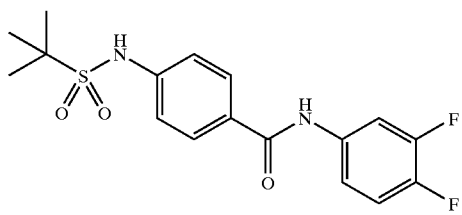
Ig-139
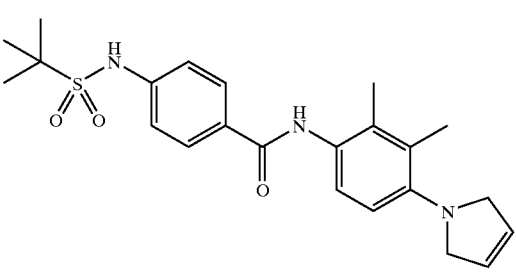
Ig-140
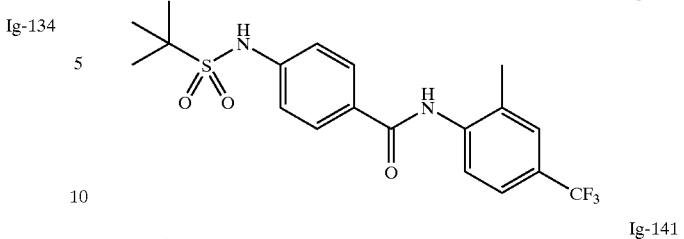
Ig-141
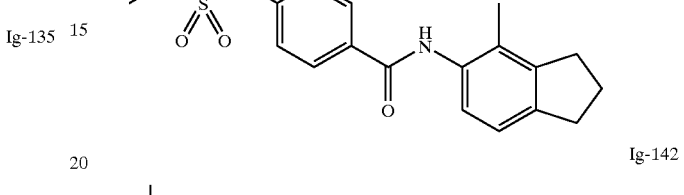
Ig-142
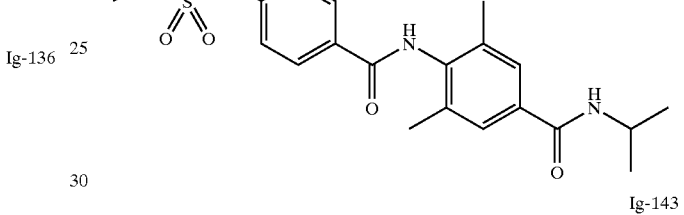
Ig-143
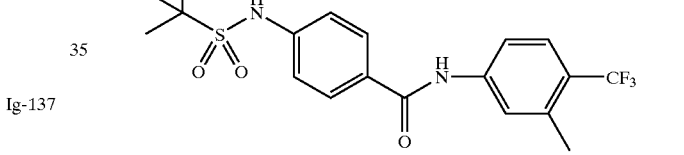
Ig-144
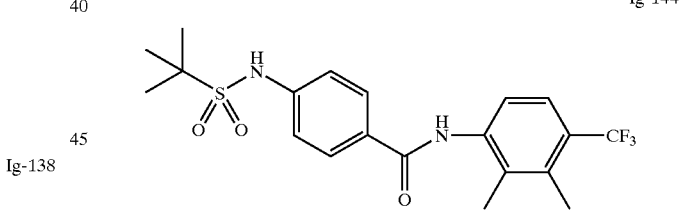
Ig-145
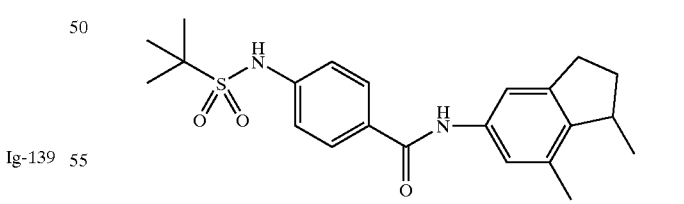
Ig-146
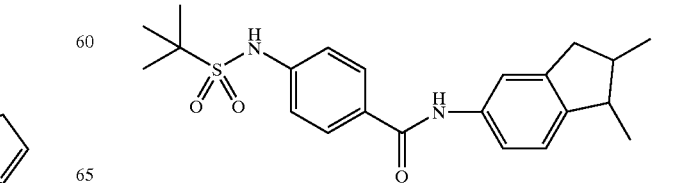

Ig-147
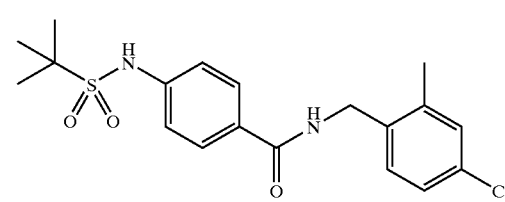
Ig-148
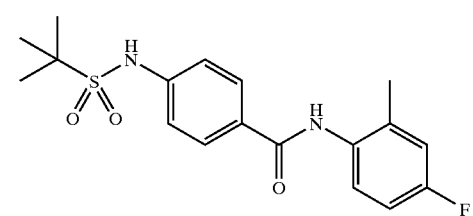
Ig-149
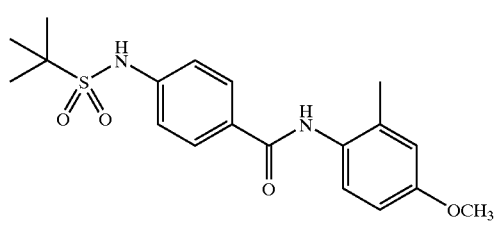
Ig-150
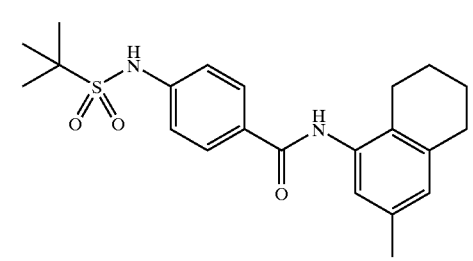
Ig-151
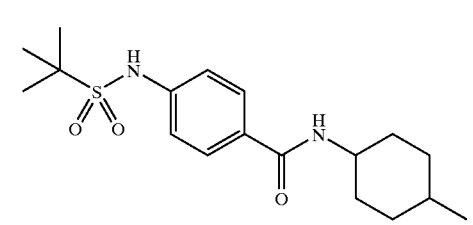
Ig-152
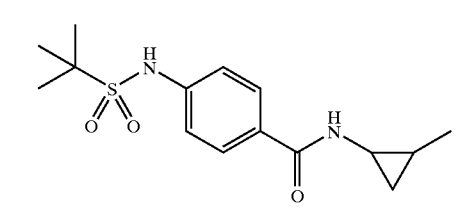
Ig-153
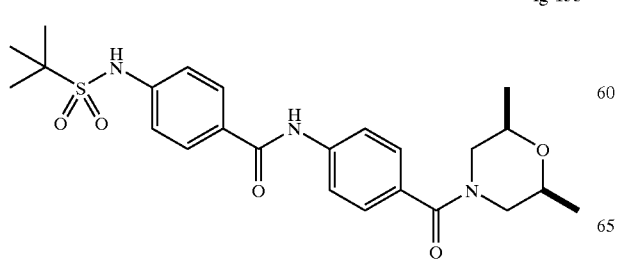
Ig-154
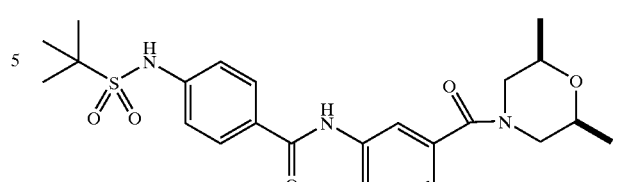
Ig-155
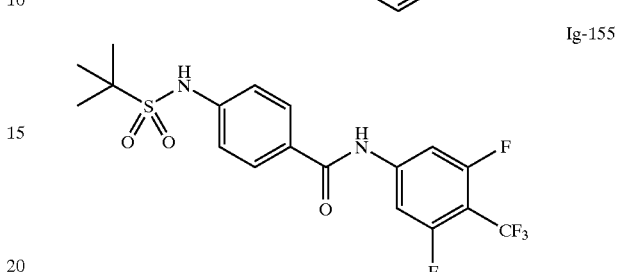
Ig-156
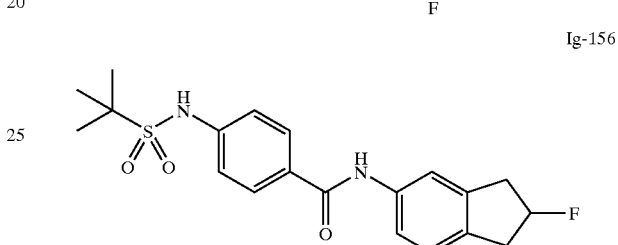
Ig-157
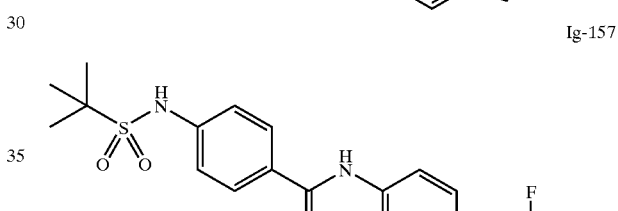
Ig-158
Ig-159
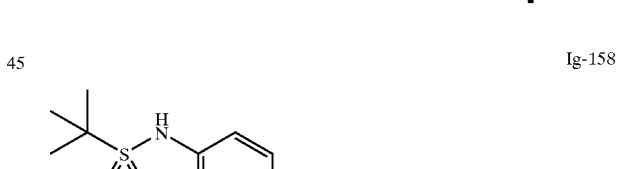

Ig-160
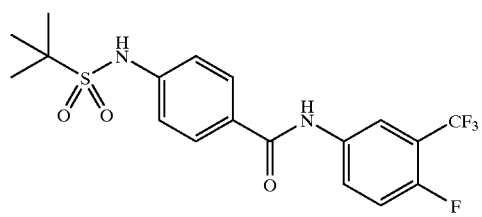
Ig-161
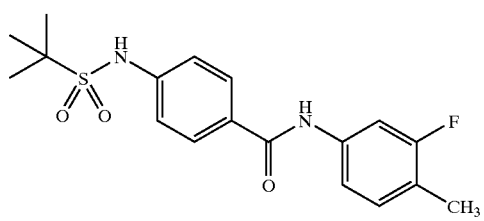
Ig-162
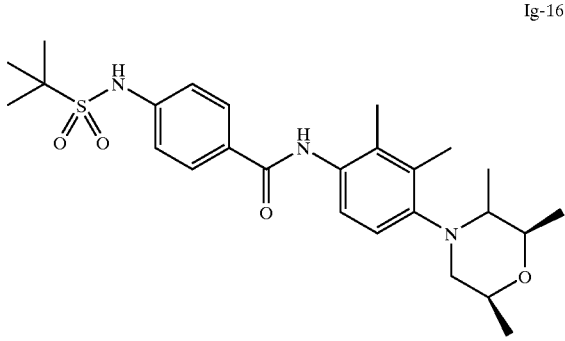
Ig-163
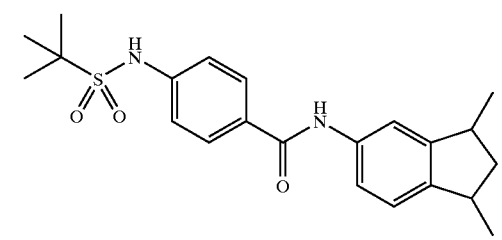
Ig-164
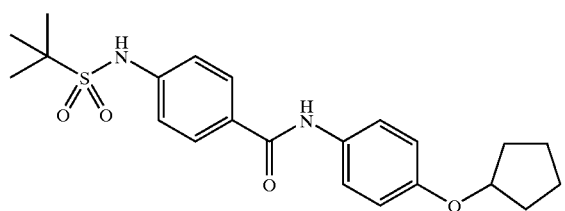
Ig-165
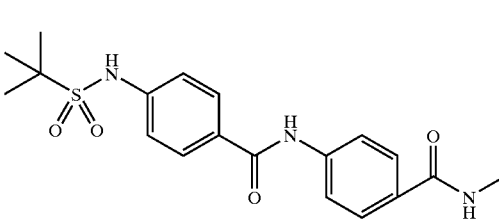
Ig-166
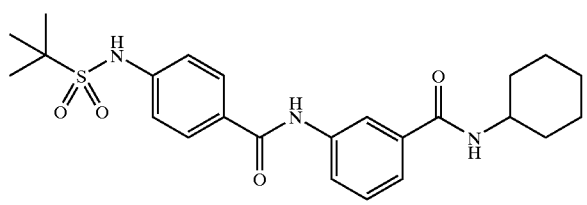
Ig-167
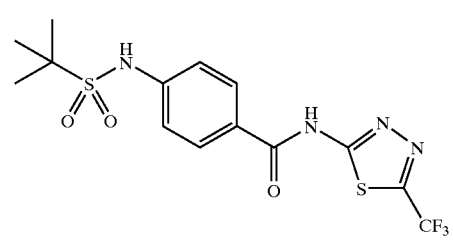
Ig-168
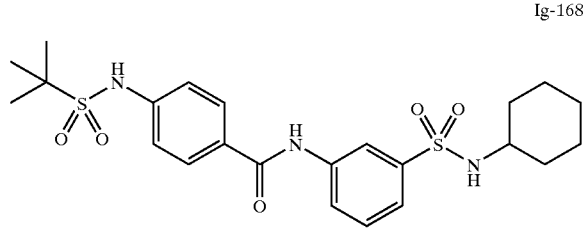
Ig-169
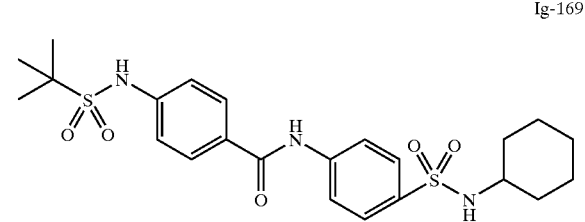
Ig-171
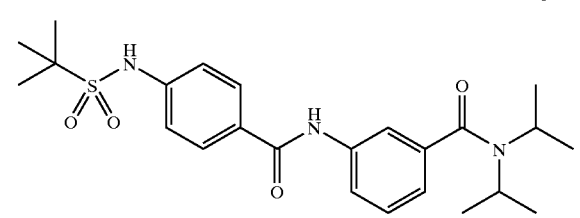
Ig-172
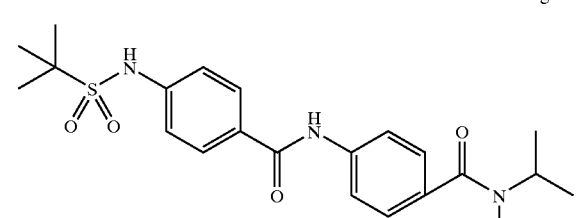

Ig-173 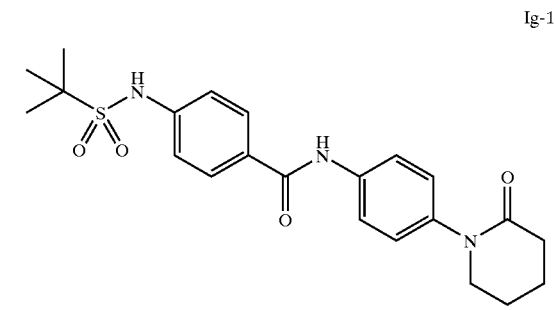
Ig-174 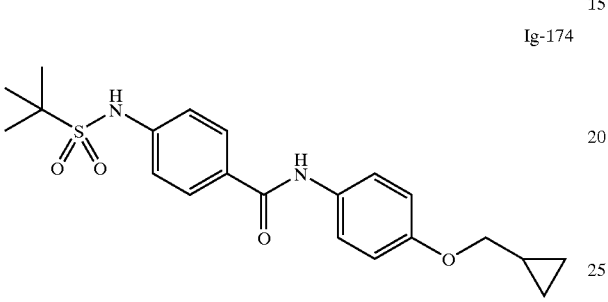
Ig-175 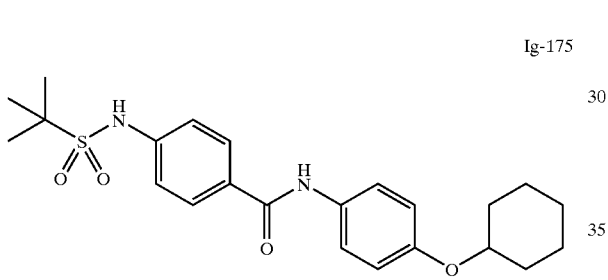
Ig-176 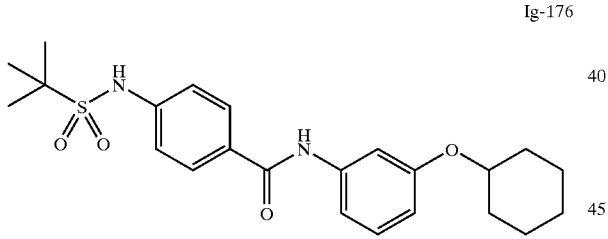
Ig-177 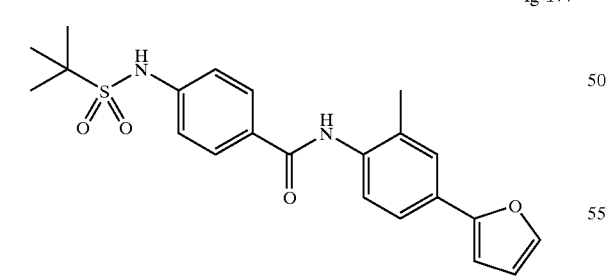
Ig-178 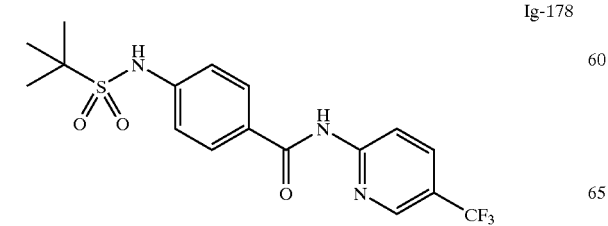
Ig-179 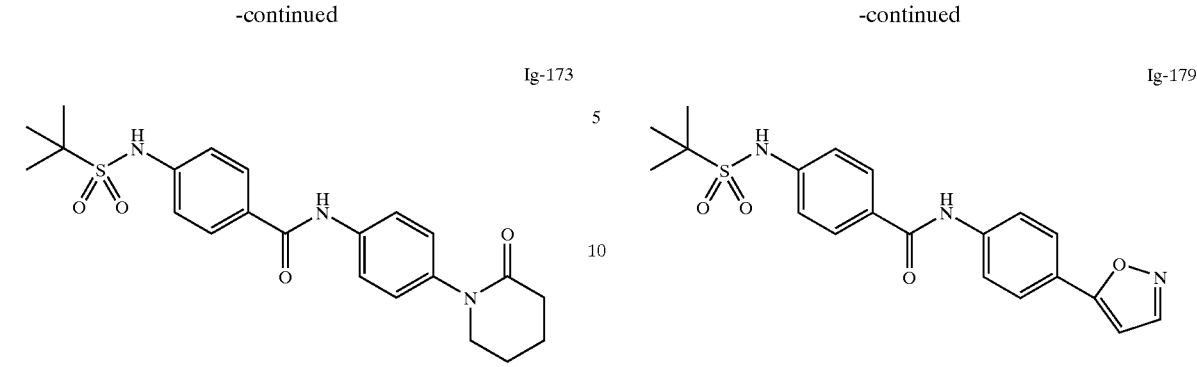
Ig-180 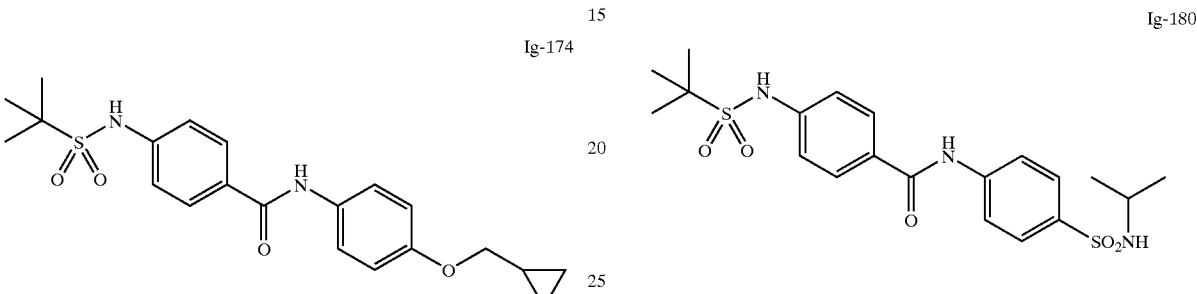
Ig-181 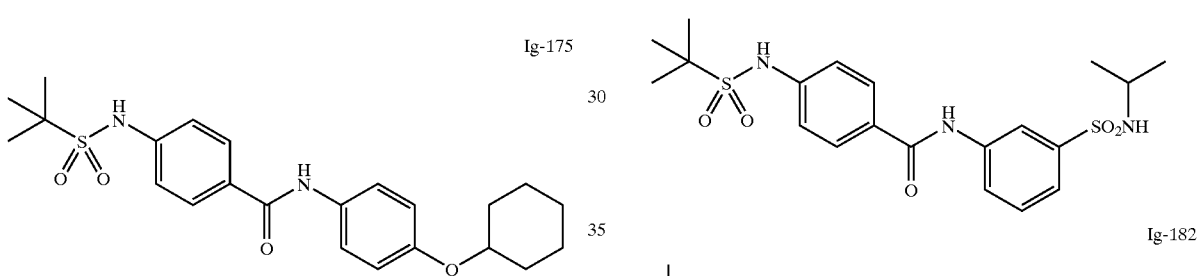
Ig-182 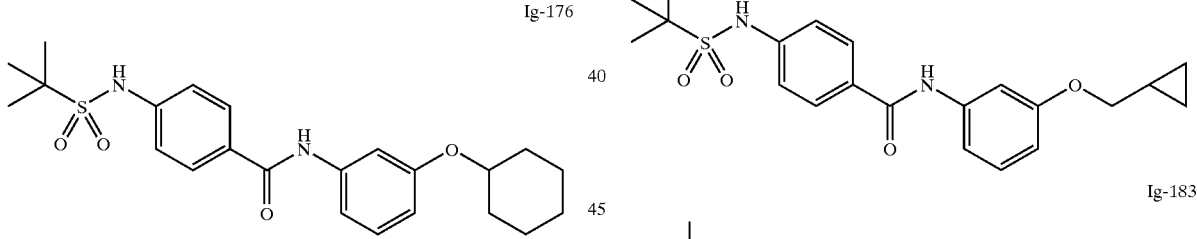
Ig-183 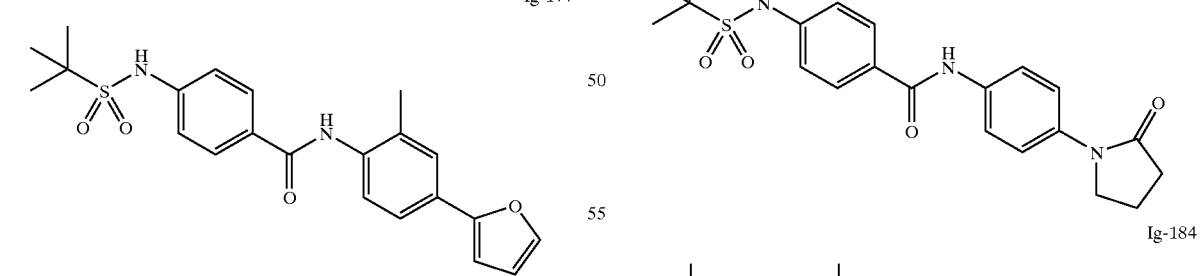
Ig-184 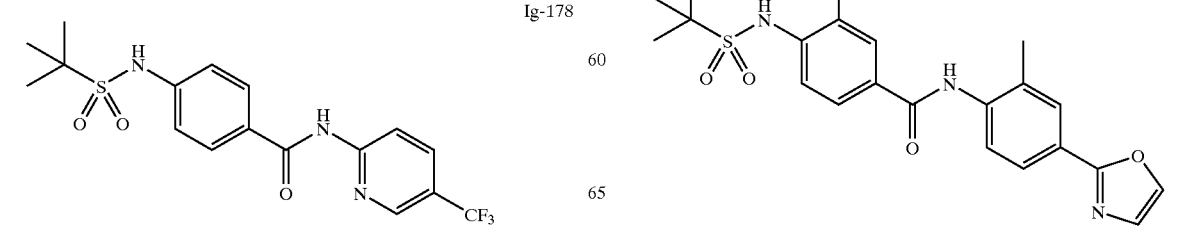

Ig-185
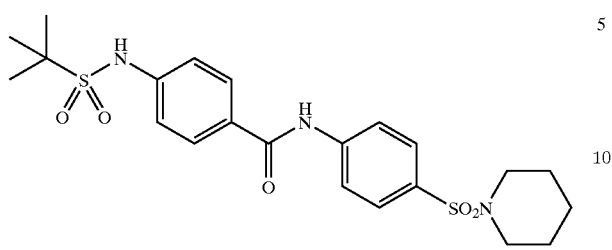
Ig-186
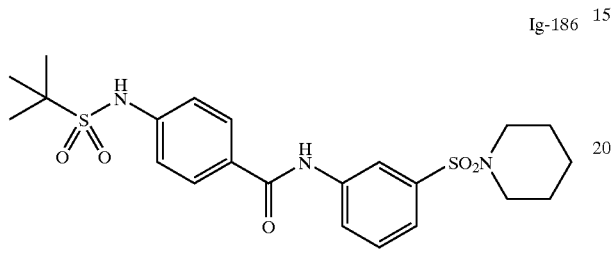
Ig-187
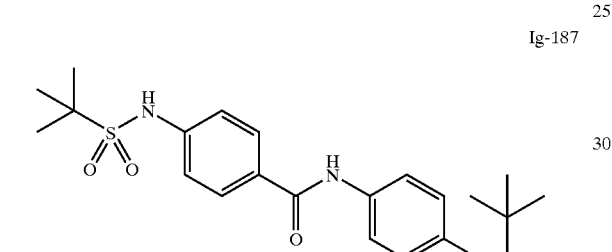
Ig-188
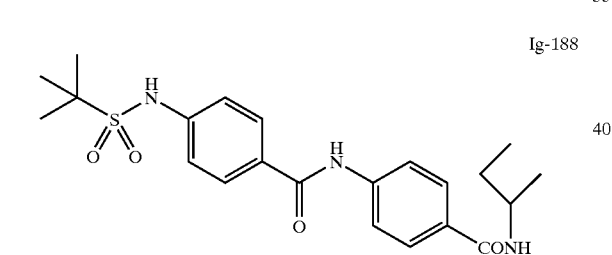
Ig-189
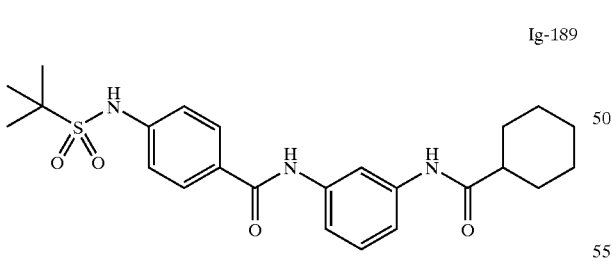
Ig-190
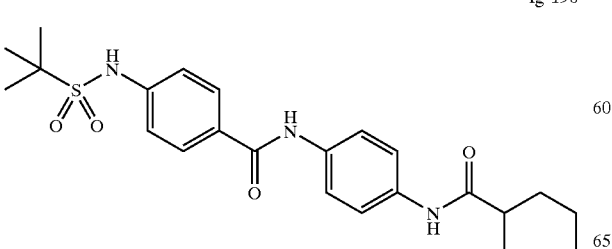
Ig-191
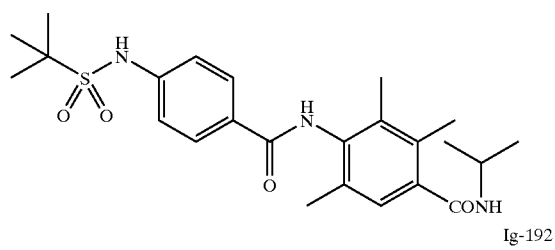
Ig-192
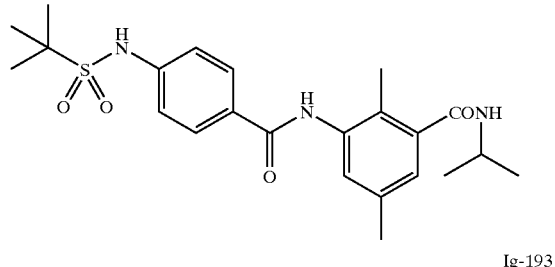
Ig-193
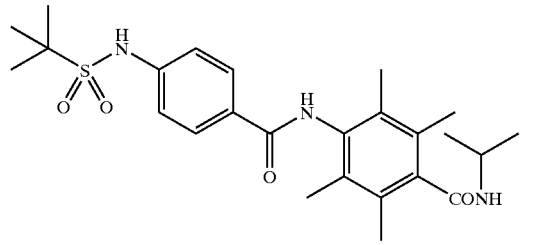
Ig-194
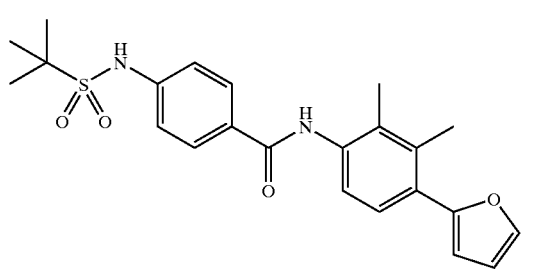
Ig-195
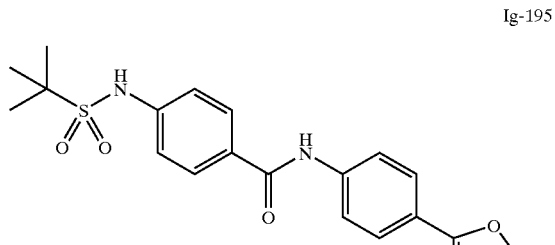
Ig-196
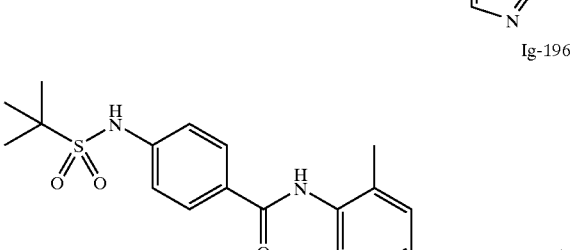

Ig-197
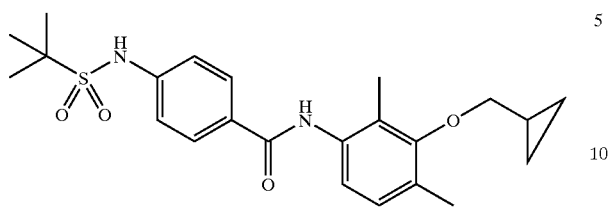
Ig-198
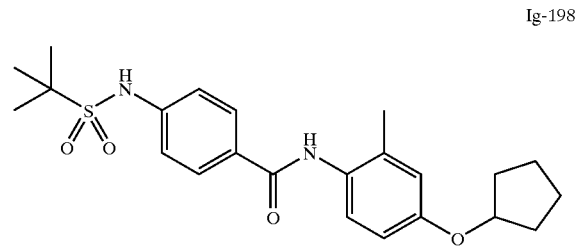
Ig-199
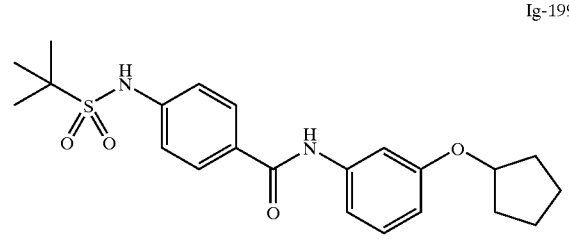
Ig-200
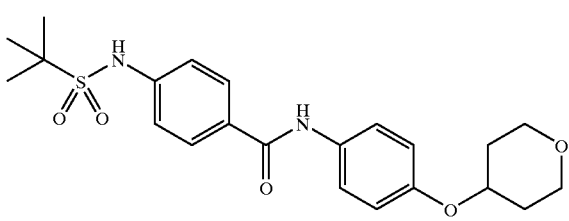
Ig-201
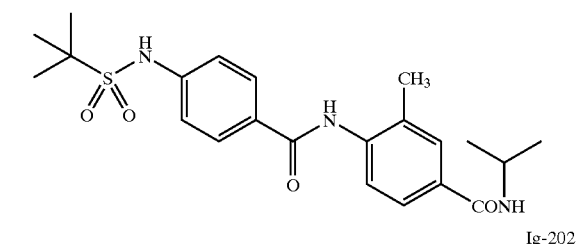
Ig-202
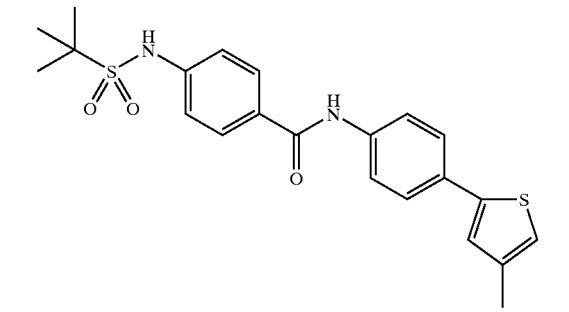
Ig-203
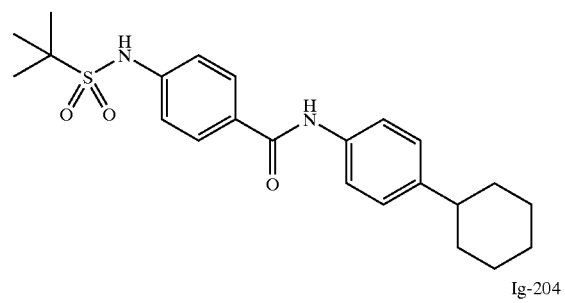
Ig-204
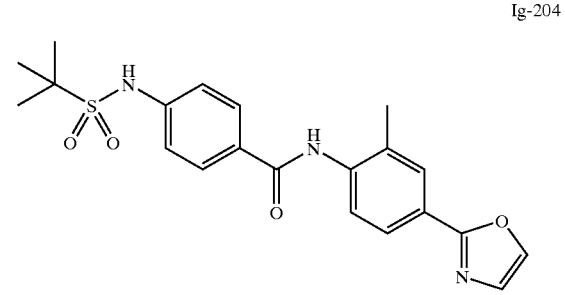
Ig-205
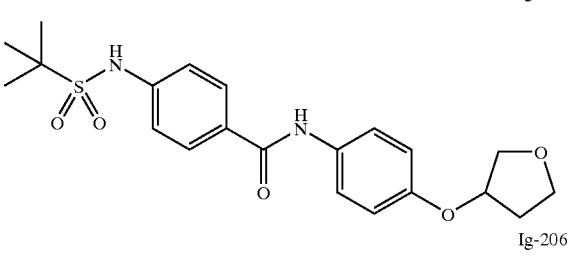
Ig-206
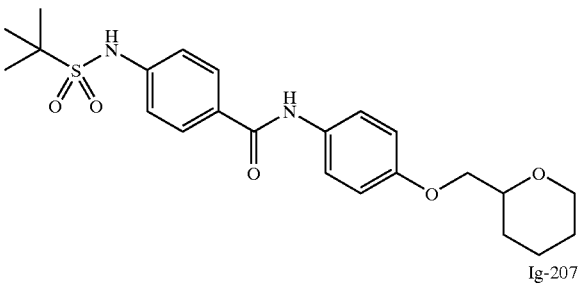
Ig-207
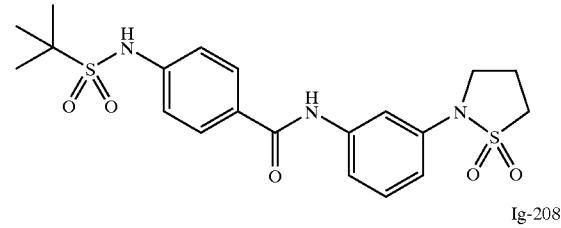
Ig-208
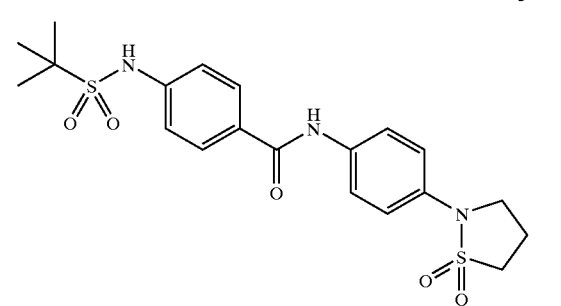

Ig-209
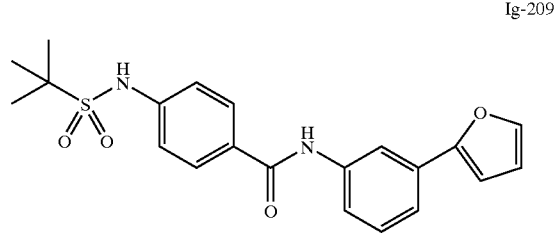
Ig-210
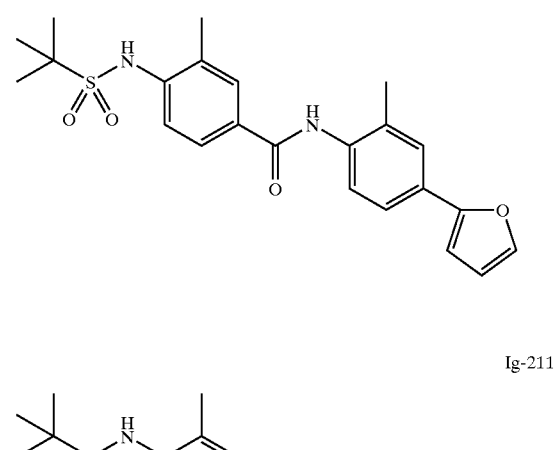
Ig-211
Ig-212
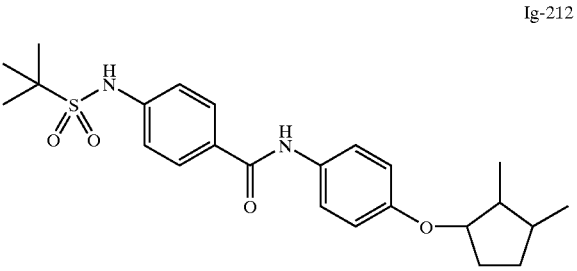
Ig-213
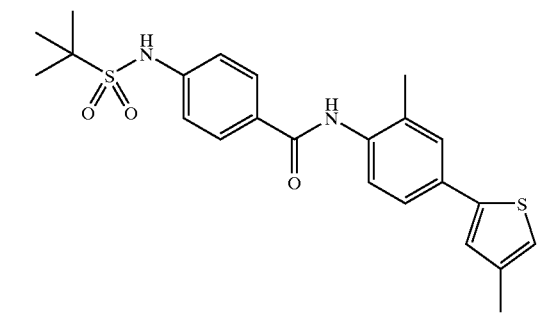
Ig-214
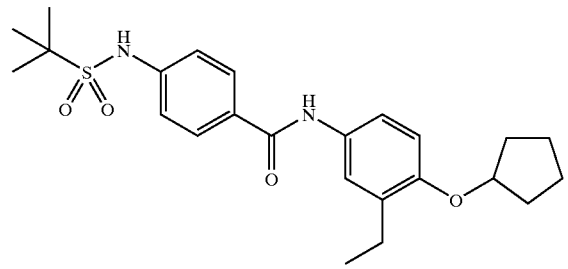
Ig-215
Ig-216
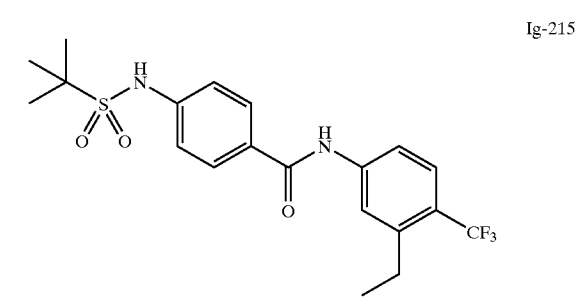
Ig-219
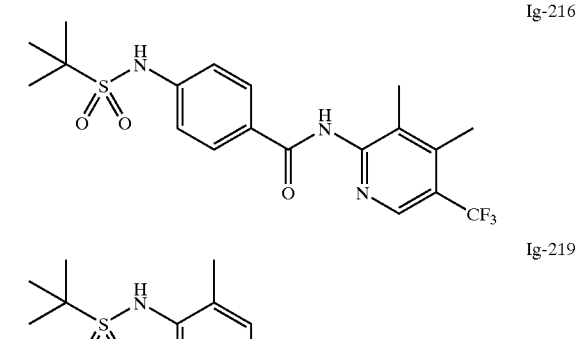
Ig-220
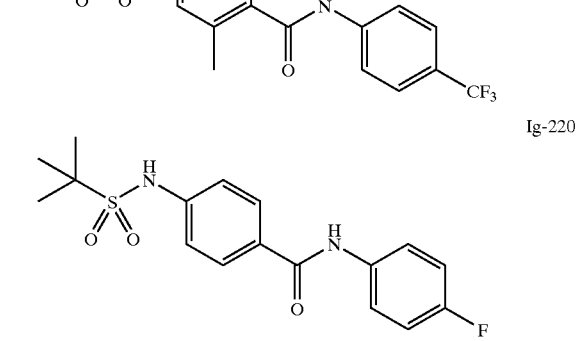
Ig-221
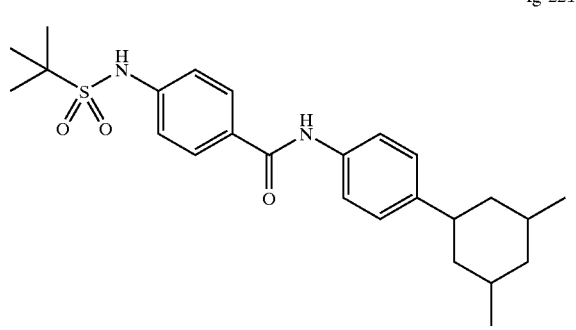

Ig-222
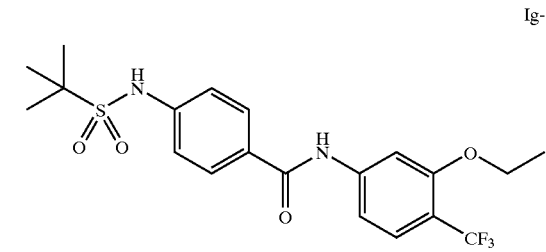
Ig-223
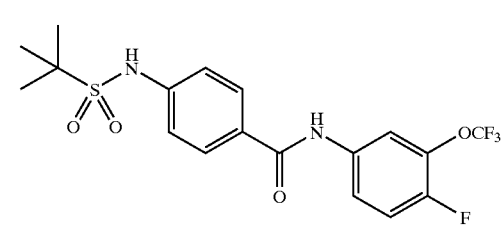
Ig-224
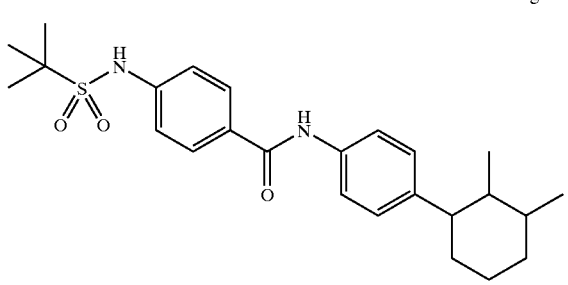
Ig-225
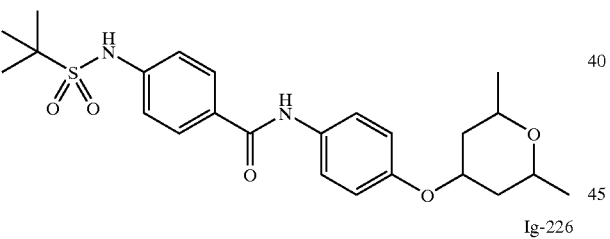
Ig-226
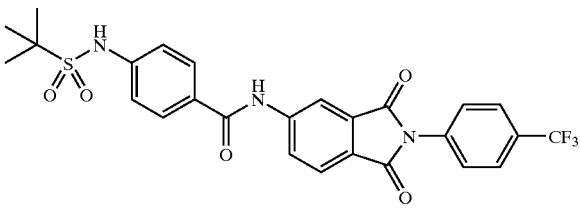
Ih-1
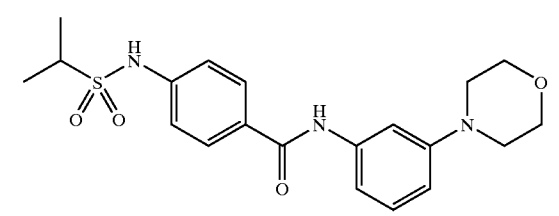
Ih-2
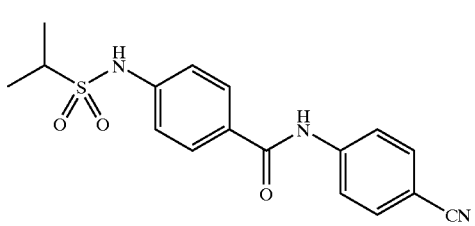
Ih-4
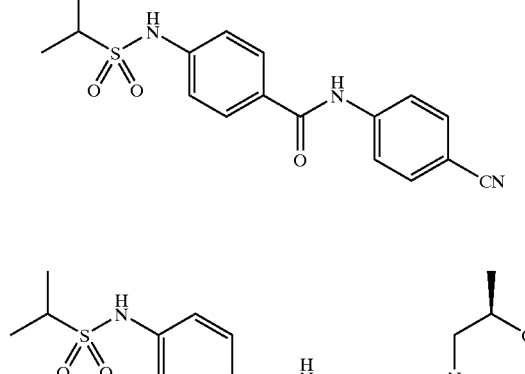
Ih-7
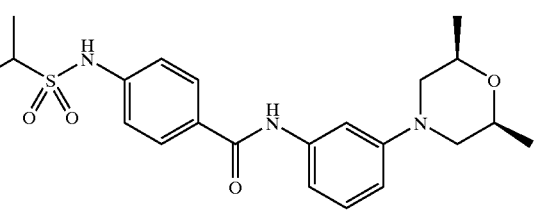
Ih-8
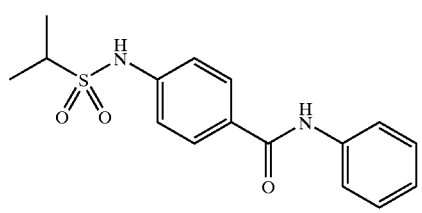
Ih-9
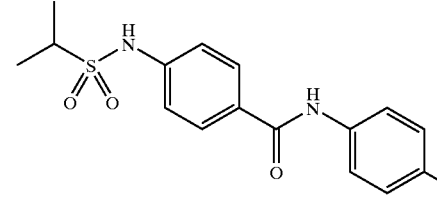
Ih-10
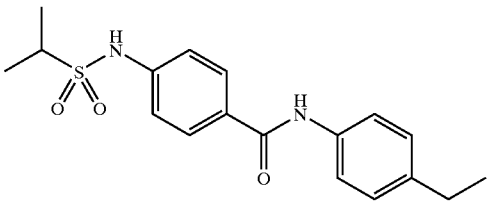
Ih-11
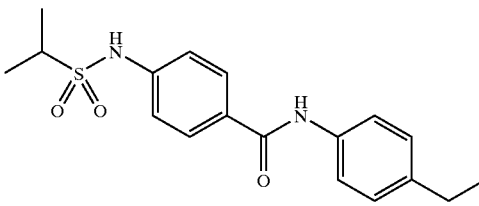

| | |
|---|---|
| Ih-12 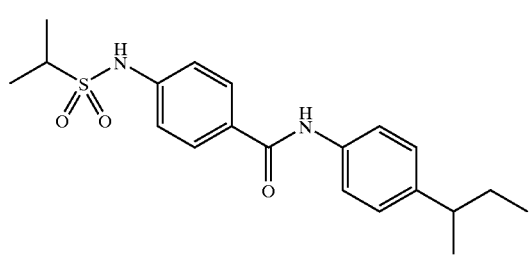 | Ih-20 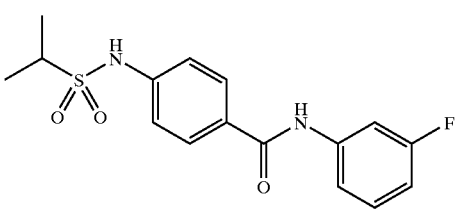 |
| Ih-13 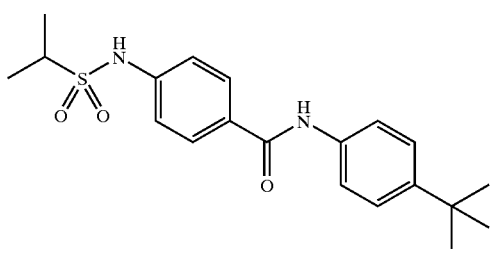 | Ih-21 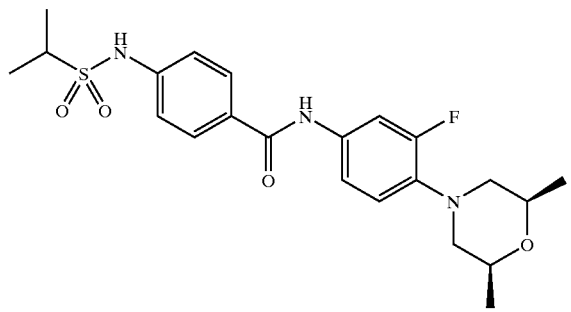 |
| Ih-14 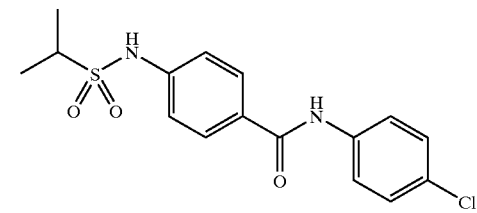 | Ih-22 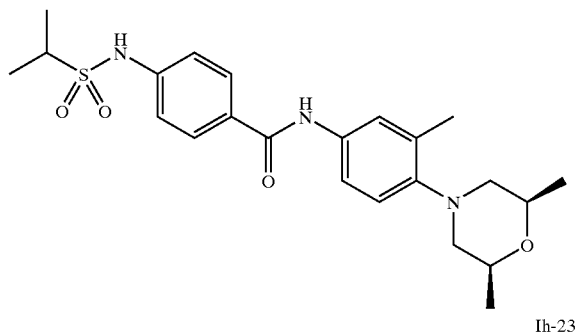 |
| Ih-16 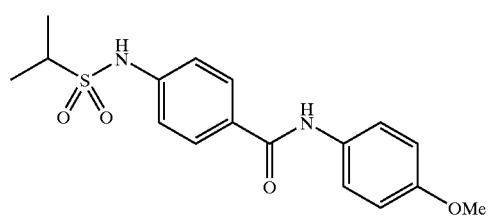 | Ih-23 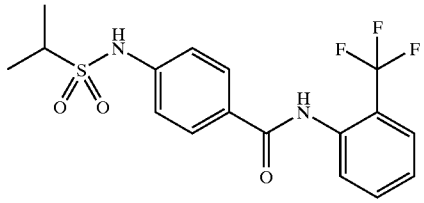 |
| Ih-17 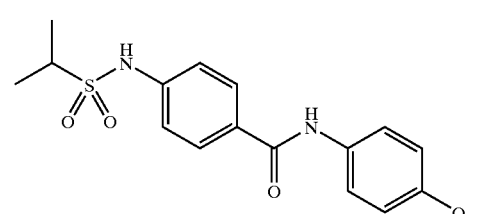 | Ih-24 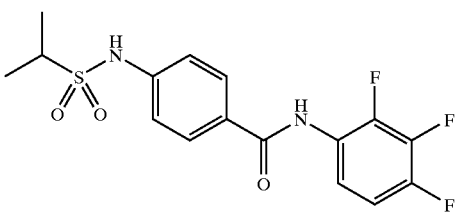 |
| Ih-18 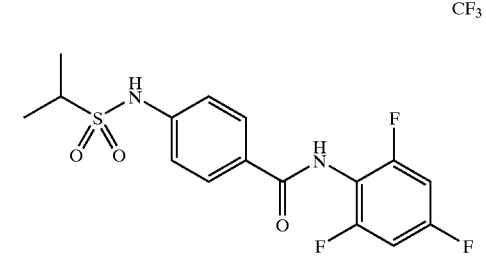 | Ih-25 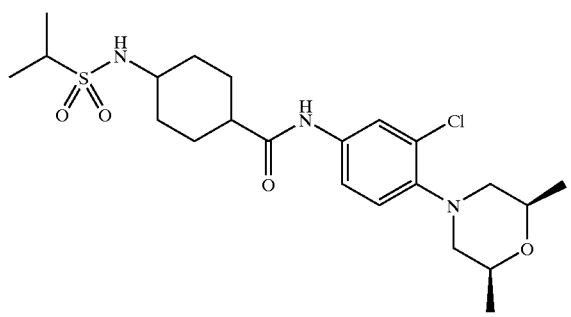 |
| Ih-19 | |

Ih-26
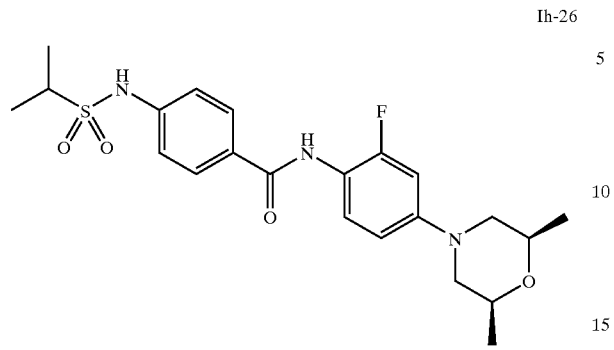
Ih-27
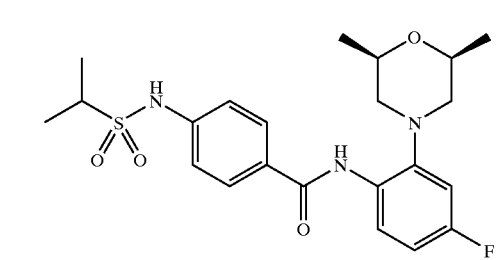
Ih-28
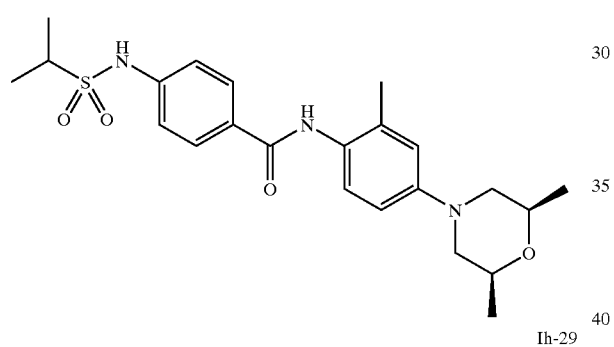
Ih-29
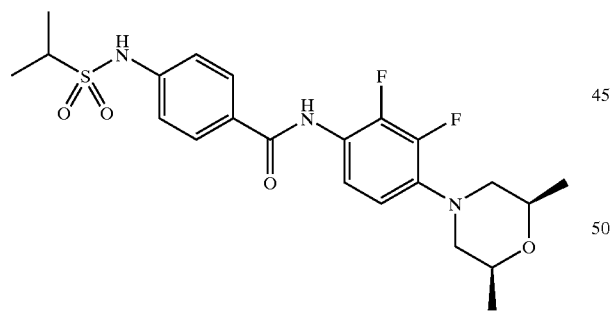
Ih-30
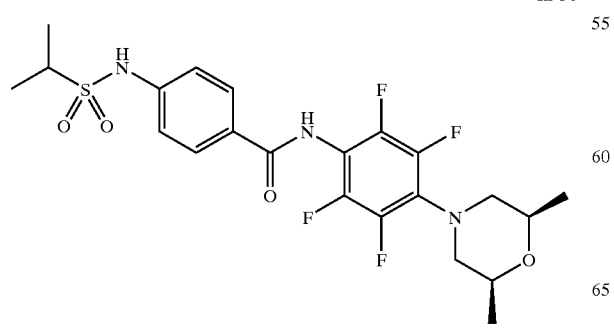
Ih-31
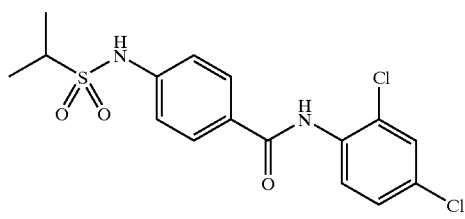
Ih-32
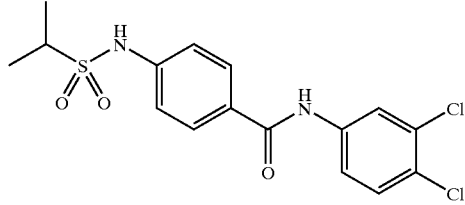
Ih-33
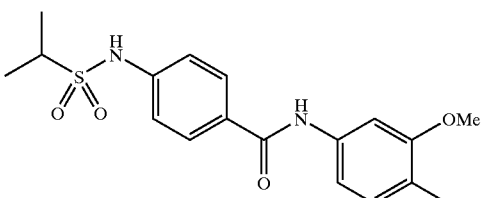
Ih-35
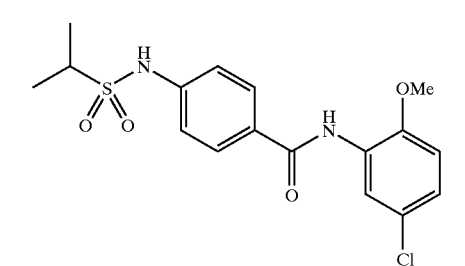
Ih-36
Ih-37
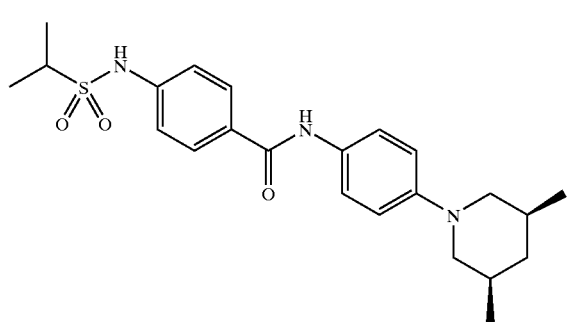

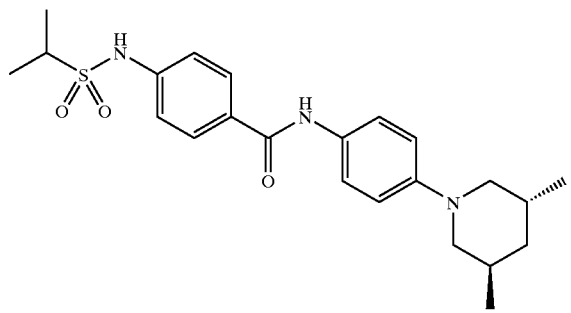
Ih-38
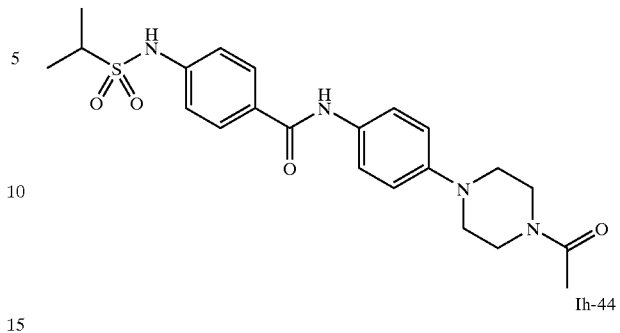
Ih-43
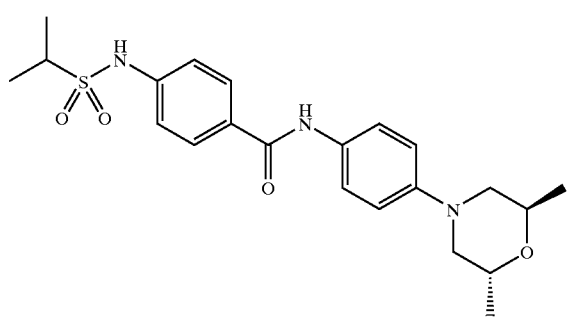
Ih-39
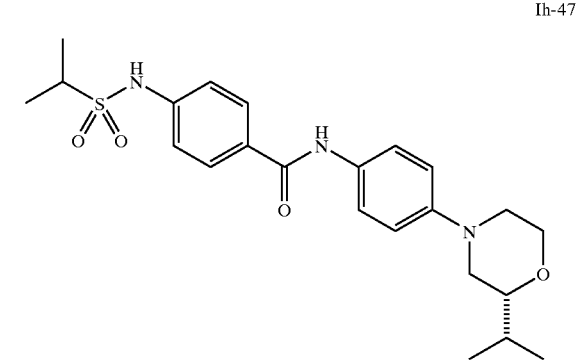
Ih-44
Ih-40
Ih-45
Ih-41
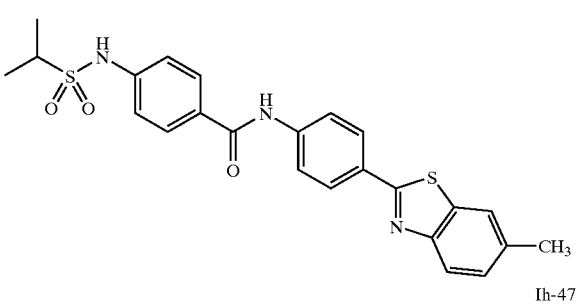
Ih-46
Ih-42
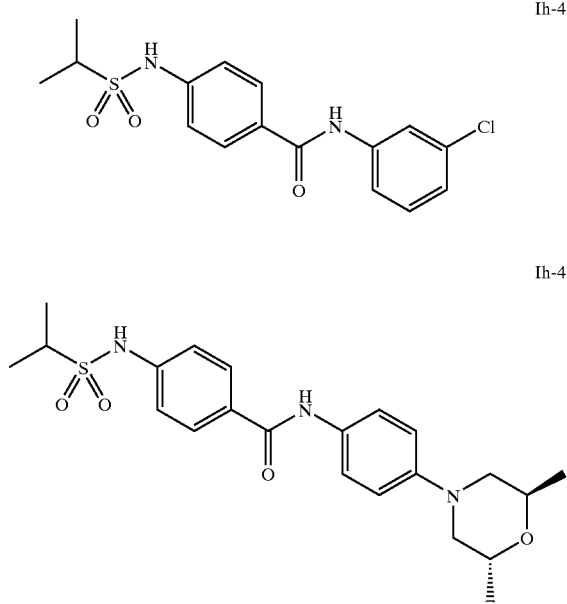
Ih-47

Ih-48
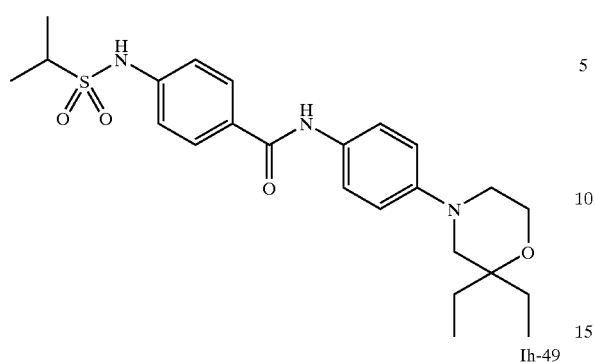
Ih-49
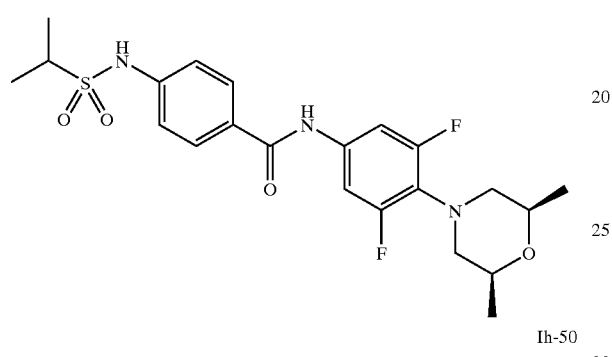
Ih-50
Ih-51
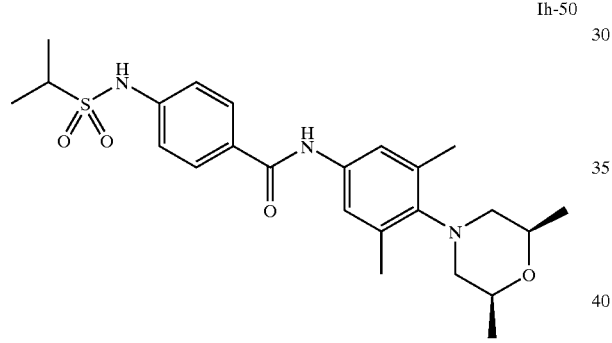
Ih-52
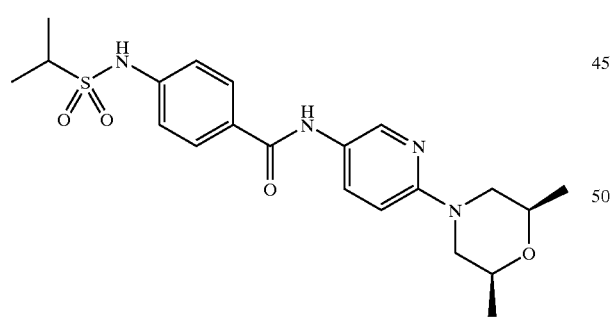
Ih-53
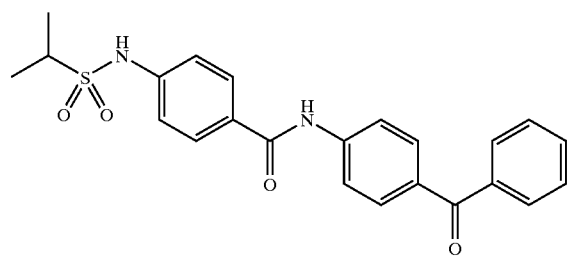
Ih-54
Ih-55
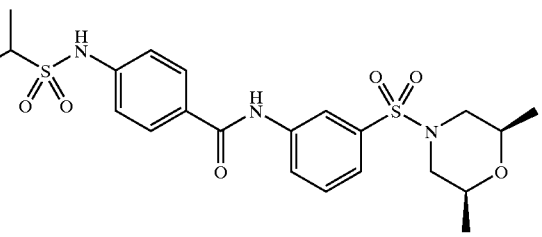
Ih-56
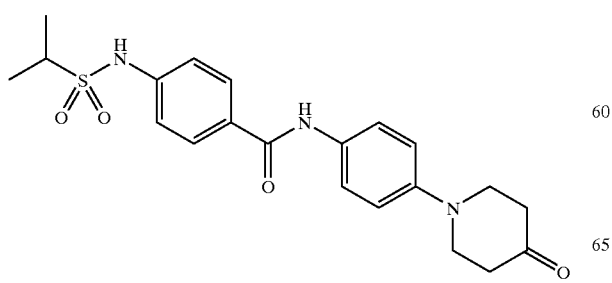
Ih-57
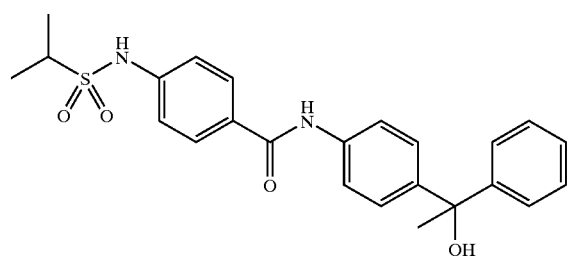

-continued
Ih-58
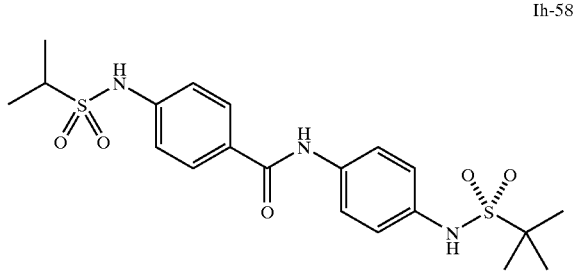
Ih-59
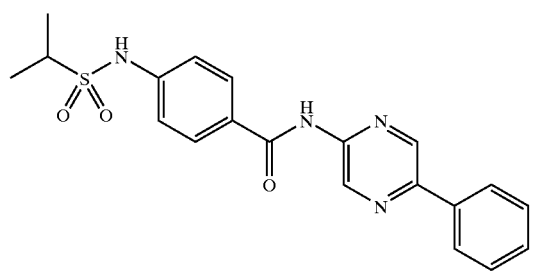
Ih-60
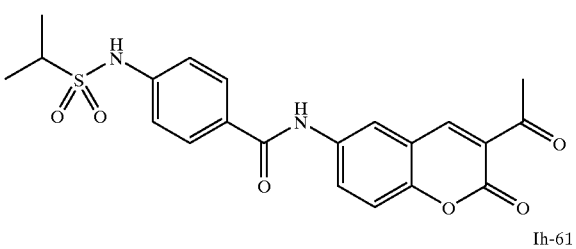
Ih-61
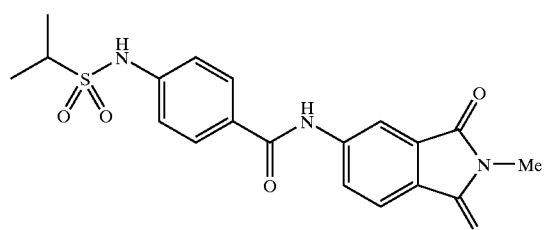
Ih-62
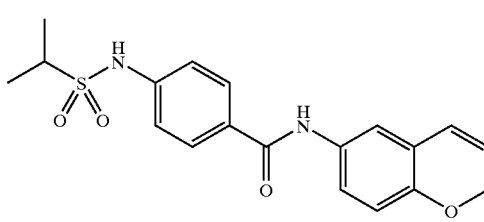
Ih-63
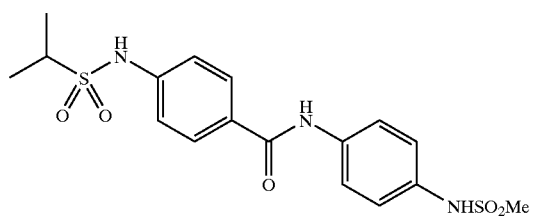
-continued
Ih-64
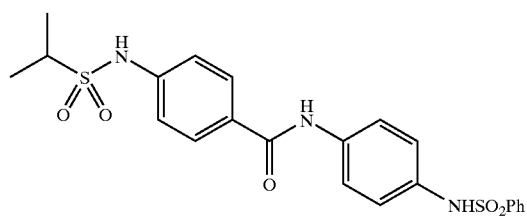
Ih-65
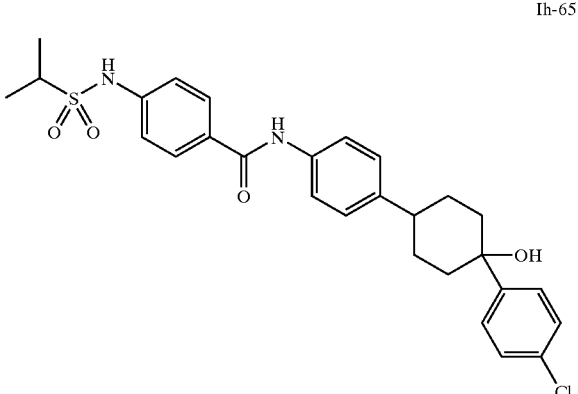
Ih-66
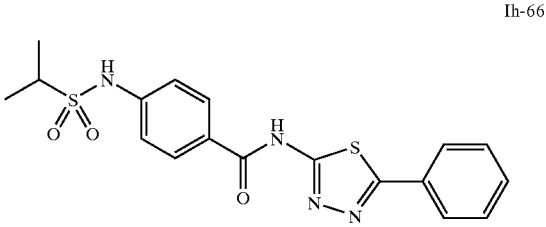
Ih-67
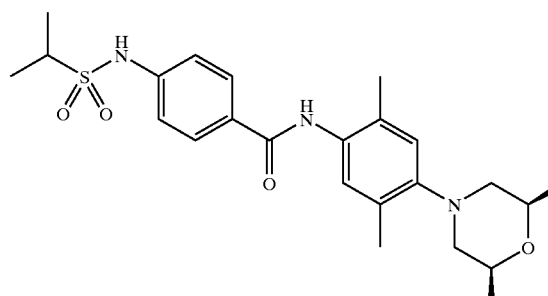
Ih-68
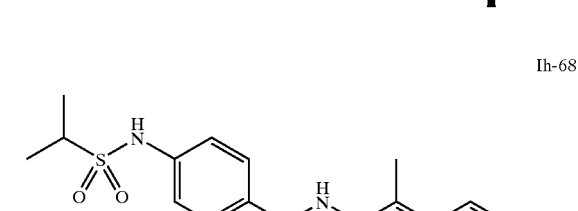

Ih-69
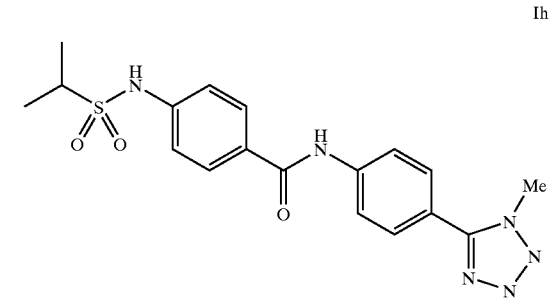
Ih-75
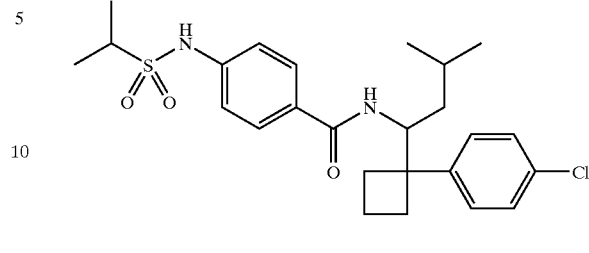
Ih-70
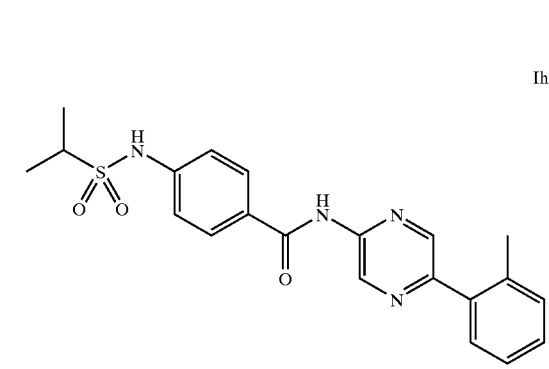
Ih-76
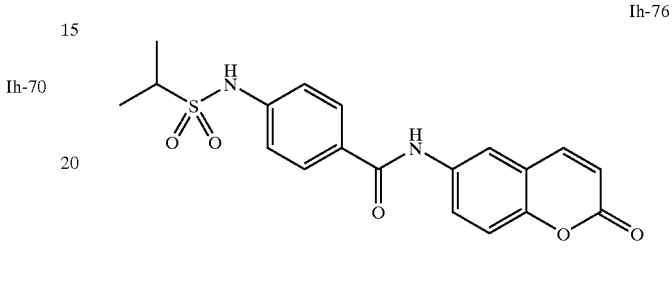
Ih-71
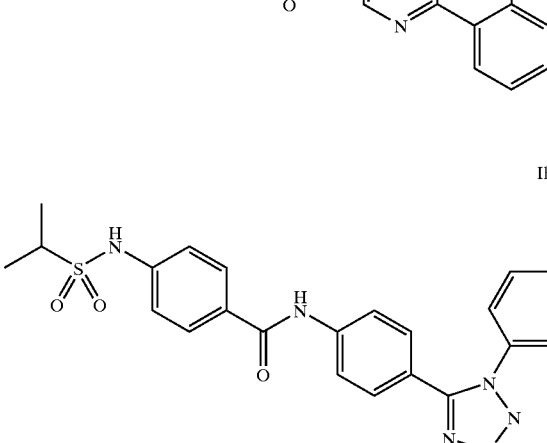
Ih-77
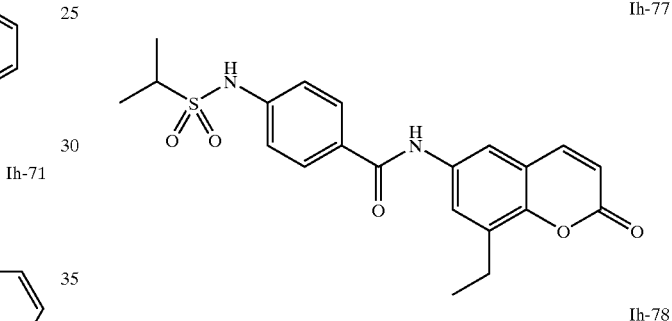
Ih-72
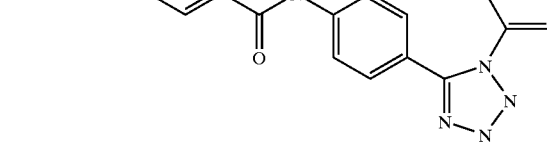
Ih-78
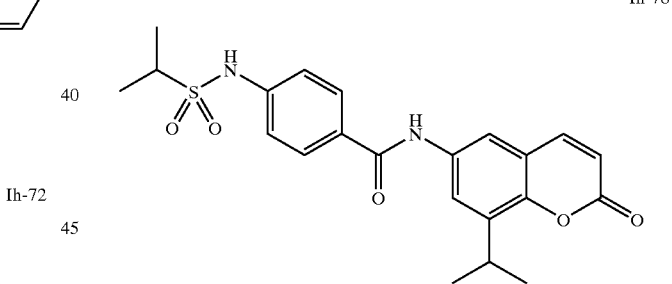
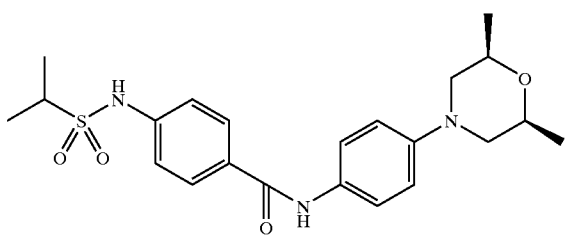
Ih-79
Ih-74
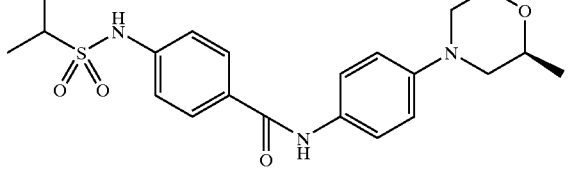
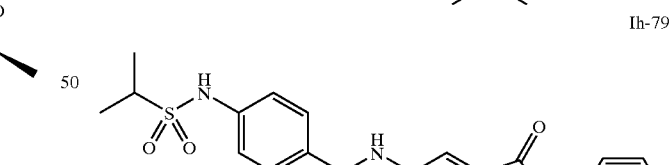
Ih-80
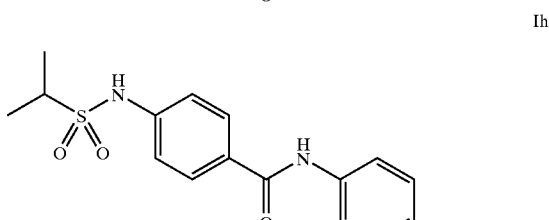
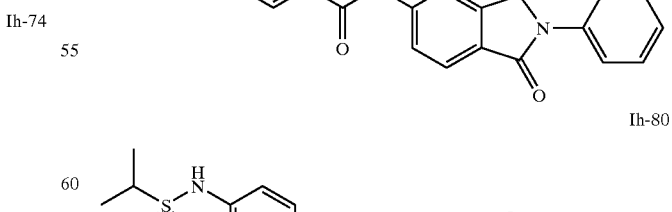

411
-continued
Ih-81
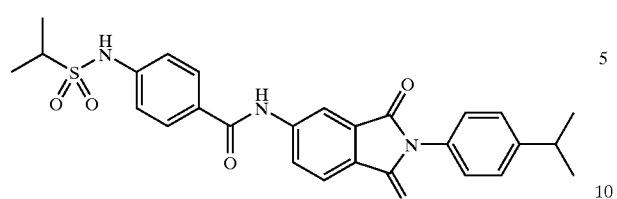
Ih-82
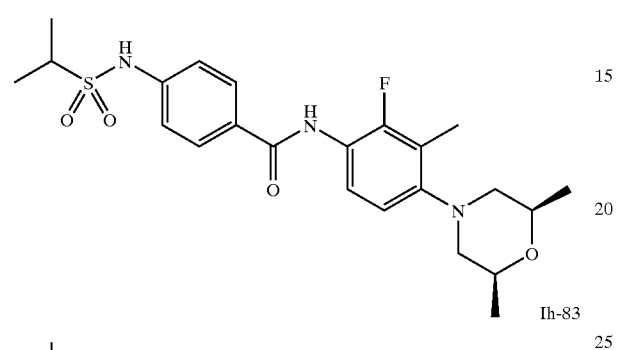
Ih-83
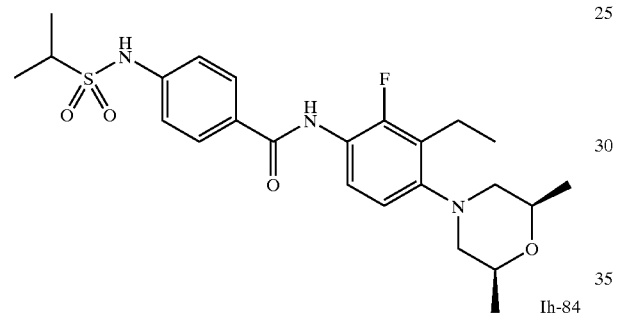
Ih-84
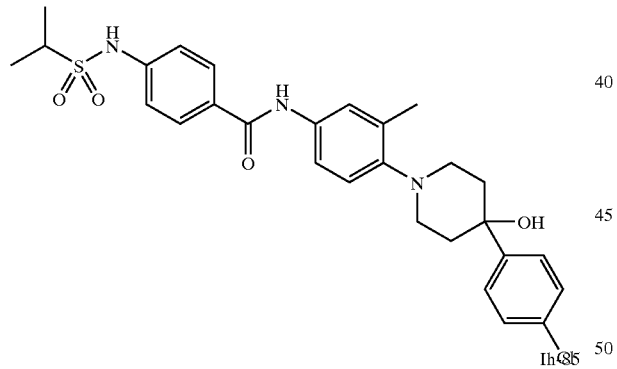
Ih-85
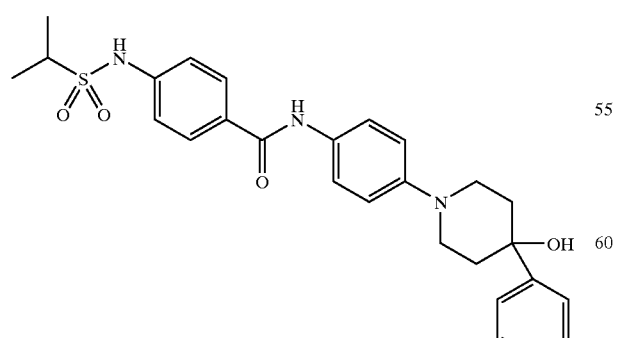
412
-continued
Ih-86
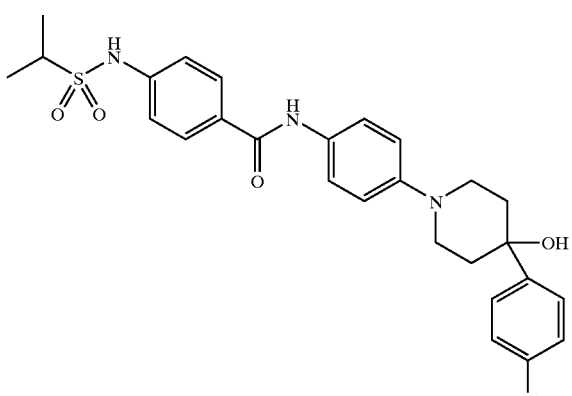
Ih-87
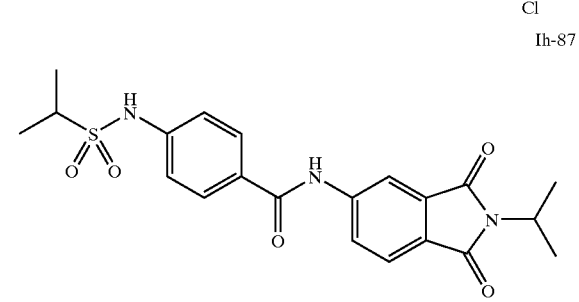
Ih-88
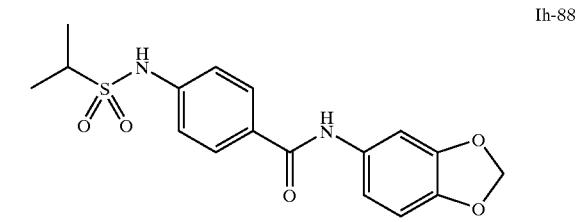
Ih-89
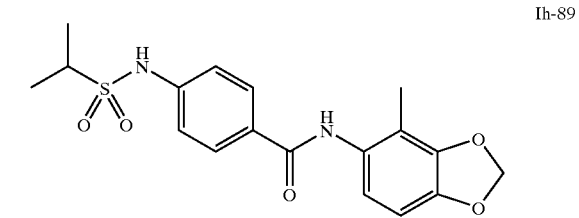
Ih-90
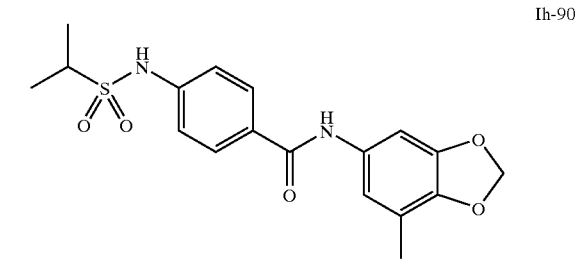
Ih-91
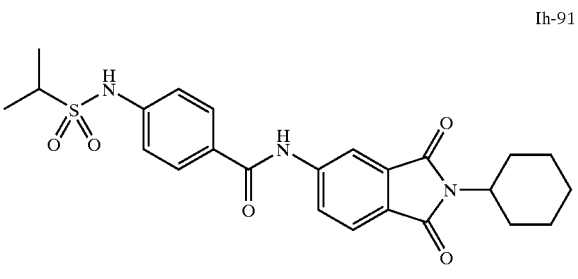

Ih-92
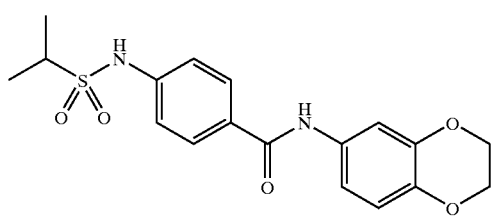
Ih-99
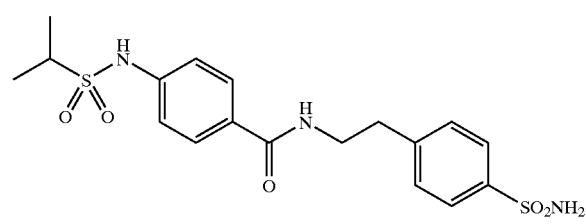
Ih-93
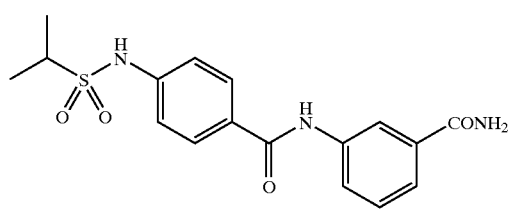
Ih-100
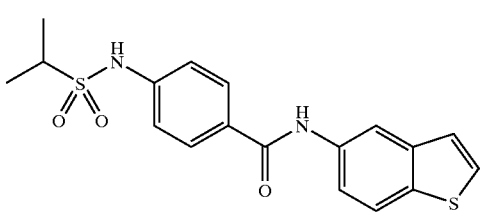
Ih-94
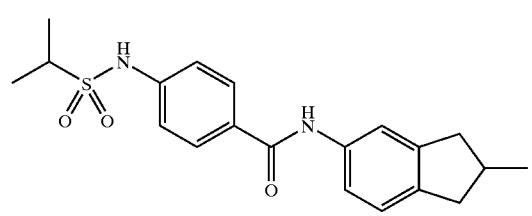
Ih-101
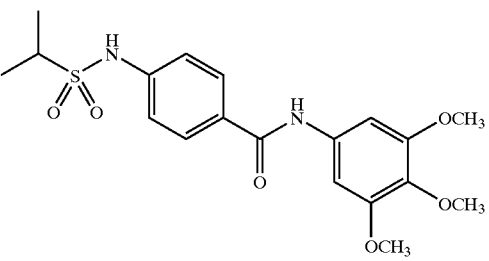
Ih-95
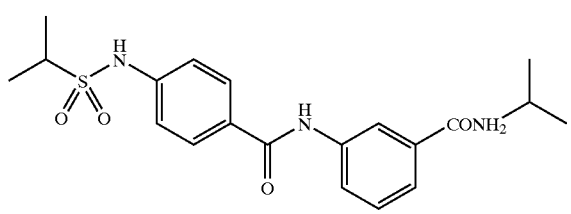
Ih-102
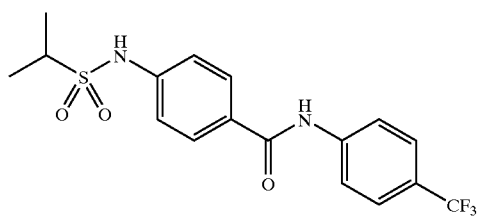
Ih-96
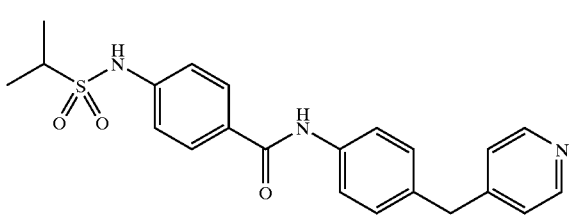
Ih-103
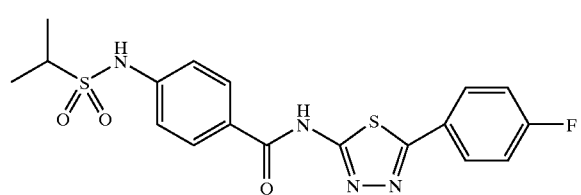
Ih-97
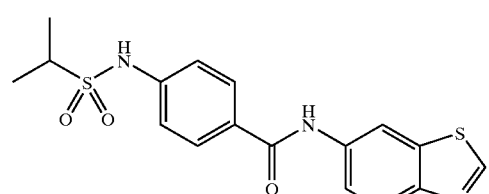
Ih-104
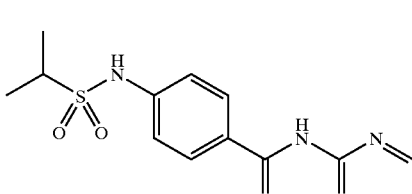
Ih-98
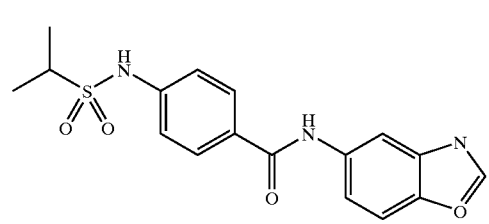
Ih-105
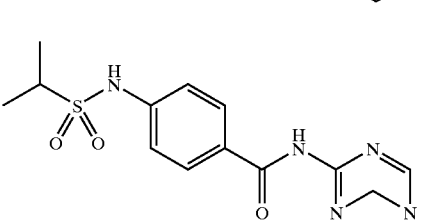

Ih-106
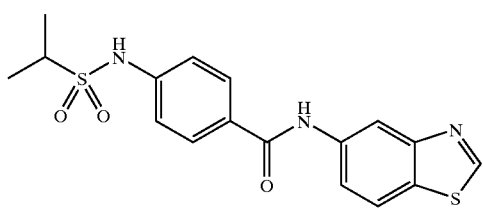
Ih-107
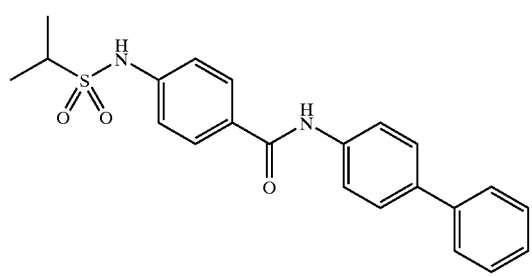
Ih-108
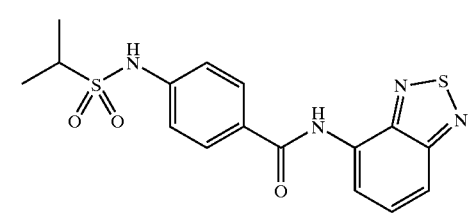
Ih-109
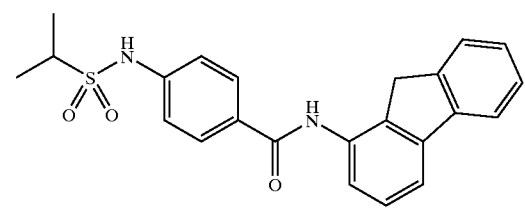
Ih-110
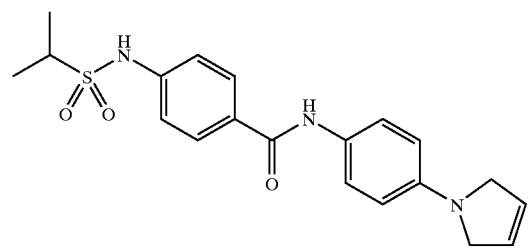
Ih-111
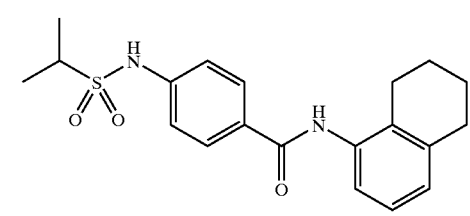
Ih-112
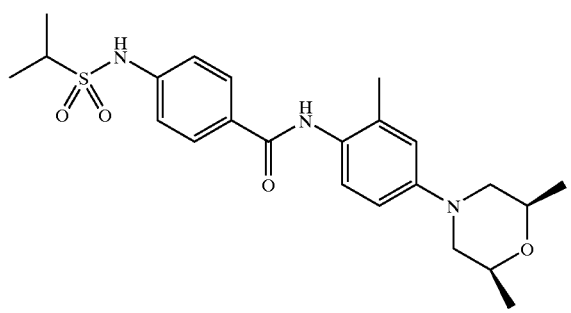
Ih-113
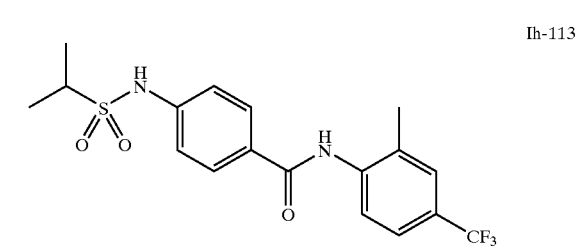
Ih-114
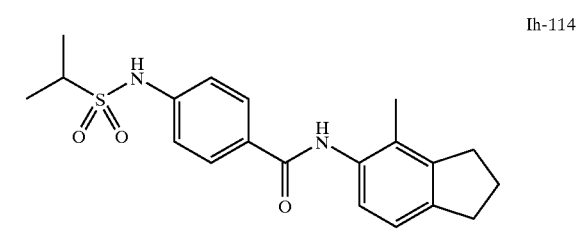
Ih-115
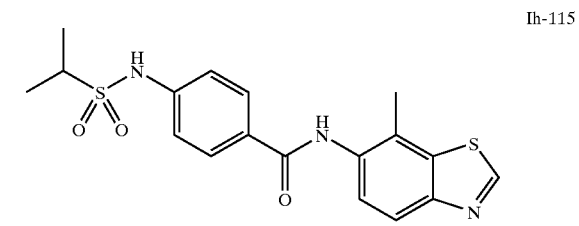
Ih-116
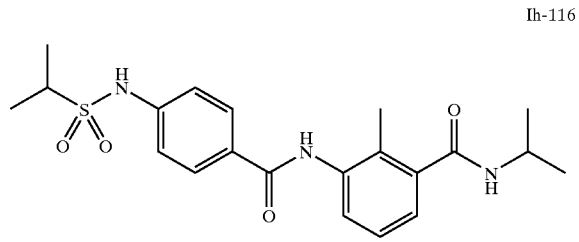
Ih-117
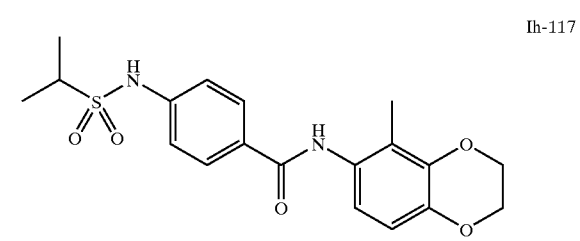

Ih-118
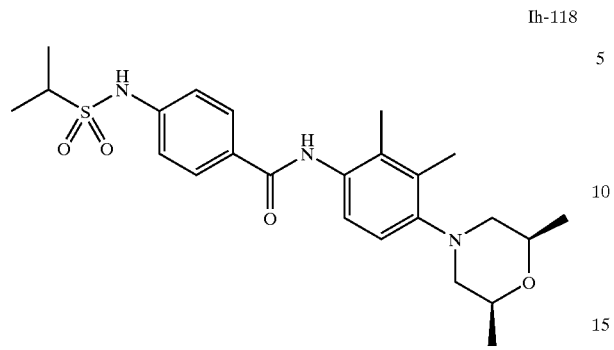
Ih-119
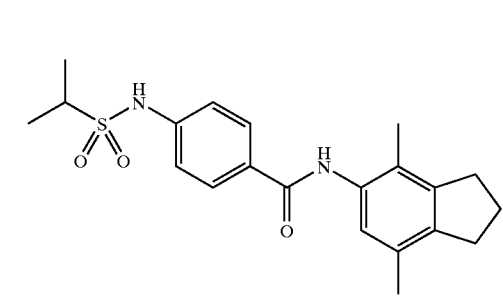
Ih-120
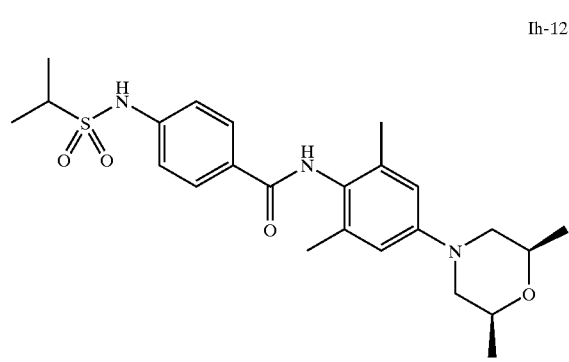
Ih-121
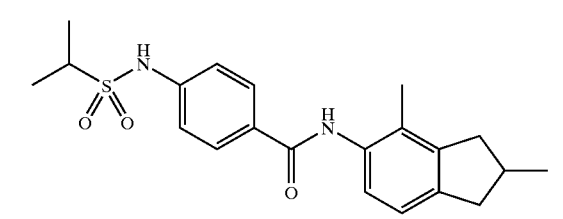
Ih-122
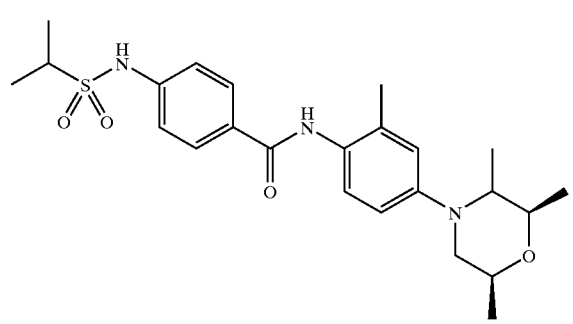
Ih-123
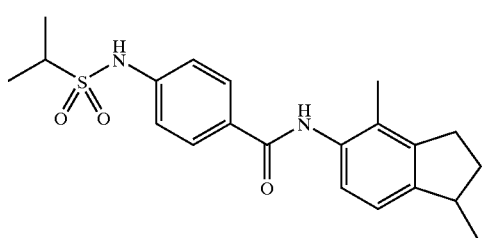
Ih-124
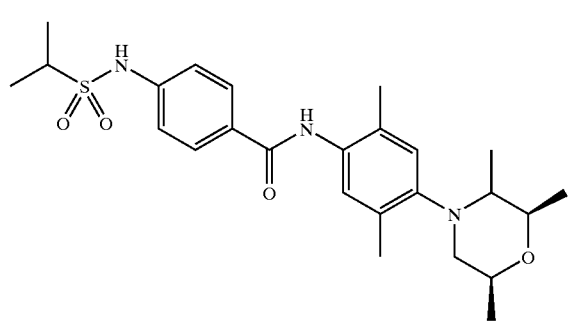
Ih-125
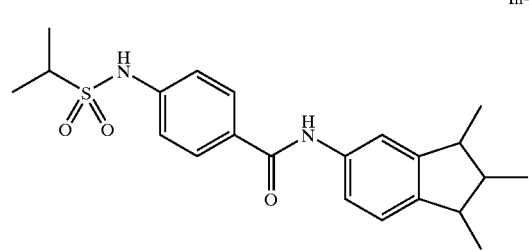
Ih-126
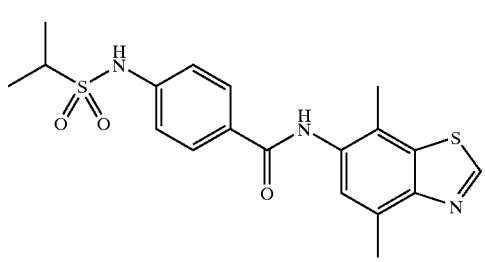
Ih-127
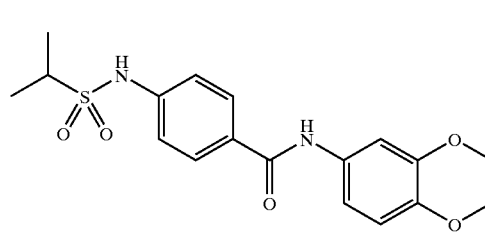
Ih-128
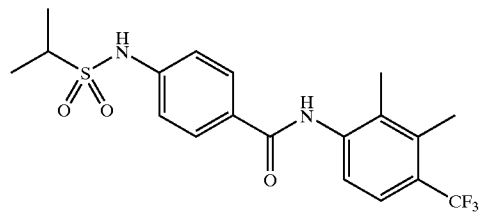

Ih-129 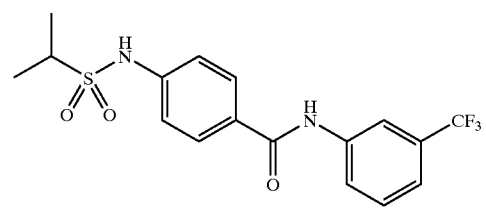
Ih-130 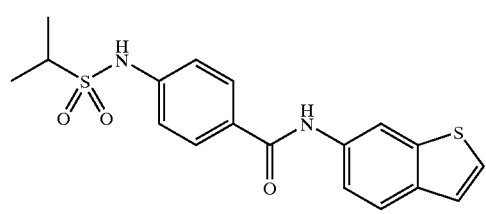
Ih-131 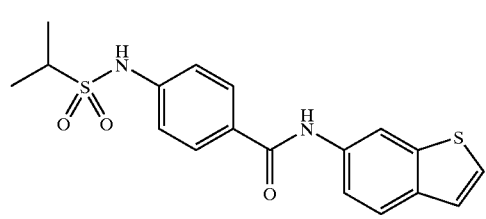
Ih-132 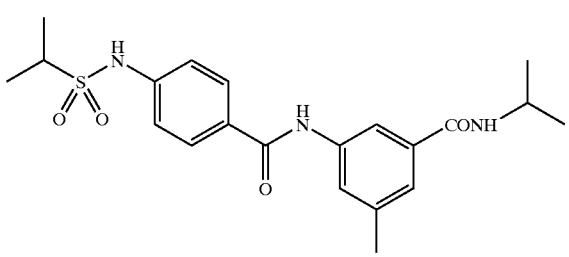
Ih-133 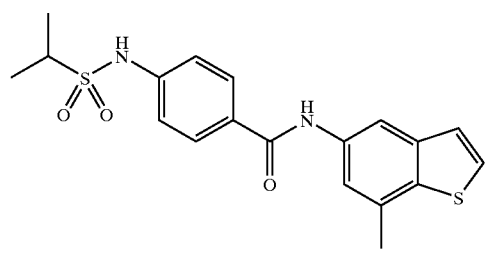
Ih-134 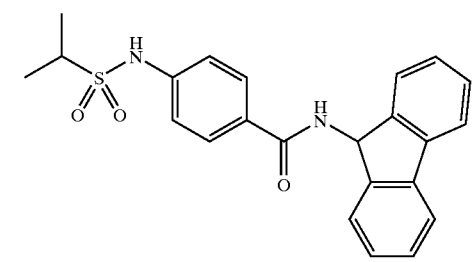
Ih-135 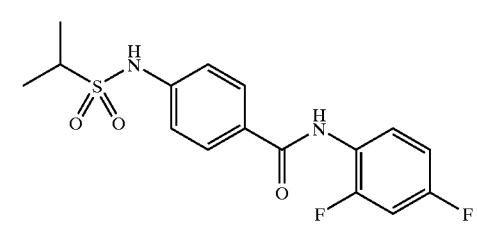
Ih-136 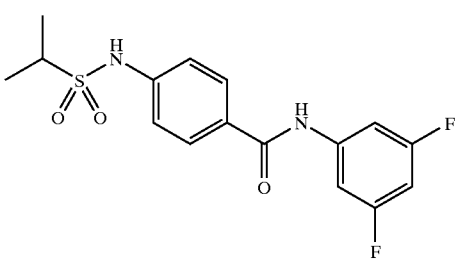
Ih-137 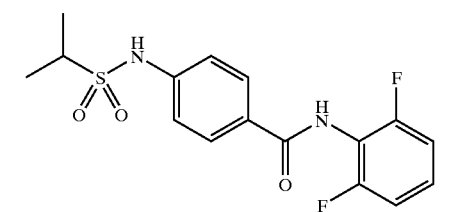
Ih-138 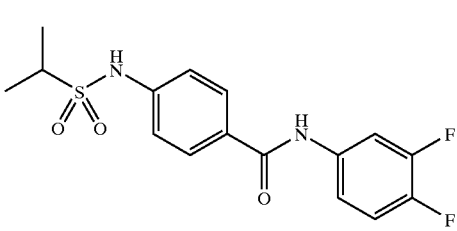
Ih-139 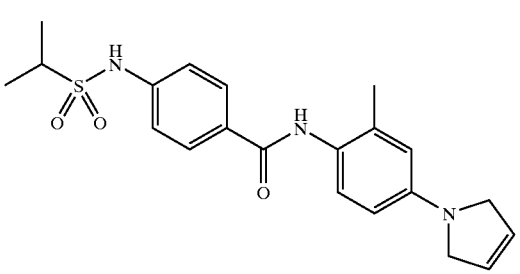
Ih-140 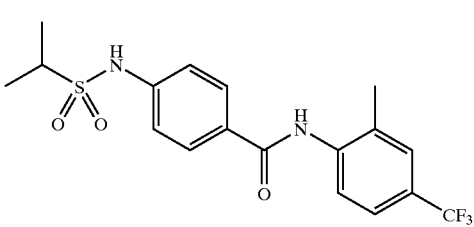
Ih-141 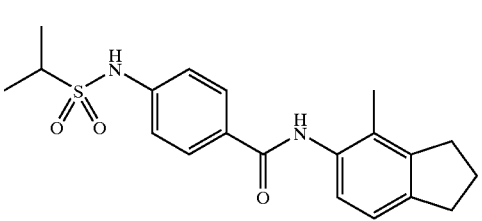

Ih-142
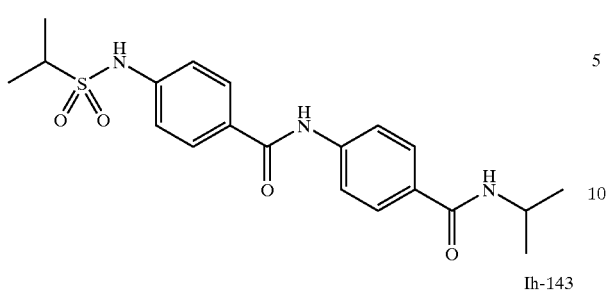
Ih-143
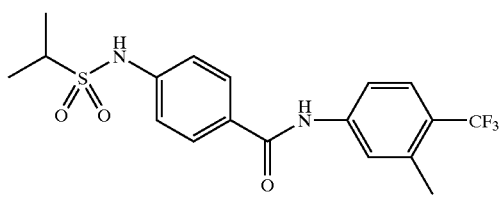
Ih-144
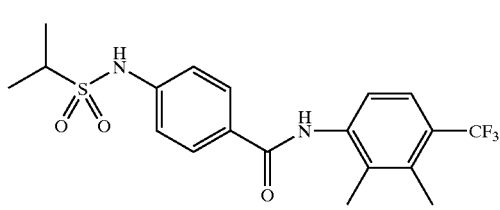
Ih-145
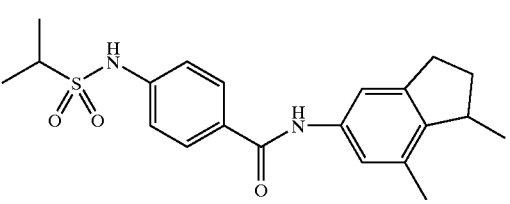
Ih-146
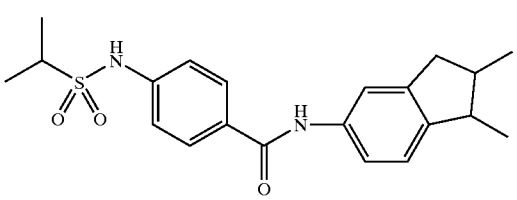
Ih-147
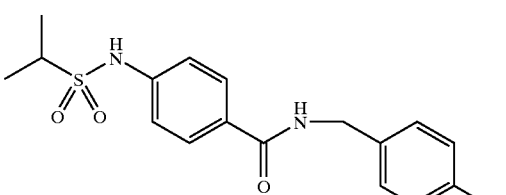
Ih-148
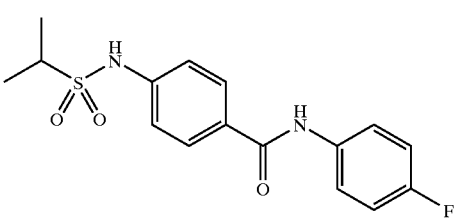
Ih-149
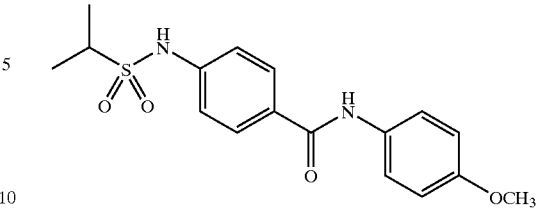
Ih-150
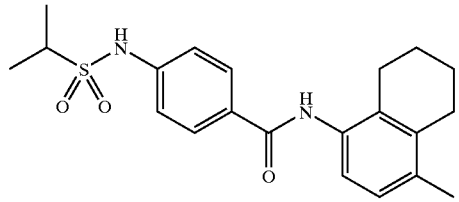
Ih-151
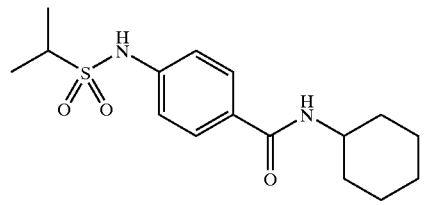
Ih-152
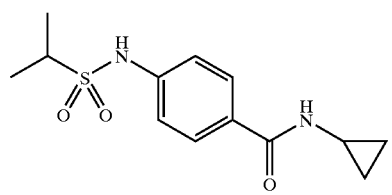
Ih-153
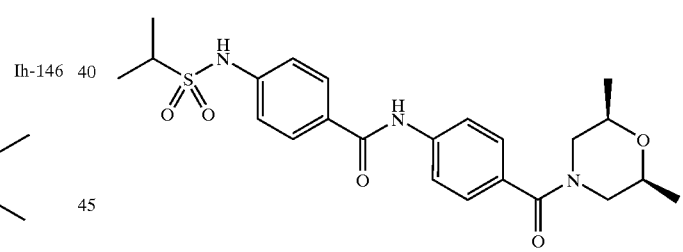
Ih-154
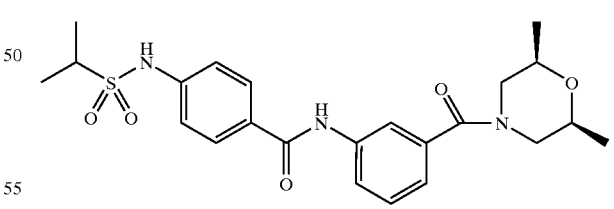
Ih-155
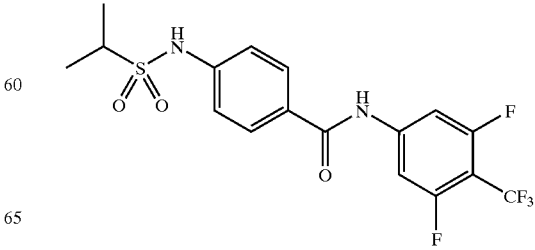

Ih-156
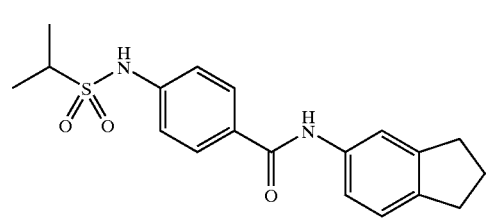
Ih-157
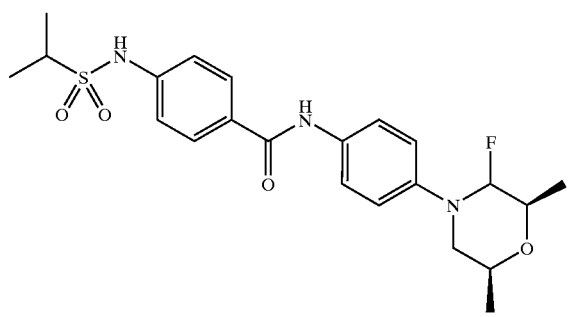
Ih-158
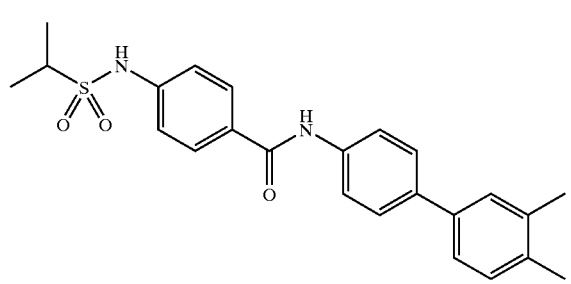
Ih-159
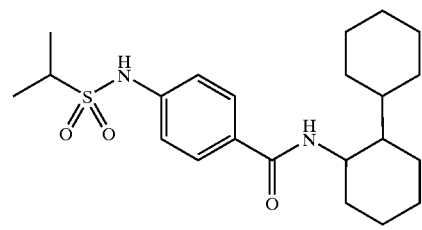
Ih-160
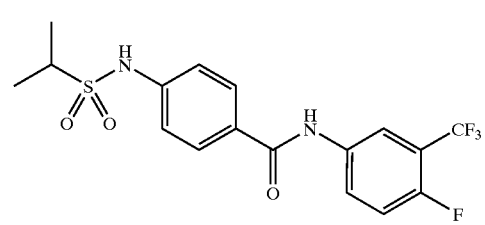
Ih-161
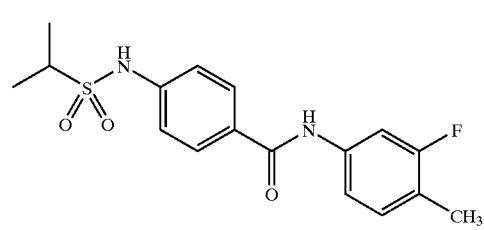
Ih-162
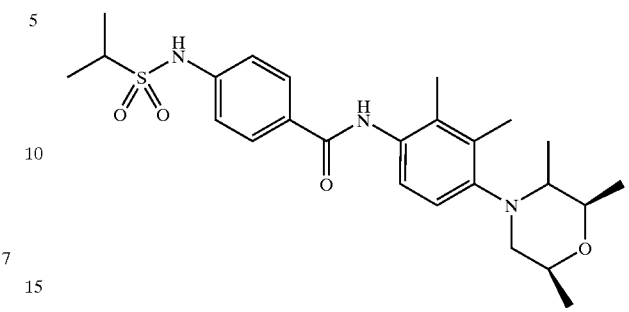
Ih-163
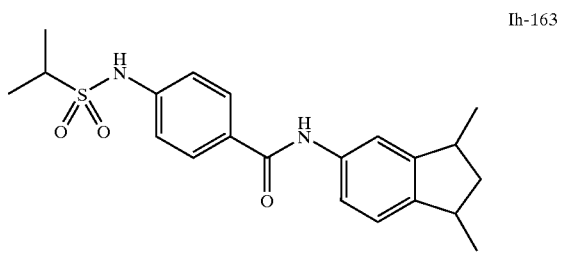
Ih-164
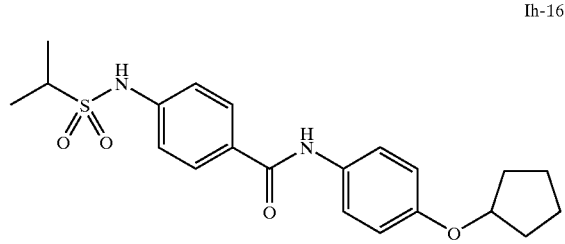
Ih-165
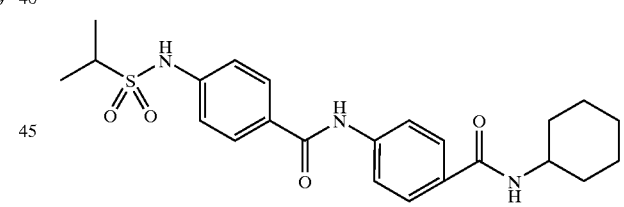
Ih-166
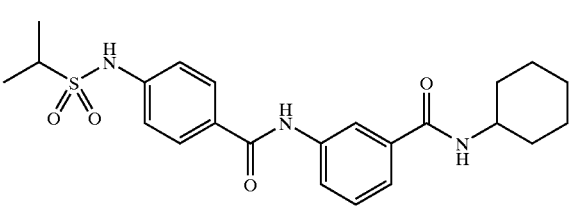
Ih-167
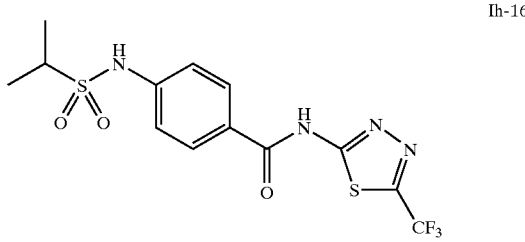

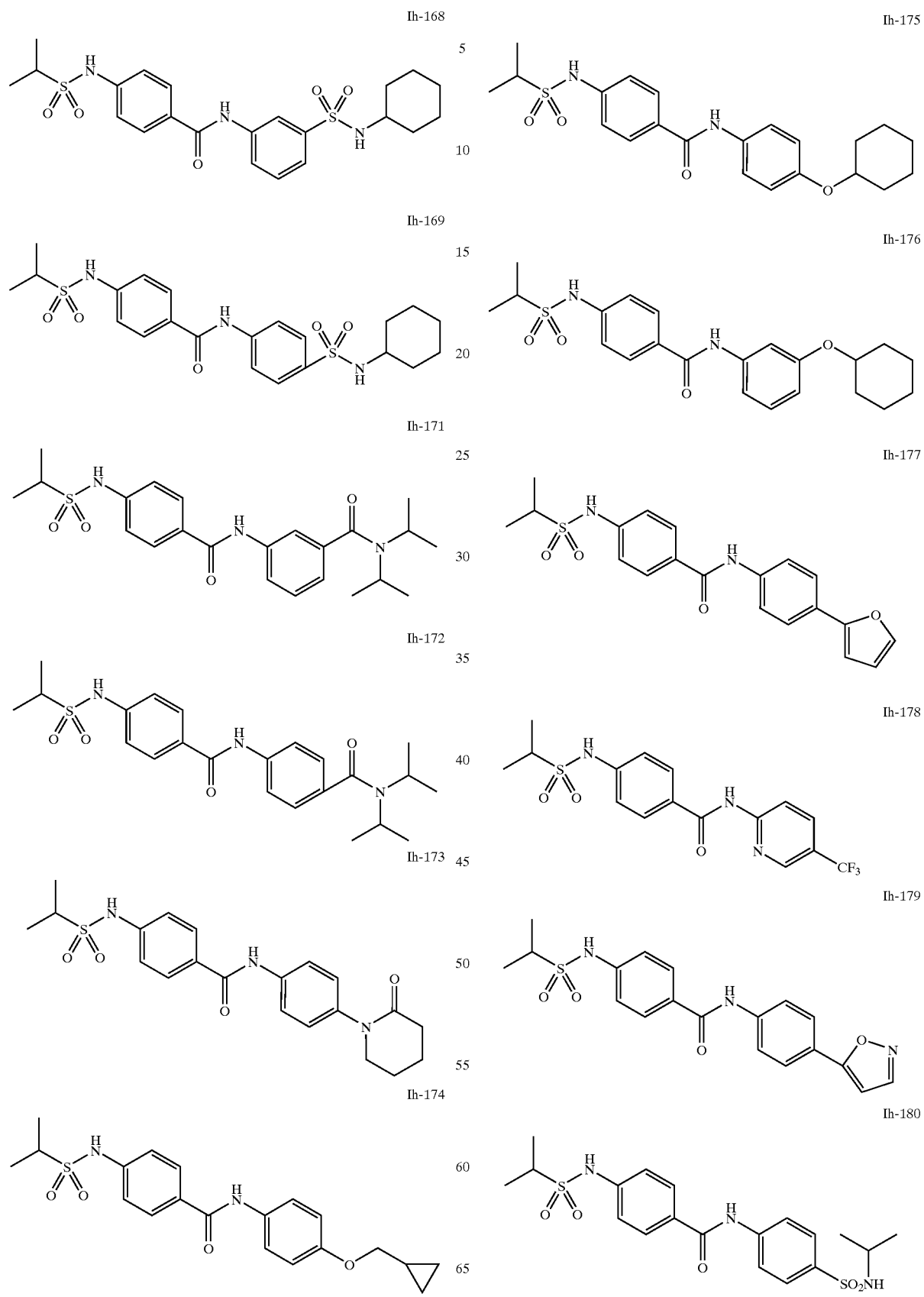

Ih-181
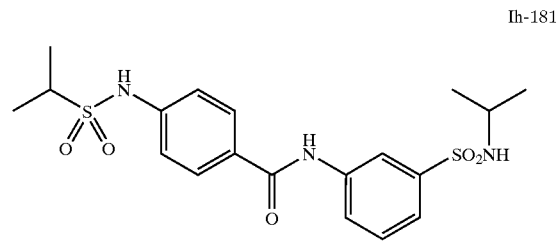
Ih-182
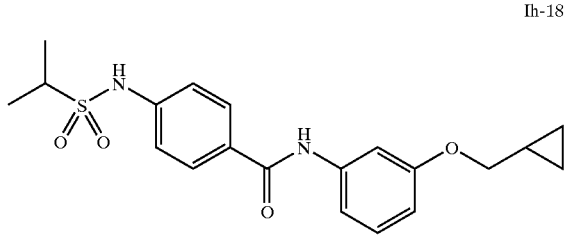
Ih-183
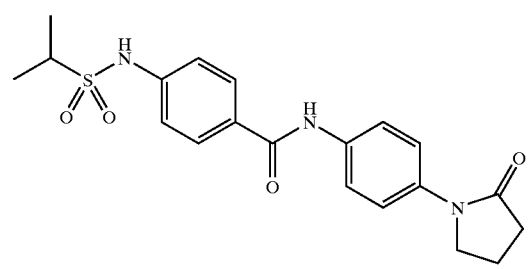
Ih-184
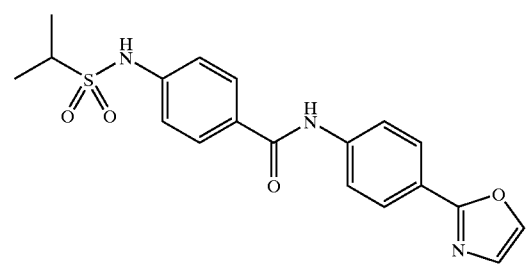
Ih-185
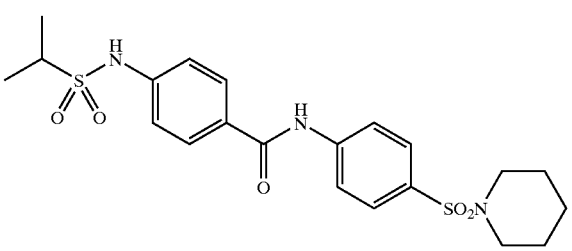
Ih-186
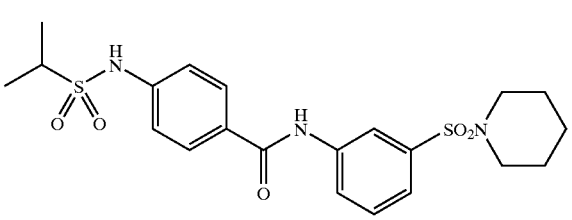
Ih-187
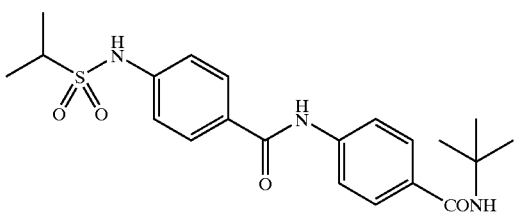
Ih-188
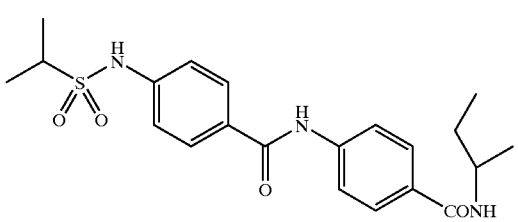
Ih-189
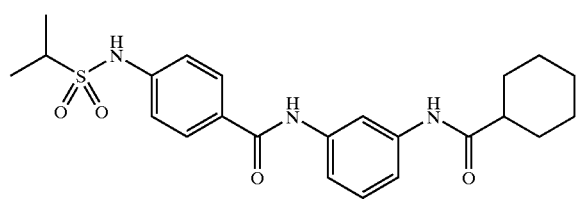
Ih-190
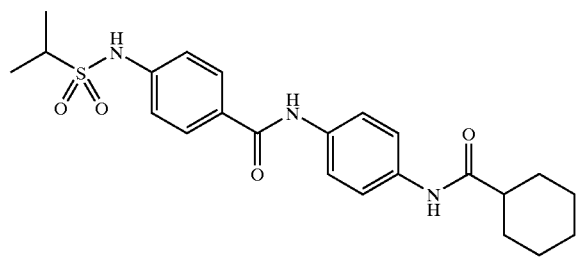
Ih-191
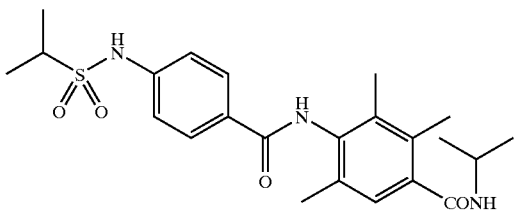
Ih-192
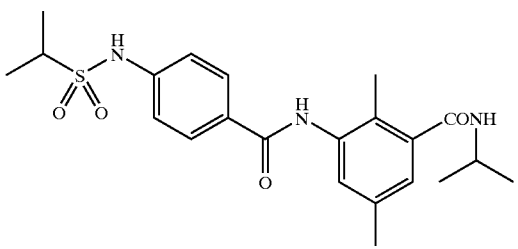

Ih-193
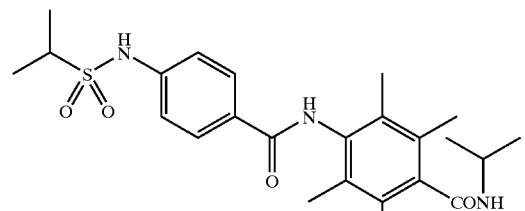
Ih-194
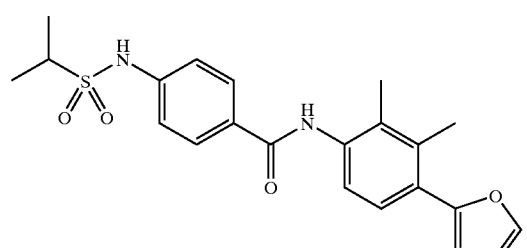
Ih-195
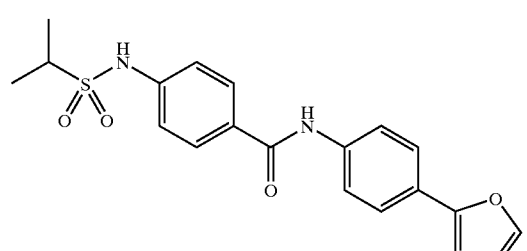
Ih-196
Ih-197
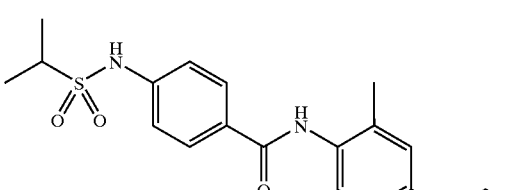
Ih-198
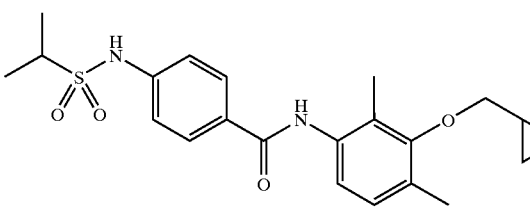
Ih-199
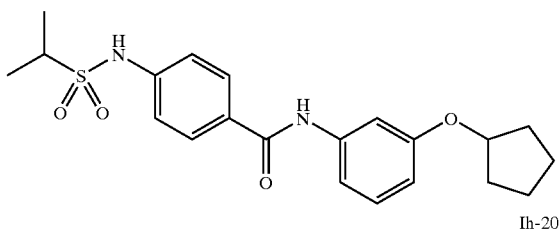
Ih-200
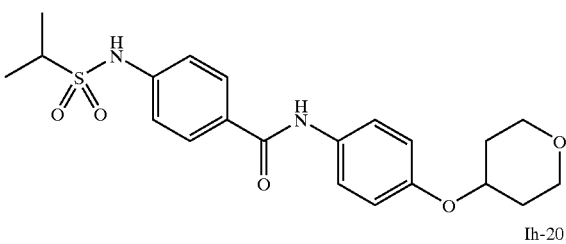
Ih-201
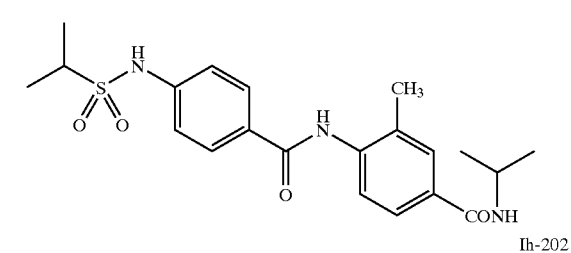
Ih-202
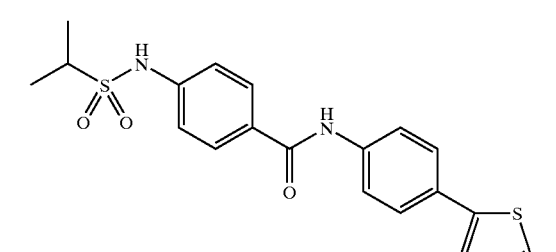
Ih-203
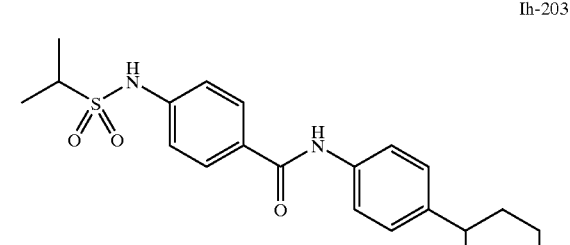
Ih-204
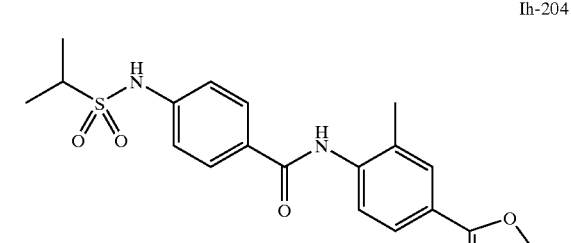

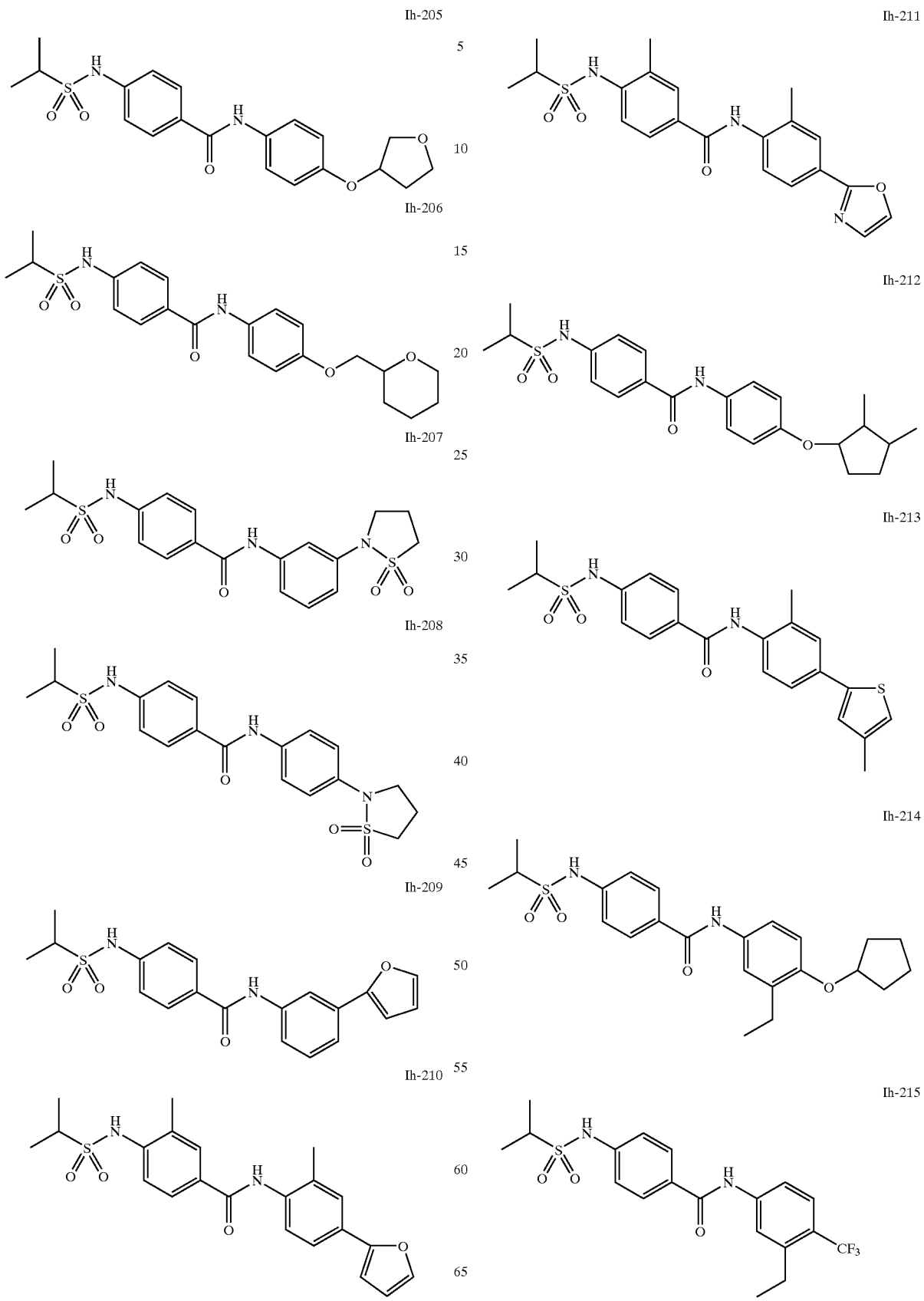

Ih-216
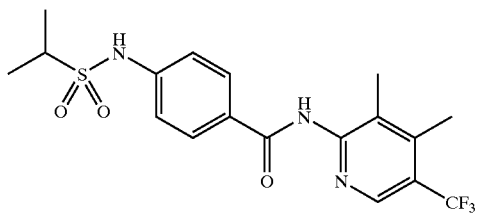

Ih-219
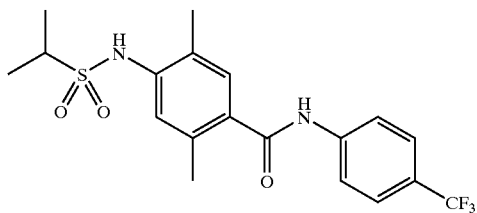

Ih-220
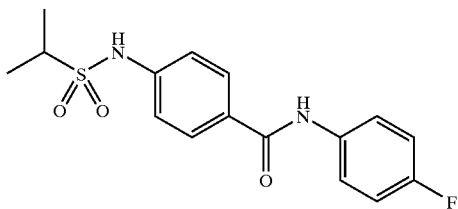

Ih-221
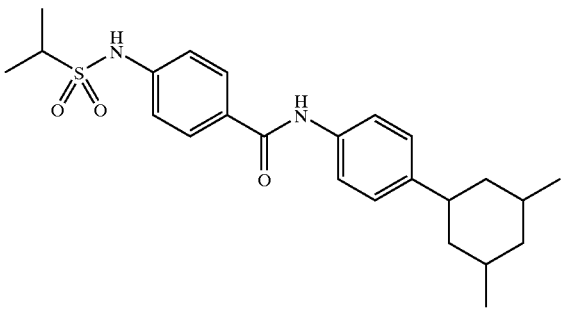

Ih-222
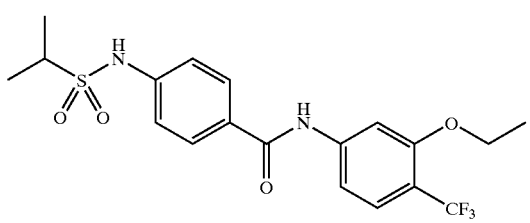

Ih-223
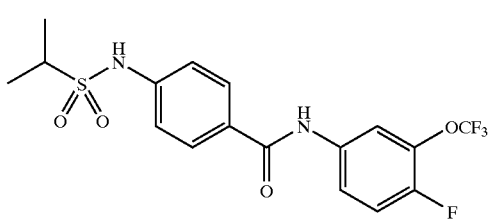

Ih-224
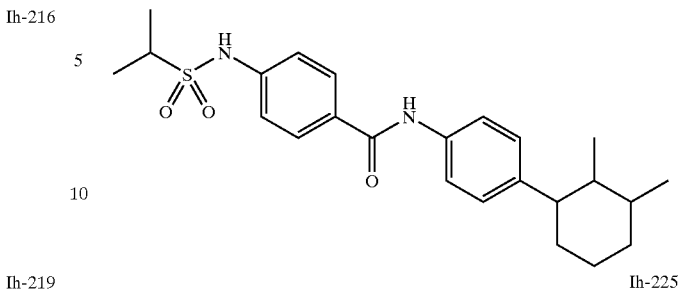

Ih-225
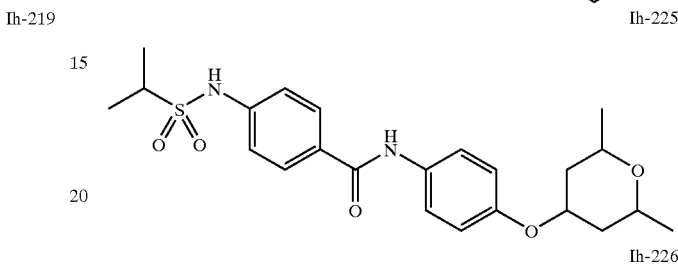

Ih-226
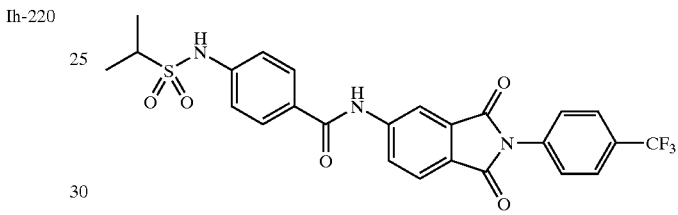

I-2

$^1$H-NMR (CDCl$_3$) δ ppm: 0.94 (t, 3H, J=7.5 Hz), 1.34–1.44 (m, 2H), 1.40 (d, 6H, J=6.6 Hz), 1.59–1.68 (m, 2H), 2.69 (t, 2H, J=7.8 Hz), 3.24–3.35 (m, 1H), 6.49 (s, 1H), 7.23–7.32 (m, 4H), 7.6 (d, 2H, J=8.7 Hz), 7.79 (d, 2H, J=8.1 Hz), 7.85 (s, 1H).

I-3

$^1$H-NMR (CDCl$_3$) δ ppm: 0.92 (t, 3H, J=7.2 Hz), 1.30–1.39 (m, 2H), 1.37 (d, 6H, J=6.9 Hz), 1.57 (quint, 2H, J=7.5 Hz), 1.96 (quint, 2H, J=6.6 Hz), 2.49 (t, 2H, J=6.6 Hz), 2.57 (t, 2H, J=7.8 Hz), 3.16–3.26 (m, 3H), 4.62 (brs, 1H), 7.12 (d, 2H, J=8.1 Hz), 7.43 (d, 2H, J=8.4 Hz), 7.64 (s, 1H).

I-4

$^1$H-NMR (CD$_3$OD) δ ppm: 0.92 (t, 3H, J=6.9 Hz), 1.28–1.41 (m, 2H), 1.46 (d, 6H), J=6.3 Hz), 1.53–1.63 (m, 2H), 2.58 (t, 2H), J=7.8 Hz), 3.33–3.43 (m, 1H), 6.27–6.29 (m, 1H), 7.14–7.16 (m, 3H), 7.50 (d, 2H, J=8.4 Hz), 7.90 (s, 1H).

I-5

$^1$H-NMR (CDCl$_3$) δ ppm: 0.92 (t, 3H, J=7.2 Hz), 1.28–1.41 (m, 2H), 1.46 (d, 6H, J=6.9 Hz), 1.53–1.63 (m, 2H), 2.59 (t, 2H, J=7.8 Hz), 3.35–3.44 (m, 1H), 7.15 (d, 2H, J=8.7 Hz), 7.38 (s, 1H), 7.45 (d, 2H, J=8.7 Hz), 7.57 (s, 1H).

I-6

$^1$H-NMR (CDCl$_3$) δ ppm: 0.91 (t, 3H, J=7.5 Hz), 1.29–1.39 (m, 2H), 1.37 (d, 6H, J=6.9 Hz), 1.55 (quint, 2H, J=7.5 Hz), 2.55 (t, 2H, J=5.1 Hz), 3.18–3.27 (m, 1H), 3.92 (d, 2H, J=6.0 Hz), 5.51 (t, 1H, J=5.7 Hz), 7.10 (d, 2H, J=8.4 Hz), 7.39 (d, 2H, J=8.4 Hz), 8.23 (s, 1H).

I-7

¹H-NMR (CDCl₃) δ ppm: 0.91 (t, 3H, J=7.2 Hz), 1.28–1.38 (m, 2H), 1.37 (d, 6H, J=6.9 Hz), 1.51–1.67 (m, 4H), 1.78–1.88 (m, 2H), 2.39 (t, 2H, J=7.2 Hz), 2.57 (t, 2H, J=7.5 Hz), 3.12–3.22 (m, 3H), 4.30–4.37 (m, 1H), 7.12 (d, 2H, J=8.4 Hz), 7.36–7.42 (m, 3H).

I-8

¹H-NMR (CDCl₃) δ ppm: 0.91 (t, 3H, J=7.5 Hz), 1.21–1.47 (m, 4H), 1.35 (d, 6H, J=6.6 Hz), 1.51–1.63 (m, 4H), 1.67–1.77 (m, 2H), 2.34 (t, 2H, J=7.5 Hz), 2.55 (t, 2H, J=7.8 Hz), 3.08–3.17 (m, 3H), 4.71 (t, 1H, J=6.0 Hz), 7.09 (d, 2H, J=8.1 Hz), 7.43 (d, 2H, J=8.4 Hz), 7.74 (s, 1H).

I-9

¹H-NMR (CDCl₃) δ ppm: 0.91 (t, 3H, J=7.2 Hz), 1.29–1.39 (m, 2H), 1.35 (d, 6H, J=6.9 Hz), 1.50–1.60 (m, 2H), 2.54 (t, 2H, J=7.8 Hz), 2.64 (t, 2H, J=5.7 Hz), 3.14–3.23 (m, 1H), 3.41–3.47 (m, 2H), 5.29 (t, 1H, J=6.3 Hz), 7.10 (d, 2H, J=8.4 Hz), 7.39 (d, 2H, J=8.4 Hz), 7.91 (s, 1H).

I-10

¹H-NMR (CDCl₃) δ ppm: 0.91 (t, 3H, J=7.5 Hz), 1.22 (s, 9H), 1.30–1.37 (m, 2H), 1.51–1.68 (m, 4H), 1.76–1.86 (m, 2H), 2.31–2.40 (m, 2H), 2.56 (t, 2H, J=7.5 Hz), 3.15–3.26 (m, 3H), 7.11 (t, 2H, J=8.7 Hz), 7.42 (d, 2H, J=8.1 Hz), 7.54 (s, 1H).

I-11 mp: 128–129° C. ¹H-NMR (CDCl₃) δ ppm: 0.91 (t, 3H, J=7.5 Hz), 1.29–1.39 (m, 2H), 1.39 (s, 9H), 1.51–1.68 (m, 4H), 1.76–1.84 (m, 2H), 2.37 (t, 2H, J=7.5 Hz), 2.56 (t, 2H, J=7.8 Hz), 3.19–3.26 (m, 2H), 4.20 (t, 1H, J=5.7 Hz), 7.11 (d, 2H, J=8.1 Hz), 7.42 (d, 2H, J=8.7 Hz), 7.46 (s, 1H).

I-12

¹H-NMR (CDCl₃) δ ppm: 0.91 (t, 3H, J=7.5 Hz), 1.28–1.37 (m, 2H), 1.47–1.68 (m, 6H), 2.23 (t, 2H, J=7.2 Hz), 2.56 (t, 2H, J=7.5 Hz), 2.90–2.97 (m, 2H), 5.10 (brs, 1H), 7.11 (d, 2H, J=8.4 Hz), 7.36 (d, 2H, J=8.1 Hz), 7.50–7.68 (m, 3H), 7.93 (d, 1H, J=8.1 Hz), 8.06 (d, 1H, J=8.4 Hz), 8.24 (d, 1H, J=7.5 Hz), 8.66 (d, 1H, J=8.7 Hz).

I-13

¹H-NMR (CDCl₃) δ ppm: 0.91 (t, 3H, J=7.5 Hz), 1.28–1.40 (m, 2H), 1.45–1.73 (m, 6H), 2.23 (t, 2H, J=7.5 Hz), 2.56 (t, 2H, J=7.8 Hz), 2.88 (s, 6H), 2.88–2.95 (m, 2H), 5.04 (brs, 1H), 7.10 (d, 2H, J=8.1 Hz), 7.17 (d, 1H, J=7.2 Hz), 7.37 (d, 2H, J=8.4 Hz), 7.48–7.54 (m, 2H), 8.23 (d, 1H, J=7.2 Hz), 8.30 (d, 1H, J=8.7 Hz), 8.53 (d, 1H, J=8.4 Hz).

I-14

¹H-NMR (CDCl₃) δ ppm: 0.91 (t, 3H, J=7.2 Hz), 1.30–1.43 (m, 6H), 1.36 (d, 6H, J=6.6 Hz), 1.51–1.62 (m, 4H), 1.67–1.78 (m, 2H), 2.34 (t, 2H, J=7.5 Hz), 2.56 (t, 2H, J=7.8 Hz), 3.09–3.20 (m, 3H), 4.34 (brs, 1H), 7.10 (d, 2H, J=8.4 Hz), 7.41–7.44 (m, 3H).

I-15

¹H-NMR (CDCl₃) δ ppm: 0.91 (t, 3H, J=7.5 Hz), 1.23 (s, 9H), 1.27–1.80 (m, 12H), 2.30–2.38 (m, 2H), 2.56 (t, 2H, J=7.5 Hz), 3.15 (brs, 2H), 7.11 (d, 2H, J=7.8 Hz), 7.43 (d, 2H, J=7.8 Hz), 7.59 (s, 1H).

I-16

¹H-NMR (CDCl₃) δ ppm: 0.91 (t, 3H, J=7.5 Hz), 1.29–1.44 (m, 6H), 1.39 (s, 9H), 1.51–1.61 (m, 4H), 1.68–1.78 (m, 2H), 2.35 (t, 2H, J=7.5 Hz), 2.56 (t, 2H, J=8.1 Hz), 3.15–3.21 (m, 2H), 4.14–4.23 (m, 1H), 7.11 (d, 2H, J=7.8 Hz), 7.36–7.44 (m, 3H).

I-19

¹H-NMR (CDCl₃) δ ppm: 0.92 (t, 3H, J=7.5 Hz), 1.21 (s, 9H), 1.30–1.40 (m, 2H), 1.55–1.72 (m, 6H), 2.64 (t, 2H, J=7.8 Hz), 3.08–3.33 (m, 3H), 3.42–3.50 (m, 2H), 6.39 (s, 1H), 7.22 (d, 2H, J=8.4 Hz), 7.69 (d, 2H, J=8.1 Hz).

I-20

¹H-NMR (CDCl₃) δ ppm: 0.92 (t, 3H, J=7.2 Hz), 1.31–1.39 (m, 2H), 1.39 (s, 9H), 1.55–1.72 (m, 6H), 2.64 (t, 2H, J=7.8 Hz), 3.24 (quart, 2H, J=6.6 Hz), 3.48 (quart, 2H, J=6.6 Hz), 4.21 (t, 1H, J=6.3 Hz), 6.29 (s, 1H), 7.22 (d, 2H, J=7.8 Hz), 7.67 (d, 2H, J=8.1 Hz).

I-21

¹H-NMR (CDCl₃) δ ppm: 0.91 (t, 3H, J=7.2 Hz), 1.23 (s, 9H), 1.30–1.42 (m, 2H), 1.50–2.02 (m, 10H), 2.30–2.42 (m, 1H), 2.57 (t, 2H, J=8.1 Hz), 3.10 (brs, 1H), 3.57 (brs, 1H), 7.12 (d, 2H, J=8.4 Hz), 7.41 (d, 2H, J=7.8 Hz).

I-22 mp: 78–79° C. ¹H-NMR (CDCl₃) δ ppm: 0.91 (t, 3H, J=7.2 Hz), 1.30–1.40 (m, 2H), 1.40 (s, 9H), 1.50–1.65 (m, 4H), 1.70–1.98 (m, 8H), 2.30–2.40 (m, 1H), 2.57 (t, 2H, J=7.5 Hz), 3.58–3.70 (m, 1H), 4.16 (d, 1H, J=9.3 Hz), 7.11–7.15 (m, 3H), 7.40 (d, 2H, J=8.1 Hz).

I-23

¹H-NMR (CDCl₃) δ ppm: 0.91 (t, 3H, J=7.2 Hz), 1.21 (s, 9H), 1.21–1.41 (m, 4H), 1.51–1.64 (m, 4H), 1.86–2.01 (m, 4H), 2.12–2.25 (m, 1H), 2.56 (t, 2H, J=7.5 Hz), 2.87–2.96 (m, 1H), 3.00–3.12 (m, 1H), 3.23–3.34 (m, 1H), 3.67–3.75 (m, 1H), 7.11 (d, 2H, J=8.1 Hz), 7.40 (d, 2H, J=8.4 Hz).

I-24

¹H-NMR (CDCl₃) δ ppm: 0.91 (t, 3H, J=7.2 Hz), 1.25–1.37 (m, 2H), 1.40 (s, 9H, 1.48–1.65 (m, 6H), 1.90 (d, 2H, J=11.7 Hz), 2.02 (d, 2H, J=11.7 Hz), 2.12–2.24 (m, 1H), 2.56 (t, 2H, J=7.5 Hz), 3.04 (t, 2H, J=6.3 Hz), 4.31 (t, 1H, J=5.7 Hz), 7.11 (d, 2H, J=8.1 Hz), 7.42 (d, 2H, J=8.4 Hz).

I-25 mp: 232–233° C. ¹H-NMR (CDCl₃) δ ppm: 0.91 (t, 3H, J=7.5 Hz), 1.23–1.40 (m, 4H), 1.40 (s, 9H), 1.51–1.76 (m, 4H), 2.01–2.26 (m, 5H), 2.56 (t, 2H, J=7.5 Hz), 3.22–3.38 (m, 1H), 3.79 (d, 1H, J=9.3 Hz), 7.11 (d, 2H, J=8.7 Hz), 7.17 (s, 1H), 7.40 (d, 2H, J=8.4 Hz).

I-26

¹H-NMR (CDCl₃) δ ppm: 0.91 (t, 3H, J=7.2 Hz), 1.22 (s, 9H), 1.28–1.40 (m, 2H), 1.52–1.62 (m, 2H), 1.85–1.96 (m, 1H), 2.00–2.14 (m, 1H), 2.38–2.53 (m, 2H), 2.56 (t, 2H, J=7.5 Hz), 3.22–3.37 (m, 3H), 7.11 (d, 2H, J=8.4 Hz), 7.45 (d, 2H, J=8.4 Hz), 8.19 (s, 1H).

I-27

¹H-NMR (CDCl₃) δ ppm: 0.91 (t, 3H, J=7.2 Hz), 1.30–1.40 (m, 2H), 1.40 (s, 9H), 1.52–1.61 (m, 2H), 1.95 (quint, 2H, J=6.3 Hz), 2.50 (t, 2H, J=6.9 Hz), 2.56 (t, 2H, J=7.8 Hz), 3.31 (quart, 2H, J=6.0 Hz), 4.30–4.36 (m, 1H), 7.12 (d, 2H, J=8.4 Hz), 7.43 (d, 2H, J=8.4 Hz), 7.65 (s, 1H).

I-28

¹H-NMR (CDCl₃) δ ppm: 0.91 (t, 3H, J=7.2 Hz), 1.21 (s, 9H), 1.30–1.62 (m, 8H), 2.08 (d, 4H, J=11.1 Hz), 2.56 (t, 2H, J=7.8 Hz), 3.04 (d, 1H, J=4.8 Hz), 3.20–3.30 (m, 1H), 4.65–4.76 (m, 1H), 6.57 (s, 1H), 7.10 (d, 2H, J=8.7 Hz), 7.26 (d, 2H, J=8.1 Hz).

I-29

¹H-NMR (CDCl₃) δ ppm: 0.91 (t, 3H, J=7.2 Hz), 1.23–1.62 (m, 8H), 1.40 (s, 9H), 2.12 (d, 4H, J=14.4 Hz), 2.56 (t, 2H, J=7.8 Hz), 3.28–3.40 (m, 1H), 3.90 (s, 1H), 4.60–4.73 (m, 1H), 6.57 (s, 1H), 7.10 (d, 2H, J=8.4 Hz), 7.25 (d, 2H, J=8.4 Hz).

I-30

¹H-NMR (CDCl₃) δ ppm: 0.91 (t, 3H, J=7.5 Hz), 1.26–1.39 (m, 2H), 1.51–1.64 (m, 4H), 1.72–1.81 (m, 2H), 2.34 (t, 2H, J=6.9 Hz), 2.56 (t, 2H, J=7.8 Hz), 2.95–3.01 (m, 2H), 4.84 (t, 1H, J=5.7 Hz), 6.99–7.12 (m, 6H), 7.19–7.24 (m, 1H), 7.30 (s, 1H), 7.38–7.43 (m, 4H), 7.79 (d, 2H, J=8.7 Hz).

I-31

¹H-NMR (CDCl₃) δ ppm: 0.92 (t, 3H, J=7.5 Hz), 1.21 (s, 9H), 1.28–1.62 (m, 8H), 2.07–2.14 (m, 4H), 2.64 (t, 2H, J=7.8 Hz), 3.11 (d, 1H, J=5.1 Hz), 3.20 (brs, 1H), 3.90–4.04 (m, 1H), 6.06–6.14 (m, 1H), 7.21 (t, 2H, J=8.1 Hz), 7.67 (t, 2H, J=8.4 Hz).

I-32

$^1$H-NMR (CDCl$_3$) δ ppm: 0.92 (t, 3H, J=7.2 Hz), 1.27–1.65 (m, 8H), 1.40 (s, 9H), 2.10–2.23 (m, 4H), 2.65 (t, 2H, J=7.5 Hz), 3.23–3.35 (m, 1H), 3.49 (s, 1H), 3.88–4.02 (m, 1H), 5.84–5.92 (m, 1H), 7.13 (t, 2H, J=8.4 Hz), 7.65 (d, 2H, J=8.1 Hz).

I-33

$^1$H-NMR (CDCl$_3$) δ ppm: 0.94 (t, 3H, J=7.2 Hz), 1.30–1.42 (m, 2H), 1.32 (s, 9H), 1.57–1.66 (m, 2H), 2.67 (t, 2H, J=7.8 Hz), 5.61 (s, 1H), 6.93 (d, 2H, J=8.7 Hz), 7.25 (d, 2H, J=8.4 Hz), 7.49 (d, 2H, J=9.0 Hz), 7.80 (d, 2H, J=8.1 Hz), 8.22 (s, 1H).

I-34

$^1$H-NMR (CD$_3$OD) δ ppm: 0.95 (t, 3H, J=7.5 Hz), 1.35 (s, 9H), 1.35–1.44 (m, 2H), 1.57–1.69 (m, 2H), 2.69 (t, 2H, J=7.5 Hz), 7.28–7.33 (m, 4H), 7.56 (d, 2H, J=9.0 Hz), 7.83 (d, 2H, J=8.4 Hz).

I-36

$^1$H-NMR (CDCl$_3$) δ ppm: 0.92 (t, 3H, J=7.5 Hz), 1.31–1.70 (m, 11H), 1.39 (s, 9H), 1.75–1.85 (m, 1H), 2.65 (t, 2H, J=8.1 Hz), 3.13 (t, 2H, J=6.6 Hz), 3.40 (t, 2H, J=7.2 Hz), 4.10 (t, 1H, J=5.7 Hz), 6.21 (t, 1H, J=5.7 Hz), 7.23 (d, 2H, J=8.1 Hz), 7.67 (d, 2H, J=8.4 Hz).

I-37

$^1$H-NMR (CDCl$_3$) δ ppm: 0.92 (t, 3H, J=7.5 Hz), 0.95–1.10 (m, 2H), 1.31–1.40 (m, 2H), 1.39 (s, 9H), 1.55–1.63 (m, 4H), 1.80–1.92 (m, 4H), 2.65 (t, 2H, J=7.8 Hz), 3.03 (t, 2H, J=6.6 Hz), 3.31 (t, 2H, J=6.6 Hz), 4.06 (t, 1H, J=6.0 Hz), 6.22 (t, 1H, J=6.0 Hz), 7.23 (d, 2H, J=8.4 Hz), 7.67 (d, 2H, J=8.1 Hz).

I-39

$^1$H-NMR (CDCl$_3$) δ ppm: 1.13 (t, 3H, J=7.2 Hz), 1.39 (s, 9H), 1.69–1.97 (m, 8H), 2.27–2.38 (m, 1H), 3.29–3.35 (m, 4H), 3.60–3.70 (m, 1H), 4.52 (d, 1H, J=9.3 Hz), 6.64 (d, 2H, J=8.4 Hz), 7.22 (s, 1H), 7.31 (d, 2H, J=9.0 Hz).

I-40

$^1$H-NMR (CDCl$_3$) δ ppm: 1.38 (s, 9H), 1.68–1.96 (m, 8H), 2.30–2.40 (m, 1H), 3.11 (t, 4H, J=4.8 Hz), 3.60–3.72 (m, 1H), 3.86 (t, 4H, J=4.8 Hz), 4.51 (brs, 1H), 6.89 (d, 2H, J=9.0 Hz), 7.42 (d, 2H, J=8.7 Hz).

I-41 mp:>278° C. (dec.); $^1$H-NMR (CDCl$_3$) δ ppm: 1.18–1.40 (m, 2H), 1.40 (s, 9H), 1.62–1.75 (m, 2H), 2.01–2.27 (m, 5H), 3.10–3.13 (m, 4H), 3.22–3.38 (m, 1H), 3.72 (d, 1H, J=9.3 Hz), 3.85–3.88 (m, 4H), 6.87 (d, 2H, J=9.0 Hz), 7.10 (s, 1H), 7.40 (d, 2H, J=9.0 Hz).

I-42

$^1$H-NHR (CDCl$_3$) δ ppm: 1.40 (s, 9H), 1.61–1.97 (m, 8H), 2.16 (s, 3H), 2.33–2.43 (m, 1H), 3.60–3.70 (m, 1H), 4.66 (brs, 1H), 7.12 (d, 1H, J=8.7 Hz), 7.46–7.50 (m, 1H), 7.62 (s, H), 7.75–7.78 (m, 1H), 7.86–7.91 (m, 2H).

I-43

$^1$H-NMR (CDCl$_3$) δ ppm: 1.40 (s, 9H), 1.62–2.00 (m, 8H), 1.87 (s, 3H), 2.36–2.47 (m, 1H), 3.24 (s, 3H), 3.64–3.74 (m, 1H), 4.87 (brs, 1H), 7.13 (d, 2H, J=9.0 Hz), 7.64 (d, 2H, J=8.4 Hz), 7.81 (s, H).

I-44 mp: 235–236° C. $^1$H-NMR (CDCl$_3$) δ ppm: 1.13 (t, 6H, J=6.9 Hz), 1.18–1.33 (m, 2H), 1.40 (s, 9H), 1.60–1.77 (m, 2H), 2.00–2.26 (m, 5H), 3.28–3.35 (m, 4H), 3.73 (d, 1H, J=9.3 Hz), 6.60–6.70 (m, 2H), 7.03 (brs, 1H), 7.31 (d, 2H, J=7.8 Hz).

I-45 mp:>268° C. (dec.); $^1$H-NMR (CDCl$_3$) δ ppm: 1.20–1.34 (m, 2H), 1.40 (s, 9H), 1.56–1.76 (m, 8H), 2.00–2.26 (m, 5H), 3.06–3.14 (m, 4H), 3.24–3.36 (m, 1H), 3.72 (d, 1H, J=9.3 Hz), 6.90 (d, 2H, J=8.7 Hz), 7.09 (s, 1H), 7.36 (d, 2H, J=8.7 Hz).

I-46 mp:>272° C. (dec.); $^1$H-NMR (DMSO-d$_6$) δ ppm: 1.28 (s, 9H), 1.31–1.59 (m, 7H), 1.87–2.00 (m, 4H), 2.23–2.34 (m, 1H), 3.00–3.16 (m, 1H), 4.35–4.45 (m, 2H), 6.81 (d, 1H, J=9.0 Hz), 7.16 (t, 1H, J=7.2 Hz), 7.43 (t, 1H, J=8.4 Hz), 7.52–7.58 (m, 3H), 8.04 (d, 1H, J=7.8 Hz), 8.43 (s, 1H).

I-47

$^1$H-NMR (CDCl$_3$) δ ppm: 1.20–1.36 (m, 2H), 1.40 (s, 9H), 1.62–1.77 (m, 2H), 1.98–2.32 (m, 5H), 3.31–3.40 (m, 1H), 3.62 (d, 1H, J=9.0 Hz), 7.08 (s, 1H), 7.29 (d, 2H, J=9.0 Hz), 7.61 (d, 2H, J=9.0 Hz).

I-48

$^1$H-NMR (CDCl$_3$) δ ppm: 1.22–1.36 (m, 2H), 1.40 (s, 9H), 1.62–1.77 (m, 2H), 2.00–2.31 (m, 5H), 3.24–3.40 (m, 1H), 3.62 (d, 1H, J=10.2 Hz), 7.01 (t, 2H, J=8.7 Hz), 7.09 (s, 1H), 7.42–7.50 (m, 2H).

I-49 mp: 270° C. (dec.);

$^1$H-NMR (CDCl$_3$) δ ppm: 1.20–1.36 (m, 2H), 1.40 (s, 9H), 1.61–1.77 (m, 2H), 1.95–2.30 (m, 9H), 3.17–3.38 (m, 5H), 3.67 (d, 1H, J=9.3 Hz), 6.50 (d, 2H, J=9.0 Hz), 6.97 (s, 1H), 7.30 (d, 2H, J=9.0 Hz).

I-50 mp: 252–253° C. $^1$H-NMR (CDCl$_3$) δ ppm: 1.21–1.37 (m, 2H), 1.40 (s, 9H), 1.62–1.78 (m, 2H), 1.98–2.32 (m, 5H), 3.26–3.40 (m, 1H), 3.68 (d, 1H, J=9.6 Hz), 6.94–7.02 (m, 4H), 7.08 (t, 1H, J=7.5 Hz), 7.13 (s, 1H), 7.31 (t, 2H, J=7.5 Hz), 7.46 (d, 2H, J=9.0 Hz).

I-51 mp: 278–279° C. $^1$H-NMR (CDCl$_3$) δ ppm: 1.02 (d, 6H, J=6.9 Hz), 1.35 (s, 9H), 1.39–1.71 (m, 6H), 1.90–2.09 (m, 2H), 3.16–3.30 (m, 1H), 3.46 (d, 1H, J=9.0 Hz), 4.92–5.01 (m, 1H), 6.91–6.95 (m, 2H), 7.00–7.07 (m, 3H), 7.13–7.16 (m, 2H), 7.30–7.36 (m, 2H).

I-52 mp: 276–277° C. $^1$H-NMR (CDCl$_3$) δ ppm: 1.20–1.36 (m, 2H), 1.40 (s, 9H), 1.60–1.78 (m, 2H), 1.98–2.30 (m, 5H), 2.36 (s, 3H), 2.58 (t, 4H, J=4.5 Hz), 3.17 (t, 4H, J=4.5 Hz), 3.21–3.40 (m, 1H), 3.64 (d, 1H, J=9.0 Hz), 6.88 (d, 2H, J=9.0 Hz), 7.01 (s, 1H), 7.37 (d, 2H, J=9.0 Hz).

I-53 mp:>300° C. $^1$H-NMR (DMSO-d$_6$) δ ppm: 1.20–1.54 (m, 4H), 1.27 (s, 9H), 1.73–1.88 (m, 2H), 1.89–2.01 (m, 2H), 2.13–2.25 (m, 1H), 2.98–3.12 (m, 1H), 3.15–3.31 (m, 8H), 6.76–6.84 (m, 2H), 6.93 (d, 2H, J=9.0 Hz), 6.99 (d, 2H, J=8.1 Hz), 7.24 (d, 2H, J=8.1 Hz), 7.46 (d, 2H, J=9.0 Hz), 9.60 (s, 1H).

I-54 mp:>215° C. (dec.); $^1$H-NMR (DMSO-d$_6$) δ ppm: 1.27 (s, 9H), 1.27–2.00 (m, 18H), 2.14–2.26 (m, 1H), 2.53–2.84 (m, 4H), 2.86–3.30 (m, 2H), 3.46–3.54 (m, 1H), 3.62–3.74 (m, 2H), 6.78 (d, 1H, J=8.7 Hz), 6.87 (d, 2H, J=7.8 Hz), 7.42 (d, 2H, J=8.7 Hz), 9.58 (s, 1H).

I-55 mp:>290° C. (dec.); $^1$H-NMR (CDCl$_3$) δ ppm: 1.23–1.40 (m, 2H), 1.40 (s, 9H), 1.60–1.76 (m, 2H), 2.02–2.27 (m, 5H), 3.20 (t, 4H, J=5.4 Hz), 3.21–3.32 (m, 1H), 3.67 (d, 1H, J=9.3 Hz), 3.98 (t, 4H, J=4.8 Hz), 6.52 (t, 1H, J=4.8 Hz), 6.93 (d, 2H, J=8.4 Hz), 7.06 (s, 1H), 7.41 (d, 2H, J=8.7 Hz), 8.33 (d, 2H, J=4.8 Hz).

I-56 mp:>232° C. (dec.); $^1$H-NMR (DMSO-d$_6$) δ ppm: 1.27 (s, 9H), 1.27–1.48 (m, 4H), 1.80–1.99 (m, 4H), 2.14–2.25 (m, 1H), 3.04–3.24 (m, 8H), 3.68 (s, 3H), 3.76 (s, 3H), 6.44–6.47 (m, 1H), 6.66 (s, 1H), 6.76–6.84 (m, 2H), 6.92 (d, 2H, J=8.4 Hz), 7.46 (d, 2H, J=8.4 Hz), 9.61 (s, 1H).

I-57 mp: 284–285° C. (dec.); $^1$H-NMR (CDCl$_3$) δ ppm: 1.27 (t, 3H, J=7.2 Hz), 1.40 (s, 9H), 1.61–2.24 (m, 9H), 2.35–2.49 (m, 1H), 2.76 (t, 2H, J=10.2 Hz), 3.04–3.15 (m, 2H), 3.20–3.36 (m, 1H), 3.55–3.59 (m, 2H), 3.87 (d, 1H, J=9.6 Hz), 4.12–4.19 (m, 2H), 6.90 (d, 2H, J=8.7 Hz), 2.79 (s, 1H), 7.40 (d, 2H, J=8.7 Hz).

I-58 mp:>299° C. (dec.); $^1$H-NMR (CDCl$_3$) δ ppm: 1.26–1.33 (m, 2H), 1.40 (s, 9H), 1.56–2.42 (m, 19H), 2.73–2.81 (m, 4H), 3.16–3.26 (m, 4H), 3.64 (d, 1H, J=9.6 Hz), 6.87 (d, 2H, J=8.7 Hz), 7.04 (s, 1H), 7.37 (d, 2H, J=9.0 Hz).

I-59 mp:>270° C. (dec.); $^1$H-NMR (CDCl$_3$) δ ppm: 1.26–1.47 (m, 2H), 1.47 (s, 9H), 1.60–1.80 (m, 4H), 2.01–2.32 (m, 5H), 3.28–3.40 (m, 3H), 3.62–3.74 (m, 3H), 5.74–5.96 (m, 2H), 6.92 (d, 2H, J=8.7 Hz), 7.13 (s, 1H), 7.39 (d, 2H, J=9.0 Hz).

I-60 mp: 247–250° C. (dec.); $^1$H-NMR (CDCl$_3$) δ ppm: 1.20–1.37 (m, 2H), 1.40 (s, 9H), 1.60–1.78 (m, 2H), 1.98–2.33 (m, 5H), 2.93–3.03 (m, 2H), 3.22–3.40 (m, 1H), 3.52 (t, 2H, J=6.0 Hz), 3.62 (d, 1H, J=8.4 Hz), 4.36 (s, 2H), 6.93 (d, 2H, J=8.7 Hz), 7.00 (s, 1H), 7.11.–7.22 (m, 4H), 7.39 (d, 2H, J=8.7 Hz).

I-61 mp: 280–281° C. $^1$H-NMR (CDCl$_3$) δ ppm: 1.21–1.38 (m, 2H), 1.41 (s, 9H), 1.64–1.80 (m, 2H), 2.02–2.33 (m, 5H), 3.24–3.40 (m, 1H), 3.61 (d, 1H, J=9.0 Hz), 6.33 (t, 2H, J=2.1 Hz), 7.04 (t, 2H, J=2.1 Hz), 7.14 (s, 1H), 7.34 (d, 2H, J=9.0 Hz), 7.56 (d, 2H, J=9.0 Hz).

I-62 mp: 260–262° C. $^1$H-NMR (CDCl$_3$) δ ppm: 1.22–1.39 (m, 2H), 1.41 (s, 9H), 1.64–1.82 (m, 2H), 2.02–2.35 (m, 5H), 3.24–3.40 (m, 1H), 3.62 (d, 1H, J=9.6 Hz), 7.31 (d, 2H, J=9.0 Hz), 7.51 (s, 1H), 7.69 (d, 2H, J=9.0 Hz).

I-63 mp: 248° C. $^1$H-NMR (CDCl$_3$) δ ppm: 1.20–1.38 (m, 2H), 1.40 (s, 9H), 1.61–1.78 (m, 2H), 1.98–2.32 (m, 5H), 3.22–3.45 (m, 1H), 3.64 (d, 1H, J=9.3 Hz), 7.11 (s, 1H), 7.37–7.46 (m, 4H).

I-64 mp: 272–275° C. (dec.); $^1$H-NMR (DMSO-d$_6$) δ ppm: 1.20–1.53 (m, 4H), 1.27 (s, 9H), 1.75–1.88 (m, 2H), 1.88–2.00 (m, 2H), 2.11–2.24 (m, 1H), 2.96–3.12 (m, 1H), 5.96 (s, 2H), 6.77 (d, 1H, J=8.7 Hz), 6.82 (d, 1H, J=8.4 Hz), 6.95 (dd, 1H, J=1.8, 8.4 Hz), 7.29 (d, 1H, J=1.8 Hz), 9.70 (s, 1H).

I-65 mp: 293–296° C. (dec.); $^1$H-NMR (DMSO-d$_6$) δ ppm: 1.20–1.70 (m, 10H), 1.27 (s, 9H), 1.79–2.038 (m, 4H), 2.18–2.33 (m, 1H), 2.98–3.30 (m, 5H), 6.79 (d, 1H, J=9.0 Hz), 6.97 (d, 2H, J=8.1 Hz), 7.43–7.57 (m, 4H), 7.62 (d, 2H, J=8.1 Hz), 9.82 (s, 1H).

I-66 mp:>300° C. $^1$H-NMR (DMSO-d$_6$) δ ppm: 1.27 (s, 9H), 1.27–1.53 (m, 4H), 1.86–1.99 (m, 4H), 2.22–2.34 (m, 1H), 2.39 (s, 3H), 3.00–3.14 (m, 1H), 6.25 (s, 1H), 6.79 (d, 1H, J=9.0 Hz), 7.47–7.50 (m, 1H), 7.69–7.76 (m, 1H), 10.27 (s, 1H).

I-67 mp: 248–249° C. $^1$H-NMR (DMSO-d$_6$) δ ppm: 1.20–1.54 (m, 4H), 1.27 (s, 9H), 1.77–1.90 (m, 2H), 1.90–2.02 (m, 2H), 2.02 (s, 3H), 2.17–2.32 (m, 1H), 2.96–3.13 (m, 1H), 6.78 (d, 1H, J=8.7 Hz), 7.12–7.30 (m, 3H), 7.89 (s, 1H), 9.79 (s, 1H), 9.88 (s, 1H).

I-68 mp:>300° C. $^1$H-NMR (DMSO-d$_6$) δ ppm: 1.20–1.54 (m, 4H), 1.27 (s, 9H), 1.77–1.89 (m, 2H), 1.89–2.03 (m, 2H), 2.00 (s, 3H), 2.14–2.28 (m, 1H), 2.95–3.13 (m, 1H), 6.78 (d, 1H, J=8.7 Hz), 7.40–7.54 (m, 4H), 9.72 (s, 1H), 9.83 (s, 1H).

I-69 mp: 199–201° C. $^1$H-NMR (DMSO-d$_6$) δ ppm: 1.21–1.53 (m, 4H), 1.27 (s, 9H), 1.76–1.89 (m, 2H), 1.89–2.02 (m, 2H), 2.13–2.30 (m, 1H), 2.85 (s, 6H), 2.94–3.14 (m, 1H), 6.40 (dd, 1H, J=2.4, 8.4 Hz), 6.78 (d, 1H, J=8.7 Hz), 6.90 (d, 1H, J=8.4 Hz), 7.05 (t, 2H, J=8.4 Hz), 9.60 (s, 1H).

I-70 mp: 227–230° C. $^1$H-NMR (DMSO-d$_6$) δ ppm: 1.22–1.52 (m, 4H), 1.27 (s, 9H), 1.72–1.87 (m, 2H), 1.87–2.01 (m, 2H), 2.12–2.29 (m, 1H), 2.96–3.12 (m, 1H), 5.00 (s, 2H), 6.22 (d, 1H, J=7.5 Hz), 6.66 (d, 1H, J=7.5 Hz), 6.78 (d, 1H, J=9.0 Hz), 6.86 (d, 1H, J=7.5 Hz), 6.89–6.95 (m, 1H), 9.46 (s, 1H).

I-71 mp: 270–272° C. $^1$H-NMR (DMSO-d$_6$) δ ppm: 1.22–1.52 (m, 4H), 1.26 (s, 9H), 1.73–1.86 (m, 2H), 1.88–2.00 (m, 2H), 2.08–2.22 (m, 1H), 2.95–3.11 (m, 1H), 4.80 (s, 2H), 6.47 (d, 2H, J=8.4 Hz), 6.77 (d, 1H, J=8.4 Hz), 7.20 (d, 2H, J=8.4 Hz), 9.35 (s, 1H).

I-72 mp: 262–263° C. $^1$H-NMR (CDCl$_3$) δ ppm: 1.25 (d, 6H, J=6.3 Hz), 1.17–1.42 (m, 2H), 1.40 (s, 9H), 1.60–1.78 (m, 2H), 1.98–2.43 (m, 7H), 3.20–3.43 (m, 3H), 3.67 (d, 1H, J=9.6 Hz), 3.74–3.86 (m, 2H), 6.86 (d, 2H, J=9.0 Hz), 7.04 (s, 1H), 7.38 (d, 2H, J=9.0 Hz).

I-73 mp: 218–219° C. $^1$H-NMR (CD$_3$OD) δ ppm: 1.36 (s, 9H), 1.36–1.69 (m, 4H), 1.45 (s, 9H), 1.88–2.02 (m, 3H), 2.06–2.30 (m, 4H), 3.05–3.44 (m, 3H), 3.46–3.56 (m, 1H), 4.16–4.26 (m, 1H), 6.51 (d, 2H, J=9.0 Hz), 7.30 (d, 2H, J=8.7 Hz).

I-74 mp: 295–296° C. (dec.); $^1$H-NMR (CD$_3$OD) δ ppm: 1.36 (s, 9H), 1.36–1.67 (m, 4H), 1.92–2.13 (m, 4H), 2.26–2.40 (m, 2H), 2.62–2.75 (m, 1H), 3.16–3.25 (m, 1H), 3.58–3.98 (m, 4H), 4.16–4.25 (m, 1H), 7.20–7.30 (m, 2H), 7.62 (d, 2H, J=9.0 Hz).

I-75 mp: 250–251° C. $^1$H-NMR (DMSO-d$_6$) δ ppm: 1.23–1.55 (m, 4H), 1.27 (s, 9H), 1.78–1.90 (m, 2H), 1.90–2.02 (m, 2H), 2.15–2.28 (m, 1H), 2.98–3.14 (m, 1H), 3.06 (t, 2H, J=8.4 Hz), 3.87 (t, 2H, J=8.4 Hz), 6.67 (dd, 1H, J=1.5, 7.2 Hz), 6.80 (d, 1H, J=8.4 Hz), 6.94–7.05 (m, 2H), 7.12–7.19 (m, 1H), 7.16 (d, 2H, J=9.3 Hz), 7.57 (d, 2H, J=9.3 Hz), 9.73 (s, 1H).

I-76 mp: 265–266° C. $^1$H-NMR (DMSO-d$_6$) δ ppm: 1.23–1.58 (m, 4H), 1.28 (s, 9H), 1.83–2.04 (m, 4H), 2.20–2.36 (m, 1H), 2.97–3.16 (m, 1H), 6.67 (d, 1H, J=3.0 Hz), 6.82 (d, 1H, J=8.4 Hz), 7.07–7.22 (m, 2H), 7.47–7.53 (m, 1H), 7.50 (d, 2H, J=9.0 Hz), 7.58 (d, 1H, J=3.0 Hz), 7.64 (d, 1H, J=7.5 Hz), 7.79 (d, 2H, J=9.0 Hz), 10.02 (s, 1H).

I-77 mp: 281° C. $^1$H-NMR (DMSO-d$_6$) δ ppm: 1.21–1.56 (m, 4H), 1.27 (s, 9H), 1.80–2.03 (m, 4H), 2.18–2.31 (m, 1H), 2.97–3.14 (m, 1H), 6.51 (dd, 1H, J=2.1, 2.7 Hz), 6.81 (d, 1H, J=9.0 Hz), 7.67–7.78 (m, 5H), 8.41 (d, 1H, J=2.1 Hz), 9.96 (s, 1H).

I-78 mp:>300° C. (dec.); $^1$H-NMR (DMSO-d$_6$) δ ppm: 1.27 (s, 9H), 1.27–1.52 (m, 4H), 1.74–2.04 (m, 7H), 2.10–2.25 (m, 2H), 2.96–3.20 (m, 2H), 3.48–3.58 (m, 1H), 3.75–3.84 (m, 1H), 6.39 (d, 2H, J=8.4 Hz), 6.79 (d, 1H, J=8.4 Hz), 7.02 (s, 1H), 7.30 (s, 1H), 7.36 (d, 2H, J=8.1 Hz), 9.48 (s, 1H).
I-79
mp: 248–250° C. (dec.); $^1$H-NMR (DMSO-d$_6$) δ ppm: 1.27 (s, 9H), 1.27–1.54 (m, 4H), 1.85–1.99 (m, 4H), 2.24–2.33 (m, 1H), 3.00–3.14 (m, 1H), 6.82 (d, 1H, J=8.7 Hz), 7.77 (d, 2H, J=8.4 Hz), 8.07 (d, 2H, J=8.4 Hz).
I-80
mp:>300° C. $^1$H-NMR (DMSO-d$_6$) δ ppm: 1.22–1.58 (m, 4H), 1.27 (s, 9H), 1.80–2.03 (m, 4H), 2.18–2.32 (m, 1H), 2.98–3.14 (m, 1H), 6.80 (d, 1H, J=8.7 Hz), 7.35–7.50 (m, 2H), 7.99 (s, 1H), 8.11 (s, 1H), 9.79 (s, 1H), 12.94 (s, 1H).
I-81
mp: 261–262° C. $^1$H-NMR (DMSO-d$_6$) δ ppm: 1.21–1.57 (m, 4H), 1.27 (s, 9H), 1.78–2.02 (m, 4H), 2.17–2.30 (m, 1H), 2.96–3.16 (m, 1H), 6.34 (s, 1H), 6.80 (d, 1H, J=8.7 Hz), 7.14–7.32 (m, 3H), 7.85 (s, 1H), 9.58 (s, 1H), 10.95 (s, 1H).
I-82 $^1$H-NMR (CDCl$_3$) δ ppm: 0.86 (s, 18H), 1.24–1.37 (m, 2H), 1.37 (s, 9H), 1.56–1.74 (m, 2H), 1.95–2.19 (m, 5H), 3.18–3.32 (m, 1H), 3.44 (t, 4H, J=6.3 Hz), 3.70 (t, 4H, J=6.3 Hz), 4.39 (d, 1H, J=9.0 Hz), 6.59 (d, 2H, J=9.0 Hz), 7.31 (d, 2H, J=8.7 Hz), 7.43 (s, 1H).
I-83
mp: 264–265° C. $^1$H-NMR (DMSO-d$_6$) δ ppm: 1.27 (s, 9H), 1.27–1.52 (m, 4H), 1.78–1.88 (m, 2H), 1.90–2.00 (m, 2H), 2.14–2.26 (m, 1H), 2.96–3.14 (m, 1H), 6.72–6.82 (m, 2H), 6.99 (t, 4H, J=7.8 Hz), 7.18 (t, 2H, J=7.5 Hz), 7.46 (d, 2H, J=9.0 Hz), 8.00 (s, 1H), 9.65 (s, 1H).
I-84
mp: 27° C. (dec.); $^1$H-NMR (DMSO-d$_6$) δ ppm: 1.23–1.57 (m, 4H), 1.27 (s, 9H), 1.83–2.03 (m, 4H), 2.23–2.35 (m, 1H), 2.98–3.15 (m, 1H), 6.80 (d, 1H, J=8.1 Hz), 7.87 (d, 2H, J=9.0 Hz), 8.34 (d, 2H, J=9.0 Hz), 9.21 (s, 1H), 10.20 (s, 1H).
I-85
mp: 256–258° C. $^1$H-NMR (DMSO-d$_6$) δ ppm: 1.22–1.53 (m, 4H), 1.26 (s, 9H), 1.79–2.01 (m, 4H), 2.25 (s, 3H), 2.28–2.42 (m, 1H), 2.97–3.02 (m, 1H), 6.71 (d, 1H, J=0.9 Hz), 6.80 (d, 1H, J=8.1 Hz), 11.91 (s, 1H).
I-86
mp: 228–230° C. $^1$H-NMR (CD$_3$OD) δ ppm: 1.36 (s, 9H), 1.36–1.48 (m, 2H), 1.55–1.70 (m, 2H), 1.87–1.98 (m, 2H), 2.08–2.17 (m, 2H), 2.20–2.32 (m, 1H), 3.15–3.27 (m, 1H), 3.50 (t, 4H, J=5.7 Hz), 3.69 (t, 4H, J=5.7 Hz), 6.72 (d, 2H, J=9.0 Hz), 7.29–7.33 (m, 2H).
I-87
mp: 183–184° C. $^1$H-NMR (DMSO-d$_6$) δ ppm: 1.27 (s, 9H), 1.27–1.48 (m, 4H), 1.73–1.89 (m, 4H), 1.90–2.00 (m, 2H), 2.16–2.28 (m, 1H), 2.28 (t, 2H, J=7.5 Hz), 2.51–2.54 (m, 2H), 2.97–3.13 (m, 1H), 3.58 (s, 3H), 6.79 (d, 1H, J=8.7 Hz), 7.08 (d, 2H, J=8.7 Hz), 7.49 (d, 2H, J=8.4 Hz), 9.73 (s, 1H).
I-88
mp: 217–218° C. $^1$H-NMR (CD$_3$OD) δ ppm: 1.36 (s, 9H), 1.36–1.46 (m, 2H), 1.55–1.69 (m, 2H), 1.83–2.00 (m, 4H), 2.07–2.18 (m, 2H), 2.26–2.36 (m, 3H), 2.61 (t, 2H, J=7.5 Hz), 3.14–3.26 (m, 1H), 7.13 (d, 2H, J=8.1 Hz), 7.44 (d, 2H, J=8.1 Hz).
I-89
$^1$H-NMR (CDCl$_3$) δ ppm: 0.08 (d, 6H, J=3.3 Hz), 0.88 (s, 9H), 1.21–1.36 (m, 2H), 1.39 (s, 9H), 1.61–1.74 (m, 2H), 1.88–2.23 (m, 6H), 3.06–3.11 (m, 1H), 3.24–3.74 (m, 4H), 3.92 (d, 1H, J=9.6 Hz), 4.48–4.56 (m, 1H), 6.47 (d, 2H, J=9.0 Hz), 7.17 (s, 1H), 7.32 (d, 2H, J=9.0 Hz).
I-90
mp: amorphous $^1$H-NMR (CD$_3$OD) δ ppm: 1.36 (s, 9H), 1.36–1.47 (m, 2H), 1.56–1.70 (m, 3H), 1.88–2.30 (m, 6H), 3.05–3.49 (m, 5H), 4.50 (brs, 1H), 6.50 (d, 2H, J=9.0 Hz), 7.29 (d, 2H, J=9.0 Hz).
I-91
mp: 105–106° C. $^1$H-NMR (CDCl$_3$) δ ppm: 0.92 (t, 3H, J=7.3 Hz), 1.25–1.27 (m, 2H), 1.36 (d, 6H, J=6.9 Hz), 1.51–1.59 (m, 2H), 2.56 (t, 2H, J=7.8 Hz), 3.27 (sept, 1H, J=6.9 Hz), 7.12 (d, 2H, J=8.6 Hz), 7.32 (t, 1H, J=7.8 Hz), 7.45 (brd, 1H, J=7.8 Hz), 7.53 (d, 2H, J=8.6 Hz), 7.58 (d, 1H, J=7.8 Hz), 7.71–7.72 (m, 2H), 8.27 (s, 1H).
I-92
mp: 163–164° C. $^1$H-NMR (CDCl$_3$) δ ppm: 0.93 (t, 3H, J=7.3 Hz), 1.32–1.39 (m, 2H), 1.55–1.65 (m, 2H), 1.87 (s, 3H), 1.95 (s, 3H), 2.60 (t, 2H, J=7.6 Hz), 7.07 (d, 2H, J=8.4 Hz), 7.18 (d, 2H, J=8.5 Hz), 7.54 (d, 2H, J=8.5 Hz), 7.91 (brs, 1H), 8.18 (d, 2H, J=8.4 Hz), 8.77 (s, 1H).
I-93
mp: 173° C. $^1$H-NMR (CDCl$_3$) δ ppm: 0.93 (t, 3H, J=7.3 Hz), 1.32–1.40 (m, 2H), 1.39 (d, 6H, J=6.9 Hz), 1.55–1.62 (m, 2H), 2.60 (t, 2H, J=7.8 Hz), 3.13 (sept, 1H, J=6.9 Hz), 4.39 (d, 2H, J=6.3 Hz), 4.45 (t, 1H, J=6.3 Hz), 7.18 (d, 2H, J=8.7 Hz), 7.46 (d, 2H, J=8.7 Hz), 7.54 (d, 2H, J=8.7 Hz), 7.80 (s, 1H), 7.85 (d, 2H, J=8.7 Hz).
I-94
mp: 159–160° C. $^1$H-NMR (CDCl$_3$) δ ppm: 0.93 (t, 3H, J=7.3 Hz), 1.32–1.39 (m, 2H), 1.54–1.80 (m, 2H), 1.79 (s, 3H), 1.80 (s, 3H), 2.60t, 2H, J=7.7 Hz), 3.18 (s, 3H), 7.18 (d, 2H, J=8.5 Hz), 7.30 (d, 2H, J=8.8 Hz), 7.52 (d, 2H, J=8.5 Hz), 7.70 (brs, 1H), 7.84 (d, 2H, J=8.8 Hz), 8.77 (s, 1H).
I-95
mp: 177–178° C. $^1$H-NMR (CDCl$_3$) δ ppm: 0.94 (t, 3H, J=7.2 Hz), 1.31–1.48 (m, 8H), 1.54–1.66 (m, 2H), 2.55 (s, 3H), 2.62 (t, 2H, J=7.6 Hz), 3.92 (sept, 1H, J=6.6 Hz), 7.20 (d, 2H, J=8.45 Hz), 7.74 (d, 2H, J=8.5 Hz), 9.01 (brs, 1H), 9.17 (s, 1H).
I-96
mp: 220–223° C. $^1$H-NMR (CDCl$_3$) δ ppm: 0.93 (t, 3H, J=7.3 Hz), 1.28–1.42 (m, 2H), 1.50 (d, 6H, J=6.8 Hz), 1.54–1.65 (m, 2H), 2.62 (t, 2H, J=7.6 Hz), 4.08 (sept, 1H, J=7.1 Hz), 7.20 (d, 2H, J=8.5 Hz), 7.48 (d, 2H, J=8.5 Hz), 7.71 (brs, 1H), 8.51 (brs, 1H), 8.95 (s, 1H).
I-97
mp: 195–197° C. $^1$H-NMR (CDCl$_3$) δ ppm: 0.91 (t, 3H, J=7.6 Hz), 0.94 (t, 3H, J=7.3 Hz), 1.32–1.44 (m, 6H), 1.54–1.64 (m, 2H), 1.66–1.78 (m, 2H), 2.62 (t, 2H, J=7.7 Hz), 2.86 (brs, 2H), 3.98 (sept, 1H, J=7.1 Hz), 7.19 (d, 2H, J=8.5 Hz), 7.63 (d, 2H, J=8.4 Hz), 8.72 (brs, 1H), 8.81 (brs, 1H).
I-98
mp: 216–218° C. $^1$H-NMR (CDCl$_3$+CD$_3$OD) δ ppm: 0.93 (t, 3H, J=7.4 Hz), 1.29–1.40 (m, 2H), 1.43 (d, 2H), J=6.9 Hz), 1.51–1.63 (m, 2H), 2.60 (t, 2H, J=7.8 Hz), 3.65 (sept, 1H, J=6.9 Hz), 7.18 (d, 2H, J=8.5 Hz), 7.22 (d, 1H, J=8.8 Hz), 7.55 (d, 2H, J=8.5 Hz), 8.18 (dd, 1H, J=8.8, 2.4 Hz), 8.63 (d, 1H, J=2.4 Hz).
I-99
mp: 201–202° C. $^1$H-NMR (CDCl$_3$) δ ppm: 0.93 (t, 3H, J=7.3 Hz), 1.22–1.40 (m, 2H), 1.49 (d, 2H, J=7.1 Hz), 1.51–1.63 (m, 2H), 2.59 (t, 2H, J=7.7 Hz), 4.22 (sept, 1H, J=7.1 Hz), 7.16 (d, 2H, J=8.4 Hz), 7.41 (brs, 1H), 7.52 (d, 2H, J=8.4 Hz), 8.10 (brs, 1H), 8.13 (d, 1H, J=2.2 Hz), 8.61 (brs, 1H).
I-100
mp: 160–162° C. $^1$H-NMR (CDCl$_3$) δ ppm: 0.93 (t, 3H, J=7.3 Hz), 1.22–1.42 (m, 2H), 1.45 (d, 2H, J=6.9 Hz), 1.51–1.63 (m, 2H), 2.61 (t, 2H, J=7.8 Hz), 3.37 (sept, 1H, J=6.9 Hz), 6.89 (brs, 1H), 7.19 (d, 2H, J=8.4 Hz), 7.65 (d, 2H, J=8.4 Hz), 7.80 (dd, 1H, J=8.4, 2.4 Hz), 8.27 (d, 1H, J=8.4 Hz), 8.45 (d, 1H, J=2.4 Hz), 9.75 (brs, 1H).

I-101, I-214 mp: 192–194° C. $^1$H-NMR (CDCl$_3$) δ ppm: 0.93 (t, 3H, J=7.3 Hz), 1.27–1.41 (m, 2H), 1.35 (s, 9H), 1.50–1.66 (m, 2H), 2.60 (t, 2H, J=7.6 Hz), 5.58 (brs, 1H), 7.07 (d, 2H, J=8.5 Hz), 7.17 (d, 2H, J=8.5 Hz), 7.52 (d, 2H, J=8.5 Hz), 7.71 (brs, 1H), 7.79 (d, 2H, J=8.5 Hz).

I-102 mp: 216–217° C. $^1$H-NMR (CDCl$_3$) δ ppm: 0.93 (t, 3H, J=7.3 Hz), 1.26–1.42 (m, 2H), 1.45 (s, 9H), 1.70–1.83 (m, 2H), 2.60 (t, 2H, J=7.7 Hz), 6.42 (brs, 1H), 7.18 (d, 2H, J=8.5 Hz), 7.35 (d, 2H, J=8.5 Hz), 7.51 (d, 2H, J=8.5 Hz), 7.68 (brs, 1H), 7.82 (d, 2H, J=8.5 Hz).

I-103

$^1$H-NMR (CDCl$_3$) δ ppm: 0.91 (t, 3H, J=7.3 Hz), 1.28–1.36 (m, 2H), 1.32 (d, 6H, J=6.9 Hz), 1.49–1.59 (m, 2H), 2.54 (t, 2H, J=7.7 Hz), 3.23 (sept, 1H, J=6.9 Hz), 3.46 (s, 3H), 6.76 (brs, 1H), 6.91 (d, 2H, J=8.2 Hz), 6.99 (d, 2H, J=8.8 Hz), 7.03 (d, 2H, J=8.2 Hz), 7.25 (d, 2H, J=8.8 Hz).

I-104 mp: 182–183° C. $^1$H-NMR (CDCl$_3$) δ ppm: 0.93 (t, 3H, J=7.3 Hz), 1.28–1.40 (m, 2H), 1.51–1.63 (m, 2H), 1.64–1.88 (m, 4H), 1.90–2.23 (m, 4H), 2.60 (t, 2H, J=7.6 Hz), 3.39 (m, 1H), 6.16 (brs, 1H), 7.07 (d, 2H, J=8.5 Hz), 7.16 (d, 2H, J=8.5 Hz), 7.52 (d, 2H, J=8.5 Hz), 7.74 (brs, 1H), 7.77 (d, 2H, J=8.5 Hz).

I-105 mp: 190–191° C. $^1$H-NMR (CDCl$_3$) δ ppm: 0.93 (t, 3H, J=7.3 Hz), 1.28–1.41 (m, 2H), 1.52–1.69 (m, 4H), 1.75–1.90 (m, 2H), 1.92–2.07 (m, 4H), 2.58 (t, 2H, J=7.6 Hz), 3.59 (m, 1H), 6.53 (brs, 1H), 7.18 (d, 2H, J=8.5 Hz), 7.31 (d, 2H, J=8.5 Hz), 7.52 (d, 2H, J=8.5 Hz), 7.67 (brs, 1H), 7.84 (d, 2H, J=8.5 Hz).

I-106 mp: 194–197° C. $^1$H-NMR (CDCl$_3$) δ ppm: 0.93 (t, 3H, J=7.3 Hz), 1.22–1.41 (m, 2H), 1.53–1.65 (m, 2H), 1.90 (s, 6H), 2.60 (t, 2H, J=7.8 Hz), 6.86 (brs, 1H), 7.18 (d, 2H, J=8.5 Hz), 7.43 (d, 2H, J=8.5 Hz), 7.51 (d, 2H, J=8.5 Hz), 7.71 (brs, 1H), 7.84 (d, 2H, J=8.5 Hz).

I-107 mp: 211–212° C. $^1$H-NMR (CDCl$_3$) δ ppm: 0.93 (t, 3H, J=7.3 Hz), 1.24–1.40 (m, 2H), 1.50–1.62 (m, 2H), 2.60 (t, 2H, J=7.6 Hz), 6.19 (brs, 1H), 7.17 (d, 2H, J=8.5 Hz), 7.18 (d, 2H, J=8.5 Hz), 7.51 (d, 2H, J=8.5 Hz), 7.66 (brs, 1H), 7.86 (d, 2H, J=8.5 Hz).

I-108 mp: 298–300° C. $^1$H-NMR (DMSO-d$_6$) δ ppm: 0.90 (t, 3H, J=7.3 Hz), 1.22–1.39 (m, 2H), 1.48–1.60 (m, 2H), 2.54 (t, 2H, J=7.3 Hz), 7.04 (d, 2H, J=8.8 Hz), 7.12 (d, 2H, J=8.5 Hz), 7.64 (d, 2H, J=8.5 Hz), 7.69 (d, 2H, J=8.8 Hz), 9.80 (s, 1H).

I-109 mp: 122–123° C. $^1$H-NMR (CDCl$_3$) δ ppm: 0.90 (t, 3H, J=7.4 Hz), 0.97 (t, 3H, J=7.7 Hz), 1.26–1.38 (m, 2H), 1.30 (s, 6H), 1.50–1.66 (m, 4H), 1.72–1.83 (m, 4H), 2.34 (t, 2H, J=7.1 Hz), 2.55 (t, 2H, J=7.6 Hz), 3.19 (q, 1H, J=6.0 Hz), 4.60 (brs, 1H), 7.08 (d, 2H, J=8.5 Hz), 7.42 (d, 2H, J=8.5 Hz), 7.85 (s, 1H).

I-110 mp: 109–110° C. $^1$H-NMR (CDCl$_3$) δ ppm: 0.91 (t, 3H, J=7.4 Hz), 1.10 (d, 6H, J=6.7 Hz), 1.29–1.38 (m, 2H), 1.55 (s, 9H), 1.60–1.70 (m, 2H), 1.78–1.89 (m, 2H), 2.26 (m, 1H), 2.39 (t, 2H, J=7.0 Hz), 2.57 (t, 2H, J=7.7 Hz), 2.90 (d, 2H, J=6.6 Hz), 3.16 (brs, 1H), 4.24 (brs, 1H), 7.12 (d, 2H, J=8.5 Hz), 7.40 (d, 2H, J=8.5 Hz).

I-111 mp: 64–65° C. $^1$H-NMR (CDCl$_3$) δ ppm: 0.91 (t, 3H, J=7.3 Hz), 1.02 (t, 3H, J=7.5 Hz), 1.35 (d, 3H, J=6.7 Hz), 1.26–1.38 (m, 2H), 1.48–1.69 (m, 5H), 1.76–1.87 (m, 2H), 2.04 (m, 1H), 2.38 (t, 2H, J=7.3 Hz), 2.56 (t, 2H, J=7.6 Hz), 2.91 (m, 1H), 3.16 (brs, 2H), 4.42 (brs, 1H), 7.11 (d, 2H, J=8.5 Hz), 7.42 (d, 2H, J=8.5 Hz), 7.47 (brs, 1H).

I-112 mp: 79–80° C. $^1$H-NMR (CDCl$_3$) δ ppm: 1.36 (s, 9H), 1.52–1.62 (m, 2H), 1.67–1.76 (m, 2H), 2.22 (t, 2H, J=7.4 Hz), 3.16 (q, 2H, J=6.3 Hz), 3.78 (s, 3H), 4.33 (d, 2H, J=5.4 Hz), 4.62 (brs, 1H), 6.20 (brs, 1H), 6.85 (d, 2H, J=8.8 Hz), 7.19 (d, 2H, J=8.8 Hz).

I-113 mp: 125–126° C. $^1$H-NMR (CDCl$_3$) δ ppm: 1.38 (s, 9H), 1.62–1.70 (m, 2H), 1.76–1.88 (m, 2H), 2.46 (t, 2H, J=7.4 Hz), 3.22 (q, 2H, J=6.1 Hz), 4.22 (t, 1H, J=6.1 Hz), 7.24 (dd, 1H, J=8.9, 2.3 Hz), 7.36 (d, 1H, J=2.3 Hz), 7.65 (brs, 1H), 8.29 (d, 1H, J=8.9 Hz).

I-114 mp: 89–91° C. $^1$H-NMR (CDCl$_3$) δ ppm: 0.92 (t, 3H, J=7.0 Hz), 1.06 (d, 6H, J=7.0 Hz), 1.36 (m, 1H), 1.50–1.72 (m, 5H), 1.94–2.06 (m, 2H), 2.26 (m, 1H), 2.60 (t, 2H, J=7.7 Hz), 2.84 (t, 2H, J=7.7 Hz), 2.93 (d, 2H, J=6.3 Hz), 3.20 (t, 2H, J=6.6 Hz), 4.30 (brs, 1H), 7.19 (d, 2H, J=8.5 Hz), 7.63 (d, 2H, J=8.5 Hz), 9.15 (brs, 1H).

I-115 mp: 94–95° C. $^1$H-NMR (CDCl$_3$) δ ppm: 0.92 (t, 3H, J=7.5 Hz), 1.03 (t, 3H, J=7.5 Hz), 1.23–1.40 (m, 5H), 1.42–1.65 (m, 6H), 1.75 (m, 1H), 2.02 (m, 1H), 2.24 (t, 2H, J=7.0 Hz), 2.59 (t, 2H, J=8.0 Hz), 2.90 (m, 1H), 3.14 (q, 2H, J=6.6 Hz), 4.20 (m, 1H), 4.40 (d, 2H, J=5.4 Hz), 5.70 (brs, 1H), 7.14 (d, 2H, J=8.1 Hz), 7.18 (d, 2H, J=8.1 Hz).

I-116 mp: 89–91° C. $^1$H-NMR (CDCl$_3$) δ ppm: 0.97 (t, 3H, J=7.3 Hz), 1.02 (t, 31, J=7.5 Hz), 1.35 (d, 3H, J=7.0 Hz), 1.40–1.90 (m, 9H), 2.04 (m, 1H), 2.37 (t, 2H, J=7.0 Hz), 2.90 (m, 1H), 3.17 (q, 2H, J=6.6 Hz), 3.93 (t, 2H, J=6.6 Hz), 4.32 (m, 1H), 6.84 (d, 2H, J=9.0 Hz), 7.31 (brs, 1H), 7.40 (d, 2H, J=9.0 Hz).

I-117 mp: 110–111° C. $^1$H-NMR (CDCl$_3$) δ ppm: 1.02 (t, 3H, J=7.5 Hz), 1.34 (d, 3H, J=6.6 Hz), 1.45–1.70 (m, 3H), 1.75–1.85 (m, 2H), 2.05 (m, 1H), 2.36 (t, 2H, J=7.5 Hz), 2.90 (m, 1H), 3.16 (q, 2H, J=6.6 Hz), 3.78 (s, 3H), 4.50 (m, 1H), 6.84 (d, 2H, J=6.8 Hz), 7.42 (d, 2H, J=6.8 Hz), 7.48 (brs, 1H).

I-118 mp: 113–115° C. $^1$H-NMR (CDCl$_3$) δ ppm: 0.92 (t, 3H, J=7.0 Hz), 1.20–1.34 (m, 1H), 1.37 (d, 6H, J=7.0 Hz), 1.48–1.70 (m, 3H), 2.43 (q, 2H, J=6.6 Hz), 2.58 (t, 2H, J=7.7 Hz), 3.10–3.31 (m, 3H), 4.75 (m, 1H), 6.04 (d, 1H, J=15.0 Hz), 6.77 (dt, 1H, J=7.7, 15.0 Hz), 7.14 (d, 2H, J=8.4 Hz), 7.55 (d, 2H, J=8.4 Hz), 7.85 (brs, 1H).

I-119 mp: 139–140° C. $^1$H-NMR (CDCl$_3$) δ ppm: 1.19 (s, 9H), 1.47 (m, 2H), 1.61 (m, 2H), 2.18 (t, 2H, J=7.6 Hz), 3.03 (q, 2H, J=6.3 Hz), 4.09 (t, 1H, J=5.9 Hz), 6.85 (brd, 1H, J=8.0 Hz), 7.00 (t, 1H, J=8.0 Hz), 7.16 (brd, 1H, J=8.0), 7.48 (brs, 1H), 7.57 (brs, 1H).

I-120 mp: 183° C. $^1$H-NMR (CDCl$_3$) δ ppm: 0.91 (t, 3H, J=7.3 Hz), 1.20–1.58 (m, 61–1), 1.40 (s, 9H), 2.07 (dd, 1H, J=12.9, 3.1 Hz), 2.52 (t, 21H, J=7.7 Hz), 2.95 (dd, 2H, J=11.5, 2.5Hz), 3.46 (m, 1H), 3.88–4.07 (m, 3H), 6.47 (s, 1H), 7.08 (d, 2H, J=8.5 Hz), 7.22 (d, 2H, J=8.5 Hz).

I-121 mp: 163–166° C. $^1$H-NMR (CDCl$_3$) δ ppm: 0.91 (t, 3H, J=7.3 Hz), 1.32–1.62 (m, 6H), 1.45 (s, 9H), 1.95–2.07 (m, 3H), 2.20 (m, 1H), 2.46 (td, 1H, J=10.4, 3.7 Hz), 2.37 (t, 2H, I-122
mp: 188–189° C. $^1$H-NMR (CDCl$_3$) δ ppm: 0.91 (t, 3H, J=7.5 Hz), 1.25–1.41 (m, 2H), 1.42 (s, 9H), 1.50–1.62 (m, 2H), 1.78–1.95 (m, 4H), 2.00–2.20 (m, 6H), 2.57 (t, 2H, J=7.5 Hz), 3.99 (brs, 1H), 7.10 (brs, 1H), 7.12 (d, 2H, J=6.5 Hz), 7.41 (d, 2H, J=6.5 Hz).
I-123
mp: 197–198° C. $^1$H-NMR (CDCl$_3$) δ ppm: 0.91 (t, 3H, J=7.5 Hz), 1.24–1.40 (m, 2H), 1.39 (s, 9H), 1.50–1.70 (m 2H), 1.99 (brs, 12H), 2.56 (t, 2H, J=7.5 Hz), 3.47 (brs, 1H), 7.10 (s, 1H), 7.11 (d, 2H, J=8.5 Hz), 7.38 (d, 2H, J=8.5 Hz).
I-124
mp: 258–260° C. $^1$H-NMR (CDCl$_3$) δ ppm: 1.20–1.40 (m, 2H), 1.41 (s, 9H), 1.62–1.81 (m, 2H), 2.03–2.35 (m, 5H), 2.37 (s, 3H), 2.71 (s, 3H), 3.32 (m, 1H), 3.64 (d, 1H, J=8.4 Hz), 7.08 (brs, 1H), 7.24 (m, 1H), 7.33 (m, 2H), 7.60 (d, 1H, J=8.1 Hz), 7.77 (s, 1H), 7.80 (d, 1H, J=8.4 Hz), 8.14 (m, 1H).
I-125
mp: 297–299° C. $^1$H-NMR (DMSO-d$_6$) δ ppm: 1.27 (s, 9H), 1.28–1.56 (m, 4H), 1.80–2.01 (m, 4H), 2.47 (m, 1H), 2.76 (brs, 1H), 3.05 (m, 2H), 6.78 (d, 1H, J=9.0 Hz), 7.23 (d, 1H, J=9.0 Hz), 7.46 (dd, 1H, J=2.0, 9.0 Hz), 8.03 (d, 1H, J=2.0 Hz).
I-126
mp: 198–199° C. $^1$H-NMR (CDCl$_3$) δ ppm: 1.18–1.39 (m, 2H), 1.40 (s, 9H), 1.60–1.79 (m, 2H), 1.98–2.35 (m, 5H), 3.30 (m, 1H), 3.67 (d, 1H, J=9.6 Hz), 5.89 (tt, 1H, J=3.0, 50.0 Hz), 6.97 (d, 1H, J=7.8 Hz), 7.21 (s, 1H), 7.30–7.40 (m, 2H), 7.55 (s, 1H).
I-127
mp: 262–264° C. $^1$H-NMR (CDCl$_3$) δ ppm: 1.20–1.39 (m, 2H), 1.41 (s, 9H), 1.60–1.80 (m, 2H), 2.00–2.36 (m, 5H), 2.57 (s, 3H), 3.33 (m, 1H), 3.62 (d, 1H, J=8.7 Hz), 7.28 (brs, 1H), 7.62 (d, 2H, J=8.7 Hz), 7.94 (d, 2H, J=8.7 Hz).
I-128
mp: 252–254° C. $^1$H-NMR (CDCl$_3$) δ ppm: 1.18–1.39 (m, 2H), 1.40 (s, 9H), 1.58–1.79 (m, 2H), 1.99–2.30 (m, 5H), 2.46 (s, 3H), 3.32 (m, 1H), 3.64 (m, 1H), 7.11 (brs, 1H), 7.23 (d, 2H, J=9.0 Hz), 7.44 (d, 2H, J=9.0 Hz).
I-129
mp:>300° C. $^1$H-NMR (CDCl$_3$+CD$_3$OD) δ ppm: 1.30–1.45 (m, 2H), 1.42 (s, 9H), 1.70–1.88 (m, 2H), 2.10–2.37 (m, 4H), 2.52 (m, 1H), 3.34 (m, 1H), 7.43–7.54 (m, 3H), 7.82 (d, 1H, J=6.7 Hz), 7.88 (d, 1H, J=8.5 Hz), 7.98–8.07 (m, 2H), 8.44 (s, 1H), 8.46 (s, 1H).
I-130
mp: 123–124° C. $^1$H-NMR (CDCl$_3$) δ ppm: 1.18–1.34 (m, 2H), 1.40 (s, 9H), 1.62–1.75 (m, 2H), 2.00–2.28 (m, 5H), 3.31 (m, 1H), 3.61 (d, 1H, J=9.5 Hz), 5.59 (s, 1H), 7.17 (s, 1H), 7.30–7.37 (m, 6H), 7.41 (d, 1H, J=8.5 Hz), 7.84 (d, 1H, J=2.1 Hz).
I-131
mp: 202–204° C. $^1$H-NMR (CDCl$_3$) δ ppm: 1.27–1.38 (m, 2H), 1.38 (s, 9H), 1.62–1.75 (m, 2H), 1.97–2.04 (m, 2H), 2.18–2.27 (m, 3H), 3.26 (m, 1H), 3.81 (s, 3H), 4.62 (d, 1H, J=7.9 Hz), 7.12 (d, 1H, J=7.8 Hz), 7.40 (t, 1H, J=7.8 Hz), 7.51 (s, 3H), 7.61 (d, 1H, J=7.8 Hz), 7.71 (s, 1H), 8.21 (brs, 1H).
I-132
mp: 236–237° C. $^1$H-NMR (CDCl$_3$) δ ppm: 1.23–1.43 (m, 2H), 1.41 (s, 9H), 1.66–1.80 (m, 2H), 2.08–2.12 (m, 2H), 2.23–2.31 (m, 3H), 3.34 (m, 1H), 3.87 (d, 1H, J=9.5 Hz), 4.02 (s, 3H), 7.30 (td, 1H, J=1.1 Hz), 7.36 (s, 1H), 7.39 (td, 1H, J=7.3, 1.5 Hz), 7.53 (brd, 1H, J=7.3 Hz), 7.84 (brd, 1H, J=7.3 Hz), 8.05 (s, 1H), 8.73 (s, 1H).
I-133
mp: 198–200° C. $^1$H-NMR (CDCl$_3$) δ ppm: 0.93 (t, 3H, J=7.3 Hz), 0.97 (t, 3H, J=6.7 Hz), 1.18–1.81 (m, 7H), 1.39 (s, 9H), 1.98–2.05 (m, 2H), 2.21–2.24 (m, 3H), 3.29 (m, 1H), 4.00 (dd, 1H, J=10.7, 6.7 Hz), 4.09 (dd, 1H, J=10.7, 6.1 Hz), 4.27 (d, 1H, J=9.8 Hz), 6.37 (d, 1H, J=15.9 Hz), 7.47 (d, 2H, J=8.5 Hz), 7.59 (d, 2H, J=8.5 Hz), 7.62 (d, 1H, J=15.9 Hz), 7.83 (brs, 1H).
I-134
mp: 212–213° C. $^1$H-NMR (CDCl$_3$) δ ppm: 1.21–1.32 (m, 2H), 1.39 (s, 9H), 1.59–1.73 (m, 2H), 1.99–2.04 (m, 2H), 2.10–2.26 (m, 3H), 3.26 (m, 1H), 3.72 (d, 1H, J=9.6 Hz), 6.74 (m, 1H), 7.02 (d, 2H, J=7.4 Hz), 7.11 (t, 1H, J=7.4 Hz), 7.13–7.19 (m, 2H), 7.22–7.26 (m, 2H), 7.34 (t, 2H, J=7.4 Hz).
I-135
mp: 294–296° C. $^1$H-NMR (DMSO-d$_6$) δ ppm: 1.27 (s, 9H), 1.28–1.55 (m, 4H), 1.81–2.05 (m, 4H), 2.26 (m, 1H), 2.98–3.20 (m, 2H), 6.78 (d, 1H, J=9.0 Hz), 7.31 (t, 1H, J=7.5 Hz), 7.54–7.72 (m, 5H), 7.94 (brs, 1H).
I-136
mp:>300° C. $^1$H-NMR (DMSO-d$_6$) δ ppm: 1.28 (s, 9H), 1.29–1.59 (m, 4H), 1.81–2.02 (m, 4H), 2.27 (m, 1H). 3.06 (m, 1H), 6.81 (d, 1H, J=8.7 Hz), 7.38 (t, 1H, J=7.2 Hz), 7.48 (t, 2H, J=7.2 Hz), 7.62–7.81 (m, 10H), 9.93 (brs, 1H).
I-137
mp: 291–292° C. $^1$H-NMR (CDCl$_3$) δ ppm: 1.25–1.39 (m, 2H), 1.41 (s, 9H), 1.61–1.80 (m, 2H), 2.01–2.36 (m, 5H), 3.32 (m, 1H), 3.63 (d, 1H, J=9.3 Hz), 7.20 (brs, 1H), 7.53–7.74 (m, 8H).
I-138
mp: 259–262° C. $^1$H-NMR (CD$_3$OD) δ ppm: 1.40 (s, 9H), 1.40–1.80 (m, 4H), 2.00–2.30 (m, 4H), 2.45 (m, 1H), 3.00 (s, 3H), 3.15–3.30 (m, 2H), 7.90 (d, 1H, J=8.4 Hz), 8.12 (d, 1H, J=9.0 Hz), 8.39 (d, 1H, J=9.0 Hz), 8.72 (s, 1H), 8.92 (d, 1H, J=8.4 Hz), 10.4 (s, 1H).
I-139
mp: 265–268° C. $^1$H-NMR (CDCl$_3$) δ ppm: 1.25–1.40 (m, 2H), 1.40 (s, 9H), 168–1.81 (m, 2H), 2.05–2.10 (m, 2H), 2.23–2.37 (m, 3H), 3.32 (m, 1H), 4.27 (d, 1H, J=9.1 Hz), 7.53 (t, 1H, J=7.9 Hz), 7.63 (td, 1H, J=7.9, 1.4 Hz), 7.77 (d, 1H, J=7.9 Hz), 8.03 (d, 1H, J=7.9 Hz), 8.37 (brs, 1H), 8.85–8.86 (m, 2H).
I-140
mp: 258–260° C. $^1$H-NMR (CDCl$_3$) δ ppm: 1.20–1.40 (m, 2H), 1.41 (s, 9H), 1.52–1.8.5 (m, 2H) 2.03–2.35 (m, 5H), 3.34 (m, 1H), 3.75 (m, 1H), 7.35–7.66 (m, 3H), 8.05 (d, 1H, J=9.0 Hz), 8.11 (d, 1H, J=9.0 Hz), 8.40 (brs, 1H), 8.83 (s, 1H).
I-141
mp: 205–206° C. $^1$H-NMR (CDCl$_3$) δ ppm: 1.20–1.37 (m, 2H), 1.40 (s, 9H), 1.43–1.62 (m, 2H), 1.90–2.01 (m, 2H), 2.02–2.23 (m, 3H), 3.27 (m, 1H), 3.63 (d, 1H, J=9.6 Hz), 3.70 (s, 3H), 6.64 (d, 1H, J=8.8 Hz), 7.28–7.41 (m, 5H), 7.45 (brs, 1H), 8.26 (d, 1H, J=8.8 Hz).
I-142
mp: 277–280° C. $^1$H-NMR (CDCl$_3$) δ ppm: 0.23–0.34 (m, 2H), 1.34 (s, 9H), 1.34–1.55 (m, 5H), 1.76–1.80 (m, 2H), 2.97 (m, 1H), 3.31 (d, 1H, J=9.6 Hz), 7.18 (s, 1H), 7.50–7.59 (m, 4H), 7.77 (dd, 1H, J=7.4, 1.0 Hz), 7.91–7.98 (m, 2H), 8.39 (dd, 1H, J=7.4, 1.9 Hz).
I-143
mp: 202–203° C. $^1$H-NMR (CDCl$_3$) δ ppm: 1.23–1.40 (m, 2H), 1.40 (s, 9H), 1.57–1.71 (m, 2H), 2.05–2.10 (m, 2H), 2.18–2.28 (m, 3H), 3.31 (m, 1H), 3.91 (s, 3H), 3.93 (s, 3H), 4.05 (d, 1H, J=9.5 Hz), 8.15 (s, 1H), 9.56 (s, 1H).

I-144
mp: 177–178° C. ¹H-NMR (CDCl₃) δ ppm: 1.27–1.39 (m, 2H), 1.40 (s, 9H), 1.65–1.79 (m, 2H), 2.04–2.07 (m, 2H), 2.12–2.34 (m, 3H), 3.22 (m, 1H), 3.93 (d, 1H, J=9.1 Hz), 6.90–7.03 (m, 3H), 7.25 (m, 1H), 7.77 (dd, 1H, J=4.9, 1.7 Hz), 7.81 (brs, 1H), 8.72 (dd, 1H, J=7.8, 1.5 Hz).

I-145
mp:>300° C. ¹H-NMR (DMSO-d₆) δ ppm: 1.30 (s, 9H), 1.44–1.70 (m, 4H), 2.05–2.19 (m, 4H), 2.73 (m, 1H), 3.18 (m, 1H), 6.86 (d, 1H, J=8.8 Hz), 7.62 (t, 2H, J=8.5 Hz), 7.86 (t, 2H, J=8.5 Hz), 7.89 (d, 2H, J=8.5 Hz), 8.16 (d, 2H, J=8.5 Hz).

I-146
mp: 240–242° C. ¹H-NMR (DMSO-d₆) δ ppm: 1.26–1.53 (m, 4H), 1.27 (s, 9H), 1.74–1.83 (m, 2H), 1.90–1.97 (m, 2H), 2.26 (m, 1H), 3.04 (m, 1H), 6.59 (brs, 1H), 6.74–6.79 (m, 3H), 7.74 (s, 1H), 10.32 (s, 1H), 12.80 (s, 1H).

I-147
mp: 167–169° C. ¹H-NMR (CDCl₃) δ ppm: 1.05–1.28 (m, 2H), 1.38 (s, 9H), 1.47–1.70 (m, 2H), 1.80–2.00 (m, 3H), 2.13–2.25 (m, 2H), 2.75 (t, 2H, J=6.9 Hz), 3.24 (m, 1H), 3.49 (dt, 2H, J=6.3, 6.9 Hz), 3.58 (d, 1H, J=8.7 Hz), 3.87 (s, 6H), 5.40 (brs, 1H), 6.71 (m, 2H), 6.82 (d, 1H, J=8.7 Hz).

I-148
mp: 171–172° C. ¹H-NMR (CDCl₃) δ ppm: 1.16–1.38 (m, 2H), 1.39 (s, 9H), 1.50–1.79 (m, 4H), 1.85–2.02 (m, 3H), 2.15–2.30 (m, 2H), 2.35–2.56 (m, 6H), 3.25 (m, 1H), 3.33 (q, 2H, J=6.0 Hz), 3.63 (d, 1H, J=9.0 Hz), 3.72 (t, 4H, J=4.6 Hz), 6.77 (brs, 1H).

I-149
¹H-NMR (CDCl₃) δ ppm: 1.20–1.36 (m, 2H), 1.28 (t, 3H, J=7.2 Hz), 1.39 (s, 9H), 1.45–1.70 (m, 2H), 1.85–2.30 (m, 7H), 2.43 (s, 3H), 3.05–3.42 (m, 3H), 3.46–3.80 (m, 3H), 7.31 (d, 1H, J=7.2 Hz), 7.40–7.52 (m, 3H), 8.18 (brs, 1H).

I-150
mp: 203–204° C. ¹H-NMR (CDCl₃) δ ppm: 1.15–1.37 (m, 2H), 1.39 (s, 9H), 1.42–1.70 (m, 2H), 1.85–2.29 (m, 5H), 2.76 (t, 2H, J=6.0 Hz), 3.26 (m, 1H), 3.49 (q, 2H, J=6.0 Hz), 3.61 (m, 1H), 4.03 (s, 2H), 5.88 (brs, 1H), 7.15 (dd, 1H, J=7.0, 8.8 Hz), 7.30–7.35 (m, 2H).

I-151
mp: 181–183° C. ¹H-NMR (CDCl₃) δ ppm: 1.15–1.30 (m, 2H), 1.39 (s, 9H), 1.45–1.64 (m, 2H), 1.88–2.05 (m, 3H), 2.15–2.25 (m, 2H), 2.69 (t, 2H, J=6.0 Hz), 3.28 (m, 1H), 3.47 (q, 2H, J=6.0 Hz), 3.58 (d, 1H, J=9.9 Hz), 3.87 (s, 2H), 5.83 (brs, 1H), 7.00 (m, 1H), 7.20 (m, 2H).

I-152
mp: 222–224° C. ¹H-NMR (CDCl₃) δ ppm: 1.16–1.37 (m, 2H), 1.39 (s, 9H), 1.49–1.70 (m, 2H), 1.90–2.25 (m, 5H), 3.26 (m, 1H), 3.36 (t, 2H, J=6.4 Hz), 3.66 (dt, 3H, J=6.0, 6.4 Hz), 5.87 (t, 1H, J=6.0 Hz), 7.58 (s, 1H), 7.68 (dd, 1H, J=7.0, 8.5 Hz), 7.83 (dd, 1H, J=7.0, 8.5 Hz), 8.19 (t, 2H, J=8.5 Hz).

I-153
mp: 207–209° C. ¹H-NMR (CDCl₃) δ ppm: 1.05–1.25 (m, 2H), 1.38 (s, 9H), 1.40–2.03 (m, 10H), 2.05–2.25 (m, 2H), 2.58 (s, 3H), 2.76 (m, 1H), 3.05–3.35 (m, 2H), 3.97 (d, 1H, J=9.5 Hz), 4.94 (t, 1H, J=4.0 Hz), 8.42 (d, 1H, J=5.5 Hz), 8.97 (d, 1H, J=5.5 Hz).

I-154
mp: 184–185° C. ¹H-NMR (CDCl₃) δ ppm: 1.05–1.25 (m, 2H), 1.37 (s, 9H), 1.50–1.69 (m, 2H), 1.85–2.05 (m, 3H), 2.10–2.21 (m, 2H), 3.24 (m, 1H), 3.64 (m, 1H), 4.87 (s, 1H), 4.88 (s, 1H), 5.67 (brs, 1H), 7.42 (d, 2H, J=5.5 Hz), 7.52 (m, 2H), 7.78 (m, 1H), 7.82 (m, 1H), 7.95 (d, 2H, J=7.0 Hz).

I-155
mp: 208–210° C. ¹H-NMR (DMSO-d₆) δ ppm: 1.26 (s, 9H), 1.27–1.50 (m, 4H), 1.75–2.00 (m, 4H), 2.16 (m, 1H), 2.81 (s, 3H), 3.02 (m, 1H), 6.79 (d, 1H, J=8.5 Hz), 10.00 (s, 1H), 10.66 (s, 1H).

I-156
mp: 256–257° C. ¹H-NMR (CDCl₃) δ ppm: 1.20–1.39 (m, 2H), 1.41 (s, 9H), 1.60–1.81 (m, 2H), 2.01–2.35 (m, 5H), 2.69 (t, 2H, J=6.0 Hz), 3.11 (t, 2H, J=6.0 Hz), 3.30 (m, 1H), 3.61 (d, 1H, J=9.3 Hz), 7.21 (d, 1H, J=8.0 Hz), 7.31 (s, 1H), 7.70 (d, 1H, J=8.0 Hz), 7.99 (s, 1H).

I-157
mp: 269–271° C. ¹H-NMR (CDCl₃) δ ppm: 1.20–1.45 (m, 2H), 1.41 (s, 9H), 1.70–1.90 (m, 2H), 2.10–2.45 (m, 5H), 3.37 (m, 1H), 3.68 (m, 1H), 7.45 (dd, 1H, J=4.0, 8.0 Hz), 7.53 (brs, 1H), 7.72 (t, 1H, J=8.0 Hz), 7.83 (d, 1H, J=8.0 Hz), 8.02 (d, 1H, J=8.0 Hz), 8.18 (d, 1H, J=8.0 Hz), 8.93 (d, 1H, J=4.0 Hz).

I-158
mp: 253–255° C. ¹H-NMR (CDCl₃) δ ppm: 1.20–1.40 (m, 2H), 1.42 (s, 9H), 1.60–1.90 (m, 2H), 2.06–2.50 (m, 5H), 2.72 (s, 3H), 3.33 (m, 1H), 3.78 (d, 1H, J=9.2 Hz), 7.52 (t, 1H, J=7.0 Hz), 7.62–7.80 (m, 2H), 7.94 (brs, 1H), 8.05 (d, 1H, J=8.5 Hz), 8.20 (s, 1H).

I-159
mp: 253–255° C. ¹H-NMR (CDCl₃) δ ppm: 1.20–1.39 (m, 2H), 1.40 (s, 9H), 1.60–1.80 (m, 2H), 1.98–2.30 (m, 5H), 2.71 (s, 3H), 3.31 (m, 1H), 3.68 (d, 1H, J=9.0 Hz), 7.41 (brs, 1H), 7.61 (d, 2H, J=9.0 Hz), 7.70 (d, 2H, J=9.0 Hz).

I-160
mp: 211–212° C. ¹H-NMR (CDCl₃) δ ppm: 1.20–1.32 (m, 2H), 1.39 (t, 3H, J=7.0 Hz), 1.40 (s, 9H), 1.55–1.79 (m, 2H), 1.98–2.35 (m, 5H), 3.31 (m, 1H), 3.65 (d, 1H, J=9.5 Hz), 4.03 (q, 2H, J=7.0 Hz), 6.64 (d, 1H, J=8.0 Hz), 6.92 (d, 1H, J=8.0 Hz), 7.10 (s, 1H), 7.19 (t, 1H, J=8.0 Hz), 7.30 (brs, 1H).

I-161
mp: 202–203° C. ¹H-NMR (CDCl₃) δ ppm: 0.96 (t, 1H, J=7.3 Hz), 1.29–1.39 (m, 2H), 1.40 (s, 9H), 1.41–1.58 (m, 2H), 1.60–1.80 (m, 4H), 1.98–2.31 (m, 5H), 3.31 (m, 1H), 3.66 (d, 1H, J=8.5 Hz), 3.96 (t, 2H, J=6.4 Hz), 6.64 (d, 1H, J=8.0 Hz), 6.90 (d, 1H, J=8.0 Hz), 7.11 (s, 1H), 7.19 (t, 1H, J=8.0 Hz), 7.31 (brs, 1H).

I-162
mp: 177–180° C. ¹H-NMR (CDCl₃) δ ppm: 1.18–1.38 (m, 2H), 1.39 (s, 9H), 1.59–1.78 (m, 2H), 1.95–2.05 (m, 2H), 2.07–2.25 (m, 3H), 3.26 (m, 1H), 3.46 (s, 3H), 4.17 (d, 1H, J=9.5 Hz), 5.15 (s, 2H), 6.77 (d, 1H, J=8.0 Hz), 7.10–7.23 (m, 2H), 7.34 (s, 1H), 7.58 (s, 1H).

I-163
mp: 175–178° C. ¹H-NMR (DMSO-d₆) δ ppm: 1.27 (s, 9H), 1.28–1.50 (m, 4H), 1.78–2.00 (m, 4H), 2.22 (m, 1H), 2.96–3.15 (m, 2H), 6.67 (m, 1H), 6.79 (d, 1H, J=8.5 Hz), 7.18 (m, 2H), 7.38 (s, 1H), 9.81 (s, 1H).

I-164
mp: 232–233° C. ¹H-NMR (CDCl₃) δ ppm: 0.97 (t, 3H, J=7.3 Hz), 1.22–1.30 (m, 2H), 1.40 (s, 9H), 1.44–1.51 (m, 2H), 1.67–1.77 (m, 4H), 2.02–2.24 (m, 5H), 3.22 (m, 1H), 3.62 (d, 1H, J=9.6 Hz), 4.25 (t, 2H, J=6.8 Hz), 6.71 (d, 1H, J=8.4 Hz), 7.01 (brs, 1H), 7.91 (dd, 1H, J=8.4, 3.3 Hz), 8.08 (d, 1H, J=3.3 Hz).

I-165
mp: 199–200° C. ¹H-NMR (CDCl₃) δ ppm: 0.96 (t, 3H, J=7.4 Hz), 1.24–1.50 (m, 4H), 1.40 (s, 9H), 1.67–1.76 (m, 3H), 2.03–2.08 (m, 2H), 2.24–2.35 (m, 3H), 3.29 (m, 1H), 3.76 (d, 1H, J=9.1 Hz), 3.91 (t, 2H, J=6.6 Hz), 6.41 (dd, 1H, J=8.8, 2.5 Hz), 6.55 (d, 1H, J=2.5 Hz), 6.82 (d, 1H, J=8.8 Hz), 7.43 (s, 1H), 8.95 (s, 1H).

I-166
mp: 215–218° C. ¹H-NMR (CDCl₃+CD₃OD) δ ppm: 0.97 (t, 3H, J=7.4 Hz), 1.24–1.40 (m, 4H), 1.39 (s, 9H), 1.42–1.50

(m, 2H), 1.54–1.72 (m, 2H), 1.76–1.82 (m, 2H), 1.91–2.00 (m, 2H), 2.06–2.22 (m, 3H), 3.24 (m, 1H), 4.00 (t, 2H, J=6.6 Hz), 6.78 (d, 1H, J=8.8 Hz), 6.98 (dd, 1H, J=8.8, 2.5 Hz), 7.09 (d, 1H, J=8.8 Hz).

I-167 mp: 212–213° C. $^1$H-NMR (CDCl$_3$) δ ppm: 0.96 (t, 3H, J=7.5 Hz), 1.26–1.34 (m, 2H), 1.40 (s, 9H), 1.45–1.50 (m, 2H), 1.68–1.77 (m, 4H), 2.03–2.08 (m, 2H), 2.17 (m, 1H), 2.26–2.29 (m, 2H), 3.29 (m, 1H), 3.60 (d, 1H, J=9.0 Hz), 4.25 (t, 2H, J=6.8 Hz), 6.71 (d, 1H, J=8.4 Hz), 7.01 (brs, 1H), 7.91 (dd, 1H, J=8.4, 3.3 Hz), 8.08 (d, 1H, J=3.3 Hz).

I-168 mp: 230–232° C. $^1$H-NMR (CDCl$_3$) δ ppm: 1.22–1.35 (m, 2H), 1.40 (s, 9H), 1.63–1.77 (m, 2H), 2.03–2.08 (m, 2H), 2.15–2.29 (m, 3H), 3.31 (m, 1H), 3.63 (d, 1H, J=9.3 Hz), 6.89 (d, 1H, J=9.4 Hz), 7.10 (brd, 2H, J=7.4 Hz), 7.12 (brs, 1H), 7.18 (t, 1H, J=7.4 Hz), 7.36 (brt, 2H, J=7.4 Hz), 8.09–8.15 (m, 2H).

I-169 mp: 159–160° C. $^1$H-NMR (CDCl$_3$) δ ppm: 0.97 (t, 3H, J=7.3), 1.20–1.35 (m, 2H), 1.40 (s, 9H), 1.37–1.49 (m, 2H), 1.61–1.78 (m, 4H), 2.05–2.08 (m, 2H), 2.23–2.26 (m, 2H), 2.36 (s, 3H), 2.97 (brs, 1H), 3.32 (m, 1H), 3.86 (brs, 1H), 4.30 (t, 2H, J=6.5 Hz), 6.25 (s, 1H), 7.92 (brs, 1H).

I-170 mp: 180–181° C. $^1$H-NMR (CDCl$_3$) δ ppm: 0.88–0.89 (m, 2H), 1.39 (s, 9H), 1.42–1.60 (m, 2H), 1.86–1.90 (m, 2H), 2.04–2.09 (m, 2H), 2.42 (s, 3H), 2.91 (m, 1H), 3.20 (m, 1H), 3.63 (d, 1H, J=9.2 Hz), 6.38 (s, 1H), 7.15 (m, 2H), 7.28 (m, 1H), 7.45 (m, 2H), 7.84 (brs, 1H).

I-171 mp: 173–174° C. $^1$H-NMR (CDCl$_3$) δ ppm: 0.98 (t, 3H, J=7.5 Hz), 1.29–1.40 (m, 2H), 1.40 (s, 9H), 1.55 (m, 2H), 1.62–1.83 (m, 4H), 2.09–2.12 (m, 2H), 2.24–2.32 (m, 3H), 3.32 (m, 1H), 3.63 (d, 1H, J=9.5 Hz), 3.99 (t, 2H, J=6.4 Hz), 7.22 (dd, 1H, J=9.4, 2.7 Hz), 7.66 (d, 1H, J=2.7 Hz), 8.63 (d, 1H, J=9.4 Hz), 10.17 (s, 1H).

I-172 mp: 238–242° C. $^1$H-NMR (CDCl$_3$) δ ppm: 0.96 (t, 3H, J=7.3 Hz), 1.23–1.52 (m, 4H), 1.40 (s, 9H), 1.61–1.78 (m, 4H), 2.05–2.28 (m, 5H), 3.30 (m, 1H), 3.66 (d, 1H, J=9.4 Hz), 3.84 (brs, 2H), 3.90 (t, 2H, J=6.4 Hz), 6.32–6.35 (m, 2H), 6.96 (brs, 1H), 6.97 (d, 1H, J=9.4 Hz).

I-173 mp: 165–166° C. $^1$H-NMR (CDCl$_3$) δ ppm: 1.23–1.26 (m, 2H), 1.40 (s, 9H), 1.67–1.72 (m, 2H), 2.01–2.06 (m, 2H), 2.11–2.28 (m, 3H), 3.31 (m, 1H), 3.60 (s, 2H), 3.69 (s, 3H), 4.02 (brs, 1H), 7.01 (d, 1H, J=8.0 Hz), 7.25 (t, 1H, J=8.0 Hz), 7.43 (d, 1H, J=8.0 Hz), 7.49 (brs, 1H), 7.51 (brs, 1H).

I-174 mp: 264–265° C. $^1$H-NMR (CDCl$_3$+CD$_3$OD) δ ppm: 1.26–1.29 (m, 2H), 1.39 (s, 9H), 1.62–1.69 (m, 2H), 1.96–2.00 (m, 2H), 2.18–2.21 (m, 3H), 3.25 (m, 1H), 3.58 (s, 2H), 7.01 (d, 1H, J=7.5 Hz), 7.26 (t, 1H, J=7.5 Hz), 7.42 (brs, 1H), 7.50 (d, 1H, J=7.5 Hz).

I-175 mp: 90–94° C. $^1$H-NMR (CDCl$_3$) δ ppm: 1.16–1.23 (m, 2H), 1.37 (s, 9H), 1.44–1.56 (m, 2H), 1.73–1.85 (m, 3H), 2.11–2.15 (m, 2H), 3.57 (t, 2H, J=6.4 Hz), 3.21 (m, 1H), 3.58 (m, 2H), 3.84 (d, 1H, J=9.3 Hz), 5.56 (brs, 1H), 7.01 (s, 1H), 7.11 (t, 1H, J=7.5 Hz), 7.21 (t, 1H, J=7.5 Hz), 7.38 (d, 1H, J=7.5 Hz), 7.59 (d, 1H, J=7.5 Hz), 8.24 (brs, 1H).

I-176 mp: 116–118° C. $^1$H-NMR (CDCl$_3$) δ ppm: 1.18–1.38 (m, 2H), 1.40 (s, 9H), 1.60–1.79 (m, 2H), 1.95–2.30 (m, 5H), 3.30 (m, 1H), 3.69 (m, 1H), 3.80 (s, 3H), 4.64 (s, 2H), 6.67 (d, 1H, J=8.0 Hz), 7.00 (d, 1H, J=8.5 Hz), 7.15–7.24 (m, 2H), 7.32 (brs, 1H).

I-177 mp: 219–220° C. $^1$H-NMR (DMSO-d$_6$) δ ppm: 1.27 (s, 9H), 1.28–1.50 (m, 4H), 1.75–2.01 (m, 4H), 2.18–2.30 (m, 1H), 2.95–3.15 (m, 2H), 4.61 (s, 2H), 6.56 (m, 1H), 6.80 (d, 1H, J=8.5 Hz), 7.16 (m, 2H), 7.28 (brs, 1H), 9.87 (brs, 1H).

I-178 mp: 170–173° C. $^1$H-NMR (CDCl$_3$) δ ppm: 1.18–1.39 (m, 2H), 1.40 (s, 9H), 1.50–1.80 (m, 2H), 1.90–2.33 (m, 5H), 2.36 (s, 6H), 2.75 (t, 2H, J=5.5 Hz), 3.30 (m, 1H), 3.70 (m, 1H), 4.08 (t, 2H, J=5.5 Hz), 6.68 (d, 1H, J=8.0 Hz), 6.94 (d, 1H, J=7.5 Hz), 7.15–7.23 (m, 2H), 7.33 (brs, 1H).

I-179 mp: 191–193° C. $^1$H-NMR (CDCl$_3$) δ ppm: 1.20–1.39 (m, 2H), 1.40 (s, 9H), 1.58–1.80 (m, 2H), 1.98–2.32 (m, 5H), 3.30 (m, 1H), 3.70 (d, 1H, J=9.5 Hz), 4.77 (s, 2H), 6.73 (d, 1H, J=8.0 Hz), 7.04 (d, 1H, J=8.0 Hz), 7.20–7.31 (m, 2H), 7.48 (brs, 1H).

I-180 mp: 174–176° C. $^1$H-NMR (CDCl$_3$) δ ppm: 1.10–1.30 (m, 2H), 1.40 (s, 9H), 1.45–1.65 (m, 2H), 1.81–2.02 (m, 3H), 2.15–2.30 (m, 2H), 2.58 (t, 2H, J=6.5 Hz), 3.25 (m, 1H), 3.37 (dt, 2H, J=5.5, 6.5 Hz), 3.60 (d, 1H, J=9.5 Hz), 3.71 (s, 2H), 5.73 (brs, 1H), 7.20–7.40 (m, 5H).

I-181 mp: 176–178° C. $^1$H-NMR (CDCl$_3$) δ ppm: 1.15–1.30 (m, 2H), 1.39 (s, 9H), 1.45–1.70 (m, 6H), 1.85–2.01 (m, 3H), 2.15–2.28 (m, 2H), 2.63 (t, 2H, J=7.0 Hz), 3.25 (dt, 2H, J=6.0, 7.0 Hz), 3.27 (m, 1H), 3.63 (m, 1H), 5.35 (brs, 1H), 7.17 (m, 3H), 7.29 (m, 2H).

I-182 mp: 152–154° C. $^1$H-NMR (CDCl$_3$) δ ppm: 1.15–1.30 (m, 2H), 1.39 (s, 9H), 1.45–1.65 (m, 2H), 1.85–2.05 (m, 3H), 2.09–2.25 (m, 2H), 3.25 (m, 1H), 3.45 (dt, 2H, J=5.0, 5.0 Hz), 3.55 (t, 2H, J=5.0 Hz), 3.60 (m, 1H), 4.51 (s, 2H), 5.81 (brs, 1H), 7.29–7.40 (m, 5H).

I-183 mp: 208–211° C. $^1$H-NMR (CDCl$_3$) δ ppm: 1.20–1.31 (m, 2H), 1.39 (s, 9H), 1.62–1.68 (m, 2H), 1.98–2.25 (m, 5H), 3.30 (m, 1H), 3.57 (d, 1H, J=9.2 Hz), 4.59 (d, 2H, J=5.8 Hz), 5.76 (brs, 1H), 7.37 (dd, 1H, J=8.4, 2.0 Hz), 7.46–7.52 (m, 2H), 7.69 (brs, 1H), 7.78–7.83 (m, 3H).

I-184 mp: 180–182° C. $^1$H-NMR (CDCl$_3$) δ ppm: 1.22–1.37 (m, 2H), 1.40 (s, 9H), 1.60–1.69 (m, 2H), 2.05–2.09 (m, 2H), 2.21–2.27 (m, 3H), 3.45 (m, 1H), 3.64 (d, 1H, J=9.6 Hz), 4.77 (d, 2H, J=4.9 Hz), 7.43 (d, 1H, J=8.6 Hz), 7.46 (brs, 1H), 7.61 (t, 1H, J=7.7 Hz), 7.73 (t, 1H, J=7.7 Hz), 7.87 (t, 1H, J=7.7 Hz), 8.20 (t, 1H, J=7.7 Hz), 8.24 (d, 1H, J=8.6 Hz).

I-185 mp: 260–261° C. $^1$H-NMR (CDCl$_3$) δ ppm: 1.22–1.32 (m, 2H), 1.39 (s, 9H), 1.60–1.70 (m, 2H), 1.97–2.01 (m, 2H), 2.11 (m, 1H), 2.21–2.24 (m, 2H), 3.30 (m, 1H), 3.61 (d, 1H, J=9.3 Hz), 4.95 (d, 2H, J=6.0 Hz), 5.85 (brs, 1H), 7.33 (d, 1H, J=4.8 Hz), 7.62 (dd, 1H, J=8.4, 6.9 Hz), 7.75 (dd, 1H, J=8.1, 6.9 Hz), 8.00 (d, 1H, J=8.1 Hz), 8.20 (d, 1H, J=8.4 Hz), 8.42 (d, 1H, J=4.8 Hz).

I-186 mp: 231–233° C. $^1$H-NMR (CDCl$_3$) δ ppm: 1.23–1.40 (m, 2H), 1.40 (s, 9H), 1.62–1.76 (m, 2H), 2.04–2.10 (m, 2H), 2.22–2.32 (m, 3H), 3.30 (m, 1H), 3.95 (d, 1H, J=9.3 Hz), 5.04 (d, 2H, J=4.1 Hz), 7.61 (d, 1H, J=5.8 Hz), 7.63 (brs, 1H), 7.65 (dd, 1H, J=8.2, 6.9 Hz), 7.73 (dd, 1H, J=8.5, 6.9 Hz), 7.86 (d, 1H, J=8.2 Hz), 8.10 (d, 1H, J=8.5 Hz), 8.42 (d, 1H, J=5.8 Hz).

I-187 mp: 184–187° C. $^1$H-NMR (CDCl$_3$) δ ppm: 0.97 (t, 3H, J=7.3 Hz), 1.18–1.30 (m, 2H), 1.39 (s, 9H), 1.42–1.65 (m, 4H), 1.70–1.80 (m, 2H), 1.94–2.08 (m, 3H), 2.18–2.26 (m, 2H), 3.29 (m, 1H), 3.61 (d, 1H, J=9.5 Hz), 3.93 (t, 2H, J=6.4 Hz), 4.39 (d, 2H, J=5.5 Hz), 5.67 (brs, 1H), 6.79–6.83 (m, 3H), 7.23 (t, 1H, J=7.6 Hz).

I-188
mp: 224–226° C. $^1$H-NMR (CDCl$_3$) δ ppm: 0.16–1.31 (m, 2H), 1.38 (s, 9H), 1.55–1.70 (m, 2H), 1.92–2.07 (m, 3H), 2.17–2.23 (m, 2H), 3.21 (m, 1H), 3.81 (s, 3H), 3.83 (s, 6H), 4.05 (d, 1H, J=9.8 Hz), 4.34 (d, 2H, J=5.8 Hz), 5.96 (brs, 1H), 6.47 (s, 2H).

I-189
mp: 217–218° C. $^1$H-NMR (CDCl$_3$) δ ppm: 1.15–1.30 (m, 2H), 1.37 (s, 9H), 1.52–1.66 (m, 2H), 1.90–2.06 (m, 3H), 2.13–2.20 (m, 2H), 2.93 (s, 6H), 3.24 (m, 1H), 3.94 (d, 1H, J=9.5 Hz), 4.30 (d, 2H, J=5.5 Hz), 5.73 (brs, 1H), 6.69 (d, 2H, J=8.9 Hz), 7.12 (d, 2H, J=8.9 Hz).

I-190
mp: amorphous solid $^1$H-NMR (CDCl$_3$) δ ppm: 1.17–1.32 (m, 2H), 1.39 (s, 9H), 1.54–1.72 (m, 2H), 1.96–2.13 (m, 3H), 2.18–2.27 (m, 2H), 3.30 (m, 1H), 3.63 (d, 1H, J=9.2 Hz), 4.51 (d, 2H, J=5.8 Hz), 5.82 (brs, 1H), 7.40 (d, 2H, J=8.5 Hz), 8.02 (d, 2H, J=8.5 Hz), 8.64 (s, 1H).

I-191
mp: 126–128° C. $^1$H-NMR (CDCl$_3$) δ ppm: 0.97 (t, 3H, J=7.4 Hz), 1.10–1.28 (m, 2H), 1.36 (s, 9H), 1.42–1.86 (m, 9H), 2.06–2.18 (m, 2H), 3.22 (m, 1H), 3.95 (t, 2H, J=4.5 Hz), 4.16 (brs, 1H), 4.85 (s, 2H), 6.82–6.95 (m, 3H), 7.26 (t, 1H, J=7.8 Hz), 8.54 (brs, 1H).

I-192
mp: 178–181° C. $^1$H-NMR (CDCl$_3$) δ ppm: 0.96 (t, 3H, J=7.3 Hz), 1.18–1.52 (m, 4H), 1.39 (s, 9H), 1.58–1.76 (m, 4H), 1.92–2.00 (m, 2H), 2.02–2.29 (m, 3H), 3.28 (m, 1H), 3.78 (d, 1H, J=9.5 Hz), 3.89 (t, 2H, J=6.6 Hz), 6.00 (brs, 1H), 6.78 (s, 4H), 7.35 (brs, 1H).

I-193
mp: 187–188° C. $^1$H-NMR (CDCl$_3$+CD$_3$OD) δ ppm: 1.21–1.40 (m, 2H), 1.38 (s, 9H), 1.52–1.69 (m, 2H), 1.90–2.00 (m, 2H), 2.02–2.20 (m, 3H), 3.22 (m, 1H), 3.75 (s, 3H), 6.79 (s, 4H).

I-194
mp: 251–253° C. $^1$H-NMR (DMSO-d$_6$) δ ppm: 1.27 (s, 9H), 1.24–1.50 (m, 4H), 1.72–1.83 (m, 2H), 1.91–1.99 (m, 2H), 2.16 (m, 1H), 3.02 (m, 1H), 3.82 (s, 3H), 6.79 (d, 1H, J=8.2 Hz), 7.01 (d, 2H, J=8.8 Hz), 7.85 (d, 2H, J=8.8 Hz), 9.72 (brs, 1H), 8.64 (brs, 1H).

I-195
mp: 183–185° C. $^1$H-NMR (CDCl$_3$) δ ppm: 1.22–1.37 (m, 2H), 1.40 (s, 9H), 1.58–1.75 (m, 2H), 2.05–2.10 (m, 2H), 2.20–2.30 (m, 3H), 3.32 (m, 1H), 3.70 (s, 2H), 3.73 (s, 3H), 6.79 (s, 1H), 8.83 (brs, 1H).

I-196
mp: 185–187° C. $^1$H-NMR (CDCl$_3$) δ ppm: 1.20–1.39 (m, 2H), 1.40 (s, 9H), 1.44 (t, 6H, J=7.0 Hz), 1.60–1.80 (m, 2H), 1.95–2.35 (m, 5H), 3.30 (m, 1H), 3.62 (d, 1H, J=8.9 Hz), 4.06 (q, 2H, J=7.0 Hz), 4.09 (q, 2H, J=7.0 Hz), 6.08 (s, 1H), 7.02 (s, 1H), 7.36 (s, 1H).

I-197
mp: 211–213° C. $^1$H-NMR (CDCl$_3$) δ ppm: 1.20–1.40 (m, 2H), 1.41 (s, 9H), 1.60–1.80 (m, 2H), 2.00–2.36 (m, 5H), 2.61 (s, 3H), 3.32 (m, 1H), 3.64 (d, 1H, J=9.2 Hz), 7.28 (s, 1H), 7.43 (t, 1H, J=7.5 Hz), 7.69 (d, 1H, J=7.5 Hz), 7.85 (d, 1H, J=7.5 Hz), 8.02 (s, 1H).

I-198
mp: 268–269° C. $^1$H-NMR (CDCl$_3$) δ ppm: 1.20–1.39 (m, 2H), 1.40 (s, 9H), 1.42–2.32 (m, 7H), 2.90–3.10 (m, 4H), 3.30 (m, 1H), 3.68 (d, 1H, J=8.8 Hz), 6.59 (s, 1H), 7.18 (d, 1H, J=8.7 Hz), 7.59 (d, 1H, J=8.7 Hz), 7.77 (brs, 1H).

I-199 mp: 221–224° C.
I-200 mp: 237–240° C.
I-201 mp: 87–90° C.
I-202 mp: 222–223° C.
I-203 mp: 255–257° C.
I-204 mp: 234–236° C.
I-205 mp: 208–210° C.
I-206 mp: 217–218° C.
I-207 mp: 275–279° C.
I-208 mp: 248–250° C.
I-209 mp: 256–258° C.
I-210 mp: 270–271° C.
I-211 mp: 219–220° C.
I-212 mp: 260–261° C.
I-213 mp:>300° C.
I-214 mp: 206–207° C.
$^1$H-NMR (CDCl$_3$) δ ppm: 0.93 (t, 3H, J=7.4 Hz), 1.30–1.42 (m, 2H), 1.49 (d, 6H, J=6.9 Hz), 1.53–1.65 (m, 2H), 2.61 (t, 2H, J=7.7 Hz), 4.15 (sept, 1H, J=6.9 Hz), 7.04 (d, 1H, J=8.2 Hz), 7.20 (d, 2H, J=8.2 Hz), 7.51 (d, 2H, J=8.2 Hz), 7.89 (d, 1H, J=8.8 Hz), 8.18 (s, 1H), 10.55 (s, 1H).

I-215
$^1$H-NMR (CDCl$_3$) δ ppm: 0.93 (t, 3H, J=7.3 Hz), 1.30–1.41 (m, 2H), 1.52–1.63 (m, 2H), 1.95 (s, 6H), 2.61 (t, 2H, J=7.8 Hz), 6.99 (brs, 1H), 7.20 (d, 2H, J=8.5 Hz), 7.65 (d, 2H, J=8.5 Hz), 7.9:3 (dd, 1H, J=8.5, 2.5 Hz), 8.28 (d, 1H, J=8.5 Hz), 8.55 (d, 1H, J=2.5 Hz), 9.76 (brs, 1H).

Ia-1
mp 221–224° C. $^1$H-NMR (CDCl$_3$) δ ppm: 1.19–1.38 (m, 2H), 1.40 (s, 9H), 1.62–1.77 (m, 2H), 2.00–2.31 (m, 5H), 3.18 (t, 4H, J=4.8 Hz), 3.21–3.38 (m, 1H), 3.85 (t, 4H, J=4.8 Hz), 6.64–6.32 (m, 2H), 7.11. (s, 1H), 7.20 (t, 1H, J=7.8 Hz), 7.45 (s, 1H).

Ia-3
mp 87–90° C. $^1$H-NMR (CDCl$_3$) δ ppm: 1.25 (d, 6H, J=6.3 Hz), 1.37 (d, 6H, J=6.9 Hz), 1.59–1.70 (m, 2H), 1.76–1.88 (m, 2H), 2.32–2.42 (m, 4H), 3.11–3.23 (m, 3H), 3.39 (d, 2H, J=10.8 Hz), 3.74–3.86 (m, 2H), 4.34 (t, 1H, J=9.0 Hz), 6.86 (d, 2H, J=9.0 Hz), 7.30 (s, 1H), 7.40 (d, 2H, J=9.0 Hz).

Ia-4
mp 233–234° C. $^1$H-NMR (CDCl$_3$) δ ppm: 1.25 (d, 6H, J=6.3 Hz), 1.40 (s, 9H), 1.26–1.37 (m, 2H), 1.62–1.78 (m, 2H), 2.00–2.22 (m, 5H), 2.42 (t, 2H, J=11.7 Hz), 3.20–3.40 (m, 1H), 3.46 (d, 2H, J=10.5 Hz), 3.67 (d, 1H, J=9.3 Hz), 3.72–3.84 (m, 2H), 6.62–6.76 (m, 2H), 7.10 (s, 1H), 7.18 (t, 1H, J=7.8 Hz), 7.42 (s, 1H).

Ia-5
mp 125–126° C. $^1$H-NMR (CDCl$_3$) δ ppm: 1.25 (d, 6H, J=6.3 Hz), 1.40 (s, 9H), 1.59–1.70 (m, 2H), 1.77–1.84 (m, 2H), 2.30–2.46 (m, 4H), 3.24 (q, 2H, J=6.6 Hz), 3.38 (d, 2H, J=11.7 Hz), 3.74–3.88 (m, 2H), 4.08 (t, 1H, J=5.7 Hz), 6.87 (d, 2H, J=8.7 Hz), 7.30 (s, 1H), 7.41 (d, 2H, J=8.7 Hz).

Ia-6
mp 229–230° C. $^1$H-NMR (CDCl$_3$) δ ppm: 1.25 (d, 6H, J=6.3 Hz), 1.26–1.34 (m, 2H), 1.39 (d, 6H, J=6.9 Hz), 1.61–1.77 (m, 2H), 1.98–1.26 (m, 5H), 2.32–2.46 (m, 4H), 3.15 (quintet, 1H, J=6.6 Hz), 3.22–3.35 (m, 1H), 3.39 (d, 2H, J=11.4 Hz), 3.74–3.92 (m, 2H), 3.88 (d, 1H, J=8.4 Hz), 6.96–6.71 (m, 2H), 7.05 (brs, 1H), 7.39 (d, 2H, J=9.3 Hz).

Ia-7
mp 253–254° C. $^1$H-NMR (DMSO) δ ppm: 1.24–1.60 (m, 4H), 1.27 (s, 9H), 1.77–2.07 (m, 4H), 2.16–2.34 (m, 1H), 2.97–3.15 (m, 1H), 6.78 (d, 1H, J=7.2 Hz), 7.01 (t, 1H, J=6.0 Hz), 7.27 (t, 2H, J=6.6 Hz), 7.58 (d, 2H, J=7.5 Hz), 9.78 (s, 1H).

Ia-8 mp 257–258° C. ¹H-NMR (DMSO) δ ppm: 1.22–1.54 (m, 4H), 1.27 (s, 9H), 1.77–1.88 (m, 2H), 1.88–2.00 (m, 2H), 2.16–2.34 (m, 1H), 2.23 (s, 3H), 2.92–3.14 (m, 1H), 6.77 (d, 1H, J=8.4 Hz), 7.07 (d, 2H, J=8.4 Hz), 7.46 (d, 2H, J=8.1 Hz), 9.68 (s, 1H).

Ia-9 mp 231–232° C. ¹H-NMR (CDCl₃) δ ppm: 1.21 (t, 3H, J=7.5 Hz), 1.22–1.38 (m, 2H), 1.40 (s, 9H), 1.62–1.78 (m, 2H), 1.98–2.31 (m, 5H), 2.61 (q, 2H, J=7.5 Hz), 3.24–3.38 (m, 1H), 3.70 (d, 1H, J=9.9 Hz), 7.11 (s, 1H), 7.14 (d, 2H, J=8.7 Hz), 7.40 (d, 2H, J=8.7 Hz).

Ia-10 mp 233–234° C. ¹H-NMR (CDCl₃) δ ppm: 0.96 (t, 3H, J=7.2 Hz), 1.20–1.37 (m, 2H), 1.40 (s, 9H), 1.56–1.78 (m, 4H), 1.98–2.32 (m, 5H), 2.54 (t, 2H, J=7.2 Hz), 3.23–3.39 (m, 1H), 3.66 (d, 1H, J=9.6 Hz), 7.08 (s, 1H), 7.12 (d, 2H, J=8.4 Hz), 7.39 (d, 2H, J=8.4 Hz).

Ia-11 mp 243–244° C. ¹H-NMR (CDCl₃) δ ppm: 1.22 (d, 6H, J=6.9), 1.22–1.77 (m, 4H), 1.40 (s, 9H), 2.01–2.30 (m, 5H), 2.83–2.92 (m, 1H), 3.24–3.40 (m, 1H), 3.66–3.69 (m, 1H), 7.09 (s, 1H), 7.17 (d, 2H, J=8.4 Hz), 7.41 (d, 2H, J=8.1 Hz).

Ia-12 mp 246–247° C.

¹H-NMR (CDCl₃) δ ppm: 0.80 (t, 3H, J=7.5), 1.20 (d, 3H, J=7.2), 1.26–1.77 (m, 6H), 1.40 (s, 9H), 2.01–2.27 (m, 5H), 2.51–2.60 (m, 1H), 3.20–3.38 (m, 1H), 3.64–3.69 (m, 1H), 7.08 (s, 1H), 7.12 (d, 2H, J=8.4 Hz), 7.41 (d, 2H, J=8.4 Hz).

Ia-13 mp 278–279° C. ¹H-NMR (CDCl₃) δ ppm: 1.22–1.52 (m, 4H), 1.29 (s, 9H), 1.40 (s, 9H), 1.61–1.77 (m, 2H), 2.02–2.30 (m, 5H), 3.20–3.38 (m, 1H), 3.66–3.69 (m, 1H), 7.10 (s, 1H), 7.33 (d, 2H, J=9.0 Hz), 7.42 (d, 2H, J=8.7 Hz).

Ia-14 mp 263–264° C. ¹H-NMR (DMSO) δ ppm: 1.24–1.51 (m, 4H), 1.27 (s, 9H), 1.82–1.99 (m, 4H), 2.19–2.28 (m, 1H), 2.98–3.12 (m, 1H), 6.78 (d, 1H, J=8.7 Hz), 7.33 (d, 2H, J=8.7 Hz), 7.61 (d, 2H, J=9.0 Hz), 9.94 (s, 1H).

Ia-15 mp 209–210° C. ¹H-NMR (CDCl₃) δ ppm: 1.25 (d, 6H, J=6.3 Hz), 1.40 (s, 9H), 1.70–1.98 (m, 8H), 2.19–2.38 (m, 3H), 3.39 (d, 2H, J=11.7 Hz), 3.58–3.92 (m, 3H), 4.12–4.26 (m, 1H), 6.82–6.96 (m, 2H), 7.10 (br, 1H), 7.41 (d, 2H, J=8.1 Hz).

Ia-16 mp 238–240° C. ¹H-NMR (DMSO) δ ppm: 1.22–1.52 (m, 4H), 1.27 (s, 9H), 1.81–1.84 (m, 2H), 1.93–1.97 (m, 2H), 2.16–2.23 (m, 1H), 2.95–3.12 (m, 1H), 3.70 (s, 3H), 6.77 (d, 1H; J=8.4 Hz), 6.85 (d, 2H, J=9.0 Hz), 7.48 (d, 2H, J=9.3 Hz), 9.64 (s, 1H).

Ia-17 mp 245–246° C. ¹H-NMR (DMSO) δ ppm: 1.22–1.52 (m, 4H), 1.27 (s, 9H), 1.83–1.87 (m, 2H), 1.94–1.99 (m, 2H), 2.20–2.28 (m, 1H), 2.98–3.12 (m, 1H), 6.78 (d, 1H, J=8.7 Hz), 7.28 (d, 2H, J=8.7 Hz), 7.69 (d, 2H, J=9.0 Hz), 9.64 (s, 1H).

Ia-18 mp 240–241° C. ¹H-NMR (CDCl₃) δ ppm: 1.22–1.78 (m, 4H), 1.40 (s, 9H), 2.05–2.33 (m, 5H), 3.22–3.44 (m, 1H), 3.64–3.67 (m, 1H), 6.61 (s, 1H), 6.69–6.77 (m, 2H).

Ia-19 mp 240–241° C. ¹H-NMR (CDCl₃) δ ppm: 1.24–1.77 (m, 4H), 1.40 (s, 9H), 2.05–2.30 (m, 5H), 3.22–3.38 (m, 1H), 3.70–3.74 (m, 1H), 7.00–7.15 (m, 3H), 7.36 (s, 1H), 8.29–8.34 (m, 1H).

Ia-20 mp 239–240° C. ¹H-NMR (CDCl₃) δ ppm: 1.24–1.78 (m, 4H), 1.40 (s, 9H), 2.02–2.30 (m, 5H), 3.22–3.40 (m, 1H), 3.63–3.66 (m, 1H), 6.89–6.84 (m, 1H), 7.10–7.17 (m, 2H), 7.22–7.34 (m, 1H), 7.48–7.51 (m, 1H).

Ia-21 mp 259–260° C. ¹H-NMR (CDCl₃/DMSO) δ ppm: 1.21 (d, 6H, J=6.0 Hz), 1.22–1.44 (m, 2H), 1.40 (s, 9H), 1.60–1.78 (m, 2H), 1.87–2.03 (m, 2H), 2.08–2.29 (m, 3H), 2.39 (t, 2H, J=10.2 Hz), 3.14–3.32 (m, 1H), 3.19 (d, 2H, J=11.4 Hz), 3.77–3.93 (m, 2H), 5.33 (d, 1H, J=9.0 Hz), 6.84 (dd, 1H, JFH, HH=8.1, 8.1 Hz), 7.20 (d, 1H, J=7.8 Hz), 7.49 (d, 1H, JFH=14.7 Hz), 8.86 (s, 1H).

Ia-22 mp 234–235° C. ¹H-NMR (CDCl₃) δ ppm: 1.20 (d, 6H, J=5.7 Hz), 1.22–1.44 (m, 2H), 1.38 (s, 9H), 1.54–1.76 (m, 2H), 1.94–2.32 (m, 5H), 2.27 (s, 3H), 2.39 (t, 2H, J=10.8 Hz), 2.87 (d, 2H, J=11.4 Hz), 3.20–3.40 (m, 1H), 3.76–3.92 (m, 2H), 3.91 (d, 1H, J=9.3 Hz), 6.93 (d, 1H, J=8.1 Hz), 7.21 (brs, 1H), 7.27 (brs, 1H), 7.36 (brs, 1H).

Ia-23 mp 195–196° C. ¹H-NMR (CDCl₃) δ ppm: 1.20–1.44 (m, 4H), 1.41 (s, 9H), 1.59–1.76 (m, 2H), 2.03–2.14 (m, 2H), 2.15–2.33 (m, 3H), 3.20–3.40 (m, 1H), 3.64 (s, 1H, J=9.0 Hz), 7.19–7.24 (m, 1H), 7.44 (brs, 1H), 7.52–7.63 (m, 2H), 8.17 (d, 1H, J=8.7 Hz).

Ia-24 mp 209–210° C. ¹H-NMR (CDCl₃) δ ppm: 1.22–1.39 (m, 2H), 1.56 (s, 9H), 1.61–1.78 (m, 2H), 2.00–2.12 (m, 2H), 2.17–2.33 (m, 3H), 3.24–3.39 (m, 1H), 3.67 (d, 1H, J=9.6 Hz), 6.90–7.01 (m, 1H), 7.21 (s, 1H), 7.95–8.06 (m, 1H).

Ia-25 mp 278–281° C. ¹H-NMR (DMSO-d₆) δ ppm: 1.10 (d, 6H, J=6.3 Hz), 1.27 (s, 9H), 1.28–1.55 (m, 4H), 1.78–2.00 (m, 4H), 2.11–2.26 (m, 1H), 2.31 (t, 2H, J=11.1 Hz), 3.00–3.10 (m, 1H), 3.08 (d, 1H, J=10.8 Hz), 3.67–3.80 (m, 2H), 6.78 (d, 1H, J=8.7 Hz), 7.08 (d, 1H, J=9.0 Hz), 7.41 (dd, 1H, J=2.4, 8.7 Hz), 7.78 (d, 1H, J=8.7 Hz), 9.85 (s, 1H).

Ia-26 mp 253–255° C. ¹H-NMR (DMSO-d₆) δ ppm: 1.13 (d, 6H, J=6.0 Hz), 1.27 (s, 9H), 1.28–1.52 (m, 4H), 1.78–2.00 (m, 4H), 2.21 (t, 2H, J=11.1 Hz), 2.26–2.36 (m, 1H), 2.96–3.10 (m, 1H), 3.56 (d, 1H, J=12.3 Hz), 3.60–3.72 (m, 2H), 6.66–6.84 (m, 4H), 7.47 (t, 1H, J=9.3 Hz), 9.28 (s, 1H).

Ia-27 mp 223–226° C. ¹H-NMR (DMSO-d₆) δ ppm: 1.09 (d, 6H, J=6.3 Hz), 1.27 (s, 9H), 1.28–1.54 (m, 4H), 1.77–2.01 (m, 4H), 2.32 (t, 2H, J=11.1 Hz), 2.32–2.42 (m, 1H), 2.90 (d, 1H, J=11.4 Hz), 2.96–3.12 (m, 1H), 3.76–3.92 (m, 2H), 6.78–6.98 (m, 3H), 7.68 (dd, 1H, J=3.3, 8.7 Hz), 8.84 (s, 1H).

Ia-28 mp 237–238° C. ¹H-NMR (CDCl₃) δ ppm: 1.22–1.44 (m, 2H), 1.25 (d, 6H, J=6.3 Hz), 1.40 (s, 9H), 1.61–1.79 (m, 2H), 2.05–2.32 (m, 5H), 2.21 (s, 3H), 2.38 (t, 2H, J=10.2 Hz), 3.22–3.42 (m, 1H), 3.40 (d, 2H, J=11.1 Hz), 3.65 (d, 1H, J=9.3 Hz), 3.72–3.90 (m, 2H), 6.70–6.78 (m, 2H), 6.81 (brs, 1H), 7.50 (d, 1H, J=9.6 Hz).

Ia-29 mp 208–209° C. ¹H-NMR (CDCl₃) δ ppm: 1.22 (d, 6H, J=6.0 Hz), 1.23–1.40 (m, 2H), 1.40 (s, 9H), 1.60–1.78 (m, 2H), 2.00–2.16 (m, 2H), 2.14–2.33 (m, 3H), 2.45 (t, 2H, J=11.1 Hz), 3.21 (d, 2H, J=10.8 Hz), 3.24–3.38 (m, 1H), 3.63 (d, 1H, J=9.3 Hz), 3.80–3.94 (m, 2H), 5.33 (d, 1H, J=9.0 Hz), 6.66 (dd, 1H, JFH, HH=6.6, 6.6 Hz), 7.16 (brs, 1H), 7.89 (dd, 1H, JFH, HH=9.0, 9.0 Hz).

Ia-30 mp 284–287° C. ¹H-NMR (DMSO-d₆) δ ppm: 1.08 (d, 6H, J=6.0 Hz), 1.26 (s, 9H), 1.28–1.53 (m, 4H), 1.82–2.22

(m, 4H), 2.25–2.39 (m, 1H), 2.78 (t, 2H, J=10.5 Hz), 2.97–3.14 (m, 1H), 3.18 (d, 2H, J=11.4 Hz), 3.65–3.76 (m, 2H), 6.79 (d, 1H, J=8.7 Hz), 9.75 (s, 1H).

Ia-31 mp 200–201° C. $^1$H-NMR (CDCl$_3$) δ ppm: 1.22–1.40 (m, 2H), 1.40 (s, 9H), 1.62–1.76 (m, 2H), 2.04–2.32 (m, 5H), 3.22–3.40 (m, 1H), 3.62–3.66 (m, 1H), 7.22–7.24 (m, 1H), 7.38–7.38 (m, 1H), 7.60 (s, 1H), 8.33–8.36 (m, 1H).

Ia-32 mp 260–261° C. $^1$H-NMR (CDCl$_3$/DMSO) δ ppm: 1.25–1.42 (m, 2H), 1.38 (s, 9H), 1.64 (q, 2H, J=13.5 Hz), 1.95 (d, 2H, J=12.3 Hz), 2.16 (d, 2H, J=10.5 Hz), 2.18–2.32 (m, 1H), 3.14–3.30 (m, 1H), 5.53 (d, 1H, J=9.0 Hz), 7.31 (d, 1H, J=8.7 Hz), 7.46 (dd, 1H, J=2.4, 8.7 Hz), 7.90 (d, 1H, J=2.1 Hz), 9.35 (s, 1H).

Ia-33 mp 227° C. $^1$H-NMR (DMSO-d$_6$) δ ppm: 1.27 (s, 9H), 1.30–1.56 (m, 4H), 1.78–2.01 (m, 2H), 2.12–2.36 (m, 2H), 2.96–3.13 (m, 1H), 3.70 (s, 3H), 3.71 (s, 3H), 6.77 (d, 1H, J=8.7 Hz), 6.85 (d, 1H, J=8.7 Hz), 7.06 (dd, 1H, J=2.4, 8.7 Hz), 7.33 (d, 1H, J=2.4 Hz), 9.65 (s, 1H).

Ia-35 mp 214–216° C. $^1$H-NMR (CDCl$_3$) δ ppm: 1.23–1.38 (m, 2H), 1.40 (s, 9H), 1.60–1.76 (m, 2H), 2.00–2.12 (m, 2H), 2.20–2.32 (m, 3H), 3.24–3.39 (m, 1H), 3.68 (d, 1H, J=9.0 Hz), 6.77 (d, 1H, J=8.7 Hz), 7.00 (dd, 1H, J=2.4, 8.7 Hz), 7.77 (s, 1H), 8.45 (d, 1H, J=2.4 Hz).

Ia-36 mp 241–242° C. $^1$H-NMR (CDCl$_3$/DMSO) δ ppm: 1.25–1.42 (m, 2H), 1.37 (s, 9H), 1.62 (q, 2H, J=11.7 Hz), 1.93 (d, 2H, J=12.0 Hz), 2.12 (d, 2H, J=10.8 Hz), 2.16–2.30 (m, 1H), 3.12–3.28 (m, 1H), 3.84 (s, 3H), 6.07 (d, 1H, J=8.4 Hz), 6.89 (dd, 1H, JFH, HH=9.3, 9.3 Hz), 7.24 (d, 1H, J=8.7 Hz), 7.55 (d, 1H, JFH=13.5 Hz), 9.32 (s, 1H).

Ia-37 mp 248–249° C. $^1$H-NMR (CDCl$_3$) δ ppm: 0.60–0.73 (m, 1H), 0.91 (d, 6H, J=6.6), 1.12–1.40 (m 2H), 1.40 (s, 9H), 1.54–1.88 (m, 5H), 1.98–2.29 (m, 7H), 3.22–3.37 (m, 1H), 3.51–3.54 (m, 2H), 3.72 (d, 1H, J=9.6), 6.88 (d, 1H, J=8.7), 7.06 (s, 1H), 7.35 (d, 1H, J=9.0).

Ia-38 mp 237–238° C. $^1$H-NMR (CDCl$_3$) δ ppm: 1.01 (d, 6H, J=6.6), 1.20–1.40 (m, 2H), 1.40 (s, 9H), 1.60–1.74 (m, 4H), 1.99–2.28 (m, 7H), 2.69–2.82 (m, 2H), 3.02–3.14 (m, 2H), 3.20–3.38 (m, 1H), 3.80–3.90 (m, 1H), 6.83–6.86 (m, 2H), 7.14 (s, 1H), 7.34 (d, 1H, J=8.4).

Ia-39 mp 234–235° C. $^1$H-NMR (CDCl$_3$) δ ppm: 1.20–1.36 (m, 2H), 1.40 (s, 9H), 1.60–1.77 (m, 2H), 1.90–2.32 (m, 5H), 3.21–3.39 (m, 1H), 3.65 (d, 1H, J=9.6 Hz), 6.87 (d, 1H, J=8.7 Hz), 7.04 (s, 1H), 7.37 (dd, 1H, J=2.7, 8.7 Hz), 7.56 (d, 1H, J=2.7 Hz).

Ia-40 mp 257–258° C. $^1$H-NMR (DMSO-d$_6$) δ ppm: 1.14 (d, 6H, J=6.0 Hz), 1.27 (s, 9H), 1.28–1.53 (m, 4H), 1.78–2.00 (m, 4H), 2.13–2.256 (m, 1H), 2.30 (t, 2H, J=11.7 Hz), 2.97–3.12 (m, 1H), 3.53–3.67 (m, 2H), 4.01 (d, 1H, J=12.3 Hz), 6.80 (dd, 1H, J=3.0, 9.0 Hz), 7.79 (d, 1H, J=9.0 Hz), 8.27 (s, 1H), 9.66 (s, 1H).

Ia-41 mp 245–246° C. $^1$H-NMR (CDCl$_3$/DMSO) δ ppm: 1.25–1.42 (m, 2H), 1.37 (s, 9H), 1.62 (q, 2H, J=12.6 Hz), 1.94 (d, 2H, J=11.1 Hz), 2.13 (d, 2H, J=11.1 Hz), 2.18–2.35 (m, 1H), 3.11–3.29 (m, 1H), 6.07 (d, 1H, J=8.1 Hz), 6.95–7.06 (m, 1H), 7.14–7.27 (m, 1H), 7.44 (d, 1H, J=7.2 Hz), 7.79 (s, 1H), 9.48 (s, 1H).

Ia-43 mp 294–295° C. $^1$H-NMR (DMSO-d$_6$) δ ppm: 1.26 (s, 9H), 1.28–1.53 (m, 4H), 1.76–1.87 (m, 2H), 1.89–2.00 (m, 2H), 2.13–2.25 (m, 1H), 2.96–3.10 (m, 5H), 3.52–3.60 (m, 4H), 6.78 (d, 1H, J=9.0 Hz), 6.88 (d, 2H, J=9.0 Hz), 7.44 (d, 2H, J=9.0 Hz), 9.59 (s, 1H).

Ia-44 mp 250–252° C. $^1$H-NMR (CDCl$_3$) δ ppm: 1.13 (d, 6H, J=6.3 Hz), 1.21–1.38 (m, 2H), 1.41 (s, 9H), 1.63–1.80 (m, 2H), 1.93 (t, 2H, J=10.8 Hz), 2.00–2.10 (m, 2H), 2.16–2.32 (m, 3H), 3.24–3.39 (m, 1H), 3.54 (d, 2H, J=10.2 Hz), 3.64–3.78 (m, 3H), 7.47 (s, 1H), 7.69 (d, 2H, J=9.0 Hz), 7.73 (d, 2H, J=9.0 Hz).

Ia-45 mp 193° C. $^1$H-NMR (DMSO-d$_6$) δ ppm: 1.10 (t, 6H, J=7.2 Hz), 1.26 (s, 9H), 1.28–1.52 (m, 4H), 1.75–1.86 (m, 2H), 1.89–2.01 (m, 2H), 2.10–2.22 (m, 1H), 2.96–3.10 (m, 1H), 3.30–3.52 (m, 12H), 6.60 (d, 2H, J=9.0 Hz), 6.80 (d, 1H, J=9.0 Hz), 7.33 (d, 2H, J=9.0 Hz), 9.46 (s, 1H).

Ia-46 mp>300° C. $^1$H-NMR (DMSO-d$_6$) δ ppm: 1.28 (s, 9H), 1.28–1.58 (m, 4H), 1.83–2.04 (m, 4H), 2.23–2.36 (m, 1H), 2.46 (s, 3H), 3.00–3.14 (m, 1H), 6.79 (d, 1H, J=8.7 Hz), 7.34 (d, 1H, J=8.7 Hz), 7.78 (d, 2H, J=8.7 Hz), 7.89 (d, 1H, J=8.4 Hz), 7.91 (s, 1H), 8.00 (d, 2H, J=8.7 Hz), 10.13 (s, 1H).

Ia-47 mp 236–237° C. $^1$H-NMR (CDCl$_3$) δ ppm: 0.97 (d, 6H, J=6.6 Hz), 1.01 (d, 6H, J=6.6 Hz), 1.20–1.37 (m, 2H), 1.40 (s, 9H), 1.60–1.84 (m, 3H), 1.97–2.31 (m, 5H), 2.50 (t, 1H, J=10.8 Hz), 2.78 (dt, 1H, J=3.3, 11.4 Hz), 3.25–3.38 (m, 1H), 3.45 (d, 1H, J=11.4 Hz), 3.75 (dt, 1H, J=2.4, 11.4 Hz), 4.02 (dt, 1H, J=2.4, 11.4 Hz), 6.88 (d, 2H, J=9.0 Hz), 7.05 (s, 1H), 7.39 (d, 2H, J=9.0 Hz).

Ia-48 mp 228–229° C. $^1$H-NMR (CDCl$_3$) δ ppm: 0.88 (t, 6H, J=7.2 Hz), 1.19–1.45 (m, 4H), 1.40 (s, 9H), 1.45–1.76 (m, 4H), 1.76–1.92 (m, 1H), 1.96–2.30 (m, 5H), 2.66–3.20 (m, 3H), 3.20–3.40 (m, 1H), 3.78 (d, 1H, J=9.3 Hz), 3.82 (s, 1H), 6.62–6.98 (m, 2H), 7.09 (brs, 1H), 7.37 (d, 2H, J=7.8 Hz).

Ia-49 mp 262–263° C. $^1$H-NMR (CDCl$_3$/DMSO) δ ppm: 1.21 (d, 6H, J=5.7 Hz), 1.26–1.34 (m, 2H), 1.37 (d, 6H), J=5.4 Hz), 1.52–1.76 (m, 2H), 1.85–2.03 (m, 2H), 2.03–2.30 (m, 3H), 2.30–2.53 (m, 2H), 3.02–3.33 (m, 4H), 3.75–3.98 (m, 2H), 5.70 (brs, 1H), 6.73–6.98 (m, 1H), 7.14–7.25 (m, 1H), 7.52 (d, 1H, JFH=13.5 Hz), 8.86 (brs, 1H).

Ia-50 mp 232–233° C. $^1$H-NMR (CDCl$_3$) δ ppm: 1.21 (d, 6H, J=6.3 Hz), 1.22–1.37 (m, 2H), 1.38 (d, 6H, J=6.9 Hz), 1.68 (q, 2H, J=12.6 Hz), 1.98–2.26 (m, 5H), 2.29 (s, 3H), 2.41 (t, 2H, J=10.2 Hz), 2.88 (d, 2H, J=11.1 Hz), 3.15 (septet, 1H, J=6.6 Hz), 3.21–3.37 (m, 1H), 3.77–3.92 (m, 2H), 3.87 (d, 1H, J=7.8 Hz), 6.88–7.06 (m, 3H), 7.35 (s, 1H).

Ia-51 mp 211–212° C. $^1$H-NMR (CDCl$_3$) δ ppm: 1.20–1.42 (m, 2H), 1.26 (d, 6H, J=6.3 Hz), 1.38 (d, 6H, J=6.9 Hz), 1.62–1.78 (m, 2H), 1.99–2.28 (m, 5H), 2.49 (dd, 2H, J=10.5, 10.5 Hz), 3.17 (quint, 1H, J=6.9 Hz), 3.20–3.38 (m, 1H), 3.66–3.99 (m, 2H), 3.90–4.01 (m, 3H), 6.62 (d, 1H, J=9.0 Hz), 7.06 (s, 1H), 7.90 (dd, 1H, J=2.4, 9.0 Hz), 8.09 (d, 1H, J=2.4 Hz).

Ia-52 mp 247–249° C. $^1$H-NMR (CDCl$_3$) δ ppm: 1.21–1.36 (m, 2H), 1.40 (s, 9H) 1.62–1.78 (m, 2H), 1.98–2.32 (m, 5H), 2.55 (t, 4H, J=6.0 Hz), 3.23–3.38 (m, 1H), 3.55 (t, 4H, J=6.0 Hz), 3.72 (d, 2H, J=9.6 Hz), 6.94 (d, 2H, J=9.0 Hz), 7.10 (s, 1H), 7.42 (d, 1H, J=9.0 Hz).

Ia-53
mp 234–235° C. ¹H-NMR (CDCl₃) δ ppm: 1.22–1.38 (m, 2H), 1.41 (s, 9H) 1.64–1.80 (m, 2H), 2.00–2.32 (m, 5H), 3.25–3.40 (m, 1H), 3.73 (d, 1H, J=9.3 Hz), 7.43 (s, 1H), 7.48 (t, 2H, J=7.5 Hz), 7.55–7.66 (m, 3H), 7.68–7.89 (m, 4H).

Ia-54
mp 235–236° C. ¹H-NMR (CDCl₃) δ ppm: 1.24–1.39 (m, 2H), 1.25 (d, 6H, J=6.3 Hz), 1.39 (d, 6H, J=6.9 Hz), 1.60–1.80 (m, 2H), 2.00–2.28 (m, 5H), 2.21 (s, 3H), 2.38 (t, 2H, J=10.8 Hz), 3.15 (septet, 1H, J=6.3 Hz), 3.23–3.38 (m, 1H), 3.40 (d, 2H, J=11.7 Hz), 3.72–3.88 (m, 2H), 3.87 (d, 1H, J=9.3 Hz), 6.78–6.86 (m, 3H), 7.50 (d, 1H, J=9.6 Hz).

Ia-55
mp 185–186° C. ¹H-NMR (CDCl₃) δ ppm: 1.14 (d, 6H, J=6.3 Hz), 1.22–1.38 (m, 2H), 1.41 (s, 9H), 1.62–1.78 (m, 2H), 2.02 (t, 2H, J=10.5 Hz), 2.02–2.10 (m, 2H), 2.16–2.31 (m, 3H), 3.24–3.39 (m, 1H), 3.56 (d, 2H, J=9.3 Hz), 3.63–3.80 (m, 3H), 7.46 (dd, 1H, J=1.5, 8.1 Hz), 7.51 (t, 1H, J=8.1 Hz), 7.63 (s, 1H), 7.81 (t, 1H, J=1.8 Hz), 7.98 (dt, 1H, J=1.8, 8.1 Hz).

Ia-56
mp 229–230° C. ¹H-NMR (DMSO) δ ppm: 1.27 (s, 9H), 1.28–1.54 (m, 4H), 1.38 (s, 6H), 1.78–1.84 (m, 2H), 1.90–2.00 (m, 2H), 2.15–2.30 (m, 1H), 2.97–3.13 (m, 1H), 4.90 (s, 1H), 6.79 (d, 1H, J=9.0 Hz), 7.34 (d, 2H, J=8.7 Hz), 7.48 (d, 2H, J=8.4 Hz), 9.72 (s, 1H).

Ia-57
mp 211–212° C. ¹H-NMR (CDCl₃/DMSO) δ ppm: 1.24–1.40 (m, 2H), 1.38 (s, 9H), 1.57–1.74 (m, 2H), 1.91 (s, 3H), 1.92–2.01 (m, 2H), 2.12–2.24 (m, 2H), 2.51 (brs, 1H), 3.18–3.33 (m, 1H), 4.96 (d, 1H, J=9.3 Hz), 7.16–7.53 (m, 9H), 7.41 (s, 1H).

Ia-58
mp 298–299° C. ¹H-NMR (DMSO-d₆) δ ppm: 1.24 (s, 9H), 1.27 (s, 9H), 1.28–1.54 (m, 4H), 1.75–2.02 (m, 4H), 2.14–2.28 (m, 1H), 2.97–3.11 (m, 1H), 6.78 (d, 1H, J=8.4 Hz), 7.18 (d, 2H, J=9.0 Hz), 7.48 (d, 2H, J=9.0 Hz), 9.46 (s, 1H), 9.76 (s, 1H).

Ia-59
mp 253–254° C. ¹H-NMR (CDCl₃) δ ppm: 1.22–1.40 (m, 2H), 1.41 (s, 9H), 1.65–1.81 (m, 2H), 2.04–2.16 (m, 2H), 2.22–2.36 (m, 2H), 3.24–3.41 (m, 1H), 3.74 (d, 1H, J=9.6 Hz), 7.40–7.54 (m, 3H), 7.88–8.01 (m, 3H), 8.66 (d, 1H, J=1.5 Hz), 9.57 (d, 1H, J=1.2 Hz).

Ia-60
mp 213–214° C. ¹H-NMR (DMSO) δ ppm: 1.32–1.50 (m, 2H), 1.35 (s, 9H), 1.52–1.70 (m, 2H), 1.88–2.00 (m, 2H), 2.04–2.16 (m, 2H), 2.22–2.38 (m, 1H), 2.65 (s, 3H), 2.99–3.15 (m, 1H), 6.46 (d, 1H, J=9.3 Hz), 7.28 (d, 1H, J=9.0 Hz), 7.81 (s, 1H), 8.20 (s, 1H), 8.47 (s, 1H), 9.89 (s, 1H).

Ia-61
mp 274–275° C. ¹H-NMR (DMSO) δ ppm: 1.27 (s, 1H), 1.28–1.58 (m, 4H), 1.84–2.08 (m, 4H), 2.22–2.40 (m, 1H), 2.99–3.15 (m, 1H), 3.01 (s, 3H), 6.81 (d, 1H, J=8.1 Hz), 7.78 (d, 2H, J=7.8 Hz), 7.84 (d, 2H, J=8.4 Hz), 8.18 (s, 1H), 10.43 (s, 1H).

Ia-62
mp 235–236° C. ¹H-NMR (CDCl₃) δ ppm: 1.22–1.39 (m, 2H), 1.41 (s, 3H), 1.66–1.80 (m, 2H), 2.01–2.12 (m, 2H), 2.14–2.22 (m, 1H), 2.23–2.34 (m, 2H), 3.24–3.42 (m, 1H), 3.69 (d, 1H, J=9.5 Hz), 6.44 (d, 1H, J=9.3 Hz), 7.27 (brs, 1H), 7.28 (d, 1H, J=9.3 Hz), 7.37 (dd, 1H, J=2.4, 9.0 Hz), 7.68 (d, 1H, J=9.6 Hz), 8.04 (d, 1H, J=2.4 Hz).

Ia-63
mp 277–279° C. ¹H-NMR (DMSO-d₆) δ ppm: 1.27 (s, 9H), 1.28–1.54 (m, 4H), 1.77–2.02 (m, 4H), 2.15–2.29 (m, 1H), 2.90 (s, 3H), 2.96–3.13 (m, 1H), 6.79 (d, 1H, J=8.7 Hz), 7.12 (d, 2H, J=9.0 Hz), 7.54 (d, 2H, J=9.0 Hz), 9.50 (s, 1H), 9.81 (s, 1H).

Ia-64
mp 259–260° C. ¹H-NMR (DMSO-d₆) δ ppm: 1.26 (s, 9H), 1.26–1.50 (m, 4H), 1.74–1.99 (m, 4H), 2.10–2.25 (m, 1H), 2.95–3.10 (m, 1H), 6.78 (d, 1H, J=8.7 Hz), 6.97 (d, 2H, J=9.0 Hz), 7.42 (d, 2H, J=9.0 Hz), 7.50–7.71 (m, 5H), 9.73 (s, 1H), 10.05 (s, 1H).

Ia-65
mp 292–293° C. ¹H-NMR (DMSO-d₆) δ ppm: 1.27 (s, 9H), 1.28–1.54 (m, 4H), 1.62–1.72 (m, 2H), 1.77–1.87 (m, 2H), 1.91–2.10 (m, 4H), 2.13–2.25 (m, 1H), 2.98–3.12 (m, 1H), 3.41–3.52 (m, 2H), 5.09 (s, 1H), 6.79 (d, 1H, J=9.0 Hz), 6.91 (d, 2H, J=9.0 Hz), 7.37 (d, 2H, J=9.0 Hz), 7.42 (d, 2H, J=9.0 Hz), 7.51 (d, 2H, J=9.0 Hz), 9.56 (s, 1H).

Ia-66
mp>300° C. ¹H-NMR (DMSO-d₆) δ ppm: 1.27 (s, 9H), 1.28–1.58 (m, 4H), 1.85–2.02 (m, 4H), 2.40–2.52 (m, 1H), 3.00–3.16 (m, 1H), 6.81 (d, 1H, J=9.0 Hz), 7.50–7.58 (m, 3H), 7.90–7.97 (m, 2H), 12.58 (s, 1H).

Ia-67
mp 199–200° C. ¹H-NMR (DMSO-d₆) δ ppm: 1.14 (d, 6H, J=6.3 Hz), 1.28 (s, 9H), 1.31–1.48 (m, 4H), 1.76–1.88 (m, 2H), 2.17 (t, 2H, J=11.1 Hz), 2.82 (t, 2H, J=11.7 Hz), 3.46 (d, 2H, J=11.4 Hz), 3.20–3.36 (m, 1H), 3.62–3.74 (m, 2H), 4.02 (d, 2H, J=12.9 Hz), 6.83 (d, 2H, J=9.0 Hz), 6.89 (d, 1H, J=8.7 Hz), 7.28 (d, 2H, J=9.0 Hz), 8.27 (s, 1H).

Ia-68
mp 2:37–239° C. ¹H-NMR (CDCl₃/DMSO) δ ppm: 1.40 (s, 9H), 1.49–1.65 (m, 2H), 1.99–2.10 (m, 2H), 1.99–2.10 (m, 2H), 2.95 (t, 2H, J=11.1 Hz), 3.36–3.52 (m, 1H), 4.17 (d, 1H, J=12.9 Hz), 5.84 (d, 1H, J=8.7 Hz), 6.39 (d, 1H, J=9.6 Hz), 7.21 (d, 1H, J=9.3 Hz), 7.51 (dd, 1H, J=2.4, 9.3 Hz), 7.72 (d, 1H, J=9.9 Hz), 7.85 (d, 1H, J=2.7 Hz), 8.04 (s, 1H).

Ia-69
mp 259–260° C. ¹H-NMR (DMSO) δ ppm: 1.25–1.55 (m, 4H), 1.27 (s, 9H), 1.82–2.05 (m, 4H), 2.22–2.36 (m, 1H), 2.98–3.17 (m, 1H), 4.16 (s, 3H), 6.80 (d, 1H, J=8.4 Hz), 7.77–7.87 (m, 4H), 10.16 (s, 1H).

Ia-70
mp 259–260° C. ¹H-NMR (DMSO) δ ppm: 1.28 (s, 9H), 1.36–1.56 (m, 2H), 1.80–1.92 (m, 2H), 2.86–3.02 (m, 2H), 3.36–3.52 (m, 1H), 4.04–4.20 (m, 2H), 6.92 (d, 1H, J=7.5 Hz), 7.38–7.58 (m, 3H), 8.00–8.14 (m, 2H), 8.90 (s, 1H), 9.08 (s, 1H), 9.63 (s, 1H).

Ia-71
mp 228–229° C. ¹H-NMR (CDCl₃/DMSO) δ ppm: 1.27–1.42 (m, 2H), 1.38 (s, 9H), 1.57–1.75 (m, 2H), 1.90–2.02 (m, 2H), 2.12–2.34 (m, 3H), 3.14–3.32 (m, 1H), 5.37 (d, 1H, J=9.3 Hz), 7.38–7.43 (m, 3H), 7.46 (d, 2H, J=8.7 Hz), 7.51–7.60 (m, 2H), 7.68 (d, 2H, J=9.0 Hz), 9.33 (s, 1H).

Ia-75
mp 169–170° C. ¹H-NMR (CDCl₃) δ ppm: 0.58–0.72 (m, 1H), 0.80 (d, 3H, J=6.6 Hz), 0.94 (d, 3H, J=6.0 Hz), 1.14–1.35 (m, 3H), 1.39 (s, 9H), 1.48–1.66 (m, 2H), 1.74–2.06 (m, 5H), 2.06–2.44 (m, 6H), 3.18–3.35 (m, 1H), 3.64–3.74 (m, 1H), 4.46–4.60 (m, 1H), 6.98–7.38 (m, 5H).

Ia-76
mp 236–237° C. ¹H-NMR (CDCl₃/DMSO) δ ppm: 1.27–1.42 (m, 2H), 1.38 (d, 6H, J=6.6 Hz), 1.60–1.78 (m, 2H), 1.94–2.06 (m, 2H), 2.12–2.30 (m, 3H), 3.06–3.34 (m, 2H), 5.10 (brs, 1H), 6.41 (d, 1H, J=9.9 Hz), 7.25 (d, 1H, J=8.4 Hz), 7.48 (dd, 1H, J=2.4, 8.7 Hz), 7.68 (d, 1H, J=9.9 Hz), 8.12 (d, 1H, J=2.4 Hz), 8.88 (brs, 1H).

Ia-77
mp 117–118° C. $^1$H-NMR (CDCl$_3$) δ ppm: 1.38 (d, 6H, J=6.9 Hz), 1.65 (quintet, 2H, J=5.4 Hz), 1.75–1.91 (m, 2H), 2.42 (t, 2H, J=7.4 Hz), 3.10–3.24 (m, 3H), 4.77 (brs, 1H), 6.41 (d, 1H, J=9.6 Hz), 7.18–7.26 (m, 1H), 7.48 (dd, 1H, J=1.8, 8.7 Hz), 7.67 (d, 1H, J=9.9 Hz), 8.01 (s, 1H), 8.23 (brs, 1H).

Ia-78
mp 138–139° C. $^1$H-NMR (CDCl$_3$) δ ppm: 1.41 (s, 9H), 1.64 (quintet, 2H, J=6.6 Hz), 1.84 (quintet, 2H, J=7.3 Hz), 2.42 (t, 2H, J=7.5 Hz), 3.26 (q, 2H, J=6.5 Hz), 4.59 (brs, 1H), 6.41 (d, 1H, J=9.3 Hz), 7.23 (d, 1H, J=8.7 Hz), 7.49 (dd, 1H, J=2.4, 9.0 Hz), 7.67 (d, 1H, J=9.9 Hz), 8.03 (d, 1H, J=2.4 Hz), 8.28 (brs, 1H).

Ia-79
mp 289–290° C. $^1$H-NMR (DMSO) δ ppm: 1.24–1.63 (m, 4H), 1.28 (s, 9H), 1.84–2.08 (m, 4H), 2.24–2.41 (m, 1H), 3.00–3.16 (m, 1H), 6.82 (d, 1H, J=8.1 Hz), 7.36–7.60 (m, 5H), 7.86–7.99 (m, 2H), 8.28 (s, 1H), 10.50 (s, 1H).

Ia-80
mp 239–240° C. $^1$H-NMR (DMSO) δ ppm: 1.22 (d, 1H, J=6.6 Hz), 1.23–1.40 (m, 2H), 1.40–1.59 (m, 2H), 1.83–2.04 (m, 4H), 2.23–2.39 (m, 1H), 2.98–3.23 (m, 2H), 7.00 (d, 1H, J=7.8 Hz), 7.36–7,59 (m, 5H), 7.85–7.97 (m, 2H), 8.29 (s, 1H), 10.50 (s, 1H).

Ia-81
mp 205–206° C. $^1$H-NMR (CDCl$_3$/DMSO) δ ppm: 1.40 (s, 9H), 1.66 (quintet, 2H, J=7.0 Hz), 1.85 (quintet, 2H, J=7.2 Hz), 2.45 (t, 2H, J=7.5 Hz), 3.24 (t, 2H, J=6.5 Hz), 5.17 (brs, 1H), 7.36–7.54 (m, 5H), 7.85 (d, 1H, J=8.4 Hz), 8.07 (dd, 1H, J=1.8, 8.1 Hz), 8.23 (d, 1H, J=1.8 Hz), 9.61 (s, 1H).

Ia-82
mp 216–217° C. $^1$H-NMR (DMSO-d$_6$) δ ppm: 1.14 (d, 6H, J=6.3 Hz), 1.22 (d, 6H, J=6.9 Hz), 1.22–1.53 (m, 4H), 1.76–1.98 (m, 2H), 2.21 (t, 2H, J=10.8 Hz), 2.22–2.36 (m, 1H), 2.96–3.20 (m, 2H), 3.57 (d, 2H, J=12.0 Hz), 3.60–3.74 (m, 1H), 6.66–6.85 (m, 2H), 6.98 (d, 1H, J=7.8 Hz), 7.47 (d, 1H, J=8.7 Hz), 9.30 (s, 1H).

Ia-83
mp 118–119° C. $^1$H-NMR (DMSO-d$_6$) δ ppm: 1.41 (d, 6H, J=6.3 Hz), 1.26 (s, 9H), 1.40–1.67 (m, 4H), 2.17–2.36 (m, 3H), 2.97–3.10 (m, 2H), 3.57 (d, 2H, J=12.0 Hz), 3.61–3.74 (m, 1H), 6.67–6.92 (m, 3H), 7.48 (t, 1H, J=9.0 Hz), 9.37 (s, 1H).

Ia-84
mp 265–267° C. $^1$H-NMR (DMSO-d$_6$) δ ppm: 1.21 (d, 6H, J=6.6 Hz), 1.20–1.57 (m, 4H), 1.60–2.30 (m, 9H), 2.99–3.20 (m, 4H), 3.40–3.52 (m, 2H), 5.09 (s, 1H), 6.91 (d, 2H, J=8.7 Hz), 6.98 (d, 1H, J=7.5 Hz), 7.37 (d, 2H, J=8.7 Hz), 7.42 (d, 2H, J=8.7 Hz), 7.51 (d, 2H, J=8.7 Hz), 9.56 (s, 1H).

Ia-85
mp 185–186° C. $^1$H-NMR (DMSO-d$_6$) δ ppm: 1.26 (s, 9H), 1.42–1.72 (m, 6H), 1.96–2.10 (m, 2H), 2.26 (t, 2H, J=6.9 Hz), 2.96–3.12 (m, 4H), 3.41–3.52 (m, 2H), 5.09 (s, 1H), 6.88 (d, 1H, J=8.7 Hz), 6.92 (d, 2H, J=9.0 Hz), 7.37 (d, 2H, J=8.7 Hz), 7.43 (d, 2H, J=9.0 Hz), 7.52 (d, 2H, J=8.7 Hz), 9.63 (s, 1H).

Ia-86
mp 162–164° C. $^1$H-NMR (DMSO-d$_6$) δ ppm: 1.21 (d, 6H, J=6.6 Hz), 1.41–1.73 (m, 6H), 1.96–2.10 (m, 2H), 2.26 (t, 2H, J=7.2 Hz), 2.91–3.20 (m, 5H), 3.42–3.52 (m, 2H), 5.09 (s, 1H), 6.92 (d, 2H, J=9.3 Hz), 6.99 (t, 1H, J=6.0 Hz), 7.37 (d, 2H, J=8.7 Hz), 7.43 (d, 2H, J=9.3 Hz), 7.52 (d, 2H, J=8.7 Hz), 9.64 (s, 1H).

Ia-87
mp 245–247° C. $^1$H-NMR (DMSO-d$_6$) δ ppm: 1.22 (d, 6H, J=6.6 Hz), 1.22–1.58 (m, 4H), 1.81–2.02 (m, 4H), 2.22–2.36 (m, 1H), 3.00–3.20 (m, 2H), 3.01 (s, 3H), 6.99 (d, 1H, J=8.4 Hz), 7.75–7.88 (m, 2H), 8.19 (d, 1H, J=1.2 Hz), 10.4.3 (s, 1H).

Ia-88
mp 208–209° C. $^1$H-NMR (DMSO-d$_6$) δ ppm: 1.22 (d, 6H, J=6.9 Hz), 1.22–1.55 (m, 4H), 1.75–1.98 (m, 4H), 2.11–2.24 (m, 1H), 2.98–3.20 (m, 2H), 5.96 (s, 2H), 6.82 (d, 1H, J=8.4 Hz), 6.91–7.03 (m, 2H), 7.30 (d, 1H, J=1.8 Hz), 9.72 (s, 1H).

Ia-89
mp 142–143° C. $^1$H-NMR (DMSO-d$_6$) δ ppm: 1.27 (s, 9H), 1.40–1.66 (m, 4H), 2.26 (t, 2H, J=7.5 Hz), 3.02 (q, 2H, J=6.6 Hz), 5.96 (s, 2H), 6.82 (d, 1H, J=8.4 Hz), 6.88 (t, 1H, J=8.4 Hz), 6.94 (dd, 1H, J=1.8, 8.4 Hz), 7.30 (d, 1H, J=1.8 Hz), 9.78 (s, 1H).

Ia-90
mp 100° C. $^1$H-NMR (DMSO-d$_6$) δ ppm: 1.20 (d, 6H, J=6.9 Hz), 1.40–1.66 (m, 4H), 2.26 (t, 2H, J=7.5 Hz), 2.89–2.99 (m, 2H), 3.13 (quint, 1H, J=6.6 Hz), 5.96 (s, 2H), 6.83 (d, 1H, J=8.1 Hz), 6.91–7.02 (m, 2H), 7.30 (d, 1H, J=1.8 Hz), 9.78 (s, 1H).

Ia-91
mp 189–190° C. $^1$H-NMR (DMSO-d$_6$) δ ppm: 1.26 (s, 9H), 1.43–1.71 (m, 4H), 2.40 (t, 2H, J=7.5 Hz), 2.97–3.09 (m, 2H), 3.01 (s, 3H), 6.85–6.93 (m, 1H), 7.76–7.88 (m, 2H), 8.20 (d, 1H, J=1.2 Hz), 10.49 (s, 1H).

Ia-104
mp 238–241° C. $^1$H-NMR (DMSO) δ ppm: 1.27 (s, 9H), 1.3–1.5 (m, 4H), 1.8–2.0 (m, 4H), 2.50 (m, 1H), 3.05 (m, 1H), 6.55 (br s, 1H), 6.79 (d, 1H, J=8.2), 7.15 (t, 1H, J=4.8), 8.64 (d, 2H, J=4.8 Hz).

Ia-105
mp 232–234° C. $^1$H-NMR (DMSO) δ ppm: 1.26 (s, 9H), 1.2–1.5. (m, 4H), 1.8–2.0 (m, 4H), 2.55 (m, 1H), 3.05 (m, 1H), 6.77 (d, 1H, J=8.7), 9.92 (s, 2H), 10.93 (s, 1H).

Ia-106
mp 226–228° C. $^1$H-NMR (DMSO) δ ppm: 1.28 (s, 9H), 1.22–1.58 (m, 4H), 1.82–2.04 (m, 4H), 2.29 (m, 1H), 3.07 (m, 1H), 6.79 (d, 1H, J=8.7 Hz), 7.61 (d-d, 1H, J=1.8 Hz, 8.7 Hz), 8.04 (d, 1H, J=8.7 Hz), 8.48 (d, 1H, 2.1 Hz), 9.35 (s, 1H), 10.05 (s, 1H).

Ia-107
mp 282–283° C. $^1$H-NMR (DMSO) δ ppm: 1.22–1.57 (m, 4H), 1.27 (s, 914), 1.80–2.04 (m, 4H), 2.27 (m, 1H), 3.06 (m, 1H), 6.81 (d, 1H, J=8.7 Hz), 7.32 (m, 1H), 7.44 (t, 2H, J=7.5 Hz), 7.57–7.72 (m, 6H), 9.91 (s, 1H).

Ia-108
mp 191–192° C. $^1$H-NMR (DMSO) δ ppm: 1.24–1.58 (m, 4H), 1.28 (s, 9H), 1.86–2.04 (m, 4H), 2.70 (m, 1H), 3.08 (m, 1H), 6.83 (d, 1H, J=8.7 Hz), 7.63–7.79 (m, 2H), 8.31 (d, 1H, J=7.2 Hz), 10.27 (s, 1H).

Ia-109
mp 283–285° C. $^1$H-NMR (DMSO) δ ppm: 1.24–1.60 (m, 4H), 1.28 (s, 9H), 1.87–2.04 (m, 4H), 2.42 (m, 1H), 3.09 (m, 1H), 3.87 (s, 2H), 6.82 (d, 1H, J=8.7 Hz), 7.28–7.43 (m, 3H), 7.60 (d, 2H, J=7.8 Hz), 7.68 (d, 2H, J=7.2 Hz), 7.89 (d, 1H, J=7.5 Hz), 9.48 (s, 1H).

Ia-110
mp 263–265° C. $^1$H-NMR (DMSO) δ ppm: 1.24–1.54 (m, 4H), 1.27 (s, 9H), 1.76–1.87 (m, 2H), 1.89–2.01 (m, 2H), 2.17 (m, 1H), 3.04 (m, 1H), 4.01 (s, 4H), 6.01 (s, 2H), 6.44 (d, 2H, J=8.7 Hz), 6.77 (d, 1H, J=8.7 Hz), 7.39 (d, 2H, J=9,0 Hz), 9.44 (s, 1H).

Ia-111
mp 239–241° C. $^1$H-NMR (DMSO) δ ppm: 1.24–1.54 (m, 4H), 1.27 (s, 9H), 1.62–1.76 (m, 4H), 1.80–2.02 (m, 4H), 2.30 (m, 1H), 2.47–2.59 (m, 2H), 2.66–2.76 (m, 2H), 6.08 (m, 1H), 6.79 (d, 1H, J=9.0 Hz), 6.88 (d, 1H, J=6.9 Hz), 7.02 (t, 1H, J=7.5 Hz), 7.13 (d, 1H, J=7.5 Hz), 8.98 (s, 1H).

Ia-124 mp 247–249° C. $^1$H-NMR (DMSO) δ ppm: 1.15 (d, 6H, J=6.3 Hz), 1.30 (s, 9H), 2.15–2.26 (m, 2H), 3.48–3.57 (m, 2H), 3.63–3.76 (m, 2H), 6.92 (d, 2H, J=8.7 Hz), 7.59 (d, 2H, J=9.0 Hz), 7.38 (d, 2H, J=9.0 Hz), 7.87 (d, 2H, J=8.7 Hz), 9.92 (brs, 1H), 9.98 (brs, 1H).

Ia-125 mp 228–232° C. $^1$H-NMR (DMSO) δ ppm: 1.30 (s, 9H), 1.95–2.08 (m, 2H), 2.77–2.89 (m, 4H), 7.17 (d, 1H, J=8.4 Hz), 7.39 (d, 2H, J=9.0 Hz), 7.42–7.48 (m, 1H), 7.64 (brs, 1H), 7.87 (d, 2H, J=9.0 Hz), 9.99 (brs, 2H).

Ia-126 mp 244–246° C. $^1$H-NMR (DMSO) δ ppm: 1.31 (s, 9H), 7.42 (d, 2H, J=8.4 Hz), 7.81 (d-d, 1H, J=2.1 Hz, 8.7 Hz), 7.93 (d, 2H, J=9.0 Hz), 8.05 (d, 1H, J=9.0 Hz), 8.66 (d, 1H, J=2.1 Hz), 9.29 (s, 1H), 10.05 (brs, 1H), 10.39 (brs, 1H).

Ia-127 mp 238–239° C. $^1$H-NMR (DMSO) δ ppm: 1.30 (s, 9H), 4.18–4.27 (m, 4H), 6.81 (d, 1H, J=8.4 Hz), 7.16 (d-d, 1H, J=2.7 Hz, 9.0 Hz), 7.34–7.42 (m, 3H), 7.85 (d, 2H, J=8.4 Hz), 9.94 (brs, 1H), 9.99 (brs, 1H).

Ia-128 mp 286–287° C. $^1$H-NMR (DMSO) δ ppm: 1.31 (s, 9H), 7.41 (d, 2H, J=8.7 Hz), 7.71 (d, 2H, J=8.4 Hz), 7.91 (d, 2H, J=8.7 Hz), 7.99 (d, 2H, J=8.7 Hz), 10.05 (brs, 1H), 10.44 (brs, 1H).

Ia-129 mp 232–234° C. $^1$H-NMR (DMSO) δ ppm: 1.27 (s, 9H), 1.3–1.5 (m, 4H), 1.8–2.0 (m, 4H), 2.25 (1H, m), 3.07 (m, 1H), 6.80 (d, 1H, J=9.0), 7.37 (d, 1H, J=8.1), 7.53 (t, 1H, J=8.1), 7.75 (t, 1H, J=8.1), 8.12 (s, 1H), 10.16 (s, 1H).

Ia-130 mp 274–277° C. $^1$H-NMR (DMSO) δ ppm: 1.27 (s, 9H), 1.23–1.58 (m, 4H), 1.81–2.03 (m, 4H), 2.28 (m, 1H), 3.07 (m, 1H), 6.80 (d, 1H, J=8.4 Hz), 7.36 (d-d, 1H, J=0.9 Hz, 5.7 Hz), 7.43 (d-d, 1H, J=2.1 Hz, 8.7 Hz), 7.60 (d, 1H, J=5.4 Hz), 7.78 (d, 1H, J=8.7 Hz), 8.40 (d, 1H, 1.8 Hz), 9.97 (brs, 1H).

Ia-131 mp 259–260° C. $^1$H-NMR (DMSO) δ ppm: 1.31 (s, 9H), 7.40 (d, 1H, J=4.8 Hz), 7.41 (d, 2H, J=8.7 Hz), 7.66 (d, 1H, J=5.1 Hz), 7.67 (d-d, 1H, J=1.8 Hz, 8.7 Hz), 7.84 (d, 1H, J=9.0 Hz), 7.92 (d, 2H, J=8.7 Hz), 8.50 (s, 1H), 10,03 brs, 1H), 10,27 (brs 1H).

Ia-132 mp 265–266° C. $^1$H-NMR (DMSO) δ ppm: 1.17 (d, 6H, J=6.6 Hz), 1.31 (s, 9H), 4.10 (m, 1H), 7.35–7.46 (m, 3H), 7.54 (d, 1H, J=7.5 Hz), 7.87–7.97 (m, 3H), 8.15 brs, 1H), 8.20 (d, 1H, J=7.5 Hz), 10.03 brs, 1H), 10.25 (brs, 1H).

Ia-133 mp 249–250° C. $^1$H-NMR (DMSO) δ ppm: 1.31 (s, 9H), 7.41 (d, 2H, J=8.7 Hz), 7.45 (d, 1H, J=5.4 Hz), 7.67 (d-d, 1H, J=1.8 Hz, 8.7 Hz), 7.76 (d, 1H, J=5.4 Hz), 7.92 (d, 2H, J=8.7 Hz), 7.95 (d, 1H, J=8.1 Hz), 8.39 (d, 1H, J=1.8 Hz), 10.02 (brs, 1H), 10 23 (brs, 1H).

Ia-134 mp 305–306° C. $^1$H-NMR (DMSO) δ ppm: 1.25 (m, 2H), 1.25 (s, 9H), 1.52 (m, 21), 1.82 (m, 2H), 1.94 (m, 2H), 2.13 (m, 1H), 3.04 (m, 1H), 6.00 (d, 1H, J=8.1), 6.74 (d, 1H, J=8.4), 7.3–7.5 (m, 6H), 7.85 (d, 1H, J=7.5), 8.31 (d, 1H, J=8.4).

Ia-135 mp 220–222° C. $^1$H-NMR (DMSO) δ ppm: 1.27 (s, 9H), 1.3–1.5 (m, 4H), 1.8–2.0 (m, 4H), 2.37 (m, 1H), 3.03 (m, 1H), 6.80 (d, 1H, J=8.7), 7.04 (m, 1H), 7.29 (m, 1H), 7.79 (m, 1H), 9.60 (s, 1H).

Ia-136 mp 263–264° C. $^1$H-NMR (DMSO) δ ppm: 1.27 (s, 9H), 1.3–1.5 (m 4H), 1.8–2.0 (m, 4H), 2.20 (m, 1H), 3.03 (m, 1H), 6.80 (d, 1H, J=8.4), 6.87 (m, 1H), 7.31 (m, 2H), 10.21 (s, 1H).

Ia-137 mp 260–262° C. $^1$H-NMR (DMSO) δ ppm: 1.27 (s, 9H), 1.3–1.5 (m, 4H), 1.8–2.0 (m, 4H), 2.30 (m, 1H), 3.05 (m, 1H), 6.80 (d, 1H, J=8.4), 7.13 (t, 2H, J=8.1), 7.31 (m, 1H), 9.52 (s, 1H).

Ia-138 mp 270–273° C. $^1$H-NMR (DMSO) δ ppm: 1.27 (s, 9H), 1.3–1.5 (m, 4H), 1.8–2.0 (m, 4H), 2.12 (m, 1H), 3.05 (m, 1H), 6.79 (d, 1H, J=9.0), 7.31 (m, 2H), 7.80 (m, 1H), 10.05 (s, 1H).

Ia-139 mp 267–270° C. $^1$H-NMR (DMSO) δ ppm: 1.30 (s, 9H), 4.05 (s, 4H), 6.04 (s, 2H), 6.51 (d, 2H, J=8.7 Hz), 7.34 (d, 2H, J=8.4 Hz), 7.54 (d, 2H, J=8.4 Hz), 7.87 (d, 2H, J=8.4 Hz), 9.82 (brs, 1H), 9.97 (brs, 1H).

Ia-140 mp 227–229° C. $^1$H-NMR (DMSO) δ ppm: 1.22 (d, 6H, J=6.6 Hz), 1.20–1.57 (m 4H), 1.80–2.01 (m, 4H), 2.27 (m, 1H), 2.95–3.22 (m, 2H), 6.99 (d, 1H, J=7.8 Hz), 7.65 (d, 2H, J=8.7 Hz), 7.80 (d, 2H, J=8.4 Hz), 10.18 (brs, 1H).

Ia-141 mp 205–207° C. $^1$H-NMR (DMSO) δ ppm: 1.22 (d, 6H, J=6.9 Hz), 1.20–1.55 (m, 4H), 1.75–2.05 (m, 6H), 2.21 (m, 1H), 2.72–2.85 (m, 4H), 2.93–3.20 (m, 2H), 6.98 (d, 1H, J=8.1 Hz), 7.10 (d, 1H, J=8.1 Hz), 7.26 (d-d, 1H, J=2.1 Hz, 8.1 Hz), 7.51 (s, 1H), 9.67 (brs, 1H).

Ia-142 mp 295–296° C. $^1$H-NMR (DMSO) δ ppm: 1.15 (d, 6H, J=6.6), 1.27 (s, 9H), 1.3–1.5 (m, 4H), 1.8–2.0 (m, 4H), 2.27 (m, 1H), 3.05 (m, 1H), 4.07 (m, 1H), 6.80 (d, 1H, J=8.7), 7.64 (d, 2H, J=8.7), 7.79 (d, 2H, J=8.7), 8.06 (d, 1H, J=7.5), 10.01 (s, 1H).

Ia-143 mp 146–147° C. $^1$H-NMR (DMSO) δ ppm: 1.26 (s, 9H), 1.5–1.7 (m, 4H), 2.36 (t, 2H, J=7.8), 3.03 (q, 2H, J=6.3), 6.89 (t, 1H, J=6.3), 7.66 (d, 2H, J=8.4), 7.80 (d, 2H, J=8.4), 10.25 (s, 1H).

Ia-144 mp 138–140° C. $^1$H-NMR (DMSO) δ ppm: 1.21 (d, 6H, J=6.0), 1.4–1.7 (m, 4H), 2.37 (t, 2H, J=7.5), 2.96 (q, 2H, J=6.3), 3.14 (m, 1H), 6.99 (t, 1H, J=5.4), 7.66 (d, 2H, J=7.8), 7.81 (d, 2H, J=7.8), 10.25 (s, 1H).

Ia-145 mp 134–136° C. $^1$H-NMR (DMSO) δ ppm: 1.26 (s, 9H), 1.39 (m, 2H), 1.4–1.7 (m, 4H), 2.28 (t, 2H, J=7.2), 2.79 (m, 4H), 3.02 (q, 2H, J=7.2), 6.88 (t, 1H, J=6.0), 7.10 (t, 1H, J=6.0), 7.51 (s, 1H), 9.73 (s, 1H).

Ia-146 mp 135–137° C. $^1$H-NMR (DMSO) δ ppm: 1.20 (d, 6H, J=6.6), 1.4–1.7 (m, 4H), 1.99 (m, 2H), 2.28 (t, 2H, J=7.2), 2.79 (m, 4H), 2.94 (q, 2H, J=6.3), 3.13 (m, 1H), 6.98 (t, 1H, J=6.9), 7.10 (d, 2H, J=8.1), 7.26 (d, 2H, J=8.1), 7.51 (s, 1H), 9.73 (s, 1H).

Ia-147 mp 206–207° C. $^1$H-NMR (DMSO) δ ppm: 1.29 (s, 9H), 4.54 (d, 2H, J=5.7 Hz), 7.35 (d, 2H, J=9.0 Hz), 7.52 (d, 2H, J=7.8 Hz), 7.69 (d, 2H, J=8.1 Hz), 7.83 (d, 2H, J=8.7 Hz), 9.02 (t, 1H, J=5.7 Hz), 9.97 (brs, 1H).

Ia-148 mp 250–251° C. $^1$H-NMR (DMSO) δ ppm: 1.30 (s, 9H), 7.18 (t, 2H, J=9.3 Hz), 7.40 (d, 2H, J=8.7 Hz), 7.76 (d-d, 2H, J=5.1 Hz, 9.3 Hz), 7.88 (d, 2H, J=9.0 Hz), 10.02 (brs, 1H), 10.17 (brs, 1H).

Ia-149 mp 220–222° C. $^1$H-NMR (DMSO) δ ppm: 1.30 (s, 9H), 3.74 (s, 3H), 6.92 (d, 2H, J=9.0 Hz), 7.38 (d, 2H, J=9.0 Hz), 7.64 (d, 2H, J=9.0 Hz), 7.87 (d, 2H, J=9.0 Hz), 9.99 (s, 2H).

Ia-150 mp 264–266° C. $^1$H-NMR (DMSO) δ ppm: 1.31 (s, 9H), 1.66–1.76 (m, 4H), 2.57–2.66 (m, 2H), 2.71–2.80 (m, 2H), 6.98 (m, 1H), 7.06–7.16 (m, 2H), 7.38 (d, 2H, J=9.0 Hz), 7.90 (d, 2H, J=8.7 Hz), 9.60 (s, 1H), 9.99 (s, 1H).

Ia-151 mp 235–236° C. $^1$H-NMR (DMSO) δ ppm: 1.03–1.39 (m, 5H), 1.27 (s, 9H), 1.55–1.87 (m, 5H), 3.73 (m, 1H), 7.31 (d, 2H, J=8.7 Hz), 7.76 (d, 2H, J=8.4 Hz), 8.01 (d, 1H, J=7.8 Hz), 9.90 (s, 1H).

Ia-152 mp 244–246° C. $^1$H-NMR (DMSO) δ ppm: 0.50–0.72 (m, 4H), 1.27 (s, 9H), 2.81 (m, 1H), 7.31 (d, 2H, J=8.7 Hz), 7.73 (d, 2H, J=8.7 Hz), 8.30 (d, 1H, J=4.2 Hz), 9.91 (brs, 1H).

Ia-153 mp>300° C. $^1$H-NMR (DMSO) δ ppm: 1.06 (m, 6H), 1.27 (s, 9H), 1.2–1.5 (m, 4H), 1.8–2.0 (m, 4H), 2.25 (m, 1H), 2.7 (m, 1H), 3.05 (m, 1H), 3.51 (m, 4H), 4.30 (m, 1H), 6.80 (d, 1H, J=8.4), 7.34 (d, 2H, J=8.4), 7.65 (d, 2H, J=8.4), 10.01 (s, 1H).

Ia-154 mp 247–249° C. $^1$H-NMR (DMSO) δ ppm: 1.05 (m, 6H), 1.27 (s, 9H), 1.2–1.5 (m, 4H), 1.8–2.0 (m, 4H), 2.23 (m, 1H), 2.77 (m, 1H), 3.05 (m, 1H), 3.52 (m, 4H), 4.33 (m, 1H), 6.80 (d, 1H, J=9.0), 7.03 (d, 1H, J=7.8), 7.35 (t, 1H, J=7.8), 7.59 (d, 1H, J=7.8), 7.68 (s, 1H), 9.96 (s, 1H).

Ia-155 mp 258–259° C. $^1$H-NMR (DMSO) δ ppm: 1.25 (m, 2H), 1.50 (m, 2H), 1.86 (m, 2H), 1.99 (m, 2H), 2.28 (m, 1H), 2.93 (s, 3H), 3.10 (m, 1H), 7.02 (d, 1H, J=7.5), 7.65 (d, 2H, J=8.4), 7.80 (d, 2H, J=8.4), 10.20 (s, 1H).

Ia-156 mp 250–253° C. $^1$H-NMR (DMSO) δ ppm: 1.28 (m, 2H), 1.50 (m, 2H), 1.82 (m, 2H), 2.00 (m, 4H), 2.22 (m, 1H), 2.79 (m, 4H), 2.92 (s, 3H), 3.11 (m, 1H), 7.01 (d, 1H, J=(0.1), 7.26 (d, 1H, J=8.1), 7.51 (s, 1H), 9.68 (s, 1H).

Ia-157 mp 259–262° C. $^1$H-NMR (DMSO) δ ppm: 1.13 (d, 6H, J=6.0), 1.25 (m, 2H), 1.50 (m, 2H), 1.80 (m, 2H), 1.95 (m, 2H), 2.17 (m, 3H), 2.92 (s, 3H), 3.10 (m, 1H), 3.70 (m, 2H), 3.68 (m, 2H), 6.86 (d, 2H J=9.3), 7.00 (d, 1H, J=7.2), 7.43 (d, 2H, J=9.3), 9.58 (s, 1H).

Ia-158 mp 298–300° C. $^1$H-NMR (DMSO) δ ppm: 1.31 (s, 9H), 7.30–7.50 (m, 5H), 7.63–7.71 (m, 4H), 7.87 (d, 2H, J=8.7 Hz), 7.91 (d, 2H, J=9.0 Hz), 10.03 (brs, 1H), 10.22 (brs, 1H).

Ia-159 mp 278–281° C. $^1$H-NMR (DMSO) δ ppm: 0.74–1.87 (m, 20H), 1.29 (s, 9H), 3.76 (m, 1H), 7.32 (d, 2H, J=8.4 Hz), 7.75 (d, 2H, J=8.7 Hz), 7.75 (d, 1H, J=8.7 Hz), 7.90 (brs, 1H).

Ia-160 mp 227–228° C. $^1$H-NMR (DMSO) δ ppm: 1.22–1.55 (m, 4H), 1.27 (s, 9H), 1.80–2.02 (m, 4H), 2.23 (m, 1H), 3.06 (m, 1H), 6.78 (d, 1H, J=8.7 Hz), 7.45 (t, 1H, J=9.9 Hz), 7.82 (m, 1H), 8.12 (d-d, 1H, J=2.4 Hz, 6.3 Hz), 10.17 (brs, 1H).

Ia-161 mp 259–260° C. $^1$H-NMR (DMSO) δ ppm: 1.22–1.54 (m, 4H), 1.27 (s, 9H), 1.78–2.01 (m, 4H), 2.16 (s, 3H), 2.21 (m, 1H), 3.05 (m, 1H), 6.77 (d, 1H, J=8.4 Hz), 7.12–7.21 (m, 2H), 7.53 (m, 1H), 9.90 (brs, 1H).

Ia-162 mp 222–226° C. $^1$H-NMR (DMSO) δ ppm: 1.15 (d, 6H, J=6.3 Hz), 1.26 (d, 6H, J=6.9 Hz), 2.16–2.26 (m, 2H), 3.31 (m, 1H), 3.48–3.58 (m, 2H), 3.63–3.76 (m, 2H), 6.92 (d, 2H, J=9.0 Hz), 7.32 (d, 2H, J=8.7 Hz), 7.59 (d, 2H, 9.0 Hz), 7.89 (d, 2H, J=9.0 Hz), 9.92 (s, 1H), 10.13 (brs, 1H).

Ia-163 mp 197–200° C. $^1$-NMR (DMSO) δ ppm: 1.26 (d, 6H, J=6.3 Hz), 1.95–2.09 (m, 2H), 2.77–2.90 (m, 4H), 3.32 (m, 1H), 7.17 (d, 1H, J=8.1 Hz), 7.32 (d, 2H, J=8.7 Hz), 7.45 (d-d, 1H, J=1.8 Hz, 8.1 Hz), 7.64 (brs, 1H), 7.90 (d, 2H, J=8.7 Hz), 9.99 (brs, 1H), 10.13 (brs, 1H).

Ia-164 mp 145–247° C. $^1$H-NMR (DMSO) δ ppm: 1.27 (s, 9H), 1.3–2.0 (m, 16H), 2.19 (m, 1H), 3.05 (m, 1H), 4.74 (m, 1H), 6.79 (d, 1H, J=9.0), 6.80 (d, 2H, J=9.0), 7.47 (d, 2H, J=9.0), 9.63 (s, 1H).

Ia-165 mp>300° C. $^1$H-NMR (DMSO) δ ppm: 1.03–2.02 (m, 18H), 1.27 (s, 9H), 2.26 (m, 1H), 3.06 (m, 1H), 3.73 (m, 1H), 6.78 (d, 1H, J=8.7 Hz), 7.6:3 (d, 2H, J=9.0 Hz), 7.78 (d, 2H, J=8.7 Hz), 8.02 (d, 1H, J=8.1 Hz), 10.00 (brs, 1H).

Ia-166 mp 200–201° C. $^1$H-NMR (DMSO) δ ppm: 1.03–2.02 (m, 18H), 1.27 (s, 9H), 2.25 (m, 1H), 3.06 (m, 1H), 3.73 (m, 1H), 6.78 (d, 1H, J=8.7 Hz), 7.33 (t, 1H, J=8.1 Hz), 7.46 (d, 1H, J=8.1 Hz), 7.76 (m, 1H), 7.94 (m, 1H), 8.14 (d, 1H, J=8.1 Hz), 9.92 (brs, 1H).

Ia-167 mp 282–285° C. $^1$H-NMR (DMSO) δ ppm: 1.22–1.57 (m, 4H), 1.27 (s, 9H), 1.87–2.03 (m, 4H), 2.49 (m, 1H), 3.07 (m, 1H), 6.83 (d, 1H, J=8.7 Hz), 13.20 (brs, 1H).

Ia-168 mp 120–124° C. $^1$H-NMR (DMSO) δ ppm: 0.94–1.66 (m, 14H), 1.27 (s, 9H), 1.80–2.04 (m, 4H), 2.25 (m, 1H), 2.92 (m, 1H), 3.06 (m, 1H), 6.78 (d, 1H, J=8.7 Hz), 7.42–7.53 (m, 2H), 7.63 (d, 1H, J=7.2 Hz), 7.73 (m, 1H), 8.17 (m, 1H), 10.11 (brs, 1H).

Ia-169 mp 256–257° C. $^1$H-NMR (DMSO) δ ppm: 0.93–1.20 (m, 5H), 1.24–1.64 (m, 9H), 1.27 (s, 9H), 1.80–2.02 (m, 4H), 2.27 (m, 1H), 2.87 (m, 1H), 3.06 (m, 1H), 6.79 (d, 1H, J=9.0 Hz), 7.48 (d, 1H, J=7.2 Hz), 7.68–7.79 (m, 4H), 10.17 (brs, 1H).

Ia-171 mp 242–244° C. $^1$H-NMR (DMSO) δ ppm: 1.27 (m, 12H), 1.45 (m, 4H), 1.90 (m, 4H), 2.25 (m, 1H), 3.07 (m, 1H), 3.67 (m, 2H), 6.77 (d, 1H, J=8.7), 6.90 (d, 1H, J=7.8), 7.31 (t, 1H, J=7.5), 7.53 (d, 1H, J=7.8), 7.59 (s, 1H), 9.89 (s, 1H).

Ia-172 mp>310° C. $^1$H-NMR (DMSO) δ ppm: 1.27 (m, 12H), 1.38 (m, 4H), 1.84 (m, 2H), 1.97 (m, 2H), 2.25 (m, 1H), 3.07 (m, 1H), 3.66 (m, 2H), 6.81 (d, 1H, J=8.7), 7.20 (d, 2H, J=6.7), 7.61 (d, 2H, J=8.7), 9.94 (s, 1H).

Ia-173 mp 279–281° C. $^1$H-NMR (DMSO) δ ppm: 1.27 (s, 9H), 1.3–1.5 (m, 4H), 1.83 (m, 6H), 1.93 (m, 2H), 2.21 (m, 1H), 2.36 (m, 2H), 3.05 (m, 1H), 3.54 (m, 2H), 6.79 (d, 1H, J=8.7), 7.16 (d, 2H, J=9.0), 7.56 (d, 2H, J=9.0), 9.83 (s, 1H).

Ia-174 mp 258–262° C. $^1$H-NMR (DMSO) δ ppm: 0.29 (m, 2H), 0.53 (m, 2H), 1.20 (m, 1H), 1.27 (s, 9H), 1.3–1.5 (m, 4H), 1.7–2.0 (m, 4H), 2.20 (m, 1H), 3.05 (m, 1H), 3.75 (d, 2H, J=6.9), 6.79 (d, 1H, J=9.0), 6.83 (d, 2H, J=9.0), 7.46 (d, 2H, J=9.0), 9.64 (s, 1H).

Ia-175
mp 246–248° C. ¹H-NMR (DMSO) δ ppm: 1.27 (s, 9H), 1.3–2.0 (m, 18H), 2.19 (m, 1H), 3.04 (m, 1H), 4.23 (m, 1H), 6.79 (d, 1H, J=8.7), 6.84 (d, 2H, J=9.0), 7.45 (d, 2H, J=9.0), 9.64 (s, 1H).

Ia-176
mp 200–202° C. ¹H-NMR (DMSO) δ ppm: 1.27 (s, 9H), 1.3–2.0 (m, 18H), 2.21 (m, 1H), 3.05 (m, 1H), 4.23 (m, 1H), 6.57 (d, 1H, J=6.9), 6.80 (d, 1H, J=9.0), 7.0–7.2 (m, 2H), 7.28 (s, 1H), 9.74 (s, 1H).

Ia-177
mp 266–268° C. ¹H-NMR (DMSO) δ ppm: 1.22–1.56 (m, 4H), 1.27 (s, 9H), 1.79–2.02 (m, 4H), 2.25 (m, 1H), 3.05 (m, 1H), 6.56 (m, 1H), 6.77–6.84 (m, 2H), 7.58–7.71 (m, 5H), 9.92 (brs, 1H).

Ia-178
mp 223–224° C. ¹H-NMR (DMSO) δ ppm: 1.26–1.54 (m, 4H), 1.27 (s, 9H), 1.81–2.02 (m, 4H), 2.45 (m, 1H), 3.06 (m, 1H), 6.80 (d, 1H, J=8.7 Hz), 8.15 (d-d, 1H, J=2.4 Hz, 9.0 Hz), 8.27 (d, 1H, J=9.0 Hz), 8.70 (m, 1H), 10.85 brs, 1H).

Ia-179
mp 224–227° C. ¹H-NMR (DMSO) δ ppm: 1.24–1.56 (m, 4H), 1.27 (s, 9H), 1.80–2.03 (m, 4H), 2.27 (m, 1H), 3.06 (m, 1H), 6.80 (d, 1H, J=8.7 Hz), 6.90 (d, 1H, J=1.8 Hz), 7.72–7.84 (m, 4H), 8.60 (d, 1H, J=1.8 Hz), 10.09 (brs, 1H).

Ia-180
mp 226–227° C. ¹H-NMR (DMSO) δ ppm: 0.92 (d, 6H, J=6.6 Hz), 1.26–1.55 (m, 4H), 1.27 (s, 9H), 1.80–2.03 (m, 4H), 2.27 (m, 1H), 3.05 (m, 1H), 3.20 (m, 1H), 6.80 (d, 1H, J=8.7 Hz), 7.42 (d, 1H, J=7.2 Hz), 7.67–7.79 (m, 4H), 10.19 brs, 1H).

Ia-181
mp 191–192° C. ¹H-NMR (DMSO) δ ppm: 0.95 (d, 6H, J=6.6 Hz), 1.26–1.55 (m, 4H), 1.27 (s, 9H), 1.80–2.03 (m, 4H), 2.25 (m, 1H), 3.06 (m, 1H), 3.23 (m, 1H), 6.80 (d, 1H, J=8.4 Hz), 7.41–7.53 (m, 2H), 7.58 (d, 1H, J=7.2 Hz), 7.73 (m, 1H), 8.18 (m, 1H), 10.13 (brs, 1H).

Ia-182
mp 192–193° C. ¹H-NMR (DMSO) δ ppm: 0.30 (m, 2H), 0.55 (m, 2H), 1.2–1.5 (m, 5H), 1.27 (s, 1H), 1.8–2.0 (m, 4H), 2.20 (m, 1H), 3.04 (m, 1H), 3.75 (d, 2H, J=6.9), 6.58 (m, 1H), 6.79 (d, 1H, J=8.7), 7.0–7.2 (m, 2H), 7.31 (s, 1H), 9.76 (s, 1H).

Ia-183
mp>310° C. ¹H-NMR (DMSO) δ ppm: 1.27 (s, 9H), 1.3–1.5 (m, 4H), 1.82 (m, 2H), 1.97 (m, 2H), 2.04 (m, 2H), 2.39 (m, 1H), 2.46 (t, 2H, J=7.8), 3.07 (m, 1H), 3.79 (t, 2H, J=7.5), 6.79 (d, 1H, J=8.7), 7.56 (m, 4H), 9.80 (s, 1H).

Ia-184
mp 281–283° C. ¹H-NMR DMSO) δ ppm: 1.24–1.57 (m, 4H), 1.27 (s, 9H), 1.80–2.04 (m, 4H), 2.27 (m, 1H), 3.06 (m, 1H), 6.80 (d, 1H, J=9,0 Hz), 7.33 (s, 1H), 7.75 (d, 2H, J=9.3 Hz), 7.91 (d, 2H, J=8.7 Hz), 8.16 (s, 1H), 10.09 (brs, 1H).

Ia-185
mp 226–227° C. ¹H-NMR (DMSO) δ ppm: 1.24–1.58 (m, 10H), 1.27 (s, 9H), 1.81–2.02 (m, 4H), 2.28 (m, 1H), 2.78–2.88 (m, 4H), 3.06 (m, 1H), 6.80 (d, 1H, J=8.7 Hz), 7.64 (d, 2H, J=8.7 Hz), 7.82 (d, 2H, J=8.7 Hz), 10.25 brs, 1H).

Ia-186
mp 148–150° C. ¹H-NMR (DMSO) δ ppm: 1.25–1.60 (m, 10H), 1.27 (s, 9H), 1.82–2.03 (m, 4H), 2.24 (m, 1H), 2.82–2.92 (m, 4H), 3.06 (m, 1H), 6.79 (d, 1H, J=8.4 Hz), 7.36 (m, 1H), 7.55 (t, 1H, J=7.8 Hz), 7.84 (d, 2H, J=8.6 Hz, 1H), 10.18 (brs, 1H).

Ia-187
mp>310° C. ¹H-NMR (DMSO) δ ppm: 1.27 (s, 9H), 1.36 (s, 9H), 1.43 (m, 4H), 1.85 (m, 2H), 1.93 (m, 2H), 2.27 (m, 1H), 3.06 (m, 1H), 6.80 (d, 1H, J=8.7), 7.58 (s, 1H), 7.62 (d, 2H), 7.75 (d, 2H, J=9.0), 10.00 (s, 1H).

Ia-188
mp 285–292° C. ¹H-NMR (DMSO) δ ppm: 0.85 (t, 3H, J=7.5), 1.11 (d, 3H, J=6.3), 1.26 (s, 9H), 1.3–1.6 (m, 6H), 1.85 (m, 2H), 1.95 (m, 2H), 2.27 (m, 1H), 3.06 (m, 1H), 3.90 (m, 1H), 6.80 (d, 1H, J=8.4), 7.64 (d, 2H, J=8.7), 7.79 (d, 2H, J=8.7), 7.99 (d, 1H, J=8.1), 10.02 (s, 1H).

Ia-189
mp 278–281° C. ¹H-NMR (DMSO) δ ppm: 1.27 (s, 9H), 1.2–2.0 (m, 17H), 2.03 (m, 2H), 3.03 (m, 1H), 6.79 (d, 1H, J=8.4), 7.1–7.3 (m, 3H), 7.94 (s, 1H), 9.78 (m, 2H).

Ia-190
mp>310° C. ¹H-NMR (DMSO) δ ppm: 1.1–2.0 (m, 17H), 1.27 (s, 9H), 2.25 (m, 2H), 3.03 (m, 1H), 6.79 (d, 1H, J=8.7), 7.48 (m, 4H), 9.71 (m, 2H).

Ia-191
mp 275–277° C. ¹H-NMR (DMSO) δ ppm: 1.16 (d, 6H, J=6.6 Hz), 1.31 (s, 9H), 4.09 (m, 1H), 7.41 (d, 2H, J=8.7 Hz), 7.84 (s, 4H), 7.90 (d, 2H, J=9.0 Hz), 8.11 (d, 1H, J=7.5 Hz), 10.04 (brs, 1H), 10.30 (brs, 1H).

Ia-192
mp 204–205° C. ¹H-NMR (DMSO) δ ppm: 1.15 (d, 6H, J=6.6 Hz), 1.20–1.56 (m, 4H), 1.22 (d, 6H, J=6.6 Hz), 1.78–2.00 (m, 4H), 2.25 (m, 1H), 2.98–3.22 (m, 2H), 4.06 (m, 1H), 6.99 (d, 1H, J=8.1 Hz), 7.34 (t, 1H, J=8.1 Hz), 7.46 (d, 1H, J=7.8 Hz), 7.75 (m 1H), 7.96 (m, 1H), 8.17 (d, 1H, J=8.7 Hz), 9.94 (brs, 1H).

Ia-193
mp 285–286° C. ¹H-NMR (DMSO) δ ppm: 1.15 (d, 6H, J=6.6 Hz), 1.20–1.56 (m, 4H), 1.22 (d, 6H, J=6.9 Hz), 1.79–2.00 (m, 4H), 2.26 (m, 1H), 2.97–3.20 (m, 2H), 4.07 (m, 1H), 6.99 (d, 1H, J=7.8 Hz), 7.64 (d, 2H, J=8.7 Hz), 7.79 (d, 2H, J=8.7 Hz), 8.06 (d, 1H, J=7.5 Hz), 10.02 (brs, 1H).

Ia-194
mp 248–250° C. ¹H-NMR (DMSO) δ ppm: 1.22–1.57 (m, 4H), 1.22 (d, 6H, J=6.6 Hz), 1.78–2.00 (m, 4H), 2.25 (m, 1H), 2.98–3.22 (m, 2H), 6.56 (m, 1H), 6.82 (d, 1H, J=3.3 Hz), 6.99 (d, 1H, J=7.8 Hz), 7.58–7.71 (m, 5H), 9.92 brs, 1H).

Ia-195
mp 271–275° C. ¹H-NMR (DMSO) δ ppm: 1.27 (s, 9H), 1.28–1.56 (m, 4H), 1.80–2.02 (m, 4H), 2.25 (m, 1H), 3.06 (m, 1H), 6.80 (d, 1H, J=9.0 Hz), 7.57 (s, 1H), 7.62–7.74 (m, 4H), 8.39 (s, 1H), 9.99 (brs, 1H).

Ia-196
mp 226–228° C. ¹H-NMR (CDCl₃) δ ppm: 0.30 (m, 2H), 1.23 (d, 6H, J=6.9), 1.2–2.0 (m, 4H), 2.20 (m, 1H), 3.10 (m, 2H), 3.76 (d, 2H, J=6.9), 6.83 (d, 2H, J=8.7), 6.99 (d, 1H, J=8.1), 7.46 (d, 2H, J=8.7), 9.65 (s, 1H).

Ia-197
mp 173–175° C. ¹H-NMR (DMSO) δ ppm: 0.31 (m, 2H), 0.56 (m, 2H), 1.22 (d, 6H, J=6.6), 1.2–1.5 (m, 4H), 1.8–2.0 (m, 4H), 2.22 (m, 1H), 3.10 (m, 1H), 3.76 (d, 1H, J=7.2), 6.58 (d, 1H, J=8.1), 7.0–7.2 (m, 2H), 7.32 (s, 1H), 9.78 (s, 1H).

Ia-198
mp 233–235° C. ¹H-NMR (DMSO) δ ppm: 1.25 (d, 6H, J=6.9), 1.2–2.0 (m, 16H), 2.19 (m, 1H), 3.10 (m, 2H), 4.73 (m, 1H), 6.80 (d, 2H, J=8.7), 6.98 (d, 1H, J=7.8), 7.45 (d, 2H, J=8.7), 9.63 (s, 1H).

Ia-199
mp 185–186° C. ¹H-NMR (DMSO) δ ppm: 1.22 (d, 6H, J=6.9), 1.2–2.0 (m, 16H), 2.22 (m, 1H), 3.10 (m, 2H), 4.73 (m, 1H), 6.54 (m, 1H), 7.0–7.2 (m, 2H), 7.3 (s, 1H), 9.75 (s, 1H).

Ia-200 mp 235–237° C. ¹H-NMR (DMSO) δ ppm: 1.27 (s, 9H), 1.3–1;6 (m, 6H), 1.8–2.0 (m, 6H), 2.20 (m, 1H), 3.05 (m, 1H), 3.45 (m, 2H), 3.82 (m, 2H), 4.47 (m, 1H), 6.79 (d, 1H, J=9.0), 6.89 (d, 2H, J=9.0), 7.47 (d, 2H, J=9.0), 9.66 (s, 1H).

Ia-201 mp 300–301° C. ¹H-NMR (DMSO) δ ppm: 1.15 (d, 6H, J=6.6 Hz), 1.26–1.56 (m, 4H), 1.27 (s, 9H), 1.82–2.03 (m, 4H), 2.23 (s, 3H), 2.37 (m, 1H), 3.06 (m, 1H), 4.07 (m, 1H), 6.81 (d, 1H, J=8.7 Hz), 7.52 (d, 1H, J=8.4 Hz), 7.62 (d, 1H, J=8.4 Hz), 7.68 (s, 1H), 8.09 (d, 1H, J=7.5), 9.22 (brs, 1H).

Ia-202 mp 269–270° C. ¹H-NMR (DMSO) δ ppm: 1.25–1.26 (m, 4H), 1.27 (s, 9H), 1.80–2.03 (m, 4H), 2.25 (m, 1H), 3.07 (m, 1H), 6.80 (d, 1H, J=8.4 Hz), 7.11 (m, 1H), 7.42 (d, 1H, J=3.6 Hz), 7.48 (m, 1H), 7.58 (d, 2H, J=8.7 Hz), 7.64 (d, 2H, J=8.4 Hz), 9.92 (brs, 1H).

Ia-203 mp 271–273° C. ¹H-NMR (DMSO) δ ppm: 1.14–1.54 (m, 9H), 1.26 (s, 9H), 1.63–1.88 (m, 7H), 1.89–2.01 (m, 2H), 2.21 (m, 1H), 2.42 (m, 1H), 3.04 (m, 1H), 6.79 (d, 1H, J=9.0 Hz), 7.11 (d, 2H, J=8.4 Hz), 7.47 (d, 2H, J=8.1 Hz), 9.70 (brs, 1H).

Ia-204 mp 250–251° C. ¹H-NMR (DMSO) δ ppm: 1.22–1.39 (m, 2H), 1.22 (d, 6H, J=6.6 Hz), 1.40–1.57 (m, 2H), 1.80–2.01 (m, 4H), 2.28 (m, 1H), 2.98–3.21 (m, 2H), 7.00 (d, 1H, J=7.8 Hz), 7.34 (s, 1H), 7.75 (d, 2H, J=9.0 Hz), 7.91 (d, 2H, J=8.7 Hz), 8.17 (s, 1H), 10.10 (brs, 1H).

Ia-205 mp 239–240° C. ¹H-NMR (DMSO) δ ppm: 1.27 (s, 9H), 1.2–1.5 (m, 4H), 1.8–2.0 (m, 5H), 2.08 (m, 2H), 3.05 (m, 1H), 3.80 (m, 4H), 4.95 (m, 1H), 6.79 (d, 1H, J=8.7), 6.83 (d, 2H, J=8.7), 7.48 (d, 2H, J=8.7), 9.66 (s, 1H).

Ia-206 mp 236–2:38° C. ¹H-NMR (DMSO) δ ppm: 1.27 (s, 9H), 1.2–1.7 (m, 8H), 1.8–2.0 (m, 6H1), 2.18 (m, 1H), 3.04 (m, 1H), 3.3–3.6 (m, 2H), 3.85 (m, 3H), 6.80 (d, 1H, J=9.0), 6.84 (d, 2H, J=9.0), 7.47 (d, 2H, J=9.0), 9.65 (s, 1H).

Ia-207 mp 224–226° C. ¹H-NMR (DMSO) δ ppm: 1.27 (s, 9H), 1.2–1.5 (m, 4H), 1.8–2.0 (m, 4H), 2.24 (m, 1H), 2.39 (m, 2H), 3.06 (m, 1H), 3.50 (t, 2H, J=7.5), 3.70 (t, 2H, J=6.3), 6.78 (d, 1H, J=6.6), 6.83 (m, 1H), 7.25 (m, 1H), 7.27 (m, 1H), 7.54 (s, 1H), 9.61 (s, 1H).

Ia-208 mp 275–277° C. ¹H-NMR (DMSO) δ ppm: 1.27 (s, 9H), 1.3–1.5 (m, 4H), 1.8–2.0 (m, 4H), 2.22 (m, 1H), 2.38 (m, 2H), 3.07 (m, 1H), 3.47 (t, 2H, J=6.9), 3.69 (t, 2H, J=6.6), 6.80 (d, 1H, J=8.7), 7.14 (d, 2H, J=8.4), 7.58 (d, 2H, J=8.4), 9.83 (s, 1H).

Ia-209 mp 214–215° C. ¹H-NMR (DMSO) δ ppm: 1.26–1.56 (m, 4H), 1.27 (s, 9H), 1.80–2.03 (m, 4H), 2.25 (m, 1H), 3.06 (m, 1H), 6.59 (m, 1H), 6.81 (d, 1H, J=8.4 Hz), 6.86 (d, 1H, J=2.7 Hz), 7.28–7.40 (m, 2H), 7.47 (m, 1H), 7.75 (s, 1H), 8.01 (s, 1H), 9.91 (brs, 1H).

Ia-210 mp 272–275° C. ¹H-NMR (DMSO) δ ppm: 1.31 (s, 9H), 6.59 (m, 1H), 6.87 (d, 1H, J=3.3 Hz), 7.41 (d, 2H, J=8.7 Hz), 7.68 (d, 2H, J=8.7 Hz), 7.72 (m, 1H), 7.83 (d, 2H, J=8.7 Hz), 7.90 (d, 2H, J=8.7 Hz), 10.03 (brs, 1H), 10.22 (brs, 1H).

Ia-211 mp 251–255° C. ¹H-NMR (DMSO) δ ppm: 1.31 (s, 9H), 7.36 (s, 1H), 7.41 (d, 2H, J=8.4 Hz), 7.91 (d, 2H, J=8.4 Hz), 7.92–8.00 (m, 4H), 8.19 (s, 1.H), 10.06 (brs, 1H), 10.38 (brs, 1H).

Ia-212 mp 241–244° C. ¹H-NMR (DMSO) δ ppm: 1.30 (s, 9H), 1.50–1.78 (m, 6H), 1.81–1.97 (m, 2H), 4.78 (m, 1H), 6.87 (d, 2H, J=9.0 Hz), 7.38 (d, 2H, J=8.7 Hz), 7.61 (d, 2H, J=9.0 Hz), 7.87 (d, 2H, J=8.7 Hz), 9.97 (brs, 1H), 9.99 (brs, 1H).

Ia-213 mp 283–286° C. ¹H-NMR (DMSO) δ ppm: 1.31 (s, 9H), 7.12 (d-d, 1H, J=3.6 Hz, 5.1 Hz), 7.41 (d, 2H, J=9.0 Hz), 7.46 (m, 1H), 7.50 (d-d, 1H, J=1.2 Hz, 5.1 Hz), 7.64 (d, 2H, J=8.7 Hz), 7.82 (d, 2H, J=8.7 Hz), 7.90 (d, 2H, J=9.3 Hz), 10.03 (brs, 1H), 10.22 (brs, 1H).

Ia-216 mp 224–225° C. ¹H-NMR (CDCl₃) δ ppm: 1.22 (d, 6H, J=6.9), 1.2–1.5 (m, 4H), 1.8–2.0 (m, 4H), 2.45 (m, 1H), 3.12 (m, 2H), 6.99 (d, 1H, J=8.1), 8.15 (m, 1H), 8.27 (d, 1H, J=9.0), 8.69 (s, 1H), 10.86 (s, 1H).

Ia-219 mp 270–272° C. ¹H-NMR (DMSO) δ ppm: 1.28 (s, 9H), 1.34–1.51 (m, 2H), 1.80–1.92 (m, 2H), 2.83–2.97 (m, 2H), 3.32 (m, 1H), 3.99–4.12 (m, 2H), 6.92 (d, 1H, J=8.7 Hz), 7.57 (d, 2H, J=8.7 Hz), 7.68 (d, 2H, J=9.0 Hz), 8.90 (brs, 1H).

Ia-220 mp 187–189° C. ¹H-NMR (DMSO) δ ppm: 1.28 (s, 9H), 1.31–1.51 (m, 2H), 1.78–1.90 (m, 2H), 2.78–2.93 (m, 2H), 3.30 (m, 1H), 3.97–4.09 (m, 2H), 6.90 (d, 1H, J=8.7 Hz), 7.06 (t, 2H, J=9.0 Hz), 7.44 (d-d, 2H, J=4.8 Hz, 9.0 Hz), 8.53 (brs, 1H).

Ia-221 mp 260–262° C. ¹H-NMR (DMSO) δ ppm: 1.12–1.50 (m, 7H), 1.28 (s, 9H), 1.63–1.90 (m, 7H), 2.40 (m, 1H), 2.76–2.91 (m, 2H), 3.28 (m, 1H), 3.96–4.09 (m, 2H), 6.90 (d, 1H, J=8.7 Hz), 7.06 (d, 2H, J=8.4 Hz), 7.32 (d, 2H, J=8.4 Hz), 8.40 brs, 1H).

Ia-222 mp 265–267° C. ¹H-NMR (DMSO) δ ppm: 1.23 (d, 6H, J=6.6 Hz), 1.31–1.48 (m, 2H), 1.77–1.90 (m, 2H), 2.84–2.98 (m, 2H), 3.16 (m, 1H), 3.33 (m, 1H), 3.96–4.10 (m, 2H), 7.11 (d, 1H, J=7.8 Hz), 7.57 (d, 2H, J=8.7 Hz), 7.67 (d, 2H, J=8.4 Hz), 8.90 (brs, 1H).

Ia-223 mp 183–186° C. ¹H-NMR (DMSO) δ ppm: 1.23 (d, 6H, J=6.9 Hz), 1.28–1.47 (m, 2H), 1.76–1.88 (m, 2H), 2.80–3.16 (m, 2H), 3.16 (m, 1H), 3.32 (m, 1H), 3.94–4.07 (m, 2H), 7.00–7.14 (m, 3H), 7.44 (d-d, 2H, J=4.8 Hz, 9.0 Hz), 8.53 (brs, 1H).

Ia-224 mp 232–234° C. ¹H-NMR (DMSO) δ ppm: 1.12–1.46 (m, 7H), 1.23 (d, 6H, J=6.6 Hz), 1.63–1.87 (m, 7H), 2.40 (m, 1H), 2.78–2.93 (m, 2H), 3.15 (m, 1H), 3.31 (m, 1H), 3.94–4.07 (m, 2H), 7.06 (d, 2H, J=8.4 Hz), 7.09 (d, 1H, J=8.1 Hz), 7.32 (d, 2H, J=8.4 Hz), 8.39 brs, 1H).

Ia-225 mp 222–224° C. ¹H-NMR (DMSO) δ ppm: 1.28 (s, 9H), 1.30–1.61 (m, 4H), 1.77–1.98 (m, 4H), 2.66–2.90 (m, 2H), 3.28 (m, 1H), 3.40–3.50 (m, 2H), 3.79–3.88 (m, 2H), 3.96–4.08 (m, 2H), 4.44 (m, 1H), 6.85 (d, 2H, J=9.0 Hz), 6.91 (d, 1H, J=9.07), 7.31 (d, 2H, J=9.3 Hz), 8.34 (brs, 1H).

Ia-226 mp 194–195° C. ¹H-NMR (CDCl₃/DMSO) δ ppm: 1.39 (d, 6H, J=7.2 Hz), 1.66 (quintet, 2H, J=6.8 Hz), 1.87 (quintet, 2H, J=7.7 Hz), 2.47 (t, 2H, J=7.5 Hz), 3.11–3.22 (m, 1H), 3.21 (t, 2H, J=6.2 Hz), 5.00 (brs, 1H), 7.35–7.56 (m, 5H), 7.86 (d, 1H, J=8.4 Hz), 8.05 (dd, 1H, J=1.8, 8.1 Hz), 8.20 (d, 1H, J=1.8 Hz), 9.24 (s, 1H).

Ia-227 mp>300° C. ¹H-NMR (DMSO) δ ppm: 1.22 (d, 6H, J=6.3 Hz), 1.20–1.40 (m, 4H), 1.74–2.10 (m, 4H), 2.20–2.40 (m, 1H), 2.39 (s, 3H), 3.00–3.30 (m, 2H), 6.25 (s, 1H), 6.99 (brs, 1H), 7.43–7.57 (m, 1H), 7.71 (d, 1H, J=8.1 Hz), 7.76 (s, 1H), 10.27 (s, 1H).

Ia-228 mp 168–169° C. $^1$H-NMR (DMSO) δ ppm: 1.26 (s, 9H), 1.49 (quintet, 2H, J=7.5 Hz), 1.64 (quintet, 2H, J=7.4 Hz), 2.38 (t, 2H, J=7.2 Hz), 2.40 (s, 3H), 3.04 (q, 2H, J=6.5 Hz), 6.25 (s, 1H), 6.89 (t, 1H, J=6.0 Hz), 7.48 (dd, 1H, J=1.8, 8.4 Hz), 7.71 (d, 1H, J=8.4 Hz), 7.77 (d, 1H, J=1.8 Hz), 10.33 (s, 1H).

Ia-229 mp 174–175° C. $^1$H-NMR (DMSO) δ ppm: 1.21 (d, 6H, J=6.6 Hz), 1.42–1.56 (m, 2H), 1.56–1.70 (m, 2H), 2.33–2.42 (m, 2H), 2.40 (s, 3H), 2.90–3.02 (m, 2H), 3.14 (septet, 1H, J=6.5 Hz), 6.26 (s, 1H), 6.99 (brs, 1H), 7.48 (d, 1H, J=8.4 Hz), 7.71 (d, 1H, J=8.7 Hz), 7.77 (s, 1H), 10.33 (s, 1H).

Ia-230 mp 194–195° C. $^1$H-NMR (DMSO) δ ppm: 0.86 (d, 6H, J=6.9 Hz), 1.25–1.65 (m, 4H), 1.27 (s, 9H), 1.81–2.05 (m, 5H), 2.23–2.35 (m, 1H), 2.99–3.15 (m, 1H), 3.36 (d, 2H, J=7.2 Hz), 6.80 (d, 1H, J=8.4 Hz), 7.80 (d, 1H, J=8.4 Hz), 7.87 (d, 1H, J=8.4 Hz), 8.19 (s, 1H), 10.44 (s, 1H).

Ia-231 mp 221–222° C. $^1$H-NMR (DMSO) δ ppm: 0.86 (d, 6H, J=6.9 Hz), 1.22–1.40 (m, 2.H), 1.23 (d, 6H, J=6.9 Hz), 1.40–1.58 (m, 2H), 1.82–2.04 (m, 5H), 2.22–2.37 (m, 1H), 3.00–3.16 (m, 1H), 3.15 (septet, 1H, J=6.6 Hz), 3.36 (d, 2H, J=7.5 Hz), 6.99 (d, 1H, J=7.5 Hz), 7.80 (d, 1H, J=8.4 Hz), 7.86 (d, 1H, J=8.4 Hz), 8.19 (s, 1H), 10.45 (s, 1H).

Ia-232 mp 196–197° C. $^1$H-NMR (CDCl$_3$) δ ppm: 0.93 (d, 6H, J=6.6 Hz), 1.42 (s, 1H), 1.60–1.70 (m, 2H), 1.88 (quintet, 2H, J=7.4 Hz), 2.02–2.20 (m, 1H), 2.46 (t, 2H, J=7.7 Hz), 3.29 (q, 2H, J=6.1 Hz), 3.48 (d, 2H, J=7.8 Hz), 4.26 (t, 1H, J=6.0 Hz), 7.76 (d, 1H, J=8.1 Hz), 7.90 (dd, 1H, J=1.8,8.1 Hz), 8.07 (d, 1H, J=1.5 Hz), 8.39 (s, 1H).

Ia-233 mp 151–152° C. $^1$H-NMR (CDCl$_3$) δ ppm: 0.93 (d, 6H, J=6.6 Hz), 1.40 (d, 6H, J=6.6 Hz), 1.62–1.69 (m, 2H), 1.88 (quintet, 2H, J=7.3 Hz), 2.03–2.16 (m, 1H), 2.47 (t, 2H, J=7.5 Hz), 3.21 (septet, 1H, J=6.8 Hz), 3.23 (q, 2H, J=6.3 Hz), 3.48 (d, 2H, J=7.5 Hz), 4.43 (t, 1H, J=6.0 Hz), 7.76 (d, 1H, J=8.4 Hz), 7.91 (dd, 1H, J=1.8, 8.4 Hz), 8.06 (d, 1H, J=1.8 Hz), 8.36 (s, 1H).

Ia-234 mp 219–220° C. $^1$H-NMR (DMSO-d$_6$) δ ppm: 1.28 (s, 9H), 1.30–1.50 (m, 2H), 1.74–1.88 (m, 2H), 2.83 (t, 2H, J=11.1 Hz), 3.20–3.32 (m, 1H), 3.94–4.07 (m, 2H), 5.94 (s, 2H), 6.77 (d, 1H, J=8.8 Hz), 6.82 (dd, 1H, J=1.8, 8.7 Hz), 6.89 (d, 1H, J=8.7 Hz), 7.11 (d, 1H, J=1.8 Hz), 8.38 (s, 1H).

Ia-235 mp 280–282° C. $^1$H-NMR (DMSO-d$_6$) δ ppm: 1.27 (s, 9H), 1.26–1.57 (m, 4H), 1.86–2.03 (m, 4H), 2.38–2.50 (m, 1H), 3.00–3.14 (m, 1H), 6.81 (d, 1H, J=8.4 Hz), 7.29 (t, 1H, J=8.4 Hz), (t, 1H, J=7.5 Hz), 7.73 (d, 1H, J=8.4 Hz), 7.96 (d, 1H, J=7.5 Hz), 12.27 (s, 1H).

Ia-237 mp 204–205° C. $^1$H-NMR (DMSO) δ ppm: 1.23 (d, 6H, J=6.6 Hz), 1.29–1.61 (m, 4H), 1.75–1.98 (m, 4H), 2.78–2.92 (m, 2H), 3.15 (m, 1H), 3.29 (m, 1H), 3.38–3.51 (m, 2H), 3.78–3.89 (m, 2H), 3.94–4.06 (m, 2H), 4.44 (m, 1H), 6.85 (d, 2H, J=9.0 Hz), 7.10 (d, 1H, J=7.8 Hz), 7.31 (d, 2H, J=9.3 Hz), 8.34 (brs, 1H).

Ia-238 mp 128–130° C. $^1$H-NMR DMSO δ ppm: 1.26 (s, 9H), 1.41–1.53 (m, 2H), 1.55–1.68 (m, 2H), 2.44 (t, 2H, J=7.2 Hz), 2.98–3.07 (m, 2H), 6.90 (t, 1H, J=6.0 Hz), 8.16 (d-d, 1H, J=2.1 Hz, 8.7 Hz), 8.29 (d, 1H, J=8.7 Hz), 8.70 (m, 1H), 10.91 brs, 1H).

Ia-239 mp 256–258° C. $^1$H-NMR (DMSO) δ ppm: 1.26–1.53 (m, 4H), 1.26 (s, 9H), 1.76–2.00 (m, 4H), 2.23 (s, 3H), 2.39 (m, 1H), 3.04 (m, 1H), 6.80 (d, 1H, J=8.7 Hz), 7.57 (d-d, 1H, J=2.4 Hz, 8.4 Hz), 7.97 (d, 1H, J=8.4 Hz), 8.12 (m, 1H), 10.26 (brs, 1H).

Ia-240 mp 288–290° C. $^1$H-NMR (DMSO) δ ppm: 1.26–1.53 (m, 4H), 1.27 (s, 9H), 1.78–1.90 (m, 4H), 2.40 (m, 1H), 3.04 (m, 1H), 6.81 (d, 1H, J=8.7 Hz), 7.07 (m, 1H), 7.75 (m, 1H), 8.07 (d, 1H, J=8.4 Hz), 8.29 (m, 1H), 10.36 brs, 1H).

Ia-241 mp 249–250° C. $^1$H-NMR (DMSO) δ ppm: 1.28 (s, 9H), 1.34–1.50 (m, 2H), 1.79–1.90 (m, 2H), 2.74–2.98 (m, 2H), 3.32 (m, 1H), 4.02–4.14 (m, 2H), 6.91 (d, 1H, J=8.4 Hz), 7.94 (d, 1H, J=9.0 Hz), 8.04 (d-d, 1H, J=2.1 Hz, 9.0 Hz), 8.60 (s, 1H), 9.76 (brs, 1H).

Ia-242 mp 250–252° C. $^1$H-NMR (DMSO) δ ppm: 1.24 (s, 9H), 1.27 (s, 9H), 1.24–1.54 (m, 4H), 1.76–1.88 (m, 2H), 1.90–2.01 (m, 2H), 2.21 (m, 1H), 3.05 (m, 1H), 6.79 (d, 1H, J=8.7 Hz), 6.88 (d, 2H, J=9.0 Hz), 7.48 (d, 2H, J=9.0 Hz), 9.72 (brs, 1H).

136-0290 mp 250–252° C. $^1$H-NMR (DMSO) δ ppm: 1.15 (d, 6H, J=6.6 Hz), 1.28 (s, 9H), 1.35–1.52 (m, 2H), 1.78–1.92 (m, 2H), 2.20 (s, 3), 2.81–2.96 (m, 2H), 3.33 (m, 1H), 3.96–4.16 (m, 3H), 6.92 (d, 1H, J=8.7 Hz), 7.27 (d, 1H, J=8.1 Hz), 7.60 (m, 1H), 7.66 (m, 1H), 8.06 (d, 1H, J=7.8 Hz), 8.14 (brs, 1H).

Ia-244 mp 211–213° C. $^1$H-NMR DMSO δ ppm: 1.29 (s, 9H), 1.35–1.52 (m, 2H), 1.81–1.93 (m, 2H), 2.83–2.97 (m, 2), 3.32 (m, 1H), 4.03–4.14 (m, 2H), 6.93 (d, 1H, J=8.7 Hz), 7.55 (d-d, 1H, J=2.1 Hz, 9.0 Hz), 7.94 (d, 1H, J=9.0 Hz), 8.29 (d, 1H, J=1.8 Hz), 8.78 (brs, 1H), 9.19 (s, 1H).

Ia-245 mp 196–197° C. $^1$H-NMR (DMSO) δ ppm: 1.27 (s, 9H), 1.2–1.6 (m, 6H), 1.8–2.0 (m, 6H), 2.23 (m, 1H), 3.05 (m, 1H), 3.73 (m, 4h), 4.99 (s, 1H), 6.79 (d, 1H, J=8.7), 7.1:3 (d, 1H, J=6.8), 7.22 (t, 1H, J=6.8), 7.49 (d, 1H, J=6.8), 7.72 (s, 1H), 9.78 (s, 1H).

Ia-246 mp 242–244° C. $^1$H-NMR (DMSO) δ ppm: 1.27 (s, 9H), 1.2–1.5 (m, 4H), 1.65 (m, 4H), 1.8–2.0 (m, 4H), 2.23 (m, 1H), 2.71 (m, 1H), 3.06 (m, 1H), 3.43 (m, 2H), 3.93 (m, 2H), 6.79 (d, 1H, J=8.7), 6.91 (d, 1H, J=8.7), 7.20 (t, 1H, J=7.5), 7.40 (d, 1H, J=7.5), 7.5:3 (s, 1H), 9.76 (s, 1H).

Ia-247 mp 242–245° C. $^1$-NMR (DMSO) δ ppm: 1.27 (s, 9H), 1.2–1.6 (m, 6H), 1.8–2.0 (m, 6H), 2.23 (m, 1H), 3.05 (m, 1H), 3.74 (m, 4H), 4.94 (brs, 1H), 6.79 (d, 1h, J=8.7), 7.38 (d, 1H, J=8.7), 7.52 (d, 1H, J=8.7), 9.76 (s, 1H).

Ia-248 mp 272–274° C. $^1$H-NMR (CDCl$_3$) δ ppm: 1.27 (s, 9H), 1.2–1.5 (m, 4H), 1.62 (m, 4H), 1.8–2.0 (m, 4H), 2.22 (m, 1H), 2.68 (m, 1H), 3.05 (m, 1H), 3.41 (m, 2H), 3.92 (m, 2H), 6.79 (d, 1H, J=9.0), 7.15 (d, 2H, J=8.7), 7.50 (d, 2H, J=8.7), 9.73 (s, 1H).

Ia-249 mp 174–176° C.

Ia-250 mp 255–257° C.

Ia-252 mp 249–251° C.

Ia-253 mp 120–121° C.

Ia-254 mp 236–237° C.

Ia-255 mp 172–174° C.

Ia-256 mp 257–259° C.
Ia-257 mp 179–180° C.
Ia-258 mp 227–229° C.
Ia-259 mp 135–136° C.

Experiment 1 Affinity for NPY Y5 Receptor cDNA sequence encoding a human NPY Y5 receptor (WO96/16542) was cloned in the expression vector pME18S (Takebe et al. Mol. Cell. Biol. 8, 8957). The obtained expression vector was transfected into a host CHO cells by using a Lipofect AMINE reagent (Trademark, Gico BRL Co., Ltd.) according to an instruction protocol to obtain the cells that stably express NPY Y5 receptor.

The membranes prepared from the above CHO cells expressing NPY Y5 receptor, the compound of the present invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the mixture was filtered with a glassfilter GF/C treated with polyethyleneimine. After the glassfilter was washed with 50 mM Tris-HCl buffer (pH 7.4), the radioactivity on the filter was measured with a gamma counter. The non-specific binding was detected in the presence of 200 nM of peptide YY. The 50% inhibitory concentration of the test compound against the specific peptide YY binding ($IC_{50}$ value) was calculated (Inui, A. et al. Endocrinology 131, 2090–2096 (1992)). The results are shown in Tables 1 and 2.

The compounds of the present invention inhibited the binding of peptide YY (NPY homologue) to NPY Y5 receptors. In other words, the compounds of the present invention showed affinity for the NPY Y5 receptor.

Experiment 2 cAMP Production Inhibitory Activity in CHO Cells

After CHO cells expressing human NPY Y5 receptor were incubated in the presence of 2.5 mM isobutylmethylxanthine (SIGMA) at 37° C. for 20 min, the compound of the present invention was added and incubated for 5 min. Then, 50 nM NPY and 10 μM forskolin (SIGMA) were added to the cells and incubated for 30 min. After the reaction was terminated by adding 1N HCl, the amount of cAMP in the supernatant was measured with EIA kit (Amersham LIFE SCIENCE). The inhibitory activity of NPY against forskolin stimulated cAMP was regarded as 100% and the 50% inhibitory concentration ($IC_{50}$ value) of the compound of the present invention against the NPY activity was calculated. The results are shown in Tables 1 to 4.

TABLE 1

| Compound | binding $IC_{50}$ (nM) | cAMP $IC_{50}$ (nM) |
|---|---|---|
| I-2 | 7.5 | 72 |
| I-7 | 3 | <10 |
| I-11 | 1.3 | 5 |
| I-18 | 4.4 | 29 |
| I-20 | 7 | 21 |
| I-22 | 8.6 | 51 |
| I-24 | 9.6 | 71 |
| I-25 | 0.6 | 2.6 |
| I-41 | 5.3 | 38.2 |
| I-44 | 1.0 | 13.4 |
| I-45 | 1.2 | 27.9 |

TABLE 1-continued

| Compound | binding $IC_{50}$ (nM) | cAMP $IC_{50}$ (nM) |
|---|---|---|
| I-46 | 0.8 | 10.5 |
| I-47 | 0.6 | 14.9 |
| I-49 | 0.4 | 8.1 |
| I-50 | 0.3 | 8.4 |
| I-53 | 4.1 | 21 |
| I-55 | 9.0 | 40 |
| I-57 | 4.8 | 47 |
| I-59 | 0.8 | 35 |
| I-60 | 0.69 | 18 |
| I-61 | 0.26 | 5.3 |
| I-62 | 0.58 | 16 |
| I-63 | 1.3 | 50 |
| I-64 | 2.2 | 80 |
| I-65 | 1.8 | 72 |
| I-66 | 1.5 | 30 |
| I-67 | 2 | 17 |
| I-69 | 3.8 | 13 |
| I-72 | 2.3 | 2.1 |
| I-75 | 0.55 | 3.4 |
| I-76 | 0.61 | 5.5 |
| I-77 | 1.8 | 28 |
| I-79 | 0.59 | 25 |
| I-83 | 0.61 | 29 |
| I-84 | 1.3 | 25 |
| I-86 | 3.4 | 100 |
| I-87 | 0.66 | 21 |
| I-90 | 2.8 | 50 |
| I-92 | 7 | 61 |
| I-101 | 3.9 | 38 |
| I-102 | 1.7 | 14 |
| I-106 | 6.4 | 29 |

TABLE 2

| | binding $IC_{50}$ (nM) | cAMP $IC_{50}$ (nM) |
|---|---|---|
| I-109 | 1.2 | 3.2 |
| I-110 | 4.3 | 13.6 |
| I-111 | 1.8 | 6.1 |
| I-114 | 7 | 30 |
| I-116 | 1.2 | 11 |
| I-120 | 1.4 | 4.8 |
| I-123 | 1.8 | 168 |
| I-126 | 0.6 | 13.2 |
| I-127 | 1.4 | 30.4 |
| I-128 | 1.3 | 10.2 |
| I-129 | 2.1 | 174 |
| I-130 | 1.1 | 42.5 |
| I-131 | 1.1 | 34.8 |
| I-132 | 2.2 | 30.4 |
| I-133 | 0.9 | 21.1 |
| I-134 | 0.5 | 10.0 |
| I-135 | 0.7 | 22.0 |
| I-136 | 2.8 | — |
| I-137 | 1.4 | 68.2 |
| I-138 | 1.0 | 18.6 |
| I-139 | 0.41 | 7.6 |
| I-140 | 0.48 | 8.9 |
| I-141 | 0.42 | 7.4 |
| I-142 | 0.49 | 28 |
| I-143 | 3.5 | 44 |
| I-144 | 3.4 | 52 |
| I-146 | 2.3 | 20 |
| I-147 | 7.1 | 63 |
| I-149 | 0.83 | 15 |
| I-150 | 0.17 | 5.2 |
| I-151 | 0.17 | 2.6 |
| I-152 | 0.88 | 46 |
| I-153 | 1.7 | 29 |
| I-154 | 1.1 | 11 |
| I-156 | 0.81 | 17 |
| I-160 | 0.61 | 8.8 |
| I-161 | 0.49 | 3.1 |
| I-162 | 1.7 | 32 |
| I-163 | 2.3 | 83 |

TABLE 2-continued

| | | |
|---|---|---|
| I-164 | 0.71 | 5.9 |
| I-165 | 0.44 | 47 |
| I-166 | 0.37 | 9.7 |
| I-167 | 0.72 | 39 |
| I-168 | 2.1 | 32 |
| I-171 | 2.4 | 71 |
| I-172 | 0.91 | 36 |
| I-187 | 0.58 | 13 |
| I-191 | 1.1 | 11 |
| I-196 | 1.4 | 6.8 |
| I-197 | 6.7 | 38 |
| I-198 | 7.2 | 33 |
| I-199 | 4.8 | 31 |
| I-202 | 6.7 | 67 |
| I-204 | 1.0 | 6.3 |
| I-205 | 2.9 | 17 |
| I-206 | 5.9 | 54 |
| I-207 | 4.6 | 23 |
| I-210 | 1.1 | 13 |
| I-212 | 0.67 | 7.5 |
| I-213 | 0.44 | 4.0 |
| Ia-1 | 4.8 | 31 |
| Ia-3 | 9.2 | 150 |
| Ia-4 | 1.4 | 15 |
| Ia-5 | 1.6 | 43 |
| Ia-6 | 2.4 | 23 |
| Ia-8 | 2.9 | 34 |
| Ia-9 | 0.94 | 11 |
| Ia-10 | 0.47 | 2.7 |
| Ia-11 | 0.64 | 7.2 |
| Ia-12 | 0.94 | 5.5 |
| Ia-13 | 1.5 | 3.3 |
| Ia-14 | 4.8 | 28 |
| Ia-16 | 0.1 | — |
| Ia-17 | 0.1 | 1.9 |
| Ia-20 | 4.9 | 100 |

TABLE 3

| | | |
|---|---|---|
| Ia-21 | 3.4 | 35 |
| Ia-22 | 3.1 | 38 |
| Ia-24 | 5.2 | 74 |
| Ia-25 | 1.1 | 18 |
| Ia-26 | 1.9 | 27 |
| Ia-28 | 5.2 | 130 |
| Ia-29 | 1 | 7.3 |
| Ia-30 | 2.6 | 25 |
| Ia-31 | 3.8 | 11 |
| Ia-32 | 0.52 | 6.7 |
| Ia-33 | 1.8 | 64 |
| Ia-35 | 1.8 | — |
| Ia-36 | 1.6 | 86 |
| Ia-37 | 0.73 | 3.8 |
| Ia-38 | 1 | 2.2 |
| Ia-39 | 1.5 | 3.5 |
| Ia-40 | 2.2 | 9.3 |
| Ia-41 | 2.5 | 9 |
| Ia-42 | 3.6 | 20 |
| Ia-44 | 4.8 | 27 |
| Ia-45 | 4.8 | 42 |
| Ia-46 | 0.87 | 8.3 |
| Ia-47 | 0.82 | 3.8 |
| Ia-48 | 1.2 | 6.1 |
| Ia-49 | 2.6 | 83 |
| Ia-50 | 1.7 | 24 |
| Ia-51 | 1.3 | 3.4 |
| Ia-52 | 1.9 | 22 |
| Ia-53 | 0.22 | 8.1 |
| Ia-54 | 0.44 | 9 |
| Ia-55 | 1.1 | 27 |
| Ia-56 | 2.3 | 96 |
| Ia-57 | 0.93 | 31 |
| Ia-58 | 2.5 | 110 |
| Ia-59 | 0.71 | 16 |
| Ia-60 | 0.95 | 10 |
| Ia-61 | 0.68 | 19 |

TABLE 3-continued

| | | |
|---|---|---|
| Ia-62 | 1.1 | 29 |
| Ia-63 | 3.9 | 370 |
| Ia-64 | 7.1 | 96 |
| Ia-65 | 1.1 | 11 |
| Ia-66 | 0.59 | 3.2 |
| Ia-67 | 6.3 | 75 |
| Ia-68 | 9.5 | 180 |
| Ia-69 | 2.7 | 33 |
| Ia-70 | 1.5 | 31 |
| Ia-71 | 1.3 | 12 |
| Ia-76 | 2.2 | — |
| Ia-78 | 2 | 150 |
| Ia-79 | 0.82 | — |
| Ia-80 | 0.44 | 3.0 |
| Ia-81 | 2.7 | 4.5 |
| Ia-83 | 1.2 | 53 |
| Ia-84 | 0.25 | 13 |
| Ia-85 | 0.22 | 14 |
| Ia-86 | 0.73 | 11 |
| Ia-87 | 0.49 | 61 |
| Ia-88 | 0.62 | 48 |
| Ia-91 | 4 | 150 |
| Ia-106 | 1.9 | 24 |
| Ia-107 | 0.14 | 1.3 |
| Ia-109 | 0.6 | 3.9 |
| Ia-110 | 0.3 | 1.1 |
| Ia-111 | 5.1 | 28 |
| Ia-124 | 1.1 | 22 |
| Ia-125 | 4.1 | 46 |
| Ia-126 | 2.3 | 58 |
| Ia-127 | 6.1 | 160 |
| Ia-129 | 1.3 | 26 |
| Ia-130 | 0.21 | 3 |
| Ia-131 | 1.3 | 17 |
| Ia-132 | 2.8 | 76 |
| Ia-133 | 1.7 | 8.8 |
| Ia-135 | 8.2 | 49 |
| Ia-136 | 1.6 | 13 |
| Ia-138 | 2.2 | 28 |
| Ia-139 | 1.9 | 25 |
| Ia-140 | 1 | 24 |
| Ia-141 | 1 | 5.7 |
| Ia-142 | 0.67 | 5.5 |

TABLE 4

| | | |
|---|---|---|
| Ia-143 | 7.8 | 39 |
| Ia-144 | 6.1 | 57 |
| Ia-145 | 7 | 86 |
| Ia-146 | 9.9 | 79 |
| Ia-158 | 0.71 | 1.7 |
| Ia-160 | 0.76 | 140 |
| Ia-161 | 1.9 | 18 |
| Ia-163 | 7 | 400 |
| Ia-164 | 0.38 | 4.7 |
| Ia-168 | 0.95 | 13 |
| Ia-169 | 1.9 | 88 |
| Ia-173 | 6.9 | 140 |
| Ia-174 | 0.35 | 5.4 |
| Ia-175 | 0.49 | 9.2 |
| Ia-176 | 0.63 | 5.1 |
| Ia-177 | 0.49 | 7.5 |
| Ia-178 | 4.6 | 16 |
| Ia-179 | 0.89 | 19 |
| Ia-180 | 1.9 | 11 |
| Ia-181 | 7.7 | 25 |
| Ia-182 | 0.24 | 2.1 |
| Ia-183 | 1.9 | 7.8 |
| Ia-184 | 0.38 | — |
| Ia-185 | 0.94 | 4.4 |
| Ia-186 | 0.93 | 12 |
| Ia-187 | 1.9 | 60 |
| Ia-188 | 0.75 | 28 |
| Ia-189 | 3.5 | 95 |
| Ia-190 | 0.34 | 1000 |
| Ia-191 | 0.49 | 220 |

TABLE 4-continued

| | | |
|---|---|---|
| Ia-192 | 5.9 | 200 |
| Ia-193 | 1.4 | 43 |
| Ia-194 | 0.22 | 8.1 |
| Ia-195 | 1.4 | 31 |
| Ia-196 | 0.39 | 1.3 |
| Ia-197 | 0.44 | 2.5 |
| Ia-198 | 0.23 | 2.6 |
| Ia-199 | 0.11 | 1.6 |
| Ia-200 | 1.4 | 18 |
| Ia-201 | 3.1 | 74 |
| Ia-202 | 0.37 | 3.4 |
| Ia-203 | 0.2 | 2.6 |
| Ia-204 | 1 | 6.3 |
| Ia-205 | 2.4 | 99 |
| Ia-206 | 1.9 | 460 |
| Ia-207 | 0.55 | 5.9 |
| Ia-208 | 1.2 | 9.7 |
| Ia-209 | 0.55 | — |
| Ia-210 | 2.8 | 99 |
| Ia-211 | 4.8 | 240 |
| Ia-212 | 0.52 | 2.6 |
| Ia-213 | 0.91 | 28 |
| Ia-219 | 2.5 | 28 |
| Ia-221 | 0.47 | 1.5 |
| Ia-222 | 3.7 | 18 |
| Ia-224 | 0.1 | 1.2 |
| Ia-225 | 3.4 | 20 |
| Ia-226 | 0.37 | 21 |
| Ia-227 | 0.59 | — |
| Ia-228 | 0.96 | — |
| Ia-229 | 1.9 | — |
| Ia-230 | 0.32 | — |
| Ia-231 | 0.29 | — |
| Ia-232 | 0.7 | — |
| Ia-233 | 0.63 | — |
| Ia-235 | 5.5 | — |
| Ia-237 | 1.1 | 15 |
| Ia-241 | 1.9 | — |
| Ia-243 | 1.3 | — |
| Ia-246 | 0.26 | 20 |
| Ia-247 | 0.79 | 31 |
| Ia-248 | 0.27 | 17 |
| Ia-250 | 1.9 | — |
| Ia-252 | 1.2 | — |
| Ia-253 | 0.53 | — |
| Ia-254 | 2.0 | — |
| Ia-255 | 3.2 | — |
| Ia-256 | 5.7 | — |
| Ia-257 | 8.6 | — |
| Ia-258 | 1.8 | — |

As shown in Tables 1 to 4, the compounds of the present invention have an NPY Y5 receptor antagonistic activity.

Experiment 3

Using the membranes prepared from Y1-expression cells (human neuroblastoma, SK-N-MC) and the membranes prepared from Y2-expression cells (human neuroblastoma, SMS-KAN), the experiment was carried out in a similar way as Experiment 1 to determine the affinity for NPY Y1 receptor and NPY Y2 receptor.

Binding $IC_{50}$ values for NPY Y1 and NPY Y2 receptors of I-27, I-32, I-41, I-45, I-46, I-47, I-48, I-49, I-59, I-61, I-63, I-64, I-66, I-69, I-72, I-152, I-154, I-204, I-205, I-212, Ia-3, Ia-5, Ia-6, Ia-12, Ia-16, Ia-17, Ia-20, Ia-21, Ia-22, Ia-26, Ia-28, Ia-29, Ia-30, Ia-31, Ia-32, Ia-33, Ia-37, Ia-39, Ia-40, Ia-50, Ia-51, Ia-54, Ia-62, Ia-67, Ia-124, Ia-126, Ia-139, Ia-140, Ia-142, Ia-178, Ia-199 and Ia-200 were 100,000 nM or higher and each compound had a selectivity for NPY Y5 receptor.

Formulation Example 1

Tablets

| | |
|---|---|
| Compound (I-1) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

After all of the above ingredients except for calcium stearate are uniformly mixed, the mixture is crushed and granulated, and dried to obtain a suitable size of granules. After calcium stearate is added to the granules, tablets are formed by compression molding.

Formulation Example 2

Capsules

| | |
|---|---|
| Compound (I-2) | 10 mg |
| Magnesium stearate | 10 mg |
| Lactose | 80 mg |

After the above ingredients are mixed to prepare powders or granules, the obtained are filled in capsules.

Formulation Example 3

Granules

| | |
|---|---|
| Compound (I-3) | 30 g |
| Lactose | 265 g |
| Magnesium Stearate | 5 g |

After the above ingredients are mixed uniformly and formed by compression molding, the obtained are crushed, granulated and sieved to prepare suitable volume of granules.

Industrial Applicability

As shown in the above Experiments, the compounds of the present invention have an NPY Y5 receptor antagonistic activity. Therefore, the compounds of the present invention are useful as an anti-obestic agent and anorectic agent.

What is claimed is:

1. A pharmaceutical composition comprising a therapeutically effective amount of a compound of the formula (I):

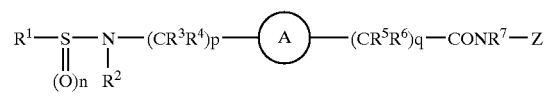

(I)

wherein $R^1$ is optionally substituted lower alkyl, optionally substituted cycloalkyl or optionally substituted aryl, $R^2$ is hydrogen or lower alkyl, and $R^1$ and $R^2$ taken together may form lower alkylene, n is 1 or 2, $R^3$, $R^4$, $R^5$ and $R^6$ are each independently hydrogen or lower alkyl,

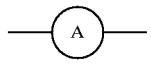

is optionally substituted cycloalkylene or optionally substituted bicycloalkylene, and p and q are each independently 0 or 1, $R^7$ is hydrogen or lower alkyl, and Z is optionally substituted pyridyl, prodrug, pharmaceutically acceptable salt or hydrate thereof together with a pharmaceutically acceptable carrier.

2. The pharmaceutical composition claimed in claim 1 wherein $R^2$ is hydrogen or lower alkyl.

3. The pharmaceutical composition claimed in claim 1 wherein $R^1$ is optionally substituted lower alkyl or optionally substituted cycloalkyl, and p and q are 0.

4. The pharmaceutical composition claimed in any one of claims 1 to 3 wherein $R^1$ is optionally substituted C3 to C10 alkyl.

5. The pharmaceutical composition claimed in any one of claims 1 to 3 which is an anti-obestic agent.

6. The pharmaceutical composition claimed in any one of claims 1 to 3 which is an anorectic agent.

7. A method for treating obesity comprising administering to a subject that is obese an effective dose of the pharmaceutical composition claimed in any one of claims 1 to 3.

8. A method for suppressing food intake comprising administering to a subject that is obese an effective dose of the pharmaceutical composition claimed in any one of claims 1 to 3.

9. A compound of the formula (I);

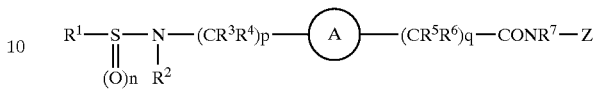

wherein $R^1$ is optionally substituted C3 to C10 alkyl or optionally substituted C5 to C6 cycloalkyl and the other symbols are the same as defined in claim 1, prodrug, pharmaceutically acceptable salt or hydrate thereof.

10. The compound described in claim 9 wherein

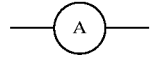

is optionally substituted cyclohexylene and p and q are simultaneously 0, prodrug, pharmaceutically acceptable salt or hydrate thereof.

* * * * *